(12) United States Patent
Beck et al.

(10) Patent No.: US 10,988,750 B2
(45) Date of Patent: *Apr. 27, 2021

(54) PHOSPHOKETOLASES FOR IMPROVED PRODUCTION OF ACETYL COENZYME A-DERIVED METABOLITES, ISOPRENE, ISOPRENOID PRECURSORS, AND ISOPRENOIDS

(71) Applicants: Danisco US Inc., Palo Alto, CA (US); The Goodyear Tire & Rubber Company, Akron, OH (US)

(72) Inventors: Zachary Q. Beck, Palo Alto, CA (US); Jeffrey W. Munos, San Francisco, CA (US); Derek H. Wells, Palo Alto, CA (US); Jian Yao, Sunnyvale, CA (US)

(73) Assignee: Danisco US Inc., Palo Alto, CA (US)

(*) Notice: Subject to any disclaimer, the term of this patent is extended or adjusted under 35 U.S.C. 154(b) by 134 days.

This patent is subject to a terminal disclaimer.

(21) Appl. No.: 16/276,558

(22) Filed: Feb. 14, 2019

(65) Prior Publication Data

US 2019/0367896 A1 Dec. 5, 2019

Related U.S. Application Data

(63) Continuation of application No. 14/783,391, filed as application No. PCT/US2014/033688 on Apr. 10, 2014, now Pat. No. 10,246,694.

(60) Provisional application No. 61/834,359, filed on Jun. 12, 2013, provisional application No. 61/810,696, filed on Apr. 10, 2013.

(51) Int. Cl.
*C12N 9/88* (2006.01)
*C12P 5/02* (2006.01)
*C12P 19/32* (2006.01)
*C12P 5/00* (2006.01)
*C12Q 1/527* (2006.01)

(52) U.S. Cl.
CPC ............. *C12N 9/88* (2013.01); *C12P 5/007* (2013.01); *C12P 5/026* (2013.01); *C12P 19/32* (2013.01); *C12Q 1/527* (2013.01); *C12Y 401/02009* (2013.01)

(58) Field of Classification Search
None
See application file for complete search history.

(56) References Cited

FOREIGN PATENT DOCUMENTS

JP  WO 2006/016705  *  2/2006  ............ C12N 9/88

* cited by examiner

*Primary Examiner* — Suzanne M Noakes
*Assistant Examiner* — Jae W Lee
(74) *Attorney, Agent, or Firm* — Mintz, Levin, Cohn, Ferris, Glovsky and Popeo, P.C.

(57) ABSTRACT

This present invention relates to cultured recombinant cells comprising a heterologous phosphoketolase (PKL) polypeptide that are capable of increased production of acetyl coenzyme A-derived metabolites, as well as methods for producing and using the same. In some embodiments, the recombinant cells further comprise one or more mevalonate (MVA) pathway polypeptides for the production of isoprenoid precursors, isoprene and isoprenoids.

20 Claims, 42 Drawing Sheets

Specification includes a Sequence Listing.

FIG. 11

PHOSPHOKETOLASES FOR IMPROVED PRODUCTION OF ACETYL COENZYME A-DERIVED METABOLITES, ISOPRENE, ISOPRENOID PRECURSORS, AND ISOPRENOIDS

CROSS-REFERENCE TO RELATED APPLICATIONS

This application is a continuation of U.S. patent application Ser. No. 14/783,391, filed Oct. 8, 2015, now U.S. Pat. No. 10,246,694, which is a U.S. National Stage Entry of International Application No. PCT/US2014/033688, filed Apr. 10, 2014, which claims priority to U.S. Provisional Patent Application No. 61/810,696, filed Apr. 10, 2013, and U.S. Provisional Patent Application No. 61/834,359, filed Jun. 12, 2013, the disclosures of each of which are incorporated by reference herein in their entireties.

INCORPORATION BY REFERENCE TO SEQUENCE LISTING

This application contains a Sequence Listing in computer readable form (file name: 048768-510C01US_SL_ST25.txt; 508,741 bytes—ASCII text file; created Aug. 15, 2019), which is incorporated herein by reference in its entirety and forms part of the disclosure.

FIELD OF THE INVENTION

This present invention relates to cultured recombinant cells comprising a heterologous phosphoketolase (PKL) polypeptide that are capable of increased production of acetyl coenzyme A-derived metabolites, as well as methods for producing and using the same. In some embodiments, the recombinant cells further comprise one or more mevalonate (MVA) pathway polypeptides for the production of isoprenoid precursors, isoprene and isoprenoids.

BACKGROUND OF THE INVENTION

Glycolysis allows the metabolic conversion of a carbon source into intermediate compounds such as acetyl-Coenzyme A (acetyl-CoA) which is an important intermediate in the synthesis of essential biological compounds, including polyketides, fatty acids, amino acids, vitamins, isoprene, isoprenoids, phenolics, and alkaloids. Several of these acetyl-CoA derived metabolites have industrial utility. For example, isoprene (2-methyl-1,3-butadiene) is the critical starting material for a variety of synthetic polymers, most notably synthetic rubbers. Isoprene can be obtained by fractionating petroleum; however, the purification of this material is expensive and time-consuming Petroleum cracking of the C5 stream of hydrocarbons produces only about 15% isoprene. About 800,000 tons per year of cis-polyisoprene are produced from the polymerization of isoprene; most of this polyisoprene is used in the tire and rubber industry. Isoprene is also copolymerized for use as a synthetic elastomer in other products such as footwear, mechanical products, medical products, sporting goods, and latex. Isoprene can also be naturally produced by a variety of microbial, plant, and animal species. In particular, two pathways have been identified for the natural biosynthesis of isoprene: the mevalonate (MVA) pathway and the non-mevalonate (DXP) pathway.

Isoprenoids are also acetyl-CoA-derived metabolites that demonstrate industrial utility. For example, isoprenoids are used in pharmaceutical products and as biofuels, food additives, and other specialty chemicals. Over 29,000 isoprenoid compounds have been identified and new isoprenoids are being discovered each year. Isoprenoids can be isolated from natural products, such as microorganisms and species of plants that use isoprenoid precursor molecules as a basic building block to form the relatively complex structures of isoprenoids. Isoprenoids are vital to most living organisms and cells, providing a means to maintain cellular membrane fluidity and electron transport. In nature, isoprenoids function in roles as diverse as natural pesticides in plants to contributing to the scents associated with cinnamon, cloves, and ginger. Moreover, the pharmaceutical and chemical communities use isoprenoids as pharmaceuticals, nutraceuticals, flavoring agents, and agricultural pest control agents. Given their importance in biological systems and usefulness in a broad range of applications, isoprenoids have been the focus of much attention by scientists.

Recent developments in the production of isoprene, isoprenoid precursor molecules, and isoprenoids disclose methods for the production of isoprene and isoprenoids at rates, titers, and purities that can be sufficient to meet the demands of robust commercial processes (see, for example, International Patent Application Publication No. WO 2009/076676 A2 and U.S. Pat. No. 7,915,026); however, alternate pathways to improve production and yields of the same are still needed.

For example, theoretically, three molecules of acetyl-CoA can be derived from a single molecule of glucose in a balanced reaction. However, organisms typically produce only up to two molecules of acetyl-CoA, with the remainder mass being lost as $CO_2$. The release of $CO_2$ occurs during the formation of acetyl-CoA from pyruvate, a reaction catalyzed by pyruvate dehydrogenase. The loss of one carbon atom results in decreased production yields of acetyl-CoA-derived metabolites, isoprenoid precursors, isoprene, and isoprenoid molecules. An exception to this reaction loss is the Wood-Ljungdahl pathway, which relies on carbon monoxide dehydrogenase and acetyl-CoA synthase enzymes to reduce the carbon dioxide to acetyl-CoA in anaerobic acetogens.

What is needed, therefore, are recombinant cells that utilize alternate metabolic process which can potentially produce three molecules of acetyl-CoA from one molecule of glucose using a pathway which does not rely on the Wood-Ljungdahl pathway enzymes in the production of isoprene, isoprenoid precursor molecules, and isoprenoids.

The invention described herein addresses these problems and provides additional benefits as well.

Throughout this specification, various patents, patent applications and other types of publications (e.g., journal articles) are referenced. The disclosure of all patents, patent applications, and publications cited herein are hereby incorporated by reference in their entirety for all purposes.

SUMMARY OF THE INVENTION

The invention provided herein discloses, inter alia, cultured recombinant cells, compositions of these cells and methods of using these cells to increase production of metabolic intermediates such as erythrose 4-phosphate (E4P), glyceraldehyde 3-phosphate (GAP), and acetyl-phosphate (Ac-P) as well as to increase production of isoprenoid precursors, isoprene, isoprenoids, and/or molecules derived from Acetyl-CoA such as amino acids.

Accordingly, in one aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:1.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:2.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:3.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:4.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:5.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:6.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:7.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:8.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:9.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:10.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:11.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:12.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:13.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:14.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:15.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:16

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:17.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:18.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:19.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:20.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:21.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:22.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:23.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:24.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:25.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:26.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:27.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:28.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:29.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:30.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:31.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:32.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:33.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:34.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:35.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:36.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:37.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:38.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:39.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:40.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:41.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:42.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:43.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:44.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:45.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:46.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:47.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:48.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:49.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:50.

In another aspect, provided herein is a recombinant cell capable of increased carbon flux through the phosphoketolase pathway, wherein the recombinant cell comprises a heterologous nucleic acid sequence encoding a polypeptide having phosphoketolase activity, wherein the polypeptide comprises at least 65% sequence identity to SEQ ID NO:51.

In some aspects, in any of the embodiments above and/or herein, culturing of the recombinant cell in a suitable media increases one or more of an intracellular amount of erythrose 4-phosphate, an intracellular amount of glyceraldehyde 3-phosphate, or intracellular amount phosphate. In other aspects, in any of the embodiments above and/or herein, the polypeptide having phosphoketolase activity is capable of synthesizing glyceraldehyde 3-phosphate and acetyl phosphate from xylulose 5-phosphate. In other aspects, in any of the embodiments above and/or herein, the polypeptide having phosphoketolase activity is capable of synthesizing erythrose 4-phosphate and acetyl phosphate from fructose 6-phosphate.

In other aspects, provided herein is a recombinant cell disclosed in any of the embodiments above and/or herein capable of producing isoprene, wherein the recombinant cell further comprises (i) one or more nucleic acids encoding one or more polypeptides of the complete MVA pathway and (ii) a heterologous nucleic acid encoding an isoprene synthase polypeptide, wherein culturing of the recombinant cell in a suitable media provides for the production of isoprene. In another aspect of the cells disclosed in any of the embodiments above and/or herein, the one or more polypeptides of the complete MVA pathway is selected from (a) an enzyme that condenses two molecules of acetyl-CoA to form acetoacetyl-CoA; (b) an enzyme that condenses acetoacetyl-CoA with acetyl-CoA to form HMG-CoA (e.g., HMG synthase); (c) an enzyme that converts HMG-CoA to mevalonate; (d) an enzyme that phosphorylates mevalonate to mevalonate 5-phosphate; (e) an enzyme that converts mevalonate 5-phosphate to mevalonate 5-pyrophosphate; and (f) an enzyme that converts mevalonate 5-pyrophosphate to isopentenyl pyrophosphate. In another aspect of the cells disclosed in any of the embodiments above and/or herein, the heterologous nucleic acid encoding an isoprene synthase polypeptide is a plant isoprene synthase polypeptide. In another aspect of the cells disclosed in any of the embodiments above and/or herein, the plant isoprene synthase polypeptide is a polypeptide from *Pueraria* or *Populus* or a hybrid, *Populus alba*×*Populus tremula*. In another aspect of the cells disclosed in any of the embodiments above and/or herein, the isoprene synthase polypeptide is selected from the group consisting of *Pueraria montana* or *Pueraria lobata*, *Populus tremuloides*, *Populus alba*, *Populus nigra*, and *Populus trichocarpa*. In another aspect of the cells disclosed in any of the embodiments above and/or herein, the recombinant cells further comprise one or more nucleic acids encoding one or more 1-deoxy-D-xylulose 5-phosphate (DXP) pathway polypeptides.

In other aspects, provided herein is a recombinant cell disclosed in any of the embodiments above and/or herein capable of producing isoprenoid precursors, wherein the recombinant cell further comprises one or more nucleic acids encoding one or more polypeptides of the complete MVA pathway, wherein culturing of the recombinant cell in a suitable media provides for the production of isoprenoid precursors.

In other aspects, provided herein is a recombinant cell disclosed in any of the embodiments above and/or herein capable of producing isoprenoids, wherein the recombinant cell further comprises (i) one or more nucleic acids encoding one or more polypeptides of the complete MVA pathway and (ii) a heterologous nucleic acid encoding an polyprenyl pyrophosphate synthase polypeptide, wherein culturing of the recombinant cell in a suitable media provides for the production of isoprenoids.

In other aspects, provided herein is a recombinant cell capable of producing an acetyl CoA-derived metabolite, wherein culturing of the recombinant cells disclosed in any of the embodiments above and/or herein in a suitable media provides for the production of the acetyl CoA-derived metabolite.

In some aspects, in any of the embodiments above and/or herein, the nucleic acid is placed under an inducible promoter or a constitutive promoter. In other aspects of any of the embodiments above and/or herein, the nucleic acid is cloned into one or more multicopy plasmids. In other aspects of any of the embodiments above and/or herein, the nucleic acid is integrated into a chromosome of the cells.

In other aspects of any of the embodiments above and/or herein, the recombinant cells are gram-positive bacterial cells, gram-negative bacterial cells, fungal cells, filamentous fungal cells, algal cells or yeast cells. In other aspects of any of the embodiments above and/or herein, the recombinant cells are selected from the group consisting of *Corynebacteria* spp. (e.g., *C. glutamicum*), *Bacillus subtilis*, *Streptomyces lividans*, *Streptomyces coelicolor*, *Streptomyces griseus*, *Escherichia coli*, *Pantoea citrea*, *Trichoderma reesei*, *Aspergillus oryzae* and *Aspergillus niger*, *Saccharomyces cerevisiae* and *Yarrowia lipolytica*.

In other aspects of any of the embodiments above and/or herein, the isoprenoid is selected from group consisting of monoterpenes, diterpenes, triterpenes, tetraterpenes, sequiterpene, and polyterpene. In other aspects of any of the embodiments above and/or herein, the isoprenoid is a sesquiterpene. In other aspects of any of the embodiments above and/or herein, the isoprenoid is selected from the group consisting of abietadiene, amorphadiene, carene, α-famesene, β-farnesene, farnesol, geraniol, geranylgeraniol, linalool, limonene, myrcene, nerolidol, ocimene, patchoulol, β-pinene, sabinene, γ-terpinene, terpindene and valencene.

In other aspects of any of the embodiments above and/or herein, the acetyl CoA-derived metabolite is selected from the group consisting of polyketides, polyhydroxybutyrate, fatty alcohols, and fatty acids. In other aspects of any of the embodiments above and/or herein, the acetyl CoA-derived metabolite is selected from the group consisting of glutamic acid, glutamine, aspartate, asparagine, proline, arginine, methionine, threonine, cysteine, succinate, lysine, leucine, and isoleucine. In other aspects of any of the embodiments above and/or herein, the acetyl CoA-derived metabolite is selected from the group consisting of acetone, isopropanol, isobutene, and propene.

In other aspects of any of the embodiments above and/or herein, the suitable media comprises a carbon source. In other aspects of any of the embodiments above and/or herein, the carbon source is a carbohydrate selected from the group consisting of monosaccharide, disaccharide, oligosaccharide, polysaccharide, C6 sugar, C5 sugar, and invert sugar.

In other aspects, provided herein is a method of producing isoprene comprising: (a) culturing the recombinant cell disclosed in any of the embodiments above and/or herein under conditions suitable for producing isoprene and (b) producing isoprene.

In other aspects, provided herein is a method of producing an isoprenoid precursor comprising: (a) culturing the recombinant cell disclosed in any of the embodiments above and/or herein under conditions suitable for producing an isoprenoid precursor and (b) producing an isoprenoid precursor.

In other aspects, provided herein is a method of producing an isoprenoid comprising: (a) culturing the recombinant cell disclosed in any of the embodiments above and/or herein under conditions suitable for producing an isoprenoid and (b) producing an isoprenoid.

In other aspects, provided herein are methods of producing an acetyl CoA-derived metabolite comprising: (a) culturing the recombinant cell disclosed in any of the embodiments above and/or herein under conditions suitable for producing an acetyl CoA-derived metabolite and (b) producing an acetyl CoA-derived metabolite.

In other aspects, provided herein are methods for detecting in vivo phosphoketolase activity of a polypeptide in a recombinant cell comprising (a) culturing a recombinant cell comprising a heterologous nucleic acid encoding said polypeptide wherein the recombinant cell is defective in transketolase activity (tktAB) under culture conditions with glucose or xylose as a carbon source; (b) assessing cell growth of the recombinant cell and (c) detecting in vivo phosphoketolase activity of said polypeptide based upon the presence of cell growth.

In other aspects, provided herein is isolated polypeptides with phosphoketolase activity produced by any methods of screening, identifying, and/or detecting disclosed herein.

In other aspects, provided herein are recombinant cells capable of increased carbon flux through the phosphoketolase pathway, wherein the recombinant cells comprise a heterologous nucleic acid sequence encoding a polypeptide having phosphoketolase activity, wherein the polypeptide comprises at least 65% sequence identity to SEQ ID NO:8. In other aspects, provided herein are recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:8 and (ii) one or more nucleic acids encoding one or more polypeptides of the complete MVA pathway, wherein said recombinant cell comprising said polypeptide having phosphoketolase activity of (i) has a Performance Index value of greater than 1.0 in one or more of the following parameters: (a) cell growth on glucose, (b) cell growth on xylose, (c) production of intracellular acetyl-phosphate or (d) cell growth on glucose-6-phosphate. In other aspects, provided herein are recombinant cells capable of increased carbon flux through the phosphoketolase pathway, wherein the recombinant cell comprises: (i) a heterologous nucleic acid sequence encoding a polypeptide having phosphoketolase activity, wherein the polypeptide comprises at least 65% sequence identity to SEQ ID NO:8 and (ii) one or more nucleic acids encoding one or more polypeptides of the complete MVA pathway, wherein said polypeptide having phosphoketolase activity of (i) has a Performance Index value of greater than 1.0 in one or more of the following parameters: (a) protein solubility, (b) protein expression, or (c) fructose-6-phosphate (F6P) Specific Activity. In some embodiments of any of the aspects described above or herein, the polypeptide comprises at least 90% sequence identity to SEQ ID NO:23. In some embodiments of any of the aspects described above or herein, the polypeptide comprises at least 90% sequence identity to SEQ ID NO:24. In some embodiments of any of the aspects described above or herein, the polypeptide comprises at least 90% sequence identity to SEQ ID NO:25. In some embodiments of any of the aspects described above or herein, the polypeptide comprises at least 90% sequence identity to SEQ ID NO:26. In some embodiments of any of the aspects described above or herein, the polypeptide comprises at least 90% sequence identity to SEQ ID NO:27. In some embodiments of any of the aspects described above or herein, the polypeptide comprises at least 90% sequence identity to SEQ ID NO:28. In some embodiments of any of the aspects described above or herein, the polypeptide comprises at least 90% sequence identity to SEQ ID NO:29. In some embodiments of any of the aspects described above or herein, the polypeptide comprises at least 90% sequence identity to SEQ ID NO:30. In some embodiments of any of the aspects described above or herein, the polypeptide comprises at least 90% sequence identity to SEQ ID NO:31.

In another aspect, provided herein are recombinant cells capable of increased carbon flux through the phosphoketolase pathway, wherein the recombinant cells comprise a heterologous nucleic acid sequence encoding a polypeptide having phosphoketolase activity, wherein the polypeptide comprises at least 65% sequence identity to SEQ ID NO:11. In another aspect, provided herein are recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:11 and (ii) one or more nucleic acids encoding one or more polypeptides of the complete MVA pathway, wherein said recombinant cell comprising said polypeptide having phosphoketolase activity of (i) has a Performance Index value of greater than 1.0 in one or more of the following parameters: (a) cell growth on glucose, (b) cell growth on xylose, (c) production of intracellular acetyl-phosphate or (d) cell growth on glucose-6-phosphate. In another aspect, provided herein are recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:11 and (ii) one or more nucleic acids encoding one or more polypeptides of the complete MVA pathway, wherein said polypeptide having phosphoketolase activity of (i) has a Performance Index value of greater than 1.0 in one or more of the following parameters: (a) protein solubility, (b) protein expression, or (c) fructose-6-phosphate (F6P) Specific Activity. In some embodiments of any of the aspects described above or herein, the polypeptide comprises at least 90% sequence identity to SEQ ID NO:32. In some embodiments of any of the aspects described above or herein, the polypeptide comprises at least 90% sequence identity to SEQ ID NO:33. In some embodiments of any of the aspects described above or herein, the polypeptide comprises at least 90% sequence identity to SEQ ID NO:34. In some embodiments of any of the aspects described above or herein, the polypeptide comprises at least 90% sequence identity to SEQ ID NO:35. In some embodiments of any of the aspects described above or herein, the polypeptide comprises at least 90% sequence identity to SEQ ID NO:36. In some embodiments of any of the aspects described above or herein, the polypeptide comprises at least 90% sequence identity to SEQ ID NO:37. In some embodiments of any of the aspects described above or herein, the polypeptide comprises at least 90% sequence identity to SEQ ID NO:38. In some embodiments of any of the aspects described above or herein, the polypeptide comprises at least 90% sequence identity to SEQ ID NO:39. In some embodiments of any of the aspects described above or herein, the polypeptide comprises at least 90% sequence identity to SEQ ID NO:40. In some embodiments of any of the aspects described above or herein, the polypeptide comprises at least 90% sequence identity to SEQ ID NO:41. In some embodiments of any of the aspects described above or herein, the polypeptide comprises at least 90% sequence identity to SEQ ID NO:42. In some embodiments of any of the aspects described above or herein, the polypeptide comprises at least 90% sequence identity to SEQ ID NO:43. In some embodiments of any of the aspects described above or herein, the polypeptide comprises at least 90% sequence identity to SEQ ID NO:44. In some embodiments of any of the aspects described above or herein, the polypeptide comprises at least 90% sequence identity to SEQ ID NO:45. In some embodiments of any of the aspects described above or herein, the polypeptide comprises at least 90% sequence identity to SEQ ID NO:46.

In some embodiments of any of the aspects described above or herein, culturing of the recombinant cell in a suitable media increases one or more of an intracellular amount of erythrose 4-phosphate, an intracellular amount of glyceraldehyde 3-phosphate, or intracellular amount of acetyl phosphate. In some embodiments of any of the aspects described above or herein, the polypeptide having phosphoketolase activity is capable of synthesizing glyceraldehyde 3-phosphate and acetyl phosphate from xylulose 5-phosphate. In some embodiments of any of the aspects described above or herein, the polypeptide having phosphoketolase activity is capable of synthesizing erythrose 4-phosphate and acetyl phosphate from fructose 6-phosphate.

In other embodiments of any of the aspects described above or herein, the one or more polypeptides of the complete MVA pathway is selected from (a) an enzyme that condenses two molecules of acetyl-CoA to form acetoacetyl-CoA; (b) an enzyme that condenses acetoacetyl-CoA with acetyl-CoA to form HMG-CoA (e.g., HMG synthase); (c) an enzyme that converts HMG-CoA to mevalonate; (d) an enzyme that phosphorylates mevalonate to mevalonate 5-phosphate; (e) an enzyme that converts mevalonate 5-phosphate to mevalonate 5-pyrophosphate; and (f) an enzyme that converts mevalonate 5-pyrophosphate to isopentenyl pyrophosphate.

In other aspects, provided herein are recombinant cells capable of producing isoprene, wherein the recombinant cell (such as any recombinant cell provided herein) further comprises a heterologous nucleic acid encoding an isoprene synthase polypeptide, wherein culturing of the recombinant cell in a suitable media provides for the production of isoprene with a Performance Index value of greater than 1.0 in one or more of the following parameters: (a) isoprene yield or (b) isoprene specific productivity. In some embodiments of any of the aspects described above or herein, the heterologous nucleic acid encoding an isoprene synthase polypeptide is a plant isoprene synthase polypeptide. In some embodiments of any of the aspects described above or herein, the plant isoprene synthase polypeptide is a polypeptide from *Pueraria* or *Populus* or a hybrid, *Populus alba*×*Populus tremula*. In some embodiments of any of the aspects described above or herein, the isoprene synthase polypeptide is selected from the group consisting of *Pueraria montana, Pueraria lobata, Populus tremuloides, Populus alba, Populus nigra*, and *Populus trichocarpa*. In some embodiments of any of the aspects described above or herein, the recombinant cells further comprise one or more nucleic acids encoding one or more 1-deoxy-D-xylulose 5-phosphate (DXP) pathway polypeptides.

In other aspects, provided herein are recombinant cells capable of producing isoprenoid precursors, wherein the recombinant cell (such as any recombinant cell provided herein) is cultured in a suitable media and produces said isoprenoid precursors.

In other aspects, provided herein are recombinant cells of producing isoprenoids, wherein the recombinant cell (such as any recombinant cell provided herein) further comprises a heterologous nucleic acid encoding an polyprenyl pyrophosphate synthase polypeptide, wherein culturing of the recombinant cell in a suitable media provides for the production of isoprenoids.

In yet other aspects, provided herein are recombinant cells capable of producing an acetyl CoA-derived metabolite, wherein culturing of the recombinant cell (such as any recombinant cell provided herein) in a suitable media provides for the production of the acetyl CoA-derived metabolite.

In some embodiments of any of the aspects described above or herein, the nucleic acid is placed under an inducible promoter or a constitutive promoter. In some embodiments of any of the aspects described above or herein, the nucleic acid is cloned into one or more multicopy plasmids. In some embodiments of any of the aspects described above or herein, the nucleic acid is integrated into a chromosome of the cells.

In some embodiments of any of the aspects described above or herein, the recombinant cells are gram-positive bacterial cells, gram-negative bacterial cells, fungal cells, filamentous fungal cells, algal cells or yeast cells. In some embodiments of any of the aspects described above or herein, the recombinant cells are selected from the group consisting of *Corynebacteria, Bacillus subtilis, Streptomyces lividans, Streptomyces coelicolor, Streptomyces griseus*,

*Escherichia coli, Pantoea citrea, Trichoderma reesei, Aspergillus oryzae* and *Aspergillus niger, Saccharomyces cerevisiae* and *Yarrowia lipolytica*.

In some embodiments of any of the aspects described above or herein, the isoprenoid is selected from group consisting of monoterpenes, diterpenes, triterpenes, tetraterpenes, sequiterpene, and polyterpene. In some embodiments of any of the aspects described above or herein, the isoprenoid is a sesquiterpene. In some embodiments of any of the aspects described above or herein, the isoprenoid is selected from the group consisting of abietadiene, amorphadiene, carene, α-famesene, β-farnesene, farnesol, geraniol, geranylgeraniol, linalool, limonene, myrcene, nerolidol, ocimene, patchoulol, β-pinene, sabinene, γ-terpinene, terpindene and valencene.

In some embodiments of any of the aspects described above or herein, the acetyl CoA-derived metabolite is selected from the group consisting of polyketides, polyhydroxybutyrate, fatty alcohols, and fatty acids. In some embodiments of any of the aspects described above or herein, the acetyl CoA-derived metabolite is selected from the group consisting of glutamic acid, glutamine, aspartate, asparagine, proline, arginine, methionine, threonine, cysteine, succinate, lysine, leucine, and isoleucine. In some embodiments of any of the aspects described above or herein, the acetyl CoA-derived metabolite is selected from the group consisting of acetone, isopropanol, isobutene, and propene.

In some embodiments of any of the aspects described above or herein, the suitable media comprises a carbon source. In some embodiments of any of the aspects described above or herein, the carbon source is a carbohydrate selected from the group consisting of monosaccharide, disaccharide, oligosaccharide, polysaccharide, C6 sugar, C5 sugar, and invert sugar.

In other aspects, also provided herein are methods for producing isoprene comprising: (a) culturing the recombinant cell (such as any recombinant cell provided herein) under conditions suitable for producing isoprene and (b) producing isoprene. In other aspects, also provided herein are methods for producing an isoprenoid precursor comprising: (a) culturing the recombinant cell (such as any recombinant cell provided herein) under conditions suitable for producing an isoprenoid precursor and (b) producing an isoprenoid precursor.

In other aspects, also provided herein are methods for producing an isoprenoid comprising: (a) culturing the recombinant cell (such as any recombinant cell provided herein) under conditions suitable for producing an isoprenoid and (b) producing an isoprenoid.

In other aspects, also provided herein are methods for producing an acetyl CoA-derived metabolite comprising: (a) culturing the recombinant cell (such as any recombinant cell provided herein) under conditions suitable for producing an acetyl CoA-derived metabolite and (b) producing an acetyl CoA-derived metabolite.

In other aspects, also provided herein are methods for detecting in vivo phosphoketolase activity of a polypeptide in a recombinant cell comprising (a) culturing a recombinant cell comprising a heterologous nucleic acid sequence encoding said polypeptide wherein the recombinant cell is defective in transketolase activity (tktAB) under culture conditions with glucose or xylose as a carbon source; (b) assessing cell growth of the recombinant cell and (c) detecting in vivo phosphoketolase activity of said polypeptide based upon the presence of cell growth.

In other aspects, also provided herein are isolated polypeptides with phosphoketolase activity detected by any of the methods described above or herein.

BRIEF DESCRIPTION OF THE DRAWINGS

Figure 11:
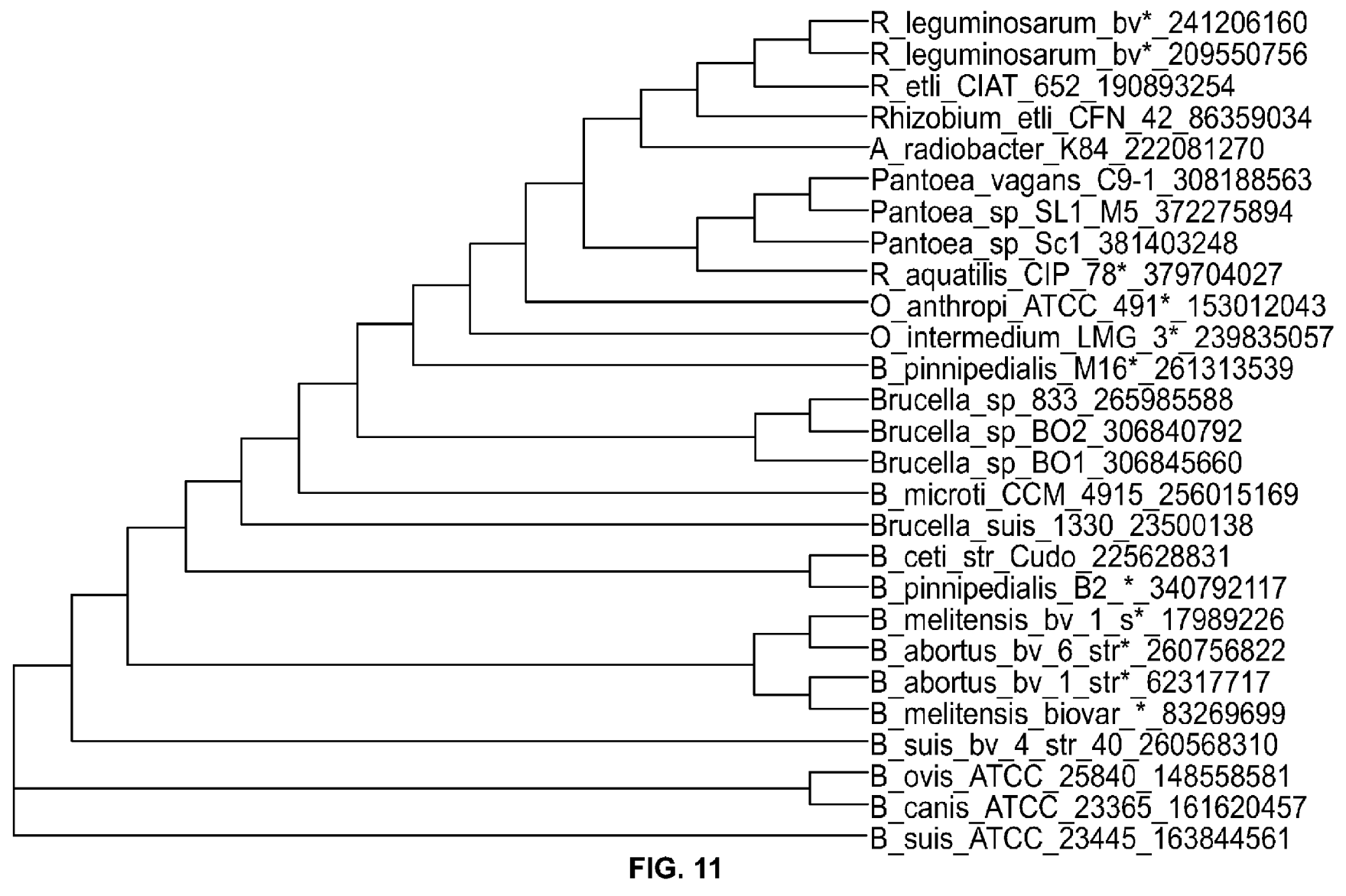

FIG. 11 is a diagram of identified phosphoketolases in Cluster 9.

DETAILED DESCRIPTION

Figure 1:
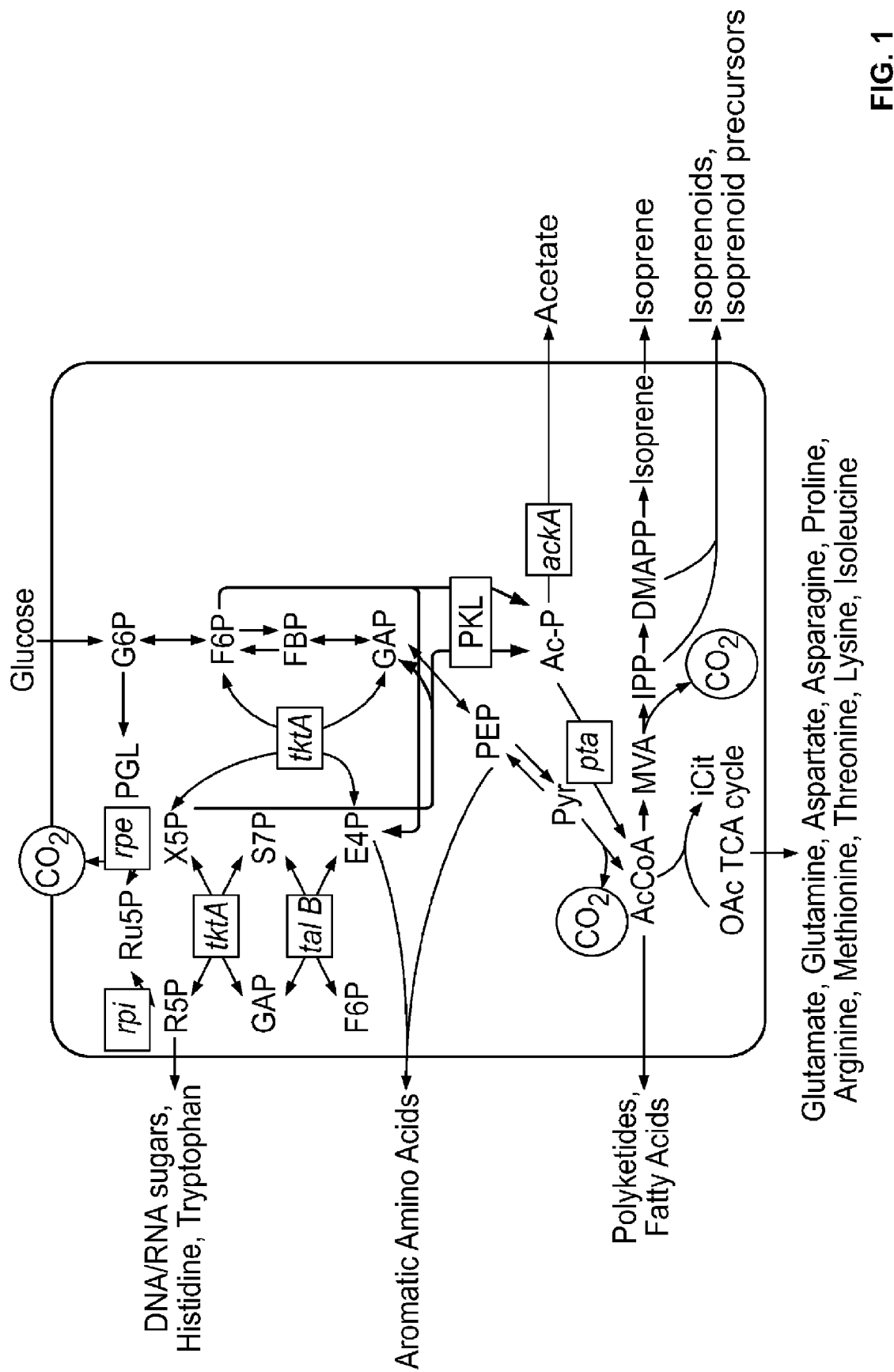
FIG. 1 depicts an engineered metabolic pathway with phosphoketolase (PKL) present. PKLs have been classified into two types based on substrate preference: xylulose-5-phosphate (X5P) phosphoketolases (EC 4.1.2.9), which only act on X5P, and xylulose-5-phosphate/fructose-6-phosphate (F6P) phosphoketolases (EC 4.1.2.22), which act on both X5P and F6P with comparable activities. acetyl phosphate (Ac-P) formed from F6P and/or X5P in PKL-catalyzed reaction(s) is subsequently converted to acetyl-CoA for use in the MVA pathway or can be converted to acetate. Other products of PKL-catalyzed reaction, namely glyceraldehyde 3-phosphate (GAP) and erythrose 4-phosphate (E4P) produced from X5P and F6P, respectively, can be recycled through manipulated metabolic pathways to maximize yield. Acetyl-Coa can be converted to many products such as polyketides, fatty acids and amino acids such as lysine.

The invention provided herein discloses, inter alia, compositions and methods for the production of acetyl coenzyme A-derived metabolites, isoprenoid precursor molecules, isoprene and/or isoprenoids in recombinant cells that have been engineered to express a phosphoketolase polypeptide. The phosphoketolase enzymes of this invention can use various substrates, as described in greater detail infra. In certain embodiments, the invention provides for compositions and methods for the production of acetyl coenzyme A-derived metabolites, isoprenoid precursor molecules, isoprene and/or isoprenoids in recombinant cells that have been engineered to express a phosphoketolase polypeptide capable of catalyzing the conversion of xylulose 5-phosphate to glyceraldehyde 3-phosphate and acetyl phosphate. In other embodiments, the invention provides for compositions and methods for the production of acetyl coenzyme A-derived metabolites, isoprenoid precursor molecules, isoprene and/or isoprenoids in recombinant cells that have been engineered to express a phosphoketolase polypeptide capable of catalyzing the conversion of fructose 6-phosphate to erythrose 4-phosphate and acetyl phosphate. In still other embodiments, the invention provides for compositions and methods for the production of acetyl coenzyme A-derived metabolites, isoprenoid precursor molecules, isoprene and/or isoprenoids in recombinant cells that have been engineered to express a phosphoketolase polypeptide capable of catalyzing the conversion of sedoheptulose-7-phosphate to ribose-5-phosphate and acetyl phosphate. In still other embodiments, the invention provides for compositions and methods for the production of acetyl coenzyme A-derived metabolites, isoprenoid precursor molecules, isoprene and/or isoprenoids in recombinant cells that have been engineered to express a phosphoketolase polypeptide capable of catalyzing the conversion of xylulose 5-phosphate to glyceraldehyde 3-phosphate and acetyl phosphate and/or the conversion of fructose 6-phosphate to erythrose 4-phosphate and acetyl phosphate and/or the conversion of sedoheptulose-7-phosphate to ribose-5-phosphate and acetyl phosphate.

Recombinantly expressed phosphoketolase has been used to engineer metabolic pathways in host cells. See U.S. Pat. No. 7,785,858. Sonderegger et al. (*Applied and Environmental Microbiology*, 2004, 70:5, 2892-97) describe the use of phosphoketolase in *Saccharomyces cerevisiae* for the overproduction of ethanol. Fleige et al. (*Appl Microbial Biotechnol.*, 2011, 91:3, 769-76) describe the expression of a *bifidobacterium* phosphoketolase gene (Meile et al., supra) in a modified *Ralstonia eutropha* strain which restored the capability for the organism to utilize fructose as a sole carbon source for growth.

Theoretically, three molecules of acetyl-CoA can be derived from a single molecule of glucose in a balanced reaction. However, organisms typically produce only up to two molecules of acetyl-CoA, with the remainder mass being lost as $CO_2$. The release of $CO_2$ occurs during the formation of acetyl-CoA from pyruvate, a reaction catalyzed by pyruvate dehydrogenase. The loss of one carbon atom results in decreased production yields of acetyl-CoA-derived metabolites, isoprenoid precursors, isoprene, and isoprenoid molecules. An exception to this reaction loss is the Wood-Ljungdahl pathway, which relies on carbon monoxide dehydrogenase and acetyl-CoA synthase enzymes to reduce the carbon dioxide to acetyl-CoA in anaerobic acetogens.

The present invention provides an alternate metabolic process which can potentially produce three molecules of acetyl-CoA from one molecule of glucose using a pathway which does not rely on the Wood-Ljungdahl pathway enzymes. Instead, it makes use of a phosphoketolase enzyme found in certain organisms [see, for example, Biology of the Prokaryotes (ed. Lengeler, Drews and Schlegel); Blackwell Science, New York, 1999, p. 299-301; Meile et al., *J. of Bacteriology*, 2001, 183:9, 2929-36; Jeong et al., *J. Microbiol. Biotechnol.*, 2007, 17:5, 822-829]. Phosphoketolase enzymes allow for formation of acetyl-CoA (via acetyl-phosphate) from xylulose 5-phosphate or fructose 6-phosphate rather than through oxidation of pyruvate as in typical metabolism.

Phosphoketolases have been classified into two types based on their substrate preference: xylulose-5-phosphate (X5P) phosphoketolases, which only act on X5P, and X5P/fructose-6-phosphate (F6P) phosphoketolases, which can act on both X5P and F6P (Suzuki et al., *Acta Cryst.* F66, 2010, 66:8, 941-43). Phosphoketolases catalyze the cleavage of X5P or F6P utilizing inorganic phosphate ($P_i$) to produce acetyl phosphate (acetyl-P), $H_2O$ and glyceraldehyde 3-phosphate or erythrose 4-phosphate. The high-energy metabolite acetyl-P is subsequently converted to acetic acid by acetate kinase to produce ATP from ADP in the pathway (FIG. 1). In addition to acetyl-phosphate, the glyceraldehyde 3-phosphate produced from the enzymatic reaction can be recycled through manipulated metabolic pathways so that the maximum yield of 3 acetyl-CoA per glucose can be achieved. Significantly, acetyl-CoA production by phosphoketolase eliminates the loss of carbon (e.g. $CO_2$) as observed from pyruvate dehydrogenase mediated reactions.

Phosphoketolases can also act upon sedoheptulose-7-phosphate to convert it to ribose-5-phosphate and acetyl phosphate. A non-limiting example of such a phosphoketolase is *Bifidobacterium longum* phosphoketolase, which has catalytic activity with sedoheptulose-7-phosphate.

The present invention is directed to the use of phosphoketolase enzymes in the production of acetyl-CoA-derived metabolites, isoprenoid precursors, isoprene and/or isoprenoids to enhance product yield. In particular, the theoretical isoprene product yield is enhanced as represented by the following balanced equations (with the assumption that an organism is capable of producing ATP from the complete oxidation of 1 mol glucose to 6 mol $CO_2$):

MVA Pathway Only

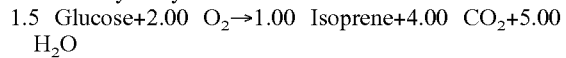

1.5 Glucose+2.00 $O_2$→1.00 Isoprene+4.00 $CO_2$+5.00 $H_2O$

Theoretical yield—0.252 g Isoprene/g Glucose

DXP Pathway

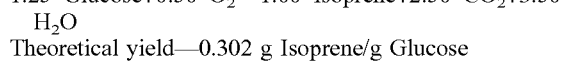

1.25 Glucose+0.50 $O_2$→1.00 Isoprene+2.50 $CO_2$+3.50 $H_2O$

Theoretical yield—0.302 g Isoprene/g Glucose

MVA+Phosphoketolase Pathways

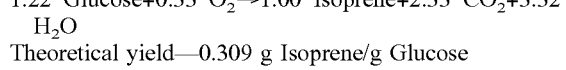

1.22 Glucose+0.33 $O_2$→1.00 Isoprene+2.33 $CO_2$+3.32 $H_2O$

Theoretical yield—0.309 g Isoprene/g Glucose

The mevalonate-dependent biosynthetic pathway is particularly important for the production of isoprenoid precursor molecules, e.g., dimethylallyl diphosphate (DMAPP) and isopentenyl pyrophosphate (IPP). The enzymes of the upper mevalonate pathway convert acetyl CoA, produced from glucose, into mevalonate via three enzymatic reactions. Without being bound to theory, it is believed that increased intracellular pools of E4P, GAP, and Ac-P produced by the use of a phosphoketolase polypeptide for the increased biosynthesis of acetyl CoA can result in increased productivity of the upper mevalonate-dependent biosynthetic pathway which will substantially increase biosynthesis of mevalonate and, consequently, of downstream isoprenoid precursor molecules such as DMAPP and IPP (FIG. 1). Furthermore, the increased biosynthesis of acetyl-CoA can result in the increased synthesis of acetyl-CoA-derived metabolites such as fatty acids, amino acids, and acetone (FIG. 1). The increased intracellular amount-CoA production by this alternate PKL pathway is therefore advantageous for commercial applications.

Acetone is produced by certain microorganisms, such as *Clostridium acetobutylicum*. It starts out with condensation of two molecules of acetyl-CoA into acetoacetyl-CoA by acetyl-CoA acetyltransferase (EC 2.3.1.9). Acetoacetyl-CoA is then converted into acetoacetate by a reaction with acetic acid or butyric acid resulting in the production of acetyl-CoA or butyryl-CoA. This reaction is catalyzed by an enzyme such as acetoacetylCoA transferase (EC 2.8.3.8). AcetoacetylCoA transferase is known from various organisms, such as *E. coli* or *C. acetobutyiicum*. However, also other enzymes can catalyze this reaction, such as 3-oxoacid CoA transferase (EC 2.8.3.5) or succinate CoA ligase (EC 6.2.1.5). In the last step of the reaction, acetoacetate is converted into acetone by a decarboxylation step catalyzed by acetoacetate decarboxylase (EC 4.1.1.4). Acetone can be subsequently converted to isopropanol, isobutene and/or propene as described in WO 2013/07786, the contents of which are expressly incorporated herein by reference in their entirety with respect to acetone, isoprene and propene.

Accordingly, in certain aspects, the invention provides recombinant cells with an increased intracellular amount of erythrose 4-phosphate, an increased intracellular amount of glyceraldehyde 3-phosphate, and/or an increased intracellular amount phosphate, wherein the cells comprise one or more heterologous nucleic acids encoding a polypeptide having phosphoketolase activity, and wherein the cells produce the increased intracellular amount of erythrose 4-phosphate, increased intracellular amount of glyceraldehyde 3-phosphate, and/or increased intracellular amount phosphate as compared to cells that do not comprise the one or more heterologous nucleic acids encoding a polypeptide having phosphoketolase activity.

In some aspects, the invention provides recombinant cells with an increased intracellular amount of acetyl-CoA, wherein the cells comprise one or more heterologous nucleic acids encoding a polypeptide having phosphoketolase activity, and wherein the cells produce the increased intracellular amount of acetyl-CoA as compared to cells that do not comprise the one or more heterologous nucleic acids encoding a polypeptide having phosphoketolase activity.

In certain aspects, the invention provides recombinant cells capable of enhanced production of mevalonate, wherein the cells comprise one or more heterologous nucleic acids encoding a polypeptide having phosphoketolase activity and one or more nucleic acids encoding one or more polypeptides of the upper MVA pathway, wherein the cells produce increased amounts of mevalonate compared to cells that do not comprise the one or more heterologous nucleic acids encoding a polypeptide having phosphoketolase activity.

In other aspects, the present invention provides recombinant cells capable of enhanced production of isoprenoid precursors, wherein the cells comprise one or more heterologous nucleic acids encoding a polypeptide having phosphoketolase activity and one or more nucleic acids encoding one or more polypeptides of the complete MVA pathway, wherein the cells produce increased amounts of isoprenoid precursors compared to cells that do not comprise the one or more heterologous nucleic acids encoding a polypeptide having phosphoketolase activity.

In still other aspects, the present invention provides recombinant cells capable of producing isoprene, wherein the cells comprise one or more heterologous nucleic acids encoding a polypeptide having phosphoketolase activity and (i) one or more nucleic acids encoding one or more polypeptides of the complete MVA pathway and (ii) a heterologous nucleic acid encoding an isoprene synthase polypeptide, wherein the cells are capable of producing recoverable amounts of isoprene. In certain embodiments, the present invention provides recombinant cells capable of enhanced production of isoprene, wherein the cells comprise one or more heterologous nucleic acids encoding a polypeptide having phosphoketolase activity and (i) one or more nucleic acids encoding one or more polypeptides of the complete MVA pathway and (ii) a heterologous nucleic acid encoding an isoprene synthase polypeptide, wherein the cells produce increased amounts of isoprene compared to isoprene-producing cells that do not comprise the one or more heterologous nucleic acids encoding a polypeptide having phosphoketolase activity.

In yet other aspects, the present invention provides recombinant cells capable of producing isoprenoids, wherein the cells comprise one or more heterologous nucleic acids encoding a polypeptide having phosphoketolase activity and (i) one or more nucleic acids encoding one or more polypeptides of the complete MVA pathway and (ii) a heterologous nucleic acid encoding an polyprenyl pyrophosphate synthase polypeptide, wherein the cells are capable of producing recoverable amounts of isoprenoids. In certain embodiments, the present invention provides recombinant cells capable of enhanced production of isoprenoids, wherein the cells comprise one or more heterologous nucleic acids encoding a polypeptide having phosphoketolase activity and (i) one or more nucleic acids encoding one or more polypeptides of the complete MVA pathway and (ii) a heterologous nucleic acid encoding an polyprenyl pyrophosphate synthase polypeptide, wherein the cells produce increased amounts of isoprenoids compared to isoprenoid producing cells that do not comprise the one or more heterologous nucleic acids encoding a polypeptide having phosphoketolase activity.

In other aspects, the present invention provides recombinant cells capable of producing an acetyl CoA-derived metabolite, wherein the cells comprise one or more heterologous nucleic acids encoding a polypeptide having phosphoketolase activity, wherein the cells are capable of producing recoverable amounts of the acetyl CoA-derived metabolite. In certain embodiments, the present invention provides recombinant cells capable of enhanced production of an acetyl CoA-derived metabolite, wherein the cells comprise one or more heterologous nucleic acids encoding a polypeptide having phosphoketolase activity, wherein the cells produce increased amounts of the acetyl CoA-derived metabolite as compared to acetyl CoA-derived metabolite producing cells that do not comprise the one or more heterologous nucleic acids encoding a polypeptide having phosphoketolase activity.

In any of the aspects herein, the present invention provides recombinant cells, wherein the cells can comprise one or more heterologous nucleic acids encoding a polypeptide having phosphoketolase activity and can be further engineered to modulate the activity of one or more of the following genes including ribose-5-phosphate isomerase (rpiA and/or rpiB), D-ribulose-5-phosphate 3-epimerase (rpe), transketolase (tktA and/or tktB), transaldolase B (tal B), phosphate acetyltransferase (pta and/or eutD), glucose-6-phosphate dehydrogenase (zwf), 6-phosphofructokinase-1 (pfkA and/or pfkB), fructose bisphosphate aldolase (fba, fbaA, fbaB, and/or fbaC), glyceraldehyde-3-phosphate dehydrogenase (gapA and/or gapB), acetate kinase (ackA), citrate synthase (gltA), EI (ptsI), EIICB$^{Glc}$ (ptsG), EIIA$^{Glc}$ (crr), and/or HPr (ptsH) to improve carbon flux through the phosphoketolase pathway.

In some embodiments, the present invention provides recombinant cells capable of producing isoprene, wherein the cells comprise one or more heterologous nucleic acids encoding a polypeptide having phosphoketolase activity and (i) one or more nucleic acids encoding one or more polypeptides of the complete MVA pathway, (ii) a heterologous nucleic acid encoding an isoprene synthase polypeptide, and (iii) is further engineered to modulate the activity of one or more genes to increases carbon flux through the phosphoketolase pathway, wherein the cells produce increased amounts of isoprene compared to isoprene-producing cells that do not comprise the one or more heterologous nucleic acids encoding a polypeptide having phosphoketolase activity.

In some embodiments, the present invention provides recombinant cells capable of producing isoprenoids, wherein the cells comprise one or more heterologous nucleic acids encoding a polypeptide having phosphoketolase activity and (i) one or more nucleic acids encoding one or more polypeptides of the complete MVA pathway, (ii) a heterologous nucleic acid encoding an polyprenyl pyrophosphate synthase polypeptide, and (iii) is further engineered to modulate the activity of one or more genes to increases carbon flux through the phosphoketolase pathway, wherein the cells produce increased amounts of isoprenoids compared to isoprenoid producing cells that do not comprise the one or more heterologous nucleic acids encoding a polypeptide having phosphoketolase activity.

In other embodiments, the present invention provides recombinant cells capable of enhanced production of an acetyl CoA-derived metabolite, wherein the cells comprise one or more heterologous nucleic acids encoding a polypeptide having phosphoketolase activity and is further engineered to modulate the activity of one or more genes to increases carbon flux through the phosphoketolase pathway, wherein the cells produce increased amounts of the acetyl CoA-derived metabolite as compared to acetyl CoA-derived metabolite producing cells that do not comprise the one or more heterologous nucleic acids encoding a polypeptide having phosphoketolase activity.

General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, "*Molecular Cloning: A Laboratory Manual*", second edition (Sambrook et al., 1989); "Oligonucleotide Synthesis" (M. J. Gait, ed., 1984); "*Animal Cell Culture*" (R. I. Freshney, ed., 1987); "*Methods in Enzymology*" (Academic Press, Inc.); "*Current Protocols in Molecular Biology*" (F. M. Ausubel et al., eds., 1987, and periodic updates); "*PCR: The Polymerase Chain Reaction*", (Mullis et al., eds., 1994). Singleton et al., *Dictionary of Microbiology and Molecular Biology* 2nd ed., J. Wiley & Sons (New York, N.Y. 1994), and March, *Advanced Organic Chemistry Reactions, Mechanisms and Structure* 4th ed., John Wiley & Sons (New York, N.Y. 1992), provide one skilled in the art with a general guide to many of the terms used in the present application.

Definitions

The term "isoprene" refers to 2-methyl-1,3-butadiene (CAS #78-79-5). It can be the direct and final volatile C5 hydrocarbon product from the elimination of pyrophosphate from 3,3-dimethylallyl diphosphate (DMAPP). It may not involve the linking or polymerization of IPP molecules to DMAPP molecules. The term "isoprene" is not generally intended to be limited to its method of production unless indicated otherwise herein.

As used herein, the term "polypeptides" includes polypeptides, proteins, peptides, fragments of polypeptides, and fusion polypeptides.

As used herein, an "isolated polypeptide" is not part of a library of polypeptides, such as a library of 2, 5, 10, 20, 50 or more different polypeptides and is separated from at least one component with which it occurs in nature. An isolated polypeptide can be obtained, for example, by expression of a recombinant nucleic acid encoding the polypeptide.

By "heterologous polypeptide" is meant a polypeptide encoded by a nucleic acid sequence derived from a different organism, species, or strain than the host cell. In some embodiments, a heterologous polypeptide is not identical to a wild-type polypeptide that is found in the same host cell in nature.

As used herein, a "nucleic acid" refers to two or more deoxyribonucleotides and/or ribonucleotides covalently joined together in either single or double-stranded form.

By "recombinant nucleic acid" is meant a nucleic acid of interest that is free of one or more nucleic acids (e.g., genes) which, in the genome occurring in nature of the organism from which the nucleic acid of interest is derived, flank the nucleic acid of interest. The term therefore includes, for example, a recombinant DNA which is incorporated into a vector, into an autonomously replicating plasmid or virus, or into the genomic DNA of a prokaryote or eukaryote, or which exists as a separate molecule (e.g., a cDNA, a genomic DNA fragment, or a cDNA fragment produced by PCR or restriction endonuclease digestion) independent of other sequences.

By "heterologous nucleic acid" is meant a nucleic acid sequence derived from a different organism, species or strain than the host cell. In some embodiments, the heterologous nucleic acid is not identical to a wild-type nucleic acid that is found in the same host cell in nature. For example, a nucleic acid encoded by the phosphoketolase gene from *Burkholderia phytofirmans, Lactobacillus buchneri, Bifidobacterium gallicum, Bifidobacterium dentium, Bifidobacterium bifidum,* and/or *Clostridium acetobutylicum* and used to transform an *E. coli* is a heterologous nucleic acid.

As used herein, the terms "phosphoketolase", "phosphoketolase enzyme" or "phosphoketolase polypeptide" are used interchangeably and refer to a polypeptide that converts 5-phosphate to glyceraldehyde 3-phosphate and acetyl phosphate and/or converts fructose 6-phosphate to erythrose 4-phosphate and acetyl phosphate. Generally, phosphoketolases act upon ketoses. In certain embodiments, the phosphoketolase polypeptide catalyzes the conversion of xylulose 5-phosphate to glyceraldehyde 3-phosphate and acetyl phosphate. In other embodiments, the phosphoketolase polypeptide catalyzes the conversion of fructose 6-phosphate to erythrose 4-phosphate and acetyl phosphate. In other embodiments, the phosphoketolase polypeptide catalyzes the conversion of sedoheptulose-7-phosphate to a product (e.g., ribose-5-phosphate) and acetyl phosphate.

As used herein, an "expression control sequence" means a nucleic acid sequence that directs transcription of a nucleic acid of interest. An expression control sequence can be a promoter, such as a constitutive or an inducible promoter, or an enhancer. An expression control sequence can be "native" or heterologous. A native expression control sequence is derived from the same organism, species, or strain as the gene being expressed. A heterologous expression control sequence is derived from a different organism, species, or strain as the gene being expressed. An "inducible promoter" is a promoter that is active under environmental or developmental regulation.

By "operably linked" is meant a functional linkage between a nucleic acid expression control sequence (such as a promoter) and a second nucleic acid sequence, wherein the expression control sequence directs transcription of the nucleic acid corresponding to the second sequence.

As used herein, the terms "minimal medium" or "minimal media" refer to growth media containing the minimum nutrients possible for cell growth, generally without the presence of amino acids. Minimal medium typically contains: (1) a carbon source for bacterial growth; (2) various salts, which can vary among bacterial species and growing conditions; and (3) water. The carbon source can vary significantly, from simple sugars like glucose to more complex hydrolysates of other biomass, such as yeast extract, as discussed in more detail below. The salts generally provide essential elements such as magnesium, nitrogen, phosphorus, and sulfur to allow the cells to synthesize proteins and nucleic acids. Minimal medium can also be supplemented with selective agents, such as antibiotics, to select for the maintenance of certain plasmids and the like. For example, if a microorganism is resistant to a certain antibiotic, such as ampicillin or tetracycline, then that antibiotic can be added to the medium in order to prevent cells lacking the resistance from growing. Medium can be supplemented with other compounds as necessary to select for desired physiological or biochemical characteristics, such as particular amino acids and the like.

As used herein, the term "isoprenoid" refers to a large and diverse class of naturally-occurring class of organic compounds composed of two or more units of hydrocarbons, with each unit consisting of five carbon atoms arranged in a specific pattern. As used herein, "isoprene" is expressly excluded from the definition of "isoprenoid."

As used herein, the term "terpenoid" refers to a large and diverse class of organic molecules derived from five-carbon isoprenoid units assembled and modified in a variety of ways and classified in groups based on the number of isoprenoid units used in group members. Hemiterpenoids have one isoprenoid unit. Monoterpenoids have two isoprenoid units. Sesquiterpenoids have three isoprenoid units. Diterpenoids have four isoprene units. Sesterterpenoids have five isoprenoid units. Triterpenoids have six isoprenoid units. Tetraterpenoids have eight isoprenoid units. Polyterpenoids have more than eight isoprenoid units.

As used herein, "isoprenoid precursor" refers to any molecule that is used by organisms in the biosynthesis of terpenoids or isoprenoids. Non-limiting examples of isoprenoid precursor molecules include, e.g., mevalonate (e.g., mevalonic acid (MVA)), isopentenyl pyrophosphate (IPP) and dimethylallyl diphosphate (DMAPP).

As used herein, the term "mass yield" refers to the mass of the product produced by the recombinant cells divided by the mass of the glucose consumed by the recombinant cells expressed as a percentage.

By "specific productivity," it is meant the mass of the product produced by the recombinant cell divided by the product of the time for production, the cell density, and the volume of the culture.

By "titer," it is meant the mass of the product produced by the recombinant cells divided by the volume of the culture.

As used herein, the term "cell productivity index (CPI)" refers to the mass of the product produced by the recombinant cells divided by the mass of the recombinant cells produced in the culture.

Unless defined otherwise herein, all technical and scientific terms used herein have the same meaning as commonly understood by one of ordinary skill in the art to which this invention pertains.

As used herein, the singular terms "a," "an," and "the" include the plural reference unless the context clearly indicates otherwise.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Recombinant Cells Expressing a Phosphoketolase Polypeptide

Phosphoketolase enzymes catalyze the conversion of xylulose 5-phosphate to glyceraldehyde 3-phosphate and acetyl phosphate and/or the conversion of fructose 6-phosphate to erythrose 4-phosphate and acetyl phosphate. In certain embodiments, the phosphoketolase enzyme is capable of catalyzing the conversion of xylulose 5-phosphate to glyceraldehyde 3-phosphate and acetyl phosphate. In other embodiments, the phosphoketolase enzyme is capable of catalyzing the conversion of fructose 6-phosphate to erythrose 4-phosphate and acetyl phosphate. In other embodiments, the phosphoketolase polypeptide catalyzes the conversion of sedoheptulose-7-phosphate to a product (e.g., ribose-5-phosphate) and acetyl phosphate. Thus, without being bound by theory, the expression of phosphoketolase as set forth herein can result in an increase in the amount of acetyl phosphate produced from a carbohydrate source. This acetyl phosphate can be converted into acetyl-CoA which can then be utilized by the enzymatic activities of the MVA pathway to produce mevalonate, isoprenoid precursor molecules, isoprene and/or isoprenoids or can be utilized to produce acetyl-CoA-derived metabolites.

As used herein, the term "acetyl-CoA-derived metabolite" can refer to a metabolite resulting from the catalytic conversion of acetyl-CoA to said metabolite. The conversion can be a one-step reaction or a multi-step reaction. For example, acetone is an acetyl-CoA derived metabolite that is produced from acetyl-CoA by a three step reaction (e.g., a multi-step reaction): 1) the condensation of two molecules of acetyl-CoA into acetoacetyl-CoA by acetyl-CoA acetyltransferase; 2) conversion of acetoacetyl-CoA into acetoacetate by a reaction with acetic acid or butyric acid resulting in the production of acetyl-CoA or butyryl-CoA; and 3) conversion of acetoacetate into acetone by a decarboxylation step catalyzed by acetoacetate decarboxylase. Acetone can be subsequently converted to isopropanol, isobutene and/or propene which are also expressly contemplated herein to be acetyl-CoA-derived metabolites. In some embodiments, the acetyl CoA-derived metabolite is selected from the group consisting of polyketides, polyhydroxybutyrate, fatty alcohols, and fatty acids. In some embodiments, the acetyl CoA-derived metabolite is selected from the group consisting of glutamic acid, glutamine, aspartate, asparagine, proline, arginine, methionine, threonine, cysteine, succinate, lysine, leucine, and isoleucine. In some embodiments, the acetyl CoA-derived metabolite is selected from the group consisting of acetone, isopropanol, isobutene, and propene. Thus the amount of these compounds (e.g., acetyl-CoA, acetyl-CoA-derived metabolite, acetyl-P, E4P, etc.) produced from a carbohydrate substrate may be increased.

Production of acetyl-P and acetyl-CoA can be increased without the increase being reflected in higher intracellular concentration. In certain embodiments, intracellular acetyl-P or acetyl-CoA concentrations will remain unchanged or even decrease, even though the phosphoketolase reaction is taking place.

Exemplary Phosphoketolase Polypeptides and Nucleic Acids

Exemplary phosphoketolase nucleic acids include nucleic acids that encode a polypeptide, fragment of a polypeptide, peptide, or fusion polypeptide that has at least one activity of a phosphoketolase polypeptide. Exemplary phosphoketolase polypeptides and nucleic acids include naturally-occurring polypeptides and nucleic acids from any of the source organisms described herein as well as mutant polypeptides and nucleic acids derived from any of the source organisms described herein (See for example, FIGS. 2-24 and Example 2). Additionally, Table 1 and Table 2 provides a non-limiting list of certain exemplary phosphoketolases from different species which may be utilized within embodiments of the invention.

Biochemical characteristics of exemplary phosphoketolases include, but are not limited to, protein expression, protein solubility, and activity. Phosphoketolases can also be selected on the basis of other characteristics, including, but not limited to, diversity amongst different types of organisms (e.g., gram positive bacteria, cyanobacteria, *actinomyces*), facultative low temperature aerobe, close relatives to a desired species (e.g., *E. coli*), and thermotolerance.

In some instances, phosphoketolases from certain organisms can be selected if the organisms lack a phosphofructokinase gene in its genome.

In yet another example, phosphoketolases can be selected based on a secondary structure of the amino acid sequence and/or the method described in Example 1.

In still another example, phosphoketolases can be selected based on an in vitro assay as described in Example 6.

In still another example, phosphoketolases can be selected based on an in vivo assay as described in Example 7. In some aspects, provided herein is a method for determining the presence of in vivo phosphoketolase activity of a polypeptide comprising (a) culturing a recombinant cell comprising a heterologous nucleic acid sequence encoding said polypeptide wherein the recombinant cell is defective in transketolase activity (tktAB) under culture conditions with glucose or xylose as a carbon source; (b) assessing cell growth of the recombinant cell and (c) determining the presence of in vivo phosphoketolase activity of said polypeptide based upon the amount of observed cell growth. In some aspects, provided herein is a method of identifying a polypeptide with phosphoketolase activity comprising (a) culturing a recombinant cell comprising a heterologous nucleic acid sequence encoding a polypeptide suspected of having phosphoketolase activity wherein the recombinant cell is defective in transketolase activity (tktAB) under culture conditions with glucose or xylose as a carbon source; (b) assessing cell growth of the recombinant cell and (c) identifying the polypeptide with phosphoketolase activity when cell growth is observed. In some aspects, provided herein is a method for detecting in vivo phosphoketolase activity of a polypeptide in a recombinant cell comprising (a) culturing a recombinant cell comprising a heterologous nucleic acid sequence encoding said polypeptide wherein the recombinant cell is defective in transketolase activity (tktAB) under culture conditions with glucose or xylose as a carbon source; (b) assessing cell growth of the recombinant cell and (c) detecting in vivo phosphoketolase activity of said polypeptide based upon the presence of cell growth.

As provided herein, phosphoketolase activity can improve production of acetyl-CoA-derived metabolites, isoprenoid precursors (e.g., IPP), isoprene, and/or isoprenoids. Provided herein is a recombinant host comprising phosphoketolase wherein the cells display at least one property of interest to improve production of acetyl-CoA-derived metabolites, isoprenoid precursors (e.g., IPP), isoprene, and/or isoprenoids.

In some aspects, at least one property of interest is selected from but not limited to the group consisting of specific productivity, yield, titer and cellular performance index (e.g., growth). As used herein, "performance index" refers to calculated activity per unit relative to a parental molecule. In some aspects of any of the embodiments disclosed herein, the parental molecule used in the calculation of the performance index is a phosphoketolase from *E. gallinarum*. In some embodiments, the parental molecule has a performance index of one, by definition. In other embodiments, a performance index greater than one (PI>1.0) indicates improved activity of a phosphoketolase compared to the parent molecule (e.g., a phosphoketolase from *E. gallinarum*).

In certain embodiments, suitable phosphoketolases for use herein include soluble phosphoketolases. Techniques for measuring protein solubility are well known in the art. Techniques for measuring protein solubility include those disclosed herein in the Examples. In some embodiments, a phosphoketolase for use herein includes those with a solubility of at least 20%. In some embodiments, phosphoketolase solubility is between about any of 5% to about 100%, between about 10% to about 100%, between about 15% to about 100%, between about 20% to about 100%, between about 25% to about 100%, between about 30% to about 100%, between about 35% to about 100%, between about 40% to about 100%, between about 45% to about 100%, between about 50% to about 100%, between about 55% to about 100%, between about 60% to about 100%, between about 65% to about 100%, between about 70% to about 100%, between about 75% to about 100%, between about 80% to about 100%, between about 85% to about 100%, or between about 90% to about 100%, In some embodiments, phosphoketolase solubility is between about 5% to about 100%. In some embodiments, solubility is between 5% and 100%. In some embodiments, phosphoketolase solubility is less than about any of 100, 90, 80, 70, 60, 50, 40, 30, 20, or 10 but no less than about 5%. In some embodiments, solubility is greater than about any of 5, 10, 15, 20, 25, 30, 35, 40, 45, 50, 55, 60, 65, 70, 75, 80, 85, 90, or 95%.

Phosphoketolases with a desired kinetic characteristic increases the production of isoprene. Kinetic characteristics include, but are not limited to, specific activity, $K_{cat}$, $K_i$, and $K_m$. In some aspects, the $k_{cat}$ is at least about 0.2, 0.4, 0.6, 0.8, 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, 5.0, 5.2, 5.4, 5.6, 5.8, 6.0, 6.2, 6.4, 6.6, 6.8, 7.0, 7.2, 7.4, 7.6, 7.8, 8.0, 8.1, 8.2, 8.4, 8.6, 8.8, 9.0, 9.2, 9.4, 9.6, 9.8, 10.0, 10.2, 10.4, 10.6, 10.8, 11.0, 11.2, 11.4, 11.6, 11.8, 12.0, 12.2, 12.4, 12.6, 12.8, 13.0, 13.2, 13.4, 13.6, 13.8, 14.0, 14.2, 14.4, 14.6, 14.8, 15.0, 15.2, 15.4, 15.6, 15.8, 16.0, 16.2, 16.4, 16.6, 16.8, 17.0, 17.2, 17.4, 17.6, 17.8, 18.0, 18.2, 18.4, 18.6, 18.8, 19.0, 19.2, 19.4, 19.6, 19.8, 20.0, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 200, 300, 400, 500, 600, 700, or 800. In other aspects, the $k_{cat}$ is at least about 0.2, 0.4, 0.6, 0.8, 1.0, 1.1, 1.2, 1.3, 1.4, 1.5, 1.6, 1.7, 1.8, 1.9 2.0, 2.1, 2.2, 2.3, 2.4, 2.5, 2.6, 2.7, 2.8, 2.9, 3.0, 3.2, 3.4, 3.6, 3.8, 4.0, 4.2, 4.4, 4.6, 4.8, 5.0, 5.2, 5.4, 5.6, 5.8, 6.0, 6.2, 6.4, 6.6, 6.8, 7.0, 7.2, 7.4, 7.6, 7.8, 8.0, 8.1, 8.2, 8.4, 8.6, 8.8, 9.0, 9.2, 9.4, 9.6, 9.8, 10.0, 10.2, 10.4, 10.6, 10.8, 11.0, 11.2, 11.4, 11.6, 11.8, 12.0, 12.2, 12.4, 12.6, 12.8, 13.0, 13.2, 13.4, 13.6, 13.8, 14.0, 14.2, 14.4, 14.6, 14.8, 15.0, 15.2, 15.4, 15.6, 15.8, 16.0, 16.2, 16.4, or 16.6.

In some aspects, the $K_m$ is at least about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 16, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, 40.5, 41, 41.5, 42, 42.5, 43, 43.5, 44, 44.5, 45, 45.5, 46, 46.5, 47, 47.5, 48, 48.5, 49, 49.5, 50, 50.5, 51, 51.5, 52, 52.5, 53, 53.5, 54, 54.5, 55, 55.5, or 56. In other aspects, the $k_m$ is at least about 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 16, 17, 17.5, 18, 18.5, 19, 19.5, 20, 20.5, 21, 21.5, or 22.

Properties of interest include, but are not limited to: increased intracellular activity, specific productivity, yield, and cellular performance index as compared to as compared to a recombinant cell that does not comprise the phosphoketolase polypeptide. In some embodiments, specific productivity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6 7, 8, 9, 10 times or more. In one embodiment, specific productivity is about 40 mg/L/OD/hr. In some embodiments, yield increase of at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more. In other embodiments, MVA yield increase of at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more. In other embodiments, isoprene yield increase of at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more.

In other embodiments, the performance index values for properties of interest, including but not limited to, (a) cell growth on glucose, (b) cell growth on xylose, (c) cell growth on glucose-6-phosphate or (d) production of intracellular Acetyl-phosphate for a recombinant cell comprising a polypeptide having phosphoketolase activity as set forth herein and one or more nucleic acids encoding one or more polypeptides of the complete MVA pathway is greater than 1, such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*).

In other embodiments, the performance index values for properties of interest, including but not limited to, (a) protein solubility, (b) protein expression, or (c) F6P specific activity for a polypeptide having phosphoketolase activity in a recombinant cell further comprising one or more nucleic acids encoding one or more polypeptides of the complete MVA pathway is greater than 1, such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*).

In other embodiments, the performance index values for properties of interest, including but not limited to, (a) isoprene yield protein solubility or (b) isoprene specific productivity for a recombinant cell comprising (i) a polypeptide having phosphoketolase activity, (ii) one or more nucleic acids encoding one or more polypeptides of the complete MVA pathway, and (iii) a heterologous nucleic acid encoding an isoprene synthase polypeptide is greater than 1, such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*).

In other embodiments, cell performance index increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Provided herein is a phosphoketolase isolated from a microorganism. In some aspects, a phosphoketolase isolated from the group consisting of a gram positive bacterium, a gram negative bacterium, an aerobic bacterium, an anaerobic bacterium, a thermophilic bacterium, a psychrophilic bacterium, a halophilic bacterium or a cyanobacterium. In some aspects, a phosphoketolase isolated from a fungi. In other aspects, exemplary phosphoketolase nucleic acids include, for example, a phosphoketolase isolated from *Burkholderia phytofirmans*, *Lactobacillus buchneri*, *Bifidobacterium gallicum*, *Bifidobacterium dentium*, *Bifidobacterium bifidum*, and/or *Clostridium acetobutylicum*. In other aspects, exemplary phosphoketolase nucleic acids include, for example, a phosphoketolase isolated from *Mycobacterium gilvum*, *Shewanella baltica*, *Lactobacillus rhamnosus*, *Lactobacillus crispatus*, *Bifidobacterium longum*, *Leuconostoc citreum*, *Bradyrhizobium* sp., *Enterococcus faecium*, *Brucella microti*, *Lactobacillus salivarius*, *Streptococcus agalactiae*, *Rhodococcus imtechensis*, *Burkholderia xenovorans*, *Mycobacterium intracellulare*, *Nitrosomonas* sp., *Schizosaccharomyces pombe*, *Leuconostoc mesenteroides*, *Streptomyces* sp., *Lactobacillus buchneri*, *Streptomyces ghanaensis*, *Cyanothece* sp., and/or *Neosartorya fischeri*. In other aspects, exemplary phosphoketolase nucleic acids include, for example, a phosphoketolase isolated from *Enterococcus faecium*, *Listeria grayi*, *Enterococcus gallinarum*, *Enterococcus saccharolyticus*, *Enterococcus casseliflavus*, *Mycoplasma alligatoris*, *Carnobacterium* sp., *Melissococcus plutonius*, *Tetragenococcus halophilus*, and/or *Mycoplasma arthritidis*. In yet other aspects, exemplary phosphoketolase nucleic acids include, for example, a phosphoketolase isolated from *Streptococcus agalactiae*, *Mycoplasma agalactiae*, *Streptococcus gordonii*, *Kingella oralis*, *Mycoplasma fermentans*, *Granulicatella adiacens*, *Mycoplasma hominis*, *Mycoplasma crocodyli*, *Mycobacterium bovis*, *Neisseria* sp., *Streptococcus* sp., *Eremococcus coleocola*, *Granulicatella elegans*, *Streptococcus parasanguinis*, *Aerococcus urinae*, *Kingella kingae*, *Streptococcus australis*, *Streptococcus criceti*, and/or *Mycoplasma columbinum*.

Other phosphoketolases that can be used include, but are not limited to, *B. longum*, *L. plantarum*, *C. acetobutylicum*, *L. reuteri*, *L. paraplantarum*, *R. palustris*, *Nostoc punctiforme*, *B. animalis*, *B. breve*, *G. vaginalis*, *E. gallinarum*, *M. paludis*, *Panteoa* sp., *R. aquatilis*, *N. punctiforme*, *S. avermetilis*, and *T. fusca*. Additional phosphoketolases that can be used, include but are not limited to, *Burkholderia phytofirmans*, *Lactobacillus buchneri*, *Bifidobacterium gallicum*, *Bifidobacterium dentium*, *Bifidobacterium bifidum*, and *Clostridium acetobutylicum*.

Standard methods can be used to determine whether a polypeptide has phosphoketolase peptide activity by measuring the ability of the peptide to convert D-fructose 6-phosphate or D-xylulose 5-phosphate into acetyl-P. Acetyl-P can then be converted into ferryl acetyl hydroxamate, which can be detected spectrophotometrically (Meile et al., J. Bact. 183:2929-2936, 2001). Any polypeptide identified as having phosphoketolase peptide activity as described herein is suitable for use in the present invention. In some embodiments, the phosphoketolase polypeptide catalyzes the conversion of xylulose 5-phosphate to glyceraldehyde 3-phosphate and acetyl phosphate. In other embodiments, the phosphoketolase polypeptide catalyzes the conversion of fructose 6-phosphate to erythrose 4-phosphate and acetyl phosphate. In still other embodiments, the phosphoketolase polypeptide capable of catalyzing the conversion of sedoheptulose-7-phosphate to ribose-5-phosphate and acetyl phosphate. In still other embodiments, the phosphoketolase polypeptide catalyzes the conversion of xylulose 5-phosphate to glyceraldehyde 3-phosphate and acetyl phosphate and/or the conversion of fructose 6-phosphate to erythrose 4-phosphate and acetyl phosphate and/or the conversion of sedoheptulose-7-phosphate to ribose-5-phosphate and acetyl phosphate.

In any of the embodiments described herein, a phosphoketolase nucleic acid can have at least about 99%, 98%, 97%, 96%, 95%, 95%, 93%, 92%, 91%, 90%, 89%, 88%, 87%, 86%, or 85% sequence identity to any of the phosphoketolase nucleic acid sequences described herein. In some embodiments, the phosphoketolase nucleic acid encoded by the *Mycobacterium gilvum* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:52. In some embodiments, the phosphoketolase nucleic acid encoded by the *Shewanella baltica* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:53. In some embodiments, the phosphoketolase nucleic acid encoded by the *Lactobacillus rhamnosus* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:54. In some embodiments, the phosphoketolase nucleic acid encoded by the *Lactobacillus crispatus* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:55. In some embodiments, the phosphoketolase nucleic acid encoded by the *Leuconostoc citreum* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:56. In some embodiments, the phosphoketolase nucleic acid encoded by the *Bradyrhizobium* sp. phosphoketolase gene can have at least about 99%, 98%, 97%, 96%, 95%, 95%, 93%, 92%, 91%, 90%, 89%, 88%, 87%, 86%, or 85% sequence identity to SEQ ID NO:57. In some embodiments, the phosphoketolase nucleic acid encoded by the *Brucella microti* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:58. In some embodiments, the phosphoketolase nucleic acid encoded by the *Lactobacillus salivarius* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:59. In some embodiments, the phosphoketolase nucleic acid encoded by the *Rhodococcus imtechensis* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:60. In some embodiments, the phosphoketolase nucleic acid encoded by the *Burkholderia xenovorans* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:61. In some embodiments, the phosphoketolase nucleic acid encoded by the *Mycobacterium intracellulare* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:62. In some embodiments, the phosphoketolase nucleic acid encoded by the *Nitrosomonas* sp. phosphoketolase gene can have at least about 99%, 98%, 97%, 96%, 95%, 95%, 93%, 92%, 91%, 90%, 89%, 88%, 87%, 86%, or 85% sequence identity to SEQ ID NO:63. In some embodiments, the phosphoketolase nucleic acid encoded by the *Schizosaccharomyces pombe* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:64. In some embodiments, the phosphoketolase nucleic acid encoded by the *Lactobacillus buchneri* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:65. In some embodiments, the phosphoketolase nucleic acid encoded by the *Streptomyces ghanaensis* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:66. In some embodiments, the phosphoketolase nucleic acid encoded by the *Cyanothece* sp. phosphoketolase gene can have at least about 99%, 98%, 97%, 96%, 95%, 95%, 93%, 92%, 91%, 90%, 89%, 88%, 87%, 86%, or 85% sequence identity to SEQ ID NO:67. In some embodiments, the phosphoketolase nucleic acid encoded by the *Neosartorya fischeri* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:68. In some embodiments, the phosphoketolase nucleic acid encoded by the *Enterococcus faecium* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:69. In some embodiments, the phosphoketolase nucleic acid encoded by the *Listeria grayi* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:70. In some embodiments, the phosphoketolase nucleic acid encoded by the *Enterococcus casseliflavus* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:71. In some embodiments, the phosphoketolase nucleic acid encoded by the *Mycoplasma alligatoris* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:72. In some embodiments, the phosphoketolase nucleic acid encoded by the *Carnobacterium* sp. phosphoketolase gene can have at least about 99%, 98%, 97%, 96%, 95%, 95%, 93%, 92%, 91%, 90%, 89%, 88%, 87%, 86%, or 85% sequence identity to SEQ ID NO:73. In some embodiments, the phosphoketolase nucleic acid encoded by the *Melissococcus plutonius* phosphoketolase gene can have at least about 99%, 98%, 97%, 96%, 95%, 95%, 93%, 92%, 91%, 90%, 89%, 88%, 87%, 86%, or 85% sequence identity to any one of SEQ ID NOs:74 and 76. In some embodiments, the phosphoketolase nucleic acid encoded by the *Tetragenococcus halophilus* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:75. In some embodiments, the phosphoketolase nucleic acid encoded by the *Mycoplasma arthritidis* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:77. In some embodiments, the phosphoketolase nucleic acid encoded by the *Streptococcus agalactiae* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:78. In some embodiments, the phosphoketolase nucleic acid encoded by the *Mycoplasma agalactiae* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:79. In some embodiments, the phosphoketolase nucleic acid encoded by the *Streptococcus gordonii* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:80. In some embodiments, the phosphoketolase nucleic acid encoded by the *Kingella oxalis* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:81. In some embodiments, the phosphoketolase nucleic acid encoded by the *Mycoplasma fermentans* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:82. In some embodiments, the phosphoketolase nucleic acid encoded by the *Granulicatella adiacens* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:83. In some embodiments, the phosphoketolase nucleic acid encoded by the *Mycoplasma hominis* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:84. In some embodiments, the phosphoketolase nucleic acid encoded by the *Mycoplasma crocodyli* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:85. In some embodiments, the phosphoketolase nucleic acid encoded by the *Neisseria* sp. phosphoketolase gene can have at least about 99%, 98%, 97%, 96%, 95%, 95%, 93%, 92%, 91%, 90%, 89%, 88%, 87%, 86%, or 85% sequence identity to SEQ ID NO:86. In some embodiments, the phosphoketolase nucleic acid encoded by the *Eremococcus coleocola* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:87. In some embodiments, the phosphoketolase nucleic acid encoded by the *Aerococcus urinae* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:88. In some embodiments, the phosphoketolase nucleic acid encoded by the *Kingella kingae* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:89. In some embodiments, the phosphoketolase nucleic acid encoded by the *Streptococcus criceti* phosphoketolase gene can have at least about 99%, 98%, 97%, 96%, 95%, 95%, 93%, 92%, 91%, 90%, 89%, 88%, 87%, 86%, or 85% sequence identity to any one of SEQ ID NOs:90 and 91. In some embodiments, the phosphoketolase nucleic acid encoded by the *Mycoplasma columbinum* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:92.

In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Mycobacterium gilvum* phosphoketolase amino acid sequence SEQ ID NO:1. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, or 70% sequence identity to the phosphoketolase polypeptide encoded by the *Shewanella baltica* phosphoketolase amino acid sequence SEQ ID NO:2. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, or 70% sequence identity to the phosphoketolase polypeptide encoded by the *Lactobacillus rhamnosus* phosphoketolase amino acid sequence SEQ ID NO:3. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, or 70% sequence identity to the phosphoketolase polypeptide encoded by the *Lactobacillus crispatus* phosphoketolase amino acid sequence SEQ ID NO:4. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Bifidobacterium longum* phosphoketolase amino acid sequence SEQ ID NO:5. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, or 70% sequence identity to the phosphoketolase polypeptide encoded by the *Leuconostoc citreum* phosphoketolase amino acid sequence SEQ ID NO:6. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, 65%, or 60% sequence identity to the phosphoketolase polypeptide encoded by the *Bradyrhizobium* sp. phosphoketolase amino acid sequence SEQ ID NO:7. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Enterococcus faecium* phosphoketolase amino acid sequence SEQ ID NO:8. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, or 70% sequence identity to the phosphoketolase polypeptide encoded by the *Brucella microti* phosphoketolase amino acid sequence SEQ ID NO:9. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, 65%, or 60% sequence identity to the phosphoketolase polypeptide encoded by the *Lactobacillus salivarius* phosphoketolase amino acid sequence SEQ ID NO:10. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Streptococcus agalactiae* phosphoketolase amino acid sequence SEQ ID NO:11. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Rhodococcus imtechensis* phosphoketolase amino acid sequence SEQ ID NO:12. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Burkholderia xenovorans* phosphoketolase amino acid sequence SEQ ID NO:13. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, 65%, or 60% sequence identity to the phosphoketolase polypeptide encoded by the *Mycobacterium intracellulare* phosphoketolase amino acid sequence SEQ ID NO:14. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, 65%, or 60% sequence identity to the phosphoketolase polypeptide encoded by the *Nitrosomonas* sp. phosphoketolase amino acid sequence SEQ ID NO:15. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, 65%, 60%, 55%, or 50% sequence identity to the phosphoketolase polypeptide encoded by the *Schizosaccharomyces pombe* phosphoketolase amino acid sequence SEQ ID NO:16. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, or 70% sequence identity to the phosphoketolase polypeptide encoded by the *Leuconostoc mesenteroides* phosphoketolase amino acid sequence SEQ ID NO:17. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, 65%, 60%, 55%, or 50% sequence identity to the phosphoketolase polypeptide encoded by the *Streptomyces* sp. phosphoketolase amino acid sequence SEQ ID NO:18. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Lactobacillus buchneri* phosphoketolase amino acid sequence SEQ ID NO:19. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, 65%, 60%, 55%, or 50% sequence identity to the phosphoketolase polypeptide encoded by the *Streptomyces ghanaensis* phosphoketolase amino acid sequence SEQ ID NO:20. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, 65%, or 60% sequence identity to the phosphoketolase polypeptide encoded by the *Cyanothece* sp. phosphoketolase amino acid sequence SEQ ID NO:21. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, or 70% sequence identity to the phosphoketolase polypeptide encoded by the *Neosartorya fischeri* phosphoketolase amino acid sequence SEQ ID NO:22. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Enterococcus faecium* phosphoketolase amino acid sequence SEQ ID NO:23. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Listeria grayi* phosphoketolase amino acid sequence SEQ ID NO:24. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Enterococcus casseliflavus* phosphoketolase amino acid sequence SEQ ID NO:25. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Mycoplasma alligatoris* phosphoketolase amino acid sequence SEQ ID NO:26. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Carnobacterium* sp. phosphoketolase amino acid sequence SEQ ID NO:27. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Melissococcus plutonius* phosphoketolase amino acid sequence SEQ ID NO:28. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Tetragenococcus halophilus* phosphoketolase amino acid sequence SEQ ID NO:29. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Melissococcus plutonius* phosphoketolase amino acid sequence SEQ ID NO:30. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Mycoplasma arthritidis* phosphoketolase amino acid sequence SEQ ID NO:31. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Streptococcus agalactiae* phosphoketolase amino acid sequence SEQ ID NO:32. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Mycoplasma agalactiae* phosphoketolase amino acid sequence SEQ ID NO:33. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Streptococcus gordonii* phosphoketolase amino acid sequence SEQ ID NO:34. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Kingella oxalis* phosphoketolase amino acid sequence SEQ ID NO:35. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Mycoplasma fermentans* phosphoketolase amino acid sequence SEQ ID NO:36. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Granulicatella adiacens* phosphoketolase amino acid sequence SEQ ID NO:37. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Mycoplasma hominis* phosphoketolase amino acid sequence SEQ ID NO:38. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Mycoplasma crocodyli* phosphoketolase amino acid sequence SEQ ID NO:39. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Neisseria* sp. phosphoketolase amino acid sequence SEQ ID NO:40. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Eremococcus coleocola* phosphoketolase amino acid sequence SEQ ID NO:41. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Aerococcus urinae* phosphoketolase amino acid sequence SEQ ID NO:42. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Kingella kingae* phosphoketolase amino acid sequence SEQ ID NO:43. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Streptococcus criceti* phosphoketolase amino acid sequence SEQ ID NO:44. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Streptococcus criceti* phosphoketolase amino acid sequence SEQ ID NO:45. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Mycoplasma columbinum* phosphoketolase amino acid sequence SEQ ID NO:46. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, 70%, or 65% sequence identity to the phosphoketolase polypeptide encoded by the *Burkholderia phytofirmans* phosphoketolase amino acid sequence SEQ ID NO:47. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, or 70% sequence identity to the phosphoketolase polypeptide encoded by the *Lactobacillus buchneri* phosphoketolase amino acid sequence SEQ ID NO:48. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, or 70% sequence identity to the phosphoketolase polypeptide encoded by the *Bifidobacterium gallicum* phosphoketolase amino acid sequence SEQ ID NO:49. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, or 70% sequence identity to the phosphoketolase polypeptide encoded by the *Bifidobacterium dentium* phosphoketolase amino acid sequence SEQ ID NO:50. In some embodiments, the phosphoketolase polypeptide can have at least about 99%, 98%, 97%, 96%, 95%, 95%, 93%, 92%, 91%, 90%, 89%, 88%, 87%, 86%, 85%, 80%, 75%, or 70% sequence identity to the phosphoketolase polypeptide encoded by the *Bifidobacterium bifidum* phosphoketolase amino acid sequence SEQ ID NO:51.

Additional examples of phosphoketolase enzymes which can be used herein are described in U.S. Pat. No. 7,785,858 and WO 2011/159853, which are incorporated by reference herein, especially with respect to all disclosure about phosphoketolase enzymes.

In some aspects, provided herein is a recombinant cell capable of increased carbon flux through the phosphoketolase pathway, wherein the recombinant cell comprises a heterologous nucleic acid sequence encoding a polypeptide having phosphoketolase activity as described herein. In some embodiments, the polypeptide having phosphoketolase activity is isolated from *Burkholderia phytofirmans*, *Lactobacillus buchneri*, *Bifidobacterium gallicum*, *Bifidobacterium dentium*, *Bifidobacterium bifidum*, and/or *Clostridium acetobutylicum*. In other aspects, the polypeptide having phosphoketolase activity isolated from *Mycobacterium gilvum*, *Shewanella baltica*, *Lactobacillus rhamnosus*, *Lactobacillus crispatus*, *Bifidobacterium longum*, *Leuconostoc citreum*, *Bradyrhizobium* sp., *Enterococcus faecium*, *Brucella microti*, *Lactobacillus salivarius*, *Streptococcus agalactiae*, *Rhodococcus imtechensis*, *Burkholderia xenovorans*, *Mycobacterium intracellulare*, *Nitrosomonas* sp., *Schizosaccharomyces pombe*, *Leuconostoc mesenteroides*, *Streptomyces* sp., *Lactobacillus buchneri*, *Streptomyces ghanaensis*, *Cyanothece* sp., and/or *Neosartorya fischeri*. In other aspects, the polypeptide having phosphoketolase activity isolated from *Enterococcus faecium*, *Listeria grayi*, *Enterococcus gallinarum*, *Enterococcus saccharolyticus*, *Enterococcus casseliflavus*, *Mycoplasma alligatoris*, *Carnobacterium* sp., *Melissococcus plutonius*, *Tetragenococcus halophilus*, and/or *Mycoplasma arthritidis*. In yet other aspects, the polypeptide having phosphoketolase activity isolated from *Streptococcus agalactiae*, *Mycoplasma agalactiae*, *Streptococcus gordonii*, *Kingella oxalis*, *Mycoplasma fermentans*, *Granulicatella adiacens*, *Mycoplasma hominis*, *Mycoplasma crocodyli*, *Mycobacterium bovis*, *Neisseria* sp., *Streptococcus* sp., *Eremococcus coleocola*, *Granulicatella elegans*, *Streptococcus parasanguinis*, *Aerococcus urinae*, *Kingella kingae*, *Streptococcus australis*, *Streptococcus criceti*, and/or *Mycoplasma columbinum*.

In any of the embodiments herein, the recombinant cells can be further engineered to increase the activity of one or more of the following genes selected from the group consisting of ribose-5-phosphate isomerase (rpiA and/or rpiB), D-ribulose-5-phosphate 3-epimerase (rpe), transketolase (tktA and/or tktB), transaldolase B (tal B), phosphate acetyltransferase (pta and/or eutD). In another embodiment, the recombinant cells can be further engineered to decrease the activity of one or more genes of the following genes including glucose-6-phosphate dehydrogenase (zwf), 6-phosphofructokinase-1 (pfkA and/or pfkB), fructose bisphosphate aldolase (fba, fbaA, fbaB, and/or fbaC), glyceraldehyde-3-phosphate dehydrogenase (gapA and/or gapB), acetate kinase (ackA), citrate synthase (gltA), EI (ptsI), EIICB$^{Glc}$ (ptsG), EIIA$^{Glc}$ (crr), and/or HPr (ptsH).

Methods of Using Recombinant Cells to Produce Increased Amounts of Acetyl-CoA and Acetyl-Derived Metabolites Also provided herein are methods for the production of acetyl-CoA. In some aspects, the method for producing acetyl-CoA comprises: (a) culturing a composition comprising recombinant cells which have been engineered to increase carbon flux through the phosphoketolase pathway as described herein (including any of the recombinant cells described above), or progeny thereof, capable of producing acetyl-CoA; and (b) producing mevalonate. In some aspects, the method of producing acetyl-CoA comprises the steps of culturing any of the recombinant cells described herein under conditions suitable for the production of acetyl-CoA and allowing the recombinant cells to produce acetyl-CoA. In some aspects, the method of producing acetyl-CoA further comprises a step of recovering the acetyl-CoA.

As described herein, the methods of producing acetyl-CoA comprise the steps of: (a) culturing recombinant cells (including, but not limited to, *E. coli* cells) that do not endogenously express a phosphoketolase polypeptide, wherein the cells heterologously express one or more copies of a gene encoding a phosphoketolase polypeptide; and (b) producing acetyl-CoA. In certain embodiments, the recombinant cells comprise one or more copies of a heterologous nucleic acid encoding a phosphoketolase isolated from *Burkholderia phytofirmans, Lactobacillus buchneri, Bifidobacterium gallicum, Bifidobacterium dentium, Bifidobacterium bifidum*, and/or *Clostridium acetobutylicum*. In some embodiments, the recombinant cells comprise one or more copies of a heterologous nucleic acid encoding a phosphoketolase isolated from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In some embodiments, the recombinant cells comprise one or more copies of a heterologous nucleic acid encoding a phosphoketolase isolated from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus, Mycoplasma arthritidis*, and/or *Mycoplasma arthritidis*. In some embodiments, the recombinant cells comprise one or more copies of a heterologous nucleic acid encoding a phosphoketolase isolated from *Streptococcus agalactiae, Mycoplasma agalactiae, Streptococcus gordonii, Kingella oxalis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*. In some embodiments, the recombinant cells comprise one or more copies of a heterologous nucleic acid encoding a phosphoketolase isolated from and organism listed in Table 1, Table 2 and/or FIGS. 3-24. In some embodiments, the recombinant cells comprise one or more copies of a heterologous nucleic acid encoding a phosphoketolase identified from an in vivo screening assay as described in Example 7. Additionally, the recombinant cells can produce acetyl-CoA in concentrations greater than that of the same cells lacking one or more heterologous copies of a gene encoding an phosphoketolase polypeptide from *Burkholderia phytofirmans, Lactobacillus buchneri, Bifidobacterium gallicum, Bifidobacterium dentium, Bifidobacterium bifidum, Clostridium acetobutylicum, Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., *Neosartorya fischeri, Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus, Mycoplasma arthritidis, Streptococcus agalactiae, Mycoplasma agalactiae, Streptococcus gordonii, Kingella oxalis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*, when the cells are cultured in minimal medium. In certain embodiments, the one or more copies of a heterologous nucleic acid encoding an phosphoketolase polypeptide described herein is a heterologous nucleic acid that is integrated into the host cell's chromosome.

Also provided herein are methods for the production of acetyl-CoA-derived metabolites. In some aspects, the method for producing acetyl-CoA-derived metabolites comprises: (a) culturing a composition comprising recombinant cells which have been engineered to increase carbon flux through the phosphoketolase pathway as described herein (including any of the recombinant cells described above), or progeny thereof, capable of producing acetyl-CoA-derived metabolites; and (b) producing mevalonate. In some aspects, the method of producing acetyl-CoA-derived metabolites comprises the steps of culturing any of the recombinant cells described herein under conditions suitable for the production of acetyl-CoA-derived metabolites and allowing the recombinant cells to produce acetyl-CoA-derived metabolites. In some aspects, the method of producing acetyl-CoA further comprises a step of recovering the acetyl-CoA-derived metabolites.

As described herein, the methods of producing acetyl-CoA-derived metabolites comprise the steps of: (a) culturing recombinant cells (including, but not limited to, *E. coli* cells) that do not endogenously express a phosphoketolase polypeptide, wherein the cells heterologously express one or more copies of a gene encoding a phosphoketolase polypeptide; and (b) producing acetyl-CoA-derived metabolites. In certain embodiments, the recombinant cells comprise one or more copies of a heterologous nucleic acid encoding a phosphoketolase isolated from *Burkholderia phytofirmans, Lactobacillus buchneri, Bifidobacterium gallicum, Bifidobacterium dentium, Bifidobacterium bifidum,* and/or *Clostridium acetobutylicum*. In some embodiments, the recombinant cells comprise one or more copies of a heterologous nucleic acid encoding a phosphoketolase isolated from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In some embodiments, the recombinant cells comprise one or more copies of a heterologous nucleic acid encoding a phosphoketolase isolated from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus,* and/or *Mycoplasma arthritidis*. In some embodiments, the recombinant cells comprise one or more copies of a heterologous nucleic acid encoding a phosphoketolase isolated from *Streptococcus agalactiae, Mycoplasma agalactiae, Streptococcus gordonii, Kingella oxalis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti,* and/or *Mycoplasma columbinum*. In some embodiments, the recombinant cells comprise one or more copies of a heterologous nucleic acid encoding a phosphoketolase isolated from and organism listed in Table 1, Table 2 and/or FIGS. 3-24. In some embodiments, the recombinant cells comprise one or more copies of a heterologous nucleic acid encoding a phosphoketolase identified from an in vivo screening assay as described in Example 7. Additionally, the recombinant cells can produce acetyl-CoA-derived metabolites in concentrations greater than that of the same cells lacking one or more heterologous copies of a gene encoding an phosphoketolase polypeptide from *Burkholderia phytofirmans, Lactobacillus buchneri, Bifidobacterium gallicum, Bifidobacterium dentium, Bifidobacterium bifidum, Clostridium acetobutylicum, Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., *Neosartorya fischeri, Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus, Mycoplasma arthritidis, Streptococcus agalactiae, Mycoplasma agalactiae, Streptococcus gordonii, Kingella oxalis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae,* *Streptococcus australis, Streptococcus criceti,* and/or *Mycoplasma columbinum*, when the cells are cultured in minimal medium. In certain embodiments, the one or more copies of a heterologous nucleic acid encoding an phosphoketolase polypeptide described herein is a heterologous nucleic acid that is integrated into the host cell's chromosome.

In any of the embodiments herein, the acetyl-CoA-derived metabolite can be one or more of polyketides, polyhydroxybutyrate, fatty alcohols, or fatty acids. In any of the embodiments herein, the acetyl-CoA-derived metabolite can be one or more of an amino acid selected from the group consisting of: glutamic acid, glutamine, aspartate, asparagine, proline, arginine, methionine, threonine, cysteine, lysine, leucine, and isoleucine. In some embodiments, the acetyl-CoA-derived metabolite is succinate. In any of the embodiments herein, the acetyl-CoA-derived metabolite can be one or more of acetone, isopropanol, isobutene, or propene.

Also provided herein are methods for producing acetyl-CoA-derived metabolites comprising culturing a recombinant cell capable of increased carbon flux through the phosphoketolase pathway, wherein the recombinant cell comprises: (i) a heterologous nucleic acid sequence encoding a polypeptide having phosphoketolase activity, wherein the polypeptide comprises at least 65% sequence identity to SEQ ID NO:8 and (ii) one or more nucleic acids encoding one or more polypeptides of the complete MVA pathway, wherein said recombinant cell comprising said polypeptide having phosphoketolase activity of (i) has a Performance Index value of greater than 1.0 in one or more of the following parameters: (a) cell growth on glucose, (b) cell growth on xylose, (c) production of intracellular acetyl-phosphate or (d) cell growth on glucose-6-phosphate and producing said acetyl-CoA-derived metabolites. In some embodiments, the polypeptide comprises at least 90% sequence identity to SEQ ID NO:23. In some embodiments, the polypeptide comprises at least 90% sequence identity to SEQ ID NO:24. In some embodiments, the polypeptide comprises at least 90% sequence identity to SEQ ID NO:25. In some embodiments, the polypeptide comprises at least 90% sequence identity to SEQ ID NO:26. In some embodiments, the polypeptide comprises at least 90% sequence identity to SEQ ID NO:27. In some embodiments, the polypeptide comprises at least 90% sequence identity to SEQ ID NO:28. In some embodiments, the polypeptide comprises at least 90% sequence identity to SEQ ID NO:29. In some embodiments, the polypeptide comprises at least 90% sequence identity to SEQ ID NO:30. In some embodiments, the polypeptide comprises at least 90% sequence identity to SEQ ID NO:31. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from E. gallinarum. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Additionally provided herein are methods for producing acetyl-CoA-derived metabolites comprising culturing a recombinant cell capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:8 and (ii) one or more nucleic acids encoding one or more polypeptides of the complete MVA pathway, wherein said polypeptide having phosphoketolase activity of (i) has a Performance Index value of greater than 1.0 in one or more of the following parameters: (a) protein solubility, (b) protein expression, or (c) fructose-6-phosphate (F6P) Specific Activity and producing said acetyl-CoA-derived metabolites. In some embodiments, the polypeptide comprises at least 90% sequence identity to SEQ ID NO:23. In some embodiments, the polypeptide comprises at least 90% sequence identity to SEQ ID NO:24. In some embodiments, the polypeptide comprises at least 90% sequence identity to SEQ ID NO:25. In some embodiments, the polypeptide comprises at least 90% sequence identity to SEQ ID NO:26. In some embodiments, the polypeptide comprises at least 90% sequence identity to SEQ ID NO:27. In some embodiments, the polypeptide comprises at least 90% sequence identity to SEQ ID NO:28. In some embodiments, the polypeptide comprises at least 90% sequence identity to SEQ ID NO:29. In some embodiments, the polypeptide comprises at least 90% sequence identity to SEQ ID NO:30. In some embodiments, the polypeptide comprises at least 90% sequence identity to SEQ ID NO:31. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from E. gallinarum). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from E. gallinarum. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Further provided herein are methods for producing acetyl-CoA-derived metabolites comprising culturing a recombinant cell capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:11 and (ii) one or more nucleic acids encoding one or more polypeptides of the complete MVA pathway, wherein said recombinant cell comprising said polypeptide having phosphoketolase activity of (i) has a Performance Index value of greater than 1.0 in one or more of the following parameters: (a) cell growth on glucose, (b) cell growth on xylose, (c) production of intracellular acetyl-phosphate or (d) cell growth on glucose-6-phosphate and producing said acetyl-CoA-derived metabolites. In some embodiments, the polypeptide comprises at least 90% sequence identity to SEQ ID NO:32. In some embodiments, the polypeptide comprises at least 90% sequence identity to SEQ ID NO:33. In some embodiments, the polypeptide comprises at least 90% sequence identity to SEQ ID NO:34. In some embodiments, the polypeptide comprises at least 90% sequence identity to SEQ ID NO:35. In some embodiments, the polypeptide comprises at least 90% sequence identity to SEQ ID NO:36. In some embodiments, the polypeptide comprises at least 90% sequence identity to SEQ ID NO:37. In some embodiments, the polypeptide comprises at least 90% sequence identity to SEQ ID NO:38. In some embodiments, the polypeptide comprises at least 90% sequence identity to SEQ ID NO:39. In some embodiments, the polypeptide comprises at least 90% sequence identity to SEQ ID NO:40. In some embodiments, the polypeptide comprises at least 90% sequence identity to SEQ ID NO:41. In some embodiments, the polypeptide comprises at least 90% sequence identity to SEQ ID NO:42. In some embodiments, the polypeptide comprises at least 90% sequence identity to SEQ ID NO:43. In some embodiments, the polypeptide comprises at least 90% sequence identity to SEQ ID NO:44. In some embodiments, the polypeptide comprises at least 90% sequence identity to SEQ ID NO:45. In some embodiments, the polypeptide comprises at least 90% sequence identity to SEQ ID NO:46. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Provided herein are methods for producing acetyl-CoA-derived metabolites comprising culturing a recombinant cell capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:11 and (ii) one or more nucleic acids encoding one or more polypeptides of the complete MVA pathway, wherein said polypeptide having phosphoketolase activity of (i) has a Performance Index value of greater than 1.0 in one or more of the following parameters: (a) protein solubility, (b) protein expression, or (c) fructose-6-phosphate (F6P) Specific Activity and producing said acetyl-CoA-derived metabolites. In some embodiments, the polypeptide comprises at least 90% sequence identity to SEQ ID NO:32. In some embodiments, the polypeptide comprises at least 90% sequence identity to SEQ ID NO:33. In some embodiments, the polypeptide comprises at least 90% sequence identity to SEQ ID NO:34. In some embodiments, the polypeptide comprises at least 90% sequence identity to SEQ ID NO:35. In some embodiments, the polypeptide comprises at least 90% sequence identity to SEQ ID NO:36. In some embodiments, the polypeptide comprises at least 90% sequence identity to SEQ ID NO:37. In some embodiments, the polypeptide comprises at least 90% sequence identity to SEQ ID NO:38. In some embodiments, the polypeptide comprises at least 90% sequence identity to SEQ ID NO:39. In some embodiments, the polypeptide comprises at least 90% sequence identity to SEQ ID NO:40. In some embodiments, the polypeptide comprises at least 90% sequence identity to SEQ ID NO:41. In some embodiments, the polypeptide comprises at least 90% sequence identity to SEQ ID NO:42. In some embodiments, the polypeptide comprises at least 90% sequence identity to SEQ ID NO:43. In some embodiments, the polypeptide comprises at least 90% sequence identity to SEQ ID NO:44. In some embodiments, the polypeptide comprises at least 90% sequence identity to SEQ ID NO:45. In some embodiments, the polypeptide comprises at least 90% sequence identity to SEQ ID NO:46. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Recombinant Cells Expressing a Phosphoketolase Polypeptide and One or More Polypeptides of the MVA Pathway The mevalonate-dependent biosynthetic pathway (MVA pathway) is a key metabolic pathway present in all higher eukaryotes and certain bacteria. In addition to being important for the production of molecules used in processes as diverse as protein prenylation, cell membrane maintenance, protein anchoring, and N-glycosylation, the mevalonate pathway provides a major source of the isoprenoid precursor molecules DMAPP and IPP, which serve as the basis for the biosynthesis of terpenes, terpenoids, isoprenoids, and isoprene.

The complete MVA pathway can be subdivided into two groups: an upper and lower pathway. In the upper portion of the MVA pathway, acetyl Co-A produced during cellular metabolism is converted to mevalonate via the actions of polypeptides having either: (a) (i) thiolase activity or (ii) acetoacetyl-CoA synthase activity, (b) HMG-CoA reductase, and (c) HMG-CoA synthase enzymatic activity. First, acetyl Co-A is converted to acetoacetyl CoA via the action of a thiolase or an acetoacetyl-CoA synthase (which utilizes acetyl-CoA and malonyl-CoA). Next, acetoacetyl-CoA is converted to 3-hydroxy-3-methylglutaryl-CoA (HMG-CoA) by the enzymatic action of HMG-CoA synthase. This Co-A derivative is reduced to mevalonate by HMG-CoA reductase, which is the rate-limiting step of the mevalonate pathway of isoprenoid production. In the lower MVA pathway, mevalonate is then converted into mevalonate-5-phosphate via the action of mevalonate kinase which is subsequently transformed into 5-diphosphomevalonate by the enzymatic activity of phosphomevalonate kinase. Finally, IPP is formed from 5-diphosphomevalonate by the activity of the enzyme mevalonate-5-pyrophosphate decarboxylase.

Thus, in certain embodiments, the recombinant cells of the present invention are recombinant cells having the ability to produce mevalonate, isoprenoid precursors, isoprene or isoprenoids via the MVA pathway wherein the recombinant cells comprise: (i) a heterologous gene encoding a phosphoketolase capable of synthesizing glyceraldehyde 3-phosphate and acetyl phosphate from xylulose 5-phosphate, (ii) one or more heterologous genes encoding one or more MVA polypeptides, and (iii) one or more heterologous genes involved in mevalonate, isoprenoid precursor, or isoprene or isoprenoid biosynthesis that enables the synthesis of mevalonate, isoprenoid precursors, isoprene or isoprenoids from acetoacetyl-CoA in the host cell. In other embodiments, recombinant cells of the present invention are recombinant cells having the ability to produce mevalonate, isoprenoid precursors, isoprene or isoprenoids wherein the recombinant cells comprise: (i) a heterologous gene encoding a phosphoketolase capable of synthesizing erythrose 4-phosphate and acetyl phosphate from fructose 6-phosphate, (ii) one or more heterologous genes encoding one or more MVA polypeptides, and (iii) one or more heterologous genes involved in mevalonate, isoprenoid precursors, isoprene or isoprenoid biosynthesis that enables the synthesis of produce mevalonate, isoprenoid precursors, isoprene or isoprenoids from acetoacetyl-CoA in the host cell.

Upper MVA Pathway Polypeptides

The upper portion of the MVA pathway uses acetyl Co-A produced during cellular metabolism as the initial substrate for conversion to mevalonate via the actions of polypeptides having either: (a) (i) thiolase activity or (ii) acetoacetyl-CoA synthase activity, (b) HMG-CoA reductase, and (c) HMG-CoA synthase enzymatic activity. First, acetyl Co-A is converted to acetoacetyl CoA via the action of a thiolase or an acetoacetyl-CoA synthase (which utilizes acetyl-CoA and malonyl-CoA). Next, acetoacetyl-CoA is converted to 3-hydroxy-3-methylglutaryl-CoA (HMG-CoA) by the enzymatic action of HMG-CoA synthase. This Co-A derivative is reduced to mevalonate by HMG-CoA reductase, which is the rate-limiting step of the mevalonate pathway of isoprenoid production.

Non-limiting examples of upper MVA pathway polypeptides include acetyl-CoA acetyltransferase (AA-CoA thiolase) polypeptides, acetoacetyl-CoA synthase polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides. Upper MVA pathway polypeptides can include polypeptides, fragments of polypeptides, peptides, and fusions polypeptides that have at least one activity of an upper MVA pathway polypeptide. Exemplary upper MVA pathway nucleic acids include nucleic acids that encode a polypeptide, fragment of a polypeptide, peptide, or fusion polypeptide that has at least one activity of an upper MVA pathway polypeptide. Exemplary MVA pathway polypeptides and nucleic acids include naturally-occurring polypeptides and nucleic acids from any of the source organisms described herein. Thus, it is contemplated herein that any gene encoding an upper MVA pathway polypeptide can be used in the present invention.

In certain embodiments, various options of mvaE and mvaS genes from L. grayi, E. faecium, E. gallinarum, E. casseliflavus and/or E. faecalis alone or in combination with one or more other mvaE and mvaS genes encoding proteins from the upper MVA pathway are contemplated within the scope of the invention. In other embodiments, an acetoacetyl-CoA synthase gene is contemplated within the scope of the present invention in combination with one or more other genes encoding: (i) 3-hydroxy-3-methylglutaryl-CoA synthase (HMG-CoA synthase) polypeptides and 3-hydroxy-3-methylglutaryl-CoA reductase (HMG-CoA reductase) polypeptides. Thus, in certain aspects, any of the combinations of genes contemplated in can be expressed in recombinant cells in any of the ways described herein.

Additional non-limiting examples of upper MVA pathway polypeptides which can be used herein are described in International Patent Application Publication No. WO2009/076676; WO2010/003007 and WO2010/148150.

Genes Encoding mvaE and mvaS Polypeptides

In certain embodiments, various options of mvaE and mvaS genes from L. grayi, E. faecium, E. gallinarum, E. casseliflavus and/or E. faecalis alone or in combination with one or more other mvaE and mvaS genes encoding proteins from the upper MVA pathway are contemplated within the scope of the invention. In L. grayi, E. faecium, E. gallinarum, E. casseliflavus, and E. faecalis, the mvaE gene encodes a polypeptide that possesses both thiolase and HMG-CoA reductase activities. In fact, the mvaE gene product represented the first bifunctional enzyme of IPP biosynthesis found in eubacteria and the first example of HMG-CoA reductase fused to another protein in nature (Hedl, et al., *J Bacteriol.* 2002 April; 184(8): 2116-2122). The mvaS gene, on the other hand, encodes a polypeptide having an HMG-CoA synthase activity.

Accordingly, recombinant cells (e.g., *E. coli*) can be engineered to express one or more mvaE and mvaS genes from L. grayi, E. faecium, E. gallinarum, E. casseliflavus and/or E. faecalis, to produce mevalonate. The one or more mvaE and mvaS genes can be expressed on a multicopy plasmid. The plasmid can be a high copy plasmid, a low copy plasmid, or a medium copy plasmid. Alternatively, the one or more mvaE and mvaS genes can be integrated into the host cell's chromosome. For both heterologous expression of the one or more mvaE and mvaS genes on a plasmid or as an integrated part of the host cell's chromosome, expression of the genes can be driven by either an inducible promoter or a constitutively expressing promoter. The promoter can be a strong driver of expression, it can be a weak driver of expression, or it can be a medium driver of expression of the one or more mvaE and mvaS genes.

Exemplary mvaE Polypeptides and Nucleic Acids

The mvaE gene encodes a polypeptide that possesses both thiolase and HMG-CoA reductase activities. The thiolase activity of the polypeptide encoded by the mvaE gene converts acetyl Co-A to acetoacetyl CoA whereas the HMG-CoA reductase enzymatic activity of the polypeptide converts 3-hydroxy-3-methylglutaryl-CoA to mevalonate. Exemplary mvaE polypeptides and nucleic acids include naturally-occurring polypeptides and nucleic acids from any of the source organisms described herein as well as mutant polypeptides and nucleic acids derived from any of the source organisms described herein that have at least one activity of a mvaE polypeptide.

Mutant mvaE polypeptides include those in which one or more amino acid residues have undergone an amino acid substitution while retaining mvaE polypeptide activity (i.e., the ability to convert acetyl Co-A to acetoacetyl CoA as well as the ability to convert 3-hydroxy-3-methylglutaryl-CoA to mevalonate). The amino acid substitutions can be conservative or non-conservative and such substituted amino acid residues can or cannot be one encoded by the genetic code. The standard twenty amino acid "alphabet" has been divided into chemical families based on similarity of their side chains. Those families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). A "conservative amino acid substitution" is one in which the amino acid residue is replaced with an amino acid residue having a chemically similar side chain (i.e., replacing an amino acid having a basic side chain with another amino acid having a basic side chain). A "non-conservative amino acid substitution" is one in which the amino acid residue is replaced with an amino acid residue having a chemically different side chain (i.e., replacing an amino acid having a basic side chain with another amino acid having an aromatic side chain).

Amino acid substitutions in the mvaE polypeptide can be introduced to improve the functionality of the molecule. For example, amino acid substitutions that increase the binding affinity of the mvaE polypeptide for its substrate, or that improve its ability to convert acetyl Co-A to acetoacetyl CoA and/or the ability to convert 3-hydroxy-3-methylglutaryl-CoA to mevalonate can be introduced into the mvaE polypeptide. In some aspects, the mutant mvaE polypeptides contain one or more conservative amino acid substitutions.

In one aspect, mvaE proteins that are not degraded or less prone to degradation can be used for the production of mevalonate, isoprenoid precursors, isoprene, and/or isoprenoids. Examples of gene products of mvaEs that are not degraded or less prone to degradation which can be used include, but are not limited to, those from the organisms *E. faecium, E. gallinarum, E. casseliflavus, E. faecalis*, and *L. grayi*. One of skill in the art can express mvaE protein in *E. coli* BL21 (DE3) and look for absence of fragments by any standard molecular biology techniques. For example, absence of fragments can be identified on Safestain stained SDS-PAGE gels following His-tag mediated purification or when expressed in mevalonate, isoprene or isoprenoid producing *E. coli* BL21 using the methods of detection described herein.

Standard methods, such as those described in Hedl et al., (*J Bacteriol.* 2002, April; 184(8): 2116-2122) can be used to determine whether a polypeptide has mvaE activity, by measuring acetoacetyl-CoA thiolase as well as HMG-CoA reductase activity. In an exemplary assay, acetoacetyl-CoA thiolase activity is measured by spectrophotometer to monitor the change in absorbance at 302 nm that accompanies the formation or thiolysis of acetoacetyl-CoA. Standard assay conditions for each reaction to determine synthesis of acetoacetyl-CoA, are 1 mM acetyl-CoA, 10 mM $MgCl_2$, 50 mM Tris, pH 10.5 and the reaction is initiated by addition of enzyme. Assays can employ a final volume of 200 μl. For the assay, 1 enzyme unit (eu) represents the synthesis or thiolysis in 1 mM of 1 μmol of acetoacetyl-CoA. In another exemplary assay, of HMG-CoA reductase activity can be monitored by spectrophotometer by the appearance or disappearance of NADP(H) at 340 nm. Standard assay conditions for each reaction measured to show reductive deacylation of HMG-CoA to mevalonate are 0.4 mM NADPH, 1.0 mM (R,S)-HMG-CoA, 100 mM KCl, and 100 mM $K_xPO_4$, pH 6.5. Assays employ a final volume of 200 μl. Reactions are initiated by adding the enzyme. For the assay, 1 eu represents the turnover, in 1 mM, of 1 μmol of NADP(H). This corresponds to the turnover of 0.5 μmol of HMG-CoA or mevalonate.

Alternatively, production of mevalonate in recombinant cells can be measured by, without limitation, gas chromatography (see U.S. Patent Application Publication No.: US 2005/0287655 A1) or HPLC (See U.S. Patent Application Publication No.: 2011/0159557 A1). As an exemplary assay, cultures can be inoculated in shake tubes containing LB broth supplemented with one or more antibiotics and incubated for 14 h at 34° C. at 250 rpm. Next, cultures can be diluted into well plates containing TM3 media supplemented with 1% Glucose, 0.1% yeast extract, and 200 μM IPTG to final OD of 0.2. The plate are then sealed with a Breath Easier membrane (Diversified Biotech) and incubated at 34° C. in a shaker/incubator at 600 rpm for 24 hours. 1 mL of each culture is then centrifuged at 3,000×g for 5 min Supernatant is then added to 20% sulfuric acid and incubated on ice for 5 mM. The mixture is then centrifuged for 5 mM at 3000× g and the supernatant was collected for HPLC analysis. The concentration of mevalonate in samples is determined by comparison to a standard curve of mevalonate (Sigma). The glucose concentration can additionally be measured by performing a glucose oxidase assay according to any method known in the art. Using HPLC, levels of mevalonate can be quantified by comparing the refractive index response of each sample versus a calibration curve generated by running various mevalonate containing solutions of known concentration.

Exemplary mvaE nucleic acids include nucleic acids that encode a polypeptide, fragment of a polypeptide, peptide, or fusion polypeptide that has at least one activity of a mvaE polypeptide. Exemplary mvaE polypeptides and nucleic acids include naturally-occurring polypeptides and nucleic acids from any of the source organisms described herein as well as mutant polypeptides and nucleic acids derived from any of the source organisms described herein. Exemplary mvaE nucleic acids include, for example, mvaE nucleic acids isolated from *Listeria grayi*_DSM 20601, *Enterococcus faecium, Enterococcus gallinarum* EG2, *Enterococcus faecalis*, and/or *Enterococcus casseliflavus*. The mvaE nucleic acid encoded by the *Listeria grayi*_DSM 20601 mvaE gene can have at least about 99%, 98%, 97%, 96%, 95%, 95%, 93%, 92%, 91%, 90%, 89%, 88%, 87%, 86%, or 85% sequence identity to SEQ ID NO:95. The mvaE nucleic acid encoded by the *Enterococcus faecium* mvaE gene can have at least about 99%, 98%, 97%, 96%, 95%, 95%, 93%, 92%, 91%, 90%, 89%, 88%, 87%, 86%, or 85% sequence identity to SEQ ID NO:96. The mvaE nucleic acid encoded by the *Enterococcus gallinarum* EG2 mvaE gene can have at least about 99%, 98%, 97%, 96%, 95%, 95%, 93%, 92%, 91%, 90%, 89%, 88%, 87%, 86%, or 85% sequence identity to SEQ ID NO:97. The mvaE nucleic acid encoded by the *Enterococcus casseliflavus* mvaE gene can have at least about 99%, 98%, 97%, 96%, 95%, 95%, 93%, 92%, 91%, 90%, 89%, 88%, 87%, 86%, or 85% sequence identity to SEQ ID NO:98. The mvaE nucleic acid encoded by the *Enterococcus faecalis* mvaE gene can have at least about 99%, 98%, 97%, 96%, 95%, 95%, 93%, 92%, 91%, 90%, 89%, 88%, 87%, 86%, or 85% sequence identity to the mvaE gene previously disclosed in *E. coli* to produce mevalonate (see US 2005/0287655 A1; Tabata, K. and Hashimoto, S.-I. Biotechnology Letters 26: 1487-1491, 2004).

The mvaE nucleic acid can be expressed in a recombinant cell on a multicopy plasmid. The plasmid can be a high copy plasmid, a low copy plasmid, or a medium copy plasmid. Alternatively, the mvaE nucleic acid can be integrated into the host cell's chromosome. For both heterologous expression of an mvaE nucleic acid on a plasmid or as an integrated part of the host cell's chromosome, expression of the nucleic acid can be driven by either an inducible promoter or a constitutively expressing promoter. The promoter can be a strong driver of expression, it can be a weak driver of expression, or it can be a medium driver of expression of the mvaE nucleic acid.

Exemplary mvaS Polypeptides and Nucleic Acids

The mvaS gene encodes a polypeptide that possesses HMG-CoA synthase activity. This polypeptide can convert acetoacetyl CoA to 3-hydroxy-3-methylglutaryl-CoA (HMG-CoA). Exemplary mvaS polypeptides and nucleic acids include naturally-occurring polypeptides and nucleic acids from any of the source organisms described herein as well as mutant polypeptides and nucleic acids derived from any of the source organisms described herein that have at least one activity of a mvaS polypeptide.

Mutant mvaS polypeptides include those in which one or more amino acid residues have undergone an amino acid substitution while retaining mvaS polypeptide activity (i.e., the ability to convert acetoacetyl CoA to 3-hydroxy-3-methylglutaryl-CoA) Amino acid substitutions in the mvaS polypeptide can be introduced to improve the functionality of the molecule. For example, amino acid substitutions that increase the binding affinity of the mvaS polypeptide for its substrate, or that improve its ability to convert acetoacetyl CoA to 3-hydroxy-3-methylglutaryl-CoA can be introduced into the mvaS polypeptide. In some aspects, the mutant mvaS polypeptides contain one or more conservative amino acid substitutions.

Standard methods, such as those described in Quant et al. (*Biochem J.,* 1989, 262:159-164), can be used to determine whether a polypeptide has mvaS activity, by measuring HMG-CoA synthase activity. In an exemplary assay, HMG-CoA synthase activity can be assayed by spectrophotometrically measuring the disappearance of the enol form of acetoacetyl-CoA by monitoring the change of absorbance at 303 nm. A standard 1 ml assay system containing 50 mm-Tris/HCl, pH 8.0, 10 mM-MgCl2 and 0.2 mM-dithiothreitol at 30° C.; 5 mM-acetyl phosphate, 10,M-acetoacetyl-CoA and 5 µl samples of extracts can be added, followed by simultaneous addition of acetyl-CoA (100 µM) and 10 units of PTA. HMG-CoA synthase activity is then measured as the difference in the rate before and after acetyl-CoA addition. The absorption coefficient of acetoacetyl-CoA under the conditions used (pH 8.0, 10 mM-MgCl$_2$), is 12.2×10$^3$ M$^{-1}$ cm$^{-1}$. By definition, 1 unit of enzyme activity causes 1 µmol of acetoacetyl-CoA to be transformed per minute.

Alternatively, production of mevalonate in recombinant cells can be measured by, without limitation, gas chromatography (see U.S. Patent Application Publication No.: US 2005/0287655 A1) or HPLC (See U.S. Patent Application Publication No.: 2011/0159557 A1). As an exemplary assay, cultures can be inoculated in shake tubes containing LB broth supplemented with one or more antibiotics and incubated for 14 h at 34° C. at 250 rpm. Next, cultures can be diluted into well plates containing TM3 media supplemented with 1% Glucose, 0.1% yeast extract, and 200 µM IPTG to final OD of 0.2. The plate are then sealed with a Breath Easier membrane (Diversified Biotech) and incubated at 34° C. in a shaker/incubator at 600 rpm for 24 hours. 1 mL of each culture is then centrifuged at 3,000×g for 5 min Supernatant is then added to 20% sulfuric acid and incubated on ice for 5 min. The mixture is then centrifuged for 5 min at 3000×g and the supernatant was collected for HPLC analysis. The concentration of mevalonate in samples is determined by comparison to a standard curve of mevalonate (Sigma). The glucose concentration can additionally be measured by performing a glucose oxidase assay according to any method known in the art. Using HPLC, levels of mevalonate can be quantified by comparing the refractive index response of each sample versus a calibration curve generated by running various mevalonate containing solutions of known concentration.

Exemplary mvaS nucleic acids include nucleic acids that encode a polypeptide, fragment of a polypeptide, peptide, or fusion polypeptide that has at least one activity of a mvaS polypeptide. Exemplary mvaS polypeptides and nucleic acids include naturally-occurring polypeptides and nucleic acids from any of the source organisms described herein as well as mutant polypeptides and nucleic acids derived from any of the source organisms described herein. Exemplary mvaS nucleic acids include, for example, mvaS nucleic acids isolated from *Listeria grayi* DSM 20601, *Enterococcus faecium, Enterococcus gallinarum* EG2, *Enterococcus faecalis*, and/or *Enterococcus casseliflavus*. The mvaS nucleic acid encoded by the *Listeria* grayi_DSM 20601 mvaS gene can have at least about 99%, 98%, 97%, 96%, 95%, 95%, 93%, 92%, 91%, 90%, 89%, 88%, 87%, 86%, or 85% sequence identity to SEQ ID NO:99. The mvaS nucleic acid encoded by the *Enterococcus faecium* mvaS gene can have at least about 99%, 98%, 97%, 96%, 95%, 95%, 93%, 92%, 91%, 90%, 89%, 88%, 87%, 86%, or 85% sequence identity to SEQ ID NO:100. The mvaS nucleic acid encoded by the *Enterococcus gallinarum* EG2 mvaS gene can have at least about 99%, 98%, 97%, 96%, 95%, 95%, 93%, 92%, 91%, 90%, 89%, 88%, 87%, 86%, or 85% sequence identity to SEQ ID NO:101. The mvaS nucleic acid encoded by the *Enterococcus casseliflavus* mvaS gene can have at least about 99%, 98%, 97%, 96%, 95%, 95%, 93%, 92%, 91%, 90%, 89%, 88%, 87%, 86%, or 85% sequence identity to SEQ ID NO:102. The mvaS nucleic acid encoded by the *Enterococcus faecalis* mvaS gene can have at least about 99%, 98%, 97%, 96%, 95%, 95%, 93%, 92%, 91%, 90%, 89%, 88%, 87%, 86%, or 85% sequence identity to the mvaE gene previously disclosed in *E. coli* to produce mevalonate (see US 2005/0287655 A1; Tabata, K. and Hashimoto, S.-I. Biotechnology Letters 26: 1487-1491, 2004).

The mvaS nucleic acid can be expressed in a recombinant cell on a multicopy plasmid. The plasmid can be a high copy plasmid, a low copy plasmid, or a medium copy plasmid. Alternatively, the mvaS nucleic acid can be integrated into the host cell's chromosome. For both heterologous expression of an mvaS nucleic acid on a plasmid or as an integrated part of the host cell's chromosome, expression of the nucleic acid can be driven by either an inducible promoter or a constitutively expressing promoter. The promoter can be a strong driver of expression, it can be a weak driver of expression, or it can be a medium driver of expression of the mvaS nucleic acid.

Acetoacetyl-CoA Synthase Gene

The acetoacetyl-CoA synthase gene (aka nphT7) is a gene encoding an enzyme having the activity of synthesizing acetoacetyl-CoA from malonyl-CoA and acetyl-CoA and having minimal activity (e.g., no activity) of synthesizing acetoacetyl-CoA from two acetyl-CoA molecules. See, e.g., Okamura et al., PNAS Vol 107, No. 25, pp. 11265-11270 (2010), the contents of which are expressly incorporated herein for teaching about nphT7. An acetoacetyl-CoA synthase gene from an actinomycete of the genus Streptomyces CL190 strain was described in JP Patent Publication (Kokai) No. 2008-61506 A and US2010/0285549. Acetoacetyl-CoA synthase can also be referred to as acetyl CoA:malonyl CoA acyltransferase. A representative acetoacetyl-CoA synthase (or acetyl CoA:malonyl CoA acyltransferase) that can be used is Genbank AB540131.1.

In any of the aspects or embodiments described herein, an enzyme that has the ability to synthesize acetoacetyl-CoA from malonyl-CoA and acetyl-CoA can be used. Non-limiting examples of such an enzyme are described herein. In certain embodiments described herein, an acetoacetyl-CoA synthase gene derived from an actinomycete of the genus Streptomyces having the activity of synthesizing acetoacetyl-CoA from malonyl-CoA and acetyl-CoA can be used. An example of such an acetoacetyl-CoA synthase gene is the gene encoding a protein having the amino Such a protein having the amino acid sequence of SEQ ID NO:103 corresponds to an acetoacetyl-CoA synthase having activity of synthesizing acetoacetyl-CoA from malonyl-CoA and acetyl-CoA and having no activity of synthesizing acetoacetyl-CoA from two acetyl-CoA molecules.

In one embodiment, the gene encoding a protein having the amino acid sequence of SEQ ID NO:103 can be obtained by a nucleic acid amplification method (e.g., PCR) with the use of genomic DNA obtained from an actinomycete of the Streptomyces sp. CL190 strain as a template and a pair of primers that can be designed with reference to JP Patent Publication (Kokai) No. 2008-61506 A.

As described herein, an acetoacetyl-CoA synthase gene for use in the present invention is not limited to a gene encoding a protein having the amino acid sequence of SEQ ID NO:103 from an actinomycete of the Streptomyces sp. CL190 strain. Any gene encoding a protein having the ability to synthesize acetoacetyl-CoA from malonyl-CoA and acetyl-CoA and which does not synthesize acetoacetyl-CoA from two acetyl-CoA molecules can be used in the presently described methods. In certain embodiments, the acetoacetyl-CoA synthase gene can be a gene encoding a protein having an amino acid sequence with high similarity or substantially identical to the amino acid sequence of SEQ ID NO:103 and having the function of synthesizing acetoacetyl-CoA from malonyl-CoA and acetyl-CoA. The expression "highly similar" or "substantially identical" refers to, for example, at least about 80% identity, at least about 85%, at least about 90%, at least about 91%, at least about 92%, at least about 93%, at least about 94%, at least about 95%, at least about 96%, at least about 97%, at least about 98%, and at least about 99% identity. As used above, the identity value corresponds to the percentage of identity between amino acid residues in a different amino acid sequence and the amino acid sequence of SEQ ID NO:103, which is calculated by performing alignment of the amino acid sequence of SEQ ID NO:103 and the different amino acid sequence with the use of a program for searching for a sequence similarity.

In other embodiments, the acetoacetyl-CoA synthase gene may be a gene encoding a protein having an amino acid sequence derived from the amino acid sequence of SEQ ID NO:103 by substitution, deletion, addition, or insertion of 1 or more amino acid(s) and having the function of synthesizing acetoacetyl-CoA from malonyl-CoA and acetyl-CoA. Herein, the expression "more amino acids" refers to, for example, 2 to 30 amino acids, preferably 2 to 20 amino acids, more preferably 2 to 10 amino acids, and most preferably 2 to 5 amino acids.

In still other embodiments, the acetoacetyl-CoA synthase gene may consist of a polynucleotide capable of hybridizing to a portion or the entirety of a polynucleotide having a nucleotide sequence complementary to the nucleotide sequence encoding the amino acid sequence of SEQ ID NO:103 under stringent conditions and capable of encoding a protein having the function of synthesizing acetoacetyl-CoA from malonyl-CoA and acetyl-CoA. Herein, hybridization under stringent conditions corresponds to maintenance of binding under conditions of washing at 60° C. two times SSC. Hybridization can be carried out by conventionally known methods such as the method described in J. Sambrook et al. Molecular Cloning, A Laboratory Manual, 3rd Ed., Cold Spring Harbor Laboratory (2001).

As described herein, a gene encoding an acetoacetyl-CoA synthase having an amino acid sequence that differs from the amino acid sequence of SEQ ID NO:103 can be isolated from potentially any organism, for example, an actinomycete that is not obtained from the Streptomyces sp. CL190 strain. In addition, acetoacetyl-CoA synthase genes for use herein can be obtained by modifying a polynucleotide encoding the amino acid sequence of SEQ ID NO:103 by a method known in the art. Mutagenesis of a nucleotide sequence can be carried out by a known method such as the Kunkel method or the gapped duplex method or by a method similar to either thereof. For instance, mutagenesis may be carried out with the use of a mutagenesis kit (e.g., product names; Mutant-K and Mutant-G (TAKARA Bio)) for site-specific mutagenesis, product name; an LA PCR in vitro Mutagenesis series kit (TAKARA Bio), and the like.

The activity of an acetoacetyl-CoA synthase having an amino acid sequence that differs from the amino acid sequence of SEQ ID NO:103 can be evaluated as described below. Specifically, a gene encoding a protein to be evaluated is first introduced into a host cell such that the gene can be expressed therein, followed by purification of the protein by a technique such as chromatography. Malonyl-CoA and acetyl-CoA are added as substrates to a buffer containing the obtained protein to be evaluated, followed by, for example, incubation at a desired temperature (e.g., 10° C. to 60° C.). After the completion of reaction, the amount of substrate lost and/or the amount of product (acetoacetyl-CoA) produced are determined. Thus, it is possible to evaluate whether or not the protein being tested has the function of synthesizing acetoacetyl-CoA from malonyl-CoA and acetyl-CoA and to evaluate the degree of synthesis. In such case, it is possible to examine whether or not the protein has the activity of synthesizing acetoacetyl-CoA from two acetyl-CoA molecules by adding acetyl-CoA alone as a substrate to a buffer containing the obtained protein to be evaluated and determining the amount of substrate lost and/or the amount of product produced in a similar manner.

Recombinant Cells Capable of Increased Production of Mevalonate

The recombinant cells (e.g., recombinant bacterial cells) described herein can produce mevalonate at an amount and/or concentration greater than that of the same cells without any manipulation to the various enzymatic pathways described herein. Thus, the recombinant cells (e.g., bacterial cells) that have been engineered for modulation in the various pathways described herein are useful in the enhance production of mevalonate.

Accordingly, in certain aspects, the invention provides recombinant cells capable of enhanced production of mevalonate, wherein the cells comprise one or more heterologous nucleic acids encoding a polypeptide having phosphoketolase activity and one or more nucleic acids encoding one or more polypeptides of the upper MVA pathway, wherein the cells produce increased amounts of mevalonate compared to cells that do not comprise the one or more heterologous nucleic acids encoding a polypeptide having phosphoketolase activity.

In certain aspects, the recombinant cells described herein comprise one or more copies of a heterologous nucleic acid encoding a phosphoketolase isolated from isolated from *Burkholderia phytofirmans*, *Lactobacillus buchneri*, *Bifidobacterium gallicum*, *Bifidobacterium dentium*, *Bifidobacterium bifidum*, and/or *Clostridium acetobutylicum*. In some embodiments, the recombinant cells comprise one or more copies of a heterologous nucleic acid encoding a phosphoketolase isolated from *Mycobacterium gilvum*, *Shewanella baltica*, *Lactobacillus rhamnosus*, *Lactobacillus crispatus*, *Bifidobacterium longum*, *Leuconostoc citreum*, *Bradyrhizobium* sp., *Enterococcus faecium*, *Brucella microti*, *Lactobacillus salivarius*, *Streptococcus agalactiae*, *Rhodococcus imtechensis*, *Burkholderia xenovorans*, *Mycobacterium intracellulare*, *Nitrosomonas* sp., *Schizosaccharomyces pombe*, *Leuconostoc mesenteroides*, *Streptomyces* sp., *Lactobacillus buchneri*, *Streptomyces ghanaensis*, *Cyanothece* sp., and/or *Neosartorya fischeri*. In another embodiment, the recombinant cells comprise one or more copies of a heterologous nucleic acid encoding a phosphoketolase isolated from *Enterococcus faecium*, *Listeria grayi*, *Enterococcus gallinarum*, *Enterococcus saccharolyticus*, *Enterococcus casseliflavus*, *Mycoplasma alligatoris*, *Carnobacterium* sp., *Melissococcus plutonius*, *Tetragenococcus halophilus*, and/or *Mycoplasma arthritidis*. In still another embodiment, the recombinant cells comprise one or more copies of a heterologous nucleic acid encoding a phosphoketolase isolated from *Streptococcus agalactiae*, *Mycoplasma agalactiae*, *Streptococcus gordonii*, *Kingella oxalis*, *Mycoplasma fermentans*, *Granulicatella adiacens*, *Mycoplasma hominis*, *Mycoplasma crocodyli*, *Mycobacterium bovis*, *Neisseria* sp., *Streptococcus* sp., *Eremococcus coleocola*, *Granulicatella elegans*, *Streptococcus parasanguinis*, *Aerococcus urinae*, *Kingella kingae*, *Streptococcus australis*, *Streptococcus criceti*, and/or *Mycoplasma columbinum*. In some embodiments, the recombinant cells comprise one or more copies of a heterologous nucleic acid encoding a phosphoketolase isolated from and organism listed in Table 1, Table 2 and/or FIGS. 3-24.

In one embodiment, the recombinant cells further comprise one or more copies of a heterologous nucleic acid encoding mvaE and mvaS polypeptides from *L. grayi*, *E. faecium*, *E. gallinarum*, *E. casseliflavus*, and/or *E. faecalis*. In another embodiment, the recombinant cells further comprise an acetoacetyl-CoA synthase and one or more nucleic acids encoding one or more polypeptides of the upper MVA pathway.

In one embodiment, the recombinant cells can be further engineered to increase the activity of one or more of the following genes selected from the group consisting of ribose-5-phosphate isomerase (rpiA and/or rpiB), D-ribulose-5-phosphate 3-epimerase (rpe), transketolase (tktA and/or tktB), transaldolase B (tal B), phosphate acetyltransferase (pta and/or eutD). In another embodiment, the recombinant cells can be further engineered to decrease the activity of one or more genes of the following genes including glucose-6-phosphate dehydrogenase (zwf), 6-phosphofructokinase-1 (pfkA and/or pfkB), fructose bisphosphate aldolase (fba, fbaA, fbaB, and/or fbaC), glyceraldehyde-3-phosphate dehydrogenase (gapA and/or gapB), acetate kinase (ackA), citrate synthase (gltA), EI (ptsf), EIICB$^{Glc}$ (ptsG), (crr), and/or HPr (ptsH).

In one aspect, the recombinant cells described herein can produce mevalonate at a higher volumetric productivity than that of the same cells lacking one or more copies of a heterologous nucleic acid encoding a polypeptide having phosphoketolase activity. In certain embodiments, the recombinant cell can produce greater than 2.00 g/L/hr of mevalonate. Alternatively, the recombinant cells can produce greater than about 1.0 g/L/hr, 1.2 g/L/hr, 1.4 g/L/hr, 1.6 g/L/hr, 1.8 g/L/hr, 2.0 g/L/hr, 2.2 g/L/hr, 2.4 g/L/hr, 2.6 g/L/hr, 2.8 g/L/hr, 3.0 g/L/hr, 3.2 g/L/hr, 3.4 g/L/hr, 3.6 g/L/hr, 3.8 g/L/hr, 4.0 g/L/hr. 4.2 g/L/hr, 4.4 g/L/hr, 4.6 g/L/hr, 4.8 g/L/hr, 5.0 g/L/hr, 5.2 g/L/hr, 5.4 g/L/hr, 5.6 g/L/hr, 5.8 g/L/hr, 6.0 g/L/hr of mevalonate, inclusive, as well as any numerical value in between these numbers.

In one aspect, the recombinant cells described herein can produce mevalonate at a higher titer than that of the same cells lacking one or more copies of a heterologous nucleic acid encoding a polypeptide having phosphoketolase activity. These recombinant cells can produce greater than about 100 g/L peak titer of mevalonate after 48 hours of fermentation. Alternatively, the recombinant cells can produce greater than about 50 g/L, 60 g/L, 70 g/L, 80 g/L, 90 g/L, 100 g/L, 110 g/L, 120 g/L, 130 g/L, 140 g/L, 150 g/L, 160 g/L, 170 g/L, 180 g/L, 190 g/L, 200 g/L, 210 g/L, 220 g/L, 230 g/L, 240 g/L, 250 g/L, 260 g/L, 270 g/L, 280 g/L, 290 g/L, 300 g/L peak titer of mevalonate after 48 hours of fermentation, inclusive, as well as any numerical value in between these numbers.

In other embodiments, the recombinant cells described herein further comprise one or more mutations which increase carbon flux towards the MVA pathway and can thus produce higher titers of mevalonate in comparison to cells which have not been similarly engineered. In such embodiments, the recombinant cells described herein produce mevalonate at a higher peak titer than that of the same cells lacking one or more copies of a heterologous nucleic acid encoding phosphoketolase polypeptide having phosphoketolase activity. In one embodiment, the recombinant cells can be further engineered to increase the activity of one or more of the following genes selected from the group consisting of ribose-5-phosphate isomerase (rpiA and/or rpiB), D-ribulose-5-phosphate 3-epimerase (rpe), transketolase (tktA and/or tktB), transaldolase B (tal B), phosphate acetyltransferase (pta and/or eutD). In another embodiment, the recombinant cells can be further engineered to decrease the activity of one or more genes of the following genes including glucose-6-phosphate dehydrogenase (zwf), 6-phosphofructokinase-1 (pfkA and/or pfkB), fructose bisphosphate aldolase (fba, fbaA, fbaB, and/or fbaC), glyceraldehyde-3-phosphate dehydrogenase (gapA and/or gapB), acetate kinase (ackA), citrate synthase (gltA), EI (ptsI), EIICB$^{Glc}$ (ptsG), EIIA$^{Glc}$ (err), and/or HPr (ptsH).

In one aspect, the recombinant cells described herein can produce mevalonate at a higher cell productivity index (CPI) for mevalonate than that of the same cells lacking one or more copies of a heterologous nucleic acid encoding a polypeptide having phosphoketolase activity. The recombinant cells can have a CPI for mevalonate of at least about 3.0 (g/g). Alternatively, the recombinant cells can have a CPI for mevalonate of at least about 1 (g/g), 2 (g/g), 3 (g/g), 4 (g/g), 5 (g/g), 6 (g/g), 7 (g/g), 8 (g/g), 9 (g/g), 10 (g/g), 11 (g/g), 12 (g/g), 13 (g/g), 14 (g/g), 15 (g/g), 20 (g/g), 25 (g/g), or 30 (g/g) inclusive, as well as any numerical value in between these numbers.

In certain embodiments, the recombinant cells described herein further comprise one or more mutations which increase carbon flux towards the MVA pathway which results in a higher cell productivity index (CPI) for mevalonate in comparison to cells which have not been similarly engineered. Additionally, the recombinant cells described herein have a higher CPI than that of the same cells lacking one or more copies of a heterologous nucleic acid encoding phosphoketolase polypeptide having phosphoketolase activity. In one embodiment, the recombinant cells can be further engineered to increase the activity of one or more of the following genes selected from the group consisting of ribose-5-phosphate isomerase (rpiA and/or rpiB), D-ribulose-5-phosphate 3-epimerase (rpe), transketolase (tktA and/or tktB), transaldolase B (tal B), phosphate acetyltransferase (pta and/or eutD). In another embodiment, these recombinant cells can be further engineered to decrease the activity of one or more genes of the following genes including glucose-6-phosphate dehydrogenase (zwf), 6-phosphofructokinase-1 (pfkA and/or pfkB), fructose bisphosphate aldolase (fba, fbaA, fbaB, and/or fbaC), glyceraldehyde-3-phosphate dehydrogenase (gapA and/or gapB), acetate kinase (ackA), citrate synthase (gltA), EI (ptsI), EIICB$^{Glc}$ (ptsG), EIIA$^{Glc}$ (err), and/or HPr (ptsH).

Additionally, the cells described herein have a higher mass yield of mevalonate from glucose than that of the same cells lacking one or more copies of a heterologous nucleic acid encoding phosphoketolase polypeptide having phosphoketolase activity. The recombinant cells can produce a mass yield of mevalonate from glucose of at least about 28%. Alternatively, the recombinant cells can produce a mass yield of mevalonate from glucose of at least about 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, or 55%, inclusive, as well as any numerical value in between these numbers.

In certain embodiments, the recombinant cells described herein further comprise one or more mutations which increase carbon flux towards the MVA pathway which results in a higher mass yield of mevalonate in comparison to cells which have not been similarly engineered. Additionally, the recombinant cells described herein have a higher mass yield of mevalonate than that of the same cells lacking one or more copies of a heterologous nucleic acid encoding phosphoketolase polypeptide having phosphoketolase activity. In one embodiment, the recombinant cells can be further engineered to increase the activity of one or more of the following genes selected from the group consisting of ribose-5-phosphate isomerase (rpiA and/or rpiB), D-ribulose-5-phosphate 3-epimerase (rpe), transketolase (tktA and/or tktB), transaldolase B (tal B), phosphate acetyltransferase (pta and/or eutD). In another embodiment, these recombinant cells can be further engineered to decrease the activity of one or more genes of the following genes including glucose-6-phosphate dehydrogenase (zwf), 6-phosphofructokinase-1 (pfkA and/or pfkB), fructose bisphosphate aldolase (fba, fbaA, fbaB, and/or fbaC), glyceraldehyde-3-phosphate dehydrogenase (gapA and/or gapB), acetate kinase (ackA), citrate synthase (gltA), EI (ptsI), EIICB$^{Glc}$ (ptsG), EIIA$^{Glc}$ (err), and/or HPr (ptsH).

In one aspect, the recombinant cells described herein produce mevalonate while accumulating less acetate in the fermentation broth as compared to the same cells lacking one or more copies of a heterologous nucleic acid encoding a polypeptide having phosphoketolase activity. The recombinant cells can produce increased levels of mevalonate while accumulating less than 4.5 g/L of acetate in the fermentation broth over a 48 hr fermentation. Alternatively, the recombinant cells can produce increased levels of mevalonate while accumulating less than about 8.0 g/L, 7.5 g/L, 7.0 g/L, 6.5 g/L, 6.0 g/L, 5.5 g/L, 5.0 g/L, 4.5 g/L, 4.0 g/L, 3.5 g/L, 3.0 g/L, 2.5 g/L, 2.0 g/L, or 1.5 g/L, of acetate in the fermentation broth over a 48 hr fermentation inclusive, as well as any numerical value in between these numbers. In certain embodiments, the decreased accumulation of acetate in the fermentation broth can improve cell viability during the fermentation run.

In certain embodiments, the recombinant cells described herein further comprise one or more mutations which increase carbon flux towards the MVA pathway which results increased levels of mevalonate while accumulating less acetate in the fermentation broth in comparison to cells which have not been similarly engineered. In certain embodiments, the decreased accumulation of acetate in the fermentation broth can improve cell viability during the fermentation run.

Also provided herein are mevalonate-producing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:8 and (ii) one or more nucleic acids encoding one or more polypeptides of the upper MVA pathway, wherein said recombinant cell comprising said polypeptide having phosphoketolase activity of (i) has a Performance Index value of greater than 1.0 in one or more of the following parameters: (a) cell growth on glucose, (b) cell growth on xylose, (c) production of intracellular acetyl-phosphate or (d) cell growth on glucose-6-phosphate. In some embodiments, the polypeptide comprises at least 90% sequence identity to SEQ ID NO:23. In some embodiments, the polypeptide comprises at least 90% sequence identity to SEQ ID NO:24. In some embodiments, the polypeptide comprises at least 90% sequence identity to SEQ ID NO:25. In some embodiments, the polypeptide comprises at least 90% sequence identity to SEQ ID NO:26. In some embodiments, the polypeptide comprises at least 90% sequence identity to SEQ ID NO:27. In some embodiments, the polypeptide comprises at least 90% sequence identity to SEQ ID NO:28. In some embodiments, the polypeptide comprises at least 90% sequence identity to SEQ ID NO:29. In some embodiments, the polypeptide comprises at least 90% sequence identity to SEQ ID NO:30. In some embodiments, the polypeptide comprises at least 90% sequence identity to SEQ ID NO:31. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Additionally provided herein are mevalonate-producing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:8 and (ii) one or more nucleic acids encoding one or more polypeptides of the upper MVA pathway, wherein said polypeptide having phosphoketolase activity of (i) has a Performance Index value of greater than 1.0 in one or more of the following parameters: (a) protein solubility, (b) protein expression, or (c) fructose-6-phosphate (F6P) Specific Activity. In some embodiments, the polypeptide comprises at least 90% sequence identity to SEQ ID NO:23. In some embodiments, the polypeptide comprises at least 90% sequence identity to SEQ ID NO:24. In some embodiments, the polypeptide comprises at least 90% sequence identity to SEQ ID NO:25. In some embodiments, the polypeptide comprises at least 90% sequence identity to SEQ ID NO:26. In some embodiments, the polypeptide comprises at least 90% sequence identity to SEQ ID NO:27. In some embodiments, the polypeptide comprises at least 90% sequence identity to SEQ ID NO:28. In some embodiments, the polypeptide comprises at least 90% sequence identity to SEQ ID NO:29. In some embodiments, the polypeptide comprises at least 90% sequence identity to SEQ ID NO:30. In some embodiments, the polypeptide comprises at least 90% sequence identity to SEQ ID NO:31. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Further provided herein are mevalonate-producing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:11 and (ii) one or more nucleic acids encoding one or more polypeptides of the upper MVA pathway, wherein said recombinant cell comprising said polypeptide having phosphoketolase activity of (i) has a Performance Index value of greater than 1.0 in one or more of the following parameters: (a) cell growth on glucose, (b) cell growth on xylose, (c) production of intracellular acetyl-phosphate or (d) cell growth on glucose-6-phosphate. In some embodiments, the polypeptide comprises at least 90% sequence identity to SEQ ID NO:32. In some embodiments, the polypeptide comprises at least 90% sequence identity to SEQ ID NO:33. In some embodiments, the polypeptide comprises at least 90% sequence identity to SEQ ID NO:34. In some embodiments, the polypeptide comprises at least 90% sequence identity to SEQ ID NO:35. In some embodiments, the polypeptide comprises at least 90% sequence identity to SEQ ID NO:36. In some embodiments, the polypeptide comprises at least 90% sequence identity to SEQ ID NO:37. In some embodiments, the polypeptide comprises at least 90% sequence identity to SEQ ID NO:38. In some embodiments, the polypeptide comprises at least 90% sequence identity to SEQ ID NO:39. In some embodiments, the polypeptide comprises at least 90% sequence identity to SEQ ID NO:40. In some embodiments, the polypeptide comprises at least 90% sequence identity to SEQ ID NO:41. In some embodiments, the polypeptide comprises at least 90% sequence identity to SEQ ID NO:42. In some embodiments, the polypeptide comprises at least 90% sequence identity to SEQ ID NO:43. In some embodiments, the polypeptide comprises at least 90% sequence identity to SEQ ID NO:44. In some embodiments, the polypeptide comprises at least 90% sequence identity to SEQ ID NO:45. In some embodiments, the polypeptide comprises at least 90% sequence identity to SEQ ID NO:46. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from E. gallinarum). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from E. gallinarum. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Provided herein are mevalonate-producing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:11 and (ii) one or more nucleic acids encoding one or more polypeptides of the upper MVA pathway, wherein said polypeptide having phosphoketolase activity of (i) has a Performance Index value of greater than 1.0 in one or more of the following parameters: (a) protein solubility, (b) protein expression, or (c) fructose-6-phosphate (F6P) Specific Activity. In some embodiments, the polypeptide comprises at least 90% sequence identity to SEQ ID NO:32. In some embodiments, the polypeptide comprises at least 90% sequence identity to SEQ ID NO:33. In some embodiments, the polypeptide comprises at least 90% sequence identity to SEQ ID NO:34. In some embodiments, the polypeptide comprises at least 90% sequence identity to SEQ ID NO:35. In some embodiments, the polypeptide comprises at least 90% sequence identity to SEQ ID NO:36. In some embodiments, the polypeptide comprises at least 90% sequence identity to SEQ ID NO:37. In some embodiments, the polypeptide comprises at least 90% sequence identity to SEQ ID NO:38. In some embodiments, the polypeptide comprises at least 90% sequence identity to SEQ ID NO:39. In some embodiments, the polypeptide comprises at least 90% sequence identity to SEQ ID NO:40. In some embodiments, the polypeptide comprises at least 90% sequence identity to SEQ ID NO:41. In some embodiments, the polypeptide comprises at least 90% sequence identity to SEQ ID NO:42. In some embodiments, the polypeptide comprises at least 90% sequence identity to SEQ ID NO:43. In some embodiments, the polypeptide comprises at least 90% sequence identity to SEQ ID NO:44. In some embodiments, the polypeptide comprises at least 90% sequence identity to SEQ ID NO:45. In some embodiments, the polypeptide comprises at least 90% sequence identity to SEQ ID NO:46. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from E. gallinarum). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from E. gallinarum. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Methods of Using Recombinant Cells to Produce Increased Amounts of Mevalonate

Also provided herein are methods for the production of mevalonate. In some aspects, the method for producing mevalonate comprises: (a) culturing a composition comprising recombinant cells which have been engineered to increase carbon flux through the phosphoketolase pathway as described herein (including any of the recombinant cells described above), or progeny thereof, capable of producing mevalonate; and (b) producing mevalonate. In some aspects, the method of producing mevalonate comprises the steps of culturing any of the recombinant cells described herein under conditions suitable for the production of mevalonate and allowing the recombinant cells to produce mevalonate. In some aspects, the method of producing mevalonate further comprises a step of recovering the mevalonate.

As described herein, the methods of producing mevalonate comprise the steps of: (a) culturing recombinant cells (including, but not limited to, *E. coli* cells) that do not endogenously express a phosphoketolase polypeptide, wherein the cells heterologously express one or more copies of a gene encoding a phosphoketolase polypeptide along with one or more heterologous nucleic acids expressing one or more MVA pathway peptides; and (b) producing mevalonate. In certain embodiments, the recombinant cells comprise one or more copies of a heterologous nucleic acid encoding a phosphoketolase isolated from *Burkholderia phytofirmans*, *Lactobacillus buchneri*, *Bifidobacterium gallicum*, *Bifidobacterium dentium*, *Bifidobacterium bifidum*, and/or *Clostridium acetobutylicum*. In some embodiments, the recombinant cells comprise one or more copies of a heterologous nucleic acid encoding a phosphoketolase isolated from *Mycobacterium gilvum*, *Shewanella baltica*, *Lactobacillus rhamnosus*, *Lactobacillus crispatus*, *Bifidobacterium longum*, *Leuconostoc citreum*, *Bradyrhizobium* sp., *Enterococcus faecium*, *Brucella microti*, *Lactobacillus salivarius*, *Streptococcus agalactiae*, *Rhodococcus imtechensis*, *Burkholderia xenovorans*, *Mycobacterium intracellulare*, *Nitrosomonas* sp., *Schizosaccharomyces pombe*, *Leuconostoc mesenteroides*, *Streptomyces* sp., *Lactobacillus buchneri*, *Streptomyces ghanaensis*, *Cyanothece* sp., and/or *Neosartorya fischeri*. In some embodiments, the recombinant cells comprise one or more copies of a heterologous nucleic acid encoding a phosphoketolase isolated from *Enterococcus faecium*, *Listeria grayi*, *Enterococcus gallinarum*, *Enterococcus saccharolyticus*, *Enterococcus casseliflavus*, *Mycoplasma alligatoris*, *Carnobacterium* sp., *Melissococcus plutonius*, *Tetragenococcus halophilus*, and/or *Mycoplasma arthritidis*. In some embodiments, the recombinant cells comprise one or more copies of a heterologous nucleic acid encoding a phosphoketolase isolated from *Streptococcus agalactiae*, *Mycoplasma agalactiae*, *Streptococcus gordonii*, *Kingella oralis*, *Mycoplasma fermentans*, *Granulicatella adiacens*, *Mycoplasma hominis*, *Mycoplasma crocodyli*, *Mycobacterium bovis*, *Neisseria* sp., *Streptococcus* sp., *Eremococcus coleocola*, *Granulicatella elegans*, *Streptococcus parasanguinis*, *Aerococcus urinae*, *Kingella kingae*, *Streptococcus australis*, *Streptococcus criceti*, and/or *Mycoplasma columbinum*. In some embodiments, the recombinant cells comprise one or more copies of a heterologous nucleic acid encoding a phosphoketolase isolated from and organism listed in Table 1, Table 2 and/or FIGS. 3-24. Additionally, the recombinant cells can produce mevalonate in concentrations greater than that of the same cells lacking one or more heterologous copies of a gene encoding an phosphoketolase polypeptide from *Burkholderia phytofirmans*, *Lactobacillus buchneri*, *Bifidobacterium gallicum*, *Bifidobacterium dentium*, *Bifidobacterium bifidum*, *Clostridium acetobutylicum*, *Mycobacterium gilvum*, *Shewanella baltica*, *Lactobacillus rhamnosus*, *Lactobacillus crispatus*, *Bifidobacterium longum*, *Leuconostoc citreum*, *Bradyrhizobium* sp., *Enterococcus faecium*, *Brucella microti*, *Lactobacillus salivarius*, *Streptococcus agalactiae*, *Rhodococcus imtechensis*, *Burkholderia xenovorans*, *Mycobacterium intracellulare*, *Nitrosomonas* sp., *Schizosaccharomyces pombe*, *Leuconostoc mesenteroides*, *Streptomyces* sp., *Lactobacillus buchneri*, *Streptomyces ghanaensis*, *Cyanothece* sp., *Neosartorya fischeri*, *Enterococcus faecium*, *Listeria grayi*, *Enterococcus gallinarum*, *Enterococcus saccharolyticus*, *Enterococcus casseliflavus*, *Mycoplasma alligatoris*, *Carnobacterium* sp., *Melissococcus plutonius*, *Tetragenococcus halophilus*, *Mycoplasma arthritidis*, *Streptococcus agalactiae*, *Mycoplasma agalactiae*, *Streptococcus gordonii*, *Kingella oralis*, *Mycoplasma fermentans*, *Granulicatella adiacens*, *Mycoplasma hominis*, *Mycoplasma crocodyli*, *Mycobacterium bovis*, *Neisseria* sp., *Streptococcus* sp., *Eremococcus coleocola*, *Granulicatella elegans*, *Streptococcus parasanguinis*, *Aerococcus urinae*, *Kingella kingae*, *Streptococcus australis*, *Streptococcus criceti*, and/or *Mycoplasma columbinum* along with one or more heterologous nucleic acids expressing one or more MVA pathway peptides, when the cells are cultured in minimal medium. In certain embodiments, the one or more copies of a heterologous nucleic acid encoding an phosphoketolase polypeptide from *Burkholderia phytofirmans*, *Lactobacillus buchneri*, *Bifidobacterium gallicum*, *Bifidobacterium dentium*, *Bifidobacterium bifidum*, *Clostridium acetobutylicum*, *Mycobacterium gilvum*, *Shewanella baltica*, *Lactobacillus rhamnosus*, *Lactobacillus crispatus*, *Bifidobacterium longum*, *Leuconostoc citreum*, *Bradyrhizobium* sp., *Enterococcus faecium*, *Brucella microti*, *Lactobacillus salivarius*, *Streptococcus agalactiae*, *Rhodococcus imtechensis*, *Burkholderia xenovorans*, *Mycobacterium intracellulare*, *Nitrosomonas* sp., *Schizosaccharomyces pombe*, *Leuconostoc mesenteroides*, *Streptomyces* sp., *Lactobacillus buchneri*, *Streptomyces ghanaensis*, *Cyanothece* sp., *Neosartorya fischeri*, *Enterococcus faecium*, *Listeria grayi*, *Enterococcus gallinarum*, *Enterococcus saccharolyticus*, *Enterococcus casseliflavus*, *Mycoplasma alligatoris*, *Carnobacterium* sp., *Melissococcus plutonius*, *Tetragenococcus halophilus*, *Mycoplasma arthritidis*, *Streptococcus agalactiae*, *Mycoplasma agalactiae*, *Streptococcus gordonii*, *Kingella oxalis*, *Mycoplasma fermentans*, *Granulicatella adiacens*, *Mycoplasma hominis*, *Mycoplasma crocodyli*, *Mycobacterium bovis*, *Neisseria* sp., *Streptococcus* sp., *Eremococcus coleocola*, *Granulicatella elegans*, *Streptococcus parasanguinis*, *Aerococcus urinae*, *Kingella kingae*, *Streptococcus australis*, *Streptococcus criceti*, and/or *Mycoplasma columbinum* is a heterologous nucleic acid that is integrated into the host cell's chromosome.

The instant methods for the production of mevalonate produce can produce mevalonate using cells having a volumetric productivity of greater than 2.00 g/L/hr of mevalonate. Alternatively, the recombinant cells can produce greater than about 1.0 g/L/hr, 1.2 g/L/hr, 1.4 g/L/hr, 1.6 g/L/hr, 1.8 g/L/hr, 2.0 g/L/hr, 2.2 g/L/hr, 2.4 g/L/hr, 2.6 g/L/hr, 2.8 g/L/hr, 3.0 g/L/hr, 3.2 g/L/hr, 3.4 g/L/hr, 3.6 g/L/hr, 3.8 g/L/hr, 4.0 g/L/hr, 4.2 g/L/hr, 4.4 g/L/hr, 4.6 g/L/hr, 4.8 g/L/hr, 5.0 g/L/hr, 5.2 g/L/hr, 5.4 g/L/hr, 5.6 g/L/hr, 5.8 g/L/hr, 6.0 g/L/hr of mevalonate, inclusive, as well as any numerical value in between these numbers. In some aspects, the method of producing mevalonate further comprises a step of recovering the mevalonate.

In other embodiments, the methods of producing mevalonate can comprise the steps of: (a) culturing recombinant cells (including, but not limited to, *E. coli* cells) that do not endogenously express a phosphoketolase polypeptide, wherein the cells heterologously express one or more copies of a gene encoding a phosphoketolase polypeptide along with one or more heterologous nucleic acids expressing one or more MVA pathway peptides; and (b) producing mevalonate, wherein the recombinant cells produce mevalonate with a higher peak titer after 48 hours of fermentation than that of the same cells lacking one or more heterologous copies of a gene encoding an phosphoketolase polypeptide. In certain embodiments, the recombinant cells comprise one or more copies of a heterologous nucleic acid encoding a phosphoketolase isolated from *Burkholderia phytofirmans, Lactobacillus buchneri, Bifidobacterium gallicum, Bifidobacterium dentium, Bifidobacterium bifidum*, and/or *Clostridium acetobutylicum*. In some embodiments, the recombinant cells comprise one or more copies of a heterologous nucleic acid encoding a phosphoketolase isolated from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In some embodiments, the recombinant cells comprise one or more copies of a heterologous nucleic acid encoding a phosphoketolase isolated from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus*, and/or *Mycoplasma arthritidis*. In some embodiments, the recombinant cells comprise one or more copies of a heterologous nucleic acid encoding a phosphoketolase isolated from *Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma* columbinum. In some embodiments, the recombinant cells comprise one or more copies of a heterologous nucleic acid encoding a phosphoketolase isolated from an organism listed in Table 1, Table 2 and/or FIGS. 3-24.

The instant methods for the production of mevalonate can produce mevalonate using cells that can produce a peak titer of greater than about 100 g/L peak titer of mevalonate after 48 hours of fermentation. Alternatively, the recombinant cells can produce greater than about 50 g/L, 60 g/L, 70 g/L, 80 g/L, 90 g/L, 100 g/L, 110 g/L, 120 g/L, 130 g/L, 140 g/L, 150 g/L, 160 g/L, 170 g/L, 180 g/L, 190 g/L, 200 g/L, 210 g/L, 220 g/L, 230 g/L, 240 g/L, 250 g/L, 260 g/L, 270 g/L, 280 g/L, 290 g/L, 300 g/L peak titer of mevalonate after 48 hours of fermentation, inclusive, as well as any numerical value in between these numbers. In some aspects, the method of producing mevalonate further comprises a step of recovering the mevalonate.

In other embodiments, the methods of producing mevalonate can comprise the steps of: (a) culturing recombinant cells (including, but not limited to, *E. coli* cells) that do not endogenously express a phosphoketolase polypeptide, wherein the cells heterologously express one or more copies of a gene encoding a phosphoketolase polypeptide along with one or more heterologous nucleic acids expressing one or more MVA pathway peptides; and (b) producing mevalonate, wherein the recombinant cells have a CPI for mevalonate higher than that of the same cells lacking one or more heterologous copies of a gene encoding an phosphoketolase polypeptide. In certain embodiments, the recombinant cells comprise one or more copies of a heterologous nucleic acid encoding a phosphoketolase isolated from *Burkholderia phytofirmans, Lactobacillus buchneri, Bifidobacterium gallicum, Bifidobacterium dentium, Bifidobacterium bifidum*, and/or *Clostridium acetobutylicum*. In some embodiments, the recombinant cells comprise one or more copies of a heterologous nucleic acid encoding a phosphoketolase isolated from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In some embodiments, the recombinant cells comprise one or more copies of a heterologous nucleic acid encoding a phosphoketolase isolated from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus*, and/or *Mycoplasma arthritidis*. In some embodiments, the recombinant cells comprise one or more copies of a heterologous nucleic acid encoding a phosphoketolase isolated from *Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*. In some embodiments, the recombinant cells comprise one or more copies of a heterologous nucleic acid encoding a phosphoketolase isolated from an organism listed in Table 1, Table 2 and/or FIGS. 3-24.

The instant methods for the production of mevalonate can produce mevalonate using cells with a CPI for mevalonate of at least about 3.0 (g/g). Alternatively, the recombinant cells can have a CPI for mevalonate of at least about 1 (g/g), 2 (g/g), 3 (g/g), 4 (g/g), 5 (g/g), 6 (g/g), 7 (g/g), 8 (g/g), 9 (g/g), 10 (g/g), 11 (g/g), 12 (g/g), 13 (g/g), 14 (g/g), 15 (g/g), 20 (g/g), 25 (g/g), or 30 (g/g) inclusive, as well as any numerical value in between these numbers. In some aspects, the method of producing mevalonate further comprises a step of recovering the mevalonate.

In certain embodiments, the methods of producing mevalonate can comprise the steps of: (a) culturing recombinant cells (including, but not limited to, *E. coli* cells) that do not endogenously express a phosphoketolase polypeptide, wherein the cells heterologously express one or more copies of a gene encoding a phosphoketolase polypeptide along with one or more heterologous nucleic acids expressing one or more MVA pathway peptides; and (b) producing mevalonate, wherein the recombinant cells display decreased oxygen uptake rate (OUR) as compared to that of the same cells lacking one or more heterologous copies of a gene encoding an phosphoketolase polypeptide. In certain embodiments, the recombinant cells expressing one or more heterologous copies of a gene encoding an phosphoketolase polypeptide display up to 1-fold, 2-fold, 3-fold, 4-fold, 5-fold, 6-fold or 7-fold decrease in OUR as compared to recombinant cells that do not express a phosphoketolase.

Provided herein are methods of using any of the cells described above for enhanced mevalonate production. The production of mevalonate by the cells can be enhanced by the expression of one or more heterologous nucleic acids encoding a phosphoketolase polypeptide. In certain embodiments, the recombinant cells comprise one or more copies of a heterologous nucleic acid encoding a phosphoketolase isolated from *Burkholderia phytofirmans, Lactobacillus buchneri, Bifidobacterium gallicum, Bifidobacterium dentium, Bifidobacterium bifidum*, and/or *Clostridium acetobutylicum*. In some embodiments, the recombinant cells comprise one or more copies of a heterologous nucleic acid encoding a phosphoketolase isolated from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In some embodiments, the recombinant cells comprise one or more copies of a heterologous nucleic acid encoding a phosphoketolase isolated from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus*, and/or *Mycoplasma arthritidis*. In some embodiments, the recombinant cells comprise one or more copies of a heterologous nucleic acid encoding a phosphoketolase isolated from *Streptococcus agalactiae, Mycoplasma agalactiae, Streptococcus gordonii, Kingella oxalis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*. In some embodiments, the recombinant cells comprise one or more copies of a heterologous nucleic acid encoding a phosphoketolase isolated from an organism listed in Table 1, Table 2 and/or FIGS. 3-24.

The production of mevalonate can be enhanced by about 1,000,000 folds (e.g., about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of mevalonate by mevalonate-producing cells without the expression of one or more heterologous nucleic acids encoding a phosphoketolase polypeptide. In certain embodiments described herein, the host cells have been further engineered increased carbon flux to MVA production. In certain embodiments, the recombinant cells comprise one or more copies of a heterologous nucleic acid encoding a phosphoketolase isolated from *Burkholderia phytofirmans, Lactobacillus buchneri, Bifidobacterium gallicum, Bifidobacterium dentium, Bifidobacterium bifidum*, and/or *Clostridium acetobutylicum*. In some embodiments, the recombinant cells comprise one or more copies of a heterologous nucleic acid encoding a phosphoketolase isolated from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In some embodiments, the recombinant cells comprise one or more copies of a heterologous nucleic acid encoding a phosphoketolase isolated from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus*, and/or *Mycoplasma arthritidis*. In some embodiments, the recombinant cells comprise one or more copies of a heterologous nucleic acid encoding a phosphoketolase isolated from *Streptococcus agalactiae, Mycoplasma agalactiae, Streptococcus gordonii, Kingella oxalis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*. In some embodiments, the recombinant cells comprise one or more copies of a heterologous nucleic acid encoding a phosphoketolase isolated from an organism listed in Table 1, Table 2 and/or FIGS. 3-24.

In other aspects, the methods described herein can provide for the enhanced production of mevalonate can by at least about any of 5%, 10%, 20%, 30%, 40%, 50%, 60%, 70%, 80%, 90%, 1 fold, 2 folds, 5 folds, 10 folds, 20 folds, 50 folds, 100 folds, 200 folds, 500 folds, 1000 folds, 2000 folds, 5000 folds, 10,000 folds, 20,000 folds, 50,000 folds, 100,000 folds, 200,000 folds, 500,000 folds, or 1,000,000 folds compared to the production of mevalonate by mevalonate-producing cells without the expression of one or more heterologous nucleic acids encoding a phosphoketolase polypeptide. In certain embodiments described herein, the host cells have been further engineered increased carbon flux to MVA production.

In addition, more specific cell culture conditions can be used to culture the cells in the methods described herein. For example, in some aspects, the method for the production of mevalonate comprises the steps of (a) culturing recombinant cells (including, but not limited to, *E. coli* cells) that do not endogenously have a phosphoketolase gene in minimal medium at 34° C., wherein the recombinant cells heterologously express one or more copies of a heterologous gene encoding a phosphoketolase polypeptide on a low to medium copy plasmid and under the control of a strong promoter; and (b) producing mevalonate. In certain embodiments, the recombinant cells comprise one or more copies of a heterologous nucleic acid encoding a phosphoketolase isolated from *Burkholderia phytofirmans, Lactobacillus*

*buchneri, Bifidobacterium gallicum, Bifidobacterium dentium, Bifidobacterium bifidum*, and/or *Clostridium acetobutylicum*. In some embodiments, the recombinant cells comprise one or more copies of a heterologous nucleic acid encoding a phosphoketolase isolated from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In some embodiments, the recombinant cells comprise one or more copies of a heterologous nucleic acid encoding a phosphoketolase isolated from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus*, and/or *Mycoplasma arthritidis*. In some embodiments, the recombinant cells comprise one or more copies of a heterologous nucleic acid encoding a phosphoketolase isolated from *Streptococcus agalactiae, Mycoplasma agalactiae, Streptococcus gordonii, Kingella oxalis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*. In some embodiments, the recombinant cells comprise one or more copies of a heterologous nucleic acid encoding a phosphoketolase isolated from an organism listed in Table 1, Table 2 and/or FIGS. 3-24. In some aspects, the method of producing mevalonate further comprises a step of recovering the mevalonate.

Also provided herein are methods for producing mevalonate comprising culturing a recombinant cell capable of increased carbon flux through the phosphoketolase pathway, wherein the recombinant cell comprises: (i) a heterologous nucleic acid sequence encoding a polypeptide having phosphoketolase activity, wherein the polypeptide comprises at least 65% sequence identity to SEQ ID NO:8 and (ii) one or more nucleic acids encoding one or more polypeptides of the upper MVA pathway, wherein said recombinant cell comprising said polypeptide having phosphoketolase activity of (i) has a Performance Index value of greater than 1.0 in one or more of the following parameters: (a) cell growth on glucose, (b) cell growth on xylose, (c) production of intracellular acetyl-phosphate or (d) cell growth on glucose-6-phosphate and producing said mevalonate. In some embodiments, the polypeptide comprises at least 90% sequence identity to SEQ ID NO:23. In some embodiments, the polypeptide comprises at least 90% sequence identity to SEQ ID NO:24. In some embodiments, the polypeptide comprises at least 90% sequence identity to SEQ ID NO:25. In some embodiments, the polypeptide comprises at least 90% sequence identity to SEQ ID NO:26. In some embodiments, the polypeptide comprises at least 90% sequence identity to SEQ ID NO:27. In some embodiments, the polypeptide comprises at least 90% sequence identity to SEQ ID NO:28. In some embodiments, the polypeptide comprises at least 90% sequence identity to SEQ ID NO:29. In some embodiments, the polypeptide comprises at least 90% sequence identity to SEQ ID NO:30. In some embodiments, the polypeptide comprises at least 90% sequence identity to SEQ ID NO:31. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Additionally provided herein are methods for producing mevalonate comprising culturing a recombinant cell capable of increased carbon flux through the phosphoketolase pathway, wherein the recombinant cell comprises: (i) a heterologous nucleic acid sequence encoding a polypeptide having phosphoketolase activity, wherein the polypeptide comprises at least 65% sequence identity to SEQ ID NO:8 and (ii) one or more nucleic acids encoding one or more polypeptides of the upper MVA pathway, wherein said polypeptide having phosphoketolase activity of (i) has a Performance Index value of greater than 1.0 in one or more of the following parameters: (a) protein solubility, (b) protein expression, or (c) fructose-6-phosphate (F6P) Specific Activity and producing said mevalonate. In some embodiments, the polypeptide comprises at least 90% sequence identity to SEQ ID NO:23. In some embodiments, the polypeptide comprises at least 90% sequence identity to SEQ ID NO:24. In some embodiments, the polypeptide comprises at least 90% sequence identity to SEQ ID NO:25. In some embodiments, the polypeptide comprises at least 90% sequence identity to SEQ ID NO:26. In some embodiments, the polypeptide comprises at least 90% sequence identity to SEQ ID NO:27. In some embodiments, the polypeptide comprises at least 90% sequence identity to SEQ ID NO:28. In some embodiments, the polypeptide comprises at least 90% sequence identity to SEQ ID NO:29. In some embodiments, the polypeptide comprises at least 90% sequence identity to SEQ ID NO:30. In some embodiments, the polypeptide comprises at least 90% sequence identity to SEQ ID NO:31. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Further provided herein are methods for producing mevalonate comprising culturing a recombinant cell capable of increased carbon flux through the phosphoketolase pathway, wherein the recombinant cell comprises: (i) a heterologous nucleic acid sequence encoding a polypeptide having phosphoketolase activity, wherein the polypeptide comprises at least 65% sequence identity to SEQ ID NO:11 and (ii) one or more nucleic acids encoding one or more polypeptides of the upper MVA pathway, wherein said recombinant cell comprising said polypeptide having phosphoketolase activity of (i) has a Performance Index value of greater than 1.0 in one or more of the following parameters: (a) cell growth on glucose, (b) cell growth on xylose, (c) production of intracellular acetyl-phosphate or (d) cell growth on glucose-6-phosphate and producing said mevalonate. In some embodiments, the polypeptide comprises at least 90% sequence identity to SEQ ID NO:32. In some embodiments, the polypeptide comprises at least 90% sequence identity to SEQ ID NO:33. In some embodiments, the polypeptide comprises at least 90% sequence identity to SEQ ID NO:34. In some embodiments, the polypeptide comprises at least 90% sequence identity to SEQ ID NO:35. In some embodiments, the polypeptide comprises at least 90% sequence identity to SEQ ID NO:36. In some embodiments, the polypeptide comprises at least 90% sequence identity to SEQ ID NO:37. In some embodiments, the polypeptide comprises at least 90% sequence identity to SEQ ID NO:38. In some embodiments, the polypeptide comprises at least 90% sequence identity to SEQ ID NO:39. In some embodiments, the polypeptide comprises at least 90% sequence identity to SEQ ID NO:40. In some embodiments, the polypeptide comprises at least 90% sequence identity to SEQ ID NO:41. In some embodiments, the polypeptide comprises at least 90% sequence identity to SEQ ID NO:42. In some embodiments, the polypeptide comprises at least 90% sequence identity to SEQ ID NO:43. In some embodiments, the polypeptide comprises at least 90% sequence identity to SEQ ID NO:44. In some embodiments, the polypeptide comprises at least 90% sequence identity to SEQ ID NO:45. In some embodiments, the polypeptide comprises at least 90% sequence identity to SEQ ID NO:46. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Provided herein are methods for producing mevalonate comprising culturing a recombinant cell capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:11 and (ii) one or more nucleic acids encoding one or more polypeptides of the upper MVA pathway, wherein said polypeptide having phosphoketolase activity of (i) has a Performance Index value of greater than 1.0 in one or more of the following parameters: (a) protein solubility, (b) protein expression, or (c) fructose-6-phosphate (F6P) Specific Activity and producing said mevalonate. In some embodiments, the polypeptide comprises at least 90% sequence identity to SEQ ID NO:32. In some embodiments, the polypeptide comprises at least 90% sequence identity to SEQ ID NO:33. In some embodiments, the polypeptide comprises at least 90% sequence identity to SEQ ID NO:34. In some embodiments, the polypeptide comprises at least 90% sequence identity to SEQ ID NO:35. In some embodiments, the polypeptide comprises at least 90% sequence identity to SEQ ID NO:36. In some embodiments, the polypeptide comprises at least 90% sequence identity to SEQ ID NO:37. In some embodiments, the polypeptide comprises at least 90% sequence identity to SEQ ID NO:38. In some embodiments, the polypeptide comprises at least 90% sequence identity to SEQ ID NO:39. In some embodiments, the polypeptide comprises at least 90% sequence identity to SEQ ID NO:40. In some embodiments, the polypeptide comprises at least 90% sequence identity to SEQ ID NO:41. In some embodiments, the polypeptide comprises at least 90% sequence identity to SEQ ID NO:42. In some embodiments, the polypeptide comprises at least 90% sequence identity to SEQ ID NO:43. In some embodiments, the polypeptide comprises at least 90% sequence identity to SEQ ID NO:44. In some embodiments, the polypeptide comprises at least 90% sequence identity to SEQ ID NO:45. In some embodiments, the polypeptide comprises at least 90% sequence identity to SEQ ID NO:46. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Recombinant Cells Capable of Producing Isoprene

Isoprene (2-methyl-1,3-butadiene) is an important organic compound used in a wide array of applications. For instance, isoprene is employed as an intermediate or a starting material in the synthesis of numerous chemical compositions and polymers, including in the production of synthetic rubber. Isoprene is also an important biological material that is synthesized naturally by many plants and animals.

Isoprene is produced from DMAPP by the enzymatic action of isoprene synthase. Therefore, without being bound to theory, it is thought that increasing the cellular production of E4P, GAP, Ac-P, and/or acetyl-CoA in recombinant cells comprising the mevalonate pathway by any of the compositions and methods described above will likewise result in the production of higher amounts of isoprene. Increasing the molar yield of mevalonate production from glucose translates into higher molar yields of isoprenoid precursors, isoprene and/or isoprenoids produced from glucose when combined with appropriate enzymatic activity levels of mevalonate kinase, phosphomevalonate kinase, diphosphomevalonate decarboxylase, isopentenyl diphosphate isomerase (e.g., the lower MVA pathway) and other appropriate enzymes for isoprene and isoprenoid production.

As described herein, the present invention provides recombinant cells capable of producing isoprene, wherein the cells comprise one or more heterologous nucleic acids encoding a polypeptide having phosphoketolase activity and (i) one or more nucleic acids encoding one or more polypeptides of the complete MVA pathway (i.e., the upper MVA pathway and the lower MVA pathway) and (ii) a heterologous nucleic acid encoding an isoprene synthase polypeptide, wherein the cells are capable of producing recoverable amounts of isoprene. In certain embodiments, the present invention provides recombinant cells capable of enhanced production of isoprene, wherein the cells comprise one or more heterologous nucleic acids encoding a polypeptide having phosphoketolase activity and (i) one or more nucleic acids encoding one or more polypeptides of the complete MVA pathway and (ii) a heterologous nucleic acid encoding an isoprene synthase polypeptide, wherein the cells produce increased amounts of isoprene compared to isoprene-producing cells that do not comprise the one or more heterologous nucleic acids encoding a polypeptide having phosphoketolase activity.

Production of isoprene can also be made by using any of the recombinant host cells described herein further comprising one or more of the enzymatic pathways manipulations wherein enzyme activity is modulated to increase carbon flow towards mevalonate production and subsequent isoprenoid precursor, isoprenoid, and/or isoprene production. The recombinant cells described herein that have various enzymatic pathways manipulated for increased carbon flux through the phosphoketolase pathway for production of acetyl-CoA that can be used for mevalonate production and subsequent isoprenoid precursor, isoprenoid, and/or isoprene production. In one embodiment, the recombinant cells can be further engineered to increase the activity of one or more of the following genes selected from the group consisting of rribose-5-phosphate isomerase (rpiA and/or rpiB), D-ribulose-5-phosphate 3-epimerase (rpe), transketolase (tktA and/or tktB), transaldolase B (tal B), phosphate acetyltransferase (pta and/or eutD). In another embodiment, these recombinant cells can be further engineered to decrease the activity of one or more genes of the following genes including glucose-6-phosphate dehydrogenase (zwf), 6-phosphofructokinase-1 (pfkA and/or pfkB), fructose bisphosphate aldolase (fba, fbaA, fbaB, and/or fbaC), glyceraldehyde-3-phosphate dehydrogenase (gapA and/or gapB), acetate kinase (ackA), citrate synthase (gltA), EI (ptsI), EIICB$^{Glc}$ (ptsG), (crr), and/or HPr (ptsH).

Nucleic Acids Encoding Polypeptides of the Lower MVA Pathway

In some aspects of the invention, the cells described in any of the compositions or methods described herein further comprise one or more nucleic acids encoding a lower mevalonate (MVA) pathway polypeptide(s). In some aspects, the lower MVA pathway polypeptide is an endogenous polypeptide. In some aspects, the endogenous nucleic acid encoding a lower MVA pathway polypeptide is operably linked to a constitutive promoter. In some aspects, the endogenous nucleic acid encoding a lower MVA pathway polypeptide is operably linked to an inducible promoter. In some aspects, the endogenous nucleic acid encoding a lower MVA pathway polypeptide is operably linked to a strong promoter. In a particular aspect, the cells are engineered to over-express the endogenous lower MVA pathway polypeptide relative to wild-type cells. In some aspects, the endogenous nucleic acid encoding a lower MVA pathway polypeptide is operably linked to a weak promoter.

The lower mevalonate biosynthetic pathway comprises mevalonate kinase (MVK), phosphomevalonate kinase (PMK), and diphosphomevalonte decarboxylase (MVD). In some aspects, the lower MVA pathway can further comprise isopentenyl diphosphate isomerase (IDI). Cells provided herein can comprise at least one nucleic acid encoding isoprene synthase, one or more upper MVA pathway polypeptides, and/or one or more lower MVA pathway polypeptides. Polypeptides of the lower MVA pathway can be any enzyme (a) that phosphorylates mevalonate to mevalonate 5-phosphate; (b) that converts mevalonate 5-phosphate to mevalonate 5-pyrophosphate; and (c) that converts mevalonate 5-pyrophosphate to isopentenyl pyrophosphate. More particularly, the enzyme that phosphorylates mevalonate to mevalonate 5-phosphate can be from the group consisting of M. mazei mevalonate kinase, Lactobacillus mevalonate kinase polypeptide, Lactobacillus sakei mevalonate kinase polypeptide, yeast mevalonate kinase polypeptide, Saccharomyces cerevisiae mevalonate kinase polypeptide, Streptococcus mevalonate kinase polypeptide, Streptococcus pneumoniae mevalonate kinase polypeptide, Streptomyces mevalonate kinase polypeptide, Streptomyces CL190 mevalonate kinase polypeptide, and M Burtonii mevalonate kinase polypeptide. In another aspect, the enzyme that phosphorylates mevalonate to mevalonate 5-phosphate is M. mazei mevalonate kinase.

In some aspects, the lower MVA pathway polypeptide is a heterologous polypeptide. In some aspects, the cells comprise more than one copy of a heterologous nucleic acid encoding a lower MVA pathway polypeptide. In some aspects, the heterologous nucleic acid encoding a lower MVA pathway polypeptide is operably linked to a constitutive promoter. In some aspects, the heterologous nucleic acid encoding a lower MVA pathway polypeptide is operably linked to an inducible promoter. In some aspects, the heterologous nucleic acid encoding a lower MVA pathway polypeptide is operably linked to a strong promoter. In some aspects, the heterologous nucleic acid encoding a lower MVA pathway polypeptide is operably linked to a weak promoter. In some aspects, the heterologous lower MVA pathway polypeptide is a polypeptide from Saccharomyces cerevisiae, Enterococcus faecalis, or Methanosarcina mazei.

The nucleic acids encoding a lower MVA pathway polypeptide(s) can be integrated into a genome of the cells or can be stably expressed in the cells. The nucleic acids encoding a lower MVA pathway polypeptide(s) can additionally be on a vector.

Exemplary lower MVA pathway polypeptides are also provided below: (i) mevalonate kinase (MVK); (ii) phosphomevalonate kinase (PMK); (iii) diphosphomevalonate decarboxylase (MVD); and (iv) isopentenyl diphosphate isomerase (IDI). In particular, the lower MVK polypeptide can be from the genus Methanosarcina and, more specifically, the lower MVK polypeptide can be from Methanosarcina mazei. In some embodiments, the lower MVK polypeptide can be from M. burtonii. Additional examples of lower MVA pathway polypeptides can be found in U.S. Patent Application Publication 2010/0086978 the contents of which are expressly incorporated herein by reference in their entirety with respect to lower MVK pathway polypeptides and lower MVK pathway polypeptide variant.

Lower MVA pathway polypeptides include polypeptides, fragments of polypeptides, peptides, and fusions polypeptides that have at least one activity of a lower MVA pathway polypeptide. Exemplary lower MVA pathway nucleic acids include nucleic acids that encode a polypeptide, fragment of a polypeptide, peptide, or fusion polypeptide that has at least one activity of a lower MVA pathway polypeptide. Exemplary lower MVA pathway polypeptides and nucleic acids include naturally-occurring polypeptides and nucleic acids from any of the source organisms described herein. In addition, variants of lower MVA pathway polypeptides that confer the result of better isoprene production can also be used as well.

In some aspects, the lower MVA pathway polypeptide is a polypeptide from Saccharomyces cerevisiae, Enterococcus faecalis, or Methanosarcina mazei. In some aspects, the MVK polypeptide is selected from the group consisting of Lactobacillus mevalonate kinase polypeptide, Lactobacillus sakei mevalonate kinase polypeptide, yeast mevalonate kinase polypeptide, Saccharomyces cerevisiae mevalonate kinase polypeptide, Streptococcus mevalonate kinase polypeptide, Streptococcus pneumoniae mevalonate kinase polypeptide, Streptomyces mevalonate kinase polypeptide, Streptomyces CL190 mevalonate kinase polypeptide, Methanosarcina mazei mevalonate kinase polypeptide, and M. Burtonii mevalonate kinase polypeptide. Any one of the promoters described herein (e.g., promoters described herein and identified in the Examples of the present disclosure including inducible promoters and constitutive promoters) can be used to drive expression of any of the MVA polypeptides described herein.

Any one of the cells described herein can comprise IDI nucleic acid(s) (e.g., endogenous or heterologous nucleic acid(s) encoding IDI). Isopentenyl diphosphate isomerase polypeptides (isopentenyl-diphosphate delta-isomerase or IDI) catalyzes the interconversion of isopentenyl diphosphate (IPP) and dimethylallyl diphosphate (DMAPP) (e.g., converting IPP into DMAPP and/or converting DMAPP into IPP). Exemplary IDI polypeptides include polypeptides, fragments of polypeptides, peptides, and fusions polypeptides that have at least one activity of an IDI polypeptide. Standard methods (such as those described herein) can be used to determine whether a polypeptide has IDI polypeptide activity by measuring the ability of the polypeptide to interconvert IPP and DMAPP in vitro, in a cell extract, or in vivo. Exemplary IDI nucleic acids include nucleic acids that encode a polypeptide, fragment of a polypeptide, peptide, or fusion polypeptide that has at least one activity of an IDI polypeptide. Exemplary IDI polypeptides and nucleic acids include naturally-occurring polypeptides and nucleic acids from any of the source organisms described herein as well as mutant polypeptides and nucleic acids derived from any of the source organisms described herein.

Nucleic Acids Encoding Isoprene Synthase Polypeptides

In some aspects of the invention, the cells described in any of the compositions or methods described herein (including host cells that have been engineered for increased carbon flux through the phosphoketolase pathway as described herein) further comprise one or more nucleic acids encoding an isoprene synthase polypeptide or a polypeptide having isoprene synthase activity. In some aspects, the isoprene synthase polypeptide is an endogenous polypeptide. In some aspects, the endogenous nucleic acid encoding an isoprene synthase polypeptide is operably linked to a constitutive promoter. In some aspects, the endogenous nucleic acid encoding an isoprene synthase polypeptide is operably linked to an inducible promoter. In some aspects, the endogenous nucleic acid encoding an isoprene synthase polypeptide is operably linked to a strong promoter. In a particular aspect, the cells are engineered to over-express the endogenous isoprene synthase pathway polypeptide relative to wild-type cells. In some aspects, the endogenous nucleic acid encoding an isoprene synthase polypeptide is operably linked to a weak promoter. In some aspects, the isoprene synthase polypeptide is a polypeptide from *Pueraria* or *Populus* or a hybrid such as *Populus alba*×*Populus tremula*.

In some aspects, the isoprene synthase polypeptide is a heterologous polypeptide. In some aspects, the cells comprise more than one copy of a heterologous nucleic acid encoding an isoprene synthase polypeptide. In some aspects, the heterologous nucleic acid encoding an isoprene synthase polypeptide is operably linked to a constitutive promoter. In some aspects, the heterologous nucleic acid encoding an isoprene synthase polypeptide is operably linked to an inducible promoter. In some aspects, the heterologous nucleic acid encoding an isoprene synthase polypeptide is operably linked to a strong promoter. In some aspects, the heterologous nucleic acid encoding an isoprene synthase polypeptide is operably linked to a weak promoter.

The nucleic acids encoding an isoprene synthase polypeptide(s) can be integrated into a genome of the host cells or can be stably expressed in the cells. The nucleic acids encoding an isoprene synthase polypeptide(s) can additionally be on a vector.

Exemplary isoprene synthase nucleic acids include nucleic acids that encode a polypeptide, fragment of a polypeptide, peptide, or fusion polypeptide that has at least one activity of an isoprene synthase polypeptide. Isoprene synthase polypeptides convert dimethylallyl diphosphate (DMAPP) into isoprene. Exemplary isoprene synthase polypeptides include polypeptides, fragments of polypeptides, peptides, and fusions polypeptides that have at least one activity of an isoprene synthase polypeptide. Exemplary isoprene synthase polypeptides and nucleic acids include naturally-occurring polypeptides and nucleic acids from any of the source organisms described herein. In addition, variants of isoprene synthase can possess improved activity such as improved enzymatic activity. In some aspects, an isoprene synthase variant has other improved properties, such as improved stability (e.g., thermo-stability), and/or improved solubility.

Standard methods can be used to determine whether a polypeptide has isoprene synthase polypeptide activity by measuring the ability of the polypeptide to convert DMAPP into isoprene in vitro, in a cell extract, or in vivo. Isoprene synthase polypeptide activity in the cell extract can be measured, for example, as described in Silver et al., *J. Biol. Chem.* 270:13010-13016, 1995. In one exemplary assay, DMAPP (Sigma) can be evaporated to dryness under a stream of nitrogen and rehydrated to a concentration of 100 mM in 100 mM potassium phosphate buffer pH 8.2 and stored at −20° C. To perform the assay, a solution of 5 µL of 1M $MgCl_2$, 1 mM (250 µg/ml) DMAPP, 65 µL of Plant Extract Buffer (PEB) (50 mM Tris-HCl, pH 8.0, 20 mM $MgCl_2$, 5% glycerol, and 2 mM DTT) can be added to 25 µL of cell extract in a 20 ml Headspace vial with a metal screw cap and teflon coated silicon septum (Agilent Technologies) and cultured at 37° C. for 15 minutes with shaking. The reaction can be quenched by adding 200 µL of 250 mM EDTA and quantified by GC/MS.

In some aspects, the isoprene synthase polypeptide is a plant isoprene synthase polypeptide or a variant thereof. In some aspects, the isoprene synthase polypeptide is an isoprene synthase from *Pueraria* or a variant thereof. In some aspects, the isoprene synthase polypeptide is an isoprene synthase from *Populus* or a variant thereof. In some aspects, the isoprene synthase polypeptide is a poplar isoprene synthase polypeptide or a variant thereof. In some aspects, the isoprene synthase polypeptide is a kudzu isoprene synthase polypeptide or a variant thereof. In some aspects, the isoprene synthase polypeptide is a polypeptide from *Pueraria* or *Populus* or a hybrid, *Populus alba*×*Populus tremula*, or a variant thereof.

In some aspects, the isoprene synthase polypeptide or nucleic acid is from the family Fabaceae, such as the Faboideae subfamily. In some aspects, the isoprene synthase polypeptide or nucleic acid is a polypeptide or nucleic acid from *Pueraria montana* (kudzu) (Sharkey et al., *Plant Physiology* 137: 700-712, 2005), *Pueraria lobata*, poplar (such as *Populus alba, Populus nigra, Populus trichocarpa*, or *Populus alba*×*tremula* (CAC35696) (Miller et al., *Planta* 213: 483-487, 2001), aspen (such as *Populus tremuloides*) (Silver et al., JBC 270(22): 13010-1316, 1995), English Oak (*Quercus robur*) (Zimmer et al., WO 98/02550), or a variant thereof. In some aspects, the isoprene synthase polypeptide is an isoprene synthase from *Pueraria montana, Pueraria lobata, Populus tremuloides, Populus alba, Populus nigra*, or *Populus trichocarpa* or a variant thereof. In some aspects, the isoprene synthase polypeptide is an isoprene synthase from *Populus alba* or a variant thereof. In some aspects, the nucleic acid encoding the isoprene synthase (e.g., isoprene synthase from *Populus alba* or a variant thereof) is codon optimized.

In some aspects, the isoprene synthase nucleic acid or polypeptide is a naturally-occurring polypeptide or nucleic acid (e.g., naturally-occurring polypeptide or nucleic acid from *Populus*). In some aspects, the isoprene synthase nucleic acid or polypeptide is not a wild-type or naturally-occurring polypeptide or nucleic acid. In some aspects, the isoprene synthase nucleic acid or polypeptide is a variant of a wild-type or naturally-occurring polypeptide or nucleic acid (e.g., a variant of a wild-type or naturally-occurring polypeptide or nucleic acid from *Populus*).

In some aspects, the isoprene synthase polypeptide is a variant. In some aspects, the isoprene synthase polypeptide is a variant of a wild-type or naturally occurring isoprene synthase. In some aspects, the variant has improved activity such as improved catalytic activity compared to the wild-type or naturally occurring isoprene synthase. The increase in activity (e.g., catalytic activity) can be at least about any of 10%, 20%, 30%, 40%, 50%, 60%, 70%, 80%, 90%, or 95%. In some aspects, the increase in activity such as catalytic activity is at least about any of 1 fold, 2 folds, 5 folds, 10 folds, 20 folds, 30 folds, 40 folds, 50 folds, 75 folds, or 100 folds. In some aspects, the increase in activity such as catalytic activity is about 10% to about 100 folds (e.g., about 20% to about 100 folds, about 50% to about 50 folds, about 1 fold to about 25 folds, about 2 folds to about 20 folds, or about 5 folds to about 20 folds). In some aspects, the variant has improved solubility compared to the wild-type or naturally occurring isoprene synthase. The increase in solubility can be at least about any of 10%, 20%, 30%, 40%, 50%, 60%, 70%, 80%, 90%, or 95%. The increase in solubility can be at least about any of 1 fold, 2 folds, 5 folds, 10 folds, 20 folds, 30 folds, 40 folds, 50 folds, 75 folds, or 100 folds. In some aspects, the increase in solubility is about 10% to about 100 folds (e.g., about 20% to about 100 folds, about 50% to about 50 folds, about 1 fold to about 25 folds, about 2 folds to about 20 folds, or about 5 folds to about 20 folds). In some aspects, the isoprene synthase polypeptide is a variant of naturally occurring isoprene synthase and has improved stability (such as thermo-stability) compared to the naturally occurring isoprene synthase.

In some aspects, the variant has at least about 10%, at least about 20%, at least about 30%, at least about 40%, at least about 50%, at least about 60%, at least about 70%, at least about 80%, at least about 90%, at least about 100%, at least about 110%, at least about 120%, at least about 130%, at least about 140%, at least about 150%, at least about 160%, at least about 170%, at least about 180%, at least about 190%, at least about 200% of the activity of a wild-type or naturally occurring isoprene synthase. The variant can share sequence similarity with a wild-type or naturally occurring isoprene synthase. In some aspects, a variant of a wild-type or naturally occurring isoprene synthase can have at least about any of 40%, 50%, 60%, 70%, 75%, 80%, 90%, 91%, 92%, 93%, 94%, 95%, 96%, 97%, 98%, 99%, 99.5%, or 99.9% amino acid sequence identity as that of the wild-type or naturally occurring isoprene synthase. In some aspects, a variant of a wild-type or naturally occurring isoprene synthase has any of about 70% to about 99.9%, about 75% to about 99%, about 80% to about 98%, about 85% to about 97%, or about 90% to about 95% amino acid sequence identity as that of the wild-type or naturally occurring isoprene synthase.

In some aspects, the variant comprises a mutation in the wild-type or naturally occurring isoprene synthase. In some aspects, the variant has at least one amino acid substitution, at least one amino acid insertion, and/or at least one amino acid deletion. In some aspects, the variant has at least one amino acid substitution. In some aspects, the number of differing amino acid residues between the variant and wild-type or naturally occurring isoprene synthase can be one or more, e.g. 1, 2, 3, 4, 5, 10, 15, 20, 30, 40, 50, or more amino acid residues. Naturally occurring isoprene synthases can include any isoprene synthases from plants, for example, kudzu isoprene synthases, poplar isoprene synthases, English oak isoprene synthases, and willow isoprene synthases. In some aspects, the variant is a variant of isoprene synthase from *Populus alba*. In some aspects, the variant of isoprene synthase from *Populus alba* has at least one amino acid substitution, at least one amino acid insertion, and/or at least one amino acid deletion. In some aspects, the variant is a truncated *Populus alba* isoprene synthase. In some aspects, the nucleic acid encoding variant (e.g., variant of isoprene synthase from *Populus alba*) is codon optimized (for example, codon optimized based on host cells where the heterologous isoprene synthase is expressed).

The isoprene synthase polypeptide provided herein can be any of the isoprene synthases or isoprene synthase variants described in WO 2009/132220, WO 2010/124146, and U.S. Patent Application Publication No.: 2010/0086978, the contents of which are expressly incorporated herein by reference in their entirety with respect to the isoprene synthases and isoprene synthase variants.

Any one of the promoters described herein (e.g., promoters described herein and identified in the Examples of the present disclosure including inducible promoters and constitutive promoters) can be used to drive expression of any of the isoprene synthases described herein.

Suitable isoprene synthases include, but are not limited to, those identified by Genbank Accession Nos. AY341431, AY316691, AY279379, AJ457070, and AY182241. Types of isoprene synthases which can be used in any one of the compositions or methods including methods of making cells encoding isoprene synthase described herein are also described in International Patent Application Publication Nos. WO2009/076676, WO2010/003007, WO2009/132220, WO2010/031062, WO2010/031068, WO2010/031076, WO2010/013077, WO2010/031079, WO2010/148150, WO2010/124146, WO2010/078457, WO2010/148256, WO 2012/058494, and U.S. Pat. No. 8,173,410.

Isoprene Biosynthetic Pathway

Isoprene can be produced from two different alcohols, 3-methyl-2-buten-1-ol and 2-methyl-3-buten-2-ol. For example, in a two-step isoprene biosynthetic pathway, dimethylallyl diphosphate is converted to 2-methyl-3-buten-2-ol by an enzyme such as a synthase (e.g., a 2-methyl-3-buten-2-ol synthase), followed by conversion of 2-methyl-3-buten-2-ol to isoprene by a 2-methyl-3-buten-2-ol dehydratase. As another example, in a three-step isoprene biosynthetic pathway, dimethylallyl diphosphate is converted to 3-methyl-2-buten-1-ol by either a phosphatase or a synthase (e.g., a geraniol synthase or farnesol synthase) capable of converting dimethylallyl diphosphate to 3-methyl-2-buten-1-ol, 3-methyl-2-buten-1-ol is converted to 2-methyl-3-buten-2-ol by a 2-methyl-3-buten-2-ol isomerase, and 2-methyl-3-buten-2-ol is converted to isoprene by a 2-methyl-3-buten-2-ol dehydratase. See for example, U.S. Patent Application Publication No.: US 20130309742 A1 and U.S. Patent Application Publication No.: US 20130309741 A1.

In some aspects of the invention, the cells described in any of the compositions or methods described herein (including host cells that have been modified as described herein) further comprise one or more nucleic acids encoding a polypeptide of an isoprene biosynthetic pathway selected from the group consisting of 2-methyl-3-buten-2-ol dehydratase, 2-methyl-3-butene-2-ol isomerase, and 3-methyl-2-buten-1-ol synthase. In some aspects, the polypeptide of an isoprene biosynthetic pathway is an endogenous polypeptide. In some aspects, the endogenous nucleic acid encoding a polypeptide of an isoprene biosynthetic pathway is operably linked to a constitutive promoter. In some aspects, the endogenous nucleic acid encoding a polypeptide of an isoprene biosynthetic pathway is operably linked to an inducible promoter. In some aspects, the endogenous nucleic acid encoding a polypeptide of an isoprene biosynthetic pathway is operably linked to a strong promoter. In a particular aspect, the cells are engineered to overexpress the endogenous polypeptide of an isoprene biosynthetic pathway relative to wild-type cells. In some aspects, the endogenous nucleic acid encoding a polypeptide of an isoprene biosynthetic pathway is operably linked to a weak promoter.

In some aspects, the polypeptide of an isoprene biosynthetic pathway is a heterologous polypeptide. In some aspects, the cells comprise more than one copy of a heterologous nucleic acid encoding a polypeptide of an isoprene biosynthetic pathway. In some aspects, the heterologous nucleic acid encoding a polypeptide of an isoprene biosynthetic pathway is operably linked to a constitutive promoter. In some aspects, the heterologous nucleic acid encoding a polypeptide of an isoprene biosynthetic pathway is operably linked to an inducible promoter. In some aspects, the heterologous nucleic acid encoding a polypeptide of an isoprene biosynthetic pathway is operably linked to a strong promoter. In some aspects, the heterologous nucleic acid encoding a polypeptide of an isoprene biosynthetic pathway is operably linked to a weak promoter.

The nucleic acids encoding a polypeptide(s) of an isoprene biosynthetic pathway can be integrated into a genome of the host cells or can be stably expressed in the cells. The nucleic acids encoding a polypeptide(s) of an isoprene biosynthetic pathway can additionally be on a vector.

Exemplary nucleic acids encoding a polypeptide(s) of an isoprene biosynthetic pathway include nucleic acids that encode a polypeptide, fragment of a polypeptide, peptide, or fusion polypeptide that has at least one activity of a polypeptide of an isoprene biosynthetic pathway such as a 2-methyl-3-buten-2-ol dehydratase polypeptide, 2-methyl-3-butene-2-ol isomerase polypeptide, and 3-methyl-2-buten-1-ol synthase polypeptide. Exemplary polypeptide(s) of an isoprene biosynthetic pathway and nucleic acids encoding polypeptide(s) of an isoprene biosynthetic pathway include naturally-occurring polypeptides and nucleic acids from any of the source organisms described herein. In addition, variants of polypeptide(s) of an isoprene biosynthetic pathway (e.g., a 2-methyl-3-buten-2-ol dehydratase polypeptide, 2-methyl-3-butene-2-ol isomerase polypeptide, and 3-methyl-2-buten-1-ol synthase polypeptide) can possess improved activity such as improved enzymatic activity. In some aspects, a polypeptide of an isoprene biosynthetic pathway is a phosphatase. Exemplary phosphatases include a phosphatase from *Bacillus subtilis* or *Escherichia coli*. In some embodiments, the phosphatase is a 3-methyl-2-buten-1-ol synthase polypeptide or variant thereof. In some aspects, a polypeptide of an isoprene biosynthetic pathway is a terpene synthase (e.g., a geraniol synthase, farnesol synthase, linalool synthase or nerolidol synthase). Exemplary terpene synthases include a terpene synthase from *Ocimum basilicum, Perilla citriodora, Perilla frutescans, Cinnamomom tenuipile, Zea mays* or *Oryza sativa*. Additional exemplary terpene synthases include a terpene synthase from *Clarkia breweri, Arabidopsis thaliana, Perilla setoyensis, Perilla frutescens, Actinidia arguta, Actinidia polygama, Artemesia annua, Ocimum basilicum, Mentha aquatica, Solanum lycopersicum, Medicago trunculata, Populus trichocarpa, Fragaria vesca,* or *Fragraria ananassa*. In some embodiments, the terpene synthase is a 3-methyl-2-buten-1-ol synthase polypeptide or variant thereof. For example, a terpene synthase described herein can catalyze the conversion of dimethylallyl diphosphate to 3-methyl-2-buten-1-ol (e.g., a 3-methyl-2-buten-1-ol synthase). In some aspects, a terpene synthase described herein can catalyze the conversion of dimethylallyl diphosphate to 2-methyl-3-buten-2-ol (e.g., a 2-methyl-3-buten-2-ol synthase). In some aspects, a polypeptide of an isoprene biosynthetic pathway is a 2-methyl-3-buten-2-ol dehydratase polypeptide (e.g., a 2-methyl-3-buten-2-ol dehydratase polypeptide from *Aquincola tertiaricarbonis*) or variant thereof. In some aspects, the 2-methyl-3-buten-2-ol dehydratase polypeptide is a linalool dehydratase-isomerase polypeptide (e.g., a linalool dehydratase-isomerase polypeptide from *Castellaniella defragrans* Genbank accession number FR669447) or variant thereof. In some aspects, a polypeptide of an isoprene biosynthetic pathway is a 2-methyl-3-buten-2-ol isomerase polypeptide or variant thereof. In some aspects, the 2-methyl-3-butene-2-ol isomerase polypeptide is a linalool dehydratase-isomerase polypeptide (e.g., a linalool dehydratase-isomerase polypeptide from *Castellaniella defragrans* Genbank accession number FR669447) or variant thereof.

Standard methods can be used to determine whether a polypeptide has the desired isoprene biosynthetic pathway enzymatic activity (e.g., a 2-methyl-3-buten-2-ol dehydratase activity, 2-methyl-3-butene-2-ol isomerase activity, and 3-methyl-2-buten-1-ol activity) by measuring the ability of the polypeptide to convert DMAPP into isoprene in vitro, in a cell extract, or in vivo. See for example, U.S. Patent Application Publication No.: US 20130309742 A1 and U.S. Patent Application Publication No.: US 20130309741 A1.

In some aspects, the polypeptide(s) of an isoprene biosynthetic pathway (e.g., a 2-methyl-3-buten-2-ol dehydratase polypeptide, 2-methyl-3-butene-2-ol isomerase polypeptide, and 3-methyl-2-buten-1-ol synthase polypeptide) is a variant. In some aspects, polypeptide(s) of an isoprene biosynthetic pathway (e.g., a 2-methyl-3-buten-2-ol dehydratase polypeptide, 2-methyl-3-butene-2-ol isomerase polypeptide, and 3-methyl-2-buten-1-ol synthase polypeptide) is a variant of a wild-type or naturally occurring polypeptide(s) of an isoprene biosynthetic pathway. In some aspects, the variant has improved activity such as improved catalytic activity compared to the wild-type or naturally occurring polypeptide(s) of an isoprene biosynthetic pathway. The increase in activity (e.g., catalytic activity) can be at least about any of 10%, 20%, 30%, 40%, 50%, 60%, 70%, 80%, 90%, or 95%. In some aspects, the increase in activity such as catalytic activity is at least about any of 1 fold, 2 folds, 5 folds, 10 folds, 20 folds, 30 folds, 40 folds, 50 folds, 75 folds, or 100 folds. In some aspects, the increase in activity such as catalytic activity is about 10% to about 100 folds (e.g., about 20% to about 100 folds, about 50% to about 50 folds, about 1 fold to about 25 folds, about 2 folds to about 20 folds, or about 5 folds to about 20 folds). In some aspects, the variant has improved solubility compared to the wild-type or naturally occurring polypeptide(s) of an isoprene biosynthetic pathway. The increase in solubility can be at least about any of 10%, 20%, 30%, 40%, 50%, 60%, 70%, 80%, 90%, or 95%. The increase in solubility can be at least about any of 1 fold, 2 folds, 5 folds, 10 folds, 20 folds, 30 folds, 40 folds, 50 folds, 75 folds, or 100 folds. In some aspects, the increase in solubility is about 10% to about 100 folds (e.g., about 20% to about 100 folds, about 50% to about 50 folds, about 1 fold to about 25 folds, about 2 folds to about 20 folds, or about 5 folds to about 20 folds). In some aspects, the polypeptide(s) of an isoprene biosynthetic pathway is a variant of naturally occurring polypeptide(s) of an isoprene biosynthetic pathway and has improved stability (such as thermo-stability) compared to the naturally occurring polypeptide(s) of an isoprene biosynthetic pathway.

In some aspects, the variant has at least about 10%, at least about 20%, at least about 30%, at least about 40%, at least about 50%, at least about 60%, at least about 70%, at least about 80%, at least about 90%, at least about 100%, at least about 110%, at least about 120%, at least about 130%, at least about 140%, at least about 150%, at least about 160%, at least about 170%, at least about 180%, at least about 190%, at least about 200% of the activity of a wild-type or naturally occurring polypeptide(s) of an isoprene biosynthetic pathway (e.g., a 2-methyl-3-buten-2-ol dehydratase polypeptide, 2-methyl-3-butene-2-ol isomerase polypeptide, and 3-methyl-2-buten-1-ol synthase polypeptide). The variant can share sequence similarity with a wild-type or naturally occurring polypeptide(s) of an isoprene biosynthetic pathway. In some aspects, a variant of a wild-type or naturally occurring polypeptide(s) of an isoprene biosynthetic pathway can have at least about any of 40%, 50%, 60%, 70%, 75%, 80%, 90%, 91%, 92%, 93%, 94%, 95%, 96%, 97%, 98%, 99%, 99.5%, or 99.9% amino acid sequence identity as that of the wild-type or naturally occurring polypeptide(s) of an isoprene biosynthetic pathway (e.g., a 2-methyl-3-buten-2-ol dehydratase polypeptide, 2-methyl-3-butene-2-ol isomerase polypeptide, and 3-methyl-2-buten-1-ol synthase polypeptide). In some aspects, a variant of a wild-type or naturally occurring polypeptide(s) of an isoprene biosynthetic pathway has any of about 70% to about 99.9%, about 75% to about 99%, about 80% to about 98%, about 85% to about 97%, or about 90% to about 95% amino acid sequence identity as that of the wild-type or naturally occurring polypeptide(s) of an isoprene biosynthetic pathway (e.g., a 2-methyl-3-buten-2-ol dehydratase polypeptide, 2-methyl-3-butene-2-ol isomerase polypeptide, and 3-methyl-2-buten-1-ol synthase polypeptide).

In some aspects, the variant comprises a mutation in the wild-type or naturally occurring polypeptide(s) of an isoprene biosynthetic pathway (e.g., a 2-methyl-3-buten-2-ol dehydratase polypeptide, 2-methyl-3-butene-2-ol isomerase polypeptide, and 3-methyl-2-buten-1-ol synthase polypeptide). In some aspects, the variant has at least one amino acid substitution, at least one amino acid insertion, and/or at least one amino acid deletion. In some aspects, the variant has at least one amino acid substitution. In some aspects, the number of differing amino acid residues between the variant and wild-type or naturally occurring polypeptide(s) of an isoprene biosynthetic pathway can be one or more, e.g. 1, 2, 3, 4, 5, 10, 15, 20, 30, 40, 50, or more amino acid residues. In some aspects, the nucleic acid encoding the variant (e.g., a 2-methyl-3-buten-2-ol dehydratase polypeptide, 2-methyl-3-butene-2-ol isomerase polypeptide, and 3-methyl-2-buten-1-ol synthase polypeptide) is codon optimized (for example, codon optimized based on host cells where the heterologous polypeptide(s) of an isoprene biosynthetic pathway is expressed).

Any one of the promoters described herein (e.g., promoters described herein and identified in the Examples of the present disclosure including inducible promoters and constitutive promoters) can be used to drive expression of any of the polypeptides of an isoprene biosynthetic pathway described herein.

Nucleic Acids Encoding DXP Pathway Polypeptides

In some aspects of the invention, the cells described in any of the compositions or methods described herein (including host cells that have been engineered for increased carbon flux through the phosphoketolase pathway as described herein) further comprise one or more heterologous nucleic acids encoding a DXS polypeptide or other DXP pathway polypeptides. In some aspects, the cells further comprise a chromosomal copy of an endogenous nucleic acid encoding a DXS polypeptide or other DXP pathway polypeptides. In some aspects, the E. coli cells further comprise one or more nucleic acids encoding an IDI polypeptide and a DXS polypeptide or other DXP pathway polypeptides. In some aspects, one nucleic acid encodes the isoprene synthase polypeptide, IDI polypeptide, and DXS polypeptide or other DXP pathway polypeptides. In some aspects, one plasmid encodes the isoprene synthase polypeptide, IDI polypeptide, and DXS polypeptide or other DXP pathway polypeptides. In some aspects, multiple plasmids encode the isoprene synthase polypeptide, IDI polypeptide, and DXS polypeptide or other DXP pathway polypeptides.

Exemplary DXS polypeptides include polypeptides, fragments of polypeptides, peptides, and fusions polypeptides that have at least one activity of a DXS polypeptide. Standard methods (such as those described herein) can be used to determine whether a polypeptide has DXS polypeptide activity by measuring the ability of the polypeptide to convert pyruvate and D-glyceraldehyde 3-phosphate into 1-deoxy-D-xylulose-5-phosphate in vitro, in a cell extract, or in vivo. Exemplary DXS polypeptides and nucleic acids and methods of measuring DXS activity are described in more detail in International Publication Nos. WO 2009/076676, WO 2010/003007, WO 2009/132220, and U.S. Patent Publ. Nos. US 2009/0203102, 2010/0003716 and 2010/0048964.

Exemplary DXP pathways polypeptides include, but are not limited to any of the following polypeptides: DXS polypeptides, DXR polypeptides, MCT polypeptides, CMK polypeptides, MCS polypeptides, HDS polypeptides, HDR polypeptides, and polypeptides (e.g., fusion polypeptides) having an activity of one, two, or more of the DXP pathway polypeptides. In particular, DXP pathway polypeptides include polypeptides, fragments of polypeptides, peptides, and fusions polypeptides that have at least one activity of a DXP pathway polypeptide. Exemplary DXP pathway nucleic acids include nucleic acids that encode a polypeptide, fragment of a polypeptide, peptide, or fusion polypeptide that has at least one activity of a DXP pathway polypeptide. Exemplary DXP pathway polypeptides and nucleic acids include naturally-occurring polypeptides and nucleic acids from any of the source organisms described herein as well as mutant polypeptides and nucleic acids derived from any of the source organisms described herein. Exemplary DXP pathway polypeptides and nucleic acids and methods of measuring DXP pathway polypeptide activity are described in more detail in International Publication No. WO 2010/148150

Exemplary DXS polypeptides include polypeptides, fragments of polypeptides, peptides, and fusions polypeptides that have at least one activity of a DXS polypeptide. Standard methods (such as those described herein) can be used to determine whether a polypeptide has DXS polypeptide activity by measuring the ability of the polypeptide to convert pyruvate and D-glyceraldehyde 3-phosphate into 1-deoxy-D-xylulose-5-phosphate in vitro, in a cell extract, or in vivo. Exemplary DXS polypeptides and nucleic acids and methods of measuring DXS activity are described in more detail in International Publication No. WO 2009/076676, WO 2010/003007, WO 2009/132220, and U.S. Patent Publ. Nos. US 2009/0203102, 2010/0003716, and 2010/0048964.

In particular, DXS polypeptides convert pyruvate and D-glyceraldehyde 3-phosphate into 1-deoxy-D-xylulose 5-phosphate (DXP). Standard methods can be used to determine whether a polypeptide has DXS polypeptide activity by measuring the ability of the polypeptide to convert pyruvate and D-glyceraldehyde 3-phosphate in vitro, in a cell extract, or in vivo.

DXR polypeptides convert 1-deoxy-D-xylulose 5-phosphate (DXP) into 2-C-methyl-D-erythritol 4-phosphate (MEP). Standard methods can be used to determine whether a polypeptide has DXR polypeptides activity by measuring the ability of the polypeptide to convert DXP in vitro, in a cell extract, or in vivo.

MCT polypeptides convert 2-C-methyl-D-erythritol 4-phosphate (MEP) into 4-(cytidine 5'-diphospho)-2-methyl-D-erythritol (CDP-ME). Standard methods can be used to determine whether a polypeptide has MCT polypeptides activity by measuring the ability of the polypeptide to convert MEP in vitro, in a cell extract, or in vivo.

CMK polypeptides convert 4-(cytidine 5'-diphospho)-2-C-methyl-D-erythritol (CDP-ME) into 2-phospho-4-(cytidine 5'-diphospho)-2-C-methyl-D-erythritol (CDP-MEP). Standard methods can be used to determine whether a polypeptide has CMK polypeptides activity by measuring the ability of the polypeptide to convert CDP-ME in vitro, in a cell extract, or in vivo.

MCS polypeptides convert 2-phospho-4-(cytidine 5'-diphospho)-2-C-methyl-D-erythritol (CDP-MEP) into 2-C-methyl-D-erythritol 2, 4-cyclodiphosphate (ME-CPP or cMEPP). Standard methods can be used to determine whether a polypeptide has MCS polypeptides activity by measuring the ability of the polypeptide to convert CDP-MEP in vitro, in a cell extract, or in vivo.

HDS polypeptides convert 2-C-methyl-D-erythritol 2, 4-cyclodiphosphate into (E)-4-hydroxy-3-methylbut-2-en-1-yl diphosphate (HMBPP or HDMAPP). Standard methods can be used to determine whether a polypeptide has HDS polypeptides activity by measuring the ability of the polypeptide to convert ME-CPP in vitro, in a cell extract, or in vivo.

HDR polypeptides convert (E)-4-hydroxy-3-methylbut-2-en-1-yl diphosphate into isopentenyl diphosphate (IPP) and dimethylallyl diphosphate (DMAPP). Standard methods can be used to determine whether a polypeptide has HDR polypeptides activity by measuring the ability of the polypeptide to convert HMBPP in vitro, in a cell extract, or in vivo.

Source Organisms for Lower MVA Pathway, Isoprene Synthase, IDI, and DXP Pathway Polypeptides Isoprene synthase, IDI, DXP pathway, and/or lower MVA pathway nucleic acids (and their encoded polypeptides) can be obtained from any organism that naturally contains isoprene synthase, IDI, DXP pathway, and/or lower MVA pathway nucleic acids. Isoprene is formed naturally by a variety of organisms, such as bacteria, yeast, plants, and animals. Some organisms contain the MVA pathway for producing isoprene. Isoprene synthase nucleic acids can be obtained, e.g., from any organism that contains an isoprene synthase. MVA pathway nucleic acids can be obtained, e.g., from any organism that contains the MVA pathway. IDI and DXP pathway nucleic acids can be obtained, e.g., from any organism that contains the IDI and DXP pathway.

The nucleic acid sequence of the isoprene synthase, DXP pathway, IDI, and/or MVA pathway nucleic acids can be isolated from a bacterium, fungus, plant, algae, or cyanobacterium. Exemplary source organisms include, for example, yeasts, such as species of *Saccharomyces* (e.g., *S. cerevisiae*), bacteria, such as species of *Escherichia* (e.g., *E. coli*), or species of *Methanosarcina* (e.g., *Methanosarcina mazei*), plants, such as kudzu or poplar (e.g., *Populus alba* or *Populus alba×tremula* CAC35696) or aspen (e.g., *Populus tremuloides*). Exemplary sources for isoprene synthases, IDI, and/or MVA pathway polypeptides which can be used are also described in International Patent Application Publication Nos. WO2009/076676, WO2010/003007, WO2009/132220, WO2010/031062, WO2010/031068, WO2010/031076, WO2010/013077, WO2010/031079, WO2010/148150, WO2010/078457, and WO2010/148256.

In some aspects, the source organism is a yeast, such as *Saccharomyces* sp., *Schizosaccharomyces* sp., *Pichia* sp., or *Candida* sp.

In some aspects, the source organism is a bacterium, such as strains of *Bacillus* such as *B. lichenformis* or *B. subtilis*, strains of *Pantoea* such as *P. citrea*, strains of *Pseudomonas* such as *P. alcaligenes*, strains of *Streptomyces* such as *S. lividans* or *S. rubiginosus*, strains of *Escherichia* such as *E. coli*, strains of *Enterobacter*, strains of *Streptococcus*, or strains of Archaea such as *Methanosarcina mazei*.

As used herein, "the genus *Bacillus*" includes all species within the genus "*Bacillus*," as known to those of skill in the art, including but not limited to *B. subtilis*, *B. licheniformis*, *B. lentus*, *B. brevis*, *B. stearothermophilus*, *B. alkalophilus*, *B. amyloliquefaciens*, *B. clausii*, *B. halodurans*, *B. megaterium*, *B. coagulans*, *B. circulans*, *B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus*, *Amphibacillus*, *Aneurinibacillus*, *Anoxybacillus*, *Brevibacillus*, *Filobacillus*, *Gracilibacillus*, *Halobacillus*, *Paenibacillus*, *Salibacillus*, *Thermobacillus*, *Ureibacillus*, and *Virgibacillus*.

In some aspects, the source organism is a gram-positive bacterium. Non-limiting examples include strains of *Streptomyces* (e.g., *S. lividans*, *S. coelicolor*, or *S. griseus*) and *Bacillus*. In some aspects, the source organism is a gram-negative bacterium, such as *E. coli* or *Pseudomonas* sp.

In some aspects, the source organism is a plant, such as a plant from the family Fabaceae, such as the Faboideae subfamily. In some aspects, the source organism is kudzu, poplar (such as *Populus alba×tremula* CAC35696), aspen (such as *Populus tremuloides*), or *Quercus robur*.

In some aspects, the source organism is an algae, such as a green algae, red algae, glaucophytes, chlorarachniophytes, euglenids, chromista, or dinoflagellates.

In some aspects, the source organism is a cyanobacteria, such as cyanobacteria classified into any of the following groups based on morphology: Chroococcales, Pleurocapsales, Oscillatoriales, Nostocales, or Stigonematales.

Recombinant Cells Capable of Increased Production of Isoprene

The recombinant cells described herein (including host cells that have been engineered for increased carbon flux through the phosphoketolase pathway as described herein) have the ability to produce isoprene concentration greater than that of the same cells lacking one or more copies of a heterologous nucleic acid phosphoketolase polypeptides, one or more copies of a heterologous nucleic acid encoding a MVA pathway polypeptide, and one or more heterologous nucleic acids encoding an isoprene synthase polypeptide when cultured under the same conditions. The cells can further comprise one or more heterologous nucleic acids encoding an IDI polypeptide. In certain embodiments, the phosphoketolase polypeptide is from *Burkholderia phyto-*

*firmans, Lactobacillus buchneri, Bifidobacterium gallicum, Bifidobacterium dentium, Bifidobacterium bifidum*, and/or *Clostridium acetobutylicum*. In other embodiments, the phosphoketolase polypeptide is from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In other embodiments, the phosphoketolase polypeptide is from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus*, and/or *Mycoplasma arthritidis*. In other embodiments, the phosphoketolase polypeptide is from *Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*. In some embodiments, the recombinant cell is a *Corynebacteria* spp. (e.g., *C. glutamicum*).

In one embodiment, the recombinant cells comprise one or more copies of a heterologous nucleic acid encoding a phosphoketolase isolated from *Burkholderia phytofirmans*. In another embodiment, the recombinant cells comprise one or more copies of a heterologous nucleic acid encoding a phosphoketolase isolated from *Lactobacillus buchneri*. In still another embodiment, the recombinant cells comprise one or more copies of a heterologous nucleic acid encoding a phosphoketolase isolated from *Bifidobacterium gallicum*. In yet another embodiment, the recombinant cells comprise one or more copies of a heterologous nucleic acid encoding a phosphoketolase isolated from *Bifidobacterium dentium*. In another embodiment, the recombinant cells comprise one or more copies of a heterologous nucleic acid encoding a phosphoketolase isolated from *Bifidobacterium bifidum*. In still another embodiment, the recombinant cells comprise one or more copies of a heterologous nucleic acid encoding a phosphoketolase isolated from *Clostridium acetobutylicum*. In other embodiments, the recombinant cells described herein comprise one or more copies of a heterologous nucleic acid encoding a phosphoketolase isolated from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In yet other embodiments, the recombinant cells described herein comprise one or more copies of a heterologous nucleic acid encoding a phosphoketolase isolated from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus*, and/or *Mycoplasma arthritidis*. In one embodiment, the recombinant cells comprise one or more copies of a heterologous nucleic acid encoding a phosphoketolase isolated from *Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*.

In some aspects, the one or more copies of a heterologous nucleic acid encoding phosphoketolase, one or more copies of a heterologous nucleic acid encoding a MVA pathway polypeptide, and one or more heterologous nucleic acids encoding an isoprene synthase polypeptide are heterologous nucleic acids that are integrated into the host cell's chromosomal nucleotide sequence. In other aspects, the one or more heterologous nucleic acids are integrated into plasmid. In still other aspects, at least one of the one or more heterologous nucleic acids is integrated into the cell's chromosomal nucleotide sequence while at least one of the one or more heterologous nucleic acid sequences is integrated into a plasmid. The recombinant cells can produce at least 5% greater amounts of isoprene compared to isoprene-producing cells that do not comprise the phosphoketolase polypeptide. Alternatively, the recombinant cells can produce greater than about 1%, 2%, 3%, 4%, 5%, 6%, 7%, 8%, 9%, 10%, 11%, 12%, 13%, 14%, or 15% of isoprene, inclusive, as well as any numerical value in between these numbers.

In one aspect of the invention, provided herein are recombinant cells comprising one or more heterologous nucleic acids encoding a phosphoketolase polypeptide as described herein, one or more heterologous nucleic acids encoding a mevalonate (MVA) pathway polypeptide(s), one or more heterologous nucleic acids encoding a DXP pathway polypeptide(s), and one or more heterologous nucleic acids encoding an isoprene synthase polypeptide. The cells can further comprise one or more heterologous nucleic acids encoding an IDI polypeptide. Any of the one or more heterologous nucleic acids can be operably linked to constitutive promoters, can be operably linked to inducible promoters, or can be operably linked to a combination of inducible and constitutive promoters. The one or more heterologous nucleic acids can additionally be operably linked to strong promoters, weak promoters, and/or medium promoters. One or more of the heterologous nucleic acids encoding phosphoketolase, a mevalonate (MVA) pathway polypeptide(s), a DXP pathway polypeptide(s), and an isoprene synthase polypeptide can be integrated into a genome of the host cells or can be stably expressed in the cells. The one or more heterologous nucleic acids can additionally be on a vector.

The production of isoprene by the cells according to any of the compositions or methods described herein can be enhanced (e.g., enhanced by the expression of one or more heterologous nucleic acids encoding a phosphoketolase polypeptide, an isoprene synthase polypeptide, MVA pathway polypeptide(s), and/or a DXP pathway polypeptide(s)). As used herein, "enhanced" isoprene production refers to an increased cell productivity index (CPI) for isoprene, an increased titer of isoprene, an increased mass yield of isoprene, and/or an increased specific productivity of isoprene by the cells described by any of the compositions and methods described herein compared to cells which do not have one or more heterologous nucleic acids encoding a phosphoketolase peptide. In certain embodiments described herein, the host cells have been further engineered increased carbon flux through the phosphoketolase pathway for E4P, GAP, Ac-P, and/or, acetyl-CoA production.

The production of isoprene by the recombinant cells described herein can be enhanced by about 5% to about 1,000,000 folds. In certain aspects, the production of isoprene can be enhanced by about 10% to about 1,000,000 folds (e.g., about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprene by cells that do not express one or more heterologous nucleic acids encoding phosphoketolase peptide. In certain embodiments described herein, the host cells have been further engineered to increased carbon flux through the phosphoketolase pathway to MVA production thereby providing enhanced production of isoprene as compared to the production of isoprene by cells that do not express one or more heterologous nucleic acids encoding phosphoketolase peptide and which have not been engineered for increased carbon flux through the phosphoketolase pathway to mevalonate production.

In other aspects, the production of isoprene by the recombinant cells described herein can also be enhanced by at least about any of 5%, 10%, 20%, 30%, 40%, 50%, 60%, 70%, 80%, 90%, 1 fold, 2 folds, 5 folds, 10 folds, 20 folds, 50 folds, 100 folds, 200 folds, 500 folds, 1000 folds, 2000 folds, 5000 folds, 10,000 folds, 20,000 folds, 50,000 folds, 100,000 folds, 200,000 folds, 500,000 folds, or 1,000,000 folds as compared to the production of isoprene by cells that do not express one or more heterologous nucleic acids encoding phosphoketolase peptide. In certain embodiments described herein, the host cells have been further engineered increased carbon flux through the phosphoketolase pathway to MVA production thereby providing enhanced production of isoprene as compared to the production of isoprene by cells that do not express one or more heterologous nucleic acids encoding phosphoketolase peptide and which have not been engineered for increased carbon flux through the phosphoketolase pathway to mevalonate production.

Also provided herein are isoprene-producing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:8, (ii) one or more nucleic acids encoding one or more polypeptides of the complete MVA pathway, and (iii) one or more heterologous nucleic acids encoding an isoprene synthase polypeptide, wherein said recombinant cell comprising said polypeptide having phosphoketolase activity of (i) has a Performance Index value of greater than 1.0 in one or more of the following parameters: (a) cell growth on glucose, (b) cell growth on xylose, (c) production of intracellular acetyl-phosphate or (d) cell growth on glucose-6-phosphate. In other embodiments, the Performance Index value parameters further include (e) isoprene yield protein solubility or (f) isoprene specific productivity. In some embodiments, the polypeptide comprises at least 90% sequence identity to SEQ ID NO:23. In some embodiments, the polypeptide comprises at least 90% sequence identity to SEQ ID NO:24. In some embodiments, the polypeptide comprises at least 90% sequence identity to SEQ ID NO:25. In some embodiments, the polypeptide comprises at least 90% sequence identity to SEQ ID NO:26. In some embodiments, the polypeptide comprises at least 90% sequence identity to SEQ ID NO:27. In some embodiments, the polypeptide comprises at least 90% sequence identity to SEQ ID NO:28. In some embodiments, the polypeptide comprises at least 90% sequence identity to SEQ ID NO:29. In some embodiments, the polypeptide comprises at least 90% sequence identity to SEQ ID NO:30. In some embodiments, the polypeptide comprises at least 90% sequence identity to SEQ ID NO:31. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, 8.6, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Additionally provided herein isoprene-producing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:8, (ii) one or more nucleic acids encoding one or more polypeptides of the complete MVA pathway, and (iii) one or more heterologous nucleic acids encoding an isoprene synthase polypeptide, wherein said polypeptide having phosphoketolase activity of (i) has a Performance Index value of greater than 1.0 in one or more of the following parameters: (a) protein solubility, (b) protein expression, or (c) fructose-6-phosphate (F6P) Specific Activity. In other embodiments, the Performance Index value parameters further include (d) isoprene yield protein solubility or (e) isoprene specific productivity. In some embodiments, the polypeptide comprises at least 90% sequence identity to SEQ ID NO:23. In some embodiments, the polypeptide comprises at least 90% sequence identity to SEQ ID NO:24. In some embodiments, the polypeptide comprises at least 90% sequence identity to SEQ ID NO:25. In some embodiments, the polypeptide comprises at least 90% sequence identity to SEQ ID NO:26. In some embodiments, the polypeptide comprises at least 90% sequence identity to SEQ ID NO:27. In some embodiments, the polypeptide comprises at least 90% sequence identity to SEQ ID NO:28. In some embodiments, the polypeptide comprises at least 90% sequence identity to SEQ ID NO:29. In some embodiments, the polypeptide comprises at least 90% sequence identity to SEQ ID NO:30. In some embodiments, the polypeptide comprises at least 90% sequence identity to SEQ ID NO:31. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Further provided herein are isoprene-producing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:11, (ii) one or more nucleic acids encoding one or more polypeptides of the complete MVA pathway, and (iii) one or more heterologous nucleic acids encoding an isoprene synthase polypeptide, wherein said recombinant cell comprising said polypeptide having phosphoketolase activity of (i) has a Performance Index value of greater than 1.0 in one or more of the following parameters: (a) cell growth on glucose, (b) cell growth on xylose, (c) production of intracellular acetyl-phosphate or (d) cell growth on glucose-6-phosphate. In other embodiments, the Performance Index value parameters further include (e) isoprene yield protein solubility or (f) isoprene specific productivity. In some embodiments, the polypeptide comprises at least 90% sequence identity to SEQ ID NO:32. In some embodiments, the polypeptide comprises at least 90% sequence identity to SEQ ID NO:33. In some embodiments, the polypeptide comprises at least 90% sequence identity to SEQ ID NO:34. In some embodiments, the polypeptide comprises at least 90% sequence identity to SEQ ID NO:35. In some embodiments, the polypeptide comprises at least 90% sequence identity to SEQ ID NO:36. In some embodiments, the polypeptide comprises at least 90% sequence identity to SEQ ID NO:37. In some embodiments, the polypeptide comprises at least 90% sequence identity to SEQ ID NO:38. In some embodiments, the polypeptide comprises at least 90% sequence identity to SEQ ID NO:39. In some embodiments, the polypeptide comprises at least 90% sequence identity to SEQ ID NO:40. In some embodiments, the polypeptide comprises at least 90% sequence identity to SEQ ID NO:41. In some embodiments, the polypeptide comprises at least 90% sequence identity to SEQ ID NO:42. In some embodiments, the polypeptide comprises at least 90% sequence identity to SEQ ID NO:43. In some embodiments, the polypeptide comprises at least 90% sequence identity to SEQ ID NO:44. In some embodiments, the polypeptide comprises at least 90% sequence identity to SEQ ID NO:45. In some embodiments, the polypeptide comprises at least 90% sequence identity to SEQ ID NO:46. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Provided herein are isoprene-producing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:11, (ii) one or more nucleic acids encoding one or more polypeptides of the complete MVA pathway, and (iii) one or more heterologous nucleic acids encoding an isoprene synthase polypeptide, wherein said polypeptide having phosphoketolase activity of (i) has a Performance Index value of greater than 1.0 in one or more of the following parameters: (a) protein solubility, (b) protein expression, or (c) fructose-6-phosphate (F6P) Specific Activity. In other embodiments, the Performance Index value parameters further include (d) isoprene yield protein solubility or (e) isoprene specific productivity. In some embodiments, the polypeptide comprises at least 90% sequence identity to SEQ ID NO:32. In some embodiments, the polypeptide comprises at least 90% sequence identity to SEQ ID NO:33. In some embodiments, the polypeptide comprises at least 90% sequence identity to SEQ ID NO:34. In some embodiments, the polypeptide comprises at least 90% sequence identity to SEQ ID NO:35. In some embodiments, the polypeptide comprises at least 90% sequence identity to SEQ ID NO:36. In some embodiments, the polypeptide comprises at least 90% sequence identity to SEQ ID NO:37. In some embodiments, the polypeptide comprises at least 90% sequence identity to SEQ ID NO:38. In some embodiments, the polypeptide comprises at least 90% sequence identity to SEQ ID NO:39. In some embodiments, the polypeptide comprises at least 90% sequence identity to SEQ ID NO:40. In some embodiments, the polypeptide comprises at least 90% sequence identity to SEQ ID NO:41. In some embodiments, the polypeptide comprises at least 90% sequence identity to SEQ ID NO:42. In some embodiments, the polypeptide comprises at least 90% sequence identity to SEQ ID NO:43. In some embodiments, the polypeptide comprises at least 90% sequence identity to SEQ ID NO:44. In some embodiments, the polypeptide comprises at least 90% sequence identity to SEQ ID NO:45. In some embodiments, the polypeptide comprises at least 90% sequence identity to SEQ ID NO:46. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Methods of Using the Recombinant Cells to Produce Isoprene

Also provided herein are methods for producing isoprene comprising culturing any of the recombinant cells described herein. In one aspect, isoprene can be produced by culturing recombinant cells comprising one or more heterologous nucleic acids encoding any phosphoketolase polypeptide as described herein, one or more MVA pathway polypeptides, and an isoprene synthase polypeptide. In certain embodiments, the recombinant cells described herein comprise one or more copies of a heterologous nucleic acid encoding a phosphoketolase isolated from *Burkholderia phytofirmans*, *Lactobacillus buchneri*, *Bifidobacterium gallicum*, *Bifidobacterium dentium*, *Bifidobacterium bifidum*, and/or *Clostridium acetobutylicum*. In other embodiments, the recombinant cells described herein comprise one or more copies of a heterologous nucleic acid encoding a phosphoketolase isolated from *Mycobacterium gilvum*, *Shewanella baltica*, *Lactobacillus rhamnosus*, *Lactobacillus crispatus*, *Bifidobacterium longum*, *Leuconostoc citreum*, *Bradyrhizobium* sp., *Enterococcus faecium*, *Brucella microti*, *Lactobacillus salivarius*, *Streptococcus agalactiae*, *Rhodococcus imtechensis*, *Burkholderia xenovorans*, *Mycobacterium intracellulare*, *Nitrosomonas* sp., *Schizosaccharomyces pombe*, *Leuconostoc mesenteroides*, *Streptomyces* sp., *Lactobacillus buchneri*, *Streptomyces ghanaensis*, *Cyanothece* sp., and/or *Neosartorya fischeri*. In yet other embodiments, the recombinant cells described herein comprise one or more copies of a heterologous nucleic acid encoding a phosphoketolase isolated from *Enterococcus faecium*, *Listeria grayi*, *Enterococcus gallinarum*, *Enterococcus saccharolyticus*, *Enterococcus casseliflavus*, *Mycoplasma alligatoris*, *Carnobacterium* sp., *Melissococcus plutonius*, *Tetragenococcus halophilus*, and/or *Mycoplasma arthritidis*. In one embodiment, the recombinant cells comprise one or more copies of a heterologous nucleic acid encoding a phosphoketolase isolated from *Streptococcus agalactiae*, *Mycoplasma agalactiae*, *Streptococcus gordonii*, *Kingella oralis*, *Mycoplasma fermentans*, *Granulicatella adiacens*, *Mycoplasma* hominis, *Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*.

In another aspect, isoprene can be produced by culturing recombinant cells comprising modulation in any of the enzymatic pathways described herein and one or more heterologous nucleic acids encoding a phosphoketolase peptide, a MVA pathway polypeptide, and an isoprene synthase polypeptide. In certain embodiments, the recombinant cells described herein comprise one or more copies of a heterologous nucleic acid encoding a phosphoketolase isolated from *Burkholderia phytofirmans, Lactobacillus buchneri, Bifidobacterium gallicum, Bifidobacterium dentium, Bifidobacterium bifidum*, and/or *Clostridium acetobutylicum*. In other embodiments, the recombinant cells described herein comprise one or more copies of a heterologous nucleic acid encoding a phosphoketolase isolated from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In yet other embodiments, the recombinant cells described herein comprise one or more copies of a heterologous nucleic acid encoding a phosphoketolase isolated from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus*, and/or *Mycoplasma arthritidis*. In one embodiment, the recombinant cells comprise one or more copies of a heterologous nucleic acid encoding a phosphoketolase isolated from *Streptococcus agalactiae, Mycoplasma agalactiae, Streptococcus gordonii, Kingella oxalis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*. The isoprene can be produced from any of the cells described herein and according to any of the methods described herein. Any of the cells can be used for the purpose of producing isoprene from carbohydrates, including, but not limited to, six carbon sugars such as glucose and/or five carbon sugars such as xylose.

Thus, provided herein are methods of producing isoprene comprising culturing cells comprising one or more heterologous nucleic acids encoding a phosphoketolase polypeptide and an isoprene synthase in a suitable condition for producing isoprene and (b) producing isoprene. In certain embodiments, the recombinant cells described herein comprise one or more copies of a heterologous nucleic acid encoding a phosphoketolase isolated from *Burkholderia phytofirmans, Lactobacillus buchneri, Bifidobacterium gallicum, Bifidobacterium dentium, Bifidobacterium bifidum*, and/or *Clostridium acetobutylicumi*. In other embodiments, the recombinant cells described herein comprise one or more copies of a heterologous nucleic acid encoding a phosphoketolase isolated from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In yet other embodiments, the recombinant cells described herein comprise one or more copies of a heterologous nucleic acid encoding a phosphoketolase isolated from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus*, and/or *Mycoplasma arthritidis*. In one embodiment, the recombinant cells comprise one or more copies of a heterologous nucleic acid encoding a phosphoketolase isolated from *Streptococcus agalactiae, Mycoplasma agalactiae, Streptococcus gordonii, Kingella oxalis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*.

The cells can further comprise one or more nucleic acid molecules encoding the MVA pathway polypeptide(s) described above (e.g., the complete MVA pathway) and any of the isoprene synthase polypeptide(s) described above (e.g. *Pueraria* isoprene synthase). In some aspects, the recombinant cells can be one of any of the cells described herein. Any of the isoprene synthases or variants thereof described herein, any of the host cell strains described herein, any of the promoters described herein, and/or any of the vectors described herein can also be used to produce isoprene using any of the energy sources (e.g. glucose or xylose) described herein can be used in the methods described herein. In some aspects, the method of producing isoprene further comprises a step of recovering the isoprene. In other embodiments, the phosphoketolase polypeptide is from *Burkholderia phytofirmans, Lactobacillus buchneri, Bifidobacterium gallicum, Bifidobacterium dentium, Bifidobacterium bifidum, Clostridium acetobutylicum, Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., *Neosartorya fischeri, Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus, Mycoplasma arthritidis, Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*.

In certain aspects, provided herein are methods of making isoprene comprising culturing recombinant cells comprising one or more heterologous nucleic acids encoding a phosphoketolase polypeptide from *Burkholderia phytofirmans, Lactobacillus buchneri, Bifidobacterium gallicum, Bifidobacterium dentium, Bifidobacterium bifidum, Clostridium acetobutylicum, Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., *Neosartorya fischeri, Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus, Mycoplasma arthritidis, Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*, an mvaE and an mvaS polypeptide from *L. grayi, E. faecium, E. gallinarum, E. casseliflavus*, and/or *E. faecalis*, in a suitable condition for producing isoprene and (b) producing isoprene. The cells can further comprise one or more nucleic acid molecules encoding the lower MVA pathway polypeptide(s) described above (e.g., MVK, PMK, MVD, and/or IDI) and any of the isoprene synthase polypeptide(s) described above. In some aspects, the recombinant cells can be any of the cells described herein.

In certain aspects, provided herein are methods of making isoprene comprising culturing recombinant cells comprising one or more heterologous nucleic acids encoding a phosphoketolase polypeptide from *Burkholderia phytofirmans, Lactobacillus buchneri, Bifidobacterium gallicum, Bifidobacterium dentium, Bifidobacterium bifidum, Clostridium acetobutylicum, Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., *Neosartorya fischeri, Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus, Mycoplasma arthritidis, Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*, in a suitable condition for producing isoprene and (b) producing isoprene. The cells can further comprise one or more nucleic acid molecules encoding the lower MVA pathway polypeptide(s) described above (e.g., MVK, PMK, MVD, and/or IDI) and any of the isoprene synthase polypeptide(s) described above. In some aspects, the recombinant cells can be any of the cells described herein.

The recombinant cells described herein that have various enzymatic pathways manipulated for increased carbon flow through the phosphoketolase pathway to mevalonate production can be used to produce isoprene. In some aspects, the recombinant cells can be further engineered to increase the activity of one or more of the following genes selected from the group consisting of rribose-5-phosphate isomerase (rpiA and/or rpiB), D-ribulose-5-phosphate 3-epimerase (rpe), transketolase (tktA and/or tktB), transaldolase B (tal B), phosphate acetyltransferase (pta and/or eutD). In another embodiment, these recombinant cells can be further engineered to decrease the activity of one or more genes of the following genes including glucose-6-phosphate dehydrogenase (zwf), 6-phosphofructokinase-1 (pfkA and/or pfkB), fructose bisphosphate aldolase (fba, fbaA, fbaB, and/or fbaC), glyceraldehyde-3-phosphate dehydrogenase (gapA and/or gapB), acetate kinase (ackA), citrate synthase (gltA), EI (ptsI), EIICB$^{Glc}$ (ptsG), EIIA$^{Glc}$ (crr), and/or HPr (ptsH).

In some aspects, the amount of isoprene produced is measured at the peak absolute productivity time point. In some aspects, the peak absolute productivity for the cells is about any of the amounts of isoprene disclosed herein. In some aspects, the amount of isoprene produced is measured at the peak specific productivity time point. In some aspects, the peak specific productivity for the cells is about any of the amounts of isoprene per cell disclosed herein. In some aspects, the cumulative, total amount of isoprene produced is measured. In some aspects, the cumulative total productivity for the cells is about any of the amounts of isoprene disclosed herein.

In some aspects, any of the cells described herein (for examples the cells in culture) produce isoprene at greater than about any of or about any of 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, or more nmole of isoprene/gram of cells for the wet weight of the cells/hour (nmole/$g_{wcm}$/hr). In some aspects, the amount of isoprene is between about 2 to about 5,000 nmole/$g_{wcm}$/hr, such as between about 2 to about 100 nmole/$g_{wcm}$/hr, about 100 to about 500 nmole/$g_{wcm}$/hr, about 150 to about 500 nmole/$g_{wcm}$/hr, about 500 to about 1,000 nmole/$g_{wcm}$/hr, about 1,000 to about 2,000 nmole/$g_{wcm}$/hr, or about 2,000 to about 5,000 nmole/$g_{wcm}$/hr. In some aspects, the amount of isoprene is between about 20 to about 5,000 nmole/$g_{wcm}$/hr, about 100 to about 5,000 nmole/$g_{wcm}$/hr, about 200 to about 2,000 nmole/$g_{wcm}$/hr, about 200 to about 1,000 nmole/$g_{wcm}$/hr, about 300 to about 1,000 nmole/$g_{wcm}$/hr, or about 400 to about 1,000 nmole/$g_{wcm}$/hr.

In some aspects, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/$g_{wcm}$/h). In some aspects, the amount of isoprene is between about 2 to about 5,000 ng/$g_{wcm}$/h, such as between about 2 to about 100 ng/$g_{wcm}$/h, about 100 to about 500 ng/$g_{wcm}$/h, about 500 to about 1,000 ng/$g_{wcm}$/h, about 1,000 to about 2,000 ng/$g_{wcm}$/h, or about 2,000 to about 5,000 ng/$g_{wcm}$/h. In some aspects, the amount of isoprene is between about 20 to about 5,000 ng/$g_{wcm}$/h, about 100 to about 5,000 ng/$g_{wcm}$/h, about 200 to about 2,000 ng/$g_{wcm}$/h, about 200 to about 1,000 ng/$g_{wcm}$/h, about 300 to about 1,000 ng/$g_{wcm}$/h, or about 400 to about 1,000 ng/$g_{wcm}$/h.

In some aspects, the cells in culture produce a cumulative titer (total amount) of isoprene at greater than about any of or about any of 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/$L_{broth}$, wherein the volume of broth includes the volume of the cells and the cell medium). In some aspects, the amount of isoprene is between about 2 to about 5,000 mg/$L_{broth}$, such as between about 2 to about 100 mg/$L_{broth}$, about 100 to about 500 mg/$L_{broth}$, about 500 to about 1,000 mg/$L_{broth}$, about 1,000 to about 2,000 mg/$L_{broth}$, or about 2,000 to about 5,000 mg/$L_{broth}$. In some aspects, the amount of isoprene is between about 20 to about 5,000 mg/$L_{broth}$, about 100 to about 5,000 mg/$L_{broth}$, about 200 to about 2,000 mg/$L_{broth}$, about 200 to about 1,000 mg/$L_{broth}$, about 300 to about 1,000 mg/$L_{broth}$, or about 400 to about 1,000 mg/$L_{broth}$.

In some aspects, the isoprene produced by the cells in culture comprises at least about 1, 2, 5, 10, 15, 20, or 25% by volume of the fermentation offgas. In some aspects, the isoprene comprises between about 1 to about 25% by volume of the offgas, such as between about 5 to about 15%, about 15 to about 25%, about 10 to about 20%, or about 1 to about 10%.

In certain embodiments, the methods of producing isoprene can comprise the steps of: (a) culturing recombinant cells (including, but not limited to, *E. coli* cells) that do not endogenously express a phosphoketolase polypeptide, wherein the cells heterologously express one or more copies of a gene encoding a phosphoketolase polypeptide along with (i) one or more nucleic acids expressing one or more MVA pathway peptides and (ii) an isoprene synthase and (b) producing isoprene, wherein the recombinant cells display decreased oxygen uptake rate (OUR) as compared to that of the same cells lacking one or more heterologous copies of a gene encoding an phosphoketolase polypeptide. In certain embodiments, the recombinant cells expressing one or more heterologous copies of a gene encoding an phosphoketolase polypeptide display up to 1-fold, 2-fold, 3-fold, 4-fold, 5-fold, 6-fold or 7-fold decrease in OUR as compared to recombinant cells that do not express a phosphoketolase.

Also provided herein are methods for the production of isoprene comprising cells having enhanced isoprene production capabilities. The production of isoprene by the cells described herein can be enhanced by the expression of one or more heterologous nucleic acids encoding a phosphoketolase polypeptide, one or more copies of a heterologous nucleic acid encoding one or more polypeptides of the complete MVA pathway polypeptide, and one or more heterologous nucleic acids encoding an isoprene synthase polypeptide. In certain embodiments, the phosphoketolase polypeptide is from *Burkholderia phytofirmans, Lactobacillus buchneri, Bifidobacterium gallicum, Bifidobacterium dentium, Bifidobacterium bifidum*, and/or *Clostridium acetobutylicum*. In some embodiments, the phosphoketolase polypeptide is from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In yet other embodiments, the phosphoketolase is from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus*, and/or *Mycoplasma arthritidis*. In yet other embodiments, the phosphoketolase is from *Streptococcus agalactiae, Mycoplasma agalactiae, Streptococcus gordonii, Kingella oxalis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma columbinum*. As used herein, "enhanced" isoprene production refers to an increased cell productivity index (CPI) for isoprene, an increased titer of isoprene, an increased mass yield of isoprene, and/or an increased specific productivity of isoprene by the cells described by any of the compositions and methods described herein compared to cells which do not have one or more heterologous nucleic acids encoding a phosphoketolase polypeptide, a MVA pathway polypeptide(s) and an isoprene synthase polypeptide. The production of isoprene can be enhanced by about 5% to about 1,000,000 folds. The production of isoprene can be enhanced by about 10% to about 1,000,000 folds (e.g., about 50% to about 1,000,000 folds, about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprene by the isoprene-producing cells that do not endogenously express phosphoketolase enzyme. In certain embodiments described herein, the methods described herein comprise host cells have been further engineered to increased carbon flux through the phosphoketolase pathway to MVA production thereby providing enhanced production of isoprene as compared to the production of isoprene by isoprene-producing cells that do not express one or more heterologous nucleic acids encoding phosphoketolase peptide and which have not been engineered for increased carbon flux through the phosphoketolase pathway to mevalonate production.

In other aspects, the methods described herein are directed to the enhanced production of isoprene by the cells described herein (e.g., enhanced by the expression of one or more heterologous nucleic acids encoding a phosphoketolase polypeptide). In certain embodiments, the phosphoketolase polypeptide is from *Burkholderia phytofirmans, Lactobacillus buchneri, Bifidobacterium gallicum, Bifidobacterium dentium, Bifidobacterium bifidum*, and/or *Clostridium acetobutylicum*. In some embodiments, the phosphoketolase polypeptide is from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In yet other embodiments, the phosphoketolase is from *Enterococcus faecium, Listeria grayi, Enterococcus gallinarum, Enterococcus saccharolyticus, Enterococcus casseliflavus,*

*Mycoplasma alligatoris*, *Carnobacterium* sp., *Melissococcus plutonius*, *Tetragenococcus halophilus*, and/or *Mycoplasma arthritidis*. In yet other embodiments, the phosphoketolase is from *Streptococcus agalactiae*, *Mycoplasma agalactiae*, *Streptococcus gordonii*, *Kingella oxalis*, *Mycoplasma fermentans*, *Granulicatella adiacens*, *Mycoplasma hominis*, *Mycoplasma crocodyli*, *Mycobacterium bovis*, *Neisseria* sp., *Streptococcus* sp., *Eremococcus coleocola*, *Granulicatella elegans*, *Streptococcus parasanguinis*, *Aerococcus urinae*, *Kingella kingae*, *Streptococcus australis*, *Streptococcus criceti*, and/or *Mycoplasma columbinum*. The production of isoprene can be enhanced by about 5% to about 1,000,000 folds. The production of isoprene can be enhanced by about 10% to about 1,000,000 folds (e.g., about 50% to about 1,000,000 folds, about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprene by an isoprene-producing cells without the expression of one or more heterologous nucleic acids encoding a phosphoketolase polypeptide. The production of isoprene can also enhanced by at least about any of 5%, 10%, 20%, 30%, 40%, 50%, 60%, 70%, 80%, 90%, 1 fold, 2 folds, 5 folds, 10 folds, 20 folds, 50 folds, 100 folds, 200 folds, 500 folds, 1000 folds, 2000 folds, 5000 folds, 10,000 folds, 20,000 folds, 50,000 folds, 100,000 folds, 200,000 folds, 500,000 folds, or 1,000,000 folds compared to the production of isoprene by isoprene-producing cells without the expression of one or more heterologous nucleic acids encoding phosphoketolase. In certain embodiments described herein, the methods described herein comprise host cells have been further engineered to increased carbon flux to MVA production thereby providing enhanced production of isoprene as compared to the production of isoprene by cells that do not express one or more heterologous nucleic acids encoding phosphoketolase peptide and which have not been engineered for increased carbon flux to mevalonate production.

In addition, more specific cell culture conditions can be used to culture the cells in the methods described herein. For example, in some aspects, the method for the production of isoprene comprises the steps of (a) culturing recombinant cells (including, but not limited to, *E. coli* cells) that do not endogenously have a phosphoketolase gene in minimal medium at 34° C., wherein the recombinant cells heterologously express (i) one or more copies of a heterologous gene encoding a phosphoketolase polypeptide on a low to medium copy plasmid and under the control of a strong promoter, (ii) one or more copies of a heterologous nucleic acid encoding one or more polypeptides of the MVA pathway polypeptide (upper MVA pathway and lower MVA pathway), and (iii) one or more heterologous nucleic acids encoding an isoprene synthase polypeptide; and (b) producing isoprene. In certain embodiments, the phosphoketolase polypeptide is from *Burkholderia phytofirmans*, *Lactobacillus buchneri*, *Bifidobacterium gallicum*, *Bifidobacterium dentium*, *Bifidobacterium bifidum*, and/or *Clostridium acetobutylicum*. In some embodiments, the phosphoketolase polypeptide is from *Mycobacterium gilvum*, *Shewanella baltica*, *Lactobacillus rhamnosus*, *Lactobacillus crispatus*, *Bifidobacterium longum*, *Leuconostoc citreum*, *Bradyrhizobium* sp., *Enterococcus faecium*, *Brucella microti*, *Lactobacillus salivarius*, *Streptococcus agalactiae*, *Rhodococcus imtechensis*, *Burkholderia xenovorans*, *Mycobacterium intracellulare*, *Nitrosomonas* sp., *Schizosaccharomyces pombe*, *Leuconostoc mesenteroides*, *Streptomyces* sp., *Lactobacillus buchneri*, *Streptomyces ghanaensis*, *Cyanothece* sp., and/or *Neosartorya fischeri*. In yet other embodiments, the phosphoketolase is from *Enterococcus faecium*, *Listeria grayi*, *Enterococcus gallinarum*, *Enterococcus saccharolyticus*, *Enterococcus casseliflavus*, *Mycoplasma alligatoris*, *Carnobacterium* sp., *Melissococcus plutonius*, *Tetragenococcus halophilus*, and/or *Mycoplasma arthritidis*. In yet other embodiments, the phosphoketolase is from *Streptococcus agalactiae*, *Mycoplasma agalactiae*, *Streptococcus gordonii*, *Kingella oxalis*, *Mycoplasma fermentans*, *Granulicatella adiacens*, *Mycoplasma hominis*, *Mycoplasma crocodyli*, *Mycobacterium bovis*, *Neisseria* sp., *Streptococcus* sp., *Eremococcus coleocola*, *Granulicatella elegans*, *Streptococcus parasanguinis*, *Aerococcus urinae*, *Kingella kingae*, *Streptococcus australis*, *Streptococcus criceti*, and/or *Mycoplasma columbinum*. In some aspects, the method of producing isoprene further comprises a step of recovering the isoprene.

Also provided herein are methods for producing isoprene comprising culturing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:8, (ii) one or more nucleic acids encoding one or more polypeptides of the complete MVA pathway, and (iii) one or more heterologous nucleic acids encoding an isoprene synthase polypeptide, wherein said recombinant cell comprising said polypeptide having phosphoketolase activity of (i) has a Performance Index value of greater than 1.0 in one or more of the following parameters: (a) cell growth on glucose, (b) cell growth on xylose, (c) production of intracellular acetyl-phosphate or (d) cell growth on glucose-6-phosphate and producing said isoprene. In other embodiments, the Performance Index value parameters further include (e) isoprene yield protein solubility or (f) isoprene specific productivity. In some embodiments, the polypeptide comprises at least 90% sequence identity to SEQ ID NO:23. In some embodiments, the polypeptide comprises at least 90% sequence identity to SEQ ID NO:24. In some embodiments, the polypeptide comprises at least 90% sequence identity to SEQ ID NO:25. In some embodiments, the polypeptide comprises at least 90% sequence identity to SEQ ID NO:26. In some embodiments, the polypeptide comprises at least 90% sequence identity to SEQ ID NO:27. In some embodiments, the polypeptide comprises at least 90% sequence identity to SEQ ID NO:28. In some embodiments, the polypeptide comprises at least 90% sequence identity to SEQ ID NO:29. In some embodiments, the polypeptide comprises at least 90% sequence identity to SEQ ID NO:30. In some embodiments, the polypeptide comprises at least 90% sequence identity to SEQ ID NO:31. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Additionally provided herein are methods for producing isoprene comprising culturing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:8 and, (ii) one or more nucleic acids encoding one or more polypeptides of the complete MVA pathway, and (iii) one or more heterologous nucleic acids encoding an isoprene synthase polypeptide, wherein said polypeptide having phosphoketolase activity of (i) has a Performance Index value of greater than 1.0 in one or more of the following parameters: (a) protein solubility, (b) protein expression, or (c) fructose-6-phosphate (F6P) Specific Activity and producing said isoprene. In other embodiments, the Performance Index value parameters further include (d) isoprene yield protein solubility or (e) isoprene specific productivity. In some embodiments, the polypeptide comprises at least 90% sequence identity to SEQ ID NO:23. In some embodiments, the polypeptide comprises at least 90% sequence identity to SEQ ID NO:24. In some embodiments, the polypeptide comprises at least 90% sequence identity to SEQ ID NO:25. In some embodiments, the polypeptide comprises at least 90% sequence identity to SEQ ID NO:26. In some embodiments, the polypeptide comprises at least 90% sequence identity to SEQ ID NO:27. In some embodiments, the polypeptide comprises at least 90% sequence identity to SEQ ID NO:28. In some embodiments, the polypeptide comprises at least 90% sequence identity to SEQ ID NO:29. In some embodiments, the polypeptide comprises at least 90% sequence identity to SEQ ID NO:30. In some embodiments, the polypeptide comprises at least 90% sequence identity to SEQ ID NO:31. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Further provided herein are methods for producing isoprene comprising culturing recombinant cells capable of increased carbon flux through the phosphoketolase pathway, wherein the recombinant cell comprises: (i) a heterologous nucleic acid sequence encoding a polypeptide having phosphoketolase activity, wherein the polypeptide comprises at least 65% sequence identity to SEQ ID NO:11, (ii) one or more nucleic acids encoding one or more polypeptides of the complete MVA pathway, and (iii) one or more heterologous nucleic acids encoding an isoprene synthase polypeptide, wherein said recombinant cell comprising said polypeptide having phosphoketolase activity of (i) has a Performance Index value of greater than 1.0 in one or more of the following parameters: (a) cell growth on glucose, (b) cell growth on xylose, (c) production of intracellular acetyl-phosphate or (d) cell growth on glucose-6-phosphate and producing said isoprene. In other embodiments, the Performance Index value parameters further include (e) isoprene yield protein solubility or (f) isoprene specific productivity. In some embodiments, the polypeptide comprises at least 90% sequence identity to SEQ ID NO:32. In some embodiments, the polypeptide comprises at least 90% sequence identity to SEQ ID NO:33. In some embodiments, the polypeptide comprises at least 90% sequence identity to SEQ ID NO:34. In some embodiments, the polypeptide comprises at least 90% sequence identity to SEQ ID NO:35. In some embodiments, the polypeptide comprises at least 90% sequence identity to SEQ ID NO:36. In some embodiments, the polypeptide comprises at least 90% sequence identity to SEQ ID NO:37. In some embodiments, the polypeptide comprises at least 90% sequence identity to SEQ ID NO:38. In some embodiments, the polypeptide comprises at least 90% sequence identity to SEQ ID NO:39. In some embodiments, the polypeptide comprises at least 90% sequence identity to SEQ ID NO:40. In some embodiments, the polypeptide comprises at least 90% sequence identity to SEQ ID NO:41. In some embodiments, the polypeptide comprises at least 90% sequence identity to SEQ ID NO:42. In some embodiments, the polypeptide comprises at least 90% sequence identity to SEQ ID NO:43. In some embodiments, the polypeptide comprises at least 90% sequence identity to SEQ ID NO:44. In some embodiments, the polypeptide comprises at least 90% sequence identity to SEQ ID NO:45. In some embodiments, the polypeptide comprises at least 90% sequence identity to SEQ ID NO:46. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Provided herein are methods for producing isoprene comprising culturing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:11, (ii) one or more nucleic acids encoding one or more polypeptides of the complete MVA pathway, and (iii) one or more heterologous nucleic acids encoding an isoprene synthase polypeptide, wherein said polypeptide having phosphoketolase activity of (i) has a Performance Index value of greater than 1.0 in one or more of the following parameters: (a) protein solubility, (b) protein expression, or (c) fructose-6-phosphate (F6P) Specific Activity and producing said isoprene. In other embodiments, the Performance Index value parameters further include (d) isoprene yield protein solubility or (e) isoprene specific productivity. In some embodiments, the polypeptide comprises at least 90% sequence identity to SEQ ID NO:32. In some embodiments, the polypeptide comprises at least 90% sequence identity to SEQ ID NO:33. In some embodiments, the polypeptide comprises at least 90% sequence identity to SEQ ID NO:34. In some embodiments, the polypeptide comprises at least 90% sequence identity to SEQ ID NO:35. In some embodiments, the polypeptide comprises at least 90% sequence identity to SEQ ID NO:36. In some embodiments, the polypeptide comprises at least 90% sequence identity to SEQ ID NO:37. In some embodiments, the polypeptide comprises at least 90% sequence identity to SEQ ID NO:38. In some embodiments, the polypeptide comprises at least 90% sequence identity to SEQ ID NO:39. In some embodiments, the polypeptide comprises at least 90% sequence identity to SEQ ID NO:40. In some embodiments, the polypeptide comprises at least 90% sequence identity to SEQ ID NO:41. In some embodiments, the polypeptide comprises at least 90% sequence identity to SEQ ID NO:42. In some embodiments, the polypeptide comprises at least 90% sequence identity to SEQ ID NO:43. In some embodiments, the polypeptide comprises at least 90% sequence identity to SEQ ID NO:44. In some embodiments, the polypeptide comprises at least 90% sequence identity to SEQ ID NO:45. In some embodiments, the polypeptide comprises at least 90% sequence identity to SEQ ID NO:46. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Recombinant Cells Capable of Increased Production of Isoprenoid Precursors and/or Isoprenoids Isoprenoids can be produced in many organisms from the synthesis of the isoprenoid precursor molecules which are the end products of the MVA pathway. As stated above, isoprenoids represent an important class of compounds and include, for example, food and feed supplements, flavor and odor compounds, and anticancer, antimalarial, antifungal, and antibacterial compounds.

As a class of molecules, isoprenoids are classified based on the number of isoprene units comprised in the compound. Monoterpenes comprise ten carbons or two isoprene units, sesquiterpenes comprise 15 carbons or three isoprene units, diterpenes comprise 20 carbons or four isoprene units, sesterterpenes comprise 25 carbons or five isoprene units, and so forth. Steroids (generally comprising about 27 carbons) are the products of cleaved or rearranged isoprenoids.

Isoprenoids can be produced from the isoprenoid precursor molecules IPP and DMAPP. These diverse compounds are derived from these rather simple universal precursors and are synthesized by groups of conserved polyprenyl pyrophosphate synthases (Hsieh et al., *Plant Physiol.* 2011 March; 155(3):1079-90). The various chain lengths of these linear prenyl pyrophosphates, reflecting their distinctive physiological functions, in general are determined by the highly developed active sites of polyprenyl pyrophosphate synthases via condensation reactions of allylic substrates (dimethylallyl diphosphate ($C_5$-DMAPP), geranyl pyrophosphate (Cio-GPP), farnesyl pyrophosphate (C15-FPP), geranylgeranyl pyrophosphate (C20-GGPP)) with corresponding number of isopentenyl pyrophosphates ($C_5$—IPP) (Hsieh et al., *Plant Physiol.* 2011 March; 155(3): 1079-90).

Production of isoprenoid precursors and/or isoprenoids can be made by using any of the recombinant host cells that comprise one or more copies of a heterologous nucleic acid encoding a phosphoketolase for increased production of isoprenoid precursors and/or isoprenoids. In some aspects, these cells further comprise one or more heterologous nucleic acids encoding polypeptides of the MVA pathway, IDI, and/or the DXP pathway, as described above, and a heterologous nucleic acid encoding a polyprenyl pyrophosphate synthase polypeptide. Without being bound to theory, it is thought that increasing the cellular production of mevalonate in recombinant cells by any of the compositions and methods described above will similarly result in the production of higher amounts of isoprenoid precursor molecules and/or isoprenoids. Increasing the molar yield of mevalonate production from glucose translates into higher molar yields of isoprenoid precursor molecules and/or isoprenoids, including isoprene, produced from glucose when combined with appropriate enzymatic activity levels of mevalonate kinase, phosphomevalonate kinase, diphosphomevalonate decarboxylase, isopentenyl diphosphate isomerase and other appropriate enzymes for isoprene and isoprenoid production. The recombinant cells described herein that have various enzymatic pathways manipulated for increased carbon flow to mevalonate production can be used to produce isoprenoid precursors and/or isoprenoids. In some aspects, the recombinant cells can be further engineered to increase the activity of one or more of the following genes selected from the group consisting of rpiA, rpe, tktA, tal B, pta and/or eutD. In another aspect, these strains can be further engineered to decrease the activity of one or more genes of the following genes including zwf, pfkA, fba, gapA, ackA, gltA and/or pts.

Types of Isoprenoids

The recombinant cells of the present invention are capable of increased production of isoprenoids and the isoprenoid precursor molecules DMAPP and IPP. Examples of isoprenoids include, without limitation, hemiterpenoids, monoterpenoids, sesquiterpenoids, diterpenoids, sesterterpenoids, triterpenoids, tetraterpenoids, and higher polyterpenoids. In some aspects, the hemiterpenoid is prenol (i.e., 3-methyl-2-buten-1-ol), isoprenol (i.e., 3-methyl-3-buten-1-ol), 2-methyl-3-buten-2-ol, or isovaleric acid. In some aspects, the monoterpenoid can be, without limitation, geranyl pyrophosphate, eucalyptol, limonene, or pinene. In some aspects, the sesquiterpenoid is farnesyl pyrophosphate, artemisinin, or bisabolol. In some aspects, the diterpenoid can be, without limitation, geranylgeranyl pyrophosphate, retinol, retinal, phytol, taxol, forskolin, or aphidicolin. In some aspects, the triterpenoid can be, without limitation, squalene or lanosterol. The isoprenoid can also be selected from the group consisting of abietadiene, amorphadiene, carene, α-farnesene, β-farnesene, farnesol, geraniol, geranylgeraniol, linalool, limonene, myrcene, nerolidol, ocimene, patchoulol, β-pinene, sabinene, γ-terpinene, terpindene and valencene.

In some aspects, the tetraterpenoid is lycopene or carotene (a carotenoid). As used herein, the term "carotenoid" refers to a group of naturally-occurring organic pigments produced in the chloroplasts and chromoplasts of plants, of some other photosynthetic organisms, such as algae, in some types of fungus, and in some bacteria. Carotenoids include the oxygen-containing xanthophylls and the non-oxygen-containing carotenes. In some aspects, the carotenoids are selected from the group consisting of xanthophylls and carotenes. In some aspects, the xanthophyll is lutein or zeaxanthin. In some aspects, the carotenoid is α-carotene, β-carotene, γ-carotene, β-cryptoxanthin or lycopene.

In other embodiments the isoprenoid can be a form of Vitamin A, such as, without limitation, retinol, retinyl palmitate, retinoic acid, alpha-carotene, beta-carotene, gamma-carotene, or the xanthophyll beta-cryptoxanthin. In yet other embodiments, the isoprenoid can be a form of Vitamin E, such as, without limitation a tocopherol (e.g., alpha-tocopherol, beta-tocopherol, gamma-tocopherol, or delta-tocopherol) or a tocotrienol (e.g., alpha-tocotrienol, beta-tocotrienol, gamma-tocotrienol, or delta-tocotrienol).

Heterologous Nucleic Acids Encoding Polyprenyl Pyrophosphate Synthases Polypeptides In some aspects of the invention, the cells described in any of the compositions or methods herein further comprise one or more nucleic acids encoding a phosphoketolase polypeptide, as described above, as well as one or more nucleic acids encoding a polyprenyl pyrophosphate synthase polypeptides(s). The polyprenyl pyrophosphate synthase polypeptide can be an endogenous polypeptide. The endogenous nucleic acid encoding a polyprenyl pyrophosphate synthase polypeptide can be operably linked to a constitutive promoter or can similarly be operably linked to an inducible promoter. The endogenous nucleic acid encoding a polyprenyl pyrophosphate synthase polypeptide can additionally be operably linked to a strong promoter. Alternatively, the endogenous nucleic acid encoding a polyprenyl pyrophosphate synthase polypeptide can be operably linked to a weak promoter. In particular, the cells can be engineered to over-express the endogenous polyprenyl pyrophosphate synthase polypeptide relative to wild-type cells.

In some aspects, the polyprenyl pyrophosphate synthase polypeptide is a heterologous polypeptide. The cells of the present invention can comprise more than one copy of a heterologous nucleic acid encoding a polyprenyl pyrophosphate synthase polypeptide. In some aspects, the heterologous nucleic acid encoding a polyprenyl pyrophosphate synthase polypeptide is operably linked to a constitutive promoter. In some aspects, the heterologous nucleic acid encoding a polyprenyl pyrophosphate synthase polypeptide is operably linked to an inducible promoter. In some aspects, the heterologous nucleic acid encoding a polyprenyl pyrophosphate synthase polypeptide is operably linked to a strong promoter. In some aspects, the heterologous nucleic acid encoding a polyprenyl pyrophosphate synthase polypeptide is operably linked to a weak promoter.

The nucleic acids encoding a polyprenyl pyrophosphate synthase polypeptide(s) can be integrated into a genome of the host cells or can be stably expressed in the cells. The nucleic acids encoding a polyprenyl pyrophosphate synthase polypeptide(s) can additionally be on a vector.

Exemplary polyprenyl pyrophosphate synthase nucleic acids include nucleic acids that encode a polypeptide, fragment of a polypeptide, peptide, or fusion polypeptide that has at least one activity of a polyprenyl pyrophosphate synthase. Polyprenyl pyrophosphate synthase polypeptides convert isoprenoid precursor molecules into more complex isoprenoid compounds. Exemplary polyprenyl pyrophosphate synthase polypeptides include polypeptides, fragments of polypeptides, peptides, and fusions polypeptides that have at least one activity of an isoprene synthase polypeptide. Exemplary polyprenyl pyrophosphate synthase polypeptides and nucleic acids include naturally-occurring polypeptides and nucleic acids from any of the source organisms described herein. In addition, variants of polyprenyl pyrophosphate synthase can possess improved activity such as improved enzymatic activity. In some aspects, a polyprenyl pyrophosphate synthase variant has other improved properties, such as improved stability (e.g., thermo-stability), and/or improved solubility. Exemplary polyprenyl pyrophosphate synthase nucleic acids can include nucleic acids which encode polyprenyl pyrophosphate synthase polypeptides such as, without limitation, geranyl diphosphate (GPP) synthase, farnesyl pyrophosphate (FPP) synthase, and geranylgeranyl pyrophosphate (GGPP) synthase, or any other known polyprenyl pyrophosphate synthase polypeptide.

In some aspects of the invention, the cells described in any of the compositions or methods herein further comprise one or more nucleic acids encoding a farnesyl pyrophosphate (FPP) synthase. The FPP synthase polypeptide can be an endogenous polypeptide encoded by an endogenous gene. In some aspects, the FPP synthase polypeptide is encoded by an endogenous ispA gene in *E. coli*. The endogenous nucleic acid encoding an FPP synthase polypeptide can be operably linked to a constitutive promoter or can similarly be operably linked to an inducible promoter. The endogenous nucleic acid encoding an FPP synthase polypeptide can additionally be operably linked to a strong promoter. In particular, the cells can be engineered to over-express the endogenous FPP synthase polypeptide relative to wild-type cells.

In some aspects, the FPP synthase polypeptide is a heterologous polypeptide. The cells of the present invention can comprise more than one copy of a heterologous nucleic acid encoding a FPP synthase polypeptide. In some aspects, the heterologous nucleic acid encoding a FPP synthase polypeptide is operably linked to a constitutive promoter. In some aspects, the heterologous nucleic acid encoding a FPP synthase polypeptide is operably linked to an inducible promoter. In some aspects, the heterologous nucleic acid encoding a polyprenyl pyrophosphate synthase polypeptide is operably linked to a strong promoter.

The nucleic acids encoding an FPP synthase polypeptide can be integrated into a genome of the host cells or can be stably expressed in the cells. The nucleic acids encoding an FPP synthase can additionally be on a vector.

Standard methods can be used to determine whether a polypeptide has polyprenyl pyrophosphate synthase polypeptide activity by measuring the ability of the polypeptide to convert IPP into higher order isoprenoids in vitro, in a cell extract, or in vivo. These methods are well known in the art and are described, for example, in U.S. Pat. No. 7,915,026; Hsieh et al., *Plant Physiol.* 2011 March; 155(3):1079-90; Danner et al., *Phytochemistry.* 2011 Apr. 12 [Epub ahead of print]; Jones et al., *J Biol Chem.* 2011 Mar. 24 [Epub ahead of print]; Keeling et al., *BMC Plant Biol.* 2011 Mar. 7; 11:43; Martin et al., *BMC Plant Biol.* 2010 Oct. 21; 10:226; Kumeta & Ito, *Plant Physiol.* 2010 December; 154(4):1998-2007; and Köllner & Boland, *J Org Chem.* 2010 Aug. 20; 75(16):5590-600.

Recombinant Cells Capable of Increased Production of Isoprenoid Precursors and/or Isoprenoids The recombinant cells (e.g., recombinant bacterial cells) described herein (including host cells that have been engineered for increased carbon flux through the phosphoketolase pathway as described herein) have the ability to produce isoprenoid precursors and/or isoprenoids at an amount and/or concentration greater than that of the same cells lacking one or more copies of a heterologous nucleic acid encoding phosphoketolase, one or more copies of a heterologous nucleic acid encoding a MVA pathway polypeptide, and one or more heterologous nucleic acids encoding a polyprenyl pyrophosphate synthase polypeptide when cultured under the same conditions. In certain embodiments, the phosphoketolase polypeptide is from *Burkholderia phytofirmans, Lactobacillus buchneri, Bifidobacterium gallicum, Bifidobacterium dentium, Bifidobacterium bifidum,* and/or *Clostridium acetobutylicum*. In other embodiments, the phosphoketolase polypeptide is from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In other embodiments, the phosphoketolase polypeptide is from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus,* and/or *Mycoplasma arthritidis*. In other embodiments, the phosphoketolase polypeptide is from *Streptococcus agalactiae, Mycoplasma agalactiae, Streptococcus gordonii, Kingella oxalis, Mycoplasma fermentans, Granulicatella adiacens, Mycoplasma hominis, Mycoplasma crocodyli, Mycobacte-*

*rium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti,* and/or *Mycoplasma columbinum.*

In one embodiment, the recombinant cells comprise one or more copies of a heterologous nucleic acid encoding a phosphoketolase isolated from *Burkholderia phytofirmans.* In another embodiment, the recombinant cells comprise one or more copies of a heterologous nucleic acid encoding a phosphoketolase isolated from *Lactobacillus buchneri.* In still another embodiment, the recombinant cells comprise one or more copies of a heterologous nucleic acid encoding a phosphoketolase isolated from *Bifidobacterium gallicum.* In yet another embodiment, the recombinant cells comprise one or more copies of a heterologous nucleic acid encoding a phosphoketolase isolated from *Bifidobacterium dentium.* In another embodiment, the recombinant cells comprise one or more copies of a heterologous nucleic acid encoding a phosphoketolase isolated from *Bifidobacterium bifidum.* In still another embodiment, the recombinant cells comprise one or more copies of a heterologous nucleic acid encoding a phosphoketolase isolated from *Clostridium acetobutylicum.* In other embodiments, the recombinant cells described herein comprise one or more copies of a heterologous nucleic acid encoding a phosphoketolase isolated from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri.* In yet other embodiments, the recombinant cells described herein comprise one or more copies of a heterologous nucleic acid encoding a phosphoketolase isolated from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus,* and/or *Mycoplasma arthritidis.* In one embodiment, the recombinant cells comprise one or more copies of a heterologous nucleic acid encoding a phosphoketolase isolated from *Streptococcus agalactiae, Mycoplasma agalactiae, Streptococcus gordonii, Kingella oxalis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti,* and/or *Mycoplasma columbinum.* In another embodiment, the recombinant cell is a *Corynebacteria* spp. (e.g., *C. glutamicum*).

In some aspects, the one or more copies of a heterologous nucleic acid encoding phosphoketolase, one or more copies of a heterologous nucleic acid encoding a MVA pathway polypeptide, and one or more heterologous nucleic acids encoding a polyprenyl pyrophosphate synthase polypeptide are heterologous nucleic acids that are integrated into the host cell's chromosomal nucleotide sequence. In other aspects, the one or more heterologous nucleic acids are integrated into plasmid. In still other aspects, at least one of the one or more heterologous nucleic acids is integrated into the cell's chromosomal nucleotide sequence while at least one of the one or more heterologous nucleic acid sequences is integrated into a plasmid. The recombinant cells can produce at least 5% greater amounts of isoprenoid precursors and/or isoprenoids compared to isoprenoid precursor and/or isoprenoid-producing cells that do not comprise the phosphoketolase polypeptide. Alternatively, the recombinant cells can produce greater than about 1%, 2%, 3%, 4%, 5%, 6%, 7%, 8%, 9%, 10%, 11%, 12%, 13%, 14%, or 15% of isoprenoid precursors and/or isoprenoids, inclusive, as well as any numerical value in between these numbers.

In one aspect of the invention, provided herein are recombinant cells comprising one or more heterologous nucleic acids encoding a phosphoketolase polypeptide as described herein, one or more heterologous nucleic acids encoding a mevalonate (MVA) pathway polypeptide(s), one or more heterologous nucleic acids encoding a DXP pathway polypeptide(s), and one or more heterologous nucleic acids encoding a polyprenyl pyrophosphate synthase polypeptide. The cells can further comprise one or more heterologous nucleic acids encoding an IDI polypeptide. Any of the one or more heterologous nucleic acids can be operably linked to constitutive promoters, can be operably linked to inducible promoters, or can be operably linked to a combination of inducible and constitutive promoters. The one or more heterologous nucleic acids can additionally be operably linked to strong promoters, weak promoters, and/or medium promoters. One or more of the heterologous nucleic acids encoding phosphoketolase, a mevalonate (MVA) pathway polypeptide(s), a DXP pathway polypeptide(s), and an polyprenyl pyrophosphate synthase polypeptide can be integrated into a genome of the host cells or can be stably expressed in the cells. The one or more heterologous nucleic acids can additionally be on a vector.

The production of isoprenoids and/or isoprenoid precursors by the cells according to any of the compositions or methods described herein can be enhanced (e.g., enhanced by the expression of one or more heterologous nucleic acids encoding a phosphoketolase polypeptide, a polyprenyl pyrophosphate synthase polypeptide, MVA pathway polypeptide(s), and/or a DXP pathway polypeptide(s)). As used herein, "enhanced" isoprenoid precursors and/or isoprenoids production refers to an increased cell productivity index (CPI) for isoprenoid precursors and/or isoprenoids, an increased titer of isoprenoid precursors and/or isoprenoids, an increased mass yield of isoprenoid precursors and/or isoprenoids, and/or an increased specific productivity of isoprenoid precursors and/or isoprenoids by the cells described by any of the compositions and methods described herein compared to cells which do not have one or more heterologous nucleic acids encoding a phosphoketolase peptide. In certain embodiments described herein, the host cells have been further engineered increased carbon flux through the phosphoketolase pathway for E4P, GAP, Ac-P, and/or, acetyl-CoA production.

The production of isoprenoid precursors and/or isoprenoids by the recombinant cells described herein can be enhanced by about 5% to about 1,000,000 folds. In certain aspects, the production of isoprenoid precursors and/or isoprenoids can be enhanced by about 10% to about 1,000, 000 folds (e.g., about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprenoid precursors and/or isoprenoids by cells that do not express one or more heterologous nucleic acids encoding phosphoketolase peptide. In certain embodiments described herein, the host cells have been further engineered to increased carbon flux through the phosphoketolase pathway to MVA production thereby providing enhanced production of isoprenoid precursors and/or isoprenoids as compared to the production of isoprenoid precursors and/or isoprenoids by cells that do not express one or more heterologous nucleic acids encoding phosphoketolase peptide and which have not been engineered for increased carbon flux through the phosphoketolase pathway to mevalonate production.

In other aspects, the production of isoprenoid precursors and/or isoprenoids by the recombinant cells described herein can also be enhanced by at least about any of 5%, 10%, 20%, 30%, 40%, 50%, 60%, 70%, 80%, 90%, 1 fold, 2 folds, 5 folds, 10 folds, 20 folds, 50 folds, 100 folds, 200 folds, 500 folds, 1000 folds, 2000 folds, 5000 folds, 10,000 folds, 20,000 folds, 50,000 folds, 100,000 folds, 200,000 folds, 500,000 folds, or 1,000,000 folds as compared to the production of isoprenoid precursors and/or isoprenoids by cells that do not express one or more heterologous nucleic acids encoding phosphoketolase peptide. In certain embodiments described herein, the host cells have been further engineered increased carbon flux through the phosphoketolase pathway to MVA production thereby providing enhanced production of isoprenoid precursors and/or isoprenoids as compared to the production of isoprenoid precursors and/or isoprenoids by cells that do not express one or more heterologous nucleic acids encoding phosphoketolase peptide and which have not been engineered for increased carbon flux through the phosphoketolase pathway to mevalonate production.

In one aspect of the invention, there are provided recombinant cells comprising one or more heterologous nucleic acids encoding a phosphoketolase polypeptide, one or more heterologous nucleic acids encoding one or more complete MVA pathway polypeptide(s) (i.e., the upper MVA pathway and the lower MVA pathway), one or more heterologous nucleic acids encoding polyprenyl pyrophosphate synthase and/or one or more heterologous nucleic acids encoding a DXP pathway polypeptide(s). The cells can further comprise one or more heterologous nucleic acids encoding an IDI polypeptide. Additionally, the polyprenyl pyrophosphate synthase polypeptide can be an FPP synthase polypeptide. In certain embodiments, the phosphoketolase polypeptide is from *Burkholderia phytofirmans*, *Lactobacillus buchneri*, *Bifidobacterium gallicum*, *Bifidobacterium dentium*, *Bifidobacterium bifidum*, and/or *Clostridium acetobutylicum*. In other embodiments, the phosphoketolase polypeptide is from *Mycobacterium gilvum*, *Shewanella baltica*, *Lactobacillus rhamnosus*, *Lactobacillus crispatus*, *Bifidobacterium longum*, *Leuconostoc citreum*, *Bradyrhizobium* sp., *Enterococcus faecium*, *Brucella microti*, *Lactobacillus salivarius*, *Streptococcus agalactiae*, *Rhodococcus imtechensis*, *Burkholderia xenovorans*, *Mycobacterium intracellulare*, *Nitrosomonas* sp., *Schizosaccharomyces pombe*, *Leuconostoc mesenteroides*, *Streptomyces* sp., *Lactobacillus buchneri*, *Streptomyces ghanaensis*, *Cyanothece* sp., and/or *Neosartorya fischeri*. In other embodiments, the phosphoketolase polypeptide is from *Enterococcus faecium*, *Listeria grayi*, *Enterococcus gallinarum*, *Enterococcus saccharolyticus*, *Enterococcus casseliflavus*, *Mycoplasma alligatoris*, *Carnobacterium* sp., *Melissococcus plutonius*, *Tetragenococcus halophilus*, and/or *Mycoplasma arthritidis*. In other embodiments, the phosphoketolase polypeptide is from *Streptococcus agalactiae*, *Mycoplasma agalactiae*, *Streptococcus gordonii*, *Kingella oxalis*, *Mycoplasma fermentans*, *Granulicatella adiacens*, *Mycoplasma hominis*, *Mycoplasma crocodyli*, *Mycobacterium bovis*, *Neisseria* sp., *Streptococcus* sp., *Eremococcus coleocola*, *Granulicatella elegans*, *Streptococcus parasanguinis*, *Aerococcus urinae*, *Kingella kingae*, *Streptococcus australis*, *Streptococcus criceti*, and/or *Mycoplasma columbinum*. In one embodiment, the recombinant cells comprise one or more copies of a heterologous nucleic acid encoding a phosphoketolase isolated from *Burkholderia phytofirmans*. In another embodiment, the recombinant cells comprise one or more copies of a heterologous nucleic acid encoding a phosphoketolase isolated from *Lactobacillus buchneri*. In still another embodiment, the recombinant cells comprise one or more copies of a heterologous nucleic acid encoding a phosphoketolase isolated from *Bifidobacterium gallicum*. In yet another embodiment, the recombinant cells comprise one or more copies of a heterologous nucleic acid encoding a phosphoketolase isolated from *Bifidobacterium dentium*. In another embodiment, the recombinant cells comprise one or more copies of a heterologous nucleic acid encoding a phosphoketolase isolated from *Bifidobacterium bifidum*. In still another embodiment, the recombinant cells comprise one or more copies of a heterologous nucleic acid encoding a phosphoketolase isolated from *Clostridium acetobutylicum*. In other embodiments, the recombinant cells described herein comprise one or more copies of a heterologous nucleic acid encoding a phosphoketolase isolated from *Mycobacterium gilvum*, *Shewanella baltica*, *Lactobacillus rhamnosus*, *Lactobacillus crispatus*, *Bifidobacterium longum*, *Leuconostoc citreum*, *Bradyrhizobium* sp., *Enterococcus faecium*, *Brucella microti*, *Lactobacillus salivarius*, *Streptococcus agalactiae*, *Rhodococcus imtechensis*, *Burkholderia xenovorans*, *Mycobacterium intracellulare*, *Nitrosomonas* sp., *Schizosaccharomyces pombe*, *Leuconostoc mesenteroides*, *Streptomyces* sp., *Lactobacillus buchneri*, *Streptomyces ghanaensis*, *Cyanothece* sp., and/or *Neosartorya fischeri*. In yet other embodiments, the recombinant cells described herein comprise one or more copies of a heterologous nucleic acid encoding a phosphoketolase isolated from *Enterococcus faecium*, *Listeria grayi*, *Enterococcus gallinarum*, *Enterococcus saccharolyticus*, *Enterococcus casseliflavus*, *Mycoplasma alligatoris*, *Carnobacterium* sp., *Melissococcus plutonius*, *Tetragenococcus halophilus*, and/or *Mycoplasma arthritidis*. In one embodiment, the recombinant cells comprise one or more copies of a heterologous nucleic acid encoding a phosphoketolase isolated from *Streptococcus agalactiae*, *Mycoplasma agalactiae*, *Streptococcus gordonii*, *Kingella oxalis*, *Mycoplasma fermentans*, *Granulicatella adiacens*, *Mycoplasma hominis*, *Mycoplasma crocodyli*, *Mycobacterium bovis*, *Neisseria* sp., *Streptococcus* sp., *Eremococcus coleocola*, *Granulicatella elegans*, *Streptococcus parasanguinis*, *Aerococcus urinae*, *Kingella kingae*, *Streptococcus australis*, *Streptococcus criceti*, and/or *Mycoplasma columbinum*. In another embodiment, the recombinant cell is a *Corynebacteria* spp. (e.g., *C. glutamicum*). The one or more heterologous nucleic acids can additionally be on one or more vectors.

Provided herein are recombinant cells which can provide enhanced isoprenoid precursor and/or isoprenoid production. The production of isoprenoid precursors and/or isoprenoids by the cells can be enhanced by the expression of one or more heterologous nucleic acids encoding a phosphoketolase polypeptide, one or more heterologous nucleic acids encoding one or more polypeptide(s) of the complete MVA pathway (i.e., the upper MVA pathway and lower MVA pathway), and one or more heterologous nucleic acids encoding a polyprenyl pyrophosphate synthase polypeptide. In certain embodiments, the phosphoketolase polypeptide is from *Burkholderia phytofirmans*, *Lactobacillus buchneri*, *Bifidobacterium gallicum*, *Bifidobacterium dentium*, *Bifidobacterium bifidum*, and/or *Clostridium acetobutylicum*. In other embodiments, the phosphoketolase polypeptide is from *Mycobacterium gilvum*, *Shewanella baltica*, *Lactobacillus rhamnosus*, *Lactobacillus crispatus*, *Bifidobacterium longum*, *Leuconostoc citreum*, *Bradyrhizobium* sp., *Enterococcus faecium*, *Brucella microti*, *Lactobacillus salivarius*, *Streptococcus agalactiae*, *Rhodococcus imtechensis*, *Burkholderia xenovorans*, *Mycobacterium intracellulare*, *Nitrosomonas* sp., *Schizosaccharomyces pombe*, *Leuconostoc mesenteroides*, *Streptomyces* sp., *Lactobacillus buchneri*, *Streptomyces ghanaensis*, *Cyanothece* sp., and/or *Neosartorya fischeri*. In other embodiments, the phosphoketolase polypeptide is from *Enterococcus faecium*, *Listeria grayi*, *Enterococcus gallinarum*, *Enterococcus saccharolyticus*, *Enterococcus casseliflavus*, *Mycoplasma alligatoris*, *Carnobacterium* sp., *Melissococcus plutonius*, *Tetragenococcus halophilus*, and/or *Mycoplasma arthritidis*. In other embodiments, the phosphoketolase polypeptide is from *Streptococcus agalactiae*, *Mycoplasma agalactiae*, *Streptococcus gordonii*, *Kingella oxalis*, *Mycoplasma fermentans*, *Granulicatella adiacens*, *Mycoplasma hominis*, *Mycoplasma crocodyli*, *Mycobacterium bovis*, *Neisseria* sp., *Streptococcus* sp., *Eremococcus coleocola*, *Granulicatella elegans*, *Streptococcus parasanguinis*, *Aerococcus urinae*, *Kingella kingae*, *Streptococcus australis*, *Streptococcus criceti*, and/or *Mycoplasma columbinum*. In one embodiment, the recombinant cells comprise one or more copies of a heterologous nucleic acid encoding a phosphoketolase isolated from *Burkholderia phytofirmans*. In another embodiment, the recombinant cells comprise one or more copies of a heterologous nucleic acid encoding a phosphoketolase isolated from *Lactobacillus buchneri*. In still another embodiment, the recombinant cells comprise one or more copies of a heterologous nucleic acid encoding a phosphoketolase isolated from *Bifidobacterium gallicum*. In yet another embodiment, the recombinant cells comprise one or more copies of a heterologous nucleic acid encoding a phosphoketolase isolated from *Bifidobacterium dentium*. In another embodiment, the recombinant cells comprise one or more copies of a heterologous nucleic acid encoding a phosphoketolase isolated from *Bifidobacterium bifidum*. In still another embodiment, the recombinant cells comprise one or more copies of a heterologous nucleic acid encoding a phosphoketolase isolated from *Clostridium acetobutylicum*. In other embodiments, the recombinant cells described herein comprise one or more copies of a heterologous nucleic acid encoding a phosphoketolase isolated from *Mycobacterium gilvum*, *Shewanella baltica*, *Lactobacillus rhamnosus*, *Lactobacillus crispatus*, *Bifidobacterium longum*, *Leuconostoc citreum*, *Bradyrhizobium* sp., *Enterococcus faecium*, *Brucella microti*, *Lactobacillus salivarius*, *Streptococcus agalactiae*, *Rhodococcus imtechensis*, *Burkholderia xenovorans*, *Mycobacterium intracellulare*, *Nitrosomonas* sp., *Schizosaccharomyces pombe*, *Leuconostoc mesenteroides*, *Streptomyces* sp., *Lactobacillus buchneri*, *Streptomyces ghanaensis*, *Cyanothece* sp., and/or *Neosartorya fischeri*. In yet other embodiments, the recombinant cells described herein comprise one or more copies of a heterologous nucleic acid encoding a phosphoketolase isolated from *Enterococcus faecium*, *Listeria grayi*, *Enterococcus gallinarum*, *Enterococcus saccharolyticus*, *Enterococcus casseliflavus*, *Mycoplasma alligatoris*, *Carnobacterium* sp., *Melissococcus plutonius*, *Tetragenococcus halophilus*, and/or *Mycoplasma arthritidis*. In one embodiment, the recombinant cells comprise one or more copies of a heterologous nucleic acid encoding a phosphoketolase isolated from *Streptococcus agalactiae*, *Mycoplasma agalactiae*, *Streptococcus gordonii*, *Kingella oxalis*, *Mycoplasma fermentans*, *Granulicatella adiacens*, *Mycoplasma hominis*, *Mycoplasma crocodyli*, *Mycobacterium bovis*, *Neisseria* sp., *Streptococcus* sp., *Eremococcus coleocola*, *Granulicatella elegans*, *Streptococcus parasanguinis*, *Aerococcus urinae*, *Kingella kingae*, *Streptococcus australis*, *Streptococcus criceti*, and/or *Mycoplasma columbinum*. In another embodiment, the recombinant cell is a *Corynebacteria* spp. (e.g., *C. glutamicum*). As used herein, "enhanced" isoprenoid precursor and/or isoprenoid production refers to an increased cell productivity index (CPI) for isoprenoid precursor and/or isoprenoid production, an increased titer of isoprenoid precursors and/or isoprenoids, an increased mass yield of isoprenoid precursors and/or isoprenoids, and/or an increased specific productivity of isoprenoid precursors and/or isoprenoids by the cells described by any of the compositions and methods described herein compared to cells which do not have one or more heterologous nucleic acids encoding a phosphoketolase, one or more polypeptide(s) of the complete MVA pathway, and a polyprenyl pyrophosphate synthase polypeptide. The production of isoprenoid precursors and/or isoprenoids can be enhanced by about 5% to about 1,000,000 folds. The production of isoprenoid precursors and/or isoprenoids can be enhanced by about 10% to about 1,000,000 folds (e.g., about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprenoid and/or isoprenoid precursors by cells without the expression of one or more heterologous nucleic acids encoding a phosphoketolase. In certain embodiments described herein, the recombinant host cells have been further engineered to increased carbon flux to MVA production thereby providing enhanced production of isoprenoids and/or isoprenoid-precursors as compared to the production of isoprenoids and/or isoprenoid-precursors by isoprenoids and/or isoprenoid-precursors-producing cells that do not express one or more heterologous nucleic acids encoding phosphoketolase polypeptide and which have not been engineered for increased carbon flux to mevalonate production.

The production of isoprenoid precursors and/or isoprenoids by the cells described herein can be enhanced (e.g., enhanced by the expression of one or more heterologous nucleic acids encoding the phosphoketolase polypeptides from *Burkholderia phytofirmans*, *Lactobacillus buchneri*, *Bifidobacterium gallicum*, *Bifidobacterium dentium*, *Bifidobacterium bifidum*, *Clostridium acetobutylicum*, *Mycobacterium gilvum*, *Shewanella baltica*, *Lactobacillus rhamnosus*, *Lactobacillus crispatus*, *Bifidobacterium longum*, *Leuconostoc citreum*, *Bradyrhizobium* sp., *Enterococcus faecium*, *Brucella microti*, *Lactobacillus salivarius*, *Streptococcus agalactiae*, *Rhodococcus imtechensis*, *Burkholderia xenovorans*, *Mycobacterium intracellulare*, *Nitrosomonas* sp., *Schizosaccharomyces pombe*, *Leuconostoc mesenteroides*, *Streptomyces* sp., *Lactobacillus buchneri*, *Streptomyces ghanaensis*, *Cyanothece* sp., *Neosartorya fis-* cheri, Enterococcus faecium, Listeria grayi, Enterococcus gallinarum, Enterococcus saccharolyticus, Enterococcus casseliflavus, Mycoplasma alligatoris, Carnobacterium sp., Melissococcus plutonius, Tetragenococcus halophilus, Mycoplasma arthritidis, Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria sp., Streptococcus sp., Eremococcus coleocola, Granulicatella elegans, Streptococcus parasanguinis, Aerococcus urinae, Kingella kingae, Streptococcus australis, Streptococcus criceti, and/or Mycoplasma columbinum, one or more heterologous nucleic acids encoding a lower MVA pathway polypeptide, and one or more heterologous nucleic acids encoding a polyprenyl pyrophosphate synthase polypeptide). The production of isoprenoid precursors and/or isoprenoids can be enhanced by about 5% to about 1,000,000 folds. The production of isoprenoid precursors and/or isoprenoids can be enhanced by about 10% to about 1,000,000 folds (e.g., about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprenoid precursors and/or isoprenoids by naturally-occurring cells (e.g., cells without the expression of one or more heterologous nucleic acids encoding phosphoketolase polypeptide from Burkholderia phytofirmans, Lactobacillus buchneri, Bifidobacterium gallicum, Bifidobacterium dentium, Bifidobacterium bifidum, Clostridium acetobutylicum, Mycobacterium gilvum, Shewanella baltica, Lactobacillus rhamnosus, Lactobacillus crispatus, Bifidobacterium longum, Leuconostoc citreum, Bradyrhizobium sp., Enterococcus faecium, Brucella microti, Lactobacillus salivarius, Streptococcus agalactiae, Rhodococcus imtechensis, Burkholderia xenovorans, Mycobacterium intracellulare, Nitrosomonas sp., Schizosaccharomyces pombe, Leuconostoc mesenteroides, Streptomyces sp., Lactobacillus buchneri, Streptomyces ghanaensis, Cyanothece sp., Neosartorya fischeri, Enterococcus faecium, Listeria grayi, Enterococcus gallinarum, Enterococcus saccharolyticus, Enterococcus casseliflavus, Mycoplasma alligatoris, Carnobacterium sp., Melissococcus plutonius, Tetragenococcus halophilus, Mycoplasma arthritidis, Streptococcus agalactiae, Mycoplasma agalactiae, Streptococcus gordonii, Kingella oralis, Mycoplasma fermentans, Granulicatella adiacens, Mycoplasma hominis, Mycoplasma crocodyli, Mycobacterium bovis, Neisseria sp., Streptococcus sp., Eremococcus coleocola, Granulicatella elegans, Streptococcus parasanguinis, Aerococcus urinae, Kingella kingae, Streptococcus australis, Streptococcus criceti, and/or Mycoplasma columbinum along with one or more heterologous nucleic acids expressing one or more MVA pathway peptides and which have not been engineered for increased carbon flux to mevalonate production.

In other embodiments, the recombinant cells described herein can provide for the production of isoprenoid precursors and/or isoprenoids can also enhanced by at least about any of 5%, 10%, 20%, 30%, 40%, 50%, 60%, 70%, 80%, 90%, 1 fold, 2 folds, 5 folds, 10 folds, 20 folds, 50 folds, 100 folds, 200 folds, 500 folds, 1000 folds, 2000 folds, 5000 folds, 10,000 folds, 20,000 folds, 50,000 folds, 100,000 folds, 200,000 folds, 500,000 folds, or 1,000,000 folds compared to the production of isoprenoid precursors and/or isoprenoids by isoprenoid precursors and/or isoprenoids producing recombinant cells which do not express of one or more heterologous nucleic acids encoding a phosphoketolase polypeptide.

Also provided herein are isoprenoid and/or isoprenoid precursor-producing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:8, (ii) one or more nucleic acids encoding one or more polypeptides of the complete MVA pathway, and (iii) one or more nucleic acids encoding a polyprenyl pyrophosphate synthase polypeptide, wherein said recombinant cell comprising said polypeptide having phosphoketolase activity of (i) has a Performance Index value of greater than 1.0 in one or more of the following parameters: (a) cell growth on glucose, (b) cell growth on xylose, (c) production of intracellular acetyl-phosphate or (d) cell growth on glucose-6-phosphate. In some embodiments, the polypeptide comprises at least 90% sequence identity to SEQ ID NO:23. In some embodiments, the polypeptide comprises at least 90% sequence identity to SEQ ID NO:24. In some embodiments, the polypeptide comprises at least 90% sequence identity to SEQ ID NO:25. In some embodiments, the polypeptide comprises at least 90% sequence identity to SEQ ID NO:26. In some embodiments, the polypeptide comprises at least 90% sequence identity to SEQ ID NO:27. In some embodiments, the polypeptide comprises at least 90% sequence identity to SEQ ID NO:28. In some embodiments, the polypeptide comprises at least 90% sequence identity to SEQ ID NO:29. In some embodiments, the polypeptide comprises at least 90% sequence identity to SEQ ID NO:30. In some embodiments, the polypeptide comprises at least 90% sequence identity to SEQ ID NO:31. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from E. gallinarum). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Additionally provided herein are isoprenoid and/or isoprenoid precursor-producing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:8, (ii) one or more nucleic acids encoding one or more polypeptides of the complete MVA pathway, and (iii) one or more nucleic acids encoding a polyprenyl pyrophosphate synthase polypeptide, wherein said polypeptide having phosphoketolase activity of (i) has a Performance Index value of greater than 1.0 in one or more of the following parameters: (a) protein solubility, (b) protein expression, or (c) fructose-6-phosphate (F6P) Specific Activity. In some embodiments, the polypeptide comprises at least 90% sequence identity to SEQ ID NO:23. In some embodiments, the polypeptide comprises at least 90% sequence identity to SEQ ID NO:24. In some embodiments, the polypeptide comprises at least 90% sequence identity to SEQ ID NO:25. In some embodiments, the polypeptide comprises at least 90% sequence identity to SEQ ID NO:26. In some embodiments, the polypeptide comprises at least 90% sequence identity to SEQ ID NO:27. In some embodiments, the polypeptide comprises at least 90% sequence identity to SEQ ID NO:28. In some embodiments, the polypeptide comprises at least 90% sequence identity to SEQ ID NO:29. In some embodiments, the polypeptide comprises at least 90% sequence identity to SEQ ID NO:30. In some embodiments, the polypeptide comprises at least 90% sequence identity to SEQ ID NO:31. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Further provided herein are isoprenoid and/or isoprenoid precursor-producing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:11, (ii) one or more nucleic acids encoding one or more polypeptides of the complete MVA pathway, and (iii) one or more nucleic acids encoding a polyprenyl pyrophosphate synthase polypeptide, wherein said recombinant cell comprising said polypeptide having phosphoketolase activity of (i) has a Performance Index value of greater than 1.0 in one or more of the following parameters: (a) cell growth on glucose, (b) cell growth on xylose, (c) production of intracellular acetyl-phosphate or (d) cell growth on glucose-6-phosphate. In some embodiments, the polypeptide comprises at least 90% sequence identity to SEQ ID NO:32. In some embodiments, the polypeptide comprises at least 90% sequence identity to SEQ ID NO:33. In some embodiments, the polypeptide comprises at least 90% sequence identity to SEQ ID NO:34. In some embodiments, the polypeptide comprises at least 90% sequence identity to SEQ ID NO:35. In some embodiments, the polypeptide comprises at least 90% sequence identity to SEQ ID NO:36. In some embodiments, the polypeptide comprises at least 90% sequence identity to SEQ ID NO:37. In some embodiments, the polypeptide comprises at least 90% sequence identity to SEQ ID NO:38. In some embodiments, the polypeptide comprises at least 90% sequence identity to SEQ ID NO:39. In some embodiments, the polypeptide comprises at least 90% sequence identity to SEQ ID NO:40. In some embodiments, the polypeptide comprises at least 90% sequence identity to SEQ ID NO:41. In some embodiments, the polypeptide comprises at least 90% sequence identity to SEQ ID NO:42. In some embodiments, the polypeptide comprises at least 90% sequence identity to SEQ ID NO:43. In some embodiments, the polypeptide comprises at least 90% sequence identity to SEQ ID NO:44. In some embodiments, the polypeptide comprises at least 90% sequence identity to SEQ ID NO:45. In some embodiments, the polypeptide comprises at least 90% sequence identity to SEQ ID NO:46. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from E. gallinarum). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from E. gallinarum. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Provided herein are isoprenoid precursor and/or isoprenoid-producing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:11, (ii) one or more nucleic acids encoding one or more polypeptides of the complete MVA pathway, and (iii) one or more nucleic acids encoding a polyprenyl pyrophosphate synthase polypeptide, wherein said polypeptide having phosphoketolase activity of (i) has a Performance Index value of greater than 1.0 in one or more of the following parameters: (a) protein solubility, (b) protein expression, or (c) fructose-6-phosphate (F6P) Specific Activity. In some embodiments, the polypeptide comprises at least 90% sequence identity to SEQ ID NO:32. In some embodiments, the polypeptide comprises at least 90% sequence identity to SEQ ID NO:33. In some embodiments, the polypeptide comprises at least 90% sequence identity to SEQ ID NO:34. In some embodiments, the polypeptide comprises at least 90% sequence identity to SEQ ID NO:35. In some embodiments, the polypeptide comprises at least 90% sequence identity to SEQ ID NO:36. In some embodiments, the polypeptide comprises at least 90% sequence identity to SEQ ID NO:37. In some embodiments, the polypeptide comprises at least 90% sequence identity to SEQ ID NO:38. In some embodiments, the polypeptide comprises at least 90% sequence identity to SEQ ID NO:39. In some embodiments, the polypeptide comprises at least 90% sequence identity to SEQ ID NO:40. In some embodiments, the polypeptide comprises at least 90% sequence identity to SEQ ID NO:41. In some embodiments, the polypeptide comprises at least 90% sequence identity to SEQ ID NO:42. In some embodiments, the polypeptide comprises at least 90% sequence identity to SEQ ID NO:43. In some embodiments, the polypeptide comprises at least 90% sequence identity to SEQ ID NO:44. In some embodiments, the polypeptide comprises at least 90% sequence identity to SEQ ID NO:45. In some embodiments, the polypeptide comprises at least 90% sequence identity to SEQ ID NO:46. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from E. gallinarum). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from E. gallinarum. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Methods of Using the Recombinant Cells to Produce Isoprenoids and/or Isoprenoid Precursor Molecules Also provided herein are methods of producing isoprenoid precursor molecules and/or isoprenoids comprising culturing recombinant cells (e.g., recombinant bacterial cells) that comprise one or more heterologous nucleic acids encoding a phosphoketolase and an polyprenyl pyrophosphate synthase polypeptide. In certain embodiments, the recombinant cells further comprise one or more one or more heterologous nucleic acids encoding an upper MVA pathway polypeptide and a lower MVA pathway polypeptide. The isoprenoid precursor molecules and/or isoprenoids can be produced from any of the cells described herein and according to any of the methods described herein. Any of the cells can be used for the purpose of producing isoprenoid precursor molecules and/or isoprenoids from carbohydrates, including six carbon sugars such as glucose.

In certain aspects, provided herein are methods of making isoprenoid precursor molecules and/or isoprenoids comprising culturing recombinant cells comprising one or more heterologous nucleic acids encoding a phosphoketolase polypeptide from *Burkholderia phytofirmans, Lactobacillus buchneri, Bifidobacterium gallicum, Bifidobacterium dentium, Bifidobacterium bifidum, Clostridium acetobutylicum, Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., *Neosartorya fischeri, Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus, Mycoplasma arthritidis, Streptococcus agalactiae, Mycoplasma agalactiae, Streptococcus gordonii, Kingella oxalis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti,* and/or *Mycoplasma columbinum,* an mvaE and an mvaS polypeptide from *L. grayi, E. faecium, E. gallinarum, E. casseliflavus,* and/or *E. faecalis,* in a suitable condition for producing isoprenoid precursor molecules and/or isoprenoids, and (b) producing isoprenoid precursor molecules and/or isoprenoids. The cells can further comprise one or more nucleic acid molecules encoding the lower MVA pathway polypeptide(s) described above (e.g., MVK, PMK, MVD, and/or IDI) and any of the polyprenyl pyrophosphate synthase polypeptide(s) described above. In some aspects, the recombinant cells can be any of the cells described herein. Any of the polyprenyl pyrophosphate synthase or variants thereof described herein, any of the host cell strains described herein, any of the promoters described herein, and/or any of the vectors described herein can also be used to produce isoprenoid precursor molecules and/or isoprenoids using any of the energy sources (e.g. glucose or any other six carbon sugar) described herein. In some aspects, the method of producing isoprenoid precursor molecules and/or isoprenoids further comprises a step of recovering the isoprenoid precursor molecules and/or isoprenoids.

In certain aspects, provided herein are methods of making isoprenoid precursor molecules and/or isoprenoids comprising culturing recombinant cells comprising one or more heterologous nucleic acids encoding a phosphoketolase polypeptide from *Burkholderia phytofirmans, Lactobacillus buchneri, Bifidobacterium gallicum, Bifidobacterium dentium, Bifidobacterium bifidum, Clostridium acetobutylicum, Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., *Neosartorya fischeri, Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus, Mycoplasma arthritidis, Streptococcus agalactiae, Mycoplasma agalactiae, Streptococcus gordonii, Kingella oxalis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti,* and/or *Mycoplasma columbinum,* an mvaE and an mvaS polypeptide from *L. grayi, E. faecium, E. gallinarum, E. casseliflavus,* and/or *E. faecalis,* in a suitable condition for producing isoprenoid precursor molecules and/or isoprenoids, and (b) producing isoprenoid precursor molecules and/or isoprenoids. The cells can further comprise one or more nucleic acid molecules encoding the lower MVA pathway polypeptide(s) described above (e.g., MVK, PMK, MVD, and/or IDI) and any of the polyprenyl pyrophosphate synthase polypeptide(s) described above. In some aspects, the recombinant cells can be any of the cells described herein. Any of the polyprenyl pyrophosphate synthase or variants thereof described herein, any of the host cell strains described herein, any of the promoters described herein, and/or any of the vectors described herein can also be used to produce isoprenoid precursor molecules and/or isoprenoids using any of the energy sources (e.g. glucose or any other six carbon sugar) described herein. In some aspects, the method of producing isoprenoid precursor molecules and/or isoprenoids further comprises a step of recovering the isoprenoid precursor molecules and/or isoprenoids.

The method of producing isoprenoid precursor molecules and/or isoprenoids can similarly comprise the steps of: (a) culturing recombinant cells (including, but not limited to, *E. coli* cells) that do not endogenously have a phosphoketolase, wherein the recombinant cells heterologously express one or more copies of a gene encoding a phosphoketolase polypeptide; and (b) producing isoprenoid precursor molecules and/or isoprenoids, wherein the recombinant cells produce greater amounts of isoprenoid precursors and/or isoprenoids when compared to isoprenoids and/or isoprenoid precursor-producing cells that do not comprise the phosphoketolase polypeptide.

The instant methods for the production of isoprenoid precursor molecules and/or isoprenoids can produce at least 5% greater amounts of isoprenoid precursors and/or isoprenoids when compared to isoprenoids and/or isoprenoid precursor-producing recombinant cells that do not comprise a phosphoketolase polypeptide. Alternatively, the recombinant cells can produce greater than about 1%, 2%, 3%, 4%, 5%, 6%, 7%, 8%, 9%, 10%, 11%, 12%, 13%, 14%, or 15% of isoprenoid precursors and/or isoprenoids, inclusive. In some aspects, the method of producing isoprenoid precursor molecules and/or isoprenoids further comprises a step of recovering the isoprenoid precursor molecules and/or isoprenoids.

Provided herein are methods of using any of the cells described above for enhanced isoprenoid and/or isoprenoid precursor molecule production. The production of isoprenoid precursor molecules and/or isoprenoids by the cells can be enhanced by the expression of one or more heterologous nucleic acids encoding phosphoketolase, and/or the mvaE and mvaS polypeptides from *L. grayi, E. faecium, E. gallinarum, E. casseliflavus,* and/or *E. faecalis,* one or more heterologous nucleic acids encoding a lower MVA pathway polypeptide, and one or more heterologous nucleic acids encoding a polyprenyl pyrophosphate synthase polypeptide. As used herein, "enhanced" isoprenoid precursor and/or isoprenoid production refers to an increased cell productivity index (CPI) for isoprenoid precursor and/or isoprenoid production, an increased titer of isoprenoid precursors and/or isoprenoids, an increased mass yield of isoprenoid precursors and/or isoprenoids, and/or an increased specific productivity of isoprenoid precursors and/or isoprenoids by the cells described by any of the compositions and methods described herein compared to cells which do not have one or more heterologous nucleic acids encoding a phosphoketolase, a polyprenyl pyrophosphate synthase polypeptide, a lower MVA pathway polypeptide(s), the mvaE and mvaS polypeptides from *L. grayi*, *E. faecium*, *E. gallinarum*, *E. casseliflavus*. The production of isoprenoid precursor molecules and/or isoprenoids can be enhanced by about 5% to about 1,000,000 folds. The production of isoprenoid precursor molecules and/or isoprenoids can be enhanced by about 10% to about 1,000,000 folds (e.g., about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprenoid precursor molecules and/or isoprenoids by cells without the expression of one or more heterologous nucleic acids encoding a phosphoketolase polypeptide. In certain embodiments described herein, the methods comprise recombinant host cells that have been further engineered to increased carbon flux to MVA production thereby providing enhanced production of isoprenoids and/or isoprenoid-precursors as compared to the production of isoprenoids and/or isoprenoid-precursors by isoprenoids and/or isoprenoid-precursors-producing cells that do not express one or more heterologous nucleic acids encoding phosphoketolase peptide and which have not been engineered for increased carbon flux to mevalonate production.

The production of isoprenoid precursor molecules and/or isoprenoids can also enhanced by the methods described herein by at least about any of 10%, 20%, 30%, 40%, 50%, 60%, 70%, 80%, 90%, 1 fold, 2 folds, 5 folds, 10 folds, 20 folds, 50 folds, 100 folds, 200 folds, 500 folds, 1000 folds, 2000 folds, 5000 folds, 10,000 folds, 20,000 folds, 50,000 folds, 100,000 folds, 200,000 folds, 500,000 folds, or 1,000,000 folds compared to the production of isoprenoid precursor molecules and/or isoprenoids by isoprenoid precursors and/or isoprenoid-producing cells without the expression of one or more heterologous nucleic acids encoding a phosphoketolase polypeptide. In certain embodiments described herein, the methods comprise recombinant host cells that have been further engineered to increased carbon flux to MVA production thereby providing enhanced production of isoprenoids and/or isoprenoid-precursors as compared to the production of isoprenoids and/or isoprenoid-precursors by isoprenoids and/or isoprenoid-precursors-producing cells that do not express one or more heterologous nucleic acids encoding phosphoketolase peptide and which have not been engineered for increased carbon flux to mevalonate production.

In addition, more specific cell culture conditions can be used to culture the cells in the methods described herein. For example, in some aspects, the method for the production of isoprenoid precursor molecules and/or isoprenoids comprises the steps of (a) culturing recombinant cells (including, but not limited to, *E. coli* cells) which comprise a heterologous nucleic acid which encodes a phosphoketolase polypeptide and that do not endogenously have an mvaE gene and an mvaS gene from *L. grayi*, *E. faecium*, *E. gallinarum*, *E. casseliflavus*, and/or *E. faecalis* in minimal medium at 34° C., wherein the recombinant cells heterologously express one or more copies of a gene encoding a phosphoketolase polypeptide from *Burkholderia phytofirmans*, *Lactobacillus buchneri*, *Bifidobacterium gallicum*, *Bifidobacterium dentium*, *Bifidobacterium bifidum*, *Clostridium acetobutylicum*, *Mycobacterium gilvum*, *Shewanella baltica*, *Lactobacillus rhamnosus*, *Lactobacillus crispatus*, *Bifidobacterium longum*, *Leuconostoc citreum*, *Bradyrhizobium* sp., *Enterococcus faecium*, *Brucella microti*, *Lactobacillus salivarius*, *Streptococcus agalactiae*, *Rhodococcus imtechensis*, *Burkholderia xenovorans*, *Mycobacterium intracellulare*, *Nitrosomonas* sp., *Schizosaccharomyces pombe*, *Leuconostoc mesenteroides*, *Streptomyces* sp., *Lactobacillus buchneri*, *Streptomyces ghanaensis*, *Cyanothece* sp., *Neosartorya fischeri*, *Enterococcus faecium*, *Listeria grayi*, *Enterococcus gallinarum*, *Enterococcus saccharolyticus*, *Enterococcus casseliflavus*, *Mycoplasma alligatoris*, *Carnobacterium* sp., *Melissococcus plutonius*, *Tetragenococcus halophilus*, *Mycoplasma arthritidis*, *Streptococcus agalactiae*, *Mycoplasma agalactiae*, *Streptococcus gordonii*, *Kingella oralis*, *Mycoplasma fermentans*, *Granulicatella adiacens*, *Mycoplasma hominis*, *Mycoplasma crocodyli*, *Mycobacterium bovis*, *Neisseria* sp., *Streptococcus* sp., *Eremococcus coleocola*, *Granulicatella elegans*, *Streptococcus parasanguinis*, *Aerococcus urinae*, *Kingella kingae*, *Streptococcus australis*, *Streptococcus criceti*, and/or *Mycoplasma columbinum* on a low to medium copy plasmid and under the control of a strong promoter; and (b) producing isoprenoid precursor molecules and/or isoprenoids. In some aspects, the methods further comprise a step of recovering the isoprenoid precursor molecules and/or isoprenoids.

Also provided herein are methods for producing isoprenoid precursors and/or isoprenoids comprising culturing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:8, (ii) one or more nucleic acids encoding one or more polypeptides of the complete MVA pathway, and (iii) one or more nucleic acids encoding a polyprenyl pyrophosphate synthase polypeptide, wherein said recombinant cell comprising said polypeptide having phosphoketolase activity of (i) has a Performance Index value of greater than 1.0 in one or more of the following parameters: (a) cell growth on glucose, (b) cell growth on xylose, (c) production of intracellular acetyl-phosphate or (d) cell growth on glucose-6-phosphate and producing isoprenoid precursors and/or isoprenoids. In some embodiments, the polypeptide comprises at least 90% sequence identity to SEQ ID NO:23. In some embodiments, the polypeptide comprises at least 90% sequence identity to SEQ ID NO:24. In some embodiments, the polypeptide comprises at least 90% sequence identity to SEQ ID NO:25. In some embodiments, the polypeptide comprises at least 90% sequence identity to SEQ ID NO:26. In some embodiments, the polypeptide comprises at least 90% sequence identity to SEQ ID NO:27. In some embodiments, the polypeptide comprises at least 90% sequence identity to SEQ ID NO:28. In some embodiments, the polypeptide comprises at least 90% sequence identity to SEQ ID NO:29. In some embodiments, the polypeptide comprises at least 90% sequence identity to SEQ ID NO:30. In some embodiments, the polypeptide comprises at least 90% sequence identity to SEQ ID NO:31. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Additionally provided herein are methods for producing isoprenoid precursors and/or isoprenoids comprising culturing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:8, (ii) one or more nucleic acids encoding one or more polypeptides of the complete MVA pathway, and (iii) one or more nucleic acids encoding a polyprenyl pyrophosphate synthase polypeptide, wherein said polypeptide having phosphoketolase activity of (i) has a Performance Index value of greater than 1.0 in one or more of the following parameters: (a) protein solubility, (b) protein expression, or (c) fructose-6-phosphate (F6P) Specific Activity and producing isoprenoid precursors and/or isoprenoids. In some embodiments, the polypeptide comprises at least 90% sequence identity to SEQ ID NO:23. In some embodiments, the polypeptide comprises at least 90% sequence identity to SEQ ID NO:24. In some embodiments, the polypeptide comprises at least 90% sequence identity to SEQ ID NO:25. In some embodiments, the polypeptide comprises at least 90% sequence identity to SEQ ID NO:26. In some embodiments, the polypeptide comprises at least 90% sequence identity to SEQ ID NO:27. In some embodiments, the polypeptide comprises at least 90% sequence identity to SEQ ID NO:28. In some embodiments, the polypeptide comprises at least 90% sequence identity to SEQ ID NO:29. In some embodiments, the polypeptide comprises at least 90% sequence identity to SEQ ID NO:30. In some embodiments, the polypeptide comprises at least 90% sequence identity to SEQ ID NO:31. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Further provided herein are methods for producing isoprenoid precursors and/or isoprenoids comprising culturing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:11, (ii) one or more nucleic acids encoding one or more polypeptides of the complete MVA pathway, and (iii) one or more nucleic acids encoding a polyprenyl pyrophosphate synthase polypeptide, wherein said recombinant cell comprising said polypeptide having phosphoketolase activity of (i) has a Performance Index value of greater than 1.0 in one or more of the following parameters: (a) cell growth on glucose, (b) cell growth on xylose, (c) production of intracellular acetyl-phosphate or (d) cell growth on glucose-6-phosphate and producing isoprenoid precursors and/or isoprenoids. In some embodiments, the polypeptide comprises at least 90% sequence identity to SEQ ID NO:32. In some embodiments, the polypeptide comprises at least 90% sequence identity to SEQ ID NO:33. In some embodiments, the polypeptide comprises at least 90% sequence identity to SEQ ID NO:34. In some embodiments, the polypeptide comprises at least 90% sequence identity to SEQ ID NO:35. In some embodiments, the polypeptide comprises at least 90% sequence identity to SEQ ID NO:36. In some embodiments, the polypeptide comprises at least 90% sequence identity to SEQ ID NO:37. In some embodiments, the polypeptide comprises at least 90% sequence identity to SEQ ID NO:38. In some embodiments, the polypeptide comprises at least 90% sequence identity to SEQ ID NO:39. In some embodiments, the polypeptide comprises at least 90% sequence identity to SEQ ID NO:40. In some embodiments, the polypeptide comprises at least 90% sequence identity to SEQ ID NO:41. In some embodiments, the polypeptide comprises at least 90% sequence identity to SEQ ID NO:42. In some embodiments, the polypeptide comprises at least 90% sequence identity to SEQ ID NO:43. In some embodiments, the polypeptide comprises at least 90% sequence identity to SEQ ID NO:44. In some embodiments, the polypeptide comprises at least 90% sequence identity to SEQ ID NO:45. In some embodiments, the polypeptide comprises at least 90% sequence identity to SEQ ID NO:46. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Provided herein are methods for producing isoprenoid precursors and/or isoprenoids comprising culturing recombinant cells capable of increased carbon flux through the phosphoketolase pathway, wherein the recombinant cells comprise: (i) a heterologous nucleic acid sequence encoding a polypeptide having phosphoketolase activity, wherein the polypeptide comprises at least 65% sequence identity to SEQ ID NO:11, (ii) one or more nucleic acids encoding one or more polypeptides of the complete MVA pathway, and (iii) one or more nucleic acids encoding a polyprenyl pyrophosphate synthase polypeptide, wherein said polypeptide having phosphoketolase activity of (i) has a Performance Index value of greater than 1.0 in one or more of the following parameters: (a) protein solubility, (b) protein expression, or (c) fructose-6-phosphate (F6P) Specific Activity and producing isoprenoid precursors and/or isoprenoids. In some embodiments, the polypeptide comprises at least 90% sequence identity to SEQ ID NO:32. In some embodiments, the polypeptide comprises at least 90% sequence identity to SEQ ID NO:33. In some embodiments, the polypeptide comprises at least 90% sequence identity to SEQ ID NO:34. In some embodiments, the polypeptide comprises at least 90% sequence identity to SEQ ID NO:35. In some embodiments, the polypeptide comprises at least 90% sequence identity to SEQ ID NO:36. In some embodiments, the polypeptide comprises at least 90% sequence identity to SEQ ID NO:37. In some embodiments, the polypeptide comprises at least 90% sequence identity to SEQ ID NO:38. In some embodiments, the polypeptide comprises at least 90% sequence identity to SEQ ID NO:39. In some embodiments, the polypeptide comprises at least 90% sequence identity to SEQ ID NO:40. In some embodiments, the polypeptide comprises at least 90% sequence identity to SEQ ID NO:41. In some embodiments, the polypeptide comprises at least 90% sequence identity to SEQ ID NO:42. In some embodiments, the polypeptide comprises at least 90% sequence identity to SEQ ID NO:43. In some embodiments, the polypeptide comprises at least 90% sequence identity to SEQ ID NO:44. In some embodiments, the polypeptide comprises at least 90% sequence identity to SEQ ID NO:45. In some embodiments, the polypeptide comprises at least 90% sequence identity to SEQ ID NO:46. In other embodiments, said Performance Index value for any of said parameters are any of such as greater than 1.1, such as greater than 1.2, greater than 1.4, greater than 1.6, greater than 1.8, greater than 2, greater than 2.2, greater than 2.4, greater than 2.6, greater than 2.8, greater than 3, greater than 3.2, greater than 3.4, greater than 3.6, greater than 3.8, greater than 4, greater than 4.2, greater than 4.4, greater than 4.6, greater than 4.8, greater than 5, greater than 5.2, greater than 5.4, greater than 5.6, greater than 5.8, greater than 6, greater than 6.2, greater than 6.4, greater than 6.6, greater than 6.8, greater than 7, greater than 7.2, greater than 7.4, greater than 7.6, greater than 7.8, greater than 8, greater than 8.2, greater than 8.4, greater than 8.6, greater than 8.8, 9, greater than 9.2, greater than 9.4, greater than 9.6, greater than 9.8, or greater than 10 or more compared to a parental polypeptide having phosphoketolase activity (e.g., a phosphoketolase from *E. gallinarum*). In other embodiments, cell performance index increases at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more in comparison to a parental molecule. In other embodiments, the cell performance index is greater than any of about 0.1 to 0.5, about 0.25 to 0.75, about 0.5 to 1, about 0.75 to 1.25, about 1 to 1.5, about 1.25 to 1.75, about 1.5 to 2, about 1.75 to 2.25, about 2 to 2.5, about 2.25 to 2.75, about 2.5 to 3, about 2.75 to 3.25, about 3 to 3.5, about 3.25 to 3.75, about 3.5 to 4, about 3.75 to 4.25, about 4 to 4.5, about 4.25 to 4.75, about 4.5 to 5, about 4.75 to 5.25, about 5 to 5.5, about 5.25 to 5.75, about 5.5 to 6, about 6.25 to 6.75, about 6.5 to 7, about 6.75 to 7.25, about 7 to 7.5, about 7.75 to 8.25, about 8 to 8.5, about 8.25 to 8.75, about 8.5 to 9, about 8.75 to 9.25, about 9 to 9.5, about 9.25 to 9.75, or about 9.5 to 10 or more in comparison to a parental molecule. In other embodiments, the cell performance index is greater than any of about 0.1 to 2, about 1-3, about 2-4, about 3-5, about 4-6, about 5-7, about 6-8, about 7-9, or about 8-10 or more in comparison to a parental molecule. In some embodiments, the parental molecule is a phosphoketolase from *E. gallinarum*. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

Vectors

Suitable vectors can be used for any of the compositions and methods described herein. For example, suitable vectors can be used to optimize the expression of one or more copies of a gene encoding a phosphoketolase, an upper MVA pathway polypeptide including, but not limited to, mvaE and an mvaS polypeptide, a lower MVA pathway polypeptide, an isoprene synthase, or a polyprenyl pyrophosphate synthase in a particular host cell (e.g., *E. coli*). In some aspects, the vector contains a selective marker. Examples of selectable markers include, but are not limited to, antibiotic resistance nucleic acids (e.g., kanamycin, ampicillin, carbenicillin, gentamicin, hygromycin, phleomycin, bleomycin, neomycin, or chloramphenicol) and/or nucleic acids that confer a metabolic advantage, such as a nutritional advantage on the host cell. In some aspects, one or more copies of a phosphoketolase, an upper MVA pathway polypeptide including, but not limited to, mvaE and an mvaS polypeptide, a lower MVA pathway polypeptide, an mvaE and an mvaS nucleic acid from *L. grayi, E. faecium, E. gallinarum, E. casseliflavus*, and/or *E. faecalis*, an isoprene synthase, or a polyprenyl pyrophosphate synthase nucleic acid(s) integrate into the genome of host cells without a selective marker.

Any one of the vectors characterized herein or used in the Examples of the present disclosure can be used in the present invention.

Transformation Methods

Nucleic acids encoding one or more copies of a phosphoketolase, an upper MVA pathway polypeptide including, but not limited to, mvaE and an mvaS polypeptide, a lower MVA pathway polypeptide, and/or lower MVA pathway polypeptides can be inserted into a cell using suitable techniques. Additionally, isoprene synthase, IDI, DXP pathway, and/or polyprenyl pyrophosphate synthase nucleic acids or vectors containing them can be inserted into a host cell (e.g., a plant cell, a fungal cell, a yeast cell, or a bacterial cell described herein) using standard techniques for introduction of a DNA construct or vector into a host cell, such as transformation, electroporation, nuclear microinjection, transduction, transfection (e.g., lipofection mediated or DEAE-Dextrin mediated transfection or transfection using a recombinant phage virus), incubation with calcium phosphate DNA precipitate, high velocity bombardment with DNA-coated microprojectiles, and protoplast fusion. General transformation techniques are known in the art (See, e.g., *Current Protocols in Molecular Biology* (F. M. Ausubel et al. (eds.) Chapter 9, 1987; Sambrook et al., *Molecular Cloning: A Laboratory Manual*, 2$^{nd}$ ed., Cold Spring Harbor, 1989; and Campbell et al., *Curr. Genet.* 16:53-56, 1989). The introduced nucleic acids can be integrated into chromosomal DNA or maintained as extrachromosomal replicating sequences. Transformants can be selected by any method known in the art. Suitable methods for selecting transformants are described in International Publication No. WO 2009/076676, U.S. Patent Publ. No. 2009/0203102, WO 2010/003007, US Publ. No. 2010/0048964, WO 2009/132220, and US Publ. No. 2010/0003716.

Exemplary Host Cells

One of skill in the art will recognize that expression vectors are designed to contain certain components which optimize gene expression for certain host strains. Such optimization components include, but are not limited to origin of replication, promoters, and enhancers. The vectors and components referenced herein are described for exemplary purposes and are not meant to narrow the scope of the invention.

Any cell or progeny thereof that can be used to heterologously express genes can be used to express one or more a phosphoketolase. In certain embodiments, the cells (e.g., recombinant cells) comprise one or more copies of a heterologous nucleic acid encoding a phosphoketolase isolated from *Burkholderia phytofirmans, Lactobacillus buchneri, Bifidobacterium gallicum, Bifidobacterium dentium, Bifidobacterium bifidum*, and/or *Clostridium acetobutylicum*. In some embodiments, the recombinant cells comprise one or more copies of a heterologous nucleic acid encoding a phosphoketolase isolated from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In some embodiments, the recombinant cells comprise one or more copies of a heterologous nucleic acid encoding a phosphoketolase isolated from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus*, and/or *Mycoplasma arthritidis*. In some embodiments, the recombinant cells comprise one or more copies of a heterologous nucleic acid encoding a phosphoketolase isolated from *Streptococcus agalactiae, Mycoplasma agalactiae, Streptococcus gordonii, Kingella oxalis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma* columbinum. In some embodiments, the recombinant cells comprise one or more copies of a heterologous nucleic acid encoding a phosphoketolase isolated from and organism listed in Table 1, Table 2 and/or FIGS. 3-24.

The cells (e.g., recombinant cells) with heterologous nucleic acid encoding a phosphoketolase as described above and herein can also be engineered with one or more heterologous nucleic acids expressing one or more MVA pathway peptides, isoprene synthase, IDI, DXP pathway polypeptide (e), and/or polyprenyl pyrophosphate synthase polypeptides. In some embodiments, the host cell is a gram-positive bacterium. Non-limiting examples include strains of *Corynebacteria* (e.g. *C. glutamicum*), *Streptomyces* (e.g., *S. lividans, S. coelicolor*, or *S. griseus*), *Bacillus, Listeria* (e.g., *L. monocytogenes*) or *Lactobacillus* (e.g., *L.* spp). In some embodiments, the source organism is a gram-negative bacterium, such as *E. coli, Pseudomonas* sp, or *H. pylori*.

Bacteria cells, including gram positive or gram negative bacteria can be used to express any of the heterologous genes described above. In particular, the mvaE and mvaS genes can be expressed in any one of *P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas* sp., and *P. alcaligenes* cells.

There are numerous types of anaerobic cells that can be used as host cells in the compositions and methods of the present invention. In one aspect of the invention, the cells described in any of the compositions or methods described herein are obligate anaerobic cells and progeny thereof. Obligate anaerobes typically do not grow well, if at all, in conditions where oxygen is present. It is to be understood that a small amount of oxygen may be present, that is, there is some tolerance level that obligate anaerobes have for a low level of oxygen. In one aspect, obligate anaerobes engineered to produce mevalonate, isoprenoid precursors, isoprene, and isoprenoids can serve as host cells for any of the methods and/or compositions described herein and are grown under substantially oxygen-free conditions, wherein the amount of oxygen present is not harmful to the growth, maintenance, and/or fermentation of the anaerobes.

In another aspect of the invention, the host cells described and/or used in any of the compositions or methods described herein are facultative anaerobic cells and progeny thereof. Facultative anaerobes can generate cellular ATP by aerobic respiration (e.g., utilization of the TCA cycle) if oxygen is present. However, facultative anaerobes can also grow in the absence of oxygen. This is in contrast to obligate anaerobes which die or grow poorly in the presence of greater amounts of oxygen. In one aspect, therefore, facultative anaerobes can serve as host cells for any of the compositions and/or methods provided herein and can be engineered to produce mevalonate, isoprenoid precursors, isoprene, and isoprenoids. Facultative anaerobic host cells can be grown under substantially oxygen-free conditions, wherein the amount of oxygen present is not harmful to the growth, maintenance, and/or fermentation of the anaerobes, or can be alternatively grown in the presence of greater amounts of oxygen.

The host cell can additionally be a filamentous fungal cell and progeny thereof. (See, e.g., Berka & Barnett, Biotechnology Advances, (1989), 7(2):127-154). In some aspects, the filamentous fungal cell can be any of *Trichoderma longibrachiatum, T. viride, T. koningii, T. harzianum, Penicillium* sp., *Humicola insolens, H. lanuginose, H. grisea, Chrysosporium* sp., *C. lucknowense, Gliocladium* sp., *Aspergillus* sp., such as *A. oryzae, A. niger, A sojae, A. japonicus, A. nidulans*, or *A. awamori, Fusarium* sp., such as *F. roseum, F. graminum F. cerealis, F. oxysporuim*, or *F. venenatum, Neurospora* sp., such as *N. crassa, Hypocrea* sp., *Mucor* sp., such as *M. miehei, Rhizopus* sp. or *Emericella* sp. In some aspects, the fungus is *A. nidulans, A. awamori, A. oryzae, A. aculeatus, A. niger, A. japonicus, T reesei, T viride, F. oxysporum*, or *F. solani*. In certain embodiments, plasmids or plasmid components for use herein include those described in U.S. patent pub. No. US 2011/0045563.

The host cell can also be a yeast, such as *Saccharomyces* sp., *Schizosaccharomyces* sp., *Pichia* sp., or *Candida* sp. In some aspects, the *Saccharomyces* sp. is *Saccharomyces cerevisiae* (See, e.g., Romanos et al., *Yeast*, (1992), 8(6): 423-488). In certain embodiments, plasmids or plasmid components for use herein include those described in U.S. Pat. No. 7,659,097 and U.S. patent pub. No. US 2011/0045563.

The host cell can additionally be a species of algae, such as a green algae, red algae, glaucophytes, chlorarachniophytes, euglenids, chromista, or dinoflagellates. (See, e.g., Saunders & Warmbrodt, "*Gene Expression in Algae and Fungi, Including Yeast*," (1993), National Agricultural Library, Beltsville, Md.). In certain embodiments, plasmids or plasmid components for use herein include those described in U.S. Patent Pub. No. US 2011/0045563. In some aspects, the host cell is a cyanobacterium, such as cyanobacterium classified into any of the following groups based on morphology: Chlorococcales, Pleurocapsales, Oscillatoriales, Nostocales, or Stigonematales (See, e.g., Lindberg et al., Metab. Eng., (2010) 12(1):70-79). In certain embodiments, plasmids or plasmid components for use herein include those described in U.S. patent pub. No. US 2010/0297749; US 2009/0282545 and Intl. Pat. Appl. No. WO 2011/034863.

*E. coli* host cells can be used to express one or more phosphoketolase enzymes from any number of organisms. In certain embodiments, the cells (e.g., recombinant cells) comprise one or more copies of a heterologous nucleic acid encoding a phosphoketolase isolated from *Burkholderia phytofirmans, Lactobacillus buchneri, Bifidobacterium gallicum, Bifidobacterium dentium, Bifidobacterium bifidum*, and/or *Clostridium acetobutylicum*. In some embodiments, the recombinant cells comprise one or more copies of a heterologous nucleic acid encoding a phosphoketolase isolated from *Mycobacterium gilvum, Shewanella baltica, Lactobacillus rhamnosus, Lactobacillus crispatus, Bifidobacterium longum, Leuconostoc citreum, Bradyrhizobium* sp., *Enterococcus faecium, Brucella microti, Lactobacillus salivarius, Streptococcus agalactiae, Rhodococcus imtechensis, Burkholderia xenovorans, Mycobacterium intracellulare, Nitrosomonas* sp., *Schizosaccharomyces pombe, Leuconostoc mesenteroides, Streptomyces* sp., *Lactobacillus buchneri, Streptomyces ghanaensis, Cyanothece* sp., and/or *Neosartorya fischeri*. In some embodiments, the recombinant cells comprise one or more copies of a heterologous nucleic acid encoding a phosphoketolase isolated from *Enterococcus faecium, Listeria grayi, Enterococcus gallinarum, Enterococcus saccharolyticus, Enterococcus casseliflavus, Mycoplasma alligatoris, Carnobacterium* sp., *Melissococcus plutonius, Tetragenococcus halophilus*, and/or *Mycoplasma arthritidis*. In some embodiments, the recombinant cells comprise one or more copies of a heterologous nucleic acid encoding a phosphoketolase isolated from *Streptococcus agalactiae, Mycoplasma agalactiae, Streptococcus gordonii, Kingella oxalis, Mycoplasma fermentans, Granulicatella adiacens, Mycoplasma hominis, Mycoplasma crocodyli, Mycobacterium bovis, Neisseria* sp., *Streptococcus* sp., *Eremococcus coleocola, Granulicatella elegans, Streptococcus parasanguinis, Aerococcus urinae, Kingella kingae, Streptococcus australis, Streptococcus criceti*, and/or *Mycoplasma* columbinum. In some embodiments, the recombinant cells comprise one or more copies of a heterologous nucleic acid encoding a phosphoketolase isolated from and organism listed in Table 1, Table 2 and/or FIGS. 3-24.

These cells can also be engineered with one or more heterologous nucleic acids encoding one or more MVA pathway polypeptides, isoprene synthase, IDI, DXP pathway polypeptide(s), and/or polyprenyl pyrophosphate synthase polypeptides. In one aspect, the host cell is a recombinant cell of an *Escherichia coli* (*E. coli*) strain, or progeny thereof, capable of producing mevalonate that expresses one or more nucleic acids encoding phosphoketolase described above and herein along with one or more heterologous nucleic acids expressing one or more MVA pathway peptides. The *E. coli* host cells can produce mevalonate in amounts, peak titers, and cell productivities greater than that of the same cells lacking one or more heterologously expressed nucleic acids encoding phosphoketolase polypeptides described above and herein along with one or more heterologous nucleic acids expressing one or more MVA pathway peptides. In addition, the one or more heterologously expressed nucleic acids encoding phosphoketolase polypeptide described above and herein along with one or more heterologous nucleic acids expressing one or more MVA pathway peptides in *E. coli* can be chromosomal copies (e.g., integrated into the *E. coli* chromosome). In other aspects, the *E. coli* cells are in culture. In some aspects the one or more phosphoketolase enzymes is from *Clostridium acetobutylicum, Bifidobacterium longum,* and/or *Enterococcus gallinarum.* In any aspects, the one or more phosphoketolase enzymes are any phosphoketolase enzymes as disclosed herein.

Exemplary Host Cell Modifications

Citrate Synthase Pathway

Citrate synthase catalyzes the condensation of oxaloacetate and acetyl-CoA to form citrate, a metabolite of the tricarboxylic acid (TCA) cycle (Ner, S. et al. 1983. Biochemistry, 22: 5243-5249; Bhayana, V. and Duckworth, H. 1984. Biochemistry 23: 2900-2905). In *E. coli*, this enzyme, encoded by gltA, behaves like a trimer of dimeric subunits. The hexameric form allows the enzyme to be allosterically regulated by NADH. This enzyme has been widely studied (Wiegand, G., and Remington, S. 1986. Annual Rev. Biophysics Biophys. Chem.15: 97-117; Duckworth et al. 1987. Biochem Soc Symp. 54:83-92; Stockell, D. et al. 2003. J. Biol. Chem. 278: 35435-43; Maurus, R. et al. 2003. Biochemistry. 42:5555-5565). To avoid allosteric inhibition by NADH, replacement by or supplementation with the *Bacillus subtilis* NADH-insensitive citrate synthase has been considered (Underwood et al. 2002. Appl. Environ. Microbiol. 68:1071-1081; Sanchez et al. 2005. Met. Eng. 7:229-239).

The reaction catalyzed by citrate synthase is directly competing with the thiolase catalyzing the first step of the mevalonate pathway, as they both have acetyl-CoA as a substrate (Hedl et al. 2002. J. Bact. 184:2116-2122). Therefore, one of skill in the art can modulate citrate synthase expression (e.g., decrease enzyme activity) to allow more carbon to flux into the mevalonate pathway, thereby increasing the eventual production of mevalonate, isoprene and isoprenoids. Decrease of citrate synthase activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, 99%, or 100%. In some aspects, the activity of citrate synthase is modulated by decreasing the activity of an endogenous citrate synthase gene. This can be accomplished by chromosomal replacement of an endogenous citrate synthase gene with a transgene encoding an NADH-insensitive citrate synthase or by using a transgene encoding an NADH-insensitive citrate synthase that is derived from *Bacillus subtilis*. The activity of citrate synthase can also be modulated (e.g., decreased) by replacing the endogenous citrate synthase gene promoter with a synthetic constitutively low expressing promoter. The gene encoding citrate synthase can also be deleted. The decrease of the activity of citrate synthase can result in more carbon flux into the mevalonate dependent biosynthetic pathway in comparison to cells that do not have decreased expression of citrate synthase. In any aspects of the invention, provided herein are recombinant cells comprising one or more heterologously expressed nucleic acids encoding phosphoketolase polypeptides as disclosed herein and further engineered to decrease the activity of citrate synthase (gltA). Activity modulation (e.g., decreased) of citrate synthase isozymes is also contemplated herein. In any aspects of the invention, provided herein are recombinant cells comprising one or more heterologously expressed nucleic acids encoding phosphoketolase polypeptides as disclosed herein and further engineered to decrease the activity of a citrate synthase isozyme.

Pathways Involving Phosphotransacetylase and/or Acetate Kinase

Phosphotransacetylase ((encoded in *E. coli* by (i) pta (Shimizu et al. 1969. Biochim Biophys. Acta 191: 550-558 or (ii) eutD (Bologna et al. 2010. J of Microbiology. 48:629-636) catalyzes the reversible conversion between acetyl-CoA and acetyl phosphate (acetyl-P), while acetate kinase (encoded in *E. coli* by ackA) (Kakuda, H. et al. 1994. J. Biochem. 11:916-922) uses acetyl-P to form acetate. These genes can be transcribed as an operon in *E. coli*. Together, they catalyze the dissimilation of acetate, with the release of ATP. Thus, it is possible to increase the amount of acetyl-P going towards acetyl-CoA by enhancing the activity of phosphotransacetylase. In certain embodiments, enhancement is achieved by placing an upregulated promoter upstream of the gene in the chromosome, or to place a copy of the gene behind an adequate promoter on a plasmid. In order to decrease the amount of acetyl-coA going towards acetate, the activity of acetate kinase gene (e.g., the endogenous acetate kinase gene) can be decreased or attenuated. In certain embodiments, attenuation is achieved by deleting acetate kinase (ackA). This is done by replacing the gene with a chloramphenicol cassette followed by looping out of the cassette. In some aspects, the activity of acetate kinase is modulated by decreasing the activity of an endogenous acetate kinase. This can be accomplished by replacing the endogenous acetate kinase gene promoter with a synthetic constitutively low expressing promoter. In certain embodiments, it the attenuation of the acetated kinase gene should be done disrupting the expression of the phosphotransacetylase (pta) gene. Acetate is produced by *E. coli* for a variety of reasons (Wolfe, A. 2005. Microb. Mol. Biol. Rev. 69:12-50). Without being bound by theory, deletion of ackA could result in decreased carbon being diverted into acetate production (since ackA use acetyl-CoA) and thereby increase the yield of mevalonate, isoprenoid precursors, isoprene and/or isoprenoids.

In some aspects, the recombinant cells described herein produce decreased amounts of acetate in comparison to cells that do not have attenuated endogenous acetate kinase gene expression or enhanced phosphotransacetylase. Decrease in the amount of acetate produced can be measured by routine assays known to one of skill in the art. The amount of acetate reduction is at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99% as compared when no molecular manipulations are done to the endogenous acetate kinase gene expression or phosphotransacetylase gene expression.

The activity of phosphotransacetylase (pta and/or eutD) can be increased by other molecular manipulations of the enzymes. The increase of enzyme activity can be an increase in any amount of specific activity or total activity as compared to when no manipulation has been effectuated. In some instances, the increase of enzyme activity is increased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%. In one embodiment the activity of pta is increased by altering the promoter and/or rbs on the chromosome, or by expressing it from a plasmid. In any aspects of the invention, provided herein are recombinant cells comprising one or more heterologously expressed nucleic acids encoding phosphoketolase polypeptides as disclosed herein and further engineered to increase the activity of phosphotransacetylase (pta and/or eutD). Activity modulation (e.g., increased) of phosphotransacetylase isozymes is also contemplated herein. In any aspects of the invention, provided herein are recombinant cells comprising one or more heterologously expressed nucleic acids encoding phosphoketolase polypeptides as disclosed herein and further engineered to increase the activity of a phosphotransacetylase (pta and/or eutD) isozyme.

The activity of acetate kinase (ackA) can also be decreased by other molecular manipulations of the enzymes. The decrease of enzyme activity can be any amount of reduction of specific activity or total activity as compared to when no manipulation has been effectuated. In some instances, the enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%. In any aspects of the invention, provided herein are recombinant cells comprising one or more heterologously expressed nucleic acids encoding phosphoketolase polypeptides as disclosed herein and further engineered to decrease the activity of acetate kinase (ackA). Activity modulation (e.g., decreased) of acetate kinase isozymes is also contemplated herein. In any aspects of the invention, provided herein are recombinant cells comprising one or more heterologously expressed nucleic acids encoding phosphoketolase polypeptides as disclosed herein and further engineered to decrease the activity of a acetate kinase isozyme.

In some cases, attenuating the activity of the endogenous acetate kinase gene results in more carbon flux into the mevalonate dependent biosynthetic pathway in comparison to cells that do not have attenuated endogenous acetate gene expression.

Pathways Involving Lactate Dehydrogenase

In *E. coli*, D-Lactate is produced from pyruvate through the enzyme lactate dehydrogenase (encoded by ldhA—FIG. 1) (Bunch, P. et al. 1997. Microbiol. 143:187-195). Production of lactate is accompanied with oxidation of NADH, hence lactate is produced when oxygen is limited and cannot accommodate all the reducing equivalents. Thus, production of lactate could be a source for carbon consumption. As such, to improve carbon flow through to mevalonate production (and isoprene, isoprenoid precursor and isoprenoids production, if desired), one of skill in the art can modulate the activity of lactate dehydrogenase, such as by decreasing the activity of the enzyme.

Accordingly, in one aspect, the activity of lactate dehydrogenase can be modulated by attenuating the activity of an endogenous lactate dehydrogenase gene. Such attenuation can be achieved by deletion of the endogenous lactate dehydrogenase gene. Other ways of attenuating the activity of lactate dehydrogenase gene known to one of skill in the art may also be used. By manipulating the pathway that involves lactate dehydrogenase, the recombinant cell produces decreased amounts of lactate in comparison to cells that do not have attenuated endogenous lactate dehydrogenase gene expression. Decrease in the amount of lactate produced can be measured by routine assays known to one of skill in the art. The amount of lactate reduction is at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99% as compared when no molecular manipulations are done.

The activity of lactate dehydrogenase can also be decreased by other molecular manipulations of the enzyme. The decrease of enzyme activity can be any amount of reduction of specific activity or total activity as compared to when no manipulation has been effectuated. In some instances, the enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%.

Accordingly, in some cases, attenuation of the activity of the endogenous lactate dehydrogenase gene results in more carbon flux into the mevalonate dependent biosynthetic pathway in comparison to cells that do not have attenuated endogenous lactate dehydrogenase gene expression.

Pathways Involving Glyceraldehyde 3-Phosphate

Glyceraldehyde 3-phosphate dehydrogenase (gapA and/or gapB) is a crucial enzyme of glycolysis catalyzes the conversion of glyceraldehyde 3-phosphate into 1,3-biphospho-D-glycerate (Branlant G. and Branlant C. 1985. Eur. J. Biochem. 150:61-66).

In order to direct carbon towards the phosphoketolase enzyme, glyceraldehyde 3-phosphate dehydrogenase expression can be modulated (e.g., decrease enzyme activity) to allow more carbon to flux towards fructose 6-phosphate and xylulose 5-phosphate, thereby increasing the eventual production of mevalonate, isoprene and isoprenoids. Decrease of glyceraldehyde 3-phosphate dehydrogenase activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, 99%. Or 100%. In some aspects, the activity of glyceraldehyde 3-phosphate dehydrogenase is modulated by decreasing the activity of an endogenous glyceraldehyde 3-phosphate dehydrogenase. This can be accomplished by replacing the endogenous glyceraldehyde 3-phosphate dehydrogenase gene promoter with a synthetic constitutively low expressing promoter. The gene encoding glyceraldehyde 3-phosphate dehydrogenase can also be deleted. The gene encoding glyceraldehyde 3-phosphate dehydrogenase can also be replaced by a *Bacillus* enzyme catalyzing the same reaction but producing NADPH rather than NADH. The decrease of the activity of glyceraldehyde 3-phosphate dehydrogenase can result in more carbon flux into the mevalonate-dependent biosynthetic pathway in comparison to cells that do not have decreased expression of glyceraldehyde 3-phosphate dehydrogenase. In any aspects of the invention, provided herein are recombinant cells comprising one or more heterologously expressed nucleic acids encoding phosphoketolase polypeptides as disclosed herein and further engineered to decrease the activity of glyceraldehyde 3-phosphate dehydrogenase (gapA and/or gapB). Activity modulation (e.g., decreased) of glyceraldehyde 3-phosphate dehydrogenase isozymes is also contemplated herein. In any aspects of the invention, provided herein are recombinant cells comprising one or more heterologously expressed nucleic acids encoding phosphoketolase polypeptides as disclosed herein and further engineered to decrease the activity of a glyceraldehyde 3-phosphate dehydrogenase (gapA and/or gapB) isozyme.

Pathways Involving the Entner-Doudoroff Pathway

The Entner-Doudoroff (ED) pathway is an alternative to the Emden-Meyerhoff-Parnass (EMP-glycolysis) pathway. Some organisms, like *E. coli*, harbor both the ED and EMP pathways, while others have only one or the other. *Bacillus subtilis* has only the EMP pathway, while *Zymomonas mobilis* has only the ED pathway (Peekhaus and Conway. 1998. J. Bact. 180:3495-3502; Stulke and Hillen. 2000. Annu. Rev. Microbiol. 54, 849-880; Dawes et al. 1966. Biochem. J. 98:795-803). Fructose bisphophate aldolase (fba, fbaA, fbaB, and/or fbaC) interacts with the Entner-Doudoroff pathway and reversibly catalyzes the conversion of fructose 1,6-bisphosphate into dihydroxyacetone phosphate (DHAP) and glyceraldehyde 3-phosphate (GAP) (Baldwin S. A., et. al., Biochem J. (1978) 169(3):633-41).

Phosphogluconate dehydratase (edd) removes one molecule of $H_2O$ from 6-phospho-D-gluconate to form 2-dehydro-3-deoxy-D-gluconate 6-phosphate, while 2-keto-3-deoxygluconate 6-phosphate aldolase (eda) catalyzes an aldol cleavage (Egan et al. 1992. J. Bact. 174:4638-4646). The two genes are in an operon.

Metabolites that can be directed into the phosphoketolase pathway can also be diverted into the ED pathway. To avoid metabolite loss to the ED-pathway, phosphogluconate dehydratase gene (e.g., the endogenous phosphogluconate dehydratase gene) and/or an 2-keto-3-deoxygluconate 6-phosphate aldolase gene (e.g., the endogenous 2-keto-3-deoxygluconate 6-phosphate aldolase gene) activity is attenuated. One way of achieving attenuation is by deleting phosphogluconate dehydratase (edd) and/or 2-keto-3-deoxygluconate 6-phosphate aldolase (eda). This can be accomplished by replacing one or both genes with a chloramphenicol or kanamycin cassette followed by looping out of the cassette. Without these enzymatic activities, more carbon can flux through the phosphoketolase enzyme, thus increasing the yield of mevalonate, isoprene or isoprenoids.

The activity of phosphogluconate dehydratase (edd) and/or 2-keto-3-deoxygluconate 6-phosphate aldolase (eda) can also be decreased by other molecular manipulations of the enzymes. The decrease of enzyme activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%.

In some cases, attenuating the activity of the endogenous phosphogluconate dehydratase gene and/or the endogenous 2-keto-3-deoxygluconate 6-phosphate aldolase gene results in more carbon flux into the mevalonate dependent biosynthetic pathway in comparison to cells that do not have attenuated endogenous phosphogluconate dehydratase gene and/or endogenous acetate kinase2-keto-3-deoxygluconate 6-phosphate aldolase gene expression.

Metabolites that can be directed into the phosphoketolase pathway can also be diverted into the ED pathway or EMP pathway. To avoid metabolite loss and to increase fructose-6-phosphate (F6P) concentration, fructose bisphophate aldolase (e.g., the endogenous fructose bisphophate aldolase) activity is attenuated. In some cases, attenuating the activity of the endogenous fructose bisphophate aldolase (fba, fbaA, fbaB, and/or fbaC) gene results in more carbon flux into the mevalonate dependent biosynthetic pathway in comparison to cells that do not have attenuated endogenous fructose bisphophate aldolase (fba, fbaA, fbaB, and/or fbaC) gene expression. In some aspects, attenuation is achieved by deleting fructose bisphophate aldolase (fba, fbaA, fbaB, and/or fbaC). Deletion can be accomplished by replacing the gene with a chloramphenicol or kanamycin cassette followed by looping out of the cassette. In some aspects, the activity of fructose bisphophate aldolase is modulated by decreasing the activity of an endogenous fructose bisphophate aldolase. This can be accomplished by replacing the endogenous fructose bisphophate aldolase gene promoter with a synthetic constitutively low expressing promoter. Without these enzymatic activities, more carbon can flux through the phosphoketolase enzyme, thus increasing the yield of mevalonate, isoprene or isoprenoids. The activity of fructose bisphophate aldolase can also be decreased by other molecular manipulations of the enzyme. The decrease of enzyme activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%. In any aspects of the invention, provided herein are recombinant cells comprising one or more heterologously expressed nucleic acids encoding phosphoketolase polypeptides as disclosed herein and further engineered to decrease the activity of fructose bisphophate aldolase (fba, fbaA, fbaB, and/or fbaC). Activity modulation (e.g., decreased) of fructose bisphophate aldolase isozymes is also contemplated herein. In any aspects of the invention, provided herein are recombinant cells comprising one or more heterologously expressed nucleic acids encoding phosphoketolase polypeptides as disclosed herein and further engineered to decrease the activity of a fructose bisphophate aldolase isozyme.

Pathways Involving the Oxidative Branch of the Pentose Phosphate Pathway

*E. coli* uses the pentose phosphate pathway to break down hexoses and pentoses and to provide cells with intermediates for various anabolic pathways. It is also a major producer of NADPH. The pentose phosphate pathway is composed from an oxidative branch (with enzymes like glucose 6-phosphate 1-dehydrogenase (zwf), 6-phosphogluconolactonase (pgl) or 6-phosphogluconate dehydrogenase (gnd)) and a non-oxidative branch (with enzymes such as transketolase (tktA and/or tktB), transaldolase (talA or talB), ribulose-5-phosphate-epimerase and (or) ribose-5-phosphate epimerase, ribose-5-phosphate isomerase (rpiA and/or rpiB) and/or ribulose-5-phosphate 3-epimerase (rpe)) (Sprenger. 1995. Arch. Microbiol.164:324-330).

In order to direct carbon towards the phosphoketolase enzyme, the non-oxidative branch of the pentose phosphate pathway (transketolase, transaldolase, ribulose-5-phosphate-epimerase and (or) ribose-5-phosphate epimerase, ribose-5-phosphate isomerase A, ribose-5-phosphate isomerase B, and/or ribulose-5-phosphate 3-epimerase) expression can be modulated (e.g., increase enzyme activity) to allow more carbon to flux towards fructose 6-phosphate and xylulose 5-phosphate, thereby increasing the eventual production of mevalonate, isoprene and isoprenoids. Increase of transketolase, transaldolase, ribulose-5-phosphate-epimerase and (or) ribose-5-phosphate epimerase activity can be any amount of increase of specific activity or total activity as compared to when no manipulation has been effectuated. In some instances, the enzyme activity is increased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, 99%, or 100%. In some aspects, the activity of transketolase, transaldolase, ribulose-5-phosphate-epimerase and (or) ribose-5-phosphate epimerase is modulated by increasing the activity of an endogenous transketolase, transaldolase, ribulose-5-phosphate-epimerase and (or) ribose-5-phosphate epimerase. This can be accomplished by replacing the endogenous transketolase, transaldolase, ribulose-5-phosphate-epimerase and (or) ribose-5-phosphate epimerase gene promoter with a synthetic constitutively high expressing promoter. The genes encoding transketolase, transaldolase, ribulose-5-phosphate-epimerase and (or) ribose-5-phosphate epimerase can also be cloned on a plasmid behind an appropriate promoter. The increase of the activity of transketolase, transaldolase, ribulose-5-phosphate-epimerase and (or) ribose-5-phosphate epimerase can result in more carbon flux into the mevalonate dependent biosynthetic pathway in comparison to cells that do not have increased expression of transketolase, transaldolase, ribulose-5-phosphate-epimerase and (or) ribose-5-phosphate epimerase.

In any aspects of the invention, provided herein are recombinant cells comprising one or more heterologously expressed nucleic acids encoding phosphoketolase polypeptides as disclosed herein and further engineered to increase the activity of transketolase (tktA and/or tktB). In any aspects of the invention, provided herein are recombinant cells comprising one or more heterologously expressed nucleic acids encoding phosphoketolase polypeptides as disclosed herein and further engineered to decrease the activity of transketolase (tktA and/or tktB). In any aspects of the invention, provided herein are recombinant cells comprising one or more heterologously expressed nucleic acids encoding phosphoketolase polypeptides as disclosed herein and further engineered to increase the activity of transaldolase (talA or talB). In any aspects of the invention, provided herein are recombinant cells comprising one or more heterologously expressed nucleic acids encoding phosphoketolase polypeptides as disclosed herein and further engineered to increase the activity of ribose-5-phosphate isomerase (rpiA and/or rpiB). In any aspects of the invention, provided herein are recombinant cells comprising one or more heterologously expressed nucleic acids encoding phosphoketolase polypeptides as disclosed herein and further engineered to increase the activity of ribulose-5-phosphate 3-epimerase (rpe). Activity modulation (e.g., decreased or increased) of glucose 6-phosphate 1-dehydrogenase (zwf), 6-phosphogluconolactonase (pgl), 6-phosphogluconate dehydrogenase (gnd), transketolase (tktA and/or tktB), transaldolase (talA or talB), ribulose-5-phosphate-epimerase, ribose-5-phosphate epimerase, ribose-5-phosphate isomerase (rpiA and/or rpiB) and/or ribulose-5-phosphate 3-epimerase (rpe) isozymes is also contemplated herein. In any aspects of the invention, provided herein are recombinant cells comprising one or more heterologously expressed nucleic acids encoding phosphoketolase polypeptides as disclosed herein and further engineered to increase the activity of a glucose 6-phosphate 1-dehydrogenase (zwf) isozyme. In any aspects of the invention, provided herein are recombinant cells comprising one or more heterologously expressed nucleic acids encoding phosphoketolase polypeptides as disclosed herein and further engineered to increase the activity of a transketolase (tktA and/or tktB) isozyme. In any aspects of the invention, provided herein are recombinant cells comprising one or more heterologously expressed nucleic acids encoding phosphoketolase polypeptides as disclosed herein and further engineered to decrease the activity of a transketolase (tktA and/or tktB) isozyme. In any aspects of the invention, provided herein are recombinant cells comprising one or more heterologously expressed nucleic acids encoding phosphoketolase polypeptides as disclosed herein and further engineered to increase the activity of a transaldolase (talA or talB) isozyme. In any aspects of the invention, provided herein are recombinant cells comprising one or more heterologously expressed nucleic acids encoding phosphoketolase polypeptides as disclosed herein and further engineered to increase the activity of a ribose-5-phosphate isomerase (rpiA and/or rpiB) isozyme. In any aspects of the invention, provided herein are recombinant cells comprising one or more heterologously expressed nucleic acids encoding phosphoketolase polypeptides as disclosed herein and further engineered to increase the activity of a ribulose-5-phosphate 3-epimerase (rpe) isozyme.

In order to direct carbon towards the phosphoketolase enzyme, glucose 6-phosphate 1-dehydrogenase can be modulated (e.g., decrease enzyme activity). In some aspects, the activity of glucose 6-phosphate 1-dehydrogenase (zwf) (e.g., the endogenous glucose 6-phosphate 1-dehydrogenase gene) can be decreased or attenuated. In certain embodiments, attenuation is achieved by deleting glucose 6-phosphate 1-dehydrogenase. In some aspects, the activity of glucose 6-phosphate 1-dehydrogenase is modulated by decreasing the activity of an endogenous glucose 6-phosphate 1-dehydrogenase. This can be accomplished by replacing the endogenous glucose 6-phosphate 1-dehydrogenase gene promoter with a synthetic constitutively low expressing promoter. In any aspects of the invention, provided herein are recombinant cells comprising one or more heterologously expressed nucleic acids encoding phosphoketolase polypeptides as disclosed herein and further engineered to decrease the activity of glucose 6-phosphate 1-dehydrogenase (zwf). Activity modulation (e.g., decreased) of glucose 6-phosphate 1-dehydrogenase isozymes is also contemplated herein. In any aspects of the invention, provided herein are recombinant cells comprising one or more heterologously expressed nucleic acids encoding phosphoketolase polypeptides as disclosed herein and further engineered to decrease the activity of a glucose 6-phosphate 1-dehydrogenase isozyme.

Pathways Involving Phosphofructokinase

Phosphofructokinase is a crucial enzyme of glycolysis which catalyzes the phosphorylation of fructose 6-phosphate. *E. coli* has two isozymes encoded by pfkA and pfkB. Most of the phosphofructokinase activity in the cell is due to pfkA (Kotlarz et al. 1975 Biochim Biophys. Acta 381:257-268).

In order to direct carbon towards the phosphoketolase enzyme, phosphofructokinase expression can be modulated (e.g., decrease enzyme activity) to allow more carbon to flux towards fructose 6-phosphate and xylulose 5-phosphate, thereby increasing the eventual production of mevalonate, isoprene and isoprenoids. Decrease of phosphofructokinase activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, 99%. Or 100%. In some aspects, the activity of phosphofructokinase is modulated by decreasing the activity of an endogenous phosphofructokinase. This can be accomplished by replacing the endogenous phosphofructokinase gene promoter with a synthetic constitutively low expressing promoter. The gene encoding phosphofructokinase can also be deleted. The decrease of the activity of phosphofructokinase can result in more carbon flux into the mevalonate dependent biosynthetic pathway in comparison to cells that do not have decreased expression of phosphofructokinase.

In any aspects of the invention, provided herein are recombinant cells comprising one or more heterologously expressed nucleic acids encoding phosphoketolase polypeptides as disclosed herein and further engineered to decrease the activity of fructose 6-phosphate (pfkA and/or pfkB). Activity modulation (e.g., decreased) of fructose 6-phosphate isozymes is also contemplated herein. In any aspects of the invention, provided herein are recombinant cells comprising one or more heterologously expressed nucleic acids encoding phosphoketolase polypeptides as disclosed herein and further engineered to decrease the activity of a fructose 6-phosphate isozyme.

Pathways Involving Pyruvate Dehydrogenase Complex

The pyruvate dehydrogenase complex, which catalyzes the decarboxylation of pyruvate into acetyl-CoA, is composed of the proteins encoded by the genes aceE, aceF and lpdA. Transcription of those genes is regulated by several regulators. Thus, one of skill in the art can increase acetyl-CoA by modulating the activity of the pyruvate dehydrogenase complex. Modulation can be to increase the activity and/or expression (e.g., constant expression) of the pyruvate dehydrogenase complex. This can be accomplished by different ways, for example, by placing a strong constitutive promoter, like PL.6

```
(aattcatataaaaaacatacagataaccatctgcggtgataaattatct aggcggtgttgacataaataccactggcggtgatactgagcacatcagca ggacgcactgaccaccatgaaggtg - lambda promoter, GenBank NC_001416, SEQ ID NO: 14),
``` in front of the operon or using one or more synthetic constitutively expressing promoters.

Accordingly, in one aspect, the activity of pyruvate dehydrogenase is modulated by increasing the activity of one or more enzymes of the pyruvate dehydrogenase complex consisting of (a) pyruvate dehydrogenase (E1), (b) dihydrolipoyl transacetylase, and (c) dihydrolipoyl dehydrogenase. It is understood that any one, two or three of the genes encoding these enzymes can be manipulated for increasing activity of pyruvate dehydrogenase. In another aspect, the activity of the pyruvate dehydrogenase complex can be modulated by attenuating the activity of an endogenous pyruvate dehydrogenase complex repressor, further detailed below. The activity of an endogenous pyruvate dehydrogenase complex repressor can be attenuated by deletion of the endogenous pyruvate dehydrogenase complex repressor gene.

In some cases, one or more genes encoding the pyruvate dehydrogenase complex are endogenous genes. Another way to increase the activity of the pyruvate dehydrogenase complex is by introducing into the cell one or more heterologous nucleic acids encoding one or more polypeptides from the group consisting of (a) pyruvate dehydrogenase (E1), (b) dihydrolipoyl transacetylase, and (c) dihydrolipoyl dehydrogenase.

By using any of these methods, the recombinant cells can produce increased amounts of acetyl Co-A in comparison to cells wherein the activity of pyruvate dehydrogenase is not modulated. Modulating the activity of pyruvate dehydrogenase can result in more carbon flux into the mevalonate dependent biosynthetic pathway in comparison to cells that do not have modulated pyruvate dehydrogenase expression.

Pathways Involving the Phosphotransferase System

The phosphoenolpyruvate dependent phosphotransferase system (PTS) is a multicomponent system that simultaneously transports and phosphorylates its carbohydrate substrates across a membrane in a process that is dependent on energy provided by the glycolytic intermediate phosphoenolpyruvate (PEP). The genes that regulate the PTS are mostly clustered in operons. For example, the pts operon (ptsHIcrr) of $Escherichia$ $coli$ is composed of the ptsH, ptsI and crr genes coding for three proteins central to the phosphoenolpyruvate dependent phosphotransferase system (PTS), the HPr (ptsH), enzyme I (ptsI) and EIIIGlc (crr) proteins. These three genes are organized in a complex operon in which the major part of expression of the distal gene, crr, is initiated from a promoter region within ptsI. In addition to the genes of the pts operon, ptsG encodes the glucose-specific transporter of the phosphotransferase system, ptsG Transcription from this promoter region is under the positive control of catabolite activator protein (CAP)-cyclic AMP (cAMP) and is enhanced during growth in the presence of glucose (a PTS substrate). Furthermore, the ppsA gene encodes for phosphoenolpyruvate synthetase for the production of phosphoenolpyruvate (PEP) which is required for activity of the phosphotransferase system (PTS). Carbon flux is directed by the phosphoenolpyruvate synthetase through the pyruvate dehydrogenase pathway or the PTS pathway. See Postma, P. W., et al., Microbiol Rev. (1993), 57(3):543-94) which is incorporated herein by reference in its entirety.

In certain embodiments described herein, the down regulation (e.g. attenuation) of the pts operon can enhance acetate utilization by the host cells. The down regulation of PTS operon activity can be any amount of reduction of specific activity or total activity as compared to when no manipulation has been effectuated. In some instances, the decrease of activity of the complex is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%. In certain embodiments, attenuation is achieved by deleting the pts operon. In some aspects, the activity of the PTS system is modulated by decreasing the activity of an endogenous pts operon. This can be accomplished by replacing the endogenous promoter(s) within the pts operon with synthetic constitutively low expressing promoter(s). In any aspects of the invention, provided herein are recombinant cells comprising one or more heterologously expressed nucleic acids encoding phosphoketolase polypeptides as disclosed herein and further engineered to decrease the activity of the pts operon. In any aspects of the invention, provided herein are recombinant cells comprising one or more heterologously expressed nucleic acids encoding phosphoketolase polypeptides as disclosed herein and further engineered to decrease the activity of EI (ptsI). In any aspects of the invention, provided herein are recombinant cells comprising one or more heterologously expressed nucleic acids encoding phosphoketolase polypeptides as disclosed herein and further engineered to decrease the activity of EIICB$^{Glc}$ (ptsG). In any aspects of the invention, provided herein are recombinant cells comprising one or more heterologously expressed nucleic acids encoding phosphoketolase polypeptides as disclosed herein and further engineered to decrease the activity of EIIA$^{Glc}$ (err). In any aspects of the invention, provided herein are recombinant cells comprising one or more heterologously expressed nucleic acids encoding phosphoketolase polypeptides as disclosed herein and further engineered to decrease the activity of HPr (ptsH). To decrease carbon loss through pyruvate dehydrogenase while increasing the PEP pool for glucose uptake, the activity of phosphoenolpyruvate synthetase (ppsA) can be increased. In any aspects of the invention, provided herein are recombinant cells comprising one or more heterologously expressed nucleic acids encoding phosphoketolase polypeptides as disclosed herein and further engineered to increase the activity of phosphoenolpyruvate synthetase (ppsA). In any further aspect of the invention, the PTS is downregulated and a glucose transport pathway is upregulated. A glucose transport pathway includes, but is not limited to, galactose (galP) and glucokinase (glk). In some embodiments, the pts operon is downregulated, the galactose (galP) gene is upregulated, and the glucokinase (glk) gene is upregulated. Activity modulation (e.g., decreased) of isozymes of the PTS is also contemplated herein. In any aspects of the invention, provided herein are recombinant cells comprising one or more heterologously expressed nucleic acids encoding phosphoketolase polypeptides as disclosed herein and further engineered to decrease the activity of PTS isozymes.

Pathways Involving Xylose Utilization

In certain embodiments described herein, the utilization of xylose is desirable to convert sugar derived from plant biomass into desired products, such as mevalonate, such as isoprenoid precursors, isoprene and/or isoprenoids. In some organisms, xylose utilization requires use of the pentose phosphate pathway for conversion to fructose-6-phosphate for metabolism. Organisms can be engineered for enhanced xylose utilization, either by deactivating the catabolite repression by glucose, or by heterologous expression of genes from the xylose operon found in other organisms. The xylulose pathway can be engineered as described below to enhance production of mevalonate, isoprenoid precursors, isoprene and/or isoprenoids via the phosphoketolase pathway.

Enhancement of xylose uptake and conversion to xylulose-5-phosphate followed by direct entry into the phosphoketolase pathway would be a benefit. Without being bound by theory, this allows the carbon flux to bypass the pentose phosphate pathway (although some glyceraldehyde-3-phosphate may be cycled into PPP as needed). Enhanced expression of xyulokinase can be used to increase the overall production of xylulose-5-phosphate. Optimization of xyulokinase expression and activity can be used to enhance xylose utilization in a strain with a phosphoketolase pathway. The desired xyulokinase may be either the endogenous host's enzyme, or any heterologous xyulokinase compatible with the host. In one embodiment, other components of the xylose operon can be overexpressed for increased benefit (e.g., xylose isomerase). In another embodiment, other xylose pathway enzymes (e.g. xylose reductase) may need to be attenuated (e.g., reduced or deleted activity).

Accordingly, the host cells engineered to have phosphoketolase enzymes as described herein can be further engineered to overexpress xylulose isomerase and/or xyulokinase, either the endogenous forms or heterologous forms, to improve overall yield and productivity of mevalonate, isoprenoid precursors, isoprene and/or isoprenoids.

Pathways Involving Transaldolase and Transketolase Enzymes of Pentose Phosphate Pathway Some microorganisms capable of anaerobic or heterofermentative growth incorporate a phosphoketolase pathway instead of or in addition to a glycolytic pathway. This pathway depends on the activity of the pentose phosphate pathway enzymes transaldolase and transketolase. Accordingly, the host cells engineered to have phosphoketolase enzymes as described herein can be further engineered to overexpress a transketolase and transaldolase, either the endogenous forms or heterologous forms, to improve pathway flux, decrease the levels of potentially toxic intermediates, reduce the diversion of intermediates to non-productive pathways, and improve the overall yield and productivity of mevalonate, isoprenoid precursors, isoprene and/or isoprenoids.

Combinations of Mutations

It is understood that for any of the enzymes and/or enzyme pathways described herein, molecular manipulations that modulate any combination (two, three, four, five, six, seven, eight, nine, ten, eleven, twelve, thirteen, or fourteen) of the enzymes and/or enzyme pathways described herein is expressly contemplated. For ease of the recitation of the combinations, citrate synthase (gltA) is designated as A, phosphotransacetylase (pta) is designated as B, acetate kinase (ackA) is designated as C, lactate dehydrogenase (ldhA) is designated as D, glyceraldehyde 3-phosphate dehydrogenase (gap) is designated as E, and pyruvate decarboxylase (aceE, aceF, and/or lpdA) is designated as F, phosphogluconate dehydratase (edd) is designated as G, 2-keto-3-deoxygluconate 6-phosphate aldolase (eda) is designated as H phosphofructokinase is designated as I, transaldolase is designated as J, transketolase is designated as K, ribulose-5-phosphate-epimerase is designated as L, ribose-5-phosphate epimerase is designated as M, xylukinase is designated as N, xylose isomerase is designated as O, and xylitol reductase is designated as P, ribose-5-phosphate isomerase (rpi) is designated as Q, D-ribulose-5-phosphate 3-epimerase (rpe) is designated as R, phosphoenolpyruvate synthetase (pps) is designated as S, fructose bisphosphate aldolase (fba) is designated as T, EI (ptsI) is designated as U, EIICB$^{Glc}$ (ptsG) is designated as V, ERA' (crr) is designated as W, HPr (ptsH) is designated as X, galactose (galP) is designated as Y, glucokinase (glk) is designated as Z, glucose-6-phosphate dehydrogenase (zwf) is designated as AA. As discussed above, aceE, aceF, and/or lpdA enzymes of the pyruvate decarboxylase complex can be used singly, or two of three enzymes, or three of three enzymes for increasing pyruvate decarboxylase activity. Thus, any and all combination of enzymes designated as A-M herein is expressly contemplated as well as any and all combination of enzymes designated as A-AA. Furthermore, any combination described above can be used in combination with any of the enzymes and/or enzyme pathways described herein (e.g., phosphoketolase, MVA pathway polypeptides, isoprene synthase, DXP pathway polypeptides).

Other Regulators and Factors for Increased Production

Other molecular manipulations can be used to increase the flow of carbon towards mevalonate production. One method is to reduce, decrease or eliminate the effects of negative regulators for pathways that feed into the mevalonate pathway. For example, in some cases, the genes aceEF-lpdA are in an operon, with a fourth gene upstream pdhR. The gene pdhR is a negative regulator of the transcription of its operon. In the absence of pyruvate, it binds its target promoter and represses transcription. It also regulates ndh and cyoABCD in the same way (Ogasawara, H. et al. 2007.

J. Bact. 189:5534-5541). In one aspect, deletion of pdhR regulator can improve the supply of pyruvate, and hence the production of mevalonate, isoprenoid precursors, isoprene, and isoprenoids.

In other embodiments, any of the resultant strains described above can be further engineered to modulate the activity of the Entner-Doudoroff pathway. The gene coding for phosphogluconate dehydratase or aldolase can be attenuated or deleted. In other embodiments, any of the resultant strains described above may also be engineered to decrease or remove the activity of acetate kinase or citrate synthase. In other embodiments, any of the strains the resultant strain may also be engineered to decrease or remove the activity of phosphofructokinase. In other embodiments, any of the resultant strains described above may also be engineered to modulate the activity of glyceraldehyde-3-phosphate dehydrogenase. The activity of glyceraldehyde-3-phosphate dehydrogenase can be modulated by decreasing its activity. In other embodiments, the enzymes from the non-oxidative branch of the pentose phosphate pathway, such as transketolase, transaldolase, ribulose-5-phosphate-epimerase and (or) ribose-5-phosphate epimerase can be overexpressed.

In other aspects, the host cells can be further engineered to increase intracellular acetyl-phosphate concentrations by introducing heterologous nucleic acids encoding sedoheptulose-1,7-bisphosphatase/fructose-1,6-bisphosphate aldolase and sedoheptulose-1,7-bisphosphatase/fructose-1,6-bisphosphate phosphatase. In certain embodiments, the host cells having these molecular manipulations can be combined with attenuated or deleted transaldolase (talB) and phosphofructokinase (pfkA and/or pfkB) genes, thereby allowing faster conversion of erythrose 4-phosphate, dihydroxyacetone phosphate, and glyceraldehyde 3-phosphate into sedoheptulose 7-phosphate and fructose 1-phosphate (see FIG. 5).

In other aspects, the introduction of 6-phosphogluconolactonase (PGL) into cells (such as various *E. coli* strains) which lack PGL can be used to improve production of mevalonate, isoprenoid precursors, isoprene, and isoprenoids. PGL may be introduced by introduction of the encoding gene using chromosomal integration or extra-chromosomal vehicles, such as plasmids.

In addition to the host cell (e.g., bacterial host cell) mutations for modulating various enzymatic pathways described herein that increases carbon flux towards mevalonate production, the host cells described herein comprise genes encoding phosphoketolase polypeptide, as well as other enzymes from the upper and lower MVA pathway, including but not limited to, the mvaE and mvaS gene products. Non-limiting examples of MVA pathway polypeptides include acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonte decarboxylase (MVD) polypeptides, phosphomevalonate decarboxylase (PMDC) polypeptides, isopentenyl phosphate kinase (IPK) polypeptides, IDI polypeptides, and polypeptides (e.g., fusion polypeptides) having an activity of two or more MVA pathway polypeptides. MVA pathway polypeptides can include polypeptides, fragments of polypeptides, peptides, and fusions polypeptides that have at least one activity of an MVA pathway polypeptide. Exemplary MVA pathway nucleic acids include nucleic acids that encode a polypeptide, fragment of a polypeptide, peptide, or fusion polypeptide that has at least one activity of an MVA pathway polypeptide. Exemplary MVA pathway polypeptides and nucleic acids include naturally-occurring polypeptides and nucleic acids from any of the source organisms described herein.

Non-limiting examples of MVA pathway polypeptides which can be used are described in International Patent Application Publication No. WO2009/076676; WO2010/003007 and WO2010/148150

Exemplary Cell Culture Media

As used herein, the terms "minimal medium" or "minimal media" refer to growth media containing the minimum nutrients possible for cell growth, generally, but not always, without the presence of one or more amino acids (e.g., 1, 2, 3, 4, 5, 6, 7, 8, 9, 10, or more amino acids). Minimal medium typically contains: (1) a carbon source for bacterial growth; (2) various salts, which can vary among bacterial species and growing conditions; and (3) water. The carbon source can vary significantly, from simple sugars like glucose to more complex hydrolysates of other biomass, such as yeast extract, as discussed in more detail below. The salts generally provide essential elements such as magnesium, nitrogen, phosphorus, and sulfur to allow the cells to synthesize proteins and nucleic acids. Minimal medium can also be supplemented with selective agents, such as antibiotics, to select for the maintenance of certain plasmids and the like. For example, if a microorganism is resistant to a certain antibiotic, such as ampicillin or tetracycline, then that antibiotic can be added to the medium in order to prevent cells lacking the resistance from growing. Medium can be supplemented with other compounds as necessary to select for desired physiological or biochemical characteristics, such as particular amino acids and the like.

Any minimal medium formulation can be used to cultivate the host cells. Exemplary minimal medium formulations include, for example, M9 minimal medium and TM3 minimal medium. Each liter of M9 minimal medium contains (1) 200 ml sterile M9 salts (64 g $Na_2HPO_4$-$7H_2O$, 15 g $KH_2PO_4$, 2.5 g NaCl, and 5.0 g $NH_4Cl$ per liter); (2) 2 ml of 1 M $MgSO_4$ (sterile); (3) 20 ml of 20% (w/v) glucose (or other carbon source); and (4) 100 µl of 1 M $CaCl_2$ (sterile). Each liter of TM3 minimal medium contains (1) 13.6 g $K_2HPO_4$; (2) 13.6 g $KH_2PO_4$; (3) 2 g $MgSO_4$*$7H_2O$; (4) 2 g Citric Acid Monohydrate; (5) 0.3 g Ferric Ammonium Citrate; (6) 3.2 g $(NH_4)_2SO_4$; (7) 0.2 g yeast extract; and (8) 1 ml of 1000× Trace Elements solution; pH is adjusted to ~6.8 and the solution is filter sterilized. Each liter of 1000× Trace Elements contains: (1) 40 g Citric Acid Monohydrate; (2) 30 g $MnSO_4$*$H_2O$; (3) 10 g NaCl; (4) 1 g $FeSO_4$*$7H_2O$; (4) 1 g $CoCl_2$*$6H_2O$; (5) 1 g $ZnSO_4$*$7H_2O$; (6) 100 mg $CuSO_4$*$5H_2O$; (7) 100 mg $H_3BO_3$; and (8) 100 mg $NaMoO_4$*$2H_2O$; pH is adjusted to ~3.0.

An additional exemplary minimal media includes (1) potassium phosphate $K_2HPO_4$, (2) Magnesium Sulfate $MgSO_4$*$7H_2O$, (3) citric acid monohydrate $C_6H_8O_7$*$H_2O$, (4) ferric ammonium citrate $NH_4FeC_6H_5O_7$, (5) yeast extract (from biospringer), (6) 1000× Modified Trace Metal Solution, (7) sulfuric acid 50% w/v, (8) foamblast 882 (Emerald Performance Materials), and (9) Macro Salts Solution 3.36 ml. All of the components are added together and dissolved in deionized $H_2O$ and then heat sterilized. Following cooling to room temperature, the pH is adjusted to 7.0 with ammonium hydroxide (28%) and q.s. to volume. Vitamin Solution and spectinomycin are added after sterilization and pH adjustment.

Any carbon source can be used to cultivate the host cells. The term "carbon source" refers to one or more carbon-containing compounds capable of being metabolized by a host cell or organism. For example, the cell medium used to cultivate the host cells can include any carbon source suitable for maintaining the viability or growing the host cells. In some aspects, the carbon source is a carbohydrate (such as monosaccharide, disaccharide, oligosaccharide, or polysaccharides), or invert sugar (e.g., enzymatically treated sucrose syrup).

In some aspects, the carbon source includes yeast extract or one or more components of yeast extract. In some aspects, the concentration of yeast extract is 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract. In some aspects, the carbon source includes both yeast extract (or one or more components thereof) and another carbon source, such as glucose.

Exemplary monosaccharides include glucose and fructose; exemplary oligosaccharides include lactose and sucrose, and exemplary polysaccharides include starch and cellulose. Exemplary carbohydrates include C6 sugars (e.g., fructose, mannose, galactose, or glucose) and C5 sugars (e.g., xylose or arabinose).

Exemplary Cell Culture Conditions

Materials and methods suitable for the maintenance and growth of the recombinant cells of the invention are described infra, e.g., in the Examples section. Other materials and methods suitable for the maintenance and growth of bacterial cultures are well known in the art. Exemplary techniques can be found in International Publication No. WO 2009/076676, U.S. Patent Publ. No. 2009/0203102, WO 2010/003007, US Publ. No. 2010/0048964, WO 2009/132220, US Publ. No. 2010/0003716, *Manual of Methods for General Bacteriology* Gerhardt et al., eds), *American Society for Microbiology*, Washington, D.C. (1994) or Brock in *Biotechnology: A Textbook of Industrial Microbiology*, Second Edition (1989) Sinauer Associates, Inc., Sunderland, Mass. In some aspects, the cells are cultured in a culture medium under conditions permitting the expression of phosphoketolase polypeptide, as well as other enzymes from the upper and lower MVA pathway, including but not limited to, the mvaE and mvaS gene products, isoprene synthase, DXP pathway (e.g., DXS), IDI, or PGL polypeptides encoded by a nucleic acid inserted into the host cells.

Standard cell culture conditions can be used to culture the cells (see, for example, WO 2004/033646 and references cited therein). In some aspects, cells are grown and maintained at an appropriate temperature, gas mixture, and pH (such as at about 20° C. to about 37° C., at about 6% to about 84% $CO_2$, and at a pH between about 5 to about 9). In some aspects, cells are grown at 35° C. in an appropriate cell medium. In some aspects, the pH ranges for fermentation are between about pH 5.0 to about pH 9.0 (such as about pH 6.0 to about pH 8.0 or about 6.5 to about 7.0). Cells can be grown under aerobic, anoxic, or anaerobic conditions based on the requirements of the host cells. In addition, more specific cell culture conditions can be used to culture the cells. For example, in some embodiments, the recombinant cells (such as *E. coli* cells) comprise one or more heterologous nucleic acids encoding a phosphoketolase polypeptide, as well as enzymes from the upper, including but not limited to, the mvaE and mvaS gene products mvaE and mvaS polypeptides from *L. grayi, E. faecium, E. gallinarum, E. casseliflavus* and/or *E. faecalis* under the control of a strong promoter in a low to medium copy plasmid and are cultured at 34° C.

Standard culture conditions and modes of fermentation, such as batch, fed-batch, or continuous fermentation that can be used are described in International Publication No. WO 2009/076676, U.S. Patent Publ. No. 2009/0203102, WO 2010/003007, US Publ. No. 2010/0048964, WO 2009/132220, US Publ. No. 2010/0003716. Batch and Fed-Batch fermentations are common and well known in the art and examples can be found in Brock, Biotechnology: A Textbook of Industrial Microbiology, Second Edition (1989) Sinauer Associates, Inc.

In some aspects, the cells are cultured under limited glucose conditions. By "limited glucose conditions" is meant that the amount of glucose that is added is less than or about 105% (such as about 100%, 90%, 80%, 70%, 60%, 50%, 40%, 30%, 20%, or 10%) of the amount of glucose that is consumed by the cells. In particular aspects, the amount of glucose that is added to the culture medium is approximately the same as the amount of glucose that is consumed by the cells during a specific period of time. In some aspects, the rate of cell growth is controlled by limiting the amount of added glucose such that the cells grow at the rate that can be supported by the amount of glucose in the cell medium. In some aspects, glucose does not accumulate during the time the cells are cultured. In various aspects, the cells are cultured under limited glucose conditions for greater than or about 1, 2, 3, 5, 10, 15, 20, 25, 30, 35, 40, 50, 60, or 70 hours. In various aspects, the cells are cultured under limited glucose conditions for greater than or about 5, 10, 15, 20, 25, 30, 35, 40, 50, 60, 70, 80, 90, 95, or 100% of the total length of time the cells are cultured. While not intending to be bound by any particular theory, it is believed that limited glucose conditions can allow more favorable regulation of the cells.

In some aspects, the recombinant cells are grown in batch culture. The recombinant cells can also be grown in fed-batch culture or in continuous culture. Additionally, the recombinant cells can be cultured in minimal medium, including, but not limited to, any of the minimal media described above. The minimal medium can be further supplemented with 1.0% (w/v) glucose, or any other six carbon sugar, or less. Specifically, the minimal medium can be supplemented with 1% (w/v), 0.9% (w/v), 0.8% (w/v), 0.7% (w/v), 0.6% (w/v), 0.5% (w/v), 0.4% (w/v), 0.3% (w/v), 0.2% (w/v), or 0.1% (w/v) glucose. Additionally, the minimal medium can be supplemented 0.1% (w/v) or less yeast extract. Specifically, the minimal medium can be supplemented with 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract. Alternatively, the minimal medium can be supplemented with 1% (w/v), 0.9% (w/v), 0.8% (w/v), 0.7% (w/v), 0.6% (w/v), 0.5% (w/v), 0.4% (w/v), 0.3% (w/v), 0.2% (w/v), or 0.1% (w/v) glucose and with 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract.

Exemplary Purification Methods

In some aspects, any of the methods described herein further include a step of recovering the compounds produced. In some aspects, any of the methods described herein further include a step of recovering the isoprene. In some aspects, the isoprene is recovered by absorption stripping (See, e.g., U.S. Publ. No. 2011/0178261). In some aspects, any of the methods described herein further include a step of recovering the heterologous polypeptide. In some aspects, any of the methods described herein further include a step of recovering the terpenoid or carotenoid.

Suitable purification methods are described in more detail in U.S. Patent Application Publication US2010/0196977 A1.

Throughout this specification, various patents, patent applications and other types of publications (e.g., journal articles) are referenced. The disclosure of all patents, patent applications, and publications cited herein are hereby incorporated by reference in their entirety for all purposes.

The invention can be further understood by reference to the following examples, which are provided by way of illustration and are not meant to be limiting.

EXAMPLES

Example 1: Identification of Phosphoketolases

Figure 2:
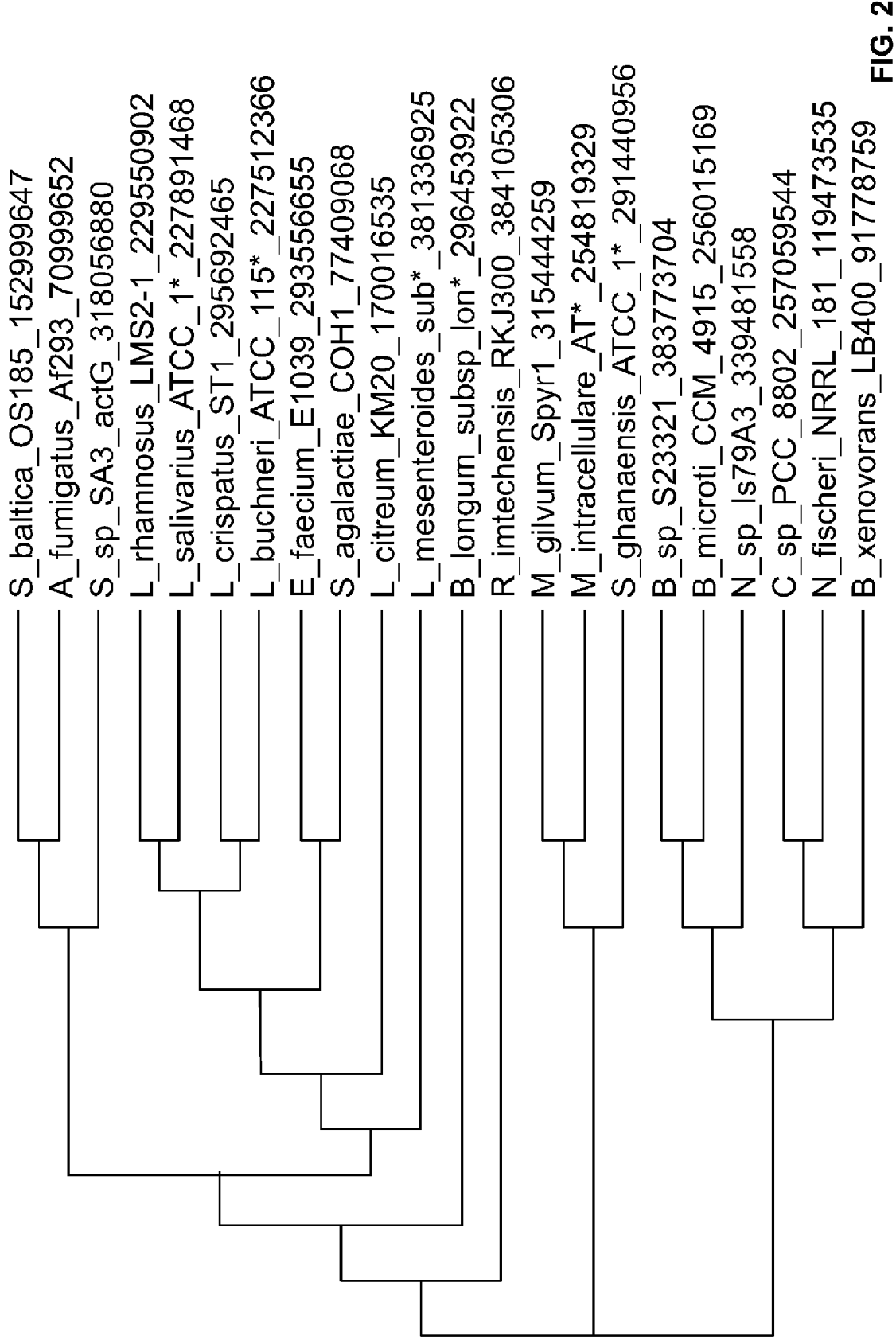
FIG. 2 is a diagram of the center representative sequences of the 22 Clusters of identified PKLs.
Figure 3:
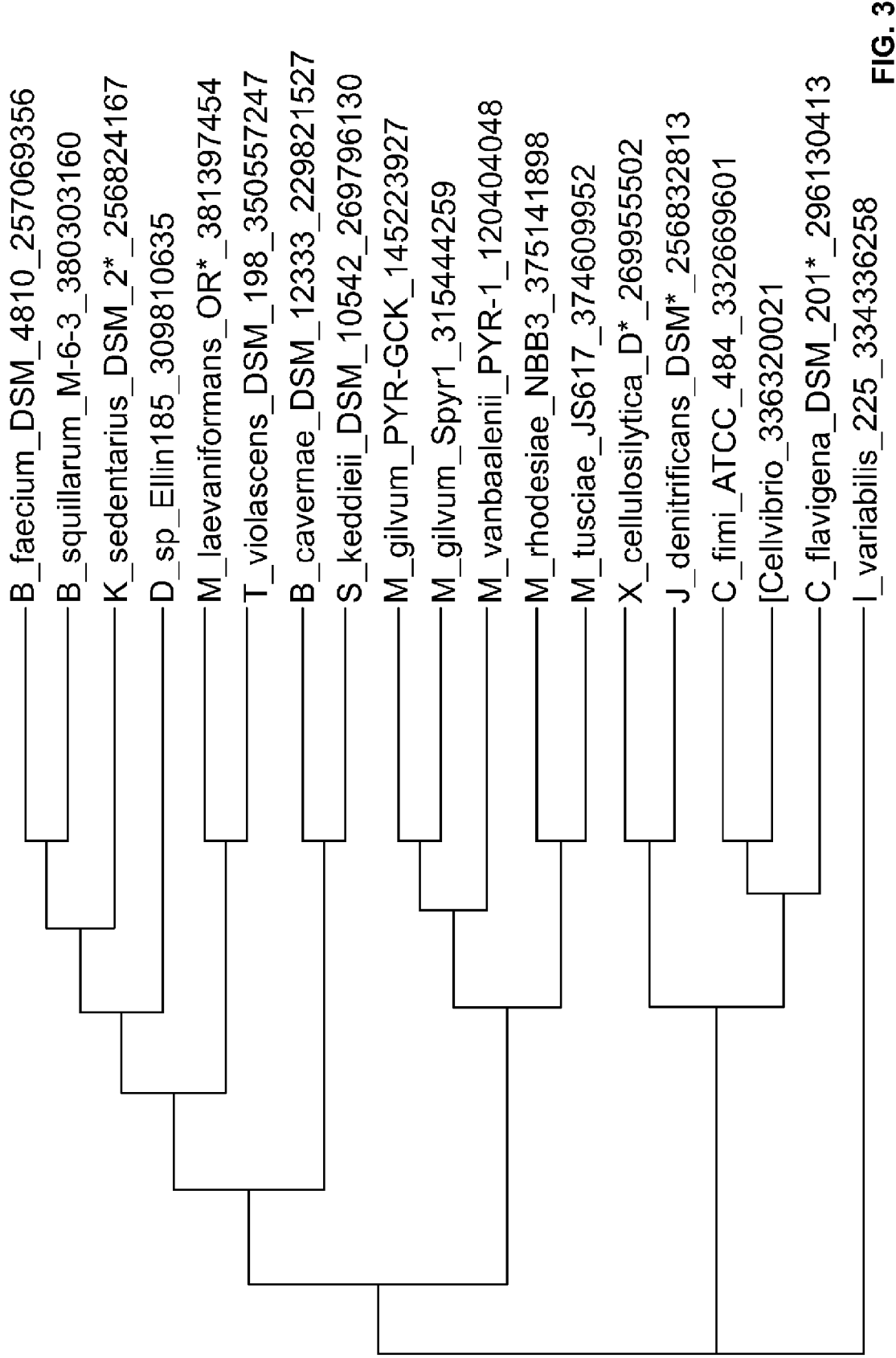
FIG. 3 is a diagram of identified phosphoketolases in Cluster 1.
Figure 4:
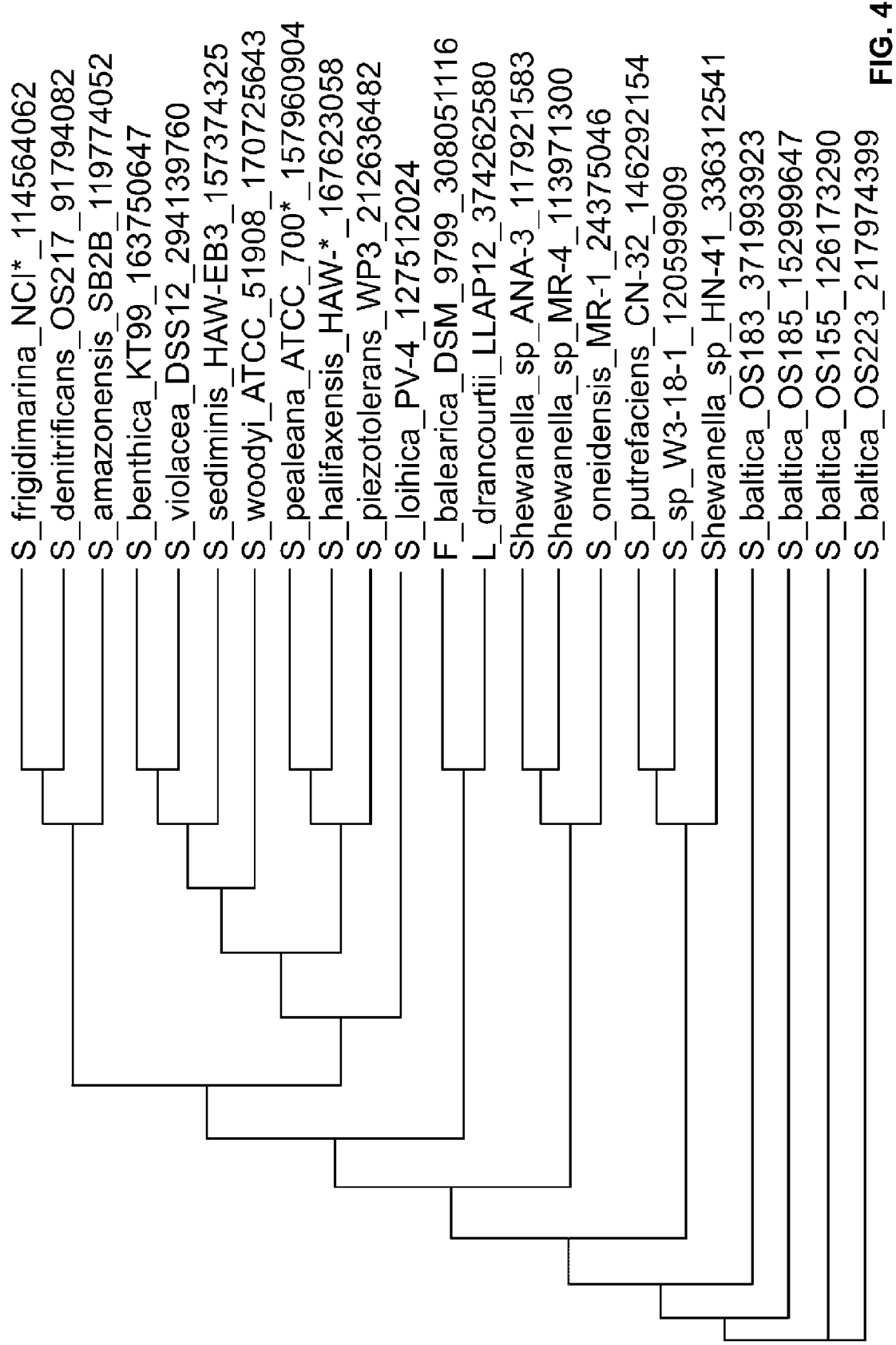
FIG. 4 is a diagram of identified phosphoketolases in Cluster 2.
Figure 5:
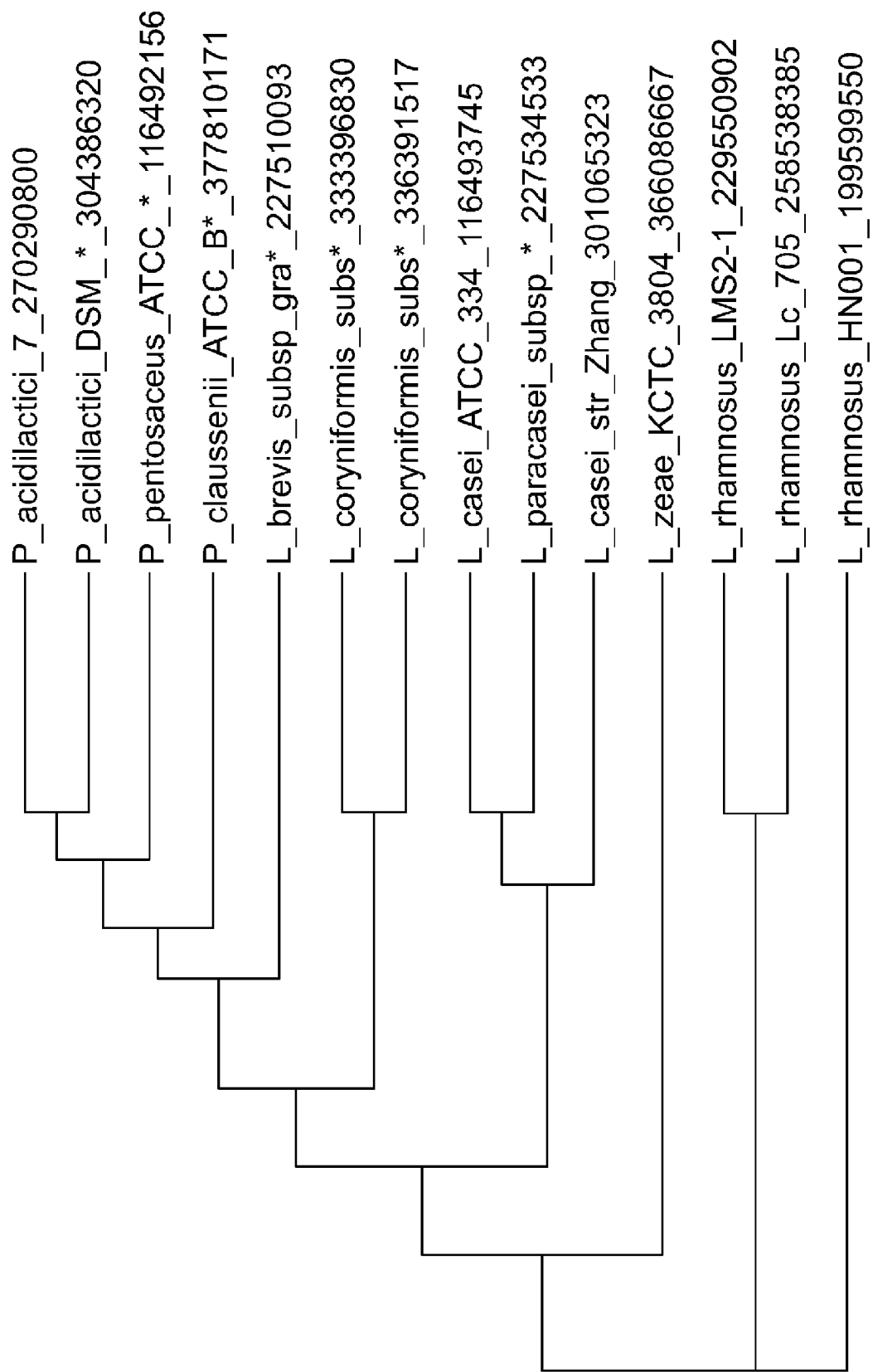
FIG. 5 is a diagram of identified phosphoketolases in Cluster 3.
Figure 6:
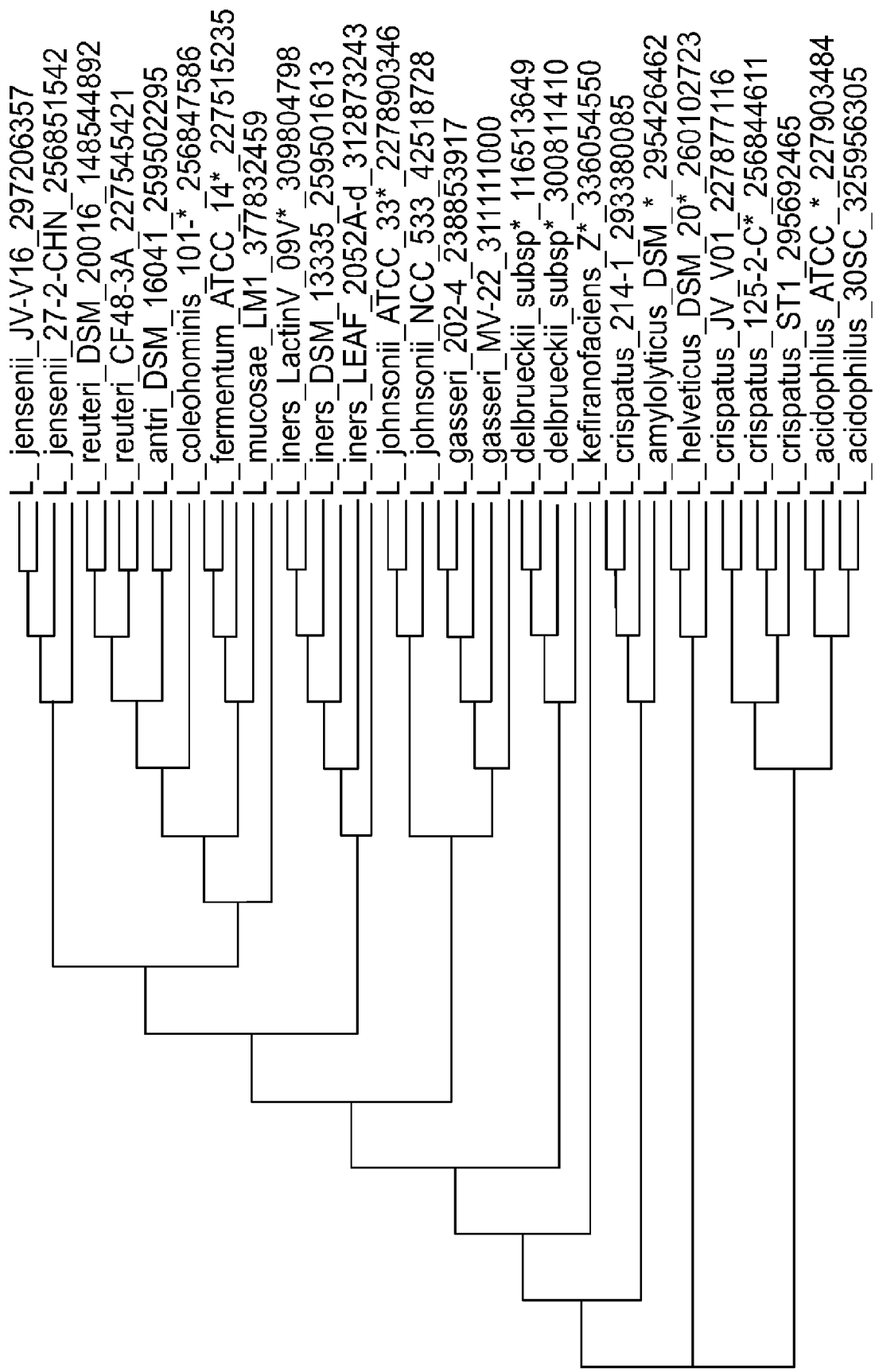
FIG. 6 is a diagram of identified phosphoketolases in Cluster 4.
Figure 7:
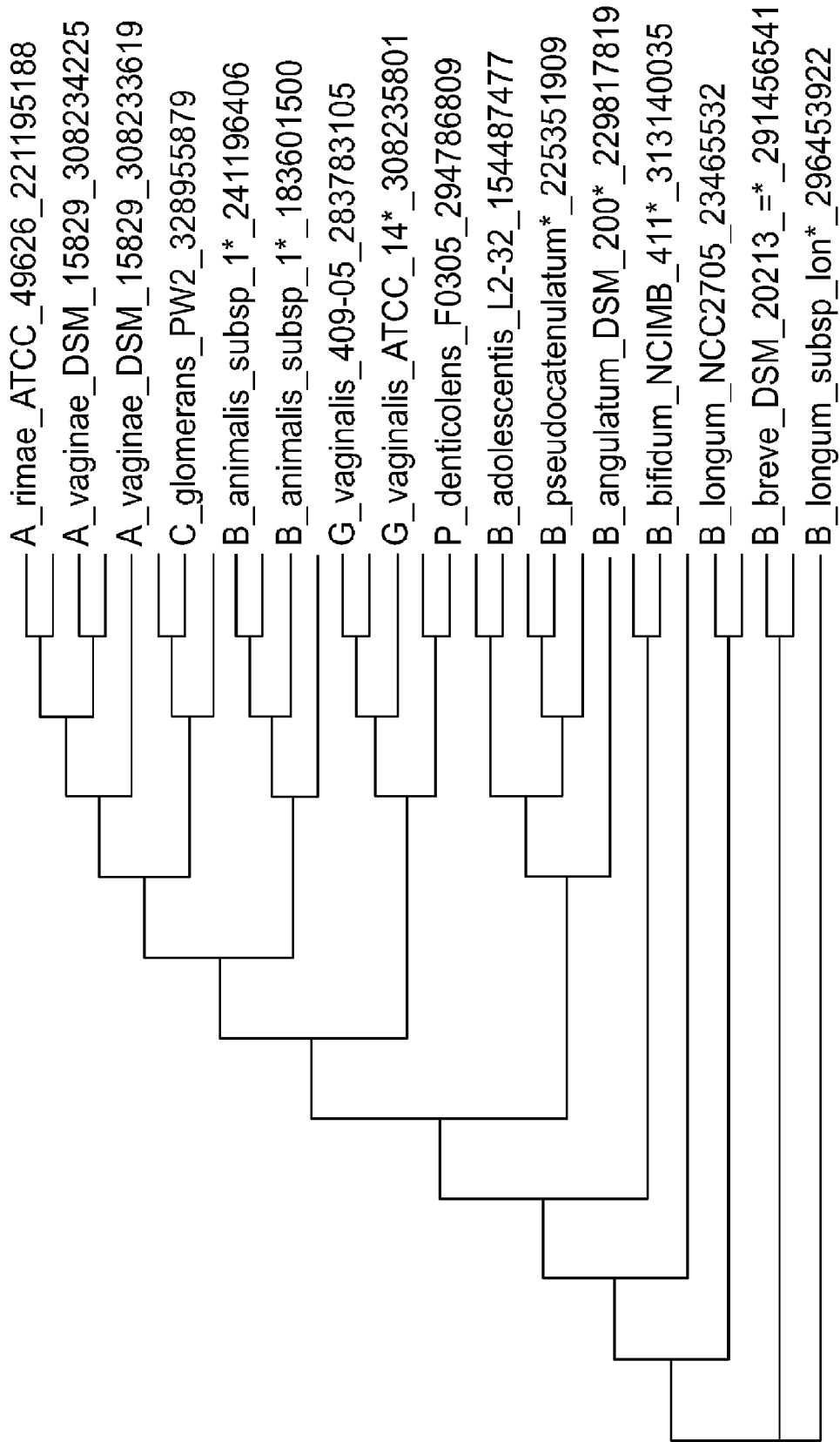
FIG. 7 is a diagram of identified phosphoketolases in Cluster 5.
Figure 8:
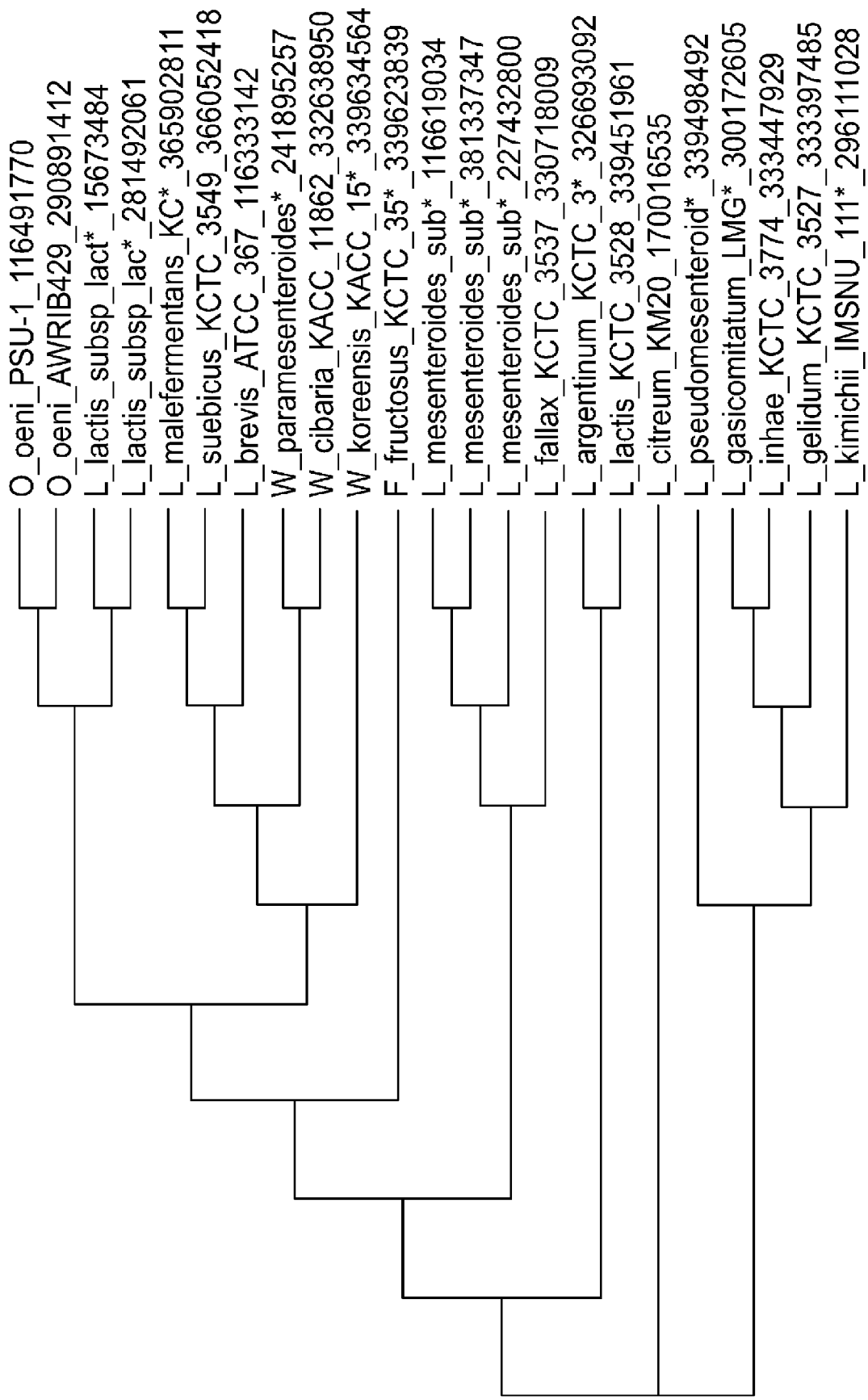
FIG. 8 is a diagram of identified phosphoketolases in Cluster 6.
Figure 9:
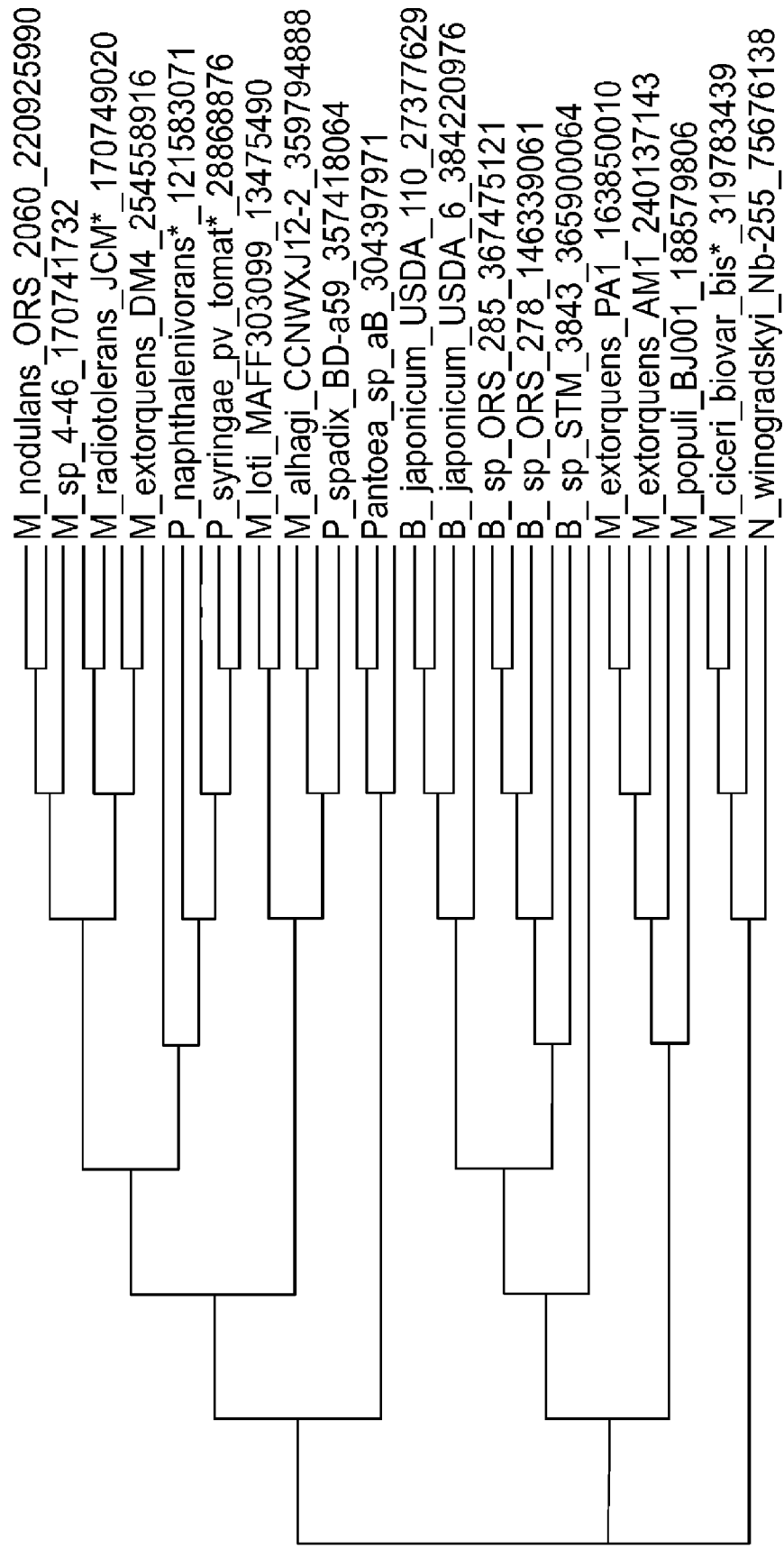
FIG. 9 is a diagram of identified phosphoketolases in Cluster 7.
Figure 10:
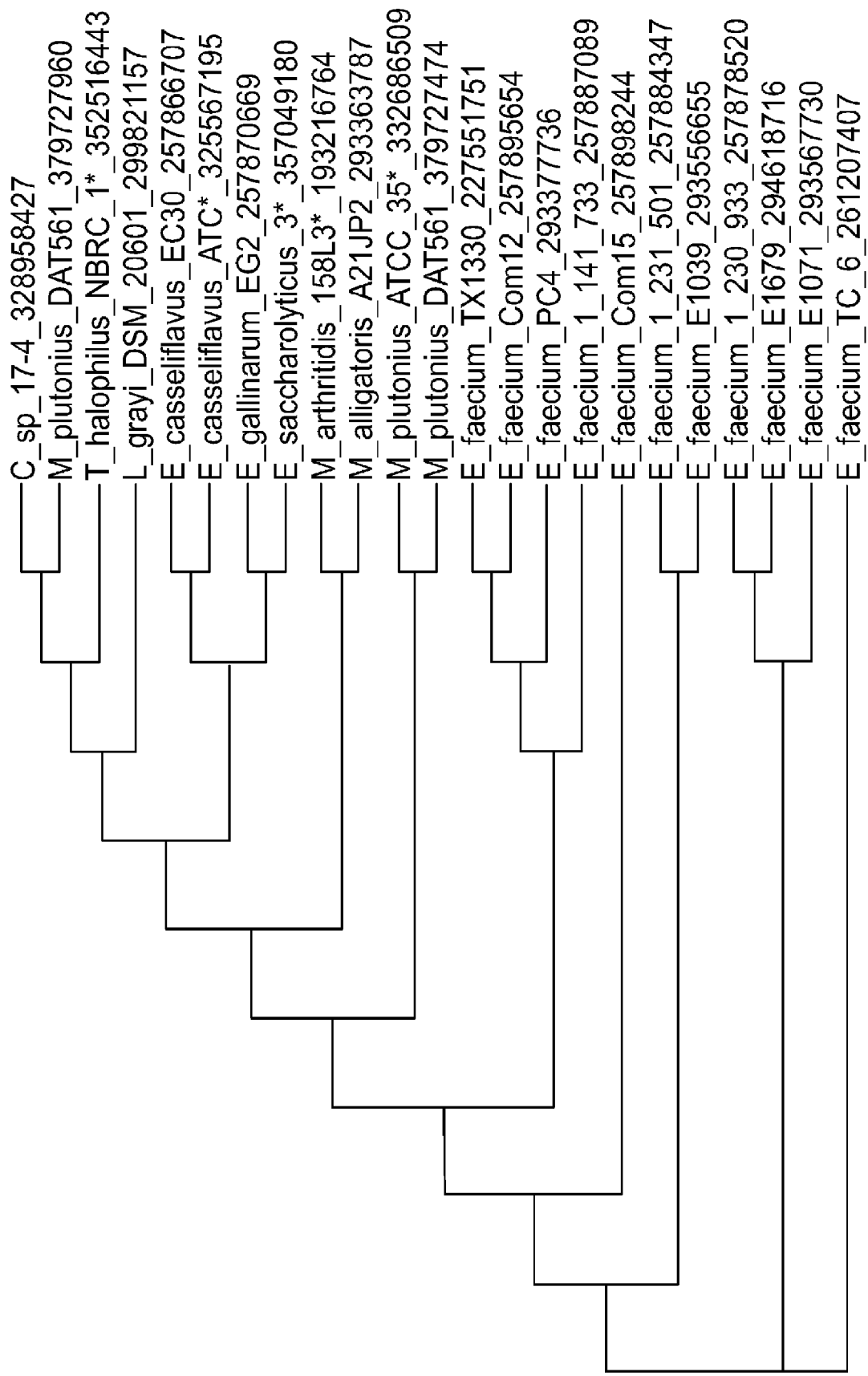
FIG. 10 is a diagram of identified phosphoketolases in Cluster 8.
Figure 12:
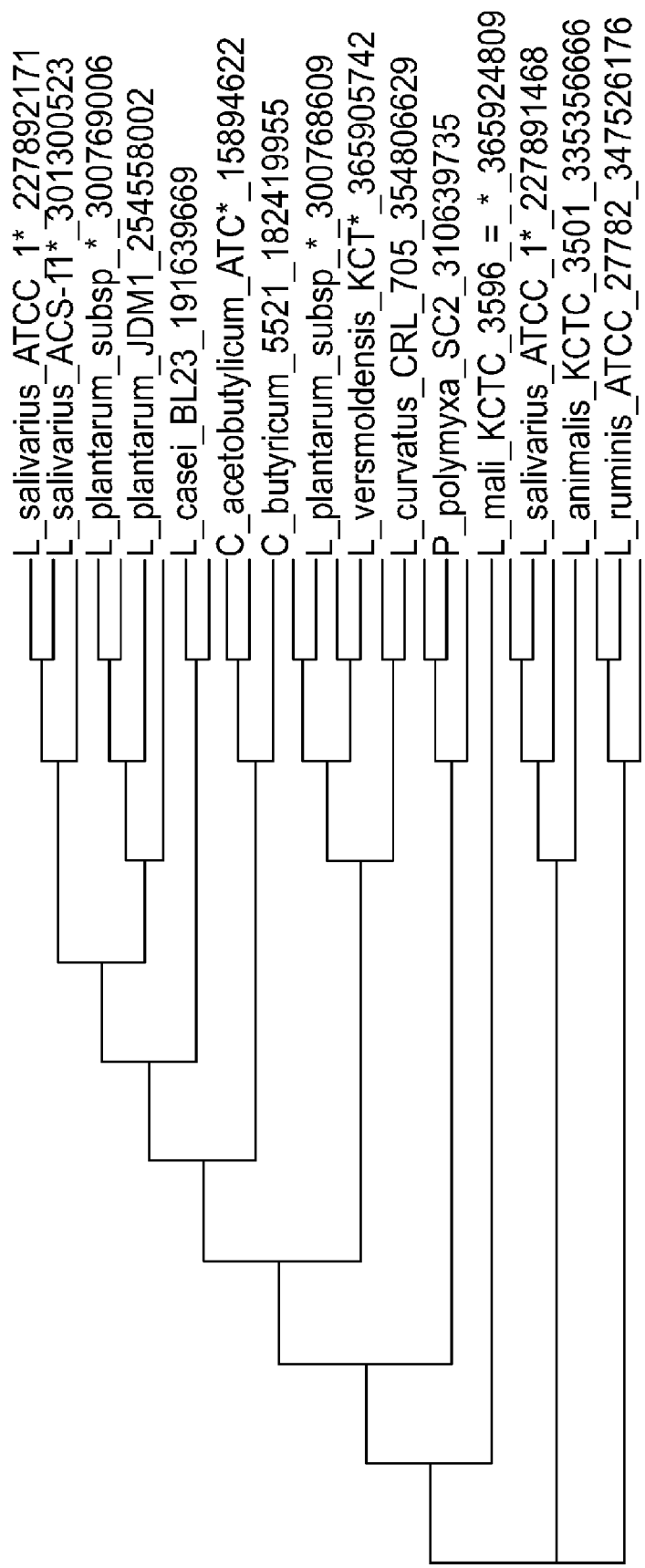
FIG. 12 is a diagram of identified phosphoketolases in Cluster 10.
Figure 13:
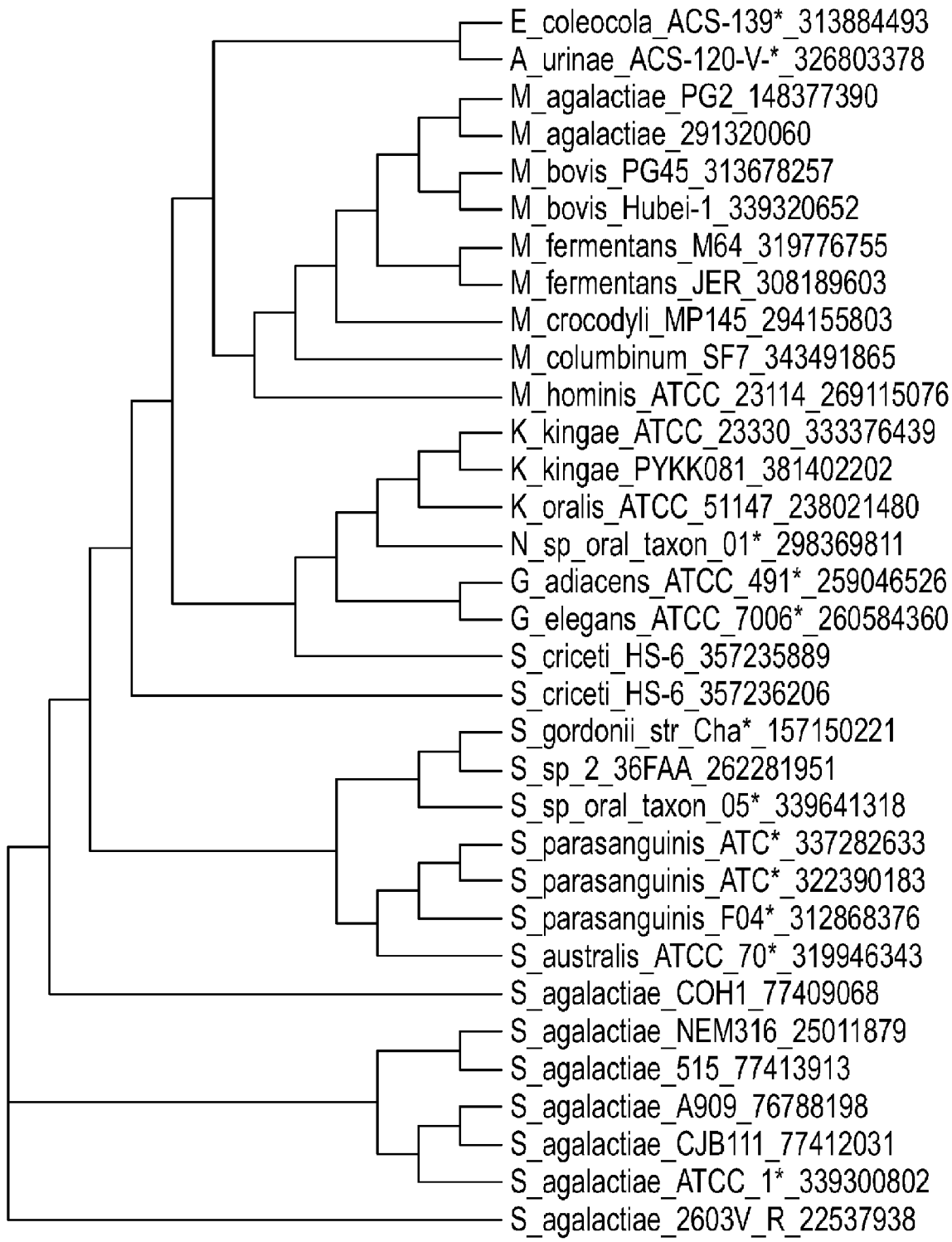
FIG. 13 is a diagram of identified phosphoketolases in Cluster 11.
Figure 14:
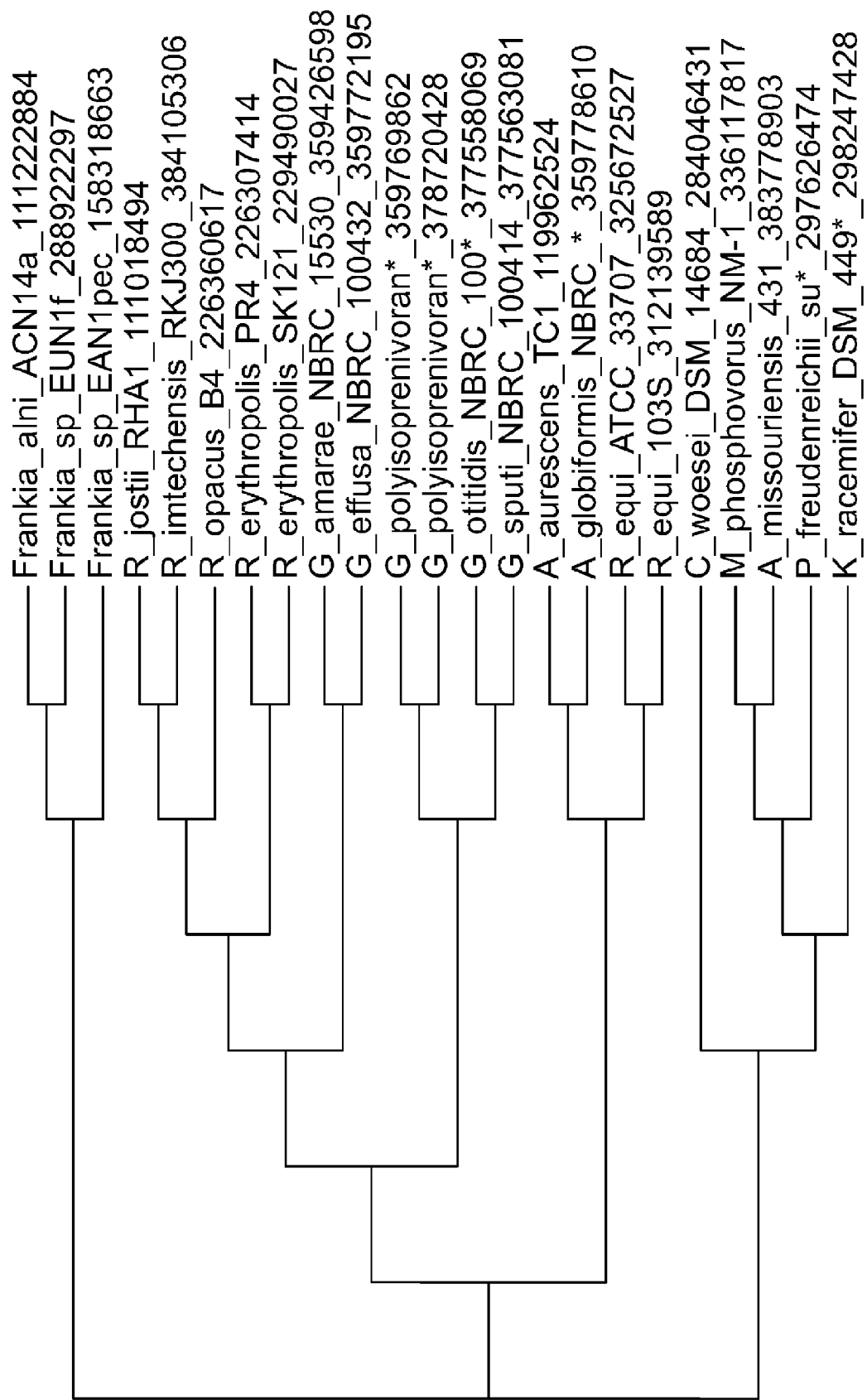
FIG. 14 is a diagram of identified phosphoketolases in Cluster 12.
Figure 15:
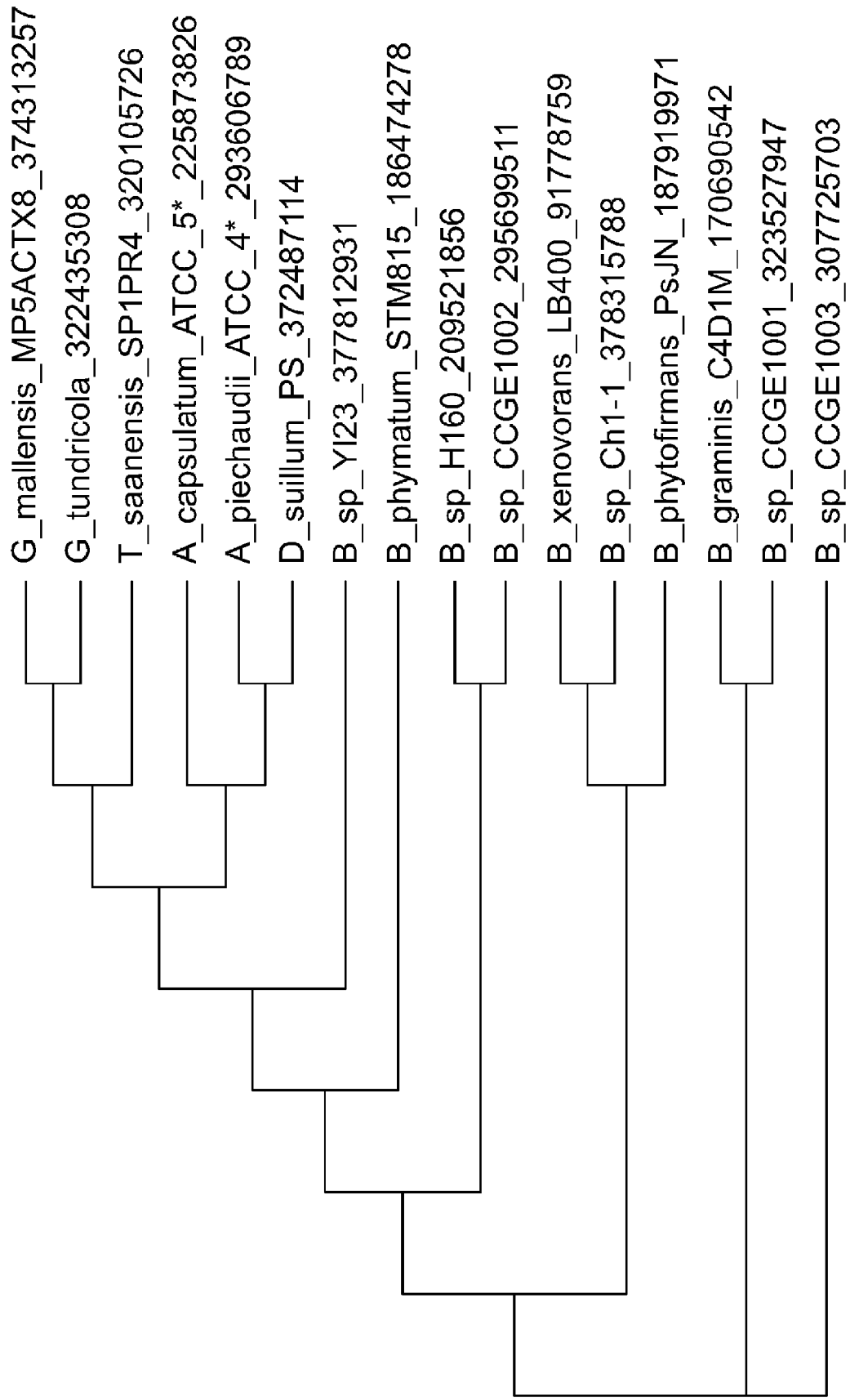
FIG. 15 is a diagram of identified phosphoketolases in Cluster 13.
Figure 16:
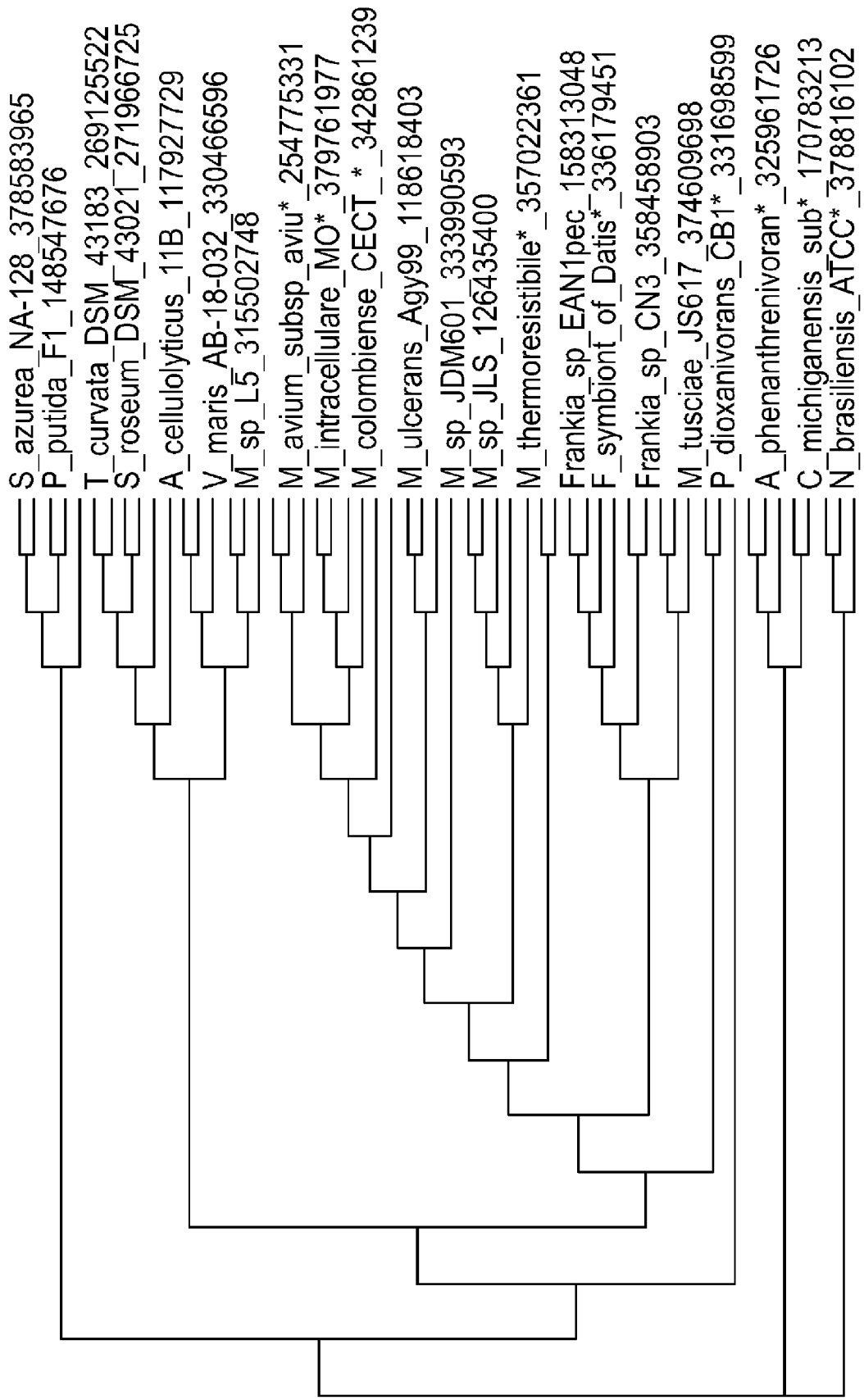
FIG. 16 is a diagram of identified phosphoketolases in Cluster 14.
Figure 17:
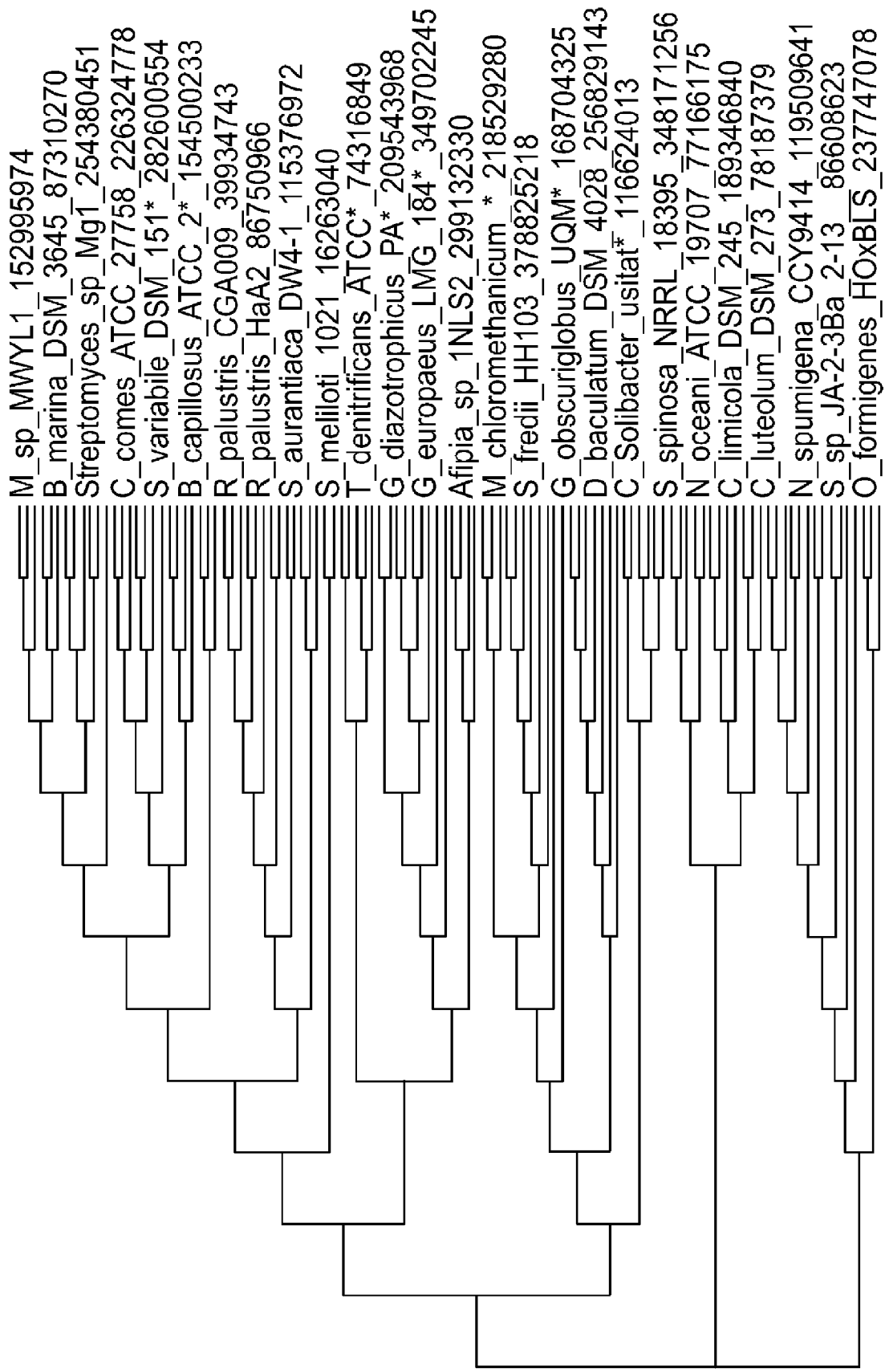
FIG. 17 is a diagram of identified phosphoketolases in Cluster 15.
Figure 18:
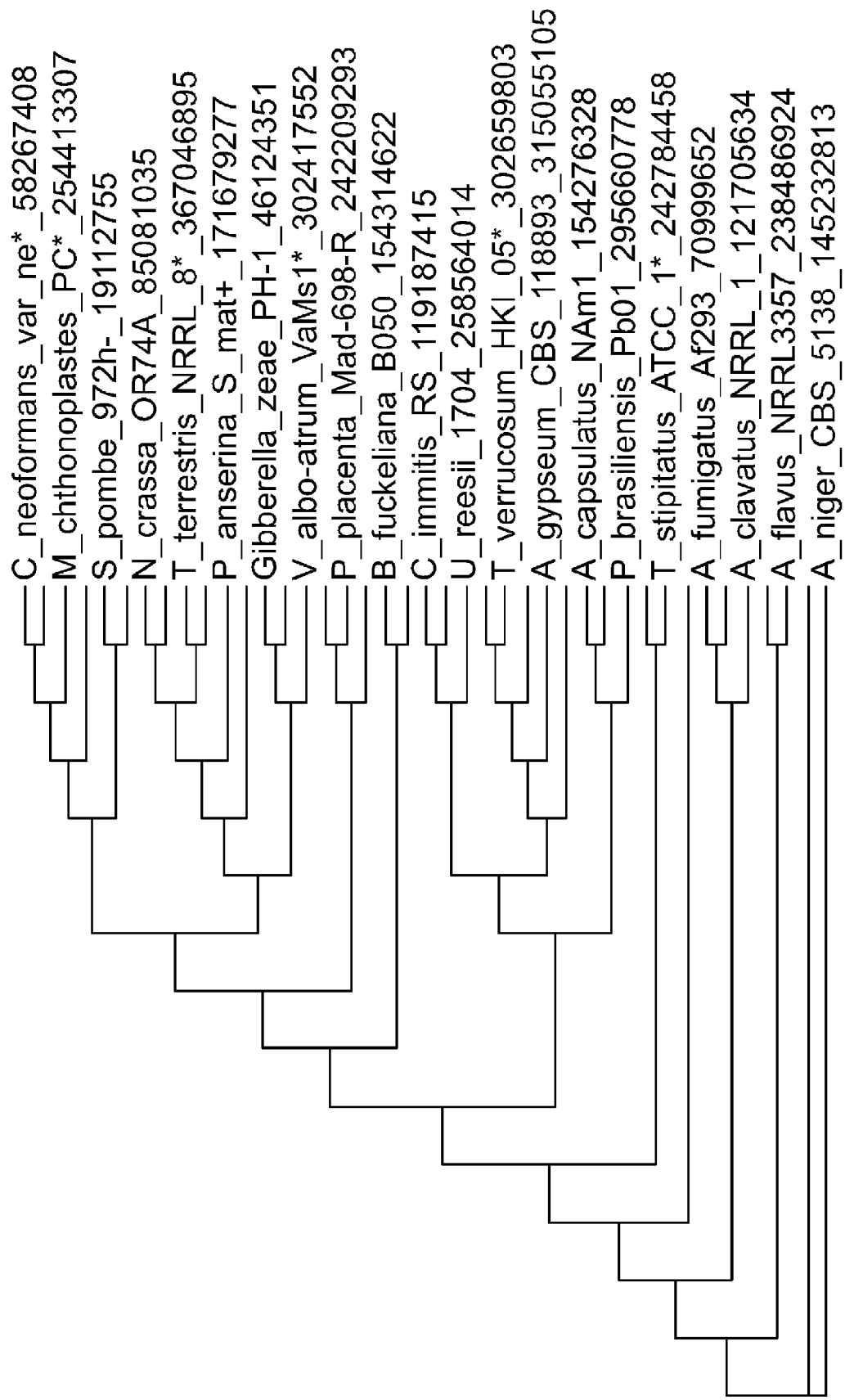
FIG. 18 is a diagram of identified phosphoketolases in Cluster 16.
Figure 19:
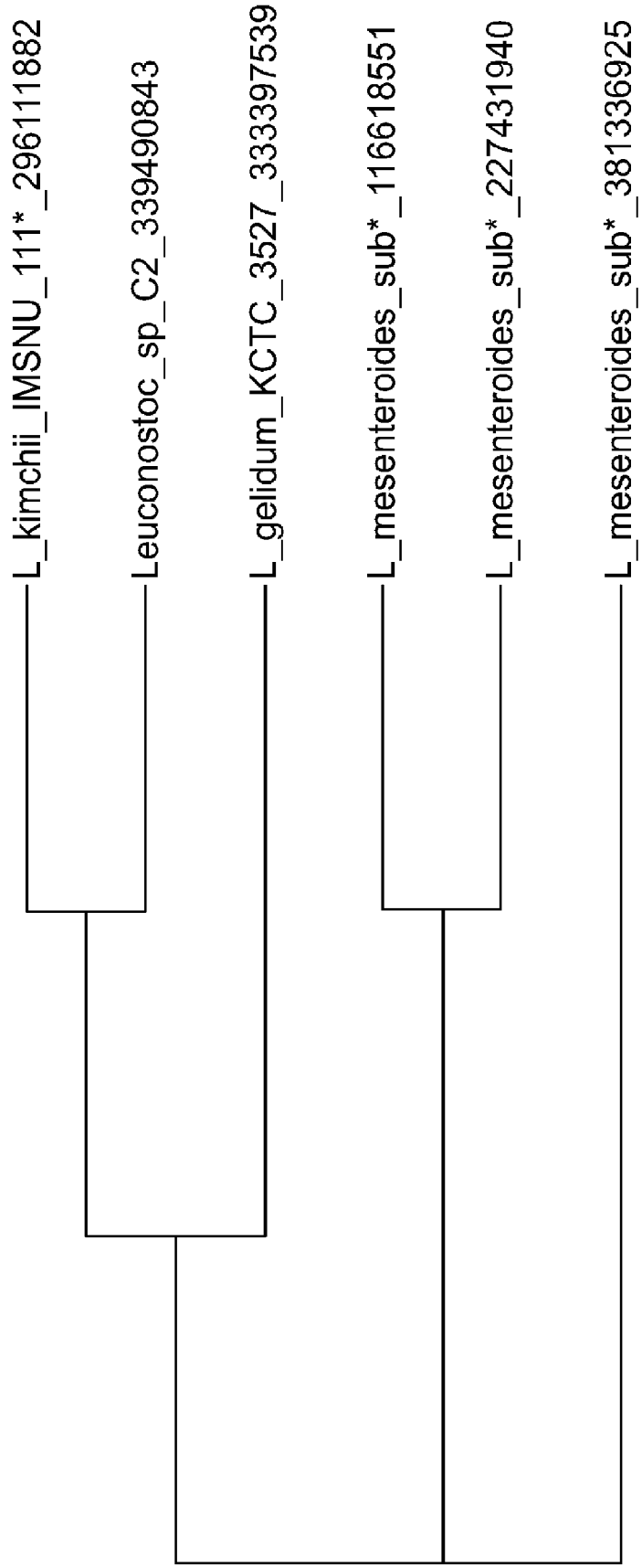
FIG. 19 is a diagram of identified phosphoketolases in Cluster 17.
Figure 20:
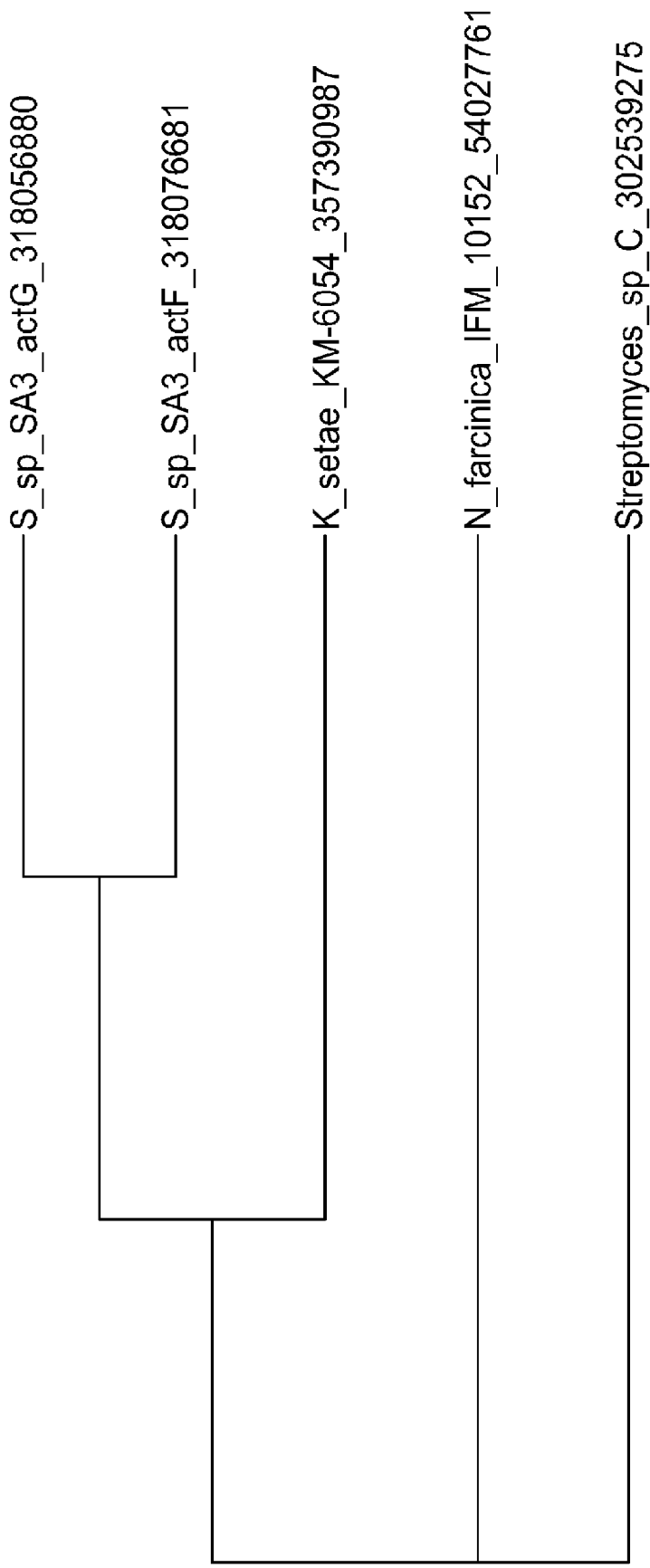
FIG. 20 is a diagram of identified phosphoketolases in Cluster 18.
Figure 21:
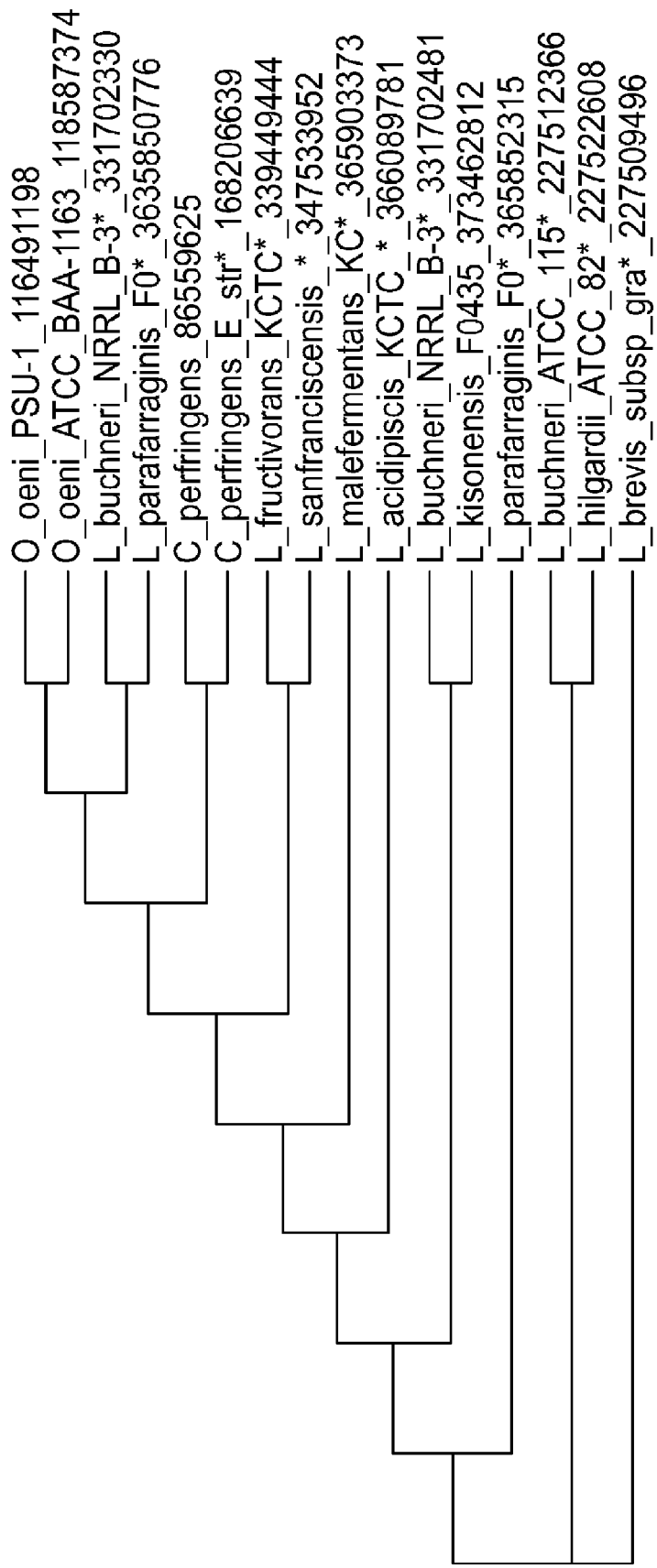
FIG. 21 is a diagram of identified phosphoketolases in Cluster 19.
Figure 22:
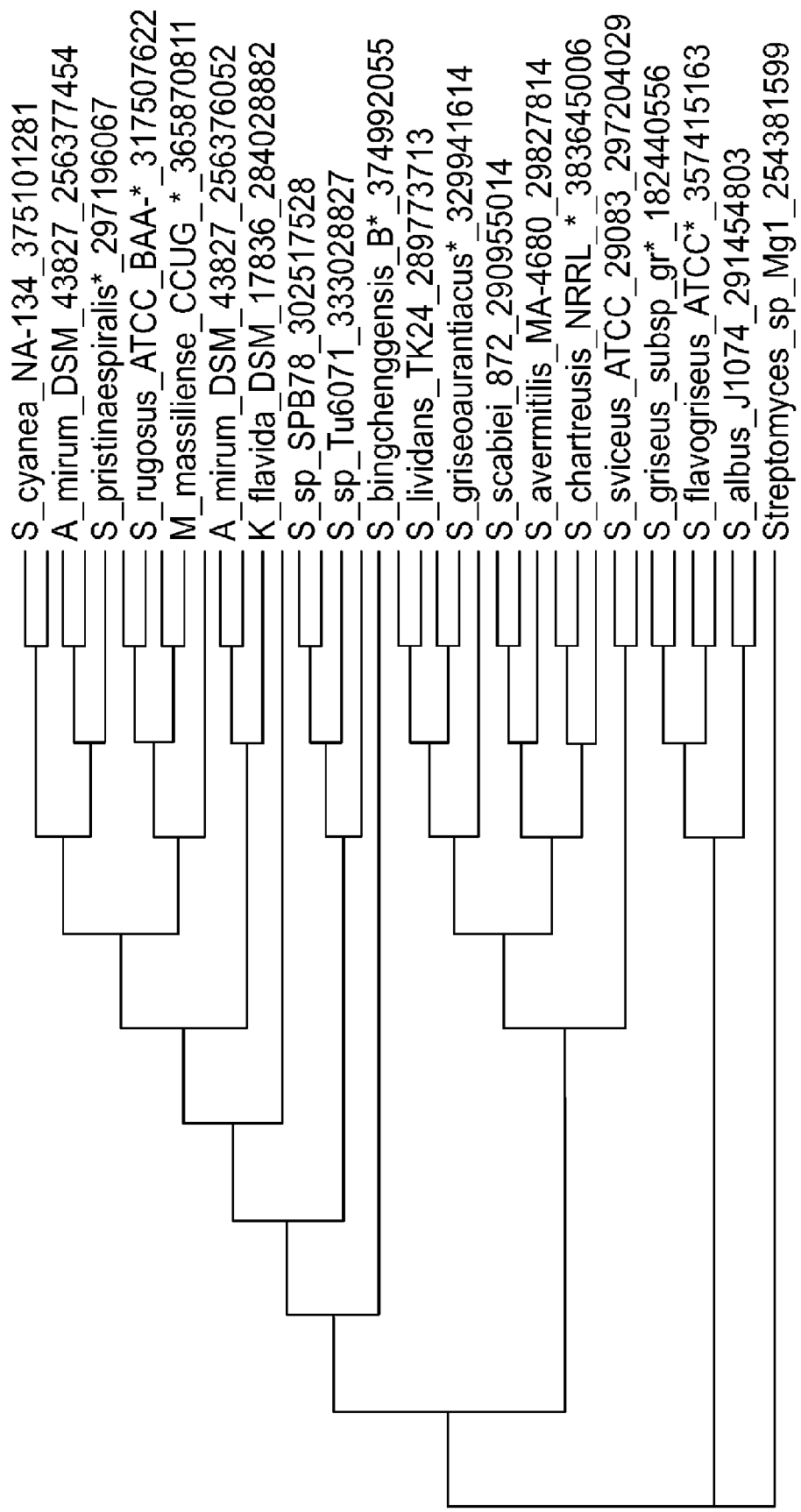
FIG. 22 is a diagram of identified phosphoketolases in Cluster 20.
Figure 23:
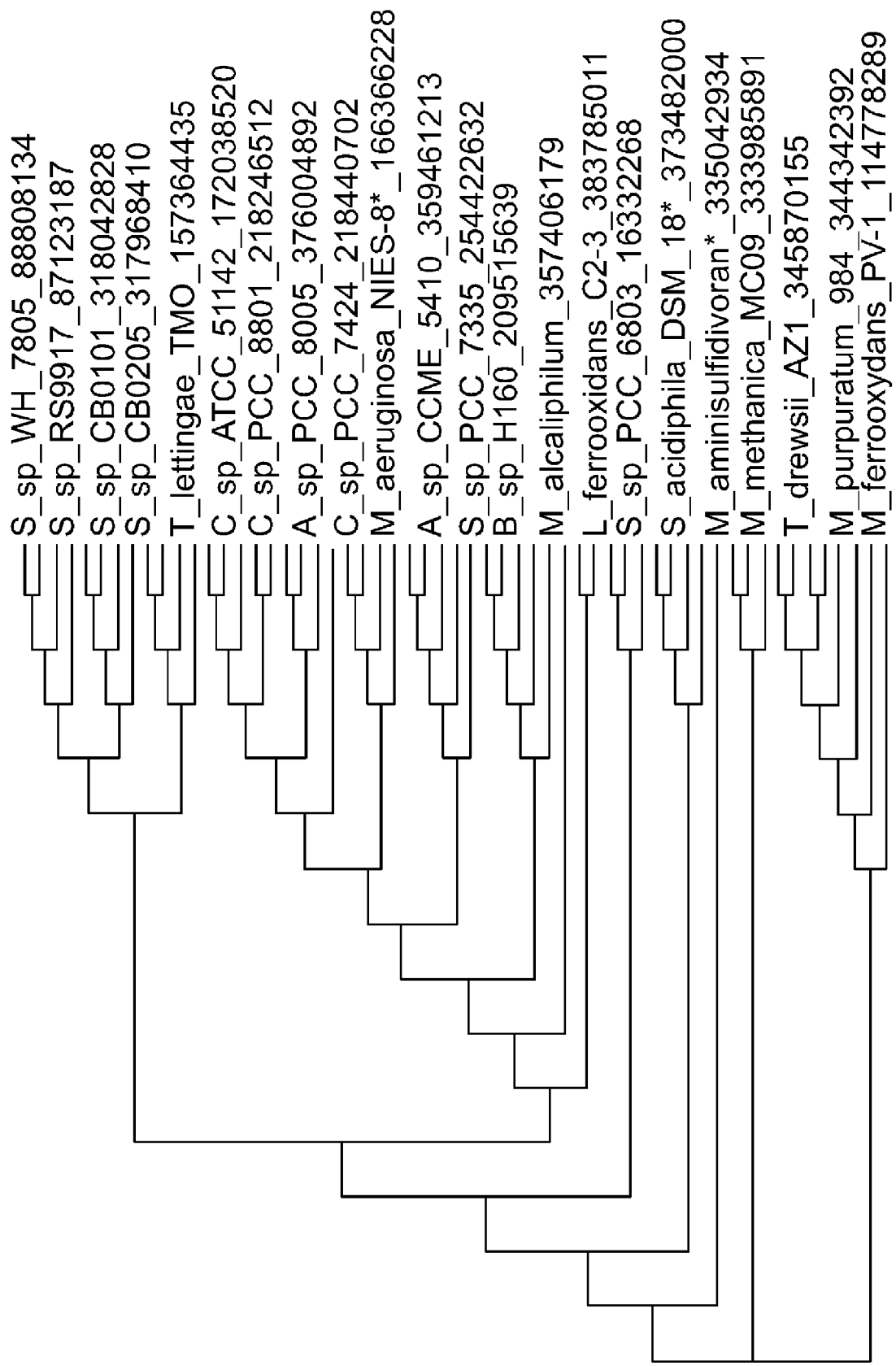
FIG. 23 is a diagram of identified phosphoketolases in Cluster 21.
Figure 24:
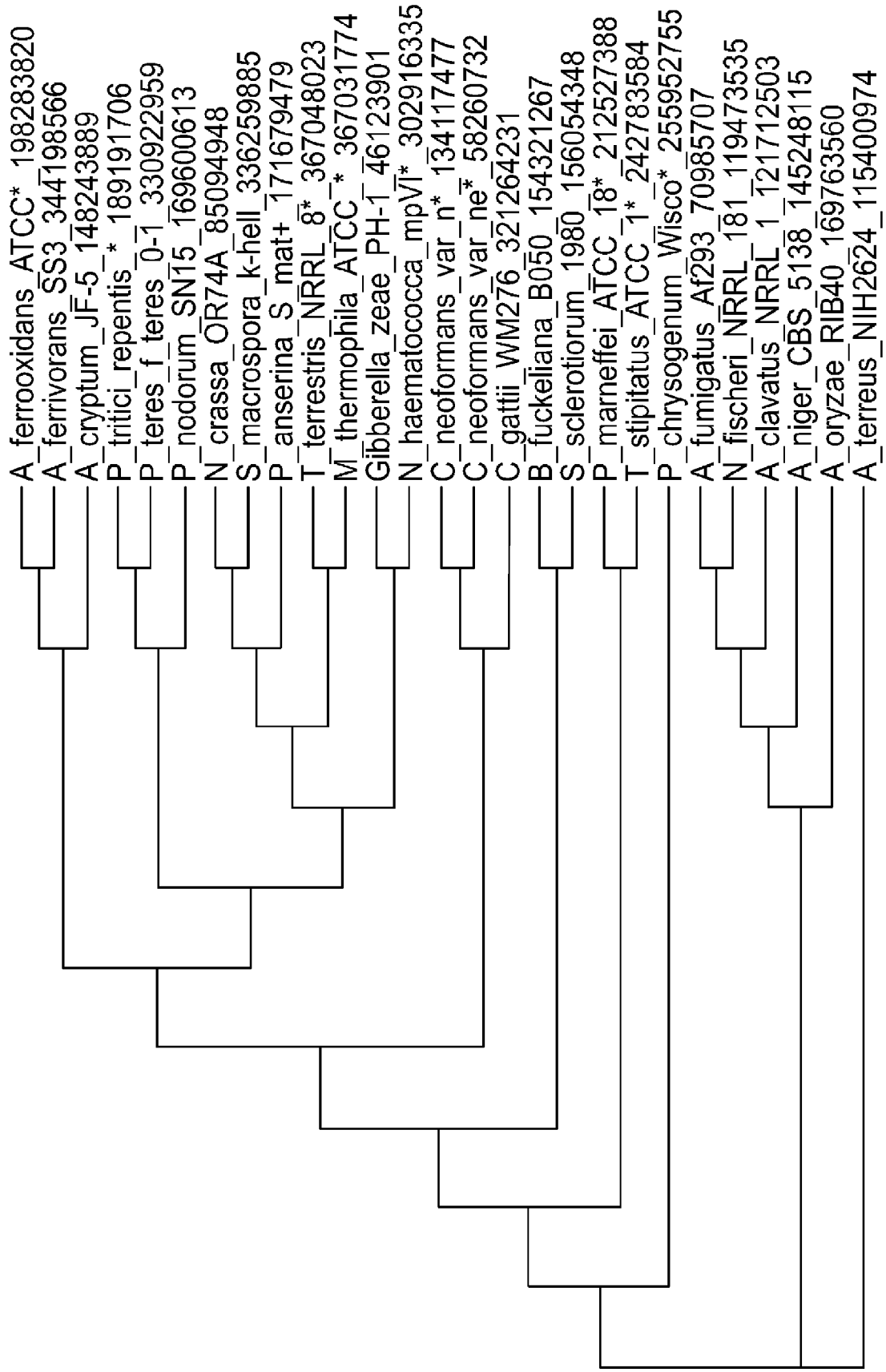
FIG. 24 is a diagram of identified phosphoketolases in Cluster 22.

To identify phosphoketolases that could be used for improved production of acetyl coenzyme A-derived (acetyl-CoA-derived) metabolites, isoprene, isoprenoid precursors, and isoprenoids in recombinant cells, the CDART program within the NCBI website was used to select all gene products that were consistent with the known phosphoketolase domain architecture (Geer L et al. (2002), "CDART: protein homology by domain architecture.", Genome Res. 12(10) 1619-23). Sequences were further refined by selecting the refseq sequences from the original domain architecture search. Next, the sequences were clustered into 22 distinct groups based on sequence similarity (Clustering by Passing Messages Between Data Points. Brendan J. Frey and Delbert Dueck, University of Toronto Science 315, 972-976, February 2007). Briefly, the amino acid sequences were multiply aligned using ClustalW. Pairwise percent identities (PIDs) were calculated. This was operationally defined and in this case it was the number of residues that were identical over residues that were aligned. The PIDs were converted to distances by way of the formula $K=-Ln(1-D-(D \cdot D)/5)$ (Kimura, M. The neutral Theory of Molecular Evolution, Camb.Univ.Press, 1983, page 75). Negative distances were used as similarity score in the above algorithm. Medium similarities were used as preferences for each data point. 22 clusters were defined using this method (FIGS. 3-24). DNA encoding the amino acid sequence of the central representative sequence from each cluster was synthesized (FIG. 2 and Table 1). In cases where the central representative from a cluster was determined to be unlikely to represent an active phosphoketolase due to the absence of complete phosphoketolase domains, an alternate phosphoketolase from that cluster was selected for DNA synthesis (Table 1).

TABLE 1

Central representative sequence

| Cluster | Organism | NCBI identifier number | Amino acid SEQ ID NO | Nucleic Acid SEQ ID NO |
|---|---|---|---|---|
| 1 | *Mycobacterium gilvum* Spyr1 | 315444259 | 1 | 52 |
| 2 | *Shewanella baltica* OS185 | 152999647 | 2 | 53 |
| 3 | *Lactobacillus rhamnosus* LMS2-1 | 229550902 | 3 | 54 |
| 4 | *Lactobacillus crispatus* ST1 | 295692465 | 4 | 55 |
| 5 | *Bifidobacterium longum* subsp. *longum* JDM301 | 296453922 | 5 | N/D |
| 6 | *Leuconostoc citreum* KM20 | 170016535 | 6 | 56 |
| 7 | *Bradyrhizobium* sp. S23321 | 383773704 | 7 | 57 |
| 8 | *Enterococcus faecium* E1039 | 293556655 | 8 | N/D |
| 9 | *Brucella microti* CCM 4915 | 256015169 | 9 | 58 |
| 10 | *Lactobacillus salivarius* ATCC 11741 | 227891468 | 10 | 59 |
| 11 | *Streptococcus agalactiae* COH1 | 77409068 | 11 | N/D |

TABLE 1-continued

Central representative sequence

| Cluster | Organism | NCBI identifier number | Amino acid SEQ ID NO | Nucleic Acid SEQ ID NO |
|---|---|---|---|---|
| 12 | *Rhodococcus imtechensis* RKJ300 | 384105306 | 12 | 60 |
| 13 | *Burkholderia xenovorans* LB400 | 91778759 | 13 | 61 |
| 14 | *Mycobacterium intracellulare* ATCC 13950 | 254819329 | 14 | 62 |
| 15 | *Nitrosomonas* sp. Is79A3 | 339481558 | 15 | 63 |
| 16* | *Schizosaccharomyces pombe* 972h- | 19112755 | 16 | 64 |
| 17 | *Leuconostoc mesenteroides* subsp. *mesenteroides* J18 | 381336925 | 17 | N/D |
| 18 | *Streptomyces* sp. SA3_actG | 318056880 | 18 | N/D |
| 19 | *Lactobacillus buchneri* ATCC 11577 | 227512366 | 19 | 65 |
| 20 | *Streptomyces ghanaensis* ATCC 14672 | 291440956 | 20 | 66 |
| 21 | *Cyanothece* sp. PCC 8802 | 257059544 | 21 | 67 |
| 22 | *Neosartorya fischeri* NRRL 181 | 119473535 | 22 | 68 |

N/D indicates not done
*Replaced the central representative *Aspergillus fumigatus* Af293 (NCBI number 70999652)

DNA encoding the protein sequences that were less than 90% identical to each other by pairwise alignment using ClustalW within Cluster 8, which contained the *Enterococcus gallinarum* phosphoketolase, and to Cluster 11, which shared the most homology with Cluster 8, were designed for protein synthesis (Table 2).

TABLE 2

Sequences from Cluster 8 and Cluster 11

| Organism | NCBI identifier number | Amino acid SEQ ID NO | Nucleic Acid SEQ ID NO |
|---|---|---|---|
| Cluster 8 | | | |
| *Enterococcus faecium* TX1330 | 227551751 | 23 | 69 |
| *Listeria grayi* DSM 20601 | 299821157 | 24 | 70 |
| *Enterococcus casseliflavus* EC30 | 257866707 | 25 | 71 |
| *Mycoplasma alligatoris* A21JP2 | 293363787 | 26 | 72 |
| *Carnobacterium* sp. 17-4 | 328958427 | 27 | 73 |
| *Melissococcus plutonius* ATCC 35311 | 332686509 | 28 | 74 |
| *Tetragenococcus halophilus* NBRC 12172 | 352516443 | 29 | 75 |
| *Melissococcus plutonius* DAT561 | 379727960 | 30 | 76 |
| *Mycoplasma arthritidis* 158L3-1 | 193216764 | 31 | 77 |
| Cluster 11 | | | |
| *Streptococcus agalactiae* NEM316 | 25011879 | 32 | 78 |
| *Mycoplasma agalactiae* PG2 | 148377390 | 33 | 79 |
| *Streptococcus gordonii* str. Challis substr. CH1 | 157150221 | 34 | 80 |
| *Kingella oralis* ATCC 51147 | 238021480 | 35 | 81 |
| *Mycoplasma fermentans* M64 | 319776755 | 36 | 82 |
| *Granulicatella adiacens* ATCC 49175 | 259046526 | 37 | 83 |
| *Mycoplasma hominis* ATCC 23114 | 269115076 | 38 | 84 |
| *Mycoplasma crocodyli* MP145 | 294155803 | 39 | 85 |

TABLE 2-continued

Sequences from Cluster 8 and Cluster 11

| Organism | NCBI identifier number | Amino acid SEQ ID NO | Nucleic Acid SEQ ID NO |
|---|---|---|---|
| Neisseria sp. oral taxon 014 str. F0314 | 298369811 | 40 | 86 |
| Eremococcus coleocola ACS-139-V-Col8 | 313884493 | 41 | 87 |
| Aerococcus urinae ACS-120-V-Col10a | 326803378 | 42 | 88 |
| Kingella kingae ATCC 23330 | 333376439 | 43 | 89 |
| Streptococcus criceti HS-6 | 357236206 | 44 | 90 |
| Streptococcus criceti HS-6 | 357235889 | 45 | 91 |
| Mycoplasma columbinum SF7 | 343491865 | 46 | 92 |

TABLE 3

Sequences from Cluster 8 - Amino Acid Percent Sequence Identity

| Cluster 8 Reference AA | Phosphoketolase AA Sequence | Amino Acid % Identity |
|---|---|---|
| SEQ ID NO: 8 | SEQ ID NO: 23 | 98 |
| SEQ ID NO: 8 | SEQ ID NO: 24 | 73 |
| SEQ ID NO: 8 | SEQ ID NO: 25 | 74 |
| SEQ ID NO: 8 | SEQ ID NO: 26 | 67 |
| SEQ ID NO: 8 | SEQ ID NO: 27 | 71 |
| SEQ ID NO: 8 | SEQ ID NO: 28 | 72 |
| SEQ ID NO: 8 | SEQ ID NO: 29 | 70 |
| SEQ ID NO: 8 | SEQ ID NO: 30 | 72 |
| SEQ ID NO: 8 | SEQ ID NO: 31 | 70 |

TABLE 4

Sequences from Cluster 11 - Amino Acid Percent Sequence Identity

| Cluster 11 Reference AA | Phosphoketolase AA Sequence | Amino Acid % Identity |
|---|---|---|
| SEQ ID NO: 11 | SEQ ID NO: 32 | 99 |
| SEQ ID NO: 11 | SEQ ID NO: 33 | 65 |
| SEQ ID NO: 11 | SEQ ID NO: 34 | 89 |
| SEQ ID NO: 11 | SEQ ID NO: 35 | 74 |
| SEQ ID NO: 11 | SEQ ID NO: 36 | 69 |
| SEQ ID NO: 11 | SEQ ID NO: 37 | 79 |
| SEQ ID NO: 11 | SEQ ID NO: 38 | 65 |
| SEQ ID NO: 11 | SEQ ID NO: 39 | 68 |
| SEQ ID NO: 11 | SEQ ID NO: 40 | 77 |
| SEQ ID NO: 11 | SEQ ID NO: 41 | 67 |
| SEQ ID NO: 11 | SEQ ID NO: 42 | 68 |
| SEQ ID NO: 11 | SEQ ID NO: 43 | 74 |
| SEQ ID NO: 11 | SEQ ID NO: 44 | 84 |
| SEQ ID NO: 11 | SEQ ID NO: 45 | 79 |
| SEQ ID NO: 11 | SEQ ID NO: 46 | 66 |

Example 2: Identification of Phosphoketolases in Bacterial Genomes Lacking Phosphofructokinase A search was conducted for bacterial genomes that had an annotated phosphoketolase (PKL) but did not have an annotated phosphofructokinase (PFK), a critical enzyme for carbon flux through glycolysis. Several organisms that fit these criteria, and from this list five PKLs, specifically PKLs from *Burkholderia phytofirmans* PsJN (SEQ ID NO:47), *Lactobacillus buchneri* NRRL B-30929 (SEQ ID NO:48), *Bifidobacterium gallicum* DSM 20093 (SEQ ID NO:49), *Bifidobacterium dentium* Bd1 (SEQ ID NO:50), and *Bifidobacterium bifidum* IPLA 20015 (SEQ ID NO:51), were chosen for investigation of high activity and increased yield of isoprene from glucose. Since most of the PKLs from the full list of organisms have not been characterized, the five PKLs that were chosen were based on sequence diversity and the best circumstantial evidence of high activity that could be obtained in the literature. The PKL from *Bifidobacterium dentium* displayed a pH optimum of 7 (Sgorbati B., et al., *Antonie van Leeuwenhoek* 1976 (42), 49-57), whereas the pH optima for other PKLs is typically around 6 (Heath EC., et al., *J Bio Chem* 1957, 1009-1029). *Lactobacillus buchneri* was isolated as a contaminant from a fuel ethanol plant, and was shown to grow on both glucose and xylose, presumably by activity of PKL on either F6P or X5P for cell mass and energy (Liu S., et al., *J Ind Microbiol Biotechnol* 2008 (35), 75-81). The PKLs from *Bifidobacterium bifidum* and *Bifidobacterium gallicum* were chosen because these strains were able to grow well on either glucose or xylose as the sole carbon source (Palframan RJ., et al., *Curr Issues Intest Microbiol* 2003 (4), 71-75).

Example 3: Cloning of Identified Phosphoketolase Enzymes

PKLs obtained from *Bifidobacterium longum* subsp. *infantis*, *Enterococcus gallinarum*, and *Clostridium acetobutylicum* were each assayed for enzyme activity. *Bifidobacterium longum* subsp. *infantis* PKL had a Km of 5.7±1.16 mM, a kcat of 4.56±0.2 sec$^{-1}$, and a kcat/Km of 0.79±0.2 mM$^{-1}$ sec$^{-1}$, *Enterococcus gallinarum* PKL had a Km of 10.4±1.03 mM, a kcat of 1.35±0.04 sec$^{-1}$, and a kcat/Km of 0.13±0.1 mM$^{-1}$ sec$^{-1}$, and *Clostridium acetobutylicum* PKL was found to have a Km of 10.3±0.67 mM, a kcat of 2.18±0.05 sec$^{-1}$, and a kcat/Km of 0.21±0.06 mM$^{-1}$ sec$^{-1}$. A construct encoding the *Bifidobacterium longum* subsp. *infantis*, *Enterococcus gallinarum*, or *Clostridium acetobutylicum* PKLs was used as a control to screen the candidate PKL enzymes for in vitro and in vivo activity.

Figure 25:
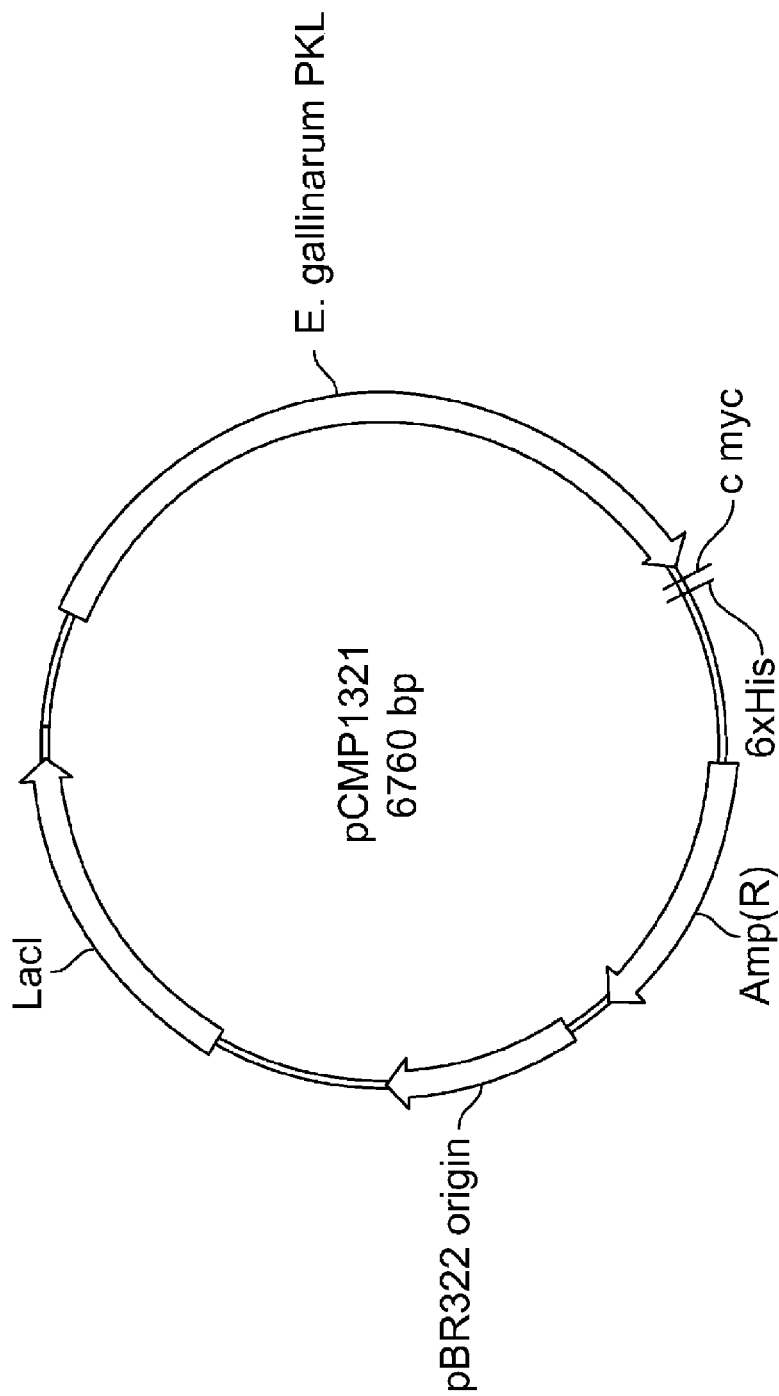
FIG. 25 depicts the plasmid map of pCMP1321, expressing *Enterococcus gallinarum* phosphoketolase.
Figure 26:
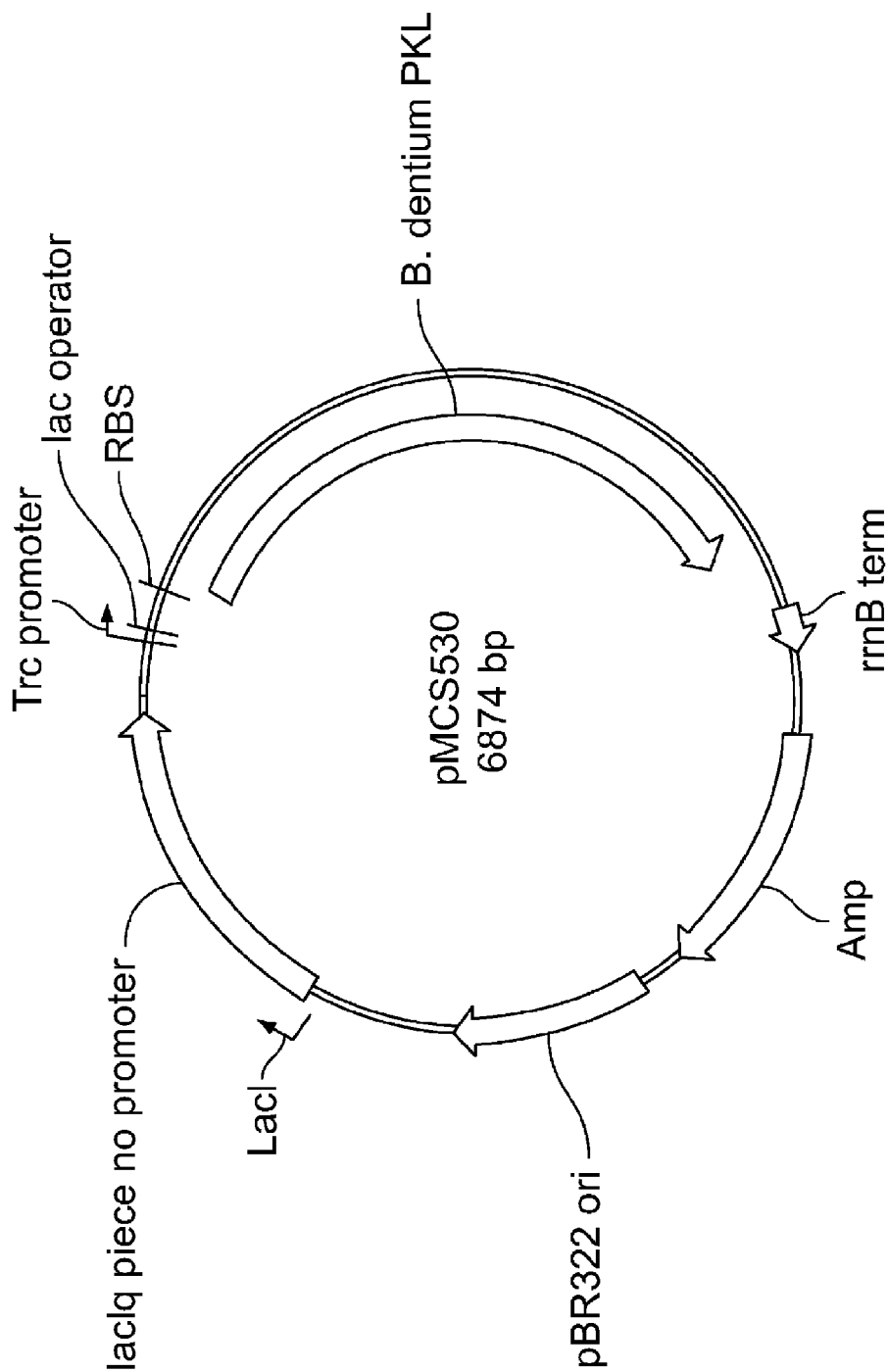
FIG. 26 depicts the plasmid map of pMCS530, expressing *Bifidobacterium dentium* phosphoketolase.
Figure 27:
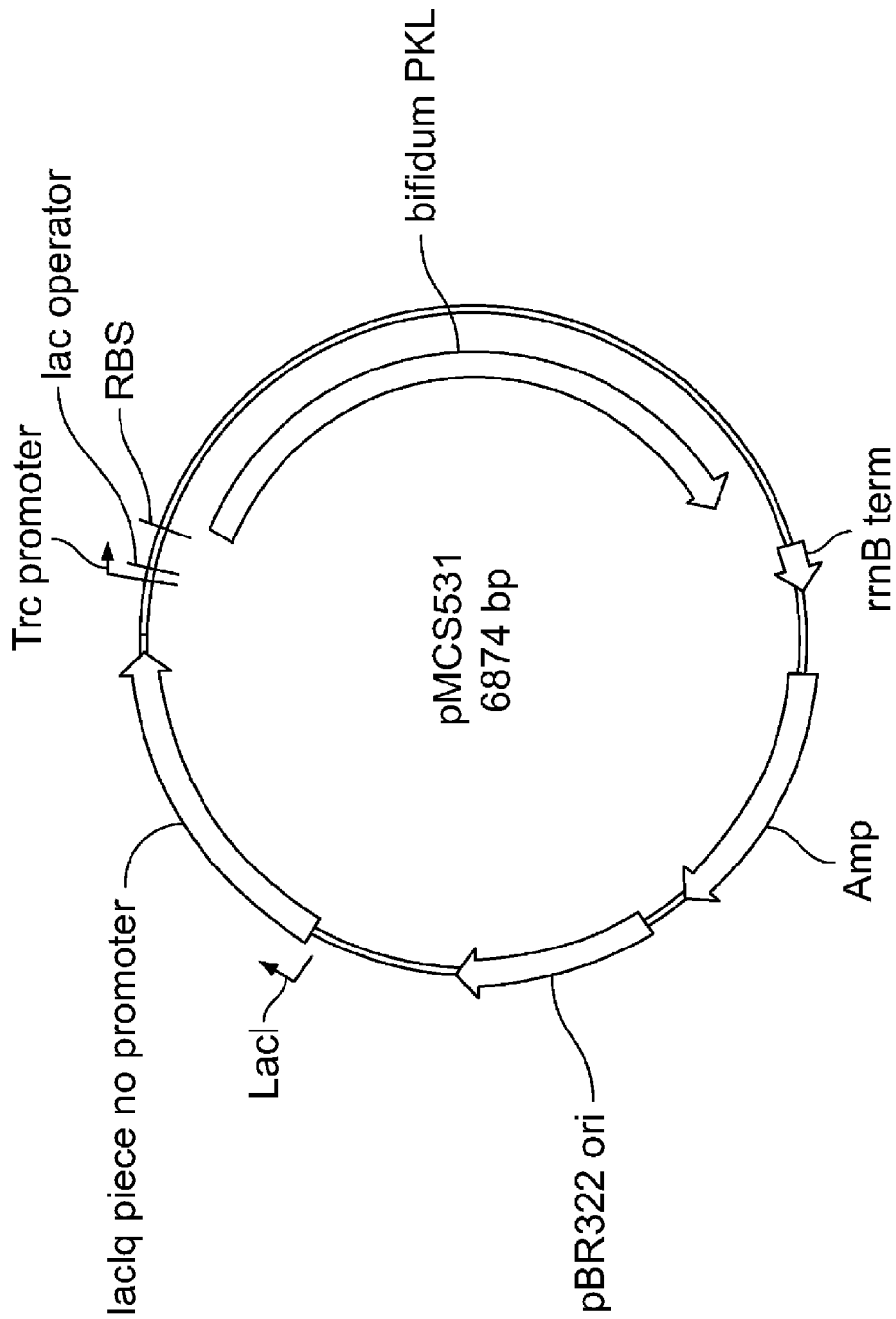
FIG. 27 depicts the plasmid map of pMCS531, expressing *Bifidobacterium bifidum* phosphoketolase.
Figure 28:
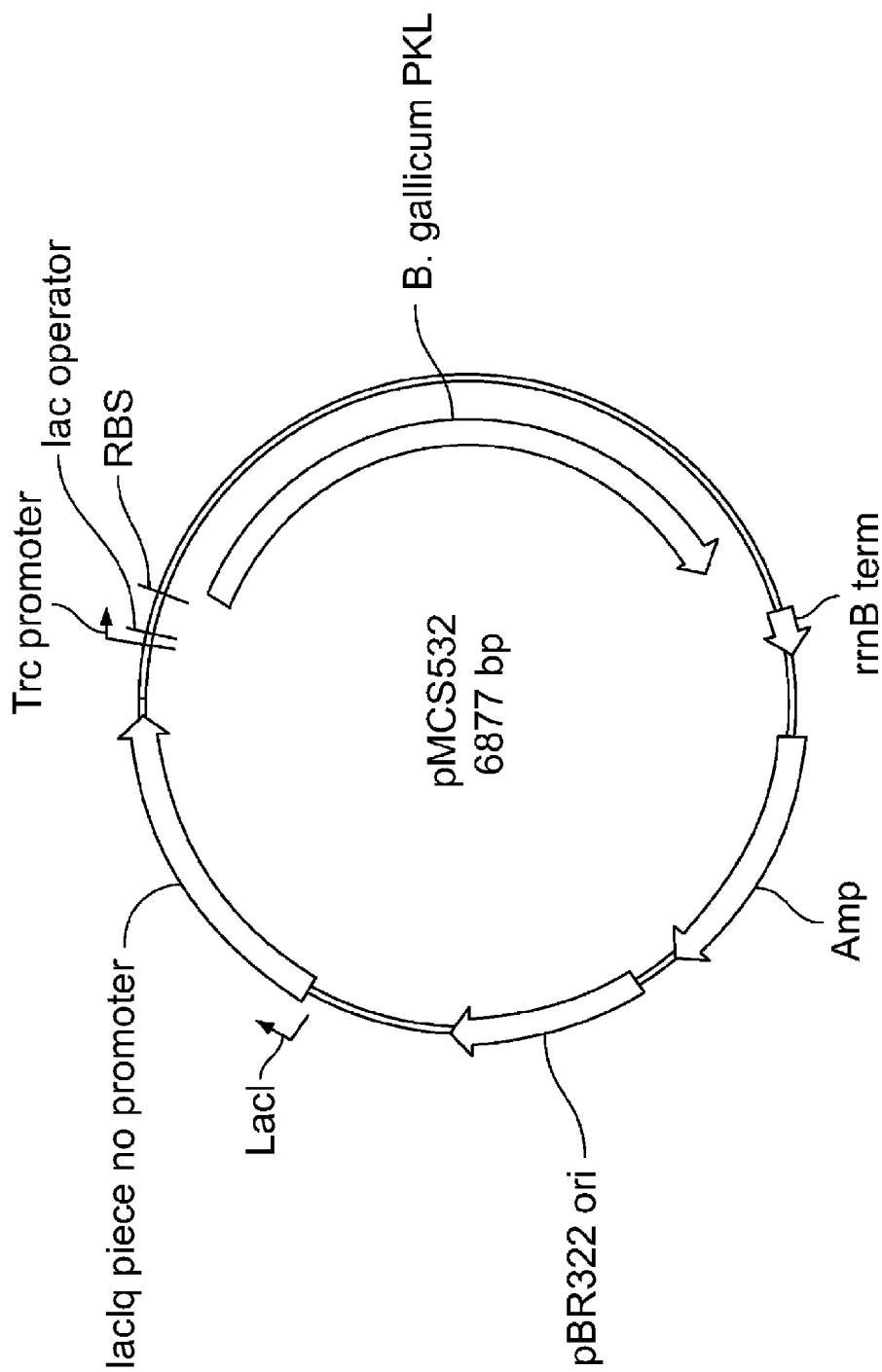
FIG. 28 depicts the plasmid map of pMCS532, expressing *Bifidobacterium gallicum* phosphoketolase.
Figure 29:
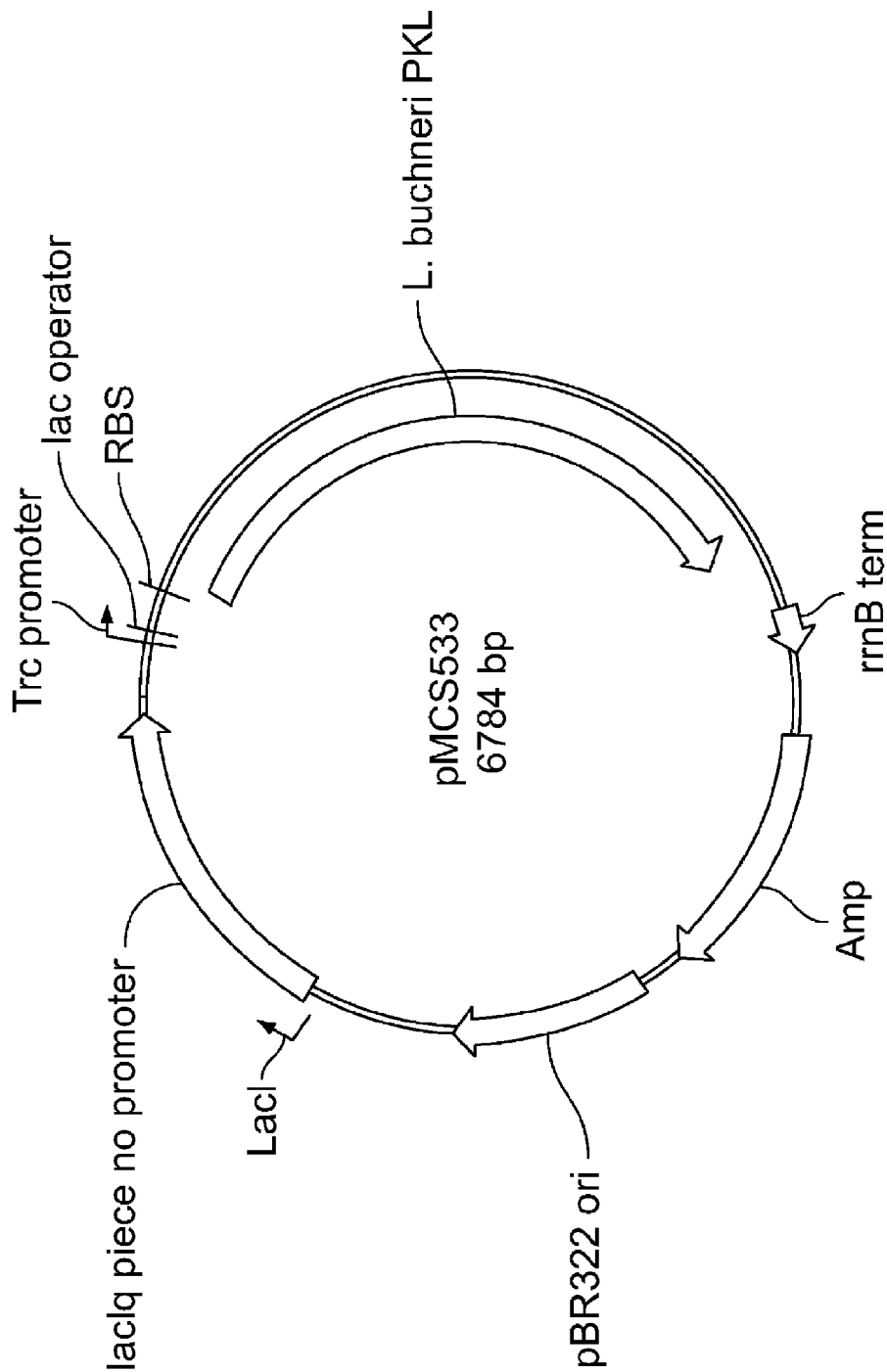
FIG. 29 depicts the plasmid map of pMCS533, expressing *Lactobacillus buchneri* phosphoketolase.
Figure 30:
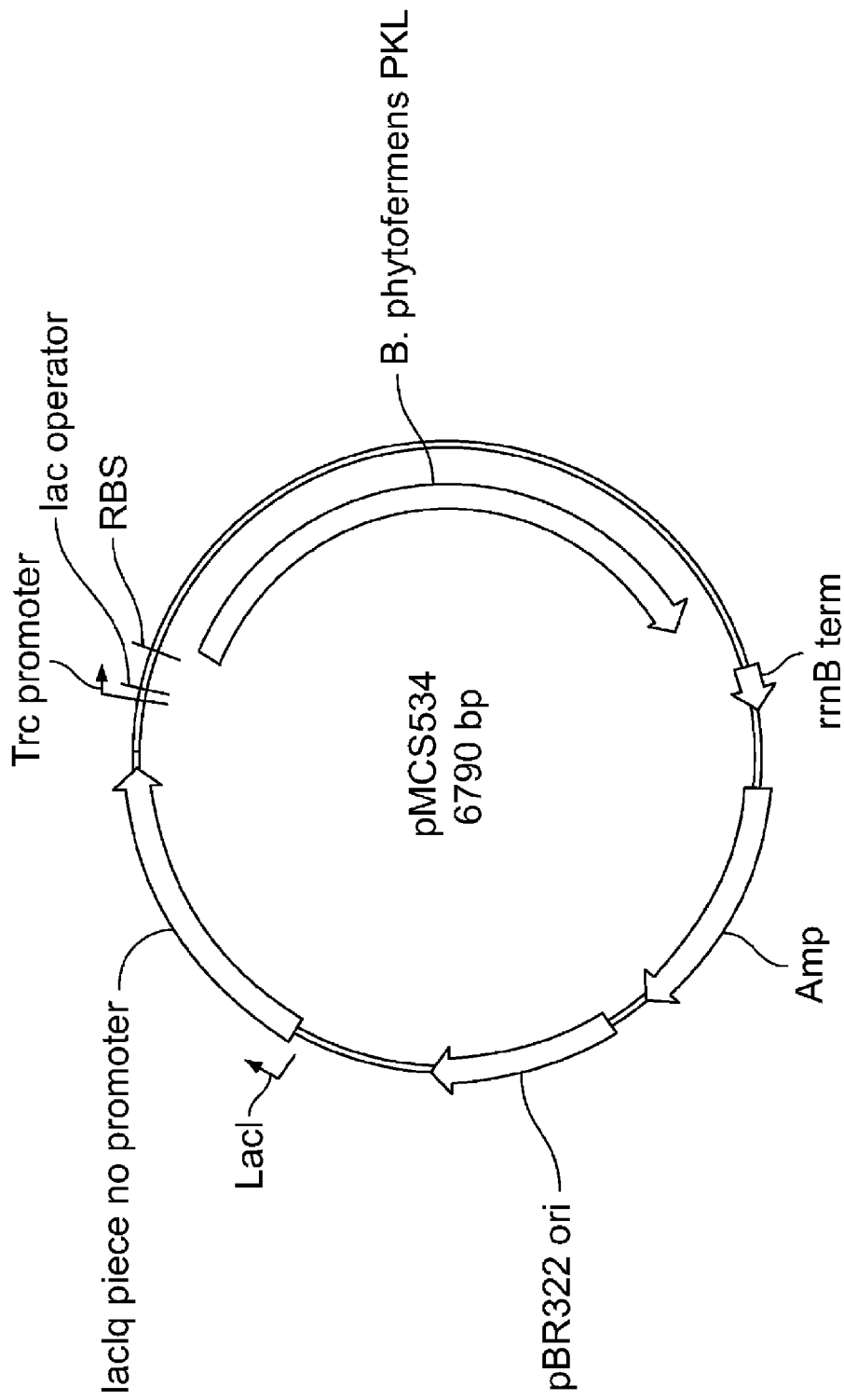
FIG. 30 depicts the plasmid map of pMCS534, expressing *Burkholderia phytofermans* phosphoketolase.
Figure 31:
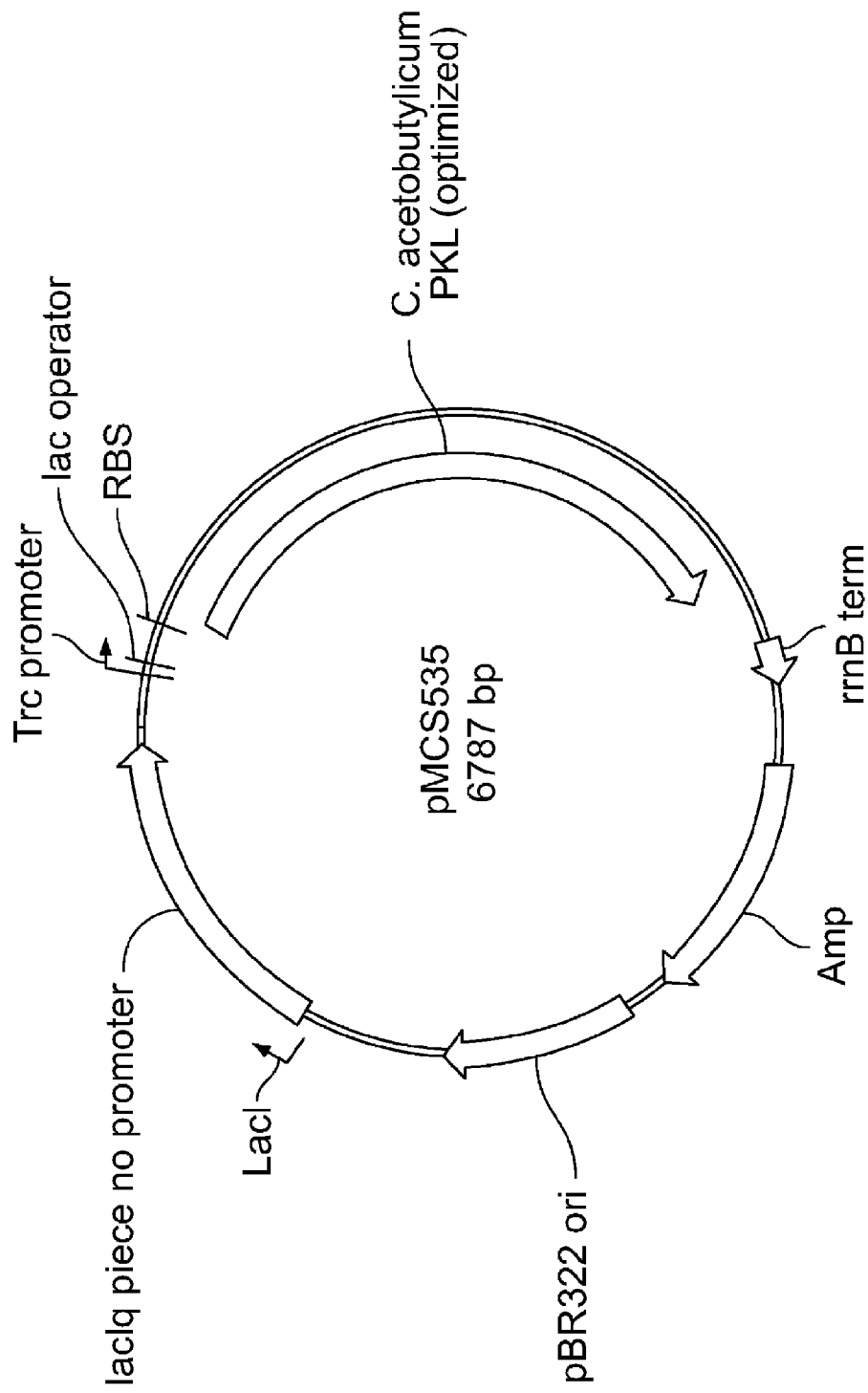
FIG. 31 depicts the plasmid map of pMCS535, expressing *Clostridium acetobutylicum* optimized phosphoketolase.

The amino acid sequence of *Enterococcus gallinarum* PKL (SEQ ID NO: 93) was obtained from GenBank and was processed in GeneArt optimization software for optimized expression in *E. coli*. Two base pairs were added in front of the PKL gene to form a BspHI site and a SacI site was inserted just after the stop codon. The synthesized PKL gene was cloned into GeneArt kanamycin-resistant cloning plasmid. The *E. gallinarum* PKL gene was then subcloned into a NcoI/SacI-digested pTrcHis2B vector (Life Technologies, Carlsbad, Calif.) to form plasmid pCMP1321 (Table 5, FIG. 25).

Chromosomal DNA of strain ATCC15697, *Bifidobacterium longum* subsp. *infantis* was obtained from ATCC (Manassas, Va.). The gene encoding *B. longum* PKL was amplified by polymerase chain reaction (PCR) from the chromosomal DNA using primers CMP283: 5'-ctgtatT-CATGAcgagtcctgttattggcacc-3' (SEQ ID NO: 107) and CMP284: 5'-ctctatGAATTCT-CACTCGTTGTCGCCAGCG-3' (SEQ ID NO: 108), and the polymerase Herculase according to the manufacturer's protocol (Life Technologies, Carlsbad, Calif.). The PCR product was digested with EcoRI and BspHI restriction enzymes before purification. After purification, the approximately 2500 bp fragment was assembled into EcoRI/NcoI-digested pTrcHis2B (Invitrogen, Carlsbad, Calif.) using the GENEART seamless cloning kit (Invitrogen, Carlsbad, Calif.) to form plasmid pCMP1090 (Table 5).

For construction of the control plasmid encoding a *Clostridium acetobutylicum* PKL, chromosomal DNA of strain ATCC BAA-98 was obtained from ATCC (Manassas, Va.). The gene encoding *Clostridium acetobutylicum* PKL was amplified by polymerase chain reaction (PCR) from the chromosomal DNA using primers CacetpTrcHisBF: 5'-taaggaggaataaaccatgcaaagtataataggaaaacataaggatgaagg-3' (SEQ ID NO: 109) and CacetpTrcHisBR: 5'-ttctagaaagcttcgttatacatgccactgccaattagttatttc-3' (SEQ ID NO: 110), and the polymerase Herculase according to the manufacturer's protocol (Life Technologies, Carlsbad, Calif.). The PCR product was purified and assembled into EcoRI/NcoI-digested pTrcHis2B (Invitrogen, Carlsbad, Calif.) using the GENEART seamless cloning kit (Invitrogen, Carlsbad, Calif.) to form plasmid pCMP1364 (Table 3).

The nucleic acid sequence encoding a PKL protein derived from each of Bifidobacterium dentium, Bifidobacterium bifidum, Bifidobacterium gallicum, Lactobacillus buchneri, Burkholderia phytofermans, and Clostridium acetobutylicum (SEQ ID NO:94) were codon optimized for expression in E. coli, and synthesized by Gene Oracle (Mountain View, Calif.). These codon-optimized PKL genes were amplified by PCR and subcloned into the pTrcHis2B expression plasmid using the GeneArt Seamless Cloning Kit (Life Technologies), according to the manufacturer's recommended protocol. Table 5 below lists the primers used for construction of plasmids pMCS530 through pMCS535. The PKL enzymes were cloned downstream of the pTrc promoter to permit inducible expression of the phosphoketolase genes by IPTG (Table 6, FIGS. 26-31).

TABLE 5

Primers used for construction of plasmids

| Primer | Sequence | Description |
|---|---|---|
| *Bifidobacterium dentium* | | |
| o430 | Tgataacgaataagagctcgagatctgcagctggtacc (SEQ ID NO: 111) | DentiumPKL into pTrcHis2B, plasmid Forward primer |
| o431 | gactcgtcatggtttattcctccttatttaatcgatacattaatatatacc SEQ ID NO: 112) | DentiumPKL into pTrcHis2B, plasmid Reverse primer |
| o432 | ggaataaaccatgacgagtccagttattggaacaccc SEQ ID NO: 113) | DentiumPKL into pTrcHis2B, PKL Forward primer |
| o433 | tctcgagctcttattcgttatcacccgcagtagcgg (SEQ ID NO: 114) | DentiumPKL into pTrcHis2B, PKL Reverse primer |
| *Bifidobacterium bifidum* | | |
| o434 | cgacaacgagtaagagctcgagatctgcagctggtacc (SEQ ID NO: 115) | Bifidum PKL into pTrcHis2B, plasmid Forward primer |
| o435 | gagaggtcatggtttattcctccttatttaatcgatacattaatatatacc (SEQ ID NO: 116) | Bifidum PKL into pTrcHis2B, plasmid Reverse primer |
| o436 | ggaataaaccatgacctctccagtaattggcactcc (SEQ ID NO: 117) | Bifidum PKL into pTrcHis2B, PKL Forward primer |
| o437 | tctcgagctcttactcgttgtcgcctgccgtg (SEQ ID NO: 118) | Bifidum PKL into pTrcHis2B, PKL Reverse primer |
| *Bifidobacterium gallicum* | | |
| o438 | cgataatgaataagagctcgagatctgcagctggtacc (SEQ ID NO: 119) | Gallicum PKL into pTrcHis2B, plasmid Forward primer |
| o439 | gagaagtcatggtttattcctccttatttaatcgatacattaatatatacc (SEQ ID NO: 120) | Gallicum PKL into pTrcHis2B, plasmid Reverse primer |
| o440 | ggaataaaccatgacttctcccgtgattggtactcc (SEQ ID NO: 121) | Gallicum PKL into pTrcHis2B, PKL Forward primer |
| o441 | tctcgagctcttattcattatcgcccgccgtagc (SEQ ID NO: 122) | Gallicum PKL into pTrcHis2B, PKL Reverse primer |
| *Lactobacillus buchneri* | | |
| o442 | gctgaaaaataagagctcgagatctgcagctggtacc (SEQ ID NO: 123) | Buchneri PKL into pTrcHis2B, plasmid Forward primer |
| o443 | ccactgtcatggtttattcctccttatttaatcgatacattaatatatacc (SEQ ID NO: 124) | Buchneri PKL into pTrcHis2B, plasmid Reverse primer |
| o444 | ggaataaaccatgacagtggactatgactcaaaagagtacttagag (SEQ ID NO: 125) | Buchneri PKL into pTrcHis2B, PKL Forward primer |
| o445 | tctcgagctcttattttttcagcccttcccatttcc (SEQ ID NO: 126) | Buchneri PKL into pTrcHis2B, PKL Reverse primer |
| *Burkholderia phytofermans* | | |
| o446 | ctggaaaggttaagagctcgagatctgcagctggtacc (SEQ ID NO: 127) | Phytofermans PKL into pTrcHis2B, plasmid Forward primer |
| o447 | cttcagccatggtttattcctccttatttaatcgatacattaatatatacc (SEQ ID NO: 128) | Phytofermans PKL into pTrcHis2B, plasmid Reverse primer |
| o448 | ggaataaaccatggctgaagccactgcccatc (SEQ ID NO: 129) | Phytofermans PKL into pTrcHis2B, PKL Forward primer |
| o449 | tctcgagctcttaacctttccaggtccaattccggattt (SEQ ID NO: 130) | Phytofermans PKL into pTrcHis2B, PKL Reverse primer |
| *Clostridium acetobutylicum* | | |
| o450 | atggcatgtataagagctcgagatctgcagctggtacc (SEQ ID NO: 131) | Acetobutylicum optimized PKL into pTrcHis2B, plasmid Forward primer |

TABLE 5-continued

Primers used for construction of plasmids

| Primer | Sequence | Description |
| --- | --- | --- |
| o451 | ttgattgcatggtttattcctccttatttaatcgatacattaatatatacc (SEQ ID NO: 132) | Acetobutylicum optimized PKL into pTrcHis2B, plasmid Reverse primer |
| o452 | ggaataaaccatgcaatcaatcatcggcaaacac (SEQ ID NO: 133) | Acetobutylicum optimized PKL into pTrcHis2B, PKL Forward primer |
| o453 | tctcgagctcttatacatgccattgccagtttgtgatc (SEQ ID NO: 134) | Acetobutylicum optimized PKL into pTrcHis2B, PKL Reverse primer |

TABLE 6

Plasmids encoding PKLs

| Plasmid | Description |
| --- | --- |
| pCMP1321 | pTrcHis2B E. gallinarum PKL, Carb |
| pCMP1090 | pTrcHis2B B. longum PKL, Carb |
| pCMP1364 | pTrcHis2B C. acetobutylicum PKL, Carb |
| pMCS530 | pTrcHis2B B. dentium PKL, Carb |
| pMCS531 | pTrcHis2B B. bifidum PKL, Carb |
| pMCS532 | pTrcHis2B B. gallicum PKL, Carb |
| pMCS533 | pTrcHis2B L. buchneri PKL, Carb |
| pMCS534 | pTrcHis2B B. phytofermans PKL, Carb |
| pMCS535 | pTrcHis2B C. acetobutylicum PKL optimized, Carb |

Carb Indicates Carbenicillin

The nucleic acid sequence encoding a PKL protein derived from each of the organisms listed in Table 1, Table 2, and Clusters 1-22 (see FIGS. 3-24) are codon optimized for expression in E. coli and synthesized. These codon-optimized PKL genes are subcloned into the pTrcHis2B expression plasmid downstream of the pTrc promoter to permit inducible expression of the phosphoketolase gene by IPTG.

Example 4: Construction of Strains Expressing Identified PKLs for In Vitro Studies PKL expressing strains were constructed by transforming strain CMP1133 (BL21, Δpgl PL.2mKKDyl, GI1.2gltA, yhfSFRTPyddVIspAyhfS, thiFRTtruncIspA) with the plasmids listed on Table 5 and selecting for colonies on Luria-Bertani plates containing 20 µg/ml kanamycin. The kanamycin marker was removed using the protocol recommended by the manufacturer (Gene Bridges, Heidelberg, Germany) to form the indicated strains (Table 7).

TABLE 7

Description of E. coli strains

| Strain Name | Genotype |
| --- | --- |
| CMP1183 | BL21, Δpgl PL.2mKKDyl, GI1.2gltA, yhfSFRTPyddVIspAyhfS, thiFRTtruncIspA, pCMP1090 (pTrcPKL B. longum) |
| CMP1328 | BL21, Δpgl PL.2mKKDyl, GI1.2gltA, yhfSFRTPyddVIspAyhfS, thiFRTtruncIspA, pCMP1321 (pTrcPKL E. gallinarum) |
| CMP1366 | BL21, Δpgl PL.2mKKDyl, GI1.2gltA, yhfSFRTPyddVIspAyhfS, thiFRTtruncIspA, pCMP1364 (pTrcPKL C. acetobutylicum) |
| MCS545 | BL21, Δpgl PL.2mKKDyl, GI1.2gltA, yhfSFRTPyddVIspAyhfS, thiFRTtruncIspA, pMCS530 (pTrcPKL B. dentium) |
| MCS546 | BL21, Δpgl PL.2mKKDyl, GI1.2gltA, yhfSFRTPyddVIspAyhfS, thiFRTtruncIspA, pMCS531 (pTrcPKL B. bifidum) |
| MCS547 | BL21, Δpgl PL.2mKKDyl, GI1.2gltA, yhfSFRTPyddVIspAyhfS, thiFRTtruncIspA, pMCS532 (pTrcPKL B. gallicum) |
| MCS548 | BL21, Δpgl PL.2mKKDyl, GI1.2gltA, yhfSFRTPyddVIspAyhfS, thiFRTtruncIspA, pMCS533 (pTrcPKL L. buchneri) |
| MCS549 | BL21, Δpgl PL.2mKKDyl, GI1.2gltA, yhfSFRTPyddVIspAyhfS, thiFRTtruncIspA, pMCS534 (pTrcPKL B. phytofermans) |
| MCS550 | BL21, Δpgl PL.2mKKDyl, GI1.2gltA, yhfSFRTPyddVIspAyhfS, thiFRTtruncIspA, pMCS535 (pTrcPKL C. acetobutylicum optimized) |

PKL expressing strains, each expressing an identified PKL, are constructed by transforming strain CMP1133 (BL21, Δpgl PL.2mKKDyl, GI1.2gltA, yhfSFRTPyddVIspAyhfS, thiFRTtruncIspA) with a plasmid encoding a PKL listed on Table 1, Table 2, and Clusters 1-22 (see FIGS. 3-24) and is selected for colonies on Luria-Bertani plates containing 20 µg/ml kanamycin. The kanamycin marker is removed using the protocol recommended by the manufacturer (Gene Bridges, Heidelberg, Germany).

Example 5: Comparison of Expression and Solubility of Identified PKLs

Strains expressing pTrcHis2B B. longum (strain CMP1183), pTrcHis2B E. gallinarum (strain CMP1328), pTrcHis2B C. acetobutylicum (strain CMP1366), pTrcHis2B B. dentium PKL (strain MCS545), pTrcHis2B B. bifidum (strain MCS546), pTrcHis2B B. gallicum PKL (strain MCS547), pTrcHis2B L. buchneri PKL (strain MCS548), pTrcHis2B B. phytofermans PKL (strain MCS549), or pTrcHis2B C. acetobutylicum PKL optimized (strain MCS550) were grown in LB media, induced at $OD_{600}$~0.5 with 200 µM IPTG, and induced for 4 hours at a temperature of 30° C. or 34° C. Cells were harvested by centrifuging 4 ml culture broth at 3000 rpm for 10 minutes. Cell pellets were re-suspended in 2 ml of 50 mM MES, 50 mM NaCl pH6.0 with 0.1% DNAase and 0.5 mM AEBSF. The cell suspension was lysed using a french pressure cell at 14,000 psi (American Instrument Company). The lysate was then centrifuged at 15,000 RPM for 10 minutes at 4° C. in an Eppendorf 5804R centrifuge. The supernatant and pellet were separated. The pellets were resuspended in the lysis 50 mM MES, 50 mM NaCl pH6.0 buffer. Supernatant and pellet samples were analyzed by 4-12% SDS-PAGE gel electrophoresis. Solubility was assessed by comparison of soluble versus pellet (insoluble) phosphoketolase fractions.

Figure 32A:
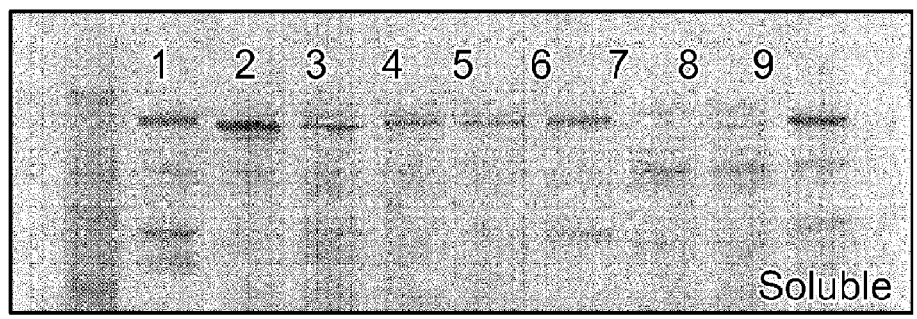
FIGS. 32A and 32B are series of SDS-PAGE coomasie stained gels showing protein expression in strains expressing phosphoketolase. A) soluble protein and B) insoluble protein from cells expressing *B. longum* PKL (lane 1), *E. gallinarum* PKL (lane 2), *C. acetobutylicum* PKL (lane 3), *B. dentium* PKL (lane 4), *B. bifidum* PKL (lane 5), *B. gallicum* PKL (lane 6), *L. buchneri* PKL (lane 7), *B. phytofermans* PKL (lane 8), and *C. acetobutylicum* codon optimized PKL (lane 9).
Figure 32B:
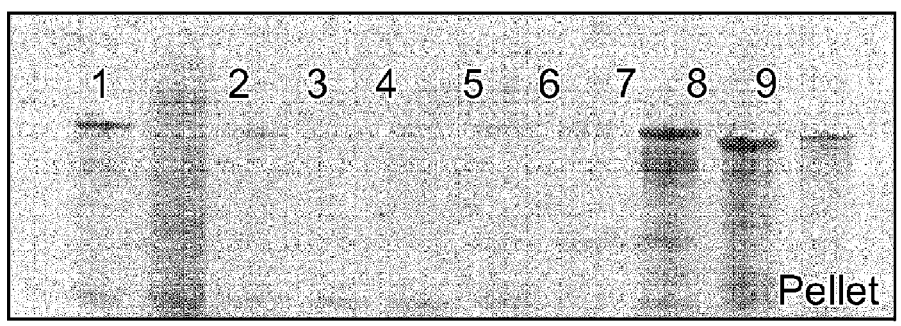

The results showed that optimized C. acetobutylicum PKL (FIG. 32A, lane 9) was expressed at a higher level as compared to *C. acetobutylicum* PKL that had not been codon-optimized (FIG. 32A, lane 3). *B. dentium* (FIG. 32A, lane 4), *B. bifidium* (FIG. 32A, lane 5), and *B. gallicum* (FIG. 32A, lane 6) PKLs were all expressed at a similar level to *C. acetobutylicum* PKL (FIG. 32A, lane 3) and were mostly soluble (FIG. 32B). In comparison, *L. buchneri* (lane 7) and *B. phytofermans* (lane 8) were almost completely insoluble (FIG. 32B).

Strains expressing an identified PKL listed on Table 1, Table 2, and Clusters 1-22 (see FIGS. 3-24) are grown in LB media, induced at $OD_{600}$~0.5 with 200 µM IPTG, and induced for 4 hours at a temperature of 30° C. or 34° C. Cells are harvested by centrifuging 4 ml culture broth at 3000 rpm for 10 minutes. Cell pellets are re-suspended in 2 ml of 50 mM MES, 50 mM NaCl pH6.0 with 0.1% DNAase and 0.5 mM AEBSF. The cell suspension is lysed using a french pressure cell at 14,000 psi (American Instrument Company). The lysate is then centrifuged at 15,000 RPM for 10 minutes at 4° C. in an Eppendorf 5804R centrifuge. The supernatant and pellet are separated. The pellets are resuspended in the lysis buffer (50 mM MES, 50 mM NaCl pH6.0). Supernatant and pellet samples are analyzed by 4-12% SDS-PAGE gel electrophoresis. Solubility is assessed by comparison of soluble versus pellet (insoluble) phosphoketolase fractions.

Example 6: In Vitro Screen for Phosphoketolase Activity in Strains Expressing Identified PKLs Strains expressing pTrcHis2B *B. longum* (strain CMP1183), pTrcHis2B *E. gallinarum* (strain CMP1328), pTrcHis2B *C. acetobutylicum* (strain CMP1366), pTrcHis2B *B. dentium* PKL (strain MCS545), pTrcHis2B *B. bifidum* (strain MCS546), pTrcHis2B *B. gallicum* PKL (strain MCS547), pTrcHis2B *L. buchneri* PKL (strain MCS548), pTrcHis2B *B. phytofermans* PKL (strain MCS549), or pTrcHis2B *C. acetobutylicum* PKL optimized (strain MCS550) were grown in LB medium with 50 µg/ml carbenicillin at 37° C. prior to induction. Following induction with 10 µM, 25 µM, 50 µM, or 100 µM IPTG, cultures were transferred to a 34° C. shaker for 30 minutes. Cells were harvested by centrifugation at 10,000 rpm for 10 mM at 4° C. Cell pellets were stored at −80° C. prior to purification. For purification, PKL cell pellets were resuspended in 50 mM MES pH 6.0, 50 mM NaCL, 0.5 mM AEBSF, 0.1 mg/ml DNaseI. Cells were lysed by repeated passage through a French press and clarified by ultracentrifugation at 50,000 rpm for 60 mM Clarified lysate containing the PKL from *B. longum*, *E. gallinarum*, *C. acetobutylicum*, *B. dentium*, *B. bifidum*, *B. gallicum*, *L. buchneri*, *B. phytofermans*, or *C. acetobutylicum* were loaded onto a DEAE HiTrap FP column equilibrated in 50 mM MES, 50 mM NaCl, pH 6 and eluted with a gradient to 50 mM MES, 1M NaCl, pH 6. The resulting fractions were analyzed by SDS-PAGE. Fractions containing PKL were pooled and desalted using a G25 desalting column into 50 mM MES, 50 mM NaCL pH 6.0. Further purification was achieved using a MonoQ 10/100 GL column equilibrated in 50 mM MES, 50 mM NaCL, pH 6 with a salt gradient to 1M NaCl. The amount of AcP formed by each PKL was measured using a scaled down version of hydroxamate assay described in L. Meile et. al., *Bacteriol.*, 2001, 183:2929-2936 and Frey et. al., *Bioorganic Chem.*, 2008, 36:121-127, which are incorporated herein in their entirety by reference. The assays were performed in a 96-well plate (Costar catalog #9017) format, at 37° C. Each 300 µl reaction contained 1 mM TPP, 10 mM potassium phosphate pH 6.0, 50 mM MES pH 6, 10 mM MgCl2, 5 mM F6P and PKL at concentration of 250 nM.

Time points were taken at various intervals. In order to stop the reaction 60 µl of the reaction mixture was mixed with 60 µl of 2M hydroxylamine at pH 6.5, incubated for 10 mM at room temperature. Addition of 40 µl of 15% TCA, 40 µl of 4M HCl, and 40 µl of 5% $FeCl_3$ in 0.1 M HCl was used to precipitate the protein and allow AcP detection. The samples were then centrifuged at 3000 rpm for 10 mM A 200 µl sample of supernatant was transferred to a microtiter plate and a plate reader, and absorbance changes associated with the amount of AcP formed were monitored at 505 nm.

Figure 33:
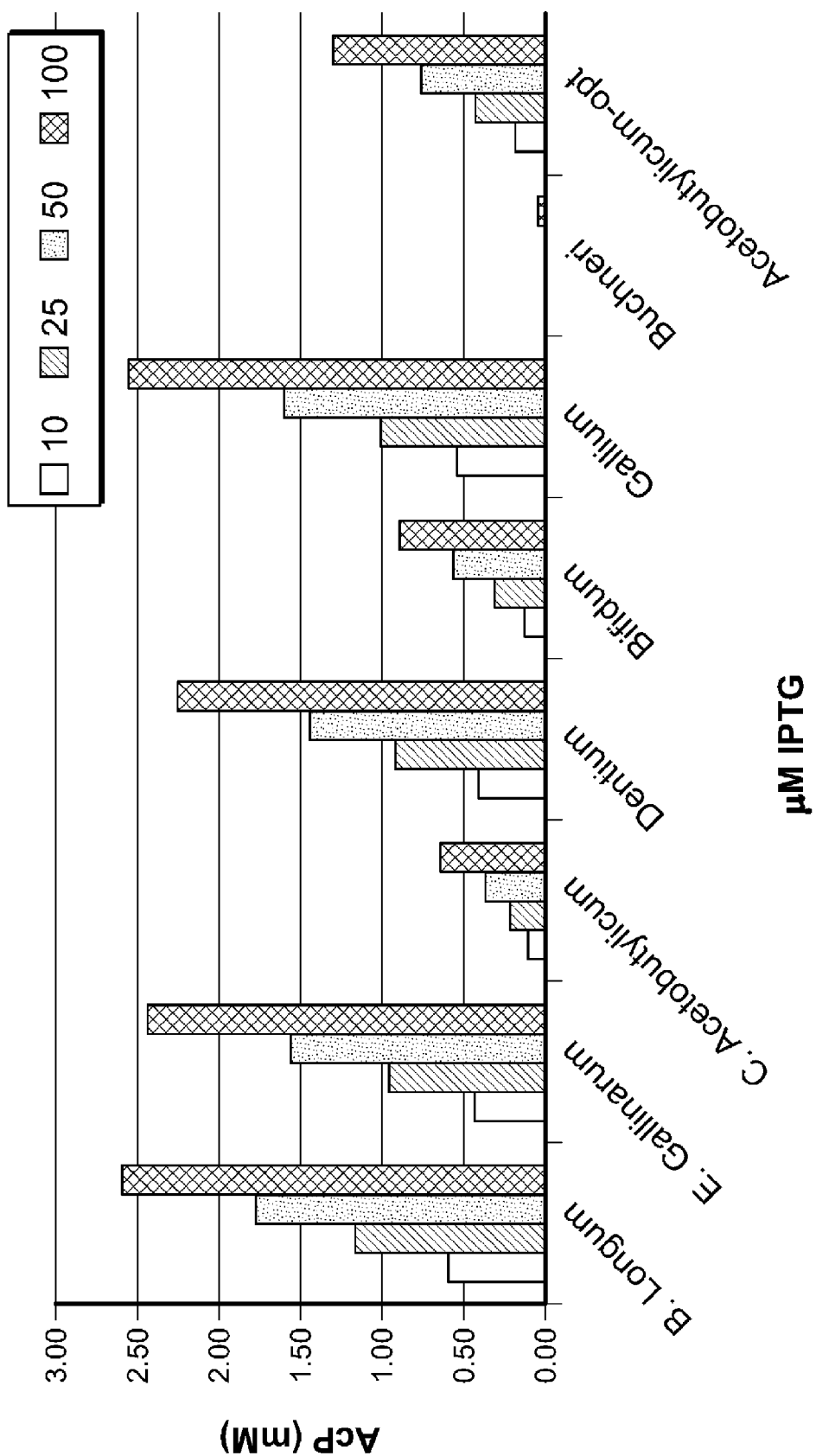
FIG. 33 is a graph showing in vitro activity of *B. longum* PKL, *E. gallinarum* PKL, *C. acetobutylicum* PKL, *B. dentium* PKL, *B. bifidum* PKL, *B. gallicum* PKL, *L. buchneri* PKL, *B. phytofermans* PKL, and *C. acetobutylicum* codon optimized PKL in the presence of F6P substrate as measured by Ac-P yield.

The results showed that optimized *C. acetobutylicum* PKL had F6P activity and produced greater amounts of AcP as compared to *C. acetobutylicum* PKL that had not been codon-optimized (FIG. 33). *B. dentium* had similar PKL F6P activity as *C. acetobutylicum* PKL that had not been codon-optimized. *B. dentium* and *B. gallicum* PKLs had significant F6P activity and were comparable to *E. gallinarum* PKL F6P activity. In comparison, *L. buchneri* PKL (FIG. 33) and *B. phytofermans* PKL did not demonstrate F6P activity which is supported by the finding that these PKLs are almost completely insoluble.

Strains expressing an identified PKL listed on Table 1, Table 2, and Clusters 1-22 (see FIGS. 3-24) are grown in LB medium with 50 µg/ml carbenicillin at 37° C. prior to induction. Following induction with 10 µM, 25 µM, 50 µM, or 100 µM IPTG, cultures are transferred to a 34° C. shaker for 30 minutes. Cells are harvested by centrifugation at 10,000 rpm for 10 min at 4° C. For purification, PKL cell pellets are resuspended in 50 mM MES pH 6.0, 50 mM NaCL, 0.5 mM AEBSF, 0.1 mg/ml DNaseI. Cells are lysed by repeated passage through a French press and clarified by ultracentrifugation at 50,000 rpm for 60 mM Clarified lysate containing the PKLs are loaded onto a DEAE HiTrap FF column equilibrated in 50 mM MES, 50 mM NaCl, pH 6 and eluted with a gradient to 50 mM MES, 1M NaCl, pH 6. The resulting fractions are analyzed by SDS-PAGE. Fractions containing PKL are pooled and desalted using a G25 desalting column into 50 mM MES, 50 mM NaCL pH 6.0. Further purification is achieved using a MonoQ 10/100 GL column equilibrated in 50 mM MES, 50 mM NaCL, pH 6 with a salt gradient to 1M NaCl. The amount of AcP formed by each PKL is measured using a scaled down version of hydroxamate assay described in L. Meile et. al., *Bacteriol.*, 2001, 183:2929-2936 and Frey et. al., *Bioorganic Chem.*, 2008, 36:121-127. The assays are performed in a 96-well plate (Costar catalog #9017) format, at 37° C. Each 300 µl reaction contains 1 mM TPP, 10 mM potassium phosphate pH 6.0, 50 mM MES pH 6, 10 mM MgCl2, 5 mM F6P and PKL at a concentration of 250 nM. Time points are taken at various intervals. In order to stop the reaction, 60 µl of the reaction mixture is mixed with 60 µl of 2M hydroxylamine at pH 6.5, incubated for 10 min at room temperature. Addition of 40 µl of 15% TCA, 40 µl of 4M HCl, and 40 µl of 5% $FeCl_3$ in 0.1 M HCl is used to precipitate the protein and allow AcP detection. The samples are then centrifuged at 3000 rpm for 10 mM. A 200 µl sample of supernatant is transferred to a microtiter plate and a plate reader, and absorbance changes associated with the amount of AcP formed are monitored at 505 nm.

Example 7: In Vivo Screen for Phosphoketolase Activity in Strains Expressing Identified Phosphoketolases (PKLs)

The in vivo activities of phosphoketolase (PKL) enzymes were evaluated in a mutant strain that has no transketolase (tkt) activity. Transketolase is responsible for producing erythrose-4-phosphate (E4P), the substrate for all aromatic vitamins and amino acids in *E. coli*. Growth of *E. coli* on minimal medium with glucose as a carbon source in the absence of transketolase activity is therefore not possible due to aromatic auxotrophy (Zhao and Winkler 1994). Transketolase is also involved in the interconversion of xylulose-5-phosphate (X5P) with sedoheptulose-7-phosphate (S7P) and glyceraldehyde-3-phosphate (GAP), and growth of a tkt mutant on minimal medium with xylose as a carbon source is also not possible, since tkt activity is the only outlet back into glycolysis from the pentose phosphate pathway. Since phosphoketolase produces E4P from F6P, and GAP from X5P, functional enzymes can rescue the growth defects of a tkt mutant when grown on glucose (indicating F6P activity) or xylose (indicating both X5P and F6P activity). Growth of complemented mutants therefore can be used to test the different in vivo activities of phosphoketolase enzymes.

Strain Construction

Standard molecular biology techniques to amplify mutations from the Keio collection by PCR, perform P1 transduction, perform GeneBridges insertions (manufacturer's protocol), PCR amplification (Pfu Turbo or Herculase, manufacturer's protocol), transform plasmids, and to grow and propagate strains were used. Briefly, since there are two transketolase enzymes in the genome of *E. coli*, both had to be knocked out to generate a transketolase null mutant. The kanamycin insert in tktB was amplified by PCR from the Keio collection and introduced by recombineering into BL21. The antibiotic resistance cassette in tktB was confirmed by PCR and then looped out using the pCP20 plasmid (Table 5). The tktA mutation was then introduced into BL21 by the same method and subsequently introduced into the tktB mutant by P1 transduction to generate a transketolase null mutant strain (Table 6). This strain, DW809, only grew on M9 glucose minimal medium with casamino acids that did not contribute substantially to the aromatic amino acid supply and an additional supplement of all aromatic compounds, including tyrosine, phenylalanine, tryptophan, p-aminobenzoate, 2-3-dihydroxybenzoate, p-hydroxybenzoate, and pyridoxine (as indicated in Zhao and Winkler, 1994). This combination of six aromatic compounds and pyridoxine is subsequently referred to herein as the "aromatic supplement." Plasmids harboring different phosphoketolase enzymes were then transformed into the transketolase mutant strain, and selected for growth on M9 glucose casamino acids with the aromatic supplement and carbenicillin (Table 6). Strains were then assayed for growth on an Enzyscreen Growth Profiler (Enzyscreen, BV) on either M9 glucose or xylose without the aromatic supplement and compared to the control strain that did not express a phosphoketolase enzyme. Phosphoketolase enzymes were induced in the transketolase null mutant at two different concentrations of IPTG, 20 µM and 60 µM.

The transektolase null mutant strain is transformed with an identified PKL listed on Table 1, Table 2, or Clusters 1-22 (see FIGS. 3-24) and selected for growth on M9 glucose casamino acids with the aromatic supplement and carbenicillin. Strains are then assayed for growth on an Enzyscreen Growth Profiler (Enzyscreen, BV) on either M9 glucose or xylose without the aromatic supplement and compared to the control strain that did not express a phosphoketolase enzyme. Phosphoketolase enzymes are induced in the transketolase null mutant at two different concentrations of IPTG, 20 µM and 60 µM.

TABLE 8

Primers for testing presence of tktA and tktB mutations

| Primer Name | Sequence |
|---|---|
| tkt A test for | catgcgagcatgatccagagatttctga (SEQ ID NO: 135) |
| tkt A test rev | gcttgtccgcaaacggacatatcaaggt (SEQ ID NO: 136) |
| tkt B test for | cagctcccatgagcgaagcggagt (SEQ ID NO: 137) |
| tkt B test rev | gacgcgtcagcgtcgcatccggca (SEQ ID NO: 138) |
| tkt B B test for | gctgcgatcgactgactatcgcaccga (SEQ ID NO: 139) |
| tkt B B test rev | cagacgcctggcccacgttgtggatca (SEQ ID NO: 140) |
| tktA B test for | gcagcggacgggcgagtagattgcgca (SEQ ID NO: 141) |
| tktA B test rev | gtgatctacaacacgccttatctat (SEQ ID NO: 142) |

TABLE 9

Engineered strains expressing PKLs

| Strain | Description |
|---|---|
| DW809 | BL21 ΔtktA ΔtktB, Kan (antibiotic marker in tktA from Keio) |
| DW816 | BL21 ΔtktA ΔtktB, pCMP1321, Kan Carb |
| DW830 | BL21 ΔtktA ΔtktB, pMCS530, Kan Carb |
| DW831 | BL21 ΔtktA ΔtktB, pMCS531, Kan Carb |
| DW832 | BL21 ΔtktA ΔtktB, pMCS532, Kan Carb |
| DW833 | BL21 ΔtktA ΔtktB, pMCS533, Kan Carb |
| DW834 | BL21 ΔtktA ΔtktB, pMCS534, Kan Carb |
| DW835 | BL21 ΔtktA ΔtktB, pMCS535, Kan Carb |

Results

Figure 34:
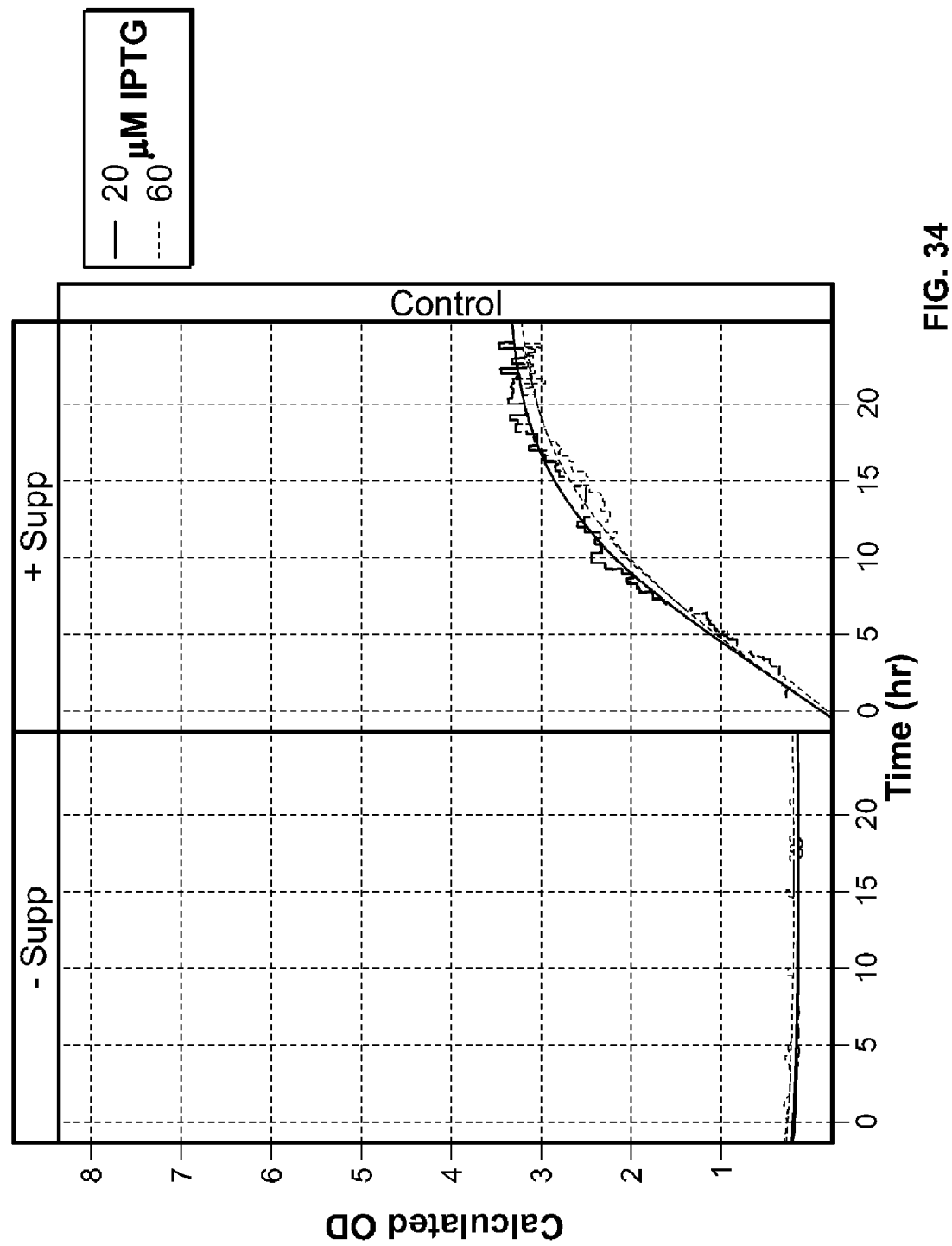
FIG. 34 is a graph showing that the transketolase mutant grew on glucose only with supplement containing six aromatic compounds and pyridoxine.
Figure 35:
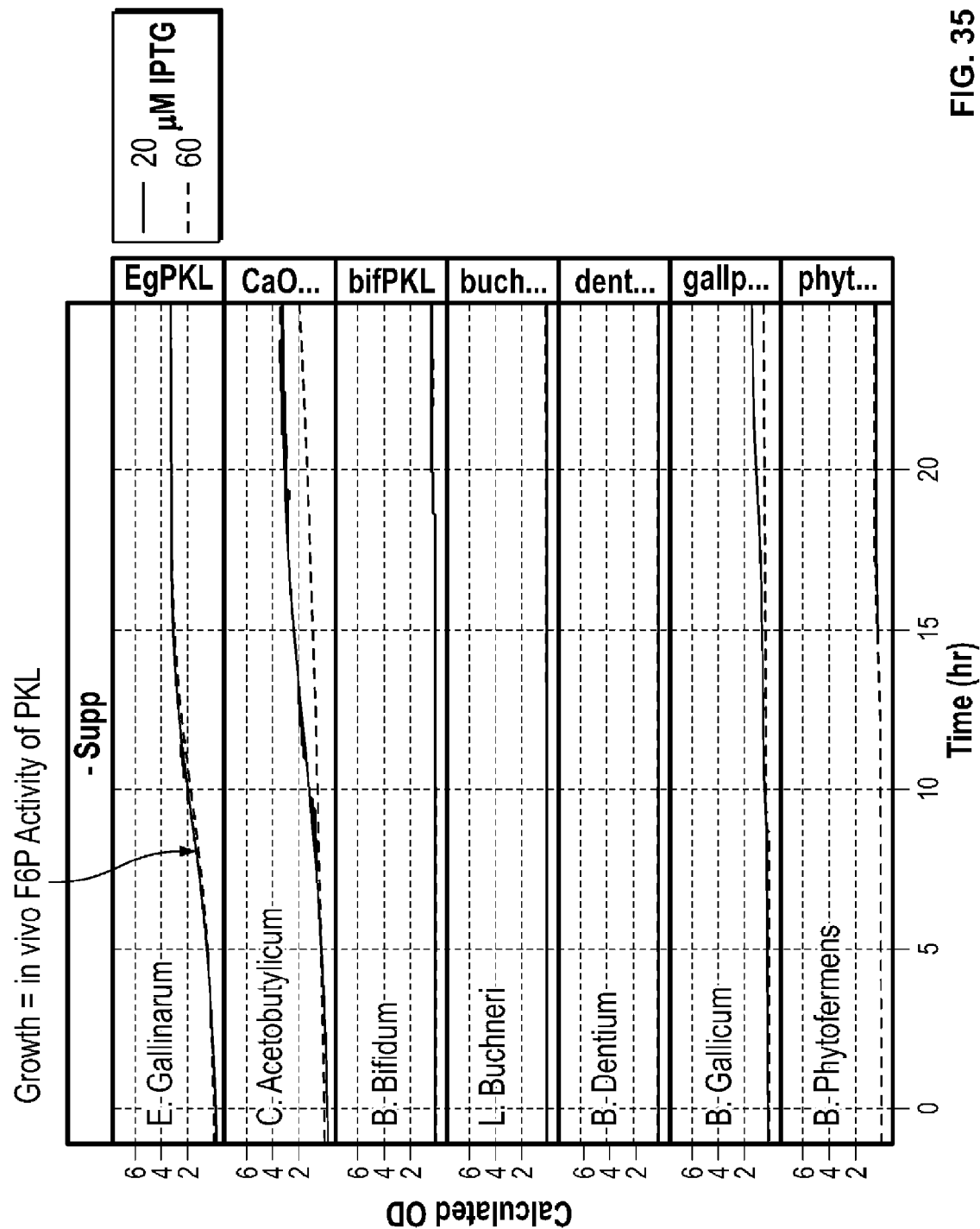
FIG. 35 is a graph showing that phosphoketolases from *E. gallinarum* and *C. acetobutylicum* restored growth to the transketolase mutant on glucose without supplement.
Figure 36:
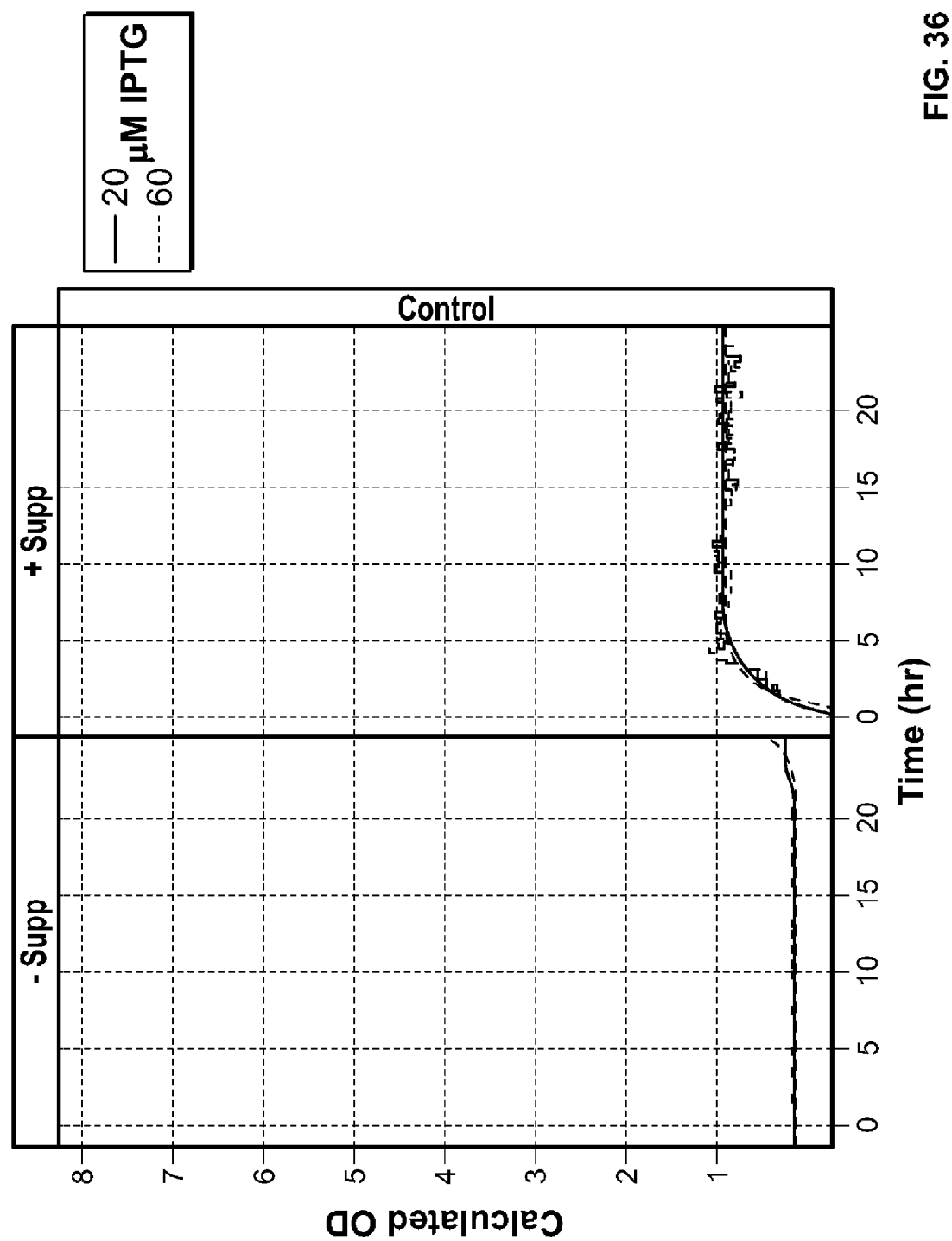
FIG. 36 is a graph showing that the transketolase mutant did not grow on xylose with or without supplement containing six aromatic compounds and pyridoxine.
Figure 37:
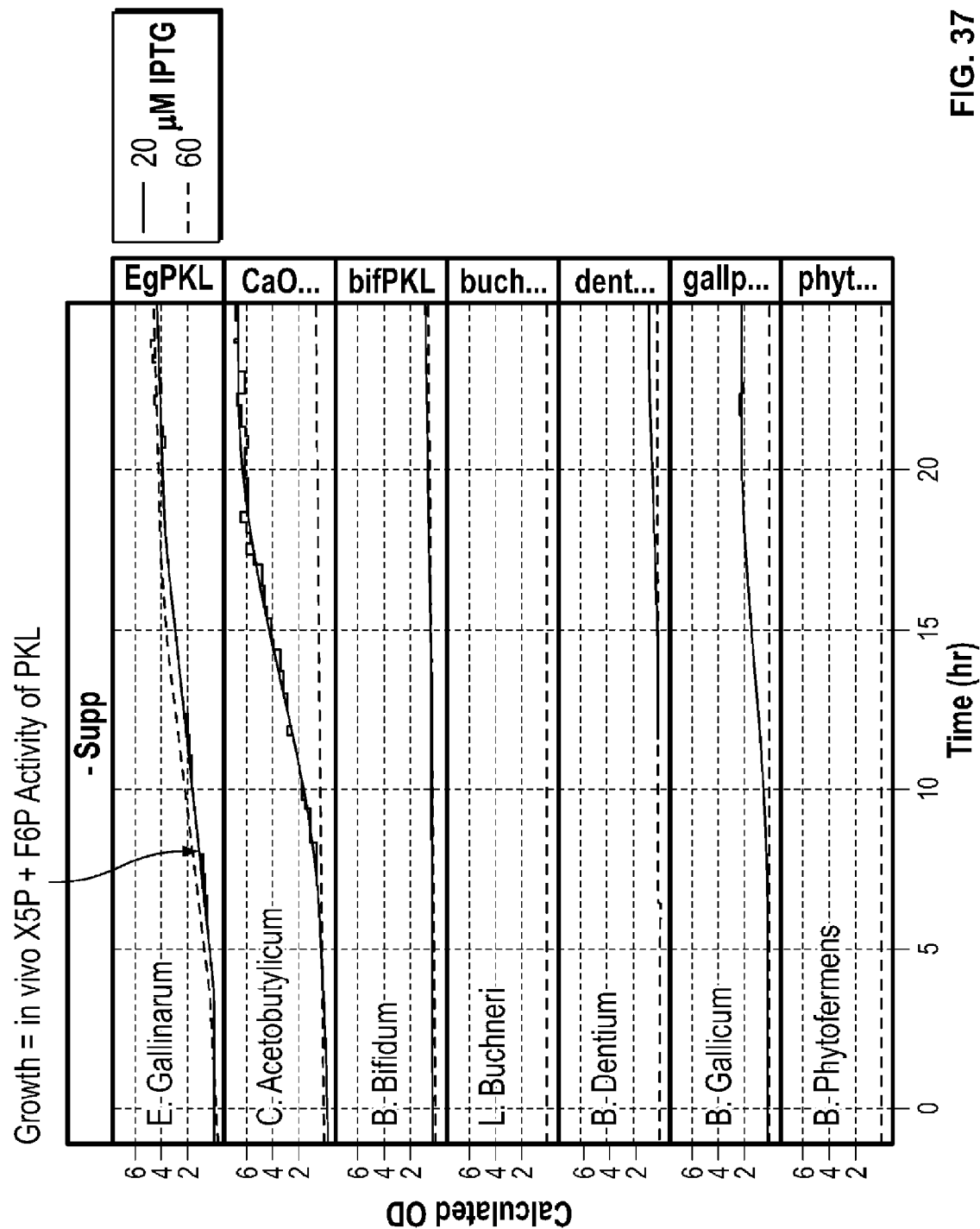
FIG. 37 is a graph showing that phosphoketolases from *E. gallinarum* and *C. acetobutylicum* restored growth to the transketolase mutant on xylose without supplement.

In this assay, the transketolase mutant grew on glucose only with supplement (FIG. 34) and did not grown on xylose with or without supplement (FIG. 36). Growth of the transketolase null mutant expressing different phosphoketolases highlighted the differential in vivo behavior of these enzymes. *E. gallinarum* PKL displayed the best performance on both glucose and xylose, indicating sufficient F6P and X5P activity to maintain growth of the transketolase mutant in the absence of supplement (see FIGS. 35 and 37). The *C. acetobutylicum* PKL also allowed for growth of the transketolase mutant in the absence of aromatic supplement on glucose and xylose (FIGS. 35 and 37), but appeared to have a deleterious effect on cell growth at the 60 µM IPTG concentration when grown on glucose (FIG. 35).

Example 8: Measurement of Intracellular Acetyl Phosphate in Strains Expressing PKLs Isoprene producing *E. coli* strains are constructed to express a phosphoketolase from *Burkholderia phytofirmans* PsJN, *Lactobacillus buchneri* NRRL B-30929, *Bifidobacterium gallicum* DSM 20093, *Bifidobacterium dentium* Bd1, or *Bifidobacterium bifidum* IPLA 20015, or a PKL from Table 1, Table 2, or Clusters 1-22 (see FIGS. 3-24). Strains that did not express a phophoketolase are used as controls.

(i) Materials

TM3 Media Recipe (Per Liter Fermentation Media):

$K_2HPO_4$ 13.6 g, $KH_2PO_4$ 13.6 g, $MgSO_4*7H_2O_2$ g, citric acid monohydrate 2 g, ferric ammonium citrate 0.3 g, $(NH_4)_2SO_4$ 3.2 g, yeast extract 0.2 g, 1000× Trace Metals Solution 1 ml. All of the components are added together and dissolved in $diH_2O$. The pH is adjusted to 6.8 with ammonium hydroxide (30%) and brought to volume. Media is filter-sterilized with a 0.22 micron filter. Glucose 10.0 g and antibiotic are added after pH adjustment and sterilization.

1000× Trace Metal Solution (Per Liter Fermentation Media)

Citric Acid*$H_2O$ 40 g, $MnSO_4$*$H_2O$ 30 g, NaCl 10 g, $FeSO_4$*$7H_2O$ 1 g, $CoCl_2$*$6H_2O$ 1 g, $ZnSO_4$*$7H_2O$ 1 g, $CuSO_4$*$5H_2O$ 100 mg, $H_3BO_3$ 100 mg, $NaMoO_4$*$2H_2O$ 100 mg. Each component is dissolved one at a time in $diH_2O$. The pH is adjusted to 3.0 with HCl/NaOH, and then the solution is brought to volume and filter-sterilized with a 0.22 micron filter.

(ii) Experimental Procedure

Cells expressing the complete MVA pathway and a PKL from *Burkholderia phytofirmans* PsJN, *Lactobacillus buchneri* NRRL B-30929, *Bifidobacterium gallicum* DSM 20093, *Bifidobacterium dentium* Bd1, or *Bifidobacterium bifidum* IPLA 20015, or a PKL from Table 1, Table 2, or Clusters 1-22 (see FIGS. 3-24) are grown overnight in Luria-Bertani broth+antibiotics. The day after, they are diluted to an OD600 of 0.05 in 20 mL TM3 medium containing 50 ug/mL carbenicillin (in a 250-mL baffled Erlenmeyer flask), and incubated at 34° C. and 200 rpm. After 2 h of growth, OD600 is measured and 200 uM IPTG is added. After 3.5 more hours, 1.5 ml sample is centrifuged, the supernatant is discarded and the pellet is resuspended in 100 uL dry-ice cold methanol.

(iii) Intracellular Acetyl Phosphate Determination.

To extract acetyl-phosphate, 1.5 mL of *E. coli* cells grown to OD 0.57-2.26 is spun down by centrifugation and 100 μL of dry-ice cold methanol is added to the pellets. Methanol-quenched samples are stored at −20° C. for several days. Further sample processing includes gentle cell re-suspension, 5-min centrifugation at −9° C. and aspiration of the supernatant into clean vials. The pellet is re-extracted twice with 75 μL of water containing 2% acetic acid. After each extraction, cell debris are pelleted by centrifugation at −9° C., the supernatants from all three extractions are pooled together and spiked with 1 μL of tributylamine. Mass spectrometric analysis of acetyl phosphate by LCMS is carried out using a Thermo Finnigan TSQ system (Thermo Electron Corporation, San Jose, Calif.). The system control, data acquisition, and mass spectral data evaluation are performed using XCalibur and LCQuan software (Thermo Electron Corp). A mobile phase gradient is applied to a Synergi MAX-RP 5 μM HPLC column (150×2 mm, Phenomenex) at a flow rate of 0.4 mL/min. The applied gradient profile is 99% A and 1% B at t=0-1 min; 80% A and 20% B at t=11 min; 75% B and 25% C at t=12-14 min; 99% A and 1% B at t=15-16 min, where solvent A is 15 mM tributylamine/10 mM acetic acid in water, solvent B is methanol, and solvent C is water. Mass detection of acetyl phosphate is carried out using electrospray ionization (ESI-MS/MS) in the negative mode (ESI spray voltage of 2.5-3.0 kV, ion transfer tube temperature 390° C.) with m/z value for the precursor ion of 138.9. Concentration of acetyl phosphate is determined based on the integrated intensity of peak generated by $PO_3^-$ product ion (m/z=79.0, collision energy 20 V, collision gas pressure 1.7 mTorr, $R_t$=13.2 min). A calibration curve obtained by injection of acetyl phosphate standard (Sigma-Aldrich) is used to calculate concentration of the metabolite in cell extracts. Intracellular concentration of acetyl phosphate is determined based on the assumption that in 1 mL of the culture at OD=200 the integrated volume of all cells is 50 Ml. Produced acetyl phosphate is assessed in strains expressing a PKL as compared to control strain not expressing phosphoketolase.

Example 9: Production of Isoprene in Recombinant Host Cells Expressing Phosphoketolase at Small Scale Isoprene producing *E. coli* strains are constructed to express a phosphoketolase from *Burkholderia phytofirmans* PsJN, *Lactobacillus buchneri* NRRL B-30929, *Bifidobacterium gallicum* DSM 20093, *Bifidobacterium dentium* Bd1, or *Bifidobacterium bifidum* IPLA 20015, or a PKL from Table 1, Table 2, or Clusters 1-22 (see FIGS. 3-24), the complete MVA pathway and an isoprene synthase. Isoprene producing strains that did not express a phophoketolase are used as controls.

TM3 Media Recipe (Per Liter Fermentation Media):

$K_2HPO_4$ 13.6 g, $KH_2PO_4$ 13.6 g, $MgSO_4$*$7H_2O$ 2 g, citric acid monohydrate 2 g, ferric ammonium citrate 0.3 g, $(NH_4)_2SO_4$ 3.2 g, yeast extract 0.2 g, 1000× Trace Metals Solution 1 ml. All of the components are added together and dissolved in $diH_2O$. The pH is adjusted to 6.8 with ammonium hydroxide (30%) and brought to volume. Media is filter-sterilized with a 0.22 micron filter. Glucose 10.0 g and antibiotics are added after pH adjustment and sterilization.

1000× Trace Metal Solution (Per Liter Fermentation Media)

Citric Acid*$H_2O$ 40 g, $MnSO_4$*$H_2O$ 30 g, NaCl 10 g, $FeSO_4$*$7H_2O$ 1 g, $CoCl_2$*$6H_2O$ 1 g, $ZnSO_4$*$7H_2O$ 1 g, $CuSO_4$*$5H_2O$ 100 mg, $H_3BO_3$ 100 mg, $NaMoO_4$*$2H_2O$ 100 mg. Each component is dissolved one at a time in $diH_2O$. The pH is adjusted to 3.0 with HCl/NaOH, and then the solution is brought to volume and filter-sterilized with a 0.22 micron filter.

(ii) Experimental Procedure

Cells are grown overnight in Luria-Bertani broth+antibiotics. The day after, they are diluted to an OD600 of 0.1 in 20 mL TM3 medium containing 50 ug/ml of spectinomycin, 25 ug/mL chloramphenicol and 50 ug/mL carbenicillin (in a 250-mL baffled Erlenmeyer flask), and incubated at 34° C. and 200 rpm. After 2 h of growth, OD600 is measured and 200 uM IPTG is added. Samples are taken regularly during the course of the fermentation. At each timepoint, OD600 is measured. Also, off-gas analysis of isoprene is performed using a gas chromatograph-mass spectrometer (GC-MS) (Agilent) headspace assay. A 100 μl sample of whole broth is placed in a 96-well glass block. The glass block is sealed with aluminum foil and incubated at 34° C. while shaking at 450 rpm, for 30 minutes using a Thermomixer. After 30 minutes, the block is kept at 70° C. water bath for 2 minutes and levels of isoprene in the headspace measurement are determined using gas chromatography-mass spectrometry. The reported specific productivity is the amount of isoprene in ug/L read by the GC divided by the incubation time (30 min) and the measured OD600.

Example 10: Production of Isoprene in Recombinant Host Cells Expressing Phosphoketolase at 15-L Scale Isoprene producing *E. coli* strains are constructed to express a phosphoketolase from *Burkholderia phytofirmans* PsJN, *Lactobacillus buchneri* NRRL B-30929, *Bifidobacterium gallicum* DSM 20093, *Bifidobacterium dentium* Bd1, or *Bifidobacterium bifidum* IPLA 20015, or a PKL from Table 1, Table 2, or Clusters 1-22 (see FIGS. 3-24), the complete MVA pathway and an isoprene synthase. Isoprene producing strains that did not express a phophoketolase are used as controls in a 15 Liter scale experiment for production of isoprene.

(i) Materials

Medium Recipe (Per Liter Fermentation Medium):

K2HPO4 7.5 g, MgSO4*7H2O 2 g, citric acid monohydrate 2 g, ferric ammonium citrate 0.3 g, yeast extract 0.5 g, 50% sulphuric acid 1.6 mL, 1000× Modified Trace Metal Solution 1 ml. All of the components are added together and dissolved in Di H2O. This solution is heat sterilized (123° C. for 20 minutes). The pH is adjusted to 7.0 with ammonium hydroxide (28%) and q.s. to volume. Glucose 10 g, Vitamin Solution 8 mL, and antibiotics are added after sterilization and pH adjustment.

1000× Modified Trace Metal Solution (Per Liter):

Citric Acids*H2O 40 g, MnSO4*H2O 30 g, NaCl 10 g, FeSO4*7H2O 1 g, CoCl2*6H2O 1 g, ZnSO*7H2O 1 g, CuSO4*5H2O 100 mg, H3BO3 100 mg, NaMoO4*2H2O 100 mg. Each component was dissolved one at a time in Di H2O, pH was adjusted to 3.0 with HO/NaOH, and then the solution was q.s. to volume and filter sterilized with a 0.22 micron filter.

Vitamin Solution (Per Liter):

Thiamine hydrochloride 1.0 g, D-(+)-biotin 1.0 g, nicotinic acid 1.0 g, pyridoxine hydrochloride 4.0 g. Each component was dissolved one at a time in Di H2O, pH was adjusted to 3.0 with HCl/NaOH, and then the solution was q.s. to volume and filter sterilized with 0.22 micron filter.

Macro Salt Solution (Per Liter):

MgSO4*7H2O 296 g, citric acid monohydrate 296 g, ferric ammonium citrate 49.6 g. All components were dissolved in water, q.s. to volume and filter sterilized with 0.22 micron filter.

Feed Solution (Per Kilogram):

Glucose 0.590 kg, Di H2O 0.393 kg, K2HPO4 7.4 g, and 100% Foamblast882 8.9 g. All components were mixed together and autoclaved. After autoclaving the feed solution, nutrient supplements are added to the feed bottle in a sterile hood. Post sterilization additions to the feed are (per kilogram of feed solution), Macro Salt Solution 5.54 ml, Vitamin Solution 6.55 ml, 1000× Modified Trace Metal Solution 0.82 ml.

(ii) Analysis

Isoprene, Oxygen, Nitrogen, and Carbon Dioxide levels in the off-gas are determined independently by two mass spectrometers, an iSCAN (Hamilton Sundstrand), and a Hiden HPR20 (Hiden Analytical) mass spectrometer. Dissolved Oxygen in the fermentation broth is measured by sanitary, sterilizable probe with an optical sensor provided Hamilton Company. The citrate, glucose, acetate, and mevalonate concentrations in the fermentor broth are determined in broth samples taken at 4 hour intervals by an HPLC analysis. Concentration in broth samples are determined by comparison of the refractive index response versus a previously generated calibration curve using standard of a known concentration.

Example 11: Production of Amorphadiene or Farnesene in Strains Expressing an Identified Phosphoketolase Isoprenoid producing *E. coli* strains are constructed to express a phosphoketolase from *Burkholderia phytofirmans* PsJN, *Lactobacillus buchneri* NRRL B-30929, *Bifidobacterium gallicum* DSM 20093, *Bifidobacterium dentium* Bd1, or *Bifidobacterium bifidum* IPLA 20015, or a PKL from Table 1, Table 2, or Clusters 1-22 (see FIGS. 3-24), the complete MVA pathway and a codon-optimized gene coding for farnesene synthase or amorphadiene synthase. Isoprenoid producing strains that did not express a phophoketolase are used as controls in an experiment for production of amorphadine or farnesene.

(i) Materials

TM3 Media Recipe (Per Liter Fermentation Media):

$K_2HPO_4$ 13.6 g, $KH_2PO_4$ 13.6 g, $MgSO_4*7H_2O$ 2 g, citric acid monohydrate 2 g, ferric ammonium citrate 0.3 g, $(NH_4)_2SO_4$ 3.2 g, yeast extract 0.2 g, 1000× Trace Metals Solution 1 ml. All of the components are added together and dissolved in $diH_2O$. The pH is adjusted to 6.8 with ammonium hydroxide (30%) and brought to volume. Media is then filter-sterilized with a 0.22 micron filter. Glucose 10.0 g and antibiotics are added after sterilization and pH adjustment.

1000× Trace Metal Solution (Per Liter Fermentation Media):

Citric Acid*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, $NaMoO_4*2H_2O$ 100 mg. Each component is dissolved one at a time in $diH_2O$. The pH is adjusted to 3.0 with HCl/NaOH, and then the solution is brought to volume and filter-sterilized with a 0.22 micron filter.

(ii) Experimental Procedure

Cells are grown overnight in Luria-Bertani broth+antibiotics. The day after, they are diluted to an OD600 of 0.05 in 20 mL TM3 medium containing 50 ug/ml of spectinomycin, 25 ug/mL chloramphenicol and 50 ug/mL carbenicillin (in a 250-mL baffled Erlenmeyer flask), and incubated at 34° C. and 200 rpm. Prior to inoculation, an overlay of 20% (v/v) dodecane (Sigma-Aldrich) is added to each culture flask to trap the volatile sesquiterpene product as described previously (Newman et al., 2006).

After 2 h of growth, OD600 is measured and 0.05-0.40 mM isopropyl β-D-1-thiogalactopyranoside (IPTG) is added. Samples are taken regularly during the course of the fermentation. At each timepoint, OD600 is measured. Also, amorphadiene or farnesene concentration in the organic layer is assayed by diluting the dodecane overlay into ethyl acetate. Dodecane/ethyl acetate extracts are analyzed by GC-MS methods as previously described (Martin et. al., *Nat. Biotechnol.* 2003, 21:96-802) by monitoring the molecular ion (204 m/z) and the 189 m/z fragment ion for amorphadiene or the molecular ion (204 m/z) for farnesene. Amorphadiene or farnesene samples of known concentration are injected to produce standard curves for amorphadiene or farnesene, respectively. The amount of amorphadiene or farnesene in samples is calculated using the amorphadiene or farnesene standard curves, respectively.

Figure 38:
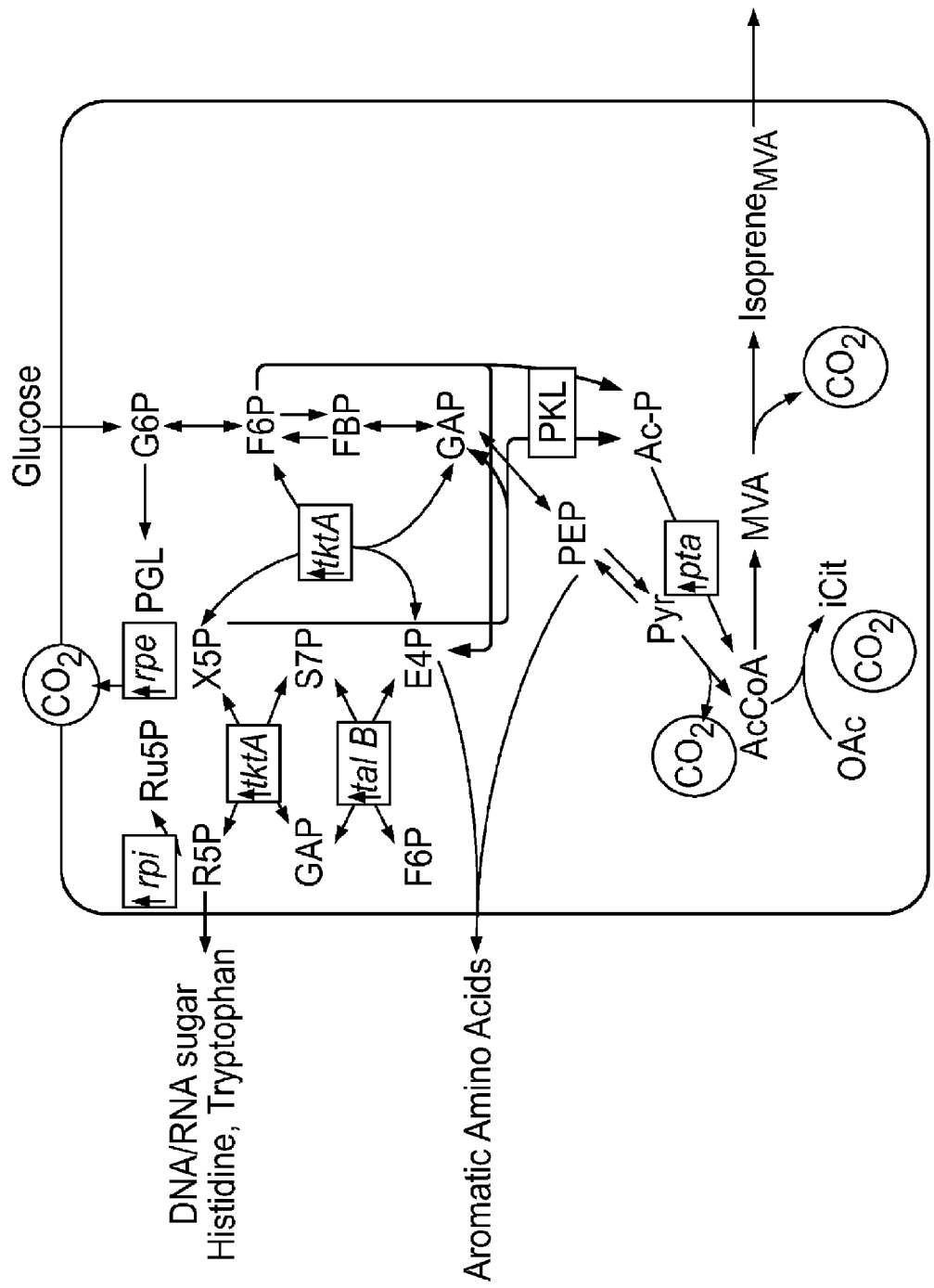
FIG. 38 is a diagram depicting host mutations that are preferably upregulated to increase carbon flux through the phosphoketolase pathway. Genes of interest for modulating carbon flux include moduribose-5-phosphate isomerase A (rpiA), D-ribulose-5-phosphate 3-epimerase (rpe), transketolase A (tktA), transaldolase B (tal B), and/or phosphate acetyltransferase (pta).

Example 12: Construction of Phosphoketolase-Expressing Strains Harboring Host Mutations for Producing Isoprene Isoprene-producing strains comprising a PKL from *Burkholderia phytofirmans* PsJN, *Lactobacillus buchneri* NRRL B-30929, *Bifidobacterium gallicum* DSM 20093, *Bifidobacterium dentium* Bd1, or *Bifidobacterium bifidum* IPLA 20015, or a PKL from Table 1, Table 2, or Clusters 1-22 (see FIGS. 3-24) can be further engineered to increase the activity of one or more of the following genes including ribose-5-phosphate isomerase (rpiA and/or rpiB), D-ribulose-5-phosphate 3-epimerase (rpe), transketolase (tktA and/or tktB), transaldolase B (tal B), phosphoenolpyruvate synthetase (ppsA), phosphate acetyltransferase (pta and/or eutD) to improve carbon flux through the phosphoketolase pathway (FIG. 38). In certain aspects, the activity of the following genes rpiA, rpiB, rpe, tktA, tktB, tal B, ppsA, eutD, and/or pta can be increased by altering the promoter and/or rbs on the chromosome, or by expressing it from a plasmid. In one embodiment the activity of ribose-5-phosphate isomerase (rpiA and/or rpiB) is increased by altering the promoter and/or rbs on the chromosome, or by expressing it from a plasmid. In another embodiment the activity of D-ribulose-5-phosphate 3-epimerase (rpe) is increased by altering the promoter and/or rbs on the chromosome, or by expressing it from a plasmid. In another embodiment the activity of transketolase (tktA and/or tktB) is increased by altering the promoter and/or rbs on the chromosome, or by expressing it from a plasmid. In yet another embodiment the activity of transaldolase B (tal B) is increased by altering the promoter and/or rbs on the chromosome, or by expressing it from a plasmid. In another embodiment the activity of phosphoenolpyruvate synthetase (ppsA) is increased by altering the promoter and/or rbs on the chromosome, or by expressing it from a plasmid. In still other embodiments the activity of phosphate acetyltransferase (pta and/or eutD) is increased by altering the promoter and/or rbs on the chromosome, or by expressing it from a plasmid. In certain aspects, isozymes of the following genes rpiA, rpiB, rpe, tktA, tktB, tal B, ppsA, eutD, and/or pta can be increased by altering the promoter and/or rbs on the chromosome, or by expressing it from a plasmid.

Figure 39:
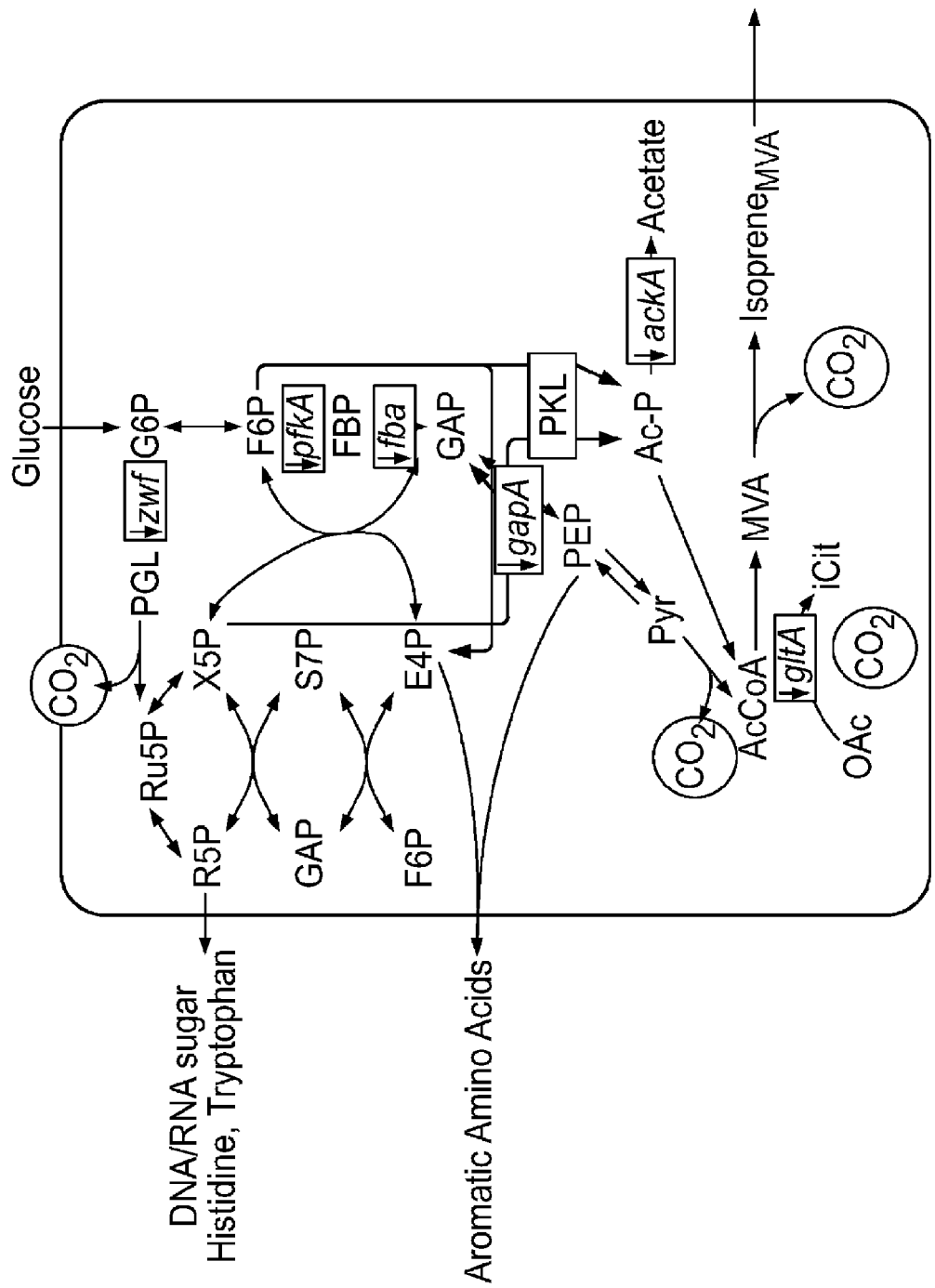
FIG. 39 is a diagram depicting host mutations that are preferably downregulated to increase carbon flux through the phosphoketolase pathway. Genes of interest for modulating carbon flux include glucose-6-phosphate dehydrogenase (zwf), 6-phosphofructokinase-1 (pfkA), fructose bisphosphate aldolase (fba), glyceraldehyde-3-phosphate dehydrogenase A (gapA), Acetate kinase (ackA), citrate synthase (gltA) and/or the pts operon.

These strains can be further engineered to decrease the activity of one or more of the following genes including glucose-6-phosphate dehydrogenase (zwf), 6-phosphofructokinase-1 (pfkA and/or pfkB), fructose bisphosphate aldolase (fba, fbaA, fbaB, and/or fbaC), glyceraldehyde-3-phosphate dehydrogenase (gapA and/or gapB), acetate kinase (ackA), citrate synthase (gltA), transketolase (tktA and/or tktB), EI (ptsI), EIICB$^{Glc}$ (ptsG), EIIA$^{Glc}$ (err), and/or HPr (ptsH) to increase carbon flux into the phosphoketolase pathway (FIG. 39). In one embodiment, a zwf gene encoding glucose-6-phosphate dehydrogenase is downregulated. In another embodiment, a pfkA gene encoding 6-phosphofructokinase-1 A is downregulated. In another embodiment, a gapA gene encoding glyceraldehyde-3-phosphate dehydrogenase A is downregulated. In another embodiment, a fba gene encoding fructose bisphosphate aldolase is downregulated. In yet another embodiment, a gltA gene encoding citrate synthase is downregulated. In an embodiment, a ackA gene encoding acetate kinase is downregulated. In another embodiment, a ptsI gene encoding EI is downregulated. In an embodiment, a ptsH gene encoding HPr is downregulated. In another embodiment, a ptsG gene encoding EIICB$^{Glc}$ is downregulated. In a yet another embodiment, a crr gene encoding EIIA$^{Glc}$ is downregulated. The pts operon encodes genes of the phosphotransferase system. In some embodiments, the strains can be engineered to decrease activity of the phosphotransferase system (PTS) to increase carbon flux into the phosphoketolase pathway. In some embodiments, the PTS is downregulated by downregulation of the pts operon. In certain aspects, the PTS is downregulated and a glucose transport pathway is upregulated. A glucose transport pathway includes, but is not limited to, galactose (galP) and glucokinase (glk) genes. In some embodiments, the pts operon is downregulated, the galactose (galP) gene is upregulated, and the glucokinase (glk) gene is upregulated. In certain aspects, isozymes of proteins encoded by the following genes zwf, pfkA, fba, gapA, ackA, gltA, tktA, ptsG, ptsH, ptsI, and/or crr can be downregulated to increase carbon flux into the phosphoketolase pathway. In some embodiments, the pfkB gene is downregulated. In some embodiments, the glyceraldehyde-3-phosphate dehydrogenase B (gapB) gene is downregulated. In some embodiments, the transketolase B (tktB) gene is downregulated.

Example 13: Production of Isoprene by Phosphoketolase-Expressing Strains Harboring Host Mutations at Small Scale The isoprene producing strains described in Example 12 are evaluated for isoprene production at small scale.
(i) Materials
TM3 Media Recipe (Per Liter Fermentation Media):
K$_2$HPO$_4$ 13.6 g, KH$_2$PO$_4$ 13.6 g, MgSO$_4$*7H$_2$O 2 g, citric acid monohydrate 2 g, ferric ammonium citrate 0.3 g, (NH$_4$)$_2$SO$_4$ 3.2 g, yeast extract 0.2 g, 1000× Trace Metals Solution 1 ml. All of the components are added together and dissolved in diH$_2$O. The pH is adjusted to 6.8 with ammonium hydroxide (30%) and brought to volume. Media is filter-sterilized with a 0.22 micron filter. Glucose 10.0 g and antibiotics are added after pH adjustment and sterilization.
1000× Trace Metal Solution (Per Liter Fermentation Media)
Citric Acid*H$_2$O 40 g, MnSO$_4$*H$_2$O 30 g, NaCl 10 g, FeSO$_4$*7H$_2$O 1 g, CoCl$_2$*6H2O 1 g, ZnSO$_4$*7H2O 1 g, CuSO$_4$*5H$_2$O 100 mg, H$_3$BO$_3$ 100 mg, NaMoO$_4$*2H2O 100 mg. Each component is dissolved one at a time in diH$_2$O. The pH is adjusted to 3.0 with HCl/NaOH, and then the solution is brought to volume and filter-sterilized with a 0.22 micron filter.
(ii) Experimental Procedure Cells are grown overnight in Luria-Bertani broth+antibiotics. The day after, they are diluted to an OD600 of 0.1 in 20 mL TM3 medium containing 50 ug/ml of spectinomycin, 25 ug/mL chloramphenicol and 50 ug/mL carbenicillin (in a 250-mL baffled Erlenmeyer flask), and incubated at 34° C. and 200 rpm. After 2 h of growth, OD600 is measured and 200 uM IPTG is added. Samples are taken regularly during the course of the fermentation. At each timepoint, OD600 is measured. Also, off-gas analysis of isoprene is performed using a gas chromatograph-mass spectrometer (GC-MS) (Agilent) headspace assay. One hundred microliters of whole broth are placed in a sealed GC vial and incubated at 34° C. and 200 rpm for a fixed time of 30 minutes. Following a heat kill step, consisting of incubation at 70° C. for 7 minutes, the sample is loaded on the GC. The reported specific productivity is the amount of isoprene in ug/L read by the GC divided by the incubation time (30 min) and the measured OD600.

Example 14: Production of Isoprene by Phosphoketolase-Expressing Strains Harboring Host Mutations at 15-L Scale The isoprene producing strains described in Example 12 are evaluated for isoprene production at 15-L scale.
(i) Materials
Medium Recipe (Per Liter Fermentation Medium):
K2HPO4 7.5 g, MgSO4*7H2O 2 g, citric acid monohydrate 2 g, ferric ammonium citrate 0.3 g, yeast extract 0.5 g, 50% sulphuric acid 1.6 mL, 1000× Modified Trace Metal Solution 1 ml. All of the components were added together and dissolved in Di H2O. This solution was heat sterilized (123° C. for 20 minutes). The pH was adjusted to 7.0 with ammonium hydroxide (28%) and q.s. to volume. Glucose 10 g, Vitamin Solution 8 mL, and antibiotics were added after sterilization and pH adjustment.

1000× Modified Trace Metal Solution (Per Liter):

Citric Acids*H2O 40 g, MnSO$_4$*H2O 30 g, NaCl 10 g, FeSO4*7H2O 1 g, CoCl2*6H2O 1 g, ZnSO*7H2O 1 g, CuSO4*5H2O 100 mg, H3BO3 100 mg, NaMoO4*2H2O 100 mg. Each component was dissolved one at a time in Di H2O, pH was adjusted to 3.0 with HO/NaOH, and then the solution was q.s. to volume and filter sterilized with a 0.22 micron filter.

Vitamin Solution (Per Liter):

Thiamine hydrochloride 1.0 g, D-(+)-biotin 1.0 g, nicotinic acid 1.0 g, pyridoxine hydrochloride 4.0 g. Each component was dissolved one at a time in Di H2O, pH was adjusted to 3.0 with HCl/NaOH, and then the solution was q.s. to volume and filter sterilized with 0.22 micron filter.

Macro Salt Solution (Per Liter):

MgSO4*7H2O 296 g, citric acid monohydrate 296 g, ferric ammonium citrate 49.6 g. All components were dissolved in water, q.s. to volume and filter sterilized with 0.22 micron filter.

Feed Solution (Per Kilogram):

Glucose 0.590 kg, Di H2O 0.393 kg, K2HPO4 7.4 g, and 100% Foamblast882 8.9 g. All components were mixed together and autoclaved. After autoclaving the feed solution, nutrient supplements are added to the feed bottle in a sterile hood. Post sterilization additions to the feed are (per kilogram of feed solution), Macro Salt Solution 5.54 ml, Vitamin Solution 6.55 ml, 1000× Modified Trace Metal Solution 0.82 ml.

(ii) Analysis

Isoprene, Oxygen, Nitrogen, and Carbon Dioxide levels in the off-gas are determined independently by two mass spectrometers, an iSCAN (Hamilton Sundstrand), and a Hiden HPR20 (Hiden Analytical) mass spectrometer. Dissolved Oxygen in the fermentation broth is measured by sanitary, sterilizable probe with an optical sensor provided Hamilton Company. The citrate, glucose, acetate, and mevalonate concentrations in the fermentor broth arephytofermans determined in broth samples taken at 4 hour intervals by an HPLC analysis. Concentration in broth samples are determined by comparison of the refractive index response versus a previously generated calibration curve using standard of a known concentration.

Example 15: Strains Used for Small Scale Evaluation of Phosphoketolases

The phosphoketolase expressing strains were generated using standard molecular biology techniques where the specified PKL was transformed into MD-891 (BL2+ GI1.2gltA yhfSFRTPyddVIspAyhfS thiFRTtruncIspA pgl ML+FRT-PL.2-3cis-RBS10000-mvk(*burtonii*) ackA::FRT) together with MCM-1225 (pMCM1225—pCL Ptrc-E. gallinarumUpper MVA)). Strains are listed in Table 10.

TABLE 10

| Strains used for Small Scale Evaluation of Phosphoketolases | | | | | |
|---|---|---|---|---|---|
| Source | PKL # | Amino Acid SEQ ID NO: | pTrc_IspS_IDI plasmid | MD891 strain | (MCM1225) |
| E. faecium | 1 | 23 | MCS811 | MCS865 | MCS932 |
| L. grayi | 2 | 24 | MCS812 | MCS866 | MCS933 |
| E. casseliflavus | 3 | 25 | MCS813 | MCS867 | MCS934 |
| M. alligatoris | 4 | 26 | MCS814 | MCS868 | MCS935 |
| Carnobacterium | 5 | 27 | MCS815 | MCS869 | MCS936 |
| M. plutonius ATCC | 6 | 28 | MCS816 | MCS870 | MCS937 |
| T. halophilus | 7 | 29 | MCS817 | MCS871 | MCS938 |
| M. plutonius DAT | 8 | 30 | MCS818 | MCS872 | MCS939 |
| M. arthritidis | 9 | 31 | MCS819 | MCS873 | MCS940 |
| S. agalactiae | 10 | 32 | MCS820 | MCS874 | MCS941 |
| M. agalacticae | 11 | 33 | MCS821 | MCS875 | MCS942 |
| S. gordonii | 12 | 34 | MCS822 | MCS876 | MCS943 |
| K. oralis | 13 | 35 | MCS823 | MCS877 | MCS944 |
| M. fermentans | 14 | 36 | MCS824 | MCS878 | MCS945 |
| G. adiacens | 15 | 37 | MCS825 | MCS879 | MCS946 |
| M. hominis | 16 | 38 | MCS826 | MCS880 | MCS947 |
| M. crocodyli | 17 | 39 | MCS827 | MCS881 | MCS948 |
| Neisseria | 18 | 40 | MCs828 | MCS882 | MCS949 |
| E. coleocola | 19 | 41 | MCS829 | MCS883 | MCS950 |
| A. urinae | 20 | 42 | MCS830 | MCS884 | MCS951 |
| K. kingae | 21 | 43 | MCS831 | MCS885 | MCS952 |
| S. criceti (#1) | 22 | 44 | MCS832 | MCS886 | MCS953 |
| S. criceti (#2) | 23 | 45 | MCS833 | MCS887 | MCS954 |
| M. columbinum | 24 | 46 | MCS834 | MCS888 | MCS955 |
| M. gilvum | 25 | 1 | MCS835 | MCS889 | MCS956 |
| S. baltica | 26 | 2 | MCs836 | MCS890 | MCS957 |
| L. rhamnosus | 27 | 3 | MCS837 | MCS891 | MCS958 |
| L. crispatus | 28 | 4 | MCS838 | MCS892 | MCS959 |
| L. citreum | 29 | 6 | MCS839 | MCS893 | MCS960 |
| Bradyrhizobium sp. | 30 | 7 | MCS840 | MCS894 | MCS961 |
| B. microti | 31 | 9 | MCS841 | MCS895 | MCS962 |
| L. salivarius | 32 | 10 | MCS842 | MCS896 | MCS963 |
| R. imtechensis | 33 | 12 | MCS843 | MCS897 | MCS964 |
| B. xenovorans | 34 | 13 | MCS844 | MCS898 | MCS965 |
| M. intracellulare | 35 | 14 | MCS845 | MCS899 | MCS966 |
| Nitrosomonas sp. | 36 | 15 | MCS846 | MCS900 | MCS967 |
| S. pombe | 37 | 16 | MCS847 | MCS901 | MCS968 |

TABLE 10-continued

Strains used for Small Scale Evaluation of Phosphoketolases

| Source | PKL # | Amino Acid SEQ ID NO: | pTrc_IspS_IDI plasmid | MD891 strain | (MCM1225) |
|---|---|---|---|---|---|
| L. buchneri | 38 | 19 | MCS848 | MCS902 | MCS969 |
| S. ghanaensis | 39 | 20 | MCs849 | MCS903 | MCS970 |
| Cyanothece sp. | 40 | 21 | MCS850 | MCS904 | MCS971 |
| N. fischeri | 41 | 22 | MCS851 | MCS905 | MCS972 |
| L. lactis | 42 | 105 | MCS852 | MCS906 | MCS973 |
| E. gallinarum (CON) | | 93 | EWL1421 | MCS908 | MCS975 |

Example 16: In Vivo Screen for Phosphoketolase Activity in Expressing Identified Phosphoketolases (PKLs)

The following in vivo screen for phosphoketolase activity was performed as set forth above in Example 7. The host cell background is DW-809 with plasmids pMCS811-pMCS852 containing distinct phosphoketolases.

For in vivo growth evaluation of this set of phosphoketolase (PKL) enzymes, strain DW809, the transketolase double mutant strain as describe in Example 7, was transformed with plasmids expressing both PKL and isoprene synthase from an IPTG-inducible promoter (see Table 11 for complete list). Individual transformants were identified by growth on M9 glucose minimal medium plates with the aromatic supplement, grown overnight, and then assayed on the Enzyscreen Growth Profiler for growth performance on either glucose or xylose without the aromatic supplement, as described in Example 7. The range of IPTG concentrations used for induction was 0, 20, 40, 60, 80, 100, 200, and 400 µM. To calculate performance index (PI) for growth on glucose or xylose, the OD of each experimental strain was normalized to the OD of the control at a specific time point in the growth curve (typically between 30 and 40 hours). The experimental strains that displayed the highest PIs for growth expressed PKL enzymes with the most preferred in vivo activity, whereas the strains with low PIs expressed PKLs that did performed as well in this assay. PIs at 0, 100, and 400 µM were calculated, and were representative of overall growth performance at different induction levels. These are illustrated in Table 11.

TABLE 11

Performance indices (PI) for growth on glucose or xylose

| Source | PKL # | DW-809 strain | PI 0 Glucose | PI 100 Glucose | PI 400 Glucose | PI 0 Xylose | PI 100 Xylose | PI 400 Xylose |
|---|---|---|---|---|---|---|---|---|
| E. faecium | 1 | MCS811 | 0.55 | 0.69 | 0.93 | 0.84 | 0.67 | 0.77 |
| L. grayi | 2 | MCS812 | 0.76 | 0.84 | 0.67 | 1.14 | 0.50 | 0.45 |
| E. casseliflavus | 3 | MCS813 | 4.73 | 0.50 | 0.47 | 2.27 | 0.77 | 0.36 |
| M. alligatoris | 4 | MCS814 | 4.54 | 0.66 | 0.99 | 1.10 | 1.11 | 1.20 |
| Carnobacterium | 5 | MCS815 | 0.72 | 0.06 | 0.06 | 0.49 | 0.09 | 0.17 |
| M. plutonius ATCC | 6 | MCS816 | 0.13 | 0.30 | 0.11 | 0.47 | 0.16 | 0.30 |
| T. halophilus | 7 | MCS817 | 0.06 | 0.02 | 0.03 | 0.39 | 0.07 | 0.05 |
| M. plutonius DAT | 8 | MCS818 | 0.17 | 0.11 | 0.08 | 0.85 | 0.18 | 0.15 |
| M. arthritidis | 9 | MCs819 | 2.26 | 0.43 | 0.66 | 9.52 | 1.33 | 0.95 |
| S. agalactiae | 10 | MCS820 | 3.23 | 0.96 | 0.79 | 0.64 | 0.61 | 0.59 |
| M. agalacticae | 11 | MCS821 | 1.26 | 0.94 | 1.19 | 11.47 | 0.88 | 0.38 |
| S. gordonii | 12 | MCS822 | 3.46 | 0.55 | 0.54 | 2.66 | 1.08 | 0.65 |
| K. oralis | 13 | MCS823 | 4.39 | 0.67 | 0.59 | 2.49 | 0.82 | 0.57 |
| M. fermentans | 14 | MCS824 | 1.48 | 0.34 | 0.32 | 5.70 | 0.12 | 0.15 |
| G. adiacens | 15 | MCS825 | 3.87 | 0.63 | 0.65 | 2.48 | 0.59 | 0.49 |
| M. hominis | 16 | MCS826 | 1.83 | 0.92 | 0.83 | 18.42 | 2.79 | 0.54 |
| M. crocodyli | 17 | MCS827 | 0.08 | 0.05 | 0.06 | 0.54 | 0.08 | 0.07 |
| Neisseria | 18 | MCs828 | 1.30 | 0.60 | 0.84 | 11.47 | 0.54 | 0.24 |
| E. coleocola | 19 | MCS829 | 0.10 | 0.08 | 0.13 | 1.18 | 0.09 | 0.05 |
| A. urinae | 20 | MCS830 | 3.79 | 0.81 | 0.84 | 2.75 | 0.53 | 1.10 |
| K. kingae | 21 | MCS831 | 5.09 | 0.81 | 1.06 | 2.36 | 0.98 | 1.28 |
| S. criceti #1 | 22 | MCS832 | 1.22 | 0.50 | 0.52 | 7.44 | 0.28 | 0.61 |
| S. criceti #2 | 23 | MCS833 | 1.46 | 1.52 | 1.44 | 16.23 | 0.64 | 0.30 |
| M. columbinum | 24 | MCS834 | 1.47 | 0.13 | 0.30 | 2.96 | 0.30 | 0.46 |
| M. gilvum | 25 | MCS835 | 0.34 | 0.08 | 0.09 | 1.38 | 0.10 | 0.16 |
| S. baltica | 26 | MCs836 | 0.11 | 0.04 | 0.08 | 1.17 | 0.07 | 0.03 |
| L. rhamnosus | 27 | MCS837 | 0.43 | 0.11 | 0.13 | 0.58 | 0.39 | 0.70 |
| L. crispatus | 28 | MCS838 | 1.02 | 0.19 | 0.25 | 0.37 | 0.05 | 0.12 |
| L. citreum | 29 | MCS839 | 1.34 | 0.84 | 0.67 | 1.43 | 0.36 | 0.75 |
| Bradyrhizobium sp. | 30 | MCS840 | 0.38 | 0.09 | 0.10 | 0.39 | 0.11 | 0.17 |
| B. microti | 31 | MCS841 | 0.38 | 0.12 | 0.10 | 0.64 | 0.13 | 0.22 |
| L. salivarius | 32 | MCS842 | 0.48 | 1.33 | 2.39 | 1.92 | 2.20 | 0.99 |

TABLE 11-continued

Performance indices (PI) for growth on glucose or xylose

| Source | PKL # | DW-809 strain | PI 0 Glucose | PI 100 Glucose | PI 400 Glucose | PI 0 Xylose | PI 100 Xylose | PI 400 Xylose |
|---|---|---|---|---|---|---|---|---|
| R. imtechensis | 33 | MCS843 | 0.22 | 1.36 | 0.06 | 0.38 | 0.01 | 0.01 |
| B. xenovorans | 34 | MCS844 | 0.72 | 0.25 | 0.25 | 0.37 | 0.07 | 0.15 |
| M. intracellulare | 35 | MCS845 | 0.12 | 0.03 | 0.07 | 0.74 | 0.11 | 0.13 |
| Nitrosomonas sp. | 36 | MCS846 | 0.08 | 0.04 | 0.07 | 0.71 | 0.13 | 0.12 |
| S. pombe | 37 | MCS847 | 0.83 | 0.27 | 0.23 | 0.43 | 0.07 | 0.12 |
| L. buchneri | 38 | MCS848 | 0.75 | 0.23 | 0.26 | 1.63 | 0.07 | 0.15 |
| S. ghanaensis | 39 | MCs849 | 0.70 | 0.28 | 0.00 | 0.33 | 0.10 | 0.12 |
| N. fischeri | 41 | MCS851 | 0.32 | 0.07 | 0.06 | 0.54 | 0.01 | 0.01 |
| L. lactis | 42 | MCS852 | 0.82 | 0.37 | 0.06 | 0.33 | 0.13 | 0.14 |
| E. gallinarum (CON) | | EWL1421 | 1.00 | 1.00 | 1.00 | 1.00 | 1.00 | 1.00 |

Example 17: Small Scale Evaluation of Isoprene Yield and Isoprene Specific Productivity in Strains Expressing Phosphoketolase The isoprene producing strains described in Example 15 were evaluated for isoprene production at small scale.

(i) Materials and Methods

Yeast extract, MgSO$_4$, glucose, IPTG, spectinomycin, and carbenicillin were purchased from Sigma. Aluminum foil seal, 48-well sterile 5 mL block, Breathe Easier sealing membrane, 96-well micro titer plates, and 96-well conical bottom plates were purchased from VWR. 96-well glass blocks were purchased from Zinsser Analytic. Equipment: Agilent 6890 GC equipped with a 5973N mass spectrometer, Eppendorf centrifuge 5417R, Sorvall legend RT.

Growth Rate Measurement:

Shake tubes containing 3 ml LB media, with appropriate antibiotics, were inoculated with glycerol culture stocks. Cultures were incubated for approximately 15 hours at 30° C., 220 rpm.

Supplemented TM3 media was prepared by combining TM3 media (without MgSO$_4$ and yeast extract), 1% Glucose, 8 mM MgSO$_4$, 0.02% yeast extract and appropriate antibiotics. 2 mL of supplemented TM3 were inoculated with overnight cultures in each well of a 48-well sterile block to a final OD$_{600}$ of 0.2. Blocks were sealed with Breathe Easier membranes and incubated for 2 hours at 34° C. at 600 rpm. After 2 hours of growth, the OD$_{600}$ was measured in the microtiter plate and cells were induced with various concentrations of IPTG. OD$_{600}$ readings were taken every hour after the IPTG induction for 4 hrs. OD600 measurements were determined using a SpectraMax Plus190 (Molecular Devices).

Isoprene Yield Assay:

Supplemented TM3 media was prepared by combining TM3 media (without MgSO$_4$ and yeast extract), 1% Glucose, 8 mM MgSO$_4$, 0.02% yeast extract and appropriate antibiotics. 2 mL of supplemented TM3 media were inoculated in each well of a 48-well sterile block to a final OD600 of 0.2. 10 µL of the inoculated cultures were transferred to 90 µL of TM3 media without glucose or yeast extract and sealed with aluminum foil in a 96-well glass block (Zinsser) and incubated at 34° C. and 450 rpm for 24 hours. After 24 hours, the amount of isoprene in the headspace was measured by GC/MS and amount of glucose left in the media in the media to calculate isoprene yield.

Isoprene Specific Productivity Measurement:

100 µl of culture was collected in a 96-well glass block. The glass block was sealed with aluminum foil seal and incubated at 34° C. while shaking at 450 rpm for 30 minutes using a Thermomixer (Eppendorf). After 30 minutes, the block was incubated at 70° C. water bath for 2 minutes. The glass block was allowed to cool to room temperature and then isoprene in the headspace of the wells was measured by GC/MS.

Glucose Measurement:

Glucose samples were collected by centrifuging 300 µl of cell culture in the 96-well conical bottom plate for 10 mM at 4° C., 3000 rpm. The supernatant was diluted 10-fold in DI water and the glucose concentration was measured using the described glucose oxidase assay.

Glucose Oxidase Assay:

ABTS was solubilized in 50 mM sodium acetate pH 5. Glucose oxidase (GOX) and horse radish peroxidase (HRP) were added to the following concentration: 2.74 mg/ml ABTS (powder), 0.1 U/ml HRP, 1 U/ml GOX. The container was wrapped in tin foil to protect from light and stored up to 7 days at 4° C. The glucose standard was prepared by dissolving glucose in MilliQ water across the desired concentration range (i.e serial 2× dilution from 1 mg/ml). 10 µl of test sample was added (dilute reaction supernatant) and/or glucose standard to a well of a microtiter plate. 90 µl of the ABTS reagent was added and quickly mixed on a plate mixer. The assay plate was transferred to the plate reader and absorbance was monitored at 420 nm for 3-5 minutes. The data file was exported to Excel. The glucose calibration curve was used to calculate the amount of glucose in each well.

TABLE 12

Parameters for isoprene detection by GC/MS
GCMS Paramaters:

| Column: ZB-5 ms | 15 m × 0.25 mm × 0.25 µm | |
|---|---|---|
| Oven: | | |
| Ramp (° C./min) | Temperature (° C.) | Hold Time (min) |
| 0 | 37 | 0.6 |

| Total Run Time: | 0.6 minutes |
|---|---|
| Front Inlet Temperature: | 110° C. |
| Split Ratio: | 50:1 |
| Flow Rate: | 2 mL/min |
| Injection Volume: | 100 µL |

TABLE 12-continued

Parameters for isoprene detection by GC/MS
GCMS Paramaters:

| | |
|---|---|
| MS Mode: | EI |
| MS Source: | 230° C. |
| MS Quadrupole: | 150° C. |
| MSD Transfer Line Heater (Aux2): | 280° C. |
| SIM Mode: | 67 amu |

(ii) Results

To calculate performance index (PI) for each of: (i) Isoprene Specific Productivity at 2 hours; (ii) Isoprene Specific Productivity at 4 hours; (iii) Growth rate; and (iv) Isoprene yield, each experimental strain was normalized to the specific parameter of the control at a specific time point in the growth curve (typically between 15-24 hours). The experimental strains that displayed PI values greater than 1.0 for these evaluated parameters indicated better performance of the evaluated PKL in this isoprene production assay.

TABLE 13

PI for each of: (i) Isoprene Specific Productivity at 2 hours; (ii) Isoprene Specific Productivity at 4 hours; (iii) Growth rate; and (iv) Isoprene yield

| Source | PKL # | MD891 strain | PI S. Prod. 2 h(mg/L/h/OD)-MTP | PI S. Prod. 4 h (mg/L/h/OD)-MTP | PI Growth rate (OD at 5 h)-MTP | PI Yield (24 h)-MTP |
|---|---|---|---|---|---|---|
| E. faecium | 1 | MCS865 | 1.29 | 1.02 | 1.01 | 1.07 |
| L. grayi | 2 | MCS866 | 1.24 | 0.75 | 0.99 | 0.73 |
| E. casseliflavus | 3 | MCS867 | 0.84 | 0.62 | 0.88 | 0.87 |
| M. alligatoris | 4 | MCS868 | 1.21 | 0.99 | 0.90 | 1.09 |
| Carnobacterium | 5 | MCS869 | 0.82 | 0.68 | 1.14 | 0.50 |
| T. halophilus | 7 | MCS871 | 1.21 | 1.17 | 1.10 | 0.99 |
| M. plutonius DAT | 8 | MCS872 | 0.00 | 0.00 | 0.00 | 0.00 |
| M. arthritidis | 9 | MCS873 | 0.61 | 0.34 | 0.72 | 0.64 |
| S. agalactiae | 10 | MCS874 | 1.06 | 0.93 | 0.95 | 1.13 |
| K. oralis | 13 | MCS877 | 0.92 | 0.71 | 0.86 | 0.99 |
| M. fermentans | 14 | MCS878 | 0.25 | 0.17 | 0.48 | 0.03 |
| G. adiacens | 15 | MCS879 | 1.02 | 0.85 | 0.86 | 0.96 |
| M. crocodyli | 17 | MCS881 | 0.67 | 0.42 | 0.68 | 1.03 |
| E. coleocola | 19 | MCS883 | 0.60 | 0.51 | 0.61 | 0.90 |
| A. urinae | 20 | MCS884 | 1.07 | 1.02 | 0.89 | 1.05 |
| S. criceti #1 | 22 | MCS886 | 1.06 | 0.83 | 0.85 | 0.85 |
| M. columbinum | 24 | MCS888 | 0.66 | 0.31 | 0.63 | 0.08 |
| M. gilvum | 25 | MCS889 | 1.00 | 1.02 | 1.00 | 0.95 |
| L. rhamnosus | 27 | MCS891 | 0.66 | 0.64 | 1.00 | 0.70 |
| L. citreum | 29 | MCS893 | 1.17 | 0.84 | 1.02 | 0.86 |
| Bradyrhizobium sp. | 30 | MCS894 | 1.10 | 1.15 | 1.06 | 0.98 |
| B. microti | 31 | MCS895 | 0.94 | 0.83 | 1.04 | 0.89 |
| R. imtechensis | 33 | MCS897 | 0.98 | 0.90 | 1.05 | 0.99 |
| B. xenovorans | 34 | MCS898 | 1.09 | 0.92 | 1.15 | 0.87 |
| M. intracellulare | 35 | MCS899 | 1.12 | 0.77 | 1.05 | 0.82 |
| Nitrosomonas sp. | 36 | MCS900 | 0.64 | 0.55 | 1.22 | 0.63 |
| S. pombe | 37 | MCS901 | 0.64 | 0.63 | 0.78 | 0.78 |
| L. buchneri | 38 | MCS902 | 0.92 | 0.74 | 1.17 | 0.65 |
| S. ghanaensis | 39 | MCS903 | 0.92 | 0.86 | 1.05 | 0.90 |
| Cyanothece sp. | 40 | MCS904 | 0.79 | 0.55 | 1.06 | 0.69 |
| N. fischeri | 41 | MCS905 | 0.79 | 0.58 | 1.19 | 0.58 |
| L. lactis | 42 | MCS906 | 1.02 | 0.85 | 1.17 | 0.72 |
| E. gallinarum (CON) | | MCS908 | 1.00 | 1.00 | 1.00 | 1.00 |

Example 18: Measurement of Intracellular Metabolites in Strains Expressing PKLs (i) Materials and Methods Metabolite Extraction:

The strains used for metabolite analysis were the same strains described in Example 17. Thus, these strains were grown under the growth conditions set forth in Example 17 and samples were taken after 4 hour of growth to determine relative concentrations of selected cellular metabolites 500 uL of cell cultures were collected by centrifugation, the supernatant was discarded, 100 uL of dry-ice-cold methanol was added to the pellets, and the tubes with the pellets were immediately frozen in dry ice and placed into a −80° C. refrigerator for storage. To extract metabolites, cell pellets covered with methanol were resuspended using glass rods, the tubes were centrifuged in microcentrifuge for 5 min and the resulting supernatants were removed and placed into clean tubes. Cell pellets obtained after the first extraction step were resuspended in 40 uL of 50% methanol/10 mM ammonium acetate mix, cell debris were centrifuged and the supernatants were collected and pooled together with the supernatants obtained after the first extraction. This extraction procedure was repeated one more time to ensure more complete removal of metabolites from cell debris.

During the extraction-centrifugation samples with cells were kept below 4° C. to minimize metabolites degradation. Final pooled extracts was mixed and then cleared by centrifugation.

Metabolite Measurements:

Analysis of metabolites was performed by LCMS on a TSQ Quantim triple quadrupole instrument (Thermo Scientific). System control, data acquisition, and data analysis were done with XCalibur and LCQuan software (Thermo Scientific). 10 uL samples were applied to a C18 Synergi MAX-RP HPLC column (150×2 mm, 4 uM, 80 A, Phenomenex) equipped with the manufacturer-recommended guard cartridge. The column was eluted with a gradient of 15 mM acetic acid+10 mM tributylamine in MilliQ-grade water (solvent A) and LCMS-grade methanol from Honeywell, Burdick & Jackson (solvent B). The 22.5 mM gradient was as follows: t=0 min, 5% B; t=2 min, 5% B; t=6 min, 10% B; t=12 min, 20% B; t=18 min, 67% B; t=19 min, 99% B; t=21 mM, 99% B; t=21.5 mM, 5% B; t=22.5 mM, 5% B flow rate 0.4 mL/min, column temperature 35° C. Mass detection was carried out using electrospray ionization in the negative mode at ESI spray voltage of 3.0-3.5 kV and ion transfer tube temperature of 350° C. The following SRM transitions were selected for metabolites of interest: 259→79 glucose-6-phosphate (G6P), 339→79 for fructose 1,6-bisphosphate, 167→479 for phosphoenolpyruvate, 275→79 for 6-phosphoglycerate, 259→79 eV for ribose-5-phosphate, 139→79 for acetyl-phosphate, and 199→79 for erythrose 4-phosphate. Scan time for each SRM transition was 0.1 s with a scan width set at 0.7 m/z. Argon was used as the collision gas at 1.7 mTorr, and the collision energies were optimized to get maximum signal intensities using corresponding standards purchased from Sigma-Aldrich. The same standards were used to verify the retention times of measured metabolites. Peaks with SRM transitions 369479 were attributed to heptose-bisphosphates. Concentrations of measured metabolites were expressed as signal intensities normalized to optical densities of the cultures during sampling.

(ii) Results

To calculate performance index (PI) for the production of Acetyl-phosphate (AcP), the amount of each metabolite from the respective experimental strain was normalized to the specific parameter of the control at a specific time point in the growth curve (typically between 30 and 40 hours). The experimental strains that displayed PI values greater than 1.0 for these evaluated parameters indicated better performance of the evaluated PKL in this assay.

TABLE 14

PI for the production of: (i) acetyl-phosphate (AcP)

| Source | PKL # | MD891 strain | PI AcP (AU/OD) - MTP |
|---|---|---|---|
| E. faecium | 1 | MCS865 | 2.49 |
| L. grayi | 2 | MCS866 | 0.94 |
| E. casseliflavus | 3 | MCS867 | 2.12 |
| M. alligatoris | 4 | MCS868 | 1.75 |
| Carnobacterium | 5 | MCS869 | 0.35 |
| M. plutonius ATCC | 6 | MCS870 | 0.00 |
| T. halophilus | 7 | MCS871 | 0.48 |
| M. plutonius DAT | 8 | MCS872 | 0.00 |
| M. arthritidis | 9 | MCS873 | 1.51 |
| S. agalactiae | 10 | MCS874 | 1.06 |
| M. agalacticae | 11 | MCS875 | 0.00 |
| S. gordonii | 12 | MCS876 | 0.00 |
| K. oralis | 13 | MCS877 | 2.26 |
| M. fermentans | 14 | MCS878 | 0.54 |
| G. adiacens | 15 | MCS879 | 1.47 |
| M. hominis | 16 | MCS880 | 0.00 |
| M. crocodyli | 17 | MCS881 | 1.71 |
| Neisseria | 18 | MCS882 | 0.00 |
| E. coleocola | 19 | MCS883 | 2.93 |
| A. urinae | 20 | MCS884 | 0.98 |
| K. kingae | 21 | MCS885 | 0.00 |
| S. criceti #1 | 22 | MCS886 | 1.31 |
| S. criceti #2 | 23 | MCS887 | 0.00 |

TABLE 14-continued

PI for the production of: (i) acetyl-phosphate (AcP)

| Source | PKL # | MD891 strain | PI AcP (AU/OD) - MTP |
|---|---|---|---|
| M. columbinum | 24 | MCS888 | 0.73 |
| M. gilvum | 25 | MCS889 | 0.52 |
| S. baltica | 26 | MCS890 | 0.00 |
| L. rhamnosus | 27 | MCS891 | 2.35 |
| L. crispatus | 28 | MCS892 | 0.00 |
| L. citreum | 29 | MCS893 | 0.76 |
| Bradyrhizobium sp. | 30 | MCS894 | 0.19 |
| B. microti | 31 | MCS895 | 0.31 |
| L. salivarius | 32 | MCS896 | 0.00 |
| R. imtechensis | 33 | MCS897 | 0.19 |
| B. xenovorans | 34 | MCS898 | 0.16 |
| M. intracellulare | 35 | MCS899 | 0.40 |
| Nitrosomonas sp. | 36 | MCS900 | 0.33 |
| S. pombe | 37 | MCS901 | 0.19 |
| L. buchneri | 38 | MCS902 | 0.19 |
| S. ghanaensis | 39 | MCS903 | 0.76 |
| Cyanothece sp. | 40 | MCS904 | 0.15 |
| N. fischeri | 41 | MCS905 | 0.15 |
| L. lactis | 42 | MCS906 | 0.19 |
| E. gallinarum (CON) | | MCS908 | 1.00 |

Example 19: Determination of Protein Expression and Solubility of Phosphoketolases (i) Materials and Methods The strains used to determine protein expression and solubility of the evaluated phosphoketolases were the same strains described in Example 17. The strains were grown in LB broth overnight at 34 C with appropriate antibiotics. The next day, 100 uL of the overnight culture was added to 5 mL of LB with appropriate antibiotics and grown at 34 C to an OD(600) of ~0.5. The cultures were then induced with 200 uM IPTG and incubated for an additional 6 hours at 34 C. The cells were then harvested by centrifugation, and the pellets were stored at −80 C.

The next day the pellets were allowed to thaw, and they were resuspended to an OD(600) of 4 in 100 mM Tris 100 mM NaCl pH 7.6 with 0.2 mg/ml DNaseI and 0.5 mM AEBSF. The cells were then individually lysed via Frenchpress, and the cell debris was removed by centrifugation. The average total protein concentration of the soluble fraction was 0.56±0.22 mg/ml as determined by the standard Bradford assay. The pellet from centrifugation was resuspended in 100 mM Tris 100 mM NaCl pH 7.6 buffer and saved to determine the percent solubility of each phosphoketolase.

The lysate was then used to determine the amount phosphoketolase (PKL) activity on fructose 6-phosphate (F6P) per unit total protein (μmol/min/mg). The PKL activity on F6P was determined by following the amount of acetyl-phosphate (AcP) generated. The reaction mixture (200 uL) contained 10 mM MgCl2, 10 mM potassium phosphate (pH 7.6), 1 mM thiamine diphosphate, 10 mM F6P, 20 mM NaF, 8 mM iodoacetomide, 1 mM dithiothreitol in 100 mM Tris 100 mM NaCl pH 7.6 with 100 uL of lysate. These incubated for 30 minutes at 34 C and were quenched by adding 60 uL of the reaction mixture to 60 uL of 2 M hydroxylamine pH 6.5. This quenched mixture incubated at room temperature for 10 minutes, and then 40 uL of 15% TCA, 40 uL of 4 M HCl and 40 uL of 5% FeCl3 in 0.1 M HCl was added. This final mixture was then centrifuged at 3000 rpm for 5 min. The supernatant (200 uL) was removed, and the absorbance was measured at 505 nm. A calibration curve of AcP was used to calculate how much AcP was produced.

Relative expression and solubility of each PKL variant, relative to the *E. gallinarum* MCS908 control, was determined by densitometry. The soluble lysates of each sample were mixed 1:1 with gel loading dye and ran on SDS-PAGE gels. Each pellet, obtained from sample centrifugation post lysis via the French press (see above), was diluted 1:1 with gel loading dye and loaded on SDS-PAGE gels. A sample of *E. gallinarum* MCS908 soluble lysate was included on each gel as a control. Gels were developed using Coomassie Brilliant Blue stain, and analyzed using ImageQuantTL v2005 (GE Health Sciences) densitometry software. The percent of soluble protein expressed and the percent soluble to insoluble were determined relative to the control strain (*E. gallinarum* MCS908).

(ii) Results

To calculate performance index (PI) for each of: (i) (F6P) Specific Activity per unit total protein (μmol/min/mg); (ii) Expression level; and (iii) Solubility each experimental strain was normalized to the specific parameter of the control. The PI for F6P Specific Activity (Activity/Expression level) was determined by dividing the PI values for (i) by the PI value to (ii). The experimental strains that displayed a PI greater than 1.0 for these evaluated parameters indicated better performance of the evaluated PKL in this assay.

Example 20: Phosphoketolase Activity on Fructose 6-Phosphate and Xylulose 5-Phosphate This example determined PKL activity when strains are grown on fructose 6-phosphate (F6P) or xylulose 5-phosphate (X5P).

(i) Materials and Methods

The strains were grown in LB broth overnight at 34 C with appropriate antibiotics. The next day, 200 uL of the overnight culture was added to 5 mL of TM3 with appropriate antibiotics and grown at 34 C for 2.5 hours. The cultures were then induced with 200 uM IPTG and incubated for an additional 4 hours at 34 C. The cells were then harvested by centrifugation, and the pellets were stored at −80 C.

The next day the pellets were allowed to thaw, and they were resuspended in 2 mL of 100 mM HEPES pH 7.8 with 0.2 mg/ml DNaseI and 0.5 mM AEBSF. The cells were then individually lysed via French-press, and the cell debris was removed by centrifugation.

Lysate Preparation and Enzyme Activity Determination:

The lysate was then used to determine the amount phosphoketolase (PKL) activity on fructose 6-phosphate (F6P) and xylulose 5-phosphate (X5P). The PKL activity on F6P and X5P was determined by following the amount of acetyl-phosphate (AcP) generated. The F6P reaction mixture (200 uL) contained 10 mM MgCl2, 10 mM potassium phosphate (pH 7.6), 1 mM thiamine diphosphate, 10 mM F6P, 20 mM NaF, 8 mM iodoacetomide, 1 mM dithiothreitol in 100 mM HEPES pH 7.8 with and 100 uL of lysate. These incubated for 30 minutes at 34 C and were quenched by adding 60 uL of the reaction mixture to 60 uL of 2 M hydroxylamine pH 6.5. This quenched mixture incubated at room temperature

TABLE 15

Solubility and expression of each PKL

| Source | MD891 strain | PI F6P S.A. (μmol/min/ mg total protein) | PI Expression level (% relative to control) | PI Solubility (% Soluble) | PI F6P Specific Activity (Activity/Expression level) |
|---|---|---|---|---|---|
| L. grayi | MCS866 | 1.22 | 0.33 | 0.30 | 3.69 |
| E. casseliflavus | MCS867 | 2.41 | 2.35 | 0.97 | 1.02 |
| M. alligatoris | MCS868 | 0.79 | 0.26 | 0.77 | 3.05 |
| Carnobacterium | MCS869 | 0.10 | 0.09 | 0.07 | 1.14 |
| T. halophilus | MCS871 | 0.15 | 0.05 | 0.16 | 3.06 |
| M. arthritidis | MCS873 | 2.52 | 1.78 | 0.87 | 1.41 |
| S. agalactiae | MCS874 | 1.25 | 0.49 | 0.82 | 2.56 |
| K. oralis | MCS877 | 2.29 | 1.81 | 0.96 | 1.26 |
| M. fermentans | MCS878 | 0.29 | 0.21 | 0.79 | 1.38 |
| G. adiacens | MCS879 | 1.87 | 1.04 | 0.99 | 1.79 |
| M. crocodyli | MCS881 | 2.21 | 1.16 | 0.61 | 1.90 |
| E. coleocola | MCS883 | 3.18 | 1.67 | 0.95 | 1.90 |
| A. urinae | MCS884 | 1.96 | 1.40 | 0.98 | 1.40 |
| M. columbinum | MCS888 | 1.77 | 1.75 | 1.06 | 1.01 |
| M. gilvum | MCS889 | 0.65 | 0.33 | 0.40 | 1.96 |
| L. citreum | MCS893 | 0.90 | 1.13 | 1.03 | 0.80 |
| Bradyrhizobium sp. | MCS894 | 0.11 | 0.10 | 0.29 | 1.10 |
| B. microti | MCS895 | 0.42 | 0.25 | 0.90 | 1.69 |
| R. imtechensis | MCS897 | 0.14 | 0.06 | 0.29 | 2.28 |
| B. xenovorans | MCS898 | 0.23 | 0.33 | 0.22 | 0.69 |
| M. intracellulare | MCS899 | 0.14 | 0.32 | 0.45 | 0.43 |
| Nitrosomonas sp. | MCS900 | 0.22 | 0.10 | 0.13 | 2.23 |
| S. pombe | MCS901 | 0.16 | 0.49 | 0.18 | 0.32 |
| L. buchneri | MCS902 | 0.06 | 0.06 | 0.08 | 0.97 |
| S. ghanaensis | MCS903 | 0.67 | 0.46 | 0.23 | 1.45 |
| Cyanothece sp. | MCS904 | 1.23 | 0.48 | 0.77 | 2.56 |
| N. fischeri | MCS905 | 0.07 | 0.44 | 0.27 | 0.15 |
| L. lactis | MCS906 | 0.23 | 0.07 | 0.07 | 3.24 |
| E. gallinarum (CON) | MCS908 | 1.00 | 1.00 | 1.00 | 1.00 | for 10 minutes, and then 40 uL of 15% TCA, 40 uL of 4 M HCl and 40 uL of 5% FeCl3 in 0.1 M HCl was added. This final mixture was then centrifuged at 3000 rpm for 5 min. The supernatant (200 uL) was removed, and the absorbance was measured at 505 nm. A calibration curve of AcP was used to calculate how much AcP was produced. The X5P activity was measured with a similar method. The X5P reaction mixture (200 uL) contained 10 mM MgCl2, 10 mM potassium phosphate (pH 7.6), 1 mM thiamine diphosphate, 10 mM ribose 5-phosphate, 60 ug/mL of ribulose-5-phosphate 3-epimerase, 200 ug/mL of ribose-5-phosphate isomerase A, 20 mM NaF, 8 mM iodoacetomide, 1 mM dithiothreitol in 100 mM HEPES pH 7.8 with and 20 uL of lysate. Due to the wide range of activities on X5P, the activities were measured at two concentrations of lysate: undiluted and five-fold diluted into 100 mM HEPES pH 7.8.

TABLE 16

PKL activity on F6P or X5P

| Strain Description (MD-891 Strain) | F6P AcP (mM) | F6P Spec Act | X5P (Undiluted) AcP (mM) | X5P (Undiluted) Spec Act | X5P (Diluted 5X) AcP (mM) | X5P (Diluted 5X) Spec Act | Ratio Undiluted (X/F) | Ratio Diluted (X/F) |
|---|---|---|---|---|---|---|---|---|
| pMCS842, pMCM1225 | 0.51 | 0.19 | 1.75 | 3.21 | 0.41 | 3.79 | 17.03 | 20.16 |
| pMC5836, pMCM1225 | 0.04 | 0.04 | 0.11 | 0.54 | 0.085 | 2.10 | 15.19 | 59.62 |
| pEWL1421, pMCM1225 | 1.19 | 0.65 | 3.59 | 9.74 | 0.76 | 10.37 | 15.06 | 16.04 |
| pMCS813, pMCM1225 | 1.99 | 1.06 | 4.97 | 13.19 | 1.26 | 16.76 | 12.49 | 15.88 |
| pMCS821, pMCM1225 | 1.98 | 1.20 | 4.82 | 14.59 | 1.27 | 19.16 | 12.20 | 16.022 |
| pMCS833, pMCM1225 | 2.02 | 1.14 | 4.70 | 13.28 | 1.12 | 15.83 | 11.68 | 13.91 |
| pMCS830, pMCM1225 | 1.45 | 0.63 | 3.10 | 6.73 | 0.81 | 8.77 | 10.67 | 13.90 |
| pMCS822, pMCM1225 | 1.52 | 1.27 | 3.23 | 13.48 | 0.67 | 13.86 | 10.61 | 10.91 |
| pMCS839, pMCM1225 | 0.37 | 0.37 | 0.77 | 3.85 | 0.19 | 4.88 | 10.45 | 13.25 |
| pMCS825, pMCM1225 | 2.02 | 1.26 | 4.14 | 12.92 | 1.16 | 18.08 | 10.22 | 14.30 |
| pMCS823, pMCM1225 | 2.51 | 1.02 | 4.65 | 9.48 | 1.25 | 12.70 | 9.28 | 12.43 |
| pMCS826, pMCM1225 | 2.43 | 1.81 | 4.36 | 16.19 | 0.94 | 17.50 | 8.95 | 9.68 |
| pMCS824, pMCM1225 | 0.37 | 6.81 | 0.64 | 59.24 | 0.19 | 89.62 | 8.69 | 13.15 |
| pMCS834, pMCM1225 | 2.04 | 1.16 | 3.39 | 9.61 | 0.87 | 12.30 | 8.32 | 10.64 |
| pMCS811, pMCM1225 | 0.87 | 0.33 | 1.45 | 2.80 | 0.39 | 3.79 | 8.31 | 11.24 |
| pMCS819, pMCM1225 | 3.53 | 1.85 | 5.13 | 13.45 | 1.34 | 17.65 | 7.26 | 9.52 |
| pMCS820, pMCM1225 | 0.81 | 0.32 | 1.16 | 2.26 | 0.32 | 3.12 | 7.18 | 9.91 |
| pMCS838, pMCM1225 | 0.24 | 0.15 | 0.34 | 1.06 | 0.16 | 2.49 | 7.05 | 16.62 |
| pMCS829, pMCM1225 | 3.30 | 2.15 | 4.45 | 14.46 | 1.16 | 18.93 | 6.73 | 8.81 |
| pMCS832, pMCM1225 | 2.10 | 1.78 | 2.76 | 11.73 | 0.69 | 14.62 | 6.59 | 8.21 |
| pMCS827, pMCM1225 | 1.33 | 2.28 | 1.73 | 14.84 | 0.36 | 15.45 | 6.51 | 6.78 |
| pMCS831, pMCM1225 | 0.78 | 0.64 | 0.99 | 4.08 | 0.23 | 4.63 | 6.41 | 7.282 |
| pMCS828, pMCM1225 | 2.62 | 2.32 | 3.30 | 14.62 | 0.87 | 19.25 | 6.31 | 8.31 |
| pMCS845, pMCM1225 | 0.19 | 0.12 | 0.17 | 0.53 | 0.09 | 1.40 | 4.36 | 11.52 |
| pMCS814, pMCM1225 | 0.54 | 0.30 | 0.37 | 1.01 | 0.17 | 2.37 | 3.36 | 7.87 |
| pMCS844, pMCM1225 | 0.21 | 0.16 | 0.12 | 0.47 | 0.09 | 1.79 | 2.89 | 11.07 |
| pMCS816, pMCM1225 | 0.19 | 0.11 | 0.11 | 0.33 | 0.12 | 1.74 | 2.87 | 15.25 |
| pMCS849, pMCM1225 | 0.82 | 0.38 | 0.47 | 1.08 | 0.14 | 1.62 | 2.83 | 4.23 |
| pMCS645, pMCM1225 | 0.22 | 0.20 | 0.13 | 0.56 | 0.10 | 2.31 | 2.81 | 11.57 |
| pMCS818, pMCM1225 | 0.18 | 0.19 | 0.09 | 0.48 | 0.10 | 2.67 | 2.54 | 13.99 |
| pMCS841, pMCM1225 | 0.78 | 0.45 | 0.37 | 1.09 | 0.11 | 1.66 | 2.42 | 3.69 |
| pMCS837, pMCM1225 | −0.07 | −0.03 | 0.61 | 1.17 | 0.10 | 1.01 | −43.14 | −37.25 |

Example 21: 14 L Evaluation of Isoprene Production in Strains Expressing Phosphoketolase This experiment was performed to evaluate the effect of expressing various phosphoketolase enzymes on isoprene production. All the strains in this experiment used a modified E. coli host (BL21 derived production host MD891) which expresses introduced genes from the mevalonate pathway, isoprene synthase and phosphoketolase (PKL), for strain details see Table 17. All of these isoprene producing strains were grown in fed-batch culture at the 15-L scale.

The relevant performance metrics are cumulative isoprene yield on glucose, and isoprene titer. The productivity metrics are found summarized in Table 18.

TABLE 17

List of strains

| Strain Name | Host | IPTG inducible Upper pathway plasmid | IPTG inducible Isoprene synthase/Phosphoketolase plasmid. |
|---|---|---|---|
| MD13-896 | MD-891 | pMCM1225 | pEWL1418 (PTrc IspS-PKL_B. longum) |

TABLE 17-continued

List of strains

| Strain Name | Host | IPTG inducible Upper pathway plasmid | IPTG inducible Isoprene synthase/Phosphoketolase plasmid. |
|---|---|---|---|
| MD13-898 | MD-891 | pMCM1225 | pEWL1436 (PTrc IspS-PKL__C. Acetobutylicum) |
| MCS674 | MD-891 | pMCM1225 | (PTrc IspS-PKL__Bifidobacterium bifidum) |
| MCS675 | MD-891 | pMCM1225 | (PTrc IspS-PKL__Bifidobacterium dentium) |
| MCS676 | MD-891 | pMCM1225 | (PTrc IspS-PKL__Bifidobacterium gallicum) |
| MCS703 | MD-891 | pMCM1225 | pMCS668 (PTrc IspS-PKL__E. gallinarum-RBS 2300) |
| MCS704 | MD-891 | pMCM1225 | pMCS669 (PTrc IspS-PKL__E. gallinarum-RBS 7700) |
| MCS706 | MD-891 | pMCM1225 | pMCS671 (PTrc IspS-PKL__E. gallinarum-RBS 73300) |
| DW891-2 | MD-891 | pMCM1225 | pMCS822 (PTrc IspS-PKL__S. gordonii) |
| DW892-1 | MD-891 | pMCM1225 | pMCS831 (PTrc IspS-PKL__K. kingae) |
| MCS935 | MD-891 | pMCM1225 | pMCS814 (PTrc IspS-PKL4[*M. alligatoris*]) |
| MCS941 | MD-891 | pMCM1225 | pMCS820 (PTrc IspS-PKL10[*S. agalacticae*]) |
| MCS946 | MD-891 | pMCM1225 | pMCS825 (PTrc IspS-PKL15 [*G. adiacens*]) |
| MCS699 | MD-891 | pMCM1225 | pMCS666 (PTrc IspS-PKL__E. gallinarum__RBS2600) |
| MCS951 | MD-891 | pMCM1225 | pMCS830 (PTrc IspS-PKL__A. urinae) |
| MCS944 | MD-891 | pMCM1225 | pMCS823 (PTrc IspS-PKL__K. oralis) |
| MCS932 | MD-891 | pMCM1225 | pMCS811 (PTrc IspS-PKL__E. faecium) |
| MCS934 | MD-891 | pMCM1225 | pMCS813 (PTrc IspS-PKL3[*E. casseliflavus*]) |
| MCS963 | MD-891 | pMCM1225 | pMCS842 (PTrc IspS-PKL__L. salivarus) |
| MCS947 | MD-891 | pMCM1225 | pMCS826 (PTrc IspS-PKL__M. hominis) |

(i) Materials and Methods

Medium Recipe (Per Liter Fermentation Medium):

$K_2HPO_4$ 7.5 g, $MgSO_4*7H_2O$ 2 g, citric acid monohydrate 2 g, ferric ammonium citrate 0.3 g, yeast extract 0.5 g, 50% sulphuric acid 1.6 mL, 1000× Modified Trace Metal Solution 1 ml. All of the components were added together and dissolved in Di H2O. This solution was heat sterilized (123° C. for 20 minutes). The pH was adjusted to 7.0 with ammonium hydroxide (28%) and q.s. to volume. Glucose 10 g, Vitamin Solution 8 mL, and antibiotics (spectinomycin and carbenicillin) were added after sterilization and pH adjustment to a target concentration of 50 mg/L.

1000× Modified Trace Metal Solution (Per Liter):

Citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO*7H_2O$ 1 g, $CuSO_4*5H_2O$ 100 mg, $H_3BO_3$ 100 mg, $NaMoO_4*2H_2O$ 100 mg. Each component was dissolved one at a time in Di H2O, pH was adjusted to 3.0 with HCl/NaOH, and then the solution was q.s. to volume and filter sterilized with a 0.22 micron filter.

Vitamin Solution (Per Liter):

Thiamine hydrochloride 1.0 g, D-(+)-biotin 1.0 g, nicotinic acid 1.0 g, pyridoxine hydrochloride 4.0 g. Each component was dissolved one at a time in Di H2O, pH was adjusted to 3.0 with HCl/NaOH, and then the solution was q.s. to volume and filter sterilized with 0.22 micron filter.

Macro Salt Solution (Per Liter):

$MgSO_4*7H_2O$ 296 g, citric acid monohydrate 296 g, ferric ammonium citrate 49.6 g. All components were dissolved in water, q.s. to volume and filter sterilized with 0.22 micron filter.

Feed Solution (Per Kilogram):

Glucose 0.590 kg, Di H2O 0.393 kg, $K_2HPO_4$ 7.4 g, and 100% Foamblast882 8.9 g. All components were mixed together and autoclaved. After autoclaving the feed solution, nutrient supplements are added to the feed bottle in a sterile hood. Post sterilization additions to the feed are (per kilogram of feed solution), Macro Salt Solution 5.54 ml, Vitamin Solution 6.55 ml, 1000× Modified Trace Metal Solution 0.82 ml. For a target of 100 µM IPTG: 1.87 ml of a sterile 10 mg/ml solution is added per kilogram of feed.

This experiment was carried out to monitor isoprene production from glucose at the desired fermentation pH (7.0) and temperature (34° C.). To start each experiment, the appropriate frozen vial of the *E. coli* production strain was thawed and inoculated into a flask with tryptone-yeast extract (LB) medium and the appropriate antibiotics. After the inoculum grew to an optical density of approximately 1.0, measured at 550 nm ($OD_{550}$), 500 mL was used to inoculate a 15-L bioreactor and bring the initial tank volume to 5 L.

The inlet gas using to maintain bioreactor backpressure at 0.7 bar gauge and to provide the oxygen to the production organisms was supplied by in house facilities that dilute the inlet gas to a known concentration (7.3 to 8.3 vol % oxygen).

The batched media had glucose batched in at 9.7 g/L. Induction was achieved by adding isopropyl-beta-D-1-thiogalactopyranoside (IPTG). A syringe containing a sterile solution of IPTG was added to bring the IPTG concentration to 100 µM when the cells were at an OD550 of 6. Once the glucose was consumed by the culture, as signaled by a rise in pH, the glucose feed solution was fed to meet metabolic demands at rates less than or equal to 10 g/min. At a fixed time after dissolved oxygen limitation was established, the temperature was raised from 34° C. to 37° C. over the course of one hour. The fermentation was run long enough to determine the maximum cumulative isoprene mass yield on glucose, typically a total of 64 hrs elapsed fermentation time (EFT).

(ii) Results and Analysis

Isoprene, Oxygen, Nitrogen, and Carbon Dioxide levels in the off-gas were determined independently by a Hiden HPR20 (Hiden Analytical) mass spectrometer.

Dissolved Oxygen in the fermentation broth is measured by sanitary, sterilizable probe with an optical sensor provided Hamilton Company.

The citrate, glucose, acetate, and mevalonate concentrations in the fermentor broth was determined in broth samples taken at 4 hour intervals by an HPLC analysis. Concentration in broth samples were determined by comparison of the refractive index response versus a previously generated calibration curve using standard of a known concentration.

HPLC Information
System: Waters Alliance 2695
Column: BioRad—Aminex HPX-87H Ion Exclusion Column 300 mm×7.8 mm Catalog #125-0140
Column Temperature: 50C
Guard column: BioRad—Microguard Cation H refill 30 mm×4.6 mm Catalog #125-0129
Running buffer: 0.01N H2SO4
Running buffer flow rate: 0.6 ml/min
Approximate running pressure: ~1100-1200 psi
Injection volume: 20 microliters
Detector: Refractive Index (Knauer K-2301)
Runtime: 26 minute Cumulative Isoprene yield on glucose is equal to Isoprene total weight (t)/[(Feed Wt(0)-Feed W(t)t+83.5)*0.5826)], where 0.5826 is the wt % of glucose in the glucose feed solution and 83.5 is the grams of this feed batched into the fermentor at t=0. Units are $g_{isoprene}/g_{glucose}*100$, expressed as percentages.

IspER is the Isoprene Evolution Rate in (mmol/L/hr).

Specific productivity (mg/L/hr/OD)=IspER*68.117 g/mol/OD.

OD=optical density=Absorbance at 550 nm*dilution factor in water.

Smoothed Specific productivity (mg/L/hr/OD)=slope of milligrams isoprene produced per hour (averaged over 8 hour interval)/broth volume*OD.

Isoprene titer ($g_{Isoprene}/L_{average\ broth}$) is the total evolved isoprene per average broth volume. It is calculated by integrating the IspER and converting the isoprene unit from mmol to grams.

Figure 40:
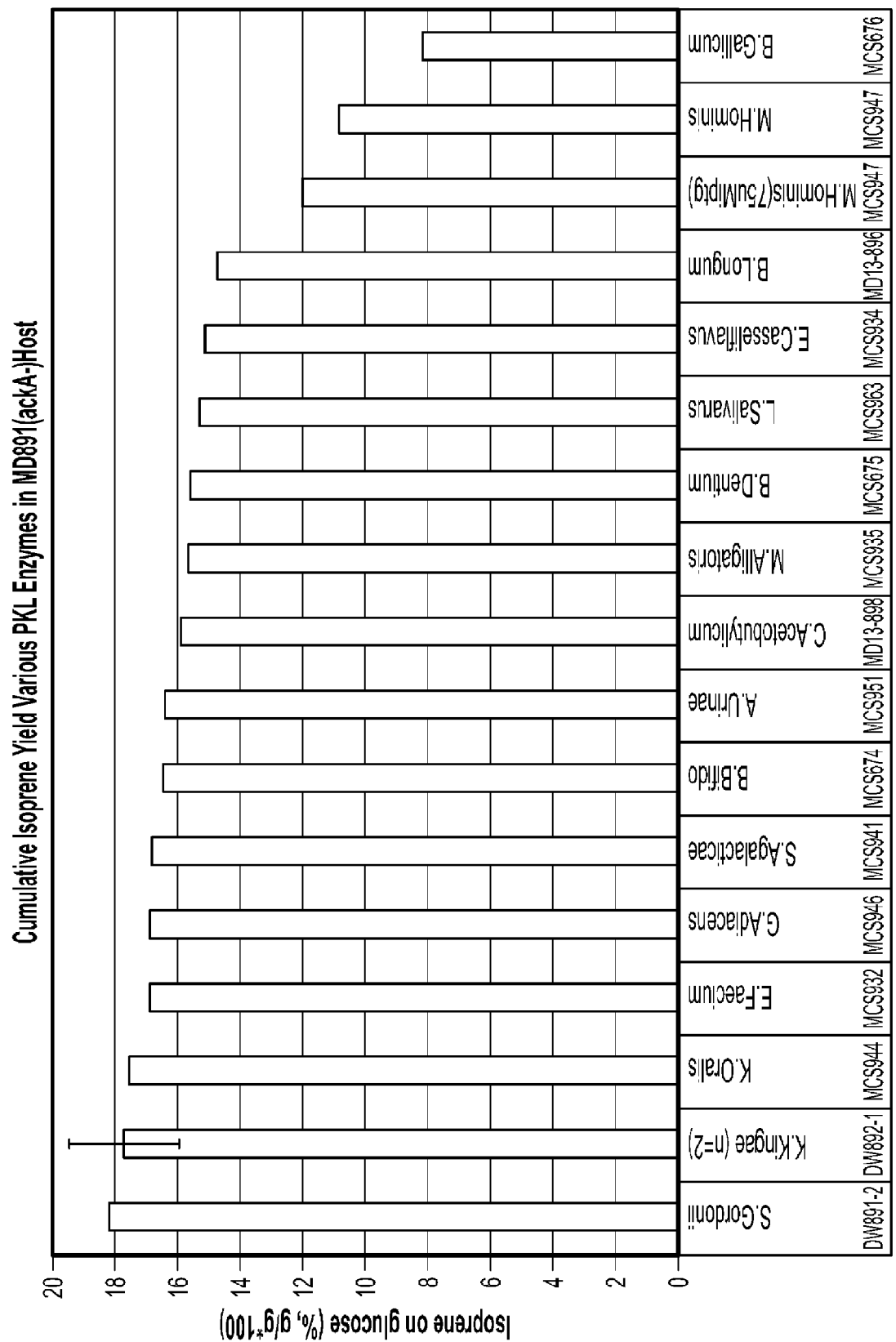
FIG. 40 depicts the cumulative isoprene yield of various PKL enzymes in an MD891 (ackA-)host.
Figure 41:
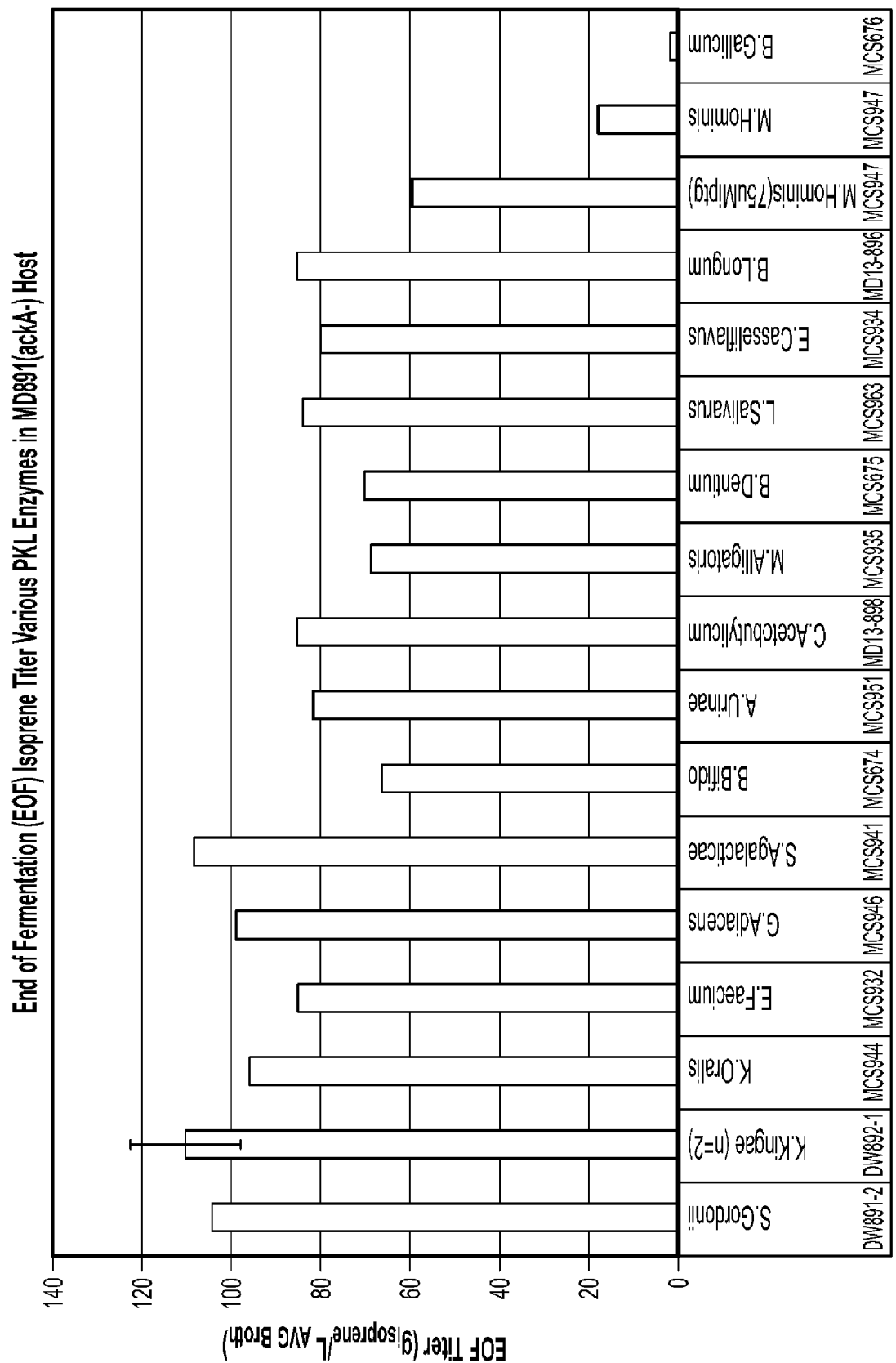
FIG. 41 depicts end of fermentation (EOF) isoprene titer of various PKL enzymes in an MD891 (ackA-)host.
Figure 42:
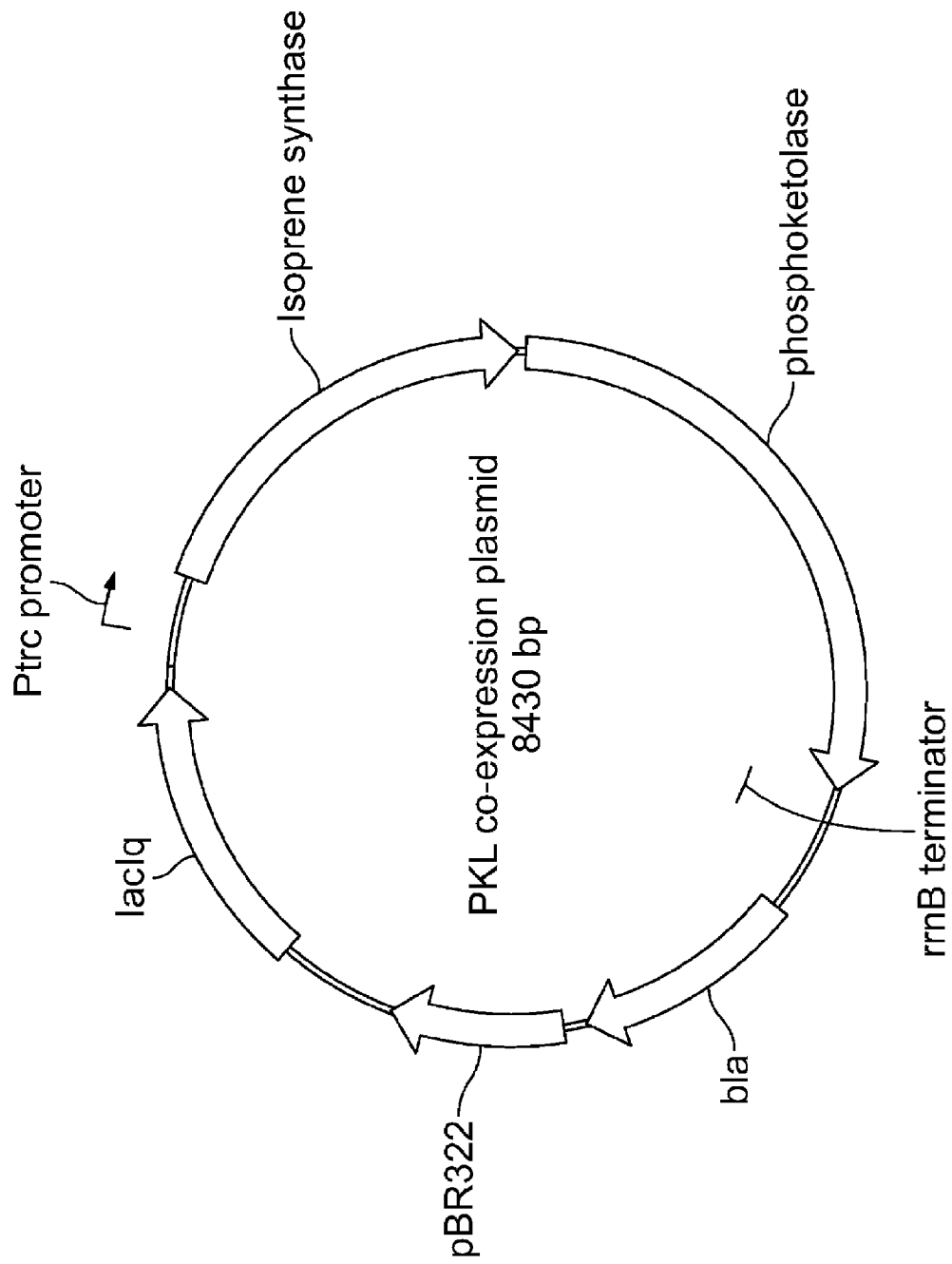
FIG. 42 depicts a generic plasmid map of a plasmid suitable for co-expression of PKL in accordance with any of the compositions, cells, or methods disclosed herein.

The results are depicted graphically in FIGS. 40 and 41 and illustrated in Table 15.

TABLE 18

Isoprene Productivity Metrics

| Strain Name | PKL (in MD891ackA-host) | Avg EOF Isoprene Titer (g/L) | Avg Cumulative Yield (g/g * 100) |
|---|---|---|---|
| DW891-2 | S. gordonii | 104.36 | 18.20 |
| DW892-1 | K. kingae | 110.32 | 17.73 |
| MCS944 | K. oralis | 96.11 | 17.57 |
| MCS932 | E. faecium | 84.76 | 16.92 |
| MCS946 | G. adiacens | 99.20 | 16.86 |
| MCS941 | S. agalactiae | 108.37 | 16.83 |
| MCS674 | B. bifido | 66.12 | 16.46 |
| MCS951 | A. urinae | 81.77 | 16.41 |
| MD13-898 | C. acetobutylicum | 85.13 | 15.90 |
| MCS935 | M. alligatoris | 68.48 | 15.67 |
| MCS675 | B. dentium | 70.15 | 15.66 |
| MCS963 | L. salivarus | 83.91 | 15.32 |
| MCS934 | E. casseliflavus | 80.17 | 15.07 |
| MD13-896 | B. longum | 85.09 | 14.74 |
| MCS947 | M. hominis (decreased IPTG) | 59.42 | 12.04 |
| MCS947 | M. hominis | 17.69 | 10.84 |
| MCS676 | B. gallicum | 2.12 | 8.17 |

Example 22: In Vivo Evaluation of Growth in PKL Expressing Strains Blocked for Glycolysis and Pentose Phosphate Pathways For analysis of PKL enzyme activity in a strain blocked for glycolysis and pentose phosphate pathways, a subset of expression plasmids was transformed into strain MD1041 (HMB GI1.2gltA yhfSFRTPyddVIspAyhfS thiFRTtruncIspA pgl ML, FRT-PL.2-2cis-RBS10000-MVK(burtonii), t zwf::FRT, t pfkA::Frt+t ackA::FRT, t pfkB::Frt) using standard molecular biology techniques. Individual transformants were grown overnight in LB, diluted into TM3 medium with 1% glucose-6-phosphate (Sigma) as the carbon source, and induced with 0, 20, 40, 60, 80, 100, 200, or 400 µM IPTG. Strains were assayed for growth performance on the Enzyscreen Growth Profiler in comparison to MD1041 control strains that did not express any PKL (and therefore did not grow), expressed the PKL enzyme from E. gallinarum (and were representative of baseline performance), or WT strains that had no metabolic block in glycolysis or pentose phosphate pathways (as a control for optimal growth).

To calculate performance index (PI) for growth, MD1041 derivative strains that expressed experimental PKL enzymes were compared to MCS1148, a strain that expressed the PKL from E. gallinarum (see Table 1 for strain list). The 35 hour time point and 100 µM IPTG induction level were chosen as representative of general performance throughout the growth curve. To normalize values between assay plates, a correction factor, based on the difference between max OD values of WT strains, of 1.279 was applied to all values in the plate that did not contain the control strain expressing E. gallinarum PKL. PI was then calculated by dividing the corrected experimental OD value by the OD value of MCS1148 at the 35 hour time point. The PI of MCS1148 was therefore 1.0, and any value higher than this indicated an X-fold improvement to growth in this assay. PI values are shown in Table 19.

TABLE 19

PI values in PKL expressing strains Blocked for Glycolysis and Pentose Phosphate Pathways

| Strain | PKL | PI Growth at 35 hours |
|---|---|---|
| MD1059 | No PKL | 0.167 |
| MCS1106 | pMCS811(pTrc_IspS_PKL1[E. faecium]) | 0.606 |
| MCS1108 | pMCS813(pTrc_IspS_PKL3[E. casseliflavus]) | 0.328 |
| MCS1109 | pMCS814(pTrc_IspS_PKL4[M. alligatoris]) | 0.740 |
| MCS1116 | pMCS821(pTrc_IspS_PKL11[M. agalacticae]) | 0.579 |
| MCS1118 | pMCS823 (pTrc_IspS_PKL13 [K. oralis]) | 1.761 |
| MCS1120 | pMCS825 (pTrc_IspS_PKL15 [G. adiacens]) | 0.560 |
| MCS1121 | pMCS826 (pTrc_IspS_PKL16 [M. hominis]) | 0.824 |
| MCS1123 | pMCS828 (pTrc_IspS_PKL18 [Neissaria]) | 0.262 |
| MCS1124 | pMCS829 (pTrc_IspS_PKL19 [E. coleocola]) | 0.164 |
| MCS1125 | pMCS830 (pTrc_IspS_PKL20 [A. urinae]) | 1.090 |
| MCS1126 | pMCS831(pTrc_IspS_PKL21 [K. kingae]) | 0.607 |
| MCS1127 | pMCS832(pTrc_IspS_PKL22 [S. criceti #1]) | 0.099 |
| MCS1128 | pMCS833(pTrc_IspS_PKL23 [S. criceti #2]) | 0.587 |
| MCS1137 | pMCS842(pTrc_IspS_PKL32 [L. salivarius]) | 0.125 |
| MCS1148 | pMCS625 (pEWL1421 = pTrc_IspS_gallinarumPKL) | 1.000 |
| MCS1150 | pMCS644 (pTrc_IspS_dentiumPKL) | 0.116 |
| MCS1152 | pMCS646 (pTrc_IspS_acetobutylicum optimizedPKL) | 0.163 |
| MCS1153 | pMCS647 (pTrc_IspS_truncatedmMVK; gi1.6_acetobutylicum optimized PKL | 1.727 |
| MCS1162 | pMCS1008 (pTrc_IspS_PKL-ANC110) | 0.239 |
| MCS1168 | pMCS1019 (pTrc_IspS_RBS3_PKL16 [M. hominis]) | 0.120 |

SEQUENCES

Amino acid sequence for a phosphoketolase enzyme from Mycobacterium gilvum Spyr1
MTTATTAERRPLSDQDVDRLDRWWRAANYLSVGQIYLLDNPLLRTPLTREDVKPRLLG
HWGTTPGLNFLYAHLNRAIAQRQQSTIYVTGPGHGGPGLVANAYLDGTYSEIYSDITQD
DEGLRRLFRQFSFPGGIPSHVAPETPGSIHEGGELGYALSHAYGAAFDNPDLLVAAVVG
DGEAETGPLATSWHSNKFVNAAKDGAVLPILHLNGYKIANPTLLARIPTDELRALMVG
YGHHPYFFEVPDDEGGPGVDHADAHRRFARLLDDVLDEIADIKTRAREGDESRPAWPM
IVFRTPKGWTGPDYIDGKKTTGSWRAHQVPLSNARDTKEHLAVLSDWLSSYRPDELFD
ADGRLLPEIAELAPSGQLRMSDNAHANGGLLLKDLRLPDFREYAVDVPAPGATVAEAT
RVLGQWLTEVIRLNPDNFRIFGPDETASNRLQAVYDATDKQWNAEFFGAEVDEHLARA
GRVVEMLSEHQCQGWLEGYLLTGRHGLFNCYEAFIHIVDSMLNQHAKWLKVTNHIPW
RRPIASLNYLLSSHVWRQDHNGFSHQDPGFIDHVVNKSAKVVRVYLPPDANTLLSTYD
HCLRSRQYVNVVVSGKQPSPNFLTMEQAVAHCTRGLGIWEWAGSEELGTDPDVVLAS
AGDIPTLEALAAADILRQHLPDLKVRFVNVVDLMRLQDSTEHPHGLPDRDFDMIFTTDR
PIIFAYHGYPWLIHRLTYRRAGHDNLHVRGYKEEGTTTTPFDMVMLNDLDRYHLVMD
VIDRVPSLGSTCAALRQQMADKRIAAREYTRAHGEDIPEVKDWVWPAARESGFGTAGA
DGASSTGGDNE (SEQ ID NO: 1)

Amino acid sequence for a phosphoketolase enzyme from Shewanella baltica OS185
MTQIHEINALKKYVRATNFLATSQIYLKQNVLHKRPLAHTDIKPRLLGHWGTCPGINFV
YANINRLIVKHNRSFIYLVGPGHGFPAVQANLFMEGSLSHFYPETIPYNETGIEDICKKFS
AAYGYPSHANPEAPGQILEGGELGYSLSVGWGAVLDNPDLIATVLIGDGEAETGPLAAS
WYANRLVSPATSGAVLPIVHINGYKISGPTRMGRMSHEELDLEFRGLGYFPIIVDNELEE
DIYVQMTNAMDTAYAMINDIQRRARSGEDVVKPKWPVILMRTAKGWTGVSEYKGKK
LEGNCESHQVIVNKCATDKGHLDALDNWLASYHFQELYQMNDKGELIFDADICSLIPPK
QLACGRQHLTYGGEVVRALTNPDLEKLSYGPEVPRGHRGYSMLKMGEWMRDAFKLN
RDQRNLRIFSPDETYSNQLQAVFEETDRAWQWPIESWDEDMSREGRVIELLSENLLFGM
LHGYTVTGRHGMFPTYESFSQVISSMADQYCKYVYASQGVHFRKPLPSCNVVLSSLLER
QDHNGYSHQNPSFLGAMLEKHPKIISAYLPADANSTLVYTERAYADRDKLNILVAGKK
ELPQWLSLEEEARKQAKDGVMVWDFASDENPDIVLAGCGDYVTQECMASLVLIRELLPR
VKIRFVSVTELSSDGLGSRKFKEKPWLMDEIFTQDKGVVFNYHGYPNTIKKLIFDYKGS
RRFRIKGYEEEGSTTTPFDMGVRNGTSRYHLVIDMAYKLFQQGVIDETMHVSITTDMLQ
RLVDHRNYIKANGVDPIEIENWIWTR (SEQ ID NO: 2)

Amino acid sequence for a phosphoketolase enzyme from Lactobacillus rhamnosus LMS2-1
MSMDTKVKTVDYSSKEYFDKMTAYWRAANYVSVGQLYLKDNPLLERPLKSEDVKPH
PIGHWGTIAGQNFIYTHLNRVINKYDLNMFYIEGPGHGGQVMVSNSYLDGSYSEIYPRV
SQDKEGMKNLFTQFSWPGGVASHASAQTPGSIHEGGELGYALSHATGAILDNPDVIAA
VVTGDGETETGPLAASWFSNTFINPISDGAILPIVHMNGFKISNPTILSRKSDEDLTKYFE
GMGWKPYFVEGDDPTKLNPEMAKVMDAAIEEIKAIQKHARETGDTTMPHWPVIIFRSP
KGWTGPKSWNGEPIEGSFRAHQIPIPVDAEDMEHADSLAGWLKSYHPEELFDENGKLIP
ELAALPPKGDKRMAANPITNGGLDPKPLVLPDYRKYALDNKEHGKQIKQDMIVWASDY
LRDLIKLNPHNFRIFGPDETMSNRLYSLFEVTNRQWLEPIKEPADQYLAPAGRIIDSQLSE
HQSEGFNEGYTLTGRHGLFTSYEAFLRVVDSMLTQHFKWIRKAHEEPWHKAYPSLNVV
STSTSFQQDHNGYTHQDPGILTHMAEKKAEYIREYLPADANSLLAISPKLFSSQNTVNVL
ITSKQPRPQFYSIDEATVLANAGLKRIDWASNDDGVEPDVIVAAAGTEPNMESLAAINLL
HDAFPDLKIRFINVLDLLKLRSPEIDPRGLSDAEFNSYFTTDKPILFAYHGBEGLIRDIFFTR
QNRNVLIHGYREEGDITTPFDMRVLNELDRFHLAKDVIQHVPAYAEKAAAFVQKMDDT
LQYHHDFIRANGEDIPEVQEWTWKSIK (SEQ ID NO: 3)

Amino acid sequence for a phosphoketolase enzyme from Lactobacillus crispatus ST1
MAVDYDSKDYLKSVDAYWRAANYLSVGQLFLMKNPLLKTPLVAEDVKPKPIGHWGTI
APQNFIYAHLNRVLKKYDLNMFYIEGSGHGGQVMVSNSYLDGSYTERYPEITQDEKGM
AKLFKRFSFPGGVASHAAPETPGSIHEGGELGYSLSHGTGAVLDNPDVIAAVEIGDGEAE
TGPLAASWFSDKFINPIKDGAVLPILQINGFKISNPTIVSRMSDQELTEYFRGMGWDPHF
VSVFKGGRFDGEKDPMQVHEEMAKTMDEVIEEIKAIQKHARENNDATLPHWPMIIFQC
PKGWTGPKKDLDGNPIENSPRAHQIPIPVAQGDMEHADMLTDWLESYKPEELFNEDGSP
KEIVTENTAKGDHRMAMNPITNGGIDPKRLNLPDYRKFALKFDKPGSVEAQDMVEWA
KYLDEVAKLNPTTFRGFGPDESKSNRLFQLLDDQKRQWEPEVHEPNDENLAPSGRVIDS
QLSEHQDEGFLEGYVLTGRHGFFATYEAFGRVVDSMLTQHMKWLRKAKEQYWRHDY
PSLNFVATSTVFQQDHNGYTHQDPGILTHLYEKNRPDLVHEYLPSDTNTLLAVGDKAL
QDRECINVLVTSKQPRPQWFSIEEAKKLVDKGLGYIDWASTDKGAKPDVVFASTETEPT
IETLAAIDILHKKFPDLKIRYINVVDVMKLMDPKDNKNGLSTEEFDRLFPKDVPVIFAWH
GYKSMMESIWFARKRYNVHIHCYEENGDITTPFDMRVLNHLDRFDLAKDAVESIDKLK
GKNADFISHMDDLLEKHHQYIRDNGKDMPEVTEWQWSGLK (SEQ ID NO: 4)

Amino acid sequence for a phosphoketolase enzyme from Bifidobacterium longum subsp.
longum JDM301
MTSPVIGTPWKKLNAPVSEEALEGVDKYWRVANYLSIGQIYLRSNPLMKEPFTREDVK
HRLVGHWGTTPGLNFLIGHINRFIADHGQNTVIIMGPGHGGPAGTSQSYLDGTYTETFPK
ITKDEAGLQKFFRQFSYPGGIPSHFAPETPGSIHEGGELGYALSHAYGAIMDNPSLFVPAI
VGDGEAETGPLATGWQSNKLVNPRTDGIVLPILHLNGYKIANPTILSRISDEELHEFFHG
MGYEPYEFVAGFDDEDHMSIHRRFAELWETIWDEICDIKAAAQTDNVHRPFYPMLIFRT
PKGWTCPKYIDGKKTEGSWRAHQVPLASARDTEAHFEVLKNWLESYKPEELFDANGA
VKDDVLAFMPKGELRIGANPNANGGVIRDDLKLPNLEDYEVKEVAEYGHGWGQLEAT
RRLGVYTRDIIKNNPRDPRIFGPDETASNRLQASYEVTNKQWDAGYISDEVDEHMHVSG
QVVEQLSEHQMEGFLEAYLLTGRHGIWSSYESFVHVIDSMLNQHAKWLEATVREIPWR
KPIASMNLLVSSHVWRQDHNGFSHQDPGVTSVLLNKCFHNDHVIGIYFATDANMLLAI
AEKCYKSTNKINAIIAGKQPAATWLTLDEARAELEKGAAAWDWASTAKNNDEAEVVL
AAAGDVPTQEIMAASDKLKELGVKFKVVNVADLLSLQSAKENDEALTDEEFADIFTAD

| SEQUENCES |
|---|
| KPVLFAYHSYAHDVRGLIYDRPNHDNFNVHGYEEEGSTTTPYDMVRVNRIDRYELTAE<br>ALRMIDADKYADKIDELEKFRDEAFQFAVDKGYDHPDYTDWVYSGVNTDKKGAVTAT<br>AATAGDNE (SEQ ID NO: 5) |
| Amino acid sequence for a phosphoketolase enzyme from *Leuconostoc citreum* KM20<br>MADFDSKEYLELVDKWWRATNYLSAGMIFLKSNPLFSVTNTPIQAEDVKVKPIGHWGT<br>ISGQTFLYAHANRLINKYDLNMFYIGGPGHGGQVMVTNAYLDGEYTEDYPEITQDLEG<br>MSRLFKRFSFPGGIGSHMTAQTPGSLHEGGELGYSLSHAFGAVLDNPDQIAFAVVGDGE<br>AETGPSMTSWHSTKFLNAKNDGAVLPILDLNGFKISNPTIFSRMSDEEITKFFEGLGYSPR<br>FIENDDIHDYAAYHELAAKVLDQAIEDIQAIQKDARENGKYEDGTIPAWPVIIARLPKG<br>WGGPTHDEDGNPIENSPRAHQVPLPLAQNKLETLSQFEDWMNSYKPEELFNADGSLKD<br>ELKAIAPKGDKRMSANPIANGGRRRGEEATDLTLPDWRQFTNDITNENRGHELPKVTQ<br>NMDMTTLSNYLEEVAKLNPTSFRVFGPDETMSNRLWSLFNTTNRQWMEEVKEPNDQY<br>VGPEGRIIDSQLSEHQAEGWLEGYTLTGRVGIFASYESFLRVVDTMVTQHFKWLRHASE<br>QAWRNDYPSLNLIATSTAFQQDHNGYTHQDPGMLTHLAEKKSNFIREYLPADGNSLLA<br>VQDRAFSERHKVNLIIASKQPRQQWFTADEADELANEGLKIIDWASTAPSGDVDITFASS<br>GTEPTIETLAALWLINQAFPEVKFRYVNVVELLRLQKKSESHMNDERELSDAEFNKFFQ<br>ADKPVIFGFHAYEDLIESFFFERKFKGDVYVHGYREDGDITTTYDMRVYSKLDRFHQAK<br>EAAEILSANSTIDQAAADTFIEKMDATLAKHFEVTRNEGRDIEEFTDWNWSALK (SEQ<br>ID NO: 6) |
| Amino acid sequence for a phosphoketolase enzyme from *Bradyrhizobium* sp. S23321<br>MNNQQQSALSRSDLDLLDRYWRAANYLSVGQIYLLDNPLLREPLRPEHIKPRLLGHWG<br>TTPGLNFIYAHLNRVIRALDLSVLYVCGPGNGGPGMVANTYLEGSYSEIYPNIARDTDG<br>LRKLFRQFSFPGGIPSHAAPETPGSIHEGGELGYALVHAYGAAFDNPDLIVACVVGDGE<br>AETGPLAASWHSNKFLNPVHDGAVLPILHLNGYKIANPTVLGRMRDEEIRDLFRGFGHE<br>PLFVEGDDPTLMHQAMADAFDVAFARIRSIQQHARDGRKEIERPRWPMIVLRSPKGWT<br>GPKEVDGLKVEGFWRAHQVPVAGCRENPAHLKILEDWMRSYEPEKLFDASGALIPELQ<br>ALAPEGNRRMGANPHANGGLLKKELKLPDPRSFALEVPQPGGVTGEATRELGKFLRDV<br>IRLNAAERNFRIMGPDETASNRLDAVFEETERVWMEPIEPYDVHLAQDGRVMEVLSEH<br>LCQGWLEGYLLTGRHGFFSCYEAFIHIVDSMFNQHAKWLKVTRHLPWRRPIASLNYLL<br>TSHVWRQDHNGFSHQDPGFVDLVANKKADIVRIYFPPDANTLLWIADHCLRTYNRINVI<br>VAGKQPAPQWLSMQDAATHCDAGIGIWSWAGNEDATGEPHVVMACAGDVPTLETLA<br>AVDLLRKALPDLKIRVVNVVDLMTLQPKEQHPHGLSDRDFDSLFTSDKPVIFAYHGYPH<br>LIHRLTYNRTNHAGLHVRGFIEEGTTTTPFDMVVLNELDRYHLAIEAIERVPGLAARAA<br>AVKQQFRDALIEHSHYIREHGEDMPEIRDWVWPGKTG (SEQ ID NO: 7) |
| Amino acid sequence for a phosphoketolase enzyme from *Enterococcus faecium* E1039<br>MDYSSKEYFDKMTAWWRAANYLSVGQLYLKDNPLLRRTLKPEDVKKHPIGHWGTIPG<br>QNFIYVHLNRVINKYDLNMFYIEGPGHGGQVMVSNAYLDGSYTEIYPEVTEDETGMQK<br>LFKRFSFPGGIASHAAPETPGSIHEGGELGYSLSHAVGAVLDNPEVISAVVIGDGEAETGP<br>LAGSWFSNVFINPVIDGAVLPILHLNGAKIANPTILARKSDGELANYFNGLGWEPFFIEG<br>NDPEKLNPVMAEKMDQAIEKIKSIQKEARLKTATDVVMPKWPVLIVRTPKGWTGEPIE<br>GTFRAHQVPIPVDQEHMDHADALLRWLKSYEPEKLFDAQGRILEEIREIAPTGDQRMAK<br>NPITNGGIDPKPLIMPDWKKYTLQFEKPGSIKAEDMTELGKFVREIIEKNPENFRIFGPDE<br>TKSNRLNQVFKTTNRQWMEKIEPENDEWLSPSGRVIDSQLSEHQDEGFLEGYVLTGRH<br>GFFASYESFLRVVDSMLTQHFKWMRKSHDLSWRNDYPSLNLIASSTVFQQDHNGYSHQ<br>DPGILTHLAEKKAEFIREYLPADANTLLAVMDKAFRSSEKINLIISSKHPRAQFYSAEEEA<br>VLVNEGLKIIDWASTAKEEEPELVIAAAGTESNLEALAAVTLLLEEFPKLKIRFINVVDLL<br>KLRHPSQDPRGLSDEEFDQYFTKDKPILFAFHGYETLVRTIFFDRHNHHLMIHGYKENG<br>DITTTPFDMRVVNELDRYHLAKDAALKIKGSQAEDFAEKMDQKLQEHQNYIRENGIDLP<br>EVLDWKWKNLDQ (SEQ ID NO: 8) |
| Amino acid sequence for a phosphoketolase enzyme from *Brucella microti* CCM 4915<br>MPAKGPLTPQQLSLINRYWRAANYLSVGQIYLMKNPLLREPLQPEHIKPRLLGHWGTTP<br>GLNFIYAHLNRIIQQRNANVIYICGPGHGGPGMVANTYLEGTYSEIYPAISEDEAGMERL<br>FRQFSFPGGIPSHAAPETPGSIHEGGELGYALVHAYGAAFDNPDLVVACVVGDGEAETG<br>ALATSWHSNKFLNPARDGAVLPILHLNGYKIANPTVLARLSDDDLDNLFRGYGYEPFFV<br>EGSEPADMHQKMAATLDTIFQRIQDIKKNADVHSPERPRWPMIILRSPKGWTGPKTVDG<br>LVVENYWRAHQVPVANCRENDAHRKILEDWMKSYDPSDLFDEKGALKPELRALAPKG<br>EARMGANPHANGGLLRKELHMPDFRQYAVNVTEPGAIEAQSTKILGDFLRDVMKLNET<br>EKNFRIFGPDETASNRLGSVLEATNRVWMAETLDMDDHLAADGRVMEVLSEHLCQGW<br>LEGYLLSGRHGFFSCYEAFIHIIDSMFNQHAKWLQVARELEWRKPISSLNYLLTSHVWR<br>QDHNGFSHQDPGFVDLVANKSADIVRVYFPPDANTLLWVGDHCLKTWNRVNIVIAGK<br>QPEPQWLTMAEAEKHCEAGLGIWEWAGTEDGLEPDIVMACAGDVPTMETLAAVDLLR<br>QSLPHLRIRVVNVVDLMVLQSPHQHPHGISDEEFDRMFTTNRPVIFAYHGYPYLIHRLV<br>YKRTNHSNFHVRGFIEQGTTTTPFDMTVLNELDRFHLAMEAVERLPLGESVAKPLIDNF<br>TEKLALHKDYIRQHGEDMPEIRDWKWTWPR (SEQ ID NO: 9) |
| Amino acid sequence for a phosphoketolase enzyme from *Lactobacillus salivarius* ATCC 11741<br>MTDYSSQEYLDKLDAYWRAANYVSVGQLYLKDNPLLRRPLKAEDVKVKPIGHWGTIA<br>GQNFIYAHLNRVINKYDLNMFYVEGPGHGGQVMVSNSYLDGSYSEIYPEISQDEQGMK<br>RLFKRFSFPGGVASHAAPETPGSIHEGGELGYSISHSVGAVLDNPDLIVAAVVGDGEAET<br>GPLAASWQSNKFINPIHDGAVLPILDLNGFKISNPTILSRESDETLTKYFEGMGWHPIFVE<br>GDDPKLMHPAMAKAMDEAIEEIKAIQKNARENNDPSLPAWPVIIFRAPKGWTGPKEWD<br>GEPIEKSFRAHQIPIPVDQNDMQHADALVDWLESYKPEELFDENGKLKAEIAEITPKGDK<br>RMAANPHTNPGKLIREVIKPDFRDFAVDTSVPGKEVAQDMTVLGKYLEKVLSDNRHNY |

| SEQUENCES |
|---|
| RVFGPDETMSNRLAPIFDVTKRQWLAEIKEPNDQYLAPSGQVIDSQLSEHQAEGFLEGY<br>VLTGRHGFFASYESFLRVVDSMLTQHFKWLRKATEQPWRTSIPSLNVIATSTVFQQDHN<br>GYTHQDPGILGHLADKKPEYIREYLPADANSLLAVFDKTINDRDKINLIVASKHPRQGFY<br>SAAEAKELVDKGLKIIDWASTDKNAEPDVVIAAAGTEPNLEALAAISILHEKLPDLKIRFI<br>NVVDILKLRSPKVDPRGLSDDEFDAYFTKDKPVIFAFHGYEGLLRDIFYYRHNHNVAFH<br>GYRENGDITTPFDMRVLSQMDRFDLVKSVALSLPDADKYGQLVAEMDAKVAKHHQYI<br>RDEGTDLPEVENWEWKPLD (SEQ ID NO: 10) |

Amino acid sequence for a phosphoketolase enzyme from *Streptococcus agalactiae* COH1
MSEFDTKSYLEKLDAWWRAANYISAAQMYLKDNPLLRRELVENDLKVHPIGHWGTVP
GQNFIYAHLNRAINKYDLDMFYIEGPGHGGQVMVSNSYLDGSYTELNPNIEQTEDGFK
QLCKIFSFPGGIASHAAPETPGSIHEGGELGYALSHATGAILDNPDVIAATVIGDGEGETG
PLMAGWLSNTFINPVNDGAVLPIFYLNGGKIHNPTIFERKTDEELSQFFEGLGWKPIFAD
VVELSEDHAAAHALFAEKLDQAIQEIKTIQSEARQKPAEEAIQAKFPVLVARIPKGWTGP
KAWEGTPIEGGFRAHQVPIPVDAHHMEHVDSLLSWLQSYRPEELFDENGKIVDEIAAISP
KGDRRMSMNPITNAGIVKAMDTADWKKFALDINVPGQIMAQDMIEFGKYAADLVDAN
PDNFRIFGPDETKSNRLQEVFTRTSRQWLGRRKPDYDEALSPAGRVIDSQLSEHQAEGFL
EGYVLTGRHGFFASYESFLRVVDSMVTQHFKWLRKSKTHTTWRKNYPALNLIAASTVF
QQDHNGYTHQDPGILTHLAEKTPEYIREYLPADTNSLLAVMDKAFKAEDKINLIVTSKH
PRPQFYSIAEAEELVAEGYKVIDWASNVSLNQEPDVVFAAAGTEPNLEALAAISILHKAF
PELKIRFVNVLDILKLRHPSQDARGLSDEEFNKVFTTDKPVIFAFHGYEDMIRDIFFSRHN
HNLHTHGYRENGDITTPFDMRVMSELDRFHLAQDAALASLGIKH (SEQ ID NO: 11)

Amino acid sequence for a phosphoketolase enzyme from *Rhodococcus imtechensis* RKJ300
MTDGRQVGSQDSDGHYSDSDLDLDLRWWAAANYLTVAQIYLQDNALLRAPLRPEHIK
PRLLGHWGTSPGLSMIYALLNRLIRRTDTDCLYVTGPGHGGPALVAATYLEGTYSEVYP
GVSRDAAGIHRLCRQFSTPGGIPSHVSVQTPGSIHEGGELGYALAHAAGAAFDHPNLLV
ACVIGDGEAETGPLSGSWKLPAFLNPERDGAVLPILHVNGAKIAGPTVYGRSSDADVEA
FLGGQGWAPTVVSGDDPRHVFPALHRALTDAHAAISDLQREARAGRRSAAKWPAIVLR
TPKGWTGPRTVDGVLVEGTHRAHQVPLSGVRTDEAHLRQLEEWMRSYGPGELFDSSG
ALVPDLERLAPQGDKRMGSSPYANGGRLRADLPVPPLEKYALAIEKPGTTLHETTRVLG
ELLRDLYAATATPDGGGYFRLFCPDETASNRLGAVFEVTDRCWQLPVTDYDDGLSARG
RVMEVLSEHLCEGWLEGYLLSGRHGLFASYEAFAMVSVSMLVQHTKWLQHAVDLPW
RAPVASLNVLLTSTCWRNDHNGFSHQGPGMIDAVIPLAPDVVRIWLPPDSNTLLSIADH
CLRSTDHVNLIVVDKQPHLQYLTLAEAHAHCAAGASVWEWAGTEGAVGADPDVVLA
AAGDVPTQEILAAAQLLREHTPDLVTRVVNVVDLMGLLTPTEHPHGPDARMFLDLFTA
DTDVVFAFHGYSRAVHELIHGRPAPDRFHVRGFSEQGTTTTPFDMVVLNRMSRYHLVL
EALRRTRREPAGAGELADFCLRQLERHGEYVVAHLEDMPEVRDWTWS (SEQ ID
NO: 12)

Amino acid sequence for a phosphoketolase enzyme from *Burkholderia xenovorans* LB400
MAEASSRPTPPQVLDADTLRNMDRYWRACNYLSAGMIYLRDNPLLREPLKPEHIKNRL
LGHWGSDPGQSFLLVHLNRLIRKLDLNVIYVAGPGHGAPATLAHCYLEGHYSEIYPDRS
EDEAGMQRFFRQFSFPGGIGSHCTPETPGSIHEGGELGYSLSHGYGAAFDNPDLIVTVMI
GDGEAETGPLATSWHSNKFLNPVRDGAVLPVLHLNGYKIANPTILARIPREELEALLTG
YGHKPYFVEGDDPAVMHQQMAATLEQCIGEIRAIQQHARANNDATRPRWPMIVLRSPK
GWTGPKEVDGHKVEGSWRAHQVPLDPVTNGKSLKLVENWMRSYEPESLFDEAGRL
VEELRELAPKGARRISANPHANGGLLCKTLDMPAFGDYAVAVKKPGGTYTSPTEVLGK
FLCDVMRRNMTNFRVFGPDETASNKLTAIYEASEKTWLAQTEPSDADGGDLAVDGRV
MEMLSEHTLEGWFEGYVLTGRHGLFATYEAFVHVIDSMFNQHAKWLEKAKRDLGWR
QPVPSINLLITSLVWRQDHNGFTHQDPGFLDVVTNKSPDVVRIYLPPDANCLLSVADHC
LRSRDYVNVIVADKQPHLQYLDMDAAVIHCTKGIGIWDWASTDQGVEPDVVIASAGDI
ATMEALAAVQILKERFADLKIRFVNVVDLFRLMPEHAHPHGLSNRDFDSLFTATKPVIF
NFHSYASLVHKLTYNRTNHDNLHVHGYHEKGNINTPLELAIINQVDRFSLAIDVIDRVPK
LRGVGDHAKEWLRGQVIEHLAYAHAEGIDREEIRNWTWKG (SEQ ID NO: 13)

Amino acid sequence for a phosphoketolase enzyme from *Mycobacterium intracellulare* ATCC 13950
MTHATALSDDELALIDKYWRAANYLSVGQIYLLDNPLLTEPLTIDHVKPRLLGHWGTTP
GLNLVYAHLNRVIRHRDADVIYVTGPGHGGPLVANAYLEGTYSEVYTGIEEDTEGLR
KLFRQFSFPGGIPSHVAAQTPGSIHEGGELGYALVHAYGAALDNPYLVACVVGDGEA
ETGPLAASWHSNKFLNPVTDGAVLPILALNGYKIANPTVLARIPHAELESLLRGYGYRPI
TVAGDDPADVHRQLAAALDDAFDDIAAIQSAARGGNGVERPVWPMIVLRTPKGWTGP
KMVDGKKVEGTWRSHQVPLAATRDNPEHRAQLEEWLRSYGPGELFDENGRLRPELRA
LAPSGDRRMSANPHANGGLLLHDLDLPDFRDYAVAVERPAAVTHEATRVLGGFLRDVI
ARNKDRFRLMGPDETASNRLDAVYGSTDKVWLSEIEPDDEHLAPDGRVMEVLSEHLCQ
GWLEGYLLTGRHGLFNCYEAFVHIVDSMLNQHAKWLATSRELPWRRPIASLNYLLSSH
VWRQDHNGASHQDPGFIDLVANKRPELTRVYLPPDGNTLLSVADHCLRSRDYINVIVA
GKQPALAYLDMDEAVHCTRGLGIWEWASTATDDPDVVLACAGDIPTLETLAAADILR
SELPELAVRVVNVVDLMRLQPDTEHPHGLPDREPDALFTPDRPVIFAYHGYPWLIHRLT
YSRTNHAHMHVRGFKERGTTTTPFDMVMLNDLDRFHLVMDVIDRVDGLASRAAMLR
QRMVDARLAARMYTREHGEDDPKISGWTWGPSD (SEQ ID NO: 14)

Amino acid sequence for a phosphoketolase enzyme from *Nitrosomonas* sp. Is79A3
MKKNTKLLSPELLHKMDAYWRAANYLSVGQIYLYDNPLLKQPLKAHIKPRLLGHWG
TTPGLNFIYVHLNRIIKEHDLNVIYITGPGHGGPGLVANTYLEGTYSEVYPNISQDEDGM
QRLFKQFSFPGGIPSHVAPETPGSIHEGGELGYSLSHAFGAAFDNPGLLVACVVGDGEAE

| SEQUENCES |
|---|
| TGPLATSWHSNKFLNPVHDGAVLPILHLNGYKIAGPTVLARIPCDELEALFRGYGYTPYF<br>IEGDDPLEMHQRMAATLDAVIANIQSIQRDARTHGFTKRPHWPMIILRSPKGWTGPKVV<br>DGKPTEGTFRSHQVPMGDMSQPGHVKILEKWLKSYRPQELFDETGKLLAELAELAPQG<br>ARRMGANPHANGGMLLRDLRLPDFRDYAVKVANPGTVSAEATRTQGEFIRDVVKLNA<br>TNFRVFSPDETASNRWGAVFEVTNRCSTAEIVPGDDHVAPDGRVMEMLSEHQCEGWLE<br>GYLLTGRHGFFSCYEAFIHIIDSMFNQHAKWLKVANEIPWRRPIASLNYLLSSHVWRQD<br>HNGFSHQDPGFIDHVINKKAEIIRIYLPPDANTLLSVTDHCLRSRNYVNVIVAGKQPQPQ<br>WLDMDAAIKHCTAGIGIWEWASNDQGEEPDVVMACAGDAPTIETLAAVELLWKHFPE<br>LKIRVINVVDLMSLQPQSEHPHGLSDKDFDGLFTKDKPIIFAYHGYPWLIHRLTYRRTNH<br>DNLHVRGYKEEGTTSTPFDMVVMNDLDRFHLVADVIDRVPQLGSRAAYVKQAIRDKLI<br>EHKQYINQYGEDMPEIRNWKWKGSSV (SEQ ID NO: 15) |

Amino acid sequence for a phosphoketolase enzyme from *Schizosaccharomyces pombe* 972h-
MATQNDIPNSTPEDLAKQVEIAEKHPDPPAMPSRLPDSLKTLEAKIDTSKITDEEVANVH
RFQRACDYLAASLIFLSNGLYTGGDLEEKDIKTRLLGHWGTCPGLSIVYSHCNRIINKYD
LNMLFVVGPGHGAPAILSALFLEDSLGPFYPRYQFTKEGLNNLINTFSLPGGFPSHVNAE
VPGAIHEGGELGYALSVSYGAVLDRPDLIVTCVVGDGEAETGPTATSWHAHKFLDPAE
SGAVIPVLELNGYKISERTIYGCMDDSELLSLFSGFGYEVAIVNDTPDQNRVMAATMDW
AVERIHDIQHRARVNREEIKPRWPMIILRTPKGKGCPKYLNGKFLEGTFRAHQVPLKLA
RTDTNQRNLLKDWLNSYNCQDFLDEHGLPTKGITEHLPPREKRMGQRHETYNSYLPLK
VPDWKKYGVKKGETTSATSVVGQYLDELLVTNDSTLRIFSPDELESNKLDGALKHSYR
TMQTDPELMAKRGRVTEVLSEHLCQGFMQGYTLTGRTAIFPSYEAFMTIVVSMLVQYS
KPFLKMGLETGWHGKFGSLNYVTSSTWARQEHNGFSHQSPRFITTMLSLKPGVSRVYFPP
DANCFLATVARCMKSENTINLMVSSKNPQPAYLSVEEAEHHCKAGASVWKFASTDNG
ENPDVVIAGVGNEIMFEVVKAAEMLQNDIPELRVRVINVTDLMVLSSLHPHGMNPAEF
DSLFTKDRHVHFNYHGYVMDLKALLFDRIQGTRVTMEGYREEGTTTTPFNMMMCNNT
SRYHVARMALQHALHNPTVAVNCNMLCAKYAWKLEEIENYIMENKDDPPEIYAAPVF
KNKTSTL (SEQ ID NO: 16)

Amino acid sequence for a phosphoketolase enzyme from *Leuconostoc mesenteroides* subsp. *mesenteroides* J18
MNIDSTDYLNNLDAYWRATNYLSVGQLYLLDNPLLKEKLTAEQVKIHPIGHWGTIPSQ
NFIYAHLNRAINKFNLNMFYIEGPGHGGQVMISNAYLDGSYTEAFPEITQDEAGMQKMF
KRFSFPGGVASHADPKVPGSIHEGGALGYSILHGAGAVLDNPDLIAAVVVGDGEAETAP
LATSWHVNKFLNPKNDGTVLPILNLNGFKIANPTVLSRESDETLTEYFHSLGWHPYFVSS
FDKPIMQVHEEMAKTMDTVFTEIKDIREKAVQQTNEEITRPLWPMIVLRSPKGWTGPKT
WDDNPIENSFRAHQIPIPADQNHPEYIPQLVDWLQSYKPDELFDENGQLTQSIQEVLPKK
ELRMANNSVTNAGKIKPLILPDIDNYLVENNQPGNNLAQDAILLGDYLRDIIKLNPTNFR
GFGPDETASNRFQDIFETTNRQWLLPIKEPNDQFMAPEGRIIDSMLSEHYDEGMLEAYTL
TGRHGFFASYEVFIREVDDMIVQHFKWLNHSHDVSWRKDVPALNIIADSTVFQQDHNG
YSHQDPGVTTMLYEKQPDFIREFFPADANSLVATFEHAAQATQQINYIVASKHPRLQWF
SPTEAKQLVTQGLRVIDWASTDKGEKPDIIISSAGSEPTTESLAAIQILHEHIPSLKIRYINV
LDLFKLRADASYGLSDDEFDAYFTTDTPVLFAFHGYEPMIESIFFKRHNHHLAVHGYRE
VGDITTPFDMRVLNKIDRFNLVKAAINLLPENIRTKQAALVQEMTDKLDLHVAYTRSKG
TDLPEVEDWRWQPLK (SEQ ID NO: 17)

Amino acid sequence for a phosphoketolase enzyme from *Streptomyces* sp. SA3 actG
MSDASVSAVADALDYLCLAQLYLRENPLLARPLTSAHVKWRPAGHWGVCPPVNRML
AALGPVQASVPDGYELRVLHGAGHAGPSALAHAYLTGRLGRVYPDLIQSPAGLLELVS
GFPRPETGGEITPMIPGHLHTGGQLGAALAIGQGTVLDAPRRLTVALLGDGECETGTTA
ASWLASRALRGTGDHGTVLPVVLLNGMRMGGPSVLSTLSRDELTAYFTGLGHQPVYS
DGLDIAQLRQAIAEAVADARPLGVPGPSSVLVLTLEKGYGAPAGLAATPAVHKTPLHDP
ASVPSEFDLLSEWLASYRPAQLLTPGGRPRPHLLPALPRPRPEPGGLSAPRGCIAASTQV
ADHASGRAFAQVVPDVLRARAAQGPFRVFSPDELASNRIDLTDGQGRTVPWAVEVLSE
ELCHAWAQGYTETGRHALVATYEAFAPITLSLVQQQLKHRSARRHAGLAPLPSLVYLL
TSLGWHNTFTHQNPSLATALLAGGDPSVHVLTPADPARAAAALTFALRKLDRCTLVIA
DKHATVQHPLETLDEELRHGMAIWPHLSAPGPEEPDLILASAGDLPAEVLTTLARRLRD
DRRELRLRYVHIHDLTALAEEDTRSLALGPAAFTHHFGTTAPLVLATSGHPADIHALFG
RRHPGPRLTVLGYRDPGRPVSQTHLRQLCGLDDTSLWHLATTLIDASKEIPAP (SEQ ID NO: 18)

Amino acid sequence for a phosphoketolase enzyme from *Lactobacillus buchneri* ATCC 11577
MTVDYDSKEYLDLLDKYWRAANYLSVGQLYLRDNPLLKRPLKSDDVKIKPIGHWGTIV
SQNFIYAQLNRAINKYDLNMFYIEGSGHGGQVMVSNSYLDGSYSDIYPNISQDEKGMQ
KLFKQFSFPGGVASHAAPETPGSIHEGGELGYSLSHGTGAILDNPDVIAAVEIGDGESET
GPLAASWFSDKFINPITDGAVLPIINMNGFKISNPTILSRMSDADLTDYFKGMGWEAHFV
EATADTDHAKVEAEFAKTLDTVIEKIKSIQKNARENETPDNVKLPVWPMIIFRSPKGWT
GPKKDLDGNPIEGSFRAHQVPIPVDANDMEHADELVDWLKSYKPEELFDENGTLKPEL
RALAPKGEQRMSVNPITNGGIKPEPLKLPNVRDFEVKFDKRGTEQKQDMIEWSKWLDA
VAKLNPTTFRGFGPDETKSNRLYSLLDDGKRQWMEDIHEPYDEDLANHGRVIDSQLSE
HQAEGWLEGYVLTGRHGFFATYESFGRVVDSMLTQHFKWLRKASEQYWRKQYPSLNF
VDTSTVFQQDHNGYTHQDPGLLTHLAEKKPEFIREYLPADANELLAVGDSAFRTYEKIN
LIVTSKHPRRQWYSMDEAQNLVKNGLGYIDWASTDQGQEPDVVFAAAGSEPNLEALA
AISILNKEFPELKIRFINVVDILKLNSPKKDPRGLSDEEFDNLFTTDKPVIFAWHGFEDMIK
DIFFFDRHNHNLYVHGYRENGDITTPFDMRVLNELDRFHLAADAIRHIPAYAVKGGYFIQ
RMNNIVDKHNRYIREVGTDLPEVTSWNWEPLNK (SEQ ID NO: 19)

| SEQUENCES |
|---|
| Amino acid sequence for a phosphoketolase enzyme from *Streptomyces ghanaensis* ATCC 14672<br>MPEAPDTRTVLSDEELRTLDAHWRAANYLAAGQIYLLANPLLTEPLRPEHIKPRLLGHW<br>GTSPGLNLVYTHLNRVIAGRGLDALCIWGPGHGGPSVLANSWLEGSYGETYPDVGRDA<br>AGMERLFRQFSFPGGVPSHVAPEVPGSVHEGGELGYSLAHAYGAALDHPGLLVACVIG<br>DGEAETGPLAASWHSNKFLDPVHDGAVLPILHLNGYKIANPTVLARLPEDELDSLLRGY<br>GHEPIHVSGDDPAAVHRAMAHAMDTALDRIAEVQRAAREDGVTERARTPVIVLRTPKG<br>WTGPAEVDGKPVEGTWRAHQVPLAGVRDNPEHLRQLEAWLRSYRPEELFDDAGRPVA<br>DVLACLPEGDRRLGSTPYANGGLLVRELPMPALDDFAVPVDKPGTTLHEPTRILGGLLE<br>RIMRDTADRRDFRLVGPDETASNRLEAVYDASGKAWQAGTLDVDEHLDRHGRVMEV<br>LSEHLCQGWLEGYLLTGRHGLFSCYEAFVHIVDSMVNQHIKWLKTSRELPWRAPIASLN<br>YLLTSHVWRQDHNGFSHQDPGFVDHVLNKSPEVVRVYLPPDANTLLSVADHALRSRD<br>YVNVVVAGKQPCFDWLSIDEARVHCARGAGIWEWAGTENGGAPDVVLACAGDVPTQ<br>EVLAAAQLLRRHLPELAVRVVNVVDIARLMPREEHPHGMTDFEYDGLFTADKPVIFAY<br>HGYPWLIHRLAYRRNGHPNLHVRGYKESGTTTTPFDMVVRNDLDRYRLVMDVIDRVP<br>GLAVRAAAVRQRMADARTRHHAWIREHGTDLPEVAEWSWNA (SEQ ID NO: 20) |
| Amino acid sequence for a phosphoketolase enzyme from *Cyanothece* sp. PCC 8802<br>MVATPERPTLEQTPLSAEELRQIQAYWRACNYLAVGMIYLRDNPLLKDPLTEDHVKNR<br>LLGHWGSSPGLSFIYIHLNRLIKKYGLDVIYMAGPGHGAPGILGPVYLEGTYSETYPDKS<br>EDEEGMKKFFKQFSFPGGIGSHCTPETPGSIHEGGELGYSLSHAYGAALDNPDLIVAAVV<br>GDGEAETGPLATAWHSNKFINPIRDGAVLPILHLNGYKIANPTILARISHEELEYLFKGYG<br>YKPYFVEGSDPEVMHQKMAATLETAIAEIKHIQQEARTSGVAKRPIWPMIVLRSPKGWT<br>GPASVDGKKTEDFWRSHQVPLSGMHGNPAHIKVLEDWLKSYTPEELFDENGTLIPELKE<br>LAPTGHHRMSANPHANGGLLRKDLKMPDFRNYGVEVAKPGTVEVGNTALLGNFLRDV<br>MANNNMTNFRVFGPDETASNRLNAIYEISKKVWMGEILPEDADGTEITTDGRVMEMLSE<br>HTLQGWLEGYLLTGRHGFFHTYEAFAHVVDSMFNQHAKWLDICKNEVPWRASVSSLN<br>ILLSSTVWRQDHNGFSHQDPGYVDLVTNKSADVVRVYFPPDANCLLSVANHCLKSTDY<br>VNVIVSDKQIHLQYLNMDQAIKHCTKGIGIWDWASNDDCGTEPDHPDVIMASCGDVAT<br>KEALAATAILREEFPDLKVRFINVVDLFKLQSEIEHPHGLSDRDFDNLFTKDKPIIFNFHG<br>YPWLIHKLTYRRTNHHNLHVRGYKEKGNINTPLELAINNQIDRFNLVIDVINRVPKLGSA<br>AAYVYERMKNAIIEHRAYAYEHGIDKPEINNWKWPH (SEQ ID NO: 21) |
| Amino acid sequence for a phosphoketolase enzyme from *Neosartorya fischeri* NRRL 181<br>MTSKGEIESLSAYGVARSTIQGTPLSQDELRKMDAYFRASMYLCLGMLYLRDNPLLKEP<br>LKVEHLKARLLGHWGSDAGQSFTWIHMNRLIKKYDLDVLFISGPGHGAPGILSQSYLEG<br>VYTEVYPEKTQDEKGLQRFFKQFSFPGGIGSHATPETPGSIHEGGELGYSISHAFGTVPD<br>HPNLITLTMVGDGEAETGPLATSWHSNKFLNPITDGAVLPVLHLNGYKINNPTILARISH<br>EELEMLLKGYGWTPYFVEGSDRESMHQAMAATLEHCVLEIKKIQKQARESNKAFRPL<br>WPMIVLRSPKGWSAPREIDGKYLEGFWRAHQIPITDVQSKPEHLKVLENWMKAYKPEE<br>VFDKNGTLIPELKELAPTGTSRMSANPVGGLLRRPMDLPDFRDYALTDIEPGVTIRPS<br>MSNMSKYLRDVVARNMTTFRVFGPDETESNKLAEIYKAGKKVWMAEYFKEDEDGGN<br>LDMQGRVMEILSEHTCEGWLEGYILSGRHGMLNSYEPPFIHVIDSMVNQHCKWIEKCLA<br>VEWRAKVSSLNILLTATVWRQDHNGFTHQDPGFLDVVANKSPEVVRIYLPPDGNTLLS<br>TMNHCFRSVNYVNVIVADKQEHVQFLNMEEAIEHCTKGVGIWNDWASNDQGCEPDVV<br>MASCGDVATHEALAATALLREHLPQLKVRFVNVVDLFRLISDINHPGMPDRQWGAIF<br>TTDKPIIFNFHSYPWLIHRLTYKRPGQHNLHVRGYKEKGNIDTPFELAVRNQTDRYSLAI<br>DAIDRIPSLGNTASGVRERLINLQLAAKNKAPDDGIDPDYIRNWTWDYPRKKC (SEQ ID NO: 22) |
| Amino acid sequence for a phosphoketolase enzyme from *Enterococcus faecium* TX1330<br>MDYSSKEYFDKMTAWWRAANYLSVGQIYLKDNPLLRRTLKPEDVKKHPIGHWGTIPG<br>QNFIYVHLNRVINKYDLNMFYIEGPGHGGQVMVSNAYLDGSYETIYPEVTEDETGMQK<br>LFKRFSFPGGIASHAAPETPGSIHEGGELGYSLSHGVGAVLDNPEVISAVVIGDGEAETGP<br>LAGSWFSNVFINPVTDGAVLPILHLNGAKIANPTILARKSDGELANYFNGLGWEPFFIEG<br>NDPEKLNPVMAEKMDQAIEKIKSIQKEARLKTAADAMMPKWPVLIVRTPKGWTGPEE<br>WDGEPIEGTFRAHQVPIPVDQEHMDHADALLRWLKSYEPEKLFDAQGRILEEIREIAPTG<br>DHRMAKNPITNGGMDPKPLIMPDWKRYTLQFEKPGSVTAEDMTELGKFVREIIEKNPEN<br>FRIFGPDETKSNRLNQVFKTTNRQWMEKIEPENDEWLSPSGRVIDSQLSEHQDEGFLEG<br>YVLTGRHGFFASYESFLRVVDSMLTQHFKWMRKSRDLSWRNNYPSLNLIASSTVFQQD<br>HNGYSHQDPGILTHLAEKKAEFIREYLPADANTLLAVMDKAFRSSEKINLIISSKHPRAQ<br>FYSAEEAAVLVNEGLKIIDWASTAKEEEPELVIAAAGTESNLEALAAVTLLLEEFPKLKI<br>RFINVVDLLKLRHPSQDPRGLSDEEFDKYFTKDKPILFAFHGYETLIRTIFFDRHNHHLMI<br>HGYKENGDITTPFDMRVVNELDRYHLAKDAALKIKGSQAEDFAKKMDQKLQEHQNYI<br>RENGIDLPEVLDWKWKNLDQ (SEQ ID NO: 23) |
| Amino acid sequence for a phosphoketolase enzyme from *Listeria grayi* DSM 20601<br>MTDYSSPNYLAKVDAWWRAADFISVGQLYLKGNPLLRRPLEKEDLKVHPIGHWGTISG<br>QNFIYAHLNRVINKYDLNMFYIEGPGHGGQVMVSNSYLDGSYTDTYPTITQDEVGLTKL<br>YKQFSFPGGIASHAAPETPGSLHEGGELGYALSHATGSILDNPDVIAATVIGDGEAETGP<br>LSAGWFSNTFINPVNDGAVLPILYLNGAKISNPTILSRKTDKELTSFFQGLGWDPIFVEGE<br>DPAKVHPLMAEKLDQAIEKIKAIQTEARKEAADKATMPTWPVILFRTPKGWTGPKEWN<br>NEPIEGSFRAHQVPIPVDQHHFDHVDALENWLQSYRPEELFTEEGSLKEEIKSLAPKNRM<br>ATNPITNGGIDPQPLRLPSWKDYAVETANKDVITQDMIELGGFVRDIVKENPDNFRIFGP<br>DETKSNRLNKVFEVTNRQWMSKAEFPRDEWLAPAGRIIDGQLSEHQAEGFLEGYVLTG<br>RHGFFASYESFLRVVDSMLTQHFKWLRKAKEQTWRNSYPSLNVIATSTVFQQDHNGYT<br>HQDPGVLTHLAEKKPEFIREYLPADTNSLLAVMNEAFRSEELINLIVSSKHPRPQFYSAEE |

| SEQUENCES |
| --- |

```
AEILVKDGLKIIDWASTVSEAEEPDVVIASAGTEPNLEALAAVTLLNEAFPSLKIRFINIVD
ILKLRHPDIDPRGLTDEEFDRYFTTDKPIIFAFHSYEGMVRDIFFNRHNHNLFIHGYRENG
DITTPFDMRVLSEMDRFHLAKDAAEAVYGEIATSFAAEMDAVLSKHHHFIRENGEDLPE
VENWKWQALKTDLLEV (SEQ ID NO: 24)
```

Amino acid sequence for a phosphoketolase enzyme from *Enterococcus casseliflavus* EC30
```
MKTTYDTPEYYQKMNAWWRAANYLSVGQIYLKDNPLLRRPIEEKDLKVNPIGHWGTI
AGQNFIYTHLNRVINKYDLNMFYIEGPGHGGQVMVANAYLDGSYSEIYPKATQDEAG
MKHLFKTFSFPGGIASHAAPETPGSIHEGGELGYSIAHATGAILDNPDVIAAVVVGDGEA
ETGPLAGSWFSNTFINPVNDGAILPILHLNGAKIANPTILARKSDQDLTKYPEGMGWTPY
FVEGDDPEAVHPQLAQKMDQAIEQIHAIQAEARKGSAEEAAMPHWPVLIVRTPKGWTG
PKVWDGEPIEGGFRAHQVPIPVNAKHMEHVDALTDWLQSYRPEELPDENGRIKAEIQEL
APKGEQRMAVNPITNGGIDPQPLRLPDWQAHAIAIETPGETTAQDMMVFGKFARDIIKE
NPDNFRIFGPDEAKSNRLNHVFEVTDRQWLEPKHPDYDEWLSSVGRVIDSQLSEHQAEG
FLEGYVLTGRHGFFASYESFLRVVDSMITQHFKWLRKAHDLDWRNPYPSLNLIASSTVF
QQDHNGYTHQDPGIMTHIAEKKADFVRVYLPADANSLMAVMAETLASEEKINLVVSSK
HPRPQFYSADEAKVLVKDGLKVIDWASTDEGQEPDIVIAAAGTEPNLEALAAVSLLIEA
FPELKVRFINVVDLLKLRRPEVDPRGLSDEAFEAYFTKDKPIVFAFHGYEGLIRDIFFGRR
NQQLHIHGYRENGDITTPFDMRILSELDRFHLAKDAAEWVYGEKATDFAQKMADTVA
YHHDFIRENGYDIAEVEEWEWKPLR (SEQ ID NO: 25)
```

Amino acid sequence for a phosphoketolase enzyme from *Mycoplasma alligatoris* A21JP2
```
MKKNTFDTQDYLDKVDAWFRAANYLSVGQMYLRNNPLLRSKITSDDVKVYPIGHWGT
IPGQNFAYAHLNRVINKYNLNMFYIEGPGHGGQVMTSNSYLDGSYTELFPHVTQDVAG
MKHLFKYFSFPGGTASHAAPETPGSIHEGGELGYSLSHATGAILDNPNVIAATIVGDGEA
ETGPLAASWFSNSFINPVNDGAVLPILHLNGGKISNPTILCRKSNKELTDYFAGMGWEA
VFVEGSDEKMHKVMAQKLDYVIEKIQSIQNEARKKPANQATRPIWPMMVLRTPKGW
TGPDSWNKDKIVGSFRAHQVPIPVNSANMEHIDALLDWLSKYKVDNLFDKNGKLVDEI
AQIAPKGDQRMGMNPITNGGLNPKKLVMPRWQDFALKFSKPGELVNQDMVELGTYFA
KMMELNKDNFRLFGPDETKSNRLYNVPKVTKRQWLEPISPILDEALSPEGRVIDSQLSEH
QAEGFLEGYVLTGRHGVFASYESFLRVVDSMLTQHLKWLKKAKDVHWRNDYPSLNVI
ATSTAFQQDHNGYTHQDPGLIGHLADKTPEIIRQYLPADTNTLLAVMDKSLKERNVINH
IIASKQPREQFYSEQEAAELVEKGLKVIDWASTTKGNEEPELVVVAAGTEPNLEALAAV
TILNKEYPSLKIRFVNVVDLMKLRHPSLDPRGLSDKEFDAIFTSNKPIVFAFHGYEGILRD
MFFKRNNHNLITHGYRENGDITTSFDIRQLSHMDRFHISASAAKAVYGNKAQEFEDKMI
QTIDFHTKYIREYGTDIPEVKEWKWADLTRK (SEQ ID NO: 26)
```

Amino acid sequence for a phosphoketolase enzyme from *Carnobacterium* sp. 17-4
```
MKNYDSKDYLKKVDAFWRAANYLSVGQLYLRDNPLLQRPLKSTDVKAHPIGHWGTIS
GQNFIYAHLNRVINKYDLNMFYIEGPGHGGQVMISNAYLDGSYTEIYPDITENKEGMKK
LFKQFSSPGGVASHAAPETPGSIHEGGELGYSLSHATGAILDNPDVIAATVIGDGEAETG
PLAAGWFSNNFINPVNDGAVLPILYLNGGKISNPTILARKSNEDLKKYFEGMGWKPYFV
EGTDPEKVHPVMANTLDVVIEEIRSIQNEARKGKAEDVEMPHWPVMIIRTPKGWTGPKE
WDNKKIEGTFRAHQVPIPVDAEHMEYVNKLVDWLKSYRPEELFTENGKLIDDLKELTP
KGNKRMATNPITNGGINAKALIIPNWKQHAIDTTIPGAVIAQDMDVFGEQARDLIVKNP
NNFRIFGPDETKSNRLDKIFEVTNRQWLESKELTDEWQSSAGRVIDGQLSEHQAEGFLE
GYVLTGRHGFFASYESFLRVVDSMLTQHFKWLRKATDQKWRNNYPSLNVIATSTVFQQ
DHNGYTHQDPGILTHLAEKKPEFIREYLPADANSLMAVMDKTLQEEQLINLIISSKHPRP
QFYSVEEAEILVKDGLKIIDWASTDNDSEPDLVIAAAGTEPNLEALAAMSILHKAFPELKI
RFINIVDILKLRHPDIDSRGLTDEKFDSYFTKEQPIIFAFHGFEGLIRDIFFNRHHNLRIHG
YRENGDITTPFDMRVLNEMDRFHLAKDAAKAVYGLKANKFMQEMENTVNFHHQYIRE
NGIDIPEVINWKWEKI (SEQ ID NO: 27)
```

Amino acid sequence for a phosphoketolase enzyme from *Melissococcus plutonius* ATCC 35311
```
MEKDKYSSTEYLDKIDKWWRAANYLSIGQLYLKDNPLLKRKIRSEDVKYHPIGHWGTI
AGQNFIYAHLNRIINKYDLNMFYIEGPGHGGQVMVSNSYLDGSYTEIYPAVTEDEAGM
QKLFKRFSFPGGVSSHAAPETPGSIHEGGELGYSLSHGVGAILDNPEVISAVVIGDGESET
GPLATSWFSNTFINPVTDGAVLPILHLNGAKIANPTILGRKSDKELEQYFRGMGWIPYFV
EGNDPNQMHPLMAKTLDQVIEKIHSIQETARKQTAETASIQKWPLIVLRTPKGWTGPKE
WDGKPIEVTFRAHQVPIPIDQDHMEHVDQLVNWLKSYKPEELFDETGRLNSEIRAIAPM
NDKRMAMNPITNGGINPKPLQMPDWREFDLHISKPGELVAQDMLEFGKMVAAIIKKNP
QNFLIFGPDETKSNLLNDAFSVTSRQWLEPIYEPQDEWLAPSGRIIDSQLSEHQDEGILEG
YVLTGRHGFFASYEAFIRIVDSMIAQHIKWMRKAMDLPWRNGYSSLNLIASSTAFQQDH
NGYTHQDPGILSHLAEKEADFIHEYVPADTNSLLAVMDKVLKSQGKVNLVISSKHPRPQ
FYSPEEAQELVNRGLMEIDWASTVAENGTPEIVIVAAGTEPNMEALAAINLINQSFPKLQ
FRFINVVDLLKRHPAVDSRGISEVEYNHLFTVDSPIIFVCQGYSSLIRSLFYDRKNRPVSI
HSYQENGAITTPFDMRVLNKIDRYHLAKDIALTAYGSRGEDFARAMDTILEKHNQYIRE
TGKDLPEVLNWKWAPLHIYNENIEQD (SEQ ID NO: 28)
```

Amino acid sequence for a phosphoketolase enzyme from *Tetragenococcus halophilus* NBRC 12172
```
MSVNIDSKEYLERMNAWWRAANYISVAQIFLRDNPLLRRPLEKEDIKINPIGHWGTISG
QNFIYVHLNRVINKYGLNMFYIEGPGHGGQVMVSNSYIDGSYSEIYPDVTQDEAGLKKL
FKQFSFPGGMGSHAAPETPGSIHEGGELGYSMSHAVGAVLDNPDVIAATVIGDGEAETG
PLAASWMSNNFINPVNDGAVLPILNLNGAKIANPTVLARKSDKDLQKYFEGLGWKPYF
VEGDNPEKMHPLMAETLDAVINEIQSIQKEARKGSAEDVTMPHWPVIVFRTPKGWEGP
EKWDNEQIAGTFRAHQVPIPIDASHMEYANDLAKWLKSYRPEELFDENGTIIDAIKELSP
```

SEQUENCES

```
KGDNRMSVNPITNGGLDPKALNMPDWHTHAVDTSKRGTDKAQDMSVLGGFIADIMEN
NPKNPRIFGPDETKSNRLNKVFDVTNRQWVEPRELSDEWQSAVGRVIDGQLSEHQAEG
FLEGYTLTGRHGFFASYEAFLRIVDSMLTQHFKWIRKANEKSWRKKYPSLNVISSSTAF
QQDHNGYTHQDPGVITHLAEKKPEYIREYFPADANSLMAVMDKALKDENVINLITSSK
HPRPQFYSVEEAQELVDYGVKKIDWASNDQDSEPDIVFAAAGSEPNLEALAAISILHEQF
PEMKIRFINVVDLLKLRHPDVDPRGLSDEAFDELFTTDKPVIFNFHGYEGLIRDIFFTRHN
RNLSIHGYREDGDITTPFDMRVKNELDRFHLAKDAANTIYAEKAADFIQEMDKTLQYH
HDYIRENGDDISEVQNWEWKDLK (SEQ ID NO: 29)
```

Amino acid sequence for a phosphoketolase enzyme from *Melissococcus plutonius* DAT561
```
MTKYDSKEYLAKVDAFWRAANYISVGQLYLKDNPLLDRPIETTDVKVHPIGHWGTISG
QNFIYAHLNRVINKYDLNMFYVEGPGHGGQVMVSNSYLDGSYTEIYPEITEDKEGLKKL
FKQFSFPGGIASHAAPETPGSIHEGGELGYSISHATGAILDNPDVIAATVVGDGEAETGPL
SAGWFANTFINPVNDGAILPILYLNGGKISNPTILERKSDEELTKYFEGMGWKPYFVEGT
VPDKVHPLMAKILDHIIEEIKDIQKEARKDKAENAKMPHWPVLIMRTPKGWTGPKIWD
DEKIEGTFRAHQVPIPVDAEHMEHIDALVDWLKSYHPEELFDKNGTLKPELKELVPKGD
RRMAKNPITNGGLDPKPLKMNGWEQHAIDTSTPGMVTAQDMIVFGNYVEDLIKANPTN
FRIFGPDETKSNRLNKVFDSTDRQWMEPISNADEWQSSVGRVIDGQLSEHQAEGFLEGY
ILTGRHGFFASYESFLRVVDSMLTQHFKWLRKAKEQSWRKEYPALNIIATSTVFQQDHN
GYTHQDPGILTHLAEKKAEYIREYLPADANCLMAVMDKAFQENEVINLIVSSKHPRPQF
YSVTEAKELVDKGVKVIDWASNDEGQTPDIVIAASGTEPNLEALAAITLLNKEFIDLKIR
FVNVVDILKLRHPSIDPRGLTDEEFDAIFTKDKPIVFAFHGFEGLIRDIFFSRSNHQLFVHG
YREKGDITTPFDMRVLSEMDRFHLAKDVADKVYNEQAADFMNRMDEILAFHHQYIRK
NGIDIPEVVNWKEDLRKKTICFN (SEQ ID NO: 30)
```

Amino acid sequence for a phosphoketolase enzyme from *Mycoplasma arthritidis* 158L3-1
```
MKKTNYDSNEYFNLIDKWFRAANYLSVGQIYLRNNPLLKTKLVADDVKIYPIGHWGTI
PGQNFIYAHLNRVINKYDLEMFYIEGPGHGGQVMISNSYLDGSYTEIYPEITEDEAGLKT
MFKRFSFPGGTASHAAPETPGSIHEGGELGYALSHATGAILDNPNVIAATVIGDGEAETG
PLAAGWFSNSFINPVNDGAVLPIIHLNGAKISNPTILSRKSNQELENYFSGLGWEPLFVEG
DDPKLMHPLMAKKLDEAIEKIQMIQASARKHKASEATRPVWPMLIVRTPKGWTGPKD
WNGEVVEGSFRAHQVPIPVNALNMTHIDKLEAWLTSYHPEELFDKNGKILEEIRALAPK
GLKRMAVHPITNGGINPRTLKLSSWEKFATKFETPGQIKGQDMIELGKYFAEIITLNKDN
FRIFGPDETKSNRMNAVFNVTKRQWLEKIAPTYDEWMSPEGRVIDSQLSEHQAEGFLEG
YVITGRHGVFASYEAFLRVVDSMLTQHMKWMKKSLELPWRKDFPSLNVIATSTAFQQD
HNGYTHQDPGLLGHLADKRPELIREYLPADTNCLLATMEKALKDRNVINLIVASKQPRE
QFYSVEEASELVQKGYKIINWASNVSKNEEPDVVFAAAGVEPNLEALAAISILNKEFPNL
KIRFVNVLDLLKLKSPKHDPRGISDEEFDQIFTKNKPIIFAFHGYEGLLRDIFFDRHNHNLI
THGYRENGDITTSFDIRQLSHMDRFHIAKDAAIAALGKDGEMFAKKMDSKLQEHTSYV
REYGYDLPEVVNWKWTNLKPIK (SEQ ID NO: 31)
```

Amino acid sequence for a phosphoketolase enzyme from *Streptococcus agalactiae* NEM316
```
MSEFDTKSYLEKLDAWWRAANYISAAQMYLKDNPLLRRELVENDLKVHPIGHWGTVP
GQNFIYAHLNRAINKYDLDMFYIEGPGHGGQVMVSNSYLDGSYTELNPNIEQTEDGFK
QLCKIFSFPGGIASHAAPETPGSIHEGGELGYALSHATGAILDNPDVIAATVIGDGEGETG
PLMAGWLSNTFINPVNDGAVLPIFYLNGGKIHNPTIFERKTDEELSQFFEGLGWKPIFAD
VVELSEDHAAAHALFAEKLDQAIQEIKTIQSEARQKPAEEAIQAKFPVLVARIPKGWTGP
KAWEGTPIEGGFRAHQVPIPVDAHHMEHVDSLLSWLQSYRPEELFDESGKIVDEIAAISP
KGDRRMSMNPITNAGIVKAMDTADWKKFALDINVPGQIMAQDMIEFGKYAADLVDAN
PDNFRIFGPDETKSNRLQEVFTRTSRQWLGRRKPDYDEALSPAGRVIDSQLSEHQAEGFL
EGYVLTGRHGFFASYESFLRVVDSMVTQHFKWLRKSKTHTTWRKNYPALNLIAASTVF
QQDHNGYTHQDPGILTHLAEKTPEYIREYLPADTNSLLAVMDKAFKAEDKINLIVTSKH
PRPQFYSIAEAEELVAEGYKVIDWASNVSLNQEPDVVFAAAGTEPNLEALAAISILHKAF
PELKIRFVNVLDILKLRHPSQDARGLSDEEFDKVFTTDKPVIFAFHSYEDMIRDIFFSRHN
HNLHTHGYRENGDITTPFDMRVMSELDRFHLAQDAALASLGNEAQAFSDEMNQMVAY
HKDYIREHGDDIPEVQNWKWENIK (SEQ ID NO: 32)
```

Amino acid sequence for a phosphoketolase enzyme from *Mycoplasma agalactiae* PG2
```
MKKSHDFDSKEYLNLVDAWWRAANYLSVGQMYLRNNPLLKIPLTSNDVKIYPIGHWG
TVPGQNFIYAHLNRIINKYDLNMFFISGPGHGGQVIASNTYLDGSYTELFPHVTKDIKGM
THLFKYFSFPGGTASHAAPECPGSIHEGGELGYSLSHAAGAVLDNPDVIAATVIGDGESE
TGPLSAGWFINSFINPANDGAVLPILHVNGGKISNPTIWSRRSNEELVSYFTGAGWKPFIV
EGNEPEYMHHEMAKALDASVELIKQYQAEARKNGANKAKRPQWPMIVLKSPKGWTG
PKEWNHEAIEGSFRAHQVPVPVSAEKMQHIDALENWLRSYRPEELFDENAQLKPEIAAI
APKGDRRMGKNPIANGGINPRAINVGDWTKFALDIKQPGKVINQDMVTLGSYLGELSL
LNKDNFRVWGPDEHKSNRLYEMFKVTDRQWLDRIDEKYDEFLSSVGRIIDSQLSEHQA
EGMLEGYVLTGRHGVFASYESFLRVVDSMLTQHMKWVKKALDIPWRNDYPSLNVIAT
SNAFQQDHNGYTHQDPGLIGHLADKRPELIREYLPADTNTLATMAKALQDRNVINLIIS
SKQPRHQFFSIEEATELVEKGIKIIDWASNIKPNEEPDLVVAASGTESTIESLATITYLRAH
FPELKIRFVNVLDLLKLRHPSIDPRGLSDSEFDSIFTKDKPILFAFHGYEAILRDIFFLRSNH
NIITHGYRENGDITTAFDIRLLSEMDRFHMTANVAKKLAPVVGESKANELVKLMEDKIK
EHRAYIKEYGTDLPEVKEWEWTPYK (SEQ ID NO: 33)
```

Amino acid sequence for a phosphoketolase enzyme from *Streptococcus gordonii* str. Challis substr. CH1
```
MTTDYNSKAYLEKVDAWWRAANYISAAQMYLKDNPLLKRDVVANDLKAHPIGHWG
TVPGQNFIYAHLNRTINKYDLDMFYIEGPGHGGQVMVSNSYLDGSYTELNPNIPQNEEG
```

| SEQUENCES |
|---|
| FKHLCKIFSFPGGIASHAAPETPGSIHEGGELGYALSHAAGAILDNPDVIAATVIGDGEGE<br>TGPLMAGWLSNTFINPVNDGAILPIFYLNGGKIHNPTIFERKTDEELTLFFEGLGWKPIFA<br>DVTAISENHEAAHALFAAKLDEAIEEIKKVQAEARKGSAEEATQAIFPVLVARIPKGWT<br>GPKSWEGTPIEGGFRAHQVPIPVDAHHMEHVDALLNWLKSYRPEELFDESGKVLPEIAA<br>IGPKGDRRMAMNPITNAGVIKPMDTADWKKHALKFGTPGEIVAQDMIEFGKYATDLVD<br>ANPDNFRIFGPDETKSNRLQEVFTRTSRQWLGRMRPEYDEALSPAGRVIDSQLSEHQAE<br>GMLEGYVLTGRHGFFASYESFLRVVDSMVTQHFKWLRKCKTHTTWRKNYPALNLIAT<br>STVFQQDHNGYTHQDPGILTHLAEKTPEFIREYLPADTNSLLAVMDKAFKAEDKVNLIV<br>TSKHPRPQFYSAEEAEELVREGYKVIDWASTVSNNEEPDVVPAAAGTEPNLEALAAVSI<br>LHKAFPELKIRFVNVVDILKLRHPSVDARGLSDEEFDQVFTTDKPVIFAFHGYEGMIRDIF<br>FNRHNHNLRVHGYRENGDITTPFDMRVMSELDRFHLAQDAANAALGEDAAVFSAKMD<br>ETVAYHNAYIRENGDDIPEVQNWKWENINK (SEQ ID NO: 34)<br><br>Amino acid sequence for a phosphoketolase enzyme from *Kingella oralis* ATCC 51147<br>MQNTQFDTPEYLAKVDAWWRAANYISAAQMYLKDNPLLKKPLTANDVKAHPIGHWG<br>TVPGQNFIYAHLNRAINKYDVDMFYIEGPGHGGQVMVSNSYLDHSYTDIYPEITQDEAG<br>LKKLCKIFSFPGGIASHAAPETPGSIHEGGELGYALSHAFGAVLDNPNIIAAAVIGDGEAE<br>TGPLCAGWFGNTFINPVNDGAVLPILYLNGGKIHNPTILARKTDAELTQYFNGMGWEPI<br>FVEVSDPAHSHAIMAQKLDEAVERILAIWQDARSRSANDATMPRWPVLVARIPKGWTG<br>PKTWNGEPIEGGFRAHQVPIPTNSHDMSTADALEAWLRSYRPEELFDDNGRFLDKWREI<br>SPKGAKRMSVHPITNGGVAPKALVMPDWTKHALKIGTPGSQDAQDMIECGRLMADVIT<br>ANPDNFRIFGPDETKSNRLNEVFKVTNRQWLGVRDAAYDEWIAPVGRVIDSQLSEHQA<br>EGFLEGYVLTGRHGFFASYESFLRVVDSMITQHFKWLRKCKTHAPWRKDYPSLNLIATS<br>TVFQQDHNGYTHQDPGLLTHLAEKKPEFVREYLPADANTLLAVMSEALTSRDRINLIVS<br>SKHLRPQFYSADEAKELVREGYKIIEWASTCHDGEPDVVIAAAGTEPNMEALAAINVLH<br>KHYPEMKIRFINVVDILKLRHPSIDPRGLSDEAFDALFTRDKPVVFCFHGYENMVRDIFF<br>PRHNRNVRIHGYRENGDITTPFDMRVLSEMDRFHVAKDAAQAVYGEKAADFANKMDE<br>TIQFHRSYIREHGKDIPEVAEWKWQPLAK (SEQ ID NO: 35)<br><br>Amino acid sequence for a phosphoketolase enzyme from *Mycoplasma fermentans* M64<br>MNKKEFDSKEYLEKVDAWWRAANYLSVGQIYLRNNPLLKHPLTSDDVKVYPIGHWGT<br>ISGQNFAYAHLNRVINKYDLNMFYIEGPGHGGQVMTSNSYLDGSYTELFPHVTQDEAG<br>MQHLFKYFSFPGGTASHAAPETPGSIHEGGELGYSISHATGAILDNPDVIAATIVGDGEA<br>ETGPLATSWFSNSFINPVNDGAVLPILHLNGGKISNPTILSRKSNEELQQYFRGMGWEPH<br>FVEGDKPEVMHELMAKTLDSVIEEIQSIQTKARKKPADKAKRPVWPMIVLRTPKGWTG<br>PKSWNKEAIEGSFRAHQVPLPINAENMEHADALEKWLRSYRPEELFDKKGKLVKEIAAI<br>APKGKRRMGMNPITNGGINPKVMKLGDWRKFALHFDRPGSVVAQDMVELGTYFADL<br>VKRNPENFRIFGPDETKSNRLYNLFKVTNRQWMERIDSKLDEALSPVGRIIDSQLSEHQA<br>QGFLEGYVLTGRHGIFASYESFLRVVDSMVTQHMKWLRKAKEINWRKDYPSLNIMATS<br>TAFQQDHNGYTHQDPGIIGHMADKRPELIREYLPADTNTLLAVMDKAFTERNVINLIVS<br>SKQPRHQFYSVEEAETLVEKGLDIIDWASTCSRNETPDLVVVASGTEPNLEALATISILN<br>KEYPSMKIRFVNVVDLLKLRHPKIDPRGLSDEEFDEIFTKDKPVLFAFHGFEGILRDIFFD<br>RHNHNLIAHGYRENGDITTSFDIRQLSHMDRFHMASDAAAAVFGSSKAKEFMDKMEET<br>IQFHNKYIREVGTDIPEVKNWKWEGLIK (SEQ ID NO: 36)<br><br>Amino acid sequence for a phosphoketolase enzyme from *Granulicatella adiacens* ATCC 49175<br>MTQFDTPEYLAKVDAWWRAANYISVAQMYLKDNPLLRRPIQKEDVKLHPIGHWGTIA<br>GQNFIYAHLNRAINKYDLDMFYIEGPGHGGQVMVSNSYLDGSYTELYPQITQDEAGFK<br>QLCKIFSFPGGIASHAAPETPGSIHEGGELGYSLSHATGAVLDNPNVIAAAVIGDGEAET<br>GPLAAGWFSNTFINPVNDGAVLPILYLNGGKIHNPTILARRTDEELTQFFNGLGWDPIFV<br>EGTDPEKVHPLMAAKLDEAIEKIQAIQKEARAKSAEEATMPHWPVLVVRTPKGWTGPK<br>EWNHEPIEGGFRAHQVPIPVSGEAMEHVDALVDWLKSYRPEELFDENGKLVEEIAAISP<br>KGPRRMSMNPITNAGVVKPMEITDWTKHAIDTSKPGAIQKQDMIEFGKFAADLVKANP<br>DNFRIFGPDETKSNRLNEVFKATNRQWVGRRDESYDEWISPVGRVIDSQLSEHQAEGFL<br>EGYVLTGRHGFFASYESFLRVVDSMITQHFKWLRKAKTHAPWRKNYPSLNLIATSTVF<br>QQDHNGYTHQDPGLLTHLAEKKPEFVREYLPADTNSLMAVMAEALSSEDKINLIVSSK<br>HPRPQFYSVEEAKELVSEGYKVIDWASTVKEGEEPDVVIAAAGTEPNLEALAGISILHKQ<br>FPELKIRFINVVDILKLRSPKVDPRGLSDEEFDKLFTTDKPVVFCFHGYEGMIRDLFFDRN<br>NHNVIHGYRENGDITTPFDMRVLSEMDRFHVAKDAAVAVYGEKASEFAAKMDETVE<br>FHHSYIREHGEDIPEVVSWQWENVNK (SEQ ID NO: 37)<br><br>Amino acid sequence for a phosphoketolase enzyme from *Mycoplasma hominis* ATCC 23114<br>MISKIYDDKKYLEKMDKWFRAANYLGVCQMYLRDNPLLKKPLTSNDIKLYPIGHWGT<br>VPGQNFIYTHLNRVIKKYDLNMFYIEGPGHGGQVMISNSYLDGSYSEIYPEISQDEAGLA<br>KMFKRFSFPGGTASHAAPETPGSIHEGGELGYSISHGTGAILDNPDVICAAVVGDGEAET<br>GPLATSWFSNAFINPVNDGAILPILHLNGGKISNPTLLSRKPKEEIKKYFEGLGWNPIFVE<br>WSEDKSNLDMHELMAKSLDKAIESIKEIQAEARKKPAEEATRPTWPMIVLRTPKGWTG<br>PKQWNNEAIEGSFRAHQVPIPVSAFKMEKIADLEKWLKSYKPEELFDENGTIIKEIRDLA<br>PEGLKRMAVNPITNGGIDSKPLKLQDWKKYALKIDYPGEIKAQDMAEMAKFAADIMK<br>DNPSSFRVFGPDETKSNRMFALFNVTNRQWLEPVSKKYDEWISPAGRIIDSQLSEHQCE<br>GFLEGYVLTGRHGFFASYEAFLRVVDSMLTQHMKWIKKASELSWRKTYPSLNIIATSNA<br>FQQDHNGYTHQDPGLLGHLADKRPEIIREYLPADTNSLLAVMNKALTERNVINLIVASK<br>QPREQFFTVEDAEELLEKGYKVVPWASNISENEEPDIVFASSGVEPNIESLAAISLINQEY<br>PHLKIRYVYVLDLLKLRSRKIDPRGISDEEFDKVFTKNKPIIFAFHGFEGLLRDIFFTRSNH<br>NLIAHGYRENGDITTSFDIRQLSEMDRYHIAKDAAEAVYGKDAKAFMNKLDQKLEYHR<br>NYIDEYGYDMPEVVEWKWKNINKEN (SEQ ID NO: 38) |

-continued

SEQUENCES

Amino acid sequence for a phosphoketolase enzyme from Mycoplasma crocodyli MP145
MKKTVYDTELYIEKLDAWFRAANYLSVGQMYLRNNPLLRNKITKDDVKVYPIGHWGT
IPGQNFAYAHLNRVINKYDLNMFYIEGPGHGGQVMTSNSYLDGSYTELFPHVTQDLDG
MKHLFKYFSFPGGTASHAAPETPGSIHEGGELGYSLSHATGAILDNPNVIAATIVGDGES
ETGPLAAGWFSNSFINPVNDGAVLPILHLNGGKISNPTILCRKSNEELTNYFLGMGWEAI
FVEGEDVQKMHKLMATKLDYAIERILSIQKEARKGKAEEEATRPLWPMIVLRTPKGWTG
PQKWNSDQIVGSFRAHQVPIPVNSENMTHIDALVDWLKSYNVDNLFDKKGKLVPEIAEI
APVGDRRMGMNPVTNGGLNPRNLALPNWQDFALNLEKPGAKIAQDMVELGSYFAKV
MEMNKDNFRLFGPDETKSNRLFNVFKVTSRQWLEPINPLFDEALSPAGRVIDSQLSEHQ
AEGFLEGYVLTGRHGVFASYESFLRVVDSMLTQHMKWLKKANDVSWRNDYPSLNVIA
TSTAFQQDHNGYTHQDPGLIGHLADKTPELIRQYLPADTNTLLAVMDKSLTERNVINHII
ASKQPREQFYSAKEAAELVEKGLKVIKWASTVEGNDEPDLVVAAAGTEPNLEALAAITI
LNKEFPKLKIRFVNVVDLMKLRHPSIDPRGITDKEFDKIFTKDKPVLFAFHGYEGILRDIF
FKRNNHNLIAHGYRENGDITTSFDIRQLSHMDRFHMAASAAVAALGKKANAFETKMLE
TIDFHTKYIREYGTDIPEVKEWKWNPLVRK (SEQ ID NO: 39)

Amino acid sequence for a phosphoketolase enzyme from Neisseria sp. oral taxon 014 str.
F0314
MSAQYDSADYLNKVDAWWRAANYISVAQMYLKDNPLLMRPIQASDVKAHPIGHWGT
IAGQNFIYAHLNRAINKYDLNMFYIEGPGHGGQVMVSNSYLDGSYSEIYPNITQDEAGL
KQLCKIFSFPGGIASHAAPETPGSIHEGGELGYALSHAVGAVLDNPDVIAATVIGDGEAE
TGPLSAGWFSNVFINPVNDGAVLPILYLNGGKIHNPTILARKSDESLRLYFEGLGWDPIF
VEATDYATTHKVMAQKLDEAIEKIKAIQTKARAGKAEEEAVMPKWPVLVARLPKGWTG
PKVWNGEPIEGGFRAHQVPIPASSHDMATVDSLVEWLKSYRPEELFDANGTFKAELREI
SPKGDRRMSTNPITNGGINPRPLNTADWKKFALDNSDRGSIMAQDMIEFGKYAAELVK
ANPDNFRIFGPDETKSNRMNEVFKVTNRQWLEPIDKAYDEWMSPAGRVIDSQLSEHQA
EGFLEGYVLTGRHGFFASYESFLRVVDSMATQHFKWLRKCKTHAPWRKSYPSLNLIAT
STVFQQDHNGYTHQDPGMLTHLAEKKPEFIREYLPADANSLLAVMSEVLSSKDKVNLI
VSSKHPRPQFYSAAEAEELVREGYKVIDWASTDKGGEPDVVIAAAATEPNLEALAAITIL
NKQFPELKIRFINVVDILKLRHPKVDPRGLTDEQFDALFTKDKPVIFCFHGYEGMVRDIF
FDRHNHNLRIHGYRENGDITTPFDMRVLSEMDRFHVAKDAALAVYGDKAQDFAKKMD
DTLAFHHSYIRENGEDIPEVRNWKWEALK (SEQ ID NO: 40)

Amino acid sequence for a phosphoketolase enzyme from Eremococcus coleocol aACS-139-V-
Col8
MTVDYNSKEYLTLVDKWWRAANYLSVGQMFLRDNPLLQEEVTADHVKLNPIGHWGT
IGGQNFLYAHLNRIINKYNVNMFYIEGPGHGGQVMVTNSYLDGSYTERYPEFTQDIAG
MKKLFKTFSFPGGIGSHAAPETPGSMHEGGELGYALSHATGAILDNPDVIAATVVGDGE
AETGPLAAGWFSNVFINPVSDGAVLPILYLNGGKIANPTILARKSNEDLTKYFEGMGWK
PYIVEGTDPEQVHPIMAKVLDEVIEEIQAIQAEARKGKAEDAKMPHWPMILYRTPKGWT
GPEEVEGKTIQGSFRAHQVPIPVSGRNMEDIDLLINWLKSYGPEELFTENGELVDELKEF
APKGDHRMAMNPLTNGGNPKPLNMPNWKDYALEIGTPGSKDAQDMIEFGGFARDIVK
ENPENFRIFGPDETKSNRLNKVFEVTNRQWLEPISEKFDENMSASGRVIDSQLSEHQNQG
FLEAYVLTGRHGFFASYESFFRTVDSMITQHFKWIRKSAKHSWRKPYQSLNLISASTVFQ
QDHNGYTHQDPGLLTHIGEKHGEYMRAYLPADTNSLLAVMDKAFRSENVINYVVTSK
HPRPQFFTADEAEELVNEGLKVIDWASTVKDNEEPDVVIAAAGTEPNFEAIAAISYLVK
AFPELKIRFVNVVDLFRLRSPEIDPRGLSDDEFDAIFTKDKPVFFAFHSYEGMLKDIFFTR
HNHNLYAHGYRENGEITTPFDMRVLNELDRFHLSAHVADVVYGDKARDYVAEMKGK
VQEHRDYVEEYGADMPEVEDWKWEDIK (SEQ ID NO: 41)

Amino acid sequence for a phosphoketolase enzyme from Aerococcus urinae ACS-120-V-
Col10a
MTDFDSKAYLDKVDAWWRAANYLSVGQMYLRDNPLLDREVTADDIKITPIGHWGTIA
GQNFVYAHLNRVINKYDLNMFYIEGPGHGGQVMQANAYLDGTWTEHYPEYPQNKEG
MQKFFKYFSFPGGTGSHATAEIPGSIHEGGELGYSLSHATGAILDNPDVIAATVIGDGESE
TGPLAASWLSNSFINPVTDGAVLPILYLNGGKIANPTILERKSNEDLIKYFQGLGWDPMV
VEGNDPEKVHPLMAKTLDQAIEKIKISIQGEARKGSADEATMGHWPMILYRTPKGWTP
KAWEGNDIEGSFRAHQVPIPVNAENMEHVDALIDWLKSYRPEELFTEEGQLRPEIAEIAP
KGDQRMASNPITDGGIDPKPLDLPDWRDYALDFETPGERDAQDMIEMGGYAAGVIEKN
PDNFRIFGPDETKSNRLNKVFNVTKRQWLEPIKDNYDEWMSPSGRVIDSQLSEHQMEGF
LEAYTLTGRHGFFASYEAFIRTVDSMITQHFKWMREASEYKWHKPYQSLNLISSSTAFQ
QDHNGYTHQDPGLLTHLAEKKGEFVRAYLPADTNSLLAVMDKALSSENVINYIVTSKH
PRPQFFSVEEAEEFVDKGYKVIDWASTVEEGEEPDVVIAASGTEPTVETIATISYLHEAFP
ELKIRYVNVVDLYRLRHPNIDPRGLSDEEFDAVFTKDKPVFFGFHSFEGLLKDIFFDRHN
HNLYPHGYREEGAITTPFDMRVLNELDRFHFAAHVAEVVYGDKAQDFIDQMNAKVEE
HRAYIVEYGTDMPEVKEWKWQPLEK (SEQ ID NO: 42)

Amino acid sequence for a phosphoketolase enzyme from Kingella kingae ATCC 23330
MTNKTQFDTPEYLGKVDAWWRAANYISVAQMYLKDNPLLKTPLVANDVKAHPIGHW
GTVPGQNFIYAHLNRAINKYDVDMFYIEGPGHGGQVMVSNSYLDGSYTEIYPDITQDTA
GLKKLCKIFSFPGGIASHAAPETPGSIHEGGELGYALSHAFGAVLDNPNVIAAAVIGDGE
AETGPLCAGWFGNTFINPVNDGAVLPILYLNGGKIHNPTILARKTDEELKQYFNGMGWE
PIFVDVNNVDNYHEIMSQKVDEAVEHILSIWQTARTQKAEDATMPHWPVLVARIPKGW
TGPKTWHGEPIEGGFRAHQVPIPASSHDMETAGELEKWLRSYRPEELFDDNGCFLDKW
RDISPKGAKRMSVHPITNGGINPKALVMPDWTQHALEIGVPGSQDAQDMVECGRLMA
DVVTANPNNFRIFGPDETKSNRLNQVFQVTKRQWLGRRDEAYDEWIAPVGRVIDSQLS
EHQAEGFLEGYVLTGRHGFFASYESFFRVVDSMITQHFKWLRKCKTHAAWRNDYPSLN

| SEQUENCES |
| --- |
| LIATSTVFQQDHNGYTHQDPGLLTHLAEKKPEFVREYLPADSNTLMAVMSEALTSRDRI<br>NLIVSSKHLRPQFFNAEEAKELVREGYKVIDWASTCHDGEPDVVIAAAGTEPNMEALA<br>AISILHKQFPELKIRFINVVDILKLRHPSIDPRGLSDEQFDALFTQEKPVVFCFHGYEGMIR<br>DLFFPRANHNVRIHGYRENGDITTPFDMRVLSEMDRFHVAKDAAQAVYGDKASEFAK<br>KMGETVAFHRSYIREHGTDIPEVAEWKWQPLAK (SEQ ID NO: 43)<br><br>Amino acid sequence for a phosphoketolase enzyme from *Streptococcus criceti* HS-6<br>MNTNFDSSDYLNKVDAWWRAANYISAAQMYLKDNPLLRREVAAEDLKSHPIGHWGT<br>VPGQNFIYAHLLRSINKYDLDMFYIEGPGHGGQVMVSNSYLDGSYTELNPQISQTEEGL<br>KQLCKIFSFPGGIASHAAPETPGSIHEGGELGYALSHATGAVLDNPDVIAATVIGDGESET<br>GPLMAGWLSNTFINPVNDGAVLPIHFLNGGKIHNPTIFERKSDDELKAFFTGLGWKPIFA<br>DVTAFASDHAAAHKLFAAKLDEAIEEIRNIQAKARKGSADEATMPAWPVIVARIPKGW<br>TGPKSWKGTPIEGGWRAHQVPIPVDSHHMEHVDALLDWLKSYQPEELFDAEGHLKSEV<br>AALSPKGNRRMSMNPITNAGVIKPMDTADWKKRAFDIQTPGEIVAQDMIEFGKYAADL<br>VEANPDNFRIFGPDESKSNRLNEVFTKTNRQWMGRRDPSYDEWLSPAGRVIDSQLSEHQ<br>AEGFLEGYVLTGRHGFFASYESFLRVVDTMITQHFKWLRKSKTHTTWRKNYPSLNLIAT<br>STVFQQDHNGYTHQDPGVLTHLSEKTPEYIREYLPADTNSLLAVMDKAFKDEDKINLIV<br>TSKHPRPQFYSVEEASELVEKGYKVIDWASTVQANEEPDVVFAAAGTEPNLEALAAISIL<br>HKTFPSLKIRFVNVVDILKLRHPDLDPRGLSDEEFDKVFTKDKPVIFAFHAYEGMIRDIFF<br>RRHNHNLHVHGYRENGDITTPFDMRVMSELDRFHLAQDAALTTLGEKAQAFSAKMDE<br>TVAYHKDYIREHGDDIPEVQNWQWENLDE (SEQ ID NO: 44)<br><br>Amino acid sequence for a phosphoketolase enzyme from *Streptococcus criceti* HS-6<br>MTEFDSKDYLAKVDAWWRAANYISVAQMYLKDNPLLRREVSKEDVKVHPIGHWGTIA<br>GQNFIYAHLNRVINKFDLNMFYIEGPGHGGQVMVSNSYIDGSYTERYPNITQDEDGLKQ<br>LCKIFSFPGGIASHAAPETPGSIHEGGELGYALSHATGAILDNPDVIAATVIGDGEAETGP<br>LNAGWFSNTFINPVNDGAVLPILYLNGGKIHNPTILSRKTDEELTHLFQGLGWEPYFVEG<br>NDPEVIHSQMAETLDKVIEKIKTIQTQARQKPAEEAQQAQWPVLIVRTPKGWTGPKEW<br>NGEPIEGGFRAHQVPIPVEAGHMEHIDALTDWLKSYRPEELFDEKGYVKEEIRVISPKGN<br>RRMSMNPITNAGIVKKLDLADWRKHAIDTSKPGSIMKQDMIEFGKYAADLVKANPDNF<br>RIFGPDETKSNRLNNVFTATNRQWLAPRDKSYDEWISPVGRVIDSQLSEHQAEGFLEGY<br>VLTGRHGFFASYESFLRVVDSMITQHFKWLRKSKTHTDWRKNYPSLNLIATSTVFQQD<br>HNGYTHQDPGLLTHLAEKTPEYVREYLPADSNSLFAVMEYALADEDKVNVIVTSKHPR<br>PQFYSVAEAQELVKEGYKVIDWASNDHDGEPDIVFAAAGTEPNLEVLAGISLLHKAFPE<br>VKIRFINVVDILKLRSPKVDPRGLSDEAFNKLFTTDKPIVFAYHGYEGQIRDLFFNRDNH<br>KVYIHGYRENGDITTPFDMRVMSEMDRFHIAKEAAQAVLGDKAQGFAQEMADKLAYH<br>TAYIREHGDDIPEVQNWQWETID (SEQ ID NO: 45)<br><br>Amino acid sequence for a phosphoketolase enzyme from *Mycoplasma columbinum* SF7<br>MSKTNFDSKKYLDKIHAWWRAANYLSVGQMYLKNNPLLQEPLKDEDIKIYPIGHWGTI<br>PGQNLIYAHLNRVINKYDLNMFYIEGPGHGGQVMISNSYLDGSYTELFPEITQDLAGLN<br>KMFKRFSFPGGTASHAAPETPGSIHEGGELGYALSHATGAILDNPDVIAATVIGDGEAET<br>GPLMAGWYSSSFINPVNDGTVLPILHINGGKISNPTILARKTDKEIKQLLAGFGWEAIFVE<br>ADVFRPEAIHLSMAKAFDKAIEKIQRIQREARANSANHAKRPIWPALVVRTPKGWTCPH<br>KIDDKVYEGSFRSHQVPLAVSSENTTKKVDLVNWLESYKPRELFNQDGSFKAHYAEIAP<br>KGNKRMAMNPITNGGINPKNLDLPNWEQFAIDFDKPGAIKAQDMVSAGTWFADVIKR<br>NPTNFRIFGPDETKSNRLFDVLKTTNRQWLERVDYDLDENIGPAGRVIDSQLSEHQAEG<br>FLEGYVLTGRHGMFASYESFLRVVDSMLTQHMKWVAKAKKVHWRNDYPSLNVIATST<br>APQQDHNGYTHQDPGILGHLADKKPELIREYLPADSNTLLAVLDKAFKERDVINLIVAS<br>KQPREQWFSPREANILVKNGLKVISWASTCTLEEEPDLVVAAAGTEPTLEALAAISYLNE<br>KFPTLKIRFVNVVDLLKLRHPSIDPRGLSNYEFDSIFTKDKPILFAHGYEALIRDIFFLRN<br>NHNLHIHGYRENGDITTSFDIRLMSEMDRFHMAQTAAKAVLGYDKAKSFVDKMQDKI<br>DQHNAYIKEHGIDMDEVRYWTWKGLNK (SEQ ID NO: 46)<br><br>Amino acid sequence for a phosphoketolase enzyme from *Burkholderia phytofirmans* PsJN<br>MAEATAHPTPPQTLDADTLRNMDRYWRACNYLSAGMIYLRDNPLLREPLKPEHIKNRL<br>LGHWGSDPGQSFLLVHLNRLIKKLDLNVIYVAGPGHGAPATLANCYLEGHYSEIYPDRS<br>QDVAGMERFFRQFSFPGGIGSHCTPETPGSIHEGGELGYSLSHGYGAAFDNPDLIVAVMI<br>GDGEAETGPLATSWHSNKFLNPIRDGAVLPVLHLNGYKIANPTILARIPREELEALLTGY<br>GHKPYFVEGEDPAVMHQQMAATLEQCIGEIRAIQQHARESNDASRPRWPMIVLRSPKG<br>WTGPKEVDGHKVEGSWRAHQVPVLDPATNSKSLKLVENWLRSYEPETLFDEAGRLVK<br>ELRELAPEGARRISANPHANGGVLCKTLAMPPFRDYAVAVKKPAGSYTSPTEVLGKFLR<br>DVMRNNMTNFRVFGPDETSSNKLTAIYEASEKTWLAQTVPSDADGGELAVDGRVMEM<br>LSEHTLEGWFEGYVLTGRHGLFATYEAFVHVIDSMFNQHAKWLEKAKRDLGWRQPVP<br>SINLLITSLVWRQDHNGFTHQDPGFLDVVTNKSPDVVRIYLPPDANCLLSVADHCLRSR<br>DYVNVIVADKQPHLQYLDMDAAVTHCTKGIGIWDWASTDQGVEPDVVMACAGDIPT<br>MEALAAVQILKEQFADLKIRFVNVVDLFRLMPEHAHPHGLSSRDFDSLFTTDKPVIFNFH<br>SYASLVHKLTYNRTNHDNLHVHGYHEKGNINTPLELAIINQVDRFSLAIDVIDRVPRLRG<br>VGDHAKEWLRGQIIEHLAYAHAEGIDKEEIRNWTWKG (SEQ ID NO: 47)<br><br>Amino acid sequence for a phosphoketolase enzyme from *Lactobacillus buchneri* NRRL B-30929<br>MTVDYDSKEYLELVDKYWRAANYLSVGQLFLRDNPLLKRPLEAKDVKVKPIGHWGTI<br>VSQNLIYAELNRVINKYDLNMFYIEGSGHGGQVMVSNSYLDGSYSDIYPNISQDEKGMA<br>KLFKQFSFPGGVASHAAPETPGSIHEGGELGYSLSHGTGAILDNPDVIAAVEIGDGESET<br>GPLAASWFSDKFINPITDGAVLPIINMNGFKISNPTILSRMSDEDLTSYFKGMGWDPYFV<br>EATADTDHAKVEEEFAKTLDHVIEEIKSIQKNARENETPDNVKLPNWPMIIFRSPKGWT |

| SEQUENCES |
|---|
| GPKKDLDGNPIEGSFRAHQVPIPVAAGSMEHKDLLNDWLKSYKPEELFDENGTVKPEIR<br>AVAPKGDKRMSVNPITNGGIKPEPLKLPDVRNFEVKFDRGVTQKQDMIEWSNWLEKVA<br>ELNPTSFRGFGPDETKSNRLYSLLDDSKRQWMEDIHEPFDEDLSNHGRVIDSQLSEHQA<br>EGWLEGYVLTGRHGFFATYESFGRVVDSMLTQHFKWLRKASEQYWRKQYPSLNFVDT<br>STVFQQDHNGYTHQDPGMLTHLAEKKPEFIREYLPADANELLAVGDVAFRTYEKINLIV<br>TSKHPRRQWYTMDEAQNLVKNGLGYIDWASTDQGQEPDVVFAAAGSEPNLEALAAISI<br>LNKEFPEMKIRFINVVDLLKLRSPKVDPRGLSDEEFDNLFTTDKPVIFAFHGFEDLIKDIFF<br>DRHNHNLHVHGYRENGDITTPFDMRVLNQLDRFDLAKEAVQDIPAYTVKGGYFIQRM<br>NDMVDKHNAYIRQEGTDLPEVVDWKWEGLKK (SEQ ID NO: 48)<br><br>Amino acid sequence for a phosphoketolase enzyme from *Bifidobacterium gallicum* DSM 20093<br>MTSPVIGTPWQKLNRPVSEEAIEGMDKYWRASNYMSIGQIYLRSNPLMKEPFTRDDVK<br>YRLVGHWGTTPGLNFLLAHINRLIADHQQNTVFIMGPGHGGPAGTAQSYLDGTYTEYY<br>PNITKDEEGLQKFFRQFSYPGGIPSHFAPETPGSIHEGGELGYALSHAYGAVMNNPSLFV<br>PCIVGDGEAETGPLATGWQSNKLVNPRTDGIVLPILHLNGYKIANPTILARVSDEELHDF<br>FRGLGYHPYEFVAGFDNEDHLSIHRRFAELFETIFDEICDIKAAANTDDMTRPFYPMLIFR<br>TPKGWTCPKFIDGKKTEGSWRAHQVPLASARDTEAHFEVLCIKNWMASYKPEELFDDKG<br>AIKDDVVDFMPKGDLRIGANPNANGGVIREELDLPALENYEVKEVKEFGHGWGQLEAT<br>RKLGEYTRDIIKNNPDSFRIFGPDETASNRLQASYEVTNKQWDNGYLSKDLVDEHMAV<br>TGQVTEQLSEHQCEGFLEAYLLTGRHGIWSSYESFVHVIDSMLNQHAKWLEATVREIP<br>WRKPISSMNLLVSSHVWRQDHNGFSHQDPGVTSVLLNKTFNNDHVIGLYFATDANVLL<br>AIAEKCYKSTNMINAIVAGKQPAATWTTLDEARELVAKGAGEFEWASNVKTNDEAEIV<br>LASAGDVPTQELMAAADRLNKLGVKFKVVNVVDLIKLQSAKENDQALSDAEFAELFTE<br>DKPVLFAYHSYAHDVRGLIFDRPNHDNFNVVGYKEQGSTTTPYDMVRVNDIDRYELTA<br>TALRMIDADKYADEIKKLEDFRIEAYQFAVDNGYDIPDYTDWVWPGVKTDLPGAVSAT<br>AATAGDNE (SEQ ID NO: 49)<br><br>Amino acid sequence for a phosphoketolase enzyme from *Bifidobacterium dentium* Bd1<br>MTSPVIGTPWKKLNAPVSEEAIEGVDKYWRAANYLSIGQIYLRSNPLMKEPFTREDVKH<br>RLVGHWGTTPGLNFLIGHINRLIADHQQNTVIIMGPGHGGPAGTAQSYLDGTYTEYFPNI<br>TKDEAGLQKFFRQFSYPGGIPSHYAPETPGSIHEGGELGYALSHAYGAVMNNPSLFVPAI<br>VGDGEAETGPLATGWQSNKLVNPRTDGIVLPILHLNGYKIANPTILSRISDEELHEFFHG<br>MGYEPYEFVAGFDNEDHLSIHRRFAELFETVFDEICDIKAAAQTDDMTRPFYPMIIFRTP<br>KGWTCPKFIDGKKTEGSWRSHQVPLASARDTEAHFEVLKNWLESYKPEELFDANGAV<br>KPEVTAFMPTGELRIGENPNANGGRIREELNLPALEDYEVKEVAEYGHGWGQLEATRR<br>LGVYTRDIIKNNPDSFRIFGPDETASNRLQAAYDVTNKQWDAGYLSAQVDEHMAVTGQ<br>VTEQLSEHQMEGFLEAYLLTGRHGIWSSYESFVHVIDSMLNQHAKWLEATVREIPWRK<br>PISSMNLLVSSHVWRQDHNGFSHQDPGVTSVLLNKCFNNDHVIGIYFPVDSNMLLAVAE<br>KCYKSTDMINAIIAGKQPAATWLTLDEARAELEKGAAEWEWASTAKSNDEAQIVLASA<br>GDVPAQEIMAAADKLDAMGIKFKVVNVVDLVKLQSTKENDEAISDADFADLFTEDKPV<br>LFAYHSYARDVRGLIYDRPNHDNFNVHGYEEQGSTTTPYDMVRVNNIDRYELVAEALR<br>MIDADKYADKIDELEAFRKEAFQFAVDNGYDHPDYTDWVYSGVNTNKQGAVSATAAT<br>AGDNE (SEQ ID NO: 50)<br><br>Amino acid sequence for a phosphoketolase enzyme from *Bifidobacterium bifidum* IPLA 20015<br>MTSPVIGTPWKKLNAPVSEEALEGVDKYWRVANYLSIGQIYLRSNPLMKEPFTREDVK<br>HRLVGHWGTTPGLNFLIGHINRFIADHGQNTVFIMGPGHGGPAGTSQSYLDGTYTETYP<br>NITKDEAGLQKFFRQFSYPGGIPSHFAPETPGSIHEGGELGYALSHAYGAIMDNPSLFVPC<br>IVGDGEAETGPLATGWQSNKLVNPRTDGIVLPILHLNGYKIANPTILSRISDEELHEFFHG<br>MGYEPYEFVAGFDDEDHMSIHRRFAELFESVWDEICDIKAAANTDNMHRPFYPMIIFRT<br>PKGWTCPKYIDGKKTEGSWRAHQVPLASARDTEAHFEVLKNWLESYKPEELFDANGA<br>VKDDVLAFMPKGELRIGANPNANGGVIRKDLVLPALEDYEVKEVKEFGHGWGQLEAT<br>RRLGVYTRDIIKNNMHDFRIFGPDETASNRLQASYEVTNKQWDAGYISDEVDEHMHVS<br>GQVVEQLSEHQMEGFLEAYLLTGRHGIWSSYESFVHVIDSMLNQHAKWLEATVREIPW<br>RKPIASMNLLVSSHVWRQDHNGFSHQDPGVTSVLLNKCFHNDHVIGIYFATDANMLLA<br>IAEKCYKSTNKINAIIAGKQPAATWLTLDEARAELAKGAAAWDWASTAKTNDEAQVV<br>LAAAGDVPTQEIMAASDKLKALGIKFKVVNVADLLSLQSAKENDEALTDEEFADIFTAD<br>KPVLFAYHSYAHDVRGLIYDRPNHDNFNVHGYEEEGSTTTPYDMVRVNELDRYELTAE<br>ALRMIDADKYADEIQKLEDFRQEAFQFAVDKGYDHPDYTDWVYSGVKTDKKGAVTAT<br>AATAGDNE (SEQ ID NO: 51)<br><br>Nucleic acid sequence encoding for a phosphoketolase enzyme from *Mycobacterium gilvum* Spyr1<br>atgaccaccgccaccaccgcagaacgtcgtccgctgagcgatcaggatgttgatcgtctggatcgttggtggcgtgcagcaaattatctga<br>gcgttggtcagatttatctgctggataatccgctgctgcgtacaccgctgacccgtgaagatgttaaacgcgtctgctgggtcattggggca<br>ccacaccgggtctgaattttctgtatgcacatctgaatcgtgcaattgcccagcgtcagcagagcaccatttatgttaccggtccgggtcatgg<br>tggtcctggtctggttgcaaatgcatatctggatggcacctatagcgaaatttacagcgatattacccagcgatgaaggtctgcgtcgtctg<br>tttcgtcagtttagcttttccgggtggtattccgagccatgttgcaccggaaactccgggtagcattcatgaaggtggtgaactgggttatgca<br>ctgagccatgcatatggtgcagcatttgataacccggacctgctggttgccgcagttgttggtgatggtgaagcagaaacaggtccgctggca<br>accagctggcatagcaacaaatttgtgaatgcagccaaagatggtgccgttctgccgattctgcatctgaacggctataaaatcgcaaatcc<br>gaccctgctggcacgcattccgaccgatgaactcgtgcactgatggttggttatggtcatcatccgtatttttcgaagaccggatgacgaa<br>ggtcctccaggtgtgatcatgcagatgccatctgtcgttttgaccgtctgttagatgatgttctggatgaaattgccgatatcaaaacccgtg<br>cacgcgaaggtgatgaaagccgtccggcatggccgatgattgttttcgtaccccgaaaggttggacgggtccggattatattgatggcaaa<br>aaaaccaccggtagctggcgtgcccatcaggttccgctgtcaaatgcacgtgataccaaagaacatctggcagttctgagtgattggctga<br>gcagctatcgtcctgatgagctgtttgatgccgatggtgcctgctgccggaaattgcagaactggcaccgagcggtcagctgcgtatgag<br>cgataatgcacatgcaaatggcggtctgctgctgaaagatctgcgtctgccggattttcgtaatatgcagttgatgttccggcaccgggtgc<br>aaccgttgccgaagcaacccgtgttctgggtcagtggctgaccgaagttattcgtctgaatccggataactttcgcattttttggtccagatgaa |

-continued

SEQUENCES accgcaagcaatcgtctgcaggcagtttatgatgcaaccgataaacagtggaacgccgaattttttggtgcggaagttgatgaacacctggc
acgtgcaggtcgtgttgttgaaatgctgagtgaacatcagtgtcagggttggctggaaggttacctgctgaccggtcgtcatggtctgtttaat
tgttatgaagcctttatccacatcgtggatagcatgctgaaccagcacgcaaaatggctgaaagttaccaatcatattccgtggcgtcgtccta
ttgcaagcctgaattatcttctgagcagtcatgtttggcgtcaggatcataatggttttagtcatcaggatccgggttttattgatcacgttgtgaat
aaaagcgccaaagttgtgcgtgtgtatctgcctccggatgccaatacactgctgagtacctatgatcattgtctgcgtagccgtcagtatgtta
atgttgttgttagcggtaaacagccgagcccgaactttctgaccatggaacaggccgttgcacattgtaccgtggcctgggtatttgggaat
gggcaggtagcgaagaactgggcacagatccggatgtggttctggcaagtgccggtgatattcctaccctggaagcactggcagcagca
gatattctgcgccagcatctgcctgatctgaaagtgcgttttgttaacgttgtggatctgatgcgcctgcaggatagcaccgaacatccgcatg
gcctgccagatcgtgattttgatatgattttttaccaccgatcgtccgatcatctttgcctatcatggttatccgtggctgattcatcgtctgacctat
cgtcgtgccggtcatgataatctgcatgttcgtggttataaagaagaaggtacaaccaccacccgttcgatatggttatgctgaatgatttag
atcgctatcacctggtcatggatgtgattgatcgtgtgccgagcctgggttcaacctgtgcagccttacgccagcagatggcagataaacgt
attgcagctcgcgaatataccgtgcgcatggcgaagatattccggaagttaaagattgggtttggcctgcagcacgtgaaagcggttttgg
tacagccggtgcggatggtgcgagcagcaccggtggtgataatgaa (SEQ ID NO: 52)

Nucleic acid sequence encoding for a phosphoketolase enzyme from Shewanella baltica OS185
atgacccagatccatgaaattaatgccctgaaaaaatacgtgcgtgccaccaattttctggcaaccagccagatttatctgaaacagaatgttc
tgcacaaacgtccgctggcacataccgatatcaaaccgcgtgctgctgggtcattggggcacctgtccgggtattaactttgtttatgcaaacat
taaccgcctgatcgtgaaacataatcgcagctttatctatctggttggtccgggtcatggttttccggcagttcaggcaaacctgtttatggaag
gtagcctgagccattttttatccggaaaccattccgtataatgaaaccggcattgaagatatttgcaaaaaattcagcgcagcctatggttatcc
gagccatgcaaatccggaagcaccgggtcagattctggaaggtggtgaactgggttatagcctgtcagttggttgggggtgcagttctggata
atccggatctgattgcaaccgttctgattggtgatggtgaagcagaaaccggtcctctggcagcaagctggtatgccaatcgtctggtttcac
cggcaacctcaggtgccgttctgccgattgttcatattaatggctataaaatcagcggtccgacccgtatgggtcgtatgagccatgaagaac
tggatctggaatttcgtggtctgggctattttccgattattgtggataatgaactggaagaggatatttacgtgcagatgaccaatgcaatggat
accgcatatgccatgattaacgatattcagcgtcgtgcacgtagcggtgaagatgtgttaaaccgaaatggcctgttattctgatgcgtaccg
caaaaggttggaccggtgttagcgaatacaaaggcaaaaaacttgaaggcaattgcgaaagccatcaggtgattgtgaataaatgtgcaac
cgataaaggtcatctgatgcactggataactggctggcaagctatcattttcaagaactgtatcagatgaacgacaaaggcgaactgattttt
gatgccgatatctgcagcctgattccgcctaaacagctggcatgtggtcgtcagcatctgacctatggtggcgaagttgttcgtgcactgacc
aatccggacctggaaaaactgagctatggtccggaagttccgcgtgctcatcgtggtttatagtatgctgaaaatgggtgaatggatgcgtga
tgcctttaaactgaatcgtgatcagcgtaatctgcgcattttttctccggatgaaacctatagcaatcagctgcaggcagttttttgaagaaaccg
atcgtcatggcagtggccgattgaaagctgggatgaggatatgagtcgtgaaggtcgtgttattgaactgctgagcgaaaatctgctgtttg
gtatgctgcatggttataccgttaccggtcgtcatggtatgtttccgacctatgaaagctttagccaggttattagcagcatggccgatcagtatt
gcaaatatgtgtatgcaagccaggtgtgcattttcgtaaaccgctgccgagctgtaatgttgttctgagcagcctgctggaacgtcaggatc
ataatggttattcacatcagaatccgagctttctgggtgccatgttagaaaaacatccgaaaattatcagcgcatatctgcctgcagtgcaaat
agcaccctggtttataccgaacgtgcctatgcagatcgtgataagctgaatattctggttcgccggaaaaaaagaactgccgcagtggctgag
cctgaagaagcacgtaaacaggcaaaagatggtgttatggttgggattttgccagtgatgaaaacccggatattgtgctggcaggttgtg
gtgattatgttacccaagaatgtatggccagcctggtgctgattcgtgaactgttaccgcgtgttaaaattcgttttgttagcgttaccgaactga
gcagtgatggcctgggtagccgtaaattcaaagaaaaaccgtggctgatggatgaaattttcacccaggataaaggcgtggtgttttaactat
catggctatccgaataccatcaaaaagctgatcttcgactataaaggcagccgtcgttttcgcattaaaggctatgaagaagaaggtagtacc
accacccgtttgatatgggtgttcgtaatggcaccagccgctatcatctggtgatcgatatggcatataactgtttcagcagggcgtgattg
atgaaacaatgcatgtgagcattaccaccgacatgctgcagcgtctggtggatcatcgtaattacattaaagccaatggtgtggatccgatcg
aaatcgaaaattggatttggacccg (SEQ ID NO: 53)

Nucleic acid sequence encoding for a phosphoketolase enzyme from Lactobacillus rhamnosus
LMS2 1
atgagcatggacaccaaagtgaaaaccgttgattatagcagcaaagaatattttgacaaaatgaccgcatattggcgtgcagcaaattatgtt
agcgttggtcagctgtatctgaaagataatccgctgctggaacgtccgctgaaaagcgaagatgttaaaccgcatccgattggtcattgggg
caccattgcaggtcagaattttatctatacccatctgaatcgcgtgatcaacaaatatgatctgaatatgttctacatcgaaggtccgggtcatg
gtggtcaggttatggttagcaatagctatctggatggtagctatagcgaaatttatccgcgtgttagccaggataaagaaggtatgaaaaacct
gtttacccagtttagctggcctggtggttgcaagccatgcaagcgcacagacaccgggtagcattcatgaaggtggtgaactgggttatg
cactgagccatgccaccggtgcaattctggataaaccggatgttattgcagcagttgttaccggtgatggtgaaaccgaaaccggtccgctg
gcagcaagctggtttagtaataccttattaacccgattagcgacggtgccatcctgccgattgttcatatgaatggctttaaaatcagcaaccc
gaccattctgagccgtaaaagtgatgaagatctgaccaaatatttcgaaggcatgggttggaaaccgtattttgttgaaggtgatgatccgac
caaactgaatccggaaatgcaaaagttatggatgcagccattgaagaaattaaagccatccagaaacatgccgtgaaacaggtgatacc
accatgccgcattggcctgttattatctttcgtagcccgaaaggttggacaggtccgaaaagctggaatggcgaaccgattgaaggtagcttt
cgtgcacatcagattccgattccggttgatgccgaagatatggaacatgcagatagcctggcaggttggctgaaatcatatccggaaga
actgtttgatgagaacggtaaactgatccctgaactggcagccctgcctccgaaaggcgataaacgtatggcagccaatccgattaccaat
ggtgcctggatccgaaacctctggttctgccggattatcgtaaatatgccctggataataaagaaacacggcaagcagattaaacaggacat
gattgtttggagcgattatctgcgtgatctgattaaactgaacccgcataacttctgtattttcggtccggatgaaaccatgagcaatcgtctgta
tagcctgtttgaagttaccaatcgtcagtggctggaaccgatcaaagaacctgcagatcagtatctgcaccggcaggtcgtattattgatag
ccagctgagcgaacatcagagcgaaggttttaatgaaggttatacccctgaccggtcgtcatggtctgtttacaagctatgaagcatttctgcgt
gttgttgatagcatgctgacccagcactttaaatggattcgtaaagcacatgaagaaccgtggcataaagcatatccgagcctgaatgttgta
gcaccagcaccagttttcagcaggatcataatggtttatacacctgaccggtcgtatcggcagaaaaaaaaaggcgaatat
attcgcgagtatctgccagcagatgccaatagcctgctggcaattagtccgaaactgtttagcagccagaataccgtttaatgttctgatcacca
gcaaacagcctcgtccgcagttttatagtattgatgaagcaccgttctggcaaatgcaggtctgaaacgtattgattgggcaagcaatgatg
atggtgttgaaccggatgtggtgattgcagccgcaggcaccgaaccgaatatggaaagtctggctgcaattaatctgctgcatgatgcattc
cggatctgaaaattcgctttatcaatgtgctggatctgctgaaactgcgttcaccggaaattgatcctcgtggtctgagtgatgcagaattaac
agctattcaccaccgataaaccgatctgtttgcctatcatggttttcgaaggttgattcgcgatatttttttaccgctcagaatcgtaacgtgct
gattcatggttatcgtgaagagggtgatattaccaccccgtttgatatgcgtgttctgaatgaactggatcgtttttcatctggccaaagatgtgat
tcagcatgttccggcatatgcggaaaaaagcagcagcatttgttcagaaaatggatgataccctgcagtatccaccatgattttattcgtgcaaat
ggtgaggatattccggaagttcaagaatggacctggaaaagcattaaa (SEQ ID NO: 54)

Nucleic acid sequence encoding for a phosphoketolase enzyme from Lactobacillus crispatus ST1
atggccgtggattatgatagcaaagactatctgaaagcgtggatgcatattggcgtgcagcaaattatctgagcgttggtcagctgtttctga
tgaaaaatccgctgctgaaaacaccgctggttgcagaagatgttaaaccgaaaccgattggtcattggggcaccattgcaccgcagaatttt
atctatgcacatctgaatcgtgttctgaaaaagtacgatctgaatatgttctatatcgaaggtagcggtcatggtggtcaggttatggttagcaat
agttatctggatggtagctataccgaacgctatccggaaattaccaggatgagaaaggtatggcaaaactgtttaaacgctttagctttccgg
gtggtgttgcaagccatgcagcaccggaaacaccgggtagcattcatgaaggtggtgaactgggttatagcctgagccatggcaccggtg -continued

SEQUENCES cagttctggataatccggatgttattgcagcagttgaaattggtgatggtgaagcagaaaccggtccgctggcagcaagctggtttagcgat
aaattcattaacccgattaaagatggtgccgttctgccgattctgcagatcaatggctttaaaatcagcaatccgaccattgttagccgtatgag
cgatcaagaactgaccgaatattttcgtggtatgggttgggatccgcattttgttagcgtttttaaaggtggtcgtttcgatggcgaaaaagatc
cgatgcaggttcacgaagaaatggccaaaaccatggatgaagtgatcgaagagattaaggccattcagaaacatgcgcgtgaaaataatg
atgcaaccctgccgcattggccgatgattatctttcagtgtccgaaaggttggacaggtccgaaaaaagatttagatggtaatccgatcgaaa
acagctttcgtgcacatcagattccgattccggttgcacagggtgatatggaacatgcagatatgctgacagattggctggaaagctataaac
cggaagaactgttcaatgaagatggcagcccgaaagaaattgttaccgaaaataccgcaaaaggtgatcatcgtatggccatgaatccgat
taccaatggtggtattgatccgaaacgtctgaatctgccggattatcgtaaattgccctgaaatttgataaacctggtagcgttgaagcacag
gatatggttgaatgggcaaaatatctggacgaagttgccaaactgaacccgaccaccttcgcggttttggtccggatgaaagcaaaagcaa
tcgtctgtttcagctgctggatgatcagaaacgccagtgggaacctgaagttcatgaaccgaacgatgaaaatctggcaccgagcggtcgt
gttattgatagccagctgagcgaacatcaggatgaaggttttctggaaggttatgttctgaccggtcgtcatggttttttttgcaacctatgaagc
atttggtcgtgtggtggatagcatgctgacccagcatatgaaatggctgtaaagccaaagaacagtactggcgtcacgattatccgagcc
tgaatttgttgcgaccagcaccgttttcagcaggatcataatggttataccccaccaggatccgggtattctgacccacctgtatgaaaaaat
cgtccggatctggtgcatgaatatcgccgagcgataccaataccctgctggcagttggtgataaagcactgcaggatcgtgaatgtattaat
gttctggttaccagcaaacagcctcgtccgcagtggtttagtattgaagaagcaaaaaaactggtcgataaaggcctgggctatattgattgg
gcaagcacagataaaggtgcaaaaccggatgtggttttgccagtaccgaaacagaaccgacaattgaaaccctggcagccattgatattct
gcataagaaatttccggacctgaagactccgttatatcaatgttgttgacgtgatgaaactgatggatccgaaggataacaaaaatggtctgag
cacggaagaatttgatcgcctgtttccgaaagatgttccggttattttgcctggcatggctataaaagcatgatggaaagtatttggtttgcccg
taaacgtataacgtgcatattcactgctatgaagaaaacggtgatattaccaccccgtttgatatgcgtgtgctgaatcatctggatcgttttga
tctgcaaaagatgccgttgaaagcatcgataaactgaaaggcaaaaacgccgattttatcagccatatggatgacctgctggaaaaacatc
atcagtatattcgcgataacggcaaagatatgccggaagttacagaatggcaatggtcaggcctgaaa (SEQ ID NO: 55)

Nucleic acid sequence encoding for a phosphoketolase enzyme from Leuconostoc citreum KM20
atggccgattcgacagcaaagagtatctggaactggttgataaatggtggcgtgcaaccaattatctgagcgcaggtatgattttttctgaaaa
gcaatccgctgtttagcgttaccaataccccgattcaggcagaagatgttaaagttaaaccgattggtcattggggcaccattagccggtcaga
cctttctgtatgcacatgcaaatcgtctgatcaacaaatacgatctgaatatgttctatattggcggtccgggtcatggtggtcaggttatggtga
ccaatgcatatctggatggtaatataccgaagattatccggaaattacccaggatctgaaggtatgagccgtctgtttaaacgtttagcttt
ccgggtggtattggtagccatatgaccgcacagacaccgggtagcctgcatgaaggtggtgaactgggttatagcctgagccatgcatttg
gtgcagttctggataatccggatcagattgcatttgcagttgttgcagttggtgatggcgaagcagaaaccggtccgagcatgaccagctggcatagc
accaaatttctgaatgcaaaaaatgatggtgccgtgctgccgattctggatctgaacggctttaaaatcagtaacccgaccattttagccgtat
gtccgatgaagaaatcaccaagtttttttgaaggtctgggctatagtccgcgttttattgaaaacgatgatatccatgattacgcagcctatcatg
aactggcagcaaaagtgctggatcaggcaattgaagatattcaggccattcagaaagatgccccgtgaaaatggtaaatatgaagatggtac
aattccggcatggccctgttattattgcacgtctgccgaaaggttgggtggtccgacccatgatgaggatggtaatccgattgaaaatagcttt
cgtgcacatcaggttccgctgccgctggcacagaataaaactggaaacccgtgagtcagttgaagattggatgaatagctacaaaccggaag
aactgtttaatgcagatggcagcctgaaagatgaactgaaagcaattgcaccgaaaggcgataaacgtatgagcgcaaaaccgattgcaa
atggcggtcgtcgtcgtggtgaagaagcaaccgatctgacctgccggattggcgtcagtttaccaatgatataaccaatgaaaaccgtggt
cacgaactgcctaaagttacccagaatatggatatgaccaccctgagcaattacctggaagaagttgcaaaactgaatccgaccagttttcgt
gttttttggtccggatgaaaccatgagcaatcgcctgtggtcactgttcaataccaccaatcgtcagtggatggaaggaggtgaaagaaccgaa
tgatcagtatgtgggtccggaaggtcgtattattgatagccagctgagcgaacatcaggcggaaggttggctggaagctatacctgacc
ggtcgtgttggtatttttgcaagctatgaaagctttctgcgtgttgttgataccatggtgacacagcacttaaatggtgcgtcatgcaagcga
acaggcatggcgtaatgattatctgagcctgaatctgattgaccaacagcaccgcatttcaggatcataatggttataccaccatcaggatcc
gggtatgctgacccatcggcagagaaaaaagcaactttatccgtgaatatctgcctgccgatgcaatagcctgctggcagttcaggatc
gtgcatttagcgaacgtcataaagtgaacctgattatcgcaagcaaacagcctcgtcagcagtggtttaccgcagatgaagcagatgagctg
gcaaatgaaggcctgaaaaattatcgattgggcaagtaccgcaccgagcggtgatgttgatattaccctttgccagcagcggcaccgaaccga
caattgaaacgctggcagccctgtggctgattaatcaagcatttccggaagttgaaatttcgctatgttaatgttgtgaacctgctgcgcctgca
gaaaaaatcagaaagtcatatgaatgatgagcgcgaactgagtgatgcagagttttaacaaatttttccaggccgataaaccggtgatctttgg
ttttcatgcatatgaggatctgatcgagagctttttttttcgagcgtaaattcaaaggtgatgtgtatgtgcatggttatcgcgaagatggcgatatt
acaaccacctatgatatgcgtgtttacagcaaactggatcgttttcatcaggccaaagaagcagcagaaattctgtcagcaaatagcacaatt
gaccaggcagcagccgatacctttatcgaaaaaatggatgcaaccctggccaaacattttgaagtgaccgtaatgaaggtcgcgatattg
aagaatttacgattggaattggagcgcactgaaa (SEQ ID NO: 56)

Nucleic acid sequence encoding for a phosphoketolase enzyme from Bradyrhizobium sp. S23321
atgaacaatcagcagcagagcgcactgagccgtagcgatctggatctgctggatcgttattggcgtgcagcaaattatctgagcgttggtca
gatttacctgctggacaatccgctgctgcgtgaaccgctgcgtccggaacacattaaaccgcgtctgctgggtcattggggcaccacaccg
ggtctgaattttatctatgcacatctgaatcgtgttatccgtgcactgagcgtgctgtatgtttgtggtccgggtaatggtggtcctggc
atggttgcaaatacctatctggaaggtagctatagcgaaatctatccgaatattgcacgtgataccgatggtctgcgtaaactgtttcgtcagttt
agctttccgggtggtattccgagccatgcagcaccggaaactccgggtagcattcatgaaggtggtgaactgggttatgcactggttcatgc
atatggtgcagcatttgataatccggatctgattgttgcatgtgttgttggtgatggtgaagcagaaaccggtccgctggcagcaagctggca
tagcaacaaatttctgaatccggttcatgatggtgccgttctgccgattctgcatctgaacggctataaaatcgcaaatccgaccgttctgggtc
gtatgcgtgatgaagaaattcgtgatttattttcgcggttttggtcatgaacctctgtttgttgaaggtgatcacgccctgatgcaccaggca
atggcagatgccttgatgttcatttgcacgtattcgtagcatccagcagcatgccgtgatgtcgtaaagaaattgaacgtccgcgttggc
cgatgattcttgctgtagccccaaaggttggacaggtccgaaaagaagttgacgtctgaaagtggaagtttctggcgtgcccatcaggtt
ccggttgcaggttgtcgtgaaaatcctgcccatctgaaaattctggaagattggatgcgtagctatgaaccggaaaaactgttcgatgcaagc
ggtgcactgattccggaactgcaggccctggctcggaaggtaatcgtcgtatgggtgccaatccgcatgcaaatggcggtctgctgaaaa
aagaactgaaactgccggatttcgtagctttgccctggaagttccgcagcctggtggtgttaccggtgaagcccacacgcgaactgggca
attcctgcgtgacgttattccgtcgaatcagcagaaacgtaattttcgcattatgctgtggataaaccggaaaacaagcaatcgtctggatgccgttt
ttgaagaaaccgaacgtgtttggatgaaccgattgaaccgtatgatgttcatctggcacaggatgtgcgcgttatgaagtgctgagcgaa
catctgtgtcagggttggctggaaggctatctgctgaccggtcgtcatggtttttttagctgttatgaagcctttatccacatcgtggatagcatg
tttaatcagcacgcaaaatggctgaaagttacccgtcatctgccgtggcgtcgtccgattgcaagcctgaattatcttctgaccagccatgtttg
gcgtcaggatcataatggttttagtcatcaggatcctggttttgttgatctggttgccaacaaaaaagcggatattgtgcgtatctattttccgcct
gatgccaaccctgctgattcattgcctgcgtacctataatcgtaattattgtggcggcaggtaaacgcctgcaacgcagt
ggctgagcagcaggatgcagcaacccattgtgcaggattggtatttggagctgggctgtaatgaagatgcaacaggcgaaccgc
atgttgttatggcatgtgccggtgatgtgccgacactggaaaccctggcagccgttgacctgctgcgcaaagcactgcctgatctgaagatt
cgtgttgttaatgttgtagatctgatgacactgcagcctaaagaacagcatcctcatggtctgagcgatcgcgattttgatagtctgtttaccag
cgataaaccggtgatttttgcctatcatggttatccgcacctgattcatcgtctgacatataatcgtaccaatcatgcaggtctgcatgtgcgtgg
ttttattgaagaaggtacaaccaccaccccgtttgatatggttgttctgaatgaactggatcgctatcacctggcaattgaagccattgaacgcg -continued

SEQUENCES ttccaggtctggcagcgcgtgccgcagcggttaaacagcagtttcgtgatgccctgattgaacatagccattatattcgtgaacacggtgaa
gatatgccggaaatccgcgattgggtttggcctggtaaaaccggt (SEQ ID NO: 57)

Nucleic acid sequence encoding for a phosphoketolase enzyme from Brucella microti CCM 4915
atgcctgcaaaaggtccgctgacaccgcagcagctgagcctgattaatcgttattggcgtgcagcaaattatctgagcgttggtcagatttac
ctgatgaaaaatccgctgctgcgtgaaccgctgcagccggaacacattaaaccgcgtctgctgggtcattggggcaccacaccgggtctg
aattttatctatgcacatctgaatcgcattatccagcagcgtaatgccaatgtgatttatatctgtggtccgggtcatggtggccctggtatggtt
gcaaatacctatctggaaggcacctatagcgaaatttatccggcaattagcgaagatgaagcaggtatggaacgtctgtttcgtcagtttagct
ttccgggtggtattccgagccatgcagcaccggaaactccgggtagcattcatgaaggtggtgaactgggttatgcactggttcatgcatat
ggtgcagcatttgataatccggatctggttgttgcatgtgttgttggtgatggtgaagcagaaaccggtgcactggcaaccagctggcatagc
aacaaatttctgaatccggcacgtgatggcgcagttctgccgattctgcatctgaacggctataaaatcgcaaatccgaccgttctggcacgt
ctgagtgatgatgatctggataacctgtttcgcggttatggttatgaaccgtttttgttgaaggtagcgaaccggcagatatgcatcagaaaat
ggcagcaaccctggataccatttttcagcgtattcaggacatcaaaaaaaacgccgatgttcatagtccggaacgtccgcgttggccgatga
ttattctgcgtagcccgaaaggttggaccggtccgaaaaccgttgatggcgtctggtggttgaaaattactggcgtgcccatcaggttccggttg
ccaattgtcgtgaaaatgatgcccatcgtaaaatcctggaagattggatgaaaagctatgatccgagcgacctgtttgatgagaaaggtgcc
ctgaaaccggaactgcgtgccctggcaccgaaaggcgaagcccgtatgggtgccaatccgcatgcgaatggtggtctgctgcgcaaaga
actgcacatgccggatttttcgccagtatgcagttaatgttaccgaaccgggtgcaattgaagcacagagcaccaaaattctgggtgatttcct
gcgtgatgtgatgaaactgaatgaaaccgaaaaaaacttccgcattttttggtccggatgaaacagcaagcaatcgtctgggtagcgttctgg
aagcgaccaatcgtgtttggatggccgaaacactggatatggatgatcacctggcagcagatggtcgtgttatggaagttctgagcgaacat
ctgtgtcagggttggctggaaggttatctgctgagcggtcgtcatggtttttttagctgttatgaagccttcatccacatcatcgatagcatgttta
atcagcatgcaaaatggctgcaggttgcacgcgaactggaatggcgtaaaccgattagcagcctgaattacctgctgaccagccatgtttg
gcgtcaggatcataatggttttagtcatcaggatcctggttttgtagatctggtggcaaataaaagcgcagatattgtgcgtgtttatttttccgcct
gatgccaataccctgctgtgggtgggtgatcattgcctgaaaacctggaatcgtgtgaatgttattgttgcaggtaaacagccagaaccgca
gtggctgaccatggcggaagccgaaaaacattgtgaagccggtctgggcatttgggaatgggcaggtacagaagatggcctggaaccg
gatattgttatggcatgtgccggtgatgttccgaccatggaaacgctggcagccgtggatttactgcgtcagagcctgccgcatctgcgtatt
cgtgttgttaatgtggttgatctgatggttctgcagagtccgcatcagcatcctcatggtattagtgatgaagaatttgatcgtatgttcaccaca
aatcgtccggtgatttttgcctatcatggttatccgtatctgattcaccgtctggtttataaacgtaccaatcacagcaattttcacgtgcgtggtttt
attgaacagggtacaaccaccaccccgtttgatatgaccgtgctgaatgagctggatcgttttcatctggcaatggaagcagttgaacgcctg
ccactgggtgaaagcgttgcaaaaccgctgattgataactttacagaaaaactggcactgcacaaagattatattcgtcagcatggcgaaga
tatgccggaaattcgtgattggaaatggacctggcctcgt (SEQ ID NO: 58)

Nucleic acid sequence encoding for a phosphoketolase enzyme from *Lactobacillus salivarius* ATCC 11741
atgaccgattatagcagccaagaatacctggataaactggatgcatattggcgtgcagcaaattatgttagcgttggtcagctgtatctgaaa
gataatccgctgctgcgtcgtccgctgaaagcagaagatgttaaagttaaaccgattggtcattggggcaccattgcaggtcagaattttatct
atgcacatctgaatcgcgtgatcaacaaatatgatctgaacatgttctatgtggaaggtccgggtcatggtggtcaggttatggttagcaatag
ctatctggatggtagctatagcgaaatctatccggaaattagccaggatgaacagggtatgaaacgtctgtttaaacgttttagctttccgggt
ggtgttgcaagccatgcagcaccggaaacaccgggtagcattcatgaaggtggtgaactgggttatagcattagccatagcgtgggtgca
gttctggataacccggatctgattgttgcagcagttgttggtgatggtgaagcagaaaccggtccgctggcagcaagctggcagagcaata
aattcattaatccgattcatgatggcgcagtgctgccgattctggatctgaatggctttaaaatcagcaatccgaccattctgagccgtgaaagt
gatgaaaccctgaccaaatatttcgaaggtatgggttggcatccgatctttgttgaaggtgatgatccgaaattaatgcatccggcaatggca
aaagcaatggatgaagcaattgaagagattaaagcgattcagaaaaacgcacgcgaaaataacgatccgagcctgcctgcatggcctgtt
attatctttcgtgcaccgaaaggttggacaggtccgaaagaatgggatggcgaaccgatcgaaaaaagctttcgcgcacatcagattccgat
tccggttgatcagaatgatatgcagcatgcagatgcactggttgattggctggaaagctataaaccggaagaactgtttgatgaaaacggca
aactgaaagccgaaattgcagaaattaccccgaaaggcgataaacgtatggcagccaatccgcataccaatccgggtaaactgattcgcg
aagttatcaaaccggattttcgtgattttgcagttgataccagcgttcctggtaaagaagttgcacaggatatgaccgttctgggtaaatatctg
gaaaaagtgctgagcgataaccgccataattatcgtgttttttggtccggatgaaacgatgagcaatcgtctggcaccgatttttgatgttacca
aacgtcagtggctggccgaaatcaaagaaccgaatgatcagtatttagcaccgagcggtcaggtgattgatagccagctgagtgaacatca
ggcagaaggttttctggaaggttatgttctgaccggtcgtcatggtttttttgcaagctatgaaagttttctgcgtgtggttgatagcatgctgac
ccagcactttaaatggctgcgtaaagcaaccgaacagccgtggcgtaccagcattccgagtctgaatgttattgcaaccagcaccgtttttca
gcaggatcataatggttatacccatcaggatcctggtattctgggtcatctggcagataaaaaacctgaatatatccgcgaatatctgcctgcc
gatgcaaatagcctgctggcagtttttgataaaaccattaatgaccgcgacaaaattaacctgattgtggcaagcaaacatccgcgtcagca
gttttatagcgcagcagaagcaaaagaactggtagataaaggcctgaaaattatcgattgggcgagcaccgataaaaatgccgaaccgga
tgtggttattgccgcagcaggcaccgaaccgaacctggaagcactggcagcgattagcattctgcatgaaaaactgccggatcttaaaatc
cgctttattaacgttgtggacattctgaaactgcgtagcccgaaagttgatccgcgtggtctgagtgatgatgaatttgatgcctatttcaccaa
agacaaaccggtgattttttgcctttcatggttatgaaggtctgctgcgatattttctattatcgccataaccataacgtggcctttcacggctat
cgtgaaaatggtgatattaccaccccgtttgatatgcgtgttctgtcacagatggatcgttttgatctggttaaaagcgttgcactgagtctgcct
gatgccgataaatatggccagctggttgccgaaatggatgcaaaagttgcaaaacatcatcagtatatccgtgatgaaggtacagatctgcc
ggaagttgaaaattgggaatggaaaccgctggat (SEQ ID NO: 59)

Nucleic acid sequence encoding for a phosphoketolase enzyme from *Rhodococcus imtechensis* RKJ300
atgaccgatggtcgtcaggttggtagccaggatagtgatggtcattatagcgatagcgatctggatctggacctgcgttggtgggcagcagc
aaattatctgaccgttgcacagatttatctgcaggataatgcactgctgcgtgctccgctgcgtccggaacacattaaaccgcgtctgctgggt
cattggggcaccagtccgggtctgagcatgatttatgccctgctgaatcgtctgattcgtcgtaccgataccgattgtctgtatgttaccggtcc
tggtcatggtggtccggcactggttgcagcaacctatctggaaggcacctatagcgaagtttatccgggtgttagccgtgatgcagcaggta
ttcatcgtctgtgtcgtcagtttagcacaccgggtggtattccgagccatgttagcgttcagactccgggtagcattcatgaaggtggtgaact
gggttatgcactggcacatgcagccggtgcagcatttgatcatccgaatctgctggttgcctgtgttattggtgatggtgaagcagaaaccgg
tccgctgagcggtagctggaaactgcctgcatttctgaatccggaacgtgatggcgcagttctgccgattctgcatgttaatggtgcaaaaatt
gcaggtccgaccgtttatggtcgtagctcagatgcagatgttgaagcctttctgggtggtcagggttgggcaccgaccgtggtgagcggtg
atgatccgcgtcatgtttttccagcactgcatcgtgcactgacagatgcacatgccgcaattagtgatctgcagcgtgaagcacgtgcaggtc
gtcgtagcgcagcaaaatggcctgcaattgttctgcgtaccccgaaaggttggacaggtccgcgtaccgttgatggtgttctggttgaaggt
acacatcgtgcccatcaggttccgctgtcaggtgttcgcaccgatgaagcacatctgcgtcagctggaagaatggatgcgtagctatggtcc
gggtgagctgtttgatagcagcggtgccctggttcctgatctggaacgtctggcaccgcagggtgataaacgtatgggtagcagcccgtat
gcaaatggtggccgtctgcgtgcagatctgccggttccgcctctggaaaaatatgcgctggcaattgaaaaaccgggtacaaccctgcatg
aaaccacccgtgtgctgggtgaattactgcgtgatctgtatgcagccaccgcaacaccggatggtggtggttattttcgtctgttttgtccggat -continued

SEQUENCES gaaaccgcaagcaatcgcctgggtgcagtttttgaagttaccgatcgttgttggcagctgccggtgaccgattatgatgatggtctgagtgca
cgtggtcgtgttatggaagttctgagcgaacatctgtgtgaaggttggctggaaggttatctgctgagtggtcgccatggtctgtttgcaagct
atgaagcatttgcaatggttagcgtgagcatgctggttcagcataccaaatggctgcagcatgcagttgatctgccttggcgtgcaccggttg
caagcctgaatgtgctgctgaccagcacctgttggcgtaatgatcataatggttttagtcatcagggtccgggaatgattgatgcagttattcc
gctggctccggatgttgttcgtatttggctgccaccggatagcaatacctgctgtcaattgcagatcattgcctgcgtagcaccgatcatgtg
aatctgattgttgttgataaacagccgcatctgcagtatctgacactggccgaagccatgcacattgtgcagcgggtgccagcgtgtggga
atgggcaggcaccgaaggtgcggttggtgcggatcctgatgttgtgctggcagcggctggtgatgttccgacccaagaaatcctggcagc
cgcacagctgctgcgcgaacatactccggatctggttacccgtgttgttaatgttgtggatctgatgggtctgctgacgccgaccgaacatcc
gcatggttttgatgcacgtatgtttctggattttgtttaccgcagatacggatgtggttttgcctttcatggttatagccgtgccgttcatgaactga
ttcatggtcgccctgcaccggatcgttttcatgttcgcggttttagcgaacagggtacgaccaccacccgtttgatatggttgttctgaaccgt
atgagccgttatcatctggtgctggaagcactgcgtcgcacccgtcgtgaacctgcgggtgcaggcgaactggcagattttttgtctgcgcca
gttagaacgccatggcgaatatgttgttgcacacctggaagatatgccggaagttcgtgattggacctggtca (SEQ ID NO: 60)

Nucleic acid sequence encoding for a phosphoketolase enzyme from Burkholderia xenovorans
LB400
atggcagaagcaagcagccgtccgaccccctccgcaggttctggatgcagataccctgcgtaatatggatcgttattggcgtgcatgtaattat
ctgagcgcaggtatgatttatctgcgtgataatccgctgctgcgtgaaccgctgaaaccggaacacattaaaaaccgtctgctgggtcattgg
ggtagcgatccgggtcagagctttctgctggtgcatctgaatcgtctgattcgtaaactggatctgaacgtgatttatgttgcaggtcctggtca
tggtgcaccggcaaccctggcacattgttatctggaaggtcattatagcgaaatttatccggatcgtagcgaagatgaagccggtatgcagc
gtttttttcgtcagtttagctttccgggtggtattggtagccattgtacaccggaaacaccgggtagcattcatgaaggtggtgaactgggttata
gcctgagccatggttatggtgccgcatttgataacccggatctgattgttaccgtgatgattggtgatggtgaagcagaaaccggtccgctgg
caaccagctggcatagcaacaaatttctgaatccggttcgtgatggcagttctgccggttctgcacctgaatggctataaaatcgcaaatc
cgaccattctggcacgtattccgcgtgaagaactggaagcactgctgaccggctatggtcataaaccgtatttcgttgaaggtgatgatccg
gcagttatgcatcagcagatggcagccaccctggaacagttgatttggtgaaattcgtgcaattcagcagcatgcacgtgcaaataatgatgc
aaaccgtccgcgttggccgatgattgttctgcgtagcccgaaaggttggacaggtccgaaagaagttgacggcataaagtggaaggtag
ctggcgtgcccatcaggttccggtgctggatccggttaccaatggtaaaagcctgaaactggttgaaaattggatgcgtagctatgaaccgg
aaagcctgtttgatgaagcaggtcgtctggttgaggaactgcgcgaactggcaccgaaaggcgcacgtcgtattagcgccaatccgcatg
caaatggtggtctgctgtgtaaaaccctggatatgcctgcatttggtgattatgcagttgcagttaaaaaaccgggtgcacctataccagcc
cgaccgaagttctgggtaaattcctgtgtgatgttatgcgtcgcaatatgaccaattttcgtgttttttggtccggatgaaaccgcaagcaataaa
ctgaccgcaatttatgaagccagcgaaaaaacctggctggcccagaccgaaccgagtgatgccgatggtggcgatctggcagttgatggt
cgtgttatggaaatgctgagcgaacatacactggaaggctggtttgaaggttatgttctgaccggtcgtcatggtctgtttgcaacctatgaag
catttgtgcatgtgatcgatacgatgctgtttaatcagcacgcaaaatggctggaaaaagcaaaacgtgatctgggtttggcgtcagccggttccg
agcattaatctgctgattaccagcctggtgtggcgtcaagatcataatggttttacacatcaggatcctggttttctggacgttgtgaccaataaa
tcaccggatgttgtgcgtatctatctgcctccggatgccaattgtctgctgagtgttgcagatcattgcctgcgtagtcgcgattatgttaatgtta
ttgttgccgataaacagccgcatctgcagtatctggacatggatgccgcagttattcattgtaccaaaggtattggcatctgggattgggcaag
caccgatcagggtgttgaacctgatgttgttattgcaagtgccggtgatattgccaccatggaagccctggcagcagttcagattctgaaaga
acgttttgccgatctgaaaatccgttttgtgaatgttgttgacctgttttcgcctgatgccggaacatgcacatccgcacgtctgagcaatcgtg
attttgatagtctgtttaccgcaaccaaaccggtgatctttaactttccatgctatgcaagcctggttcacaaactgacatataatcgtaccaacc
atgataacctgcatgtgcatggctatcatgaaaaaggcaatattaacacaccgctggaactggccattattaaccaggttgatcgttttagcct
ggcgattgatgtgattgatcgtgttccgaaactgcgtggtgtgggtgatcatgcaaaagaatggctgcgtggccaggttattgaacatctggc
atatgcacatgccgaaggcattgatcgcgaagaaattcgcaattggacctggaaaggt (SEQ ID NO: 61)

Nucleic acid sequence encoding for a phosphoketolase enzyme from Mycobacterium
intracellulare ATCC 13950
atgacccatgcaaccgcactgagtgatgatgaactggcactgattgataaatactggcgtgcagcaaattatctgagcgttggtcagatttatc
tgctggataatccgctgctgaccgaaccgctgaccattgatcatgttaaaccgcgtctgctgggtcattggggcaccacaccgggtctgaat
ctggtttatgcacatctgaatcgtgttattcgtcatcgtgatgccgatgttatttatgttaccggtccgggtcatggtggtcctggtctggttgcaa
atgcatatctggaaggcacctatagcgaagtttataccggtattgaagaagataccgaaggtctgcgtaaactgtttcgtcagtttagctttccg
ggtggtattccgagccatgttgcagcacagactccgggtagcattcatgaaggtggcgaactgggttatgcctggttcatgcatatggtgca
gcactggataacccgtatctgttgttgcatgtgttgttggtgatggtgaagcagaaacaggtccgctgcagcaagctggcatagcaacaa
atttctgaatccggtgaccgatggtgccgttctgccgattctggccctgaatggctataaaatcgcaaatccgaccgttctggcacgtattccg
catgcagaactggaaagcctgctgcgtggttatggttatcgtccgattaccgttgccggtgatgatccgcagatgttcatcgtcaactggca
gctgccctggatgatgcctttgatgatattgcagcaattcagagcgcagcacgtggtggtaatgttgaacgtccggttttggccgatgatt
gttctgcgtaccccgaaaggttggacgggtccgaaaatggttgatggcaaaaaagttgaaggtacatggcgtagccatcaggttccgttag
cagcaacccgtgataatcctgaacatcgtgcacagctggaagaatggctgcgtagctatggtccaggcgaactgtttgatgaaatggccg
tctgcgtccggaactgcgtgcactggcaccgagcggtgatcgtcgtatgagcgcaaacccgcatgccaatggtggactgctgctgcacga
tctggatctgccggatttttcgtgattatgcagttgcagtggaacgtcctgcagcagttacccatgaagcaccccgtttctgggtggttttctgc
gtgatgtgattgcacgtaataaagatcgttttcgcctgatgggtccggatgaaaccgcaagcaatcgtctggatgcagttttatggtagcaccg
ataaagtttggctgagcgaaattgaaccggatgatgagcatctggctccggatggtcgtgtgatggaagttctgagtgaacatctgtgtcagg
gttggctggaaggttatttactgaccggtcgtcatggtctgtttaattgttatgaagcctttgtgcacatcgtggatagcatgctgaaccagcatg
caaaatggctggcaaccagccgtgaactgccgtggcgtcgtcctattgcaagcctgaattacctgctgagcagccatgtgtggcgtcagga
tcataatggtcaagtcatcaggatccgggttttattgatcgtggtggccaataaacgtccagaactgcgggtgtatctgccaccggatgg
caatccctgctgtctgttgcagatcattgtctgcgttcacgcgattacattaatgttattgttgcaggtaaacagccagcctggcctatctgga
tatggatgaagccgttgcacattgtacccgtggcctgggtatttgggaatgggcaagcaccgcaaccgatgatcctgatgttgtgctggcat
gtgcaggcgatattccgaccctggaaaccctggcagccgcagatattctgcgcagcgaactgcccgaactggccgttcgtgttgttaatgtt
gttgatctgatgcgtctgcagccggatacagaacatccgcatggcctgcctgatcgtgaatttgatgcactgtttacaccggatcgtccggtg
attttgcatatcatggctatcatgcggctcatccatcgtgacctatagtcgtaccaatcatgcacatatgcatgtggcgttttaaagaacgt
ggtacaaccaccacccgtttgatatggtaatgctgaatgatctggaccgttttcacttagttatggatgttatcgatcgtgttgatgtctggca
agccgtgccgcaatgctgcgtcagcgcatggtggatcacgtctggcagcgcgtatgtatacccgtgaacatggcgaagatgatccaaaa
attagcggttggacctggggtccgagcgat (SEQ ID NO: 62)

Nucleic acid sequence encoding for a phosphoketolase enzyme from Nitrosomonas sp. Is79A3
atgaaaaagaataccaagctgctgagtccggaactgctgcacaaaatggatgcatattggcgtgcagcaaattatctgagcgttggtcagat
ttatctgtatgataatccgctgctgaaacagccgctgaaactggcacatatcaaaccgcgtctgctgggtcattgggcaccacaccgggtc
tgaattttatctatgttcatctgaaccgcattatcaaagagcacgatctgaacgttatctatattaccggtccgggtcatggtggtcctggtctggt
tgcaaataccatctggaaggcacctatagcgaagtgtatccgaatattagccaggatgaagatggtatgcagcgtctgtttcaaacagtttag
ctttccgggtggtattccgagccatgttgcaccggaaactccgggtagcattcatgaaggtggtgaactgggttatagcctgagccatgcatt -continued

SEQUENCES tggtgcagcatttgataaccctggcctgctggttgcctgtgttgttggtgatggtgaagcagaaacaggtccgctggcaaccagctggcata
gcaacaaatttctgaatccggttcatgatggtgcagttctgccgattctgcatctgaatggctataaaatcgcaggtccgaccgttctggcacg
tattccgtgtgatgaactggaagcactgtttcgtggttatggttataccccgtattttatcgaaggtgatgatcctctggaaatgcatcagcgtat
ggcagcaaccctggatgcagttattgccaatattcagagcattcagcgtgatgcacgtacccatggttttaccaaacgtccgcattggccgat
gattattctgcgtagcccgaaaggttggacgggtccgaaagttgttgatggtaaaccgaccgaaggtacatttcgtagccatcaggttccgat
gggtgatatgagccagcctggtcatgttaaaattctggaaaaatggctgaaaagctatcgtccgcaagaactgtttgataaaccggtaaact
gctggcagaactggccgagctggcaccgcagggtgcacgtcgtatgggtgcaaatccgcatgcaaatggtggtatgctgctgcgtgatct
gcgtctgccggattttcgcgattatgccgttaaagttgccaatccgggtacagttagcgcagaagcaaccccgtacccagggtgaatttattcg
tgatgttgttaaactgaacgccaccaactttcgtgtttttagtccggatgaaacggcaagcaatcgttggggtgccgttttgaagttaccaatc
gctgtagtaccgcagaaattgttcctggtgatgaccatgtggctccggatggtcgtgttatggaaatgttaagcgaacatcagtgtgaaggtt
ggctggaaggttatctgctgaccggtcgtcatggctttttttagctgttatgaagcctttatccacattattgatagcatgtttaaccagcatgccaa
gtggttaaaagtggcaaatgaaattccgtggcgtcgtccgattgcaagcctgaatacctgctgagcagccatgtgtggcgtcaggatcata
atggttttcacatcaggatccgggttttattgatcatgtgatcaacaaaaaagccgaaattattcgcatctatctgccaccggatgccaatacc
ctgctgtcagttaccgatcattgtctgcgttcacgtaattatgtgaatgttattgttgcgggtaaacagcctcagccgcagtggctggatatgga
tgccgcaatttaaacattgtacagccggtattggtatttgggaatgggccagcaatgatcagggcgaagaaccggatgttgtgatggcatgtg
ccggtgatgctccgaccattgaaacactggcagcagttgagctgctgtggaaacattttcctgaactgaaaattcgcgtgattaatgtggttga
tctgatgagcctgcagccacagagtgaacatcctcatggtctgagcgataaagattttgatggtctgtttaccaaggacaagccgattatcttt
gcctatcatggttatccgtggctgattcatcgtctgacctatcgtcgtaccaatcatgataacctgcatgttcgcggttataaagaagaaggtac
gaccagcaccccgtttgatatggttgtaatgaatgatctggatcgctttcatctggtggcagatgtgattgatcgtgttccgcagctgggtagc
cgtgcagcctatgttaaacaggcaattcgcgataaactgatcgaacacaaacagtacattaaccagtatggcgaagatatgccggaaattcg
taattggaaatggaaaggtagcagcgtg (SEQ ID NO: 63)

Nucleic acid sequence encoding for a phosphoketolase enzyme from *Schizosaccharomyces pombe* 972h
atggccacccagaatgatattccgaatagcacaccggaagatctggcaaaacaggttgaaattgcagaaaaacatccggatccgcctgca
atgccgagccgtctgccggatagcctgaaaaccctggaagcaaaaattgataccagcaaaattaccgatgaagaggttgcaaatgtgcatc
gttttcagcgtgcatgtgattatctggcagcaagcctgattttttctgagcaatggtctgtataccggtggtgatctggaagagaaagatatcaaa
acccgtctgctgggtcattggggcacctgtccgggtctgcagcattgtttatagcccatcgtcaatcgcatcatcaacaaatacgatctgaacatgc
tgtttgttgttggtcctggtcatgtgcaccggcaattctgagcgcactgtttcctggaagatagtctggttccgttttatccgcgttatcagtttac
caaagaaggcctgaataacctgattaacaccctttagcctgcctggtggttttccgagccatgttaatgccgaagttccgggtgcaattcatgaa
ggtggcgaactgggttatgcactgagcgttagctatggtgcagttctggatcgtccggatctgattgttacctgtgttgtgggtgatggtgaag
cagaaaccggtccgaccgcaaccagctggcatgcacataaaatttcttgatccggcagaaagcggtgccgttattccggttctggaactgaat
ggttacaaaattagcgaacgcaccatttatggttgcatgatgatagcgaactgctgagcctgtttagcggttttggttatgaagttgccattgt
gaatgatacaccggatcagaatcgtgttatggcagccaccatgattgggcagttgaacgtattcatgatatccagcatcgtcgcacgtgttaa
tcgcgaagaaattaaaccgcgttggccgatgattattctgcgtaccccgaaaggtaaaggttgtccgaaatatctgaatggcaaatttctgga
aggcacctttcgtgcacatcaggttccgctgaaactggcacgtaccgataccaatcagcgtaatctgctgaaagattggctgaatagctataa
ctgtcaggattttctggatgaacatggtctgccgaccaaaggtattaccgaacatcctgcctccgcgtgaaaacgtatgggtcagcgtcatga
aacctataatagttatctgccactgaaagtgccggactggaagaaatatggtgttaaaaaggtgaaaccaccagtgcgaccagcgtggttg
gccagtatctggacgagctgctggttaccaatgatagcaccctgcgcattttagtccggatgaactggaaagcaataaactggatggtgcc
ctgaaacatagctatcgtaccatgcagaccgatccggaactgatggccaaacgtggtcgtgttaccgaagtgctgagtgaacacctgtgtca
gggttttatgcagggttataccctgaccggtcgtaccgccattttccgtcatatgaccgtttatgacgtcggttgttagcatgctggttcagtat
agcaaattcctgaaaatgggtctggaaacgggttggcatggtaaatttggtagtctgaatttatgttaccagcagcacctgggcacgtcaaga
acataatggttttagccatcagagtccgcgttttattaccaccatgctgagtctgaaaacgggtgttagccgtgtttattttccgcctgatgcaaa
ttgttttctggcaaccgttgcacgttgtatgaaaagcgaaaacaccattaatctgatggtcagcagtaaaaatccgcagcctgcatatctgagc
gtggaagaagcggaacatcattgtaaagccggtgcaagcgtttggaaatttgcaagcaccgataatggtgaaaatccggatgttgttattgc
cggtgttggcaatgaaatcatgtttgaagttgttaaagcagccgaaatgctgcagaacgatatccctgaactgcgtgttcgtgtgattaatgtg
accgacctgatggtgctgagcagtctgcatccgcatggtatgaatcctgcagaatttgattcactgtttacgaaagatcgccacgtgcacttta
actatcatggttatgttatggatctgaaggcactgctgttcgatcgtattcagggcaccgtgtgaccatgaaggttatcgtgaagaaggtac
aaccaccacccgtttaatatgatgatgtgtaataataccagccgctcatcatgttgcccgtatggcactgcagcatgccctgcataatccgacc
gttgcggttaattgtaatatgctgtgtgcaaaatatgccgtgaaacttgaagagatcgagaactacatcatggaaaacaaagatgatcctccg
gaaatttatgccgcaccggttgtttaaaaacaaaaccagtaccctg (SEQ ID NO: 64)

Nucleic acid sequence encoding for a phosphoketolase enzyme from *Lactobacillus buchneri* ATCC 11577
atgaccgtggattacgatagcaaagagtatctggatctgctggataaatactggcgtgcagcaaattatctgagcgttggtcagctgtatctgc
gtgataatccgctgctgaaacgtccgctgaaaagtgatgatgttaaaatcaaaccgattggtcattggggcaccattgttagccagaattttat
ctatgcacagctgaatcgtgccatcaacaaatatgatctgaatatgtctctatattgaaggcagcggtcatggtggtcaggttatggttagcaata
gctatctggacggtagctatagcgatatttatccgaatattagccaggacgaaaaaggcatgcagaaactgttcaaacagtttagctttccgg
gtggtgttgcaagccatgcagcaccggaaaacccgggtagcattcatgaaggtggtgaactgggttatgcctgagccatgccaccggtg
caattctggataacccggatgttattgcagcagttgaaattggtgatggtgaagcgaaaccggtccgctggcagcaagcggtttagcgat
aaattcattaatccgattaccgatggtgcagttctgccgattattaacatgaacggtttcaaaattagcaatccgaccattctgagccgtatgagt
gatgcagatctgacggattatttcaaaggtatgggttgggcccatttttgttgaagcaaccgcagataccgatcatgcaaaagttgaagcc
gaatttgcaaaaaccctggataccgtgattgagaaaattaaagagcattccagaaaacgcacgcgaaaatgaaactccggataatgttaaact
gccggtttgccgatgattatctttcgtagcccgaaaggttggacaggtccgaaaaagatctggatggtaaccgattgaaggtagctttcg
tgcacatcaggttccgattccggttgatgcaaatgatatggaacatgcagatgaactggttgactggctgaaatcatataaaccggaagaact
gttgtgataaaacggcacctgaaacctgaactgcgtgcactggcaccgaaaggcgaacagcgtatgagcgtgaatccgatcacaaatgg
tggtattaaaccagaacctctgaaatgcctaatgtgcgtgatttgaaagtgaaatttgataaaacgtggaccgagcagaaacaggatatgatt
gagtggtcaaaatggctgatgcagttgcaaaactgaaccgaccaccctttcgtggttttggtccggatgaaaccaaagcaatcgtctgtat
tcactgctggacgatggtaaacgtcagtggatggaagatatccatgaaccgtatgatgaggatctggcaaatcatggtcgtgttattgatagc
cagctgagcgaacatcaggcagaaggtggctggaaggttatgttctgaccggtcgtcatggttttttttgcaacctatgaaagctttggtcgcg
ttgtggatagcatgctgacccagcattttaagtggctgcgtaaagcaagcgaacagtattggcgtaaacagtatccgagcctgaactttgttg
ataccagcaccgttttcagcaggatcataatggttatacccatcaggatccgggtctgctgacaccatcggcgtgaaaaaaccgacgggaattta
ttcgtgaatatctgcctgcagatgccaatgaactgctggcagttggtgatagcgcattcgtcacatgaaaagattaacctgatcgtgaccag
caaacatccgcgtcgccagtggtatagtatggatgaagcacagaatctggtgaaaatggtctgggctatatcgattgggcaagcaccgat
cagggtcaagaaccggatgtggttttgcagccgcaggtagcgaaccgaatctgaagccctggcagccattagtattctgaataaagaatt
cccggaactgaagatccgctttattaacgtggttgatatcctgaagctgaacagccctaaaaaggatccgcgtggtctgtcagatgaagaatt
cgataacctgttttaccaccgacaaaccggtgattttttgcatggcatggctttgaggacatgatcaaagacatctttttttgatcgccataaccaca

| SEQUENCES |
|---|
| acctgtatgtgcatggttatcgtgaaaatggcgatattaccacccccgtttgatatgcgtgttctgaacgaactggatcgttttcatctggcagc g<br>gatgccattcgtcatattccggcatatgcagttaaaggtggctatttttatccagcgcatgaacaacatcgtggataaacataatcgctatattcg<br>cgaagttggtacggatctgccggaagttaccagctggaattgggaaccgctgaacaaa (SEQ ID NO: 65) |
| Nucleic acid sequence encoding for a phosphoketolase enzyme from *Streptomyces ghanaensis* ATCC 14672<br>atgccggaagcaccggataccgtaccgttctgagtgatgaagaactgcgtaccctggatgcacattggcgtgcagcaaattatctggcag<br>caggtcagatttatctgctggcaaatccgctgctgaccgaaccgctgcgtccggaacacattaaaccgcgtctgctgggtcattggggcac<br>cagtccgggtctgaatctggtttataccatctgaatcgtgttattgcaggtcgtggtctggatgccctgtgtatttggggtcctggtcatggtg<br>gtccgagcgttctggccaatagctggctggaaggtagctatggtgaaacctatccggatgttggtcgtgatgcagccggtatggaacgtctg<br>tttcgtcagtttagctttccgggtggtgtgccgagccatgttgcaccggaagttccgggtagcgttcatgaaggtggtgaactgggttatagcc<br>tggcacatgcatatggtgcagcactggatcatccgggactgctggttgcatgcgttattggtgatggtgaagcagaaaccggtccgctggc<br>agccagctggcatagcaacaaatttctggatccggttcatgatggcgcagttctgccgattctgcatctgaacggctataaaatcgccaatcc<br>gaccgtgctggcacgtctgcctgaagatgaactggatagcctgctgcgtggttatggtcatgaaccgattcatgttagcggtgatgatccgg<br>cagcagttcatcgtgcaatggcccatgcaatggatactgccctggatcgtattgccgaagttcagcgtgccgcacgtgaagatggtgttacc<br>gaacgtgcacgtacaccggttattgttctgcgcaccccgaaaggttggaccggtcctgcggaagttgatggtaaaccggttgaaggcacct<br>ggcgtgcccatcaggttcctctggcaggcgttcgtgataaccggaacatctgcgtcagctggaagcatggctgcgtagctatcgtcctga<br>ggaactgtttgatgatgccggtcgtccggttgcagatgttctggcgtgtctgccagaaggtgatcgtcgtctgggtagcaccccgtatgcaaa<br>tggtggcctgctggtgcgcgaactgccgatgcctgcgctggatgattttgcagttccggttgataaaccgggtacaaccctgcatgaaccta<br>cccgtattctgggtggtctgttagaacgtattatgcgtgataccgcagatcgtcgcagttttcgtctggttggtccggatgaaaccgcaagcaa<br>tcgtctggaagccgtttatgatgcaagcggtaaagcgtggcaggcaggtacactggatgttgatgagcatctggatcgccatggtcgtgtga<br>tggaagttctgagcgaacacctgtgtcagggttggttagaaggttatttactgacaggtcgtcatggcctgtttagctgttatgaagcatttgtg<br>catatcgtggatagcatggttaaccagcatatcaaatggctgaaaaccagccgtgaactgccatggcgtgctccgattgcaagcctgaatta<br>cctgctgacaagccatgtgtggcgtcaggatcataatggttttagccatcagatccgggttttgttgatcatgttctgaataaaagtccggaa<br>gtggttcgtgtgtatctgcctccggatgcaaatacccctgctgtcagttgccgatcatgcactgcgtagtcgtgattatgttaatgttgttgttgcc<br>ggtaaacagccgtgttttgattggctgagcattgatgaagcacgtgttcattgtgcacgtggtcaggcatttgggaatgggcaggcaccga<br>aaatggcggtgcacctgatgtggttctggcatgtgcgggtgatgttccgacccaagaagtactggcagcggcacagctgttacgtcgtcatc<br>tgccggaactggcagttcgtgttgtgaatgttgtggatattgcccgtctcgatgcctcgtgaagaacatccgcatggtatgacagattttgaatat<br>gatggactgttcaccgcagacaaaccggtgattttttgcctatcatgtttatccgtggctgattcaccgtctggcctatcgtcgtaatgctcatcc<br>gaatctgcatgttcgtggttacaaagaaagcggtacgaccaccaccccgtttgatatggttgttcgtaatgatctggaccgttatcgcctggta<br>atggatgttattgatcgtgttcctggtctggccgttcgcgcagcagccgttcgtcagcgtatggcagatgcccgtacccgtcatcatgcatgg<br>attcgtgaacatggcaccgatttacctgaagttgcagaatggtcttggaatgca (SEQ ID NO: 66) |
| Nucleic acid sequence encoding for a phosphoketolase enzyme from *Cyanothece* sp. PCC 8802<br>atggttgcaacaccggaacgtccgaccctggaacagacaccgctgagcgcagaagaactgcgtcagattcaggcatattggcgtgcatgt<br>aattatctggcagtgggtatgatttatctgcgtgataatccgctgctgaaagatccgctgaccgaagatcatgttaaaaatcgtctgctgggtca<br>ttggggtagcagtccgggtctgagctttatctatatctcatctgaatcgcctgatcaaaaatacggcctggatgtgattttatatggcaggtcctg<br>gtcatggtgcaccgggtattctgggtccggttatctggaaggcacctatagcgaaacctatccggataaaagcgaagatgaagagggcat<br>gaaaaaattcttcaaacagtttagctttccgggtggtattggtagccattgtactccggaaacaccgggttcaattcatgaaggtggtgaactg<br>ggttatagcctgagccatgcatatggtgcagcactggataacccggatctgattgttgcagcagttgttggtgatggtgaagcagaaaccgg<br>tccgctggcaaccgcatgcgcatagcaataaatttcattaatccgattctgatgagcgcagttctgccgattctgcatctgaacggctataaaatc<br>gcaaatccgaccattctggcacgtattagccatgaggaactggaatacctgtttaaaggttatgcgtacaaaccgtattttgtcgaaggtagcg<br>atccggaagttatgcatcagaaaatggcagcaacactggaaaccgcaattgccgaaattaaacatattcagcaagaggcacgtaccagcg<br>gtgttgcaaaacgtcctatttggccgatgattgttctgcgtagcccgaaaggttggacaggtccggcaagcgttgatggcaaaaaaacgga<br>agattttttggcgtagccatcaggttccgctgagtggtatcgtcatggtaatgccggcacatcattaaagttctggaagattggctgaaagctatacc<br>cctgaagaacttttttgatgaaaacgcaccctgattccggaactgaaagaactggcaccgaccggtcatcatcgtatgagcgccaatccgc<br>atgccaatggtggtctgctgcgtaaagatctgaaaatgccggattttcgtaattatggtgttgaagttgccaaaccgggtacagttgaagtggg<br>taataccgcactgctgggcaatttttctgcgggatgttatggccaataatatgaccaattttcgtgtgtttggtccggatgaaaccgccagcaac<br>cgtctgaatgcaattatgaaatcagcaaaaagtgtggatggcgaacttctgccggaagatgcagatggtacagaaatcaccaccgatg<br>gtcgtgttatggaaatgctgagcgaacataccctgcagggcgtggctggaaggttatctgctgaccggtcgccatggttttttttcatacctatga<br>agcatttgcccatgtggtgatagcatgtttaatcagcatgcaaaatggctggacatctgcaaaaatgaagttccgtggcgtgccagcgttag<br>cagcctgaatattctgctgagcagcaccgtttggcgtcaggatcataatggttttagtcatcaggatcctggttatgttgatctggttaccaataa<br>atcagcggatgttgtgcgtgtttatttcctccggatgcgaatgtgtctgctgcagttgcaaatcattgtcgaaatcaaccgattacgtgaacgtt<br>attgttagcgataagcagatccatctgcagtatctgaatatggatcaggccatcaaacattgcaccaaaggtattggcatttgggattgggcaa<br>gcaatgatgattgcggtacggaaccggatcatcctgatgttattatggcaagctgtggtgatgttgcaaccaaagaagcactggcagccacc<br>gccattctgcgcgaagaatttccggatttaaaagtgcgttttatcaacgtggttgacctgttcaaactgcagagtgaaattgaacatcctcatgg<br>tctgagtgatcgcgattttgataacctttttcaccaaagacaaaccgatcatctttaacttttcatggttatccgtggctgatccacaaactgacctat<br>cgtcgtaccaatcatcacaatctgcatgttcgtggttataaagaaagcaataattaacactccgctggaactggccattaacaatcagattg<br>atcgttttaacctggtgatcgatgttatcaatcgtgttccgaaactgggtagcgcagcagcatatgtttatgaacgtatgaaaaacgccatcatc<br>gaacatcgtgcatatgcctatgaacatggtattgataagcccgagattaacaactggaaatggcctcat (SEQ ID NO: 67) |
| Nucleic acid sequence encoding for a phosphoketolase enzyme from *Neosartorya fischeri* NRRL 181<br>atgaccagcaaaggcgaaattgaaagcctgagcgcatatggtgttgcacgtagcaccattcagggtacaccgctgagccaggatgaactg<br>cgtaaaatggatgcatattttcgtgcaagcatgtatctgtgtctgggtatgctgtatctgcgtgataatccgctgctgaaagaaccgctgaaagt<br>tgaacatctgaaagcacgtctgctgggtcattggggtagtgatgccggtcagagctttacctggattcatatgaaccgtctgatcaaaaaata<br>cgatctggatgtgctgtttattagcggtccgggtcatggtgcaccgggtattctgtcacagactatctgaaggtgtttataccgaagtttatc<br>cggaaaaaacccaggacgaaaaaggtctgcagcgttttttcaaacagtttagctttccgggtggtattggtagccatgcaacaccggaaaca<br>ccgggttcaattcatgaaggtggtgaactgggttatagcattagtcatgcatttggcaccgttttttgatcatccgaatctgattaccctgaccatg<br>gttggtgatggtgaagcagaaaccggtccgctggcaaccagctggcatagcaacaaatttctgaatccgattacagatggtgcagttctgcc<br>ggttctgcatctgaatggctataaaatcaataacccgaccattctggcacgcattagccatgaagaactggaaatgctgttaaaggttatggt<br>tggaccccgtattttgttgaagtagcgatatgcataaaggcatacgcaaacctggaacattgtgttctggaaattaagaag<br>atccagaaacaggcacgcgaaagcaataaagcatttcgtccgctgtgccgatgattgttctgcgtagcccgaaaggttggagcgcaccg<br>cgtgaaattgatggtaaatacctggaaggcttttggcgtgcacatcagattccgatcaccgatgttcagagcaaaccggaacacttaaaagt<br>gctggaaattggatgaaagcgtataagccggaagaggtgtttgataaaaatggcaccctgattccggaactgaaagagctggcaccgac<br>cggcaccagccgtatgagcgcaaatccggtgggtaatggtggtctgctgcgtcgtccgatggatctgccggattttcgcgattatgcactga<br>ccgatattgaaccgggtgttaccattcgtccgagcatgagcaatatgagcaaatatctgcgggatgttgttgcccgtaatatgaccaccttcg |

-continued

SEQUENCES tgtttttggtccggatgaaaccgaatcaaataaactggccgaaatctacaaagccggtaaaaaggtttggatggccgaatatttcaaagaaga
tgaggacggaggtaatctggatatgcagggtcgtgtgatggaaattctgagcgaacatacatgtgaaggttggctggaaggatatattctga
gtggtcgtcatggcatgctgaatagttatgagccgtttattcatgtgatcgacagcatggttaatcagcattgcaaatggattgaaaaatgcctg
gcagttgaatggcgtgccaaagttagcagcctgaatattctgctgaccgcaaccgtttggcgtcaggatcataatggttttacccatcaggat
ccgggttttctggacgttgttgcaaataaaagtccggaagttgtgcgtatttatctgcctccggatggcaataccctgctgagcaccatgaatc
attgttttcgtagcgtgaattacgtgaatgtgattgtggcagataaacaagaacatgtgcagtttctgaacatggaagaagcaattgaacattgc
accaaaggtgttggtatttgggattgggcaagcaatgatcaggggttgcgaaccggatgtggttatggcaagctgtggtgatgttgcaaccca
tgaagccctggcagccaccgcactgctgcgcgaacatttaccgcagttaaaagttcgttttgttaatgtggttgacctgtttcgtctgattagcg
atattaatcatccgcatggtatgccggatcgtcagtggggtgcaattttttaccaccgataaaccgatcatctttaactttcatagctatccgtggc
tgattcatcgtctgacctataaacgtcctggtcagcataatctgcatgtgcgtggttataaagaaaaaggcaatatcgatacccgtttgaactg
gcggttcgtaatcagaccgatcgttatagcctggccattgatgcaattgatcgtattccgagcctgggtaataccgcaagcggtgttcgtgaa
cgcctgattaacctgcaactggcagcgaaaaacaaagcctttgatgatggtattgatccggattatattcgcaattggacctgggattatccgc
gtaaaaaatgc (SEQ ID NO: 68)

Nucleic acid sequence encoding for a phosphoketolase enzyme from *Enterococcus faecium* TX1330
atggattatagcagcaaagaatattttgataaaatgaccgcatggtggcgtgcagcaaattatctgagcgttggtcagatttatctgaaagata
atccgctgctgcgtcgtacccctgaaaccggaagatgttaaaaaacaccccgattggtcattggggcaccattccgggtcagaattttatctatgt
tcatctgaatcgcgtgatcaacaaatacgatctgaacatgtttttatatcgaaggtcctggtcatggtggtcaggttatggttagcaatgcatatct
ggatggtagctataccgaaatttatccggaagttaccgaagatgaaaccggtatgcagaaactgtttaaacgtttagcttttccgggtggtatt
gcaagccatgcagcaccggaaaacccgggtagcattcatgaaggtggtgaactgggttatagcctgagccatggtgttggtgcagttctgg
ataatcctgaagttattagcgcagttgttattggtgatggtgaagcagaaaccggtccgctggcaggtagctggtttagtaatgttttttatcaatc
cggttaccgatggtgcggtgctgccgattctgcatctgaacggtgcaaaaattgcaaatccgaccattctggcacgtaaaagtgatggcgaa
ctggccaattatttcaatggtctgggttgggaaccgtttttcattggagtaatgatccggaaaaactgaatccggtgatggcagaaaaaatgg
atcaggccattgagaaaatcaaaagcattcagaaagaagcccgtctgaaaaccgcagcagatgcaatgatgccgaaatggcctgttctgat
tgtgcgtaccccgaaaggttggacaggtccggaagaatggggatggtgagccgattgaaggcacctttcgtgcacatcaggttccgattccg
gttgatcaagaacatatggatcatgcagatgccctgctgcgctggctgaaaagctatgaaccagaaaagctgtttgatgcacagggtcgtatt
ctggaagaaattcgtgaaattgcaccgaccggtgatcatcgtatggcgcaaaaaatccgattacaaatggtggtatggtatgcgaaaccgctgat
tatgccggattggaaacgttataccctgcagtttgaaaaaccgggttcagttaccgcagaagatatgaccgaactgggcaaattgttcgcga
aatcattgaaaaaaacccgaaaactttcgcatcttttggtccggatgaaaccaaaagcaatcgtctgaatcaggtgtttaaaaccaccaatcg
tcagtggatggaaaaaattgaaccggaaaatgatgaatggctgagcccgagcggtcgtgttattgatagccagctgagcgaacatcaggat
gaaggtttttttagaaggttatgttctgaccggtcgcatggttttttttgcaagttatgaaagctttctgcgtgtggttgatagcatgctgacccagc
actttaaatggatgcgtaaaagccgtgatctgagctggcgtaataactatccgagcctgaatctgattgcaagtagcaccgtgtttcagcagg
atcataatggttatagtcaccaggatccgggtattctgacccatctggccgaaaaaaagcagaattattcgtgagtatctgcctgccgatgc
aaatacactgctggccgttatggataaagcatttcgtagcagcgaaaagatcaacctgattatcagcagtaaacatccgcgtgcacagttttat
agtgcagaagaagcagccgttctggttaatgaaggcctgaaaattatcgattgggcaagcaccgcaaaagaagaagaacctgaactggta
attgcagcagcaggcaccgaaagtaatctggaagcactggcagcagttactctgctgctggaagagtttccgaaactgaaaatccgctttat
taacgttgtggacctgctgaaactgcgtcatccgagtcaggatcctcgtggtctgagtgatgaagaatttgacaaatacttttaccaaagataaa
ccgatcctgtttgcctttcatggctatgaaacactgattcgccaccatcttttttgatcgccataatcatcatctgatgattcacggctataaagaga
atggcgatattaccacccgtttgatatgcgtgttgtgaatgaactggatcgttatcatctggcaaaagatgcagccctgaagattaaaggtag
ccaggccgaagattttgccaaaaagatggaccaaaaactgcaagaacaccagaactatatccgcgaaaatggtattgatctgccggaagt
gctggactggaaatggaagaatctggatcag (SEQ ID NO: 69)

Nucleic acid sequence encoding for a phosphoketolase enzyme from *Listeria grayi* DSM 20601
atgaccgattatagcagcccgaactatctggcaaaagttgatgcatggtggcgtgcagcagattttatcagcgttggtcagctgtatctgaaa
ggtaatccgctgctgcgtcgtccgctggaaaaagaagatttaaaagttcatccgattggtcattggggcaccattagcggtcagaattttatct
atgcacatctgaatcgcgtgatcaacaaatatgatctgaatatgttctacatcgaaggtccgggtcatggtggtcaggttatggttagcaatag
ctatctggatggtagctataccgataccctatccgaccattaccaggatgaagttggtctgaccaaactgtataaacagtttagctttccgggtg
gtattgcaagccatgcagcaccggaaacaccgggtagcctgcatgaaggtgcatcagcgactggcactgagccatgcaccaccggtagca
ttctgatatgataatccggatgttattgcagcaaccgttattggtgatggtgaagcagaaaccggtccgctgagcgcaggttggtttagtaatacctttt
attaaccggttaatgatggtgcagttctgccgattctgtacctgaatggtgcaaaaattagcaatccgacaattctgagccgcaaaaccgata
aagaactgaccagctttttcagggtctgggttgggatccgattttttgttgaaggtgaagatcctgccaaagtgcatccgctgatggcagaaa
aactggatcaggcaattgaaaaatcaaagccattcagaccgaagcacgtaaagaagccgcagataaagcaaccatgccgacctggcct
gttattctgtttcgtacccgaaaggttggacaggtccggaagaatggaataatgaaccgattgaaggtagcttcgtgcacatcaggttccg
attccggttgatcagcatcattttgatcatgttgatgccctggaaaattggctgcagagctatcgtccggaagaactgtttaccgaagaaggta
gtctgaaagaagaaatcaaaagcctggcaccgaaaaatcgtatggcaaccaatccgattaccaatggtggcattgatccgcagccgctgc
gtctgccgagctggaaagattatgcagttgaaaccgcaaacaaagatgtgattacgcaggatatgattgagctgggtggtttttgttcgtgatat
cgttaaagaaaaacccggataactttcgcattttttggtccggatgaaaccaaaagcaatcgcctgaataaagtgtttgaagtgaccaatcgtca
gtggatgagcaaagcagaatttccgcgtgatgaatggctggctccggcaggtcgtattattgatggccagctgagcgaacatcaggaca
aggttttctggaaggttatgttctgaccggtcgtcatggttttttttgcaagctatgaaagctttctgcgtgtgttgatagcatgctgacccagcac
tttaaatggctgcgtaaagcaaaagaacagacctggcgtaatagttatccgagcctgaatgtgattgcaaccagcaccgttttttcagcaggat
cataatggttataccctcaggatccggtgctgacacatctggccgaaaaaaaaccggaattttatcgtgaatatctgcctgcagatacc
aatagcctgctggcagttatgaatgaagcatttcgtagcgaggaactgattaatctgattgtgagcagcaaacatccgcgtccgcagttttata
gcgcagaagaagctgaaattctggttaaagatggcctgaaatcattgattgggcaagcaccgtgagcgaagccgaagaaccggatgtg
gttattgccagtgcaggtacagaaccgaatctggaagcactggcagcagttaccctgctgaacgaagcctttccgtcgctgaaaattcgcttt
atcaacattgtggacattctgaaactgcgccatccggatcatgatccgcgtggcctgaccgatgaagaatttgatcgttatttcaccacggac
aaaccgatcattttgcctttcattcatatgaaggtatggtgcgcataactctggcgaaaaaaaccggaatttatcaccaataatcacccagtttatcgcga
aaatggtgatattaccacccgtttgatatgcgtgttctgagtgaaatggatcgttttcacctggccaaagatgcagccgaagcagtttatggt
gaaattgcgaccagttttgccgcagaaatggacgccgttctgtcaaaacatcatcacttttattcgtgaaaacggcgaagatctgccggaagtt
gagaattggaaatggcaggcactgaaaactgacctgctgaagtg (SEQ ID NO: 70)

Nucleic acid sequence encoding for a phosphoketolase enzyme from *Enterococcus casseliflavus* EC30
atgaaaaccacctacgataccctgagtattaccagaaaatgaatgcatggtggcgtgcagcaaattatctgagcgttggtcagatttatctg
aaagataatccgctgctgcgtcgtccgattgaagaaaaagacctgaaagtgaatccgattggtcattggggcaccattgcaggtcagaattttt
atctatacccatctgaatcgcgtgatcaacaaatgatctgaatatgttctacatcgaaggtccgggtcatggtggtcaggttatggttgcaaa
tgcatatctggatggtagctatagcgaaatctatccgaaagcaacccaggatgaagcaggtatgaaacacctgtttaaaacctttagctttccg -continued

SEQUENCES ggtggtattgcaagccatgcagcaccggaaacaccgggtagcattcatgaaggtggtgaactgggttatagcattgcacatgcaaccggtg
caattctggataacccggatgttattgcagcagttgttgttggtgatggtgaagcagaaaccggtccgctggcaggtagctggtttagcaata
cctttattaacccggttaacgatggtgccattctgccgattctgcatctgaaccggtgcaaaaattgcaaatccgaccattctggcacgtaaaag
cgatcaggatctgaccaaatatttcgaaggtatgggttggacccccgtattttgttgaaggtgatgatccggaagcagttcatccgcagctggc
acaaaaaatggatcaggcaattgagcagattcatgcaattcaggcagaagcccgtaaaggttcagccgaagaggcagcaatgccgcattg
gcctgttctgattgttcgtaccccgaaaggttggacaggtccgaaagtttgggatggcgaaccgatcgaaggcggttttcgtgcacatcagg
ttccgattccggttaatgcaaaacatatggaacatgttgatgcactgaccgattggctgcagagctatcgtccggaagaactgttttgatgaaaa
tggtcgtattaaggccgaaatccaagaactggcaccgaaaggcgaacagcgtatggcagttaacccgattaccaatggcggtattgatcct
cagccgctgcgtctgccggattggcaggcacatgccattgcaattgaaactccgggtgaaaccaccgcacaggatatgatggttttggtaa
atttgcccgtgatattatcaaagagaacccggacaattttcgcattttggtcctgatgaagccaaaagcaatcgtctgaatcatgtgtttgaagt
taccgatcgtcagtggctggaaccgaaacatccggattatgatgaatggctgagcagcgtgggtcgtgttattgatagccagctgagcgaa
catcaggccgaaggttttctggaaggttatgttctgaccggtcgccatggttttttgcaagctatgaaagctttctgcgtgttgtggatagcatg
attacccagcactttaaatggctgcgtaaagcacatgatctggattggcgtaatccgtatccgagcctgaatctgattgcaagtagcaccgttt
tcagcaggatcataatggttataccaccaggatccgggtattatgacccatattgcagaaaaaaaagccgattttgtgcgtgttatctgcctg
cagatgcaaatagcctgatggccgttatggccgaaacctggcaagcgaagaaaagattaatctggttgttagcagcaaacatcctcgtcc
gcagtttatagcgcagatgaagcgaaagttctggtgaaagatggtctgaaagttatcgattgggcaagcaccgatgaaggtcaagaaccg
gatattgtgattgcagccgcaggtacagaaccgaatctggaagcactggcagccgttagcctgctgattgaagcatttccggaactgaaagt
ccgttttatcaatgttgttgacctgctgaaactgcgtcgccctgaagttgatccgcgtggtctgagcgacgaagcctttgaagcctattttacca
aagataagccgatcgtgtttgcctttcatggttatgaaggcctgattcgcgatatctttttggccgtcgtaatcagcagctgcatattcatggcta
tcgcgaaaacggcgatattaccaccccgtttgatatgcgtattctgtcagaactggatcgttttcatctggcaaaagatgcagcagaatgggtt
tatggtgaaaaagccacagattttgcacagaaagatggcagataccgttgcatatcatcatgattttatccgcgagaacggttatgatattgccg
aagttgaagaatgggaatggaaaccgctgcgc (SEQ ID NO: 71)

Nucleic acid sequence encoding for a phosphoketolase enzyme from Mycoplasma alligatoris A21JP2
atgaaaaagaataccttcgatacccaggactatctggataaagttgatgcatggtttcgtgcagcaaattatctgagcgttggtcagatgtatct
gcgtaataatccgctgctgcgtagcaaaattaccagtgatgatgttaaagtgtatccgattggtcattggggcaccattccgggtcagaatttt
gcatatgcacatctgaatcgcgtgatcaacaaatacaatctgaatatgttctacatcgaaggtcctggtcatggtggtcaggttatgaccagca
atagctacctggatggtagctatataccgaactgtttccgcatgtgacccaggatgttgcaggtatgaaacacctgtttaagtattttagctttccg
ggtggcaccgcaagccatgcagcaccggaaacaccgggtagcattcatgaaggtggtgaactgggttatagcctgagccatgccaccgg
tgcaatcctggataatccgaatgttattgcagcaaccattgttggtgatggtgaagcagaaaccggtccgctggcagcaagctggtttagca
atagttttatcaatccggttaatgatggtgccgttctgccgattctgcatctgaacggtgtggtaaaattagcaatccgaccattctgtgtcgcaaaa
gcaataaagaactgaccgattattttcgccggtatgggttggcgaagcagttttttgttgaaggtagtgatggaaagaaatgcacaagttatgg
cccagaaactggattatgtgatcgaaaaaattcagagcattcagaacgaggcacgtaaaaaaccggcaaatcaggcaacccgtccgatttg
gccgatgatggttctgcgtaccccgaaaggttggacaggtccggatagctggaataaagataaaattgtgggtagctttcgtgcccatcagg
ttccgattccggtgaatagcgcaaatatgaacatattgatgcactgctggattggctgaaatcctataaagtggataacctgttcgacaaaaa
tggcaaactggttgatgaaattgcacagattgcaccgaaaggcgcaagcagcgtatggcagttaaccgattaccaatggtggcctgaacccg
aaaaaaactggtaatgcctcgttggcaggattttgcactgaaattttcaaaaccgggtgagctggttaatcaggatatggttgagctgggcacct
attttgcaaaaatgatggaactgaacaaggacaactttcgtctgtttggtcctgatgaaaccaaaagtaatcgcctgtataacgtgttcaaagtg
accaaacgtcagtggctggaaccgattagcccctattctggatgaagcactgagtccggaaggtcgtgttattgatagccagctgagcgaac
atcaggcagaaggttttctggaaggttatgttctgaccggtcgccatggttgttttgcaagctatgaaagctttctgcgtgttgtgatagtatgc
tgacccagcacctgaaatggctgaagaaatgcaaaagatgttcattggcgtaatgattatccgagcctgaatgtgattgcgaccagcaccgc
atttcagcaggatcataatggttatacacatcaggatccgggtctgattggccatctggcagataaaactccggaaattattcgtcagtatctgc
ctgcagataccaatacccgtggcagttatggataaaagcctgaaagaacgcaacgtgattaaccatatcattgcaagcaaacagcctcgc
gaacagttttatagcgaacaagaagcagcagaactggtagaaaagaatcgtgaaagtaattgattgggcaagcaccaccaaaggtaatgaa
gaaccggaactggtggttgttgcagcaggcaccgaaccgaatctggaagcccggcagccgtgacgattctgaacaaagagtatccgtca
ctgaaaatccgttttgtgaatgtggttgatctgatgaagctgcgtcatccgagtctggatccgcgtggtctgagcgataaagaatttgatgcaat
tttcaccagcaacaagccgattgtgtttgcctttcatggttatgaaggtattctgcgcgacatgtttttcaaacgcaataaccataatctgatcacc
catggctatccggaaaatggtgatatcacaaccagctttgatattcgccagctgtacatatggatcgctttcatattagcgcaagcgcagcaa
aagcggtgtatgtaataaaagcacaagagttcgaggacaaaatgatccagaccattgatttccacaccaaatatatccgtgaatatggcacc
gatattcccgaagttaaagaatggaaatgggcagatctgacccgtaaa (SEQ ID NO: 72)

Nucleic acid sequence encoding for a phosphoketolase enzyme from Carnobacterium sp. 17 4
atgaaaaactatgatagcaaagattatctgaaaaaagtggacgcattttggcgtgcagcaaattatctgtcagttggtcagctgtatctgcgtg
ataatccgctgctgcagcgtccgctgaaaagcaccgatgttaaagcacatccgattggtcattggggcaccattagcggtcagaatttatct
atgcacatctgaatcgcgtgatcaacaaatatgatctgaatatgttctacatcgaaggtccgggtcatggtggtcaggttatgattagcaatgc
atatctggatggtagctataccgaatctatccggatatcaccgaaaacaaagaaggcatgaagaaactgttcaagcagtttagcagtccgg
gtggtgttgcaagccatgcagcaccggaaacaccgggtagcattcatgaaggtggtgggtttatagcctgagccatgccaccggtg
caattctggataacccggatgttattgcagcaaccgttattggtgatggtgaagcagaaaccggtccgctgcagcaggttggtttagcaata
attttcattaatccggtgaatgatggtgccgttctgccgattctgtacctgaatggtggtaaaattagtaacccgaccattctggcacgtaaaagc
aatgaagatctgaaagaaatatttcgagggtatgggttggaaaccgtatttgttgaaggcaccgatccggaaaaagttcatccggttatggca
aatacccctggatgttgttatcgaagaaatcgcagcattcagatcagaacgaagcccgtaaaggtaaaagcgaagtgttgaaatgccgcattggcc
tgtgatgattattcgtaccccgaaaggttggacaggtccgaaagaatgggataacaaaaaaatcgaaggcacgtttcgtgcacatcaggttc
cgattccggttgatgcagaacatatggaatgtgaataaactggtggactggctgaaatcatatcgtccggaagaactgtttaccgaaaatg
gcaaactgatcgatgacctgaaagaactgacaccgaaaggcaataaacgtatggcaaccaatccgattaccaatggtggcattaatgcaaa
agcactgattatcccgaattggaaacagcatgcaattgataccaccattccgggtgcagttattgccaggatatggatgtttttggtgaacag
gcacgtgatctgattgttaaaaatccgaacaacttcgcatcttcggtccggatgaaaccaaaaagtaatcgcctggtataaatctttgaagtga
ccaatcgtcagtggctggaaagcaaagaattaaccgatgaatggcagagcagcgcaggtcgtgttattgatggccagctgagcgaacatc
aggcagaaggttttctggaaggttatgttctgaccggtcgtcatggttttttgcaagctatgaaagctttctgcgtgttgttgatagcatgctgac
ccagcactttaaatggctgcgtaaagcaaccgatcagaaatggcgtaataactatccgagcctgaatgtgattgcaaccagcaccgtttttca
gcaggatcataatggttatacccaggatccgggtattctgacccatctggcagaaaaaaccggaatttatccgtgaatatctgcctgc
agatgcaaatagctgatggccgttatggacaaaagaacgcaacgtgattaaccatcattgcagcaaacatccgcgtcc
gcagtttatagcgttgaagaagccgaaattctggttaaagatggcctgaaaattatcgattgggctaccgataatgatagcgaaccggat
ctggttatcgcagcagccggtacagaaccgaacctggaagcactggcagccatgagcattctgcacaaagcatttccggaactgaaaatc
cgctttatcaacattgtggacattctgaaactgcgtcaccccggatattgatagcgtggtctgacagatgaaaattcgatagctatttcaccaa
agagcagccgattatctttgcctttcatggctttgaaggtctgattcgcgatatctttttaaccgccataaccataatctgcgcattcacggttatc
gtgaaaatggtgatattaccaccccgtttgatatgcgtgttctgaatgaaatggatcgttttcatctggccaaagatgccgcaaaagccgtttat -continued

SEQUENCES ggtctgaaagccaacaaattcatgcaagagatggaaaacaccgtgaactttcatcatcagtatattcgcgaaaacggcattgatattccggaa
gtgattaactggaaatgggaaaaatc (SEQ ID NO: 73)

Nucleic acid sequence encoding for a phosphoketolase enzyme from *Melissococcus plutonius* ATCC 35311 atggaaaaagataaatacagcagcaccgagtacctggacaaaattgataaatggtggcgtgcagcaaactatctgagcattggtcagctgt
atctgaaagataatccgctgctgaaacgtaaaattcgtagcgaggatgttaaatatcatccgattggtcattggggcaccattgcaggtcaga
attttatctatgcacatctgaaccgcattatcaacaaatacgatctgaatatgttttatatcgagggtccgggtcatggtggtcaggttatggttag
caatagctatctggatggtagctataccgaaatttatccggcagttaccgaagatgaagcaggtatgcagaaactgtttaaacgttttagctttc
cgggtggtgttagcagccatgccgcaccggaaacaccgggtagcattcatgaaggtggtgaactgggttatagcctgagccatggtgttg
gtgcaattctggataacccggaagttattagcgcagttgttattggtgatggtgaaagcgaaaccggtccgctggcgaccagctggtttagta
atacctttattaacccggttaccgatggtgccgttctgccgattctgcatctgaatggtgcaaaaattgcaaatccgaccattctgggtcgtaaa
agcgataaagaactggaacagtattttcgtggtatgggttggattccgtattttgtggaaggtaatgatccgaatcagatgcatccgctgatgg
caaaaaccctggatcaggtgattgaaaaaatccacagcattcaagaaaccgcacgtaaacagaccgcagaaacagcaagtattcagaaat
ggcctctgattgttctgcgtaccccgaaaggttggacaggtccgaaagaatgggatggtaaaccgattgaagttacctttcgtgcacatcag
gttccgattccgattgatcaggatcatatggaacatgttgatcagctggtgaattggctgaaaagctataaaccggaagaactgtttgatgaaa
caggtcgtctgaatagcgaaattcgtgccattgcaccgatgaatgataaacgtatggcaatgaatccgattaccaatggtggtattaatccga
aaccgctgcagatgccggattggcgtgaatttgatctgcatattagcaaaccgggtgagctggttgcacaggatatgctggaatttggtaaaa
tggttgcagccatcatcaaaaaaacccgcagaactttctgatctttggtccggatgaaaccaaaagcaatctgctgaatgatgcatttagcgt
taccagccgtcagtggctggaaccgatttatgaacctcaggatgaatggctggcaccgtcaggtcgtattattgatagccagctgagcgaac
atcaggacgaaggtattctggaaggttatgttctgaccggtcgtcatggtttttttgcaagctatgaagcctttattcgcatcgtggatagcatga
ttgcccagcatatcaaatggatgcgtaaagcaatggatctgccgtggcgtaatggttatagtagcctgaatctgattgcaagcagtaccgcat
ttcagcaggatcacaatggctatacccaccaggatccgggtatcctgagtcatctggcagaaaaagaagcagattttatccacgaatatgtg
cctgcagataccaatagcctgctggcagttatggataaagttctgaaaagtcagggcaaagtgaatctggtgattagctcaaaacatccgcg
tccgcagttttatagccctgaagaagcacaagaattagttaatcgtggcctgatggaaattgattgggcaagcaccgttgcagaaaatggca
ctccggaaattgtgattgttgccgcaggcaccgaaccgaatatggaagcactggcagcaattaatctgatcaatcagagttttccgaaactgc
agttccgctttatcaatgttgtggatttactgaaactgcgtcatcctgcagttgattcaagaggtattagcgaagtggaatataaccacctgttta
ccgttgattccccgattatctttgtttgtcagggttattcaagcctgattcgcagcctgttctatgatcgtaaaaatcgtccggttagcatccatag
ctaccaagaaaacggtgccattaccaccccgtttgatatgcgtgttctgaataaaatcgatcgttatcacctggccaaagatattgcactgacc
gcatatggtagccgtggtgaagattttgcacgtgccatggataccatcctggaaaaacacaatcagtatattcgcgaaacgggtaaagatct
gcctgaagtgctgaattggaaatgggctccgctgcatatctataacgaaaacattgaacaggat (SEQ ID NO: 74)

Nucleic acid sequence encoding for a phosphoketolase enzyme from *Tetragenococcus halophilus* NBRC 12172 atgagcgtgaacatcgacagcaaagaatatctggaacgtatgaatgcatggtggcgtgcagcaaactatattagcgttgcacagattttctg
cgtgataatccgctgctgcgtcgtccgctggaaaaagaagatatcaaaattaacccgattggtcattggggcaccattagcggtcagaatttt
atctatgttcatctgaaccgcgtgatcaacaaatatggtctgaacatgttttatatcgaaggtccgggtcatggtggtcaggttatggttagcaat
agctatattgatggcagctatagcgaaatctatccggatgttacccaggatgaagcaggtctgaaaaaactgttcaaacagtttagctttccgg
gtggtatgggtagccatgcagcaccggaaacaccgggtagcattcatgaaggtggtgaactgggttatagcatgagccatgccgttggtgc
agttctggataatcctgatgttattgcagcaaccgttattggtgatggtgaagcagaaaccggtcctctggcagcaagctggatgagcaataa
tttcattaatccggtgaatgatggcgcagtgctgccgattctgaatctgaatggtgcaaaaattgcaaatccgaccgttctggcacgtaaaagc
gataaagatctgcagaaatactttgaaggtctgggttggaaaccgtattttgtggaaggtgataacccggaaaaaatgcatccgctgatggc
cgaaaccctggatgcagttattaacgaaattcagagcattcagaaagaagcccgtaaaggttcagccgaagatgtgaccatgccgcattgg
cctgttattgtttttcgtaccccgaaaggttgggaaggtccagaaaaatgggataatgagcagattgcaggcacctttcgtgcacatcaggttc
cgattccgattgatgcaagccatatggaatatgcaaatgatctggcaaaatggctgaaaagctatcgtccggaagaactgtttgatgaaaatg
gcacaattattgatgcgattaaagaactgagtccgaaaggcgataatcgcatgagtgttaatccgattaccaatggtggcctggatccgaaa
gcactgaatatgcctgattggcatacccatgcagttgataccagcaaacgtggcaccgataaagcacaggatatgagcgttctgggtggtttt
attgccgatattatggaaaacaacccgaagaactttcgcatttttggtccggatgaaaccaaaagcaatcgcctgaataaagtttttgatgtga
caaatcgtcagtgggttgaacctcgtgaactgtcagatgaatggcagagcgcagttggtcgtgtgatcgatggtcagctgagcgaacatca
ggcagaaggttttctggaaggctataccctgaccggtcgtcatggtttttttgcaagctatgaagcatttctgcgcattgttgatagcatgctga
cccagcactttaaatggattcgtaaagccaatgaaaaagctggcgcaaaaaatacccgagcctgaatgtgattagcagcagtaccgcattt
cagcaggatcataatggttatacccatcaggatccgggtgtgattacccatctggcagaaaaaaaaccggaatatatccgcgaatattttccg
gcagatgcaaatagcctgatggcggttatggataaagccctgaaagatgaaaacgtcattaacctgattacctcgagcaaacatccgcgtcc
gcagttttatagcgttgaagaagcacaagaactggtcgattatggcgtgaaaaaaatcgattgggcaagcaatgatcaggatagcgaaccg
gatattgtgtttgcagcagcaggtagtgaaccgaatctggaagcactggcagcgattagcattctgcatgaacagtttccggaaatgaaaatc
cgctttatcaatgttgtggacctgctgaaactgcgtcatccagatgttgatccgcgtggtctgagtgatgaagcctttgatgagctgtttaccac
agataaaccggtgatctttaactttcatggttatgaaggcctgattcgcgatatctttttttacccgtcataatcgtaatctgagcatccatggctatc
gtgaagatggtgatattaccaccccgtttgatatgcgtgttaaaaatgaactggatcgctttcatctggccaaagatgcagccaataccatttat
gccgaaaaagcagccgatttcatccaagaaatggacaaaaccctgcagtatcaccatgattatattcgcgaaaacggtgatgatatcagcg
aagttcagaattgggaatggaaagacctgaaa (SEQ ID NO: 75)

Nucleic acid sequence encoding for a phosphoketolase enzyme from *Melissococcus plutonius* DAT561 atgaccaaatatgatagcaaagaatatctggccaaagtggatgcattttggcgtgcagcaaactatattagcgttggtcagctgtatctgaaag
ataatccgctgctggatcgtccgattgaaaccaccgatgttaaagttcatccgattggtcattggggcaccattagcggtcagaattttatctat
gcacatctgaatcgcgtgatcaacaaatacgatctgaacatgttttatgtggaaggtccgggtcatggtggtcaggttatggttagcaatagct
atctggatggtagctataccgaaatctatccggaaatcaccgaagataaagagggtctgaaaaaactgttcaaacagtttagctttccgggtg
gtattgcaagccatgcagcaccggaaactccgggtagcattcatgaaggtggtgaactgggttatagcattagccatgccaccggtgcaatt
ctggataacccggatgttattgcagcaaccgttgttggtgatggtgaagcagaaaccggtccgctgagcgcaggttggtttgcaaatacctttt
attaacccggttaacgatggtgccattctgccgattctgtacctgaatggtggtaaaattagcaatccgaccattctggaacgcaaaagtgatg
aagaactgaccaagtattttgaaggtatgggttggaaaccgtattttgttgaaggcaccgttccggataaagtgcatcctctgatggcaaaaat
cctggatcatatcatcgaagaaatcaaagatattcagaaagaagcccgtaaagacaaagccgaaaatgcaaaaatgccgcattggcctgtt
ctgattatgcgtaccccgaaaggttggacaggtccgaaaatttgggatgatgaaaaaattgagggcacctttcgtgcacatcaggttccgatt
ccggttgatgcagaacatatggaacatattgatgcactggttgattggctgaaaagctatcatccggaagaactttttgataaaaacggcacc
ctgaaaccggaactgaaagaactggttccgaaaggcgatcgtcgtatggccaaaaacccgattaccaatggtggcctggatccgaaaccg
ctgaaaatgaatggttgggaacagcatgcaattgataccagcacaccgggtatggttaccgcacaggatatgattgtttttggcaattatgtcg
aagatctgatcaaagcaaacccgaccaattttcgtatttttggtccggatgaaaccaaaagcaatcgcctgaataaagtgtttgatagcaccg -continued

SEQUENCES atcgtcagtggatggaaccgattagtaatgcagatgaatggcagagcagcgtgggtcgtgttattgatggccagctgagcgaacatcaggc
agaaggttttctggaaggttatattctgaccggtcgtcatggttttttttgcaagctatgaaagctttctgcgtgttgtggatagcatgctgaccca
gcactttaaatggctgcgtaaagcaaaagaacagagcgtggcgtaaagagtactgaacattattgcaaccagcaccgtttttcagc
aggatcataatggttatacccatcaggatccgggtatcctgacccatctggcagaaaaaaaagcagaatatatccgtgaatacctgcctgca
gatgcaaattgcctgatggccgttatggataaagcctttcaagaaaacgaagtgattaacctgattgtgagcagtaaacatccgcgtccgca
gttttatagcgttaccgaagccaaagaattggttgataaaggcgtgaaagtgattgattgggcaagcaatgatgaaggtcagacaccggata
ttgtgattgcagcgagcggcaccgaaccgaatctggaagcactggcagcaattaccctgctgaacaaagagtttattgatctgaaaatccgc
ttcgtgaacgtggtggatatcctgaaactgcgtcatccgagcattgatccgcgtggtctgaccgatgaagagtttgatgcaatttttcaccaagg
acaaaccgattgtgtttgcctttcatggctttgaaggcctgattcgcgatatctttttttagccgtagcaatcatcagctgtttgtgcatggttatcgt
gaaaaaggtgatattaccacccgtttgatatgcgtgttctgagtgaaatggatcgttttcacctggcaaaagatgttgccgacaaagtgtata
atgaacaggcagccgattttatgaatcgcatggatgaaattctggcctttcaccatcagtatattcgcaaaaacggtatcgatattccggaagt
ggttaactggaaatgggaggatctgcgcaaaaaaacgatttgctttaat (SEQ ID NO: 76)

Nucleic acid sequence encoding for a phosphoketolase enzyme from Mycoplasma arthritidis
158L3 1
atgaaaaaaaccaattatgatagcaatgaatattcaatctgattgataaatggtttcgcgcagccaattatctgagcgttggtcagatttatctg
cgtaataatccgctgctgaaaaccaaactggttgcagatgatgttaaaatctatccgattggtcattggggcaccattccgggtcagaatttttat
ctatgcacatctgaatcgcgtgattaacaaatacgatctggaaatgttctatatcgaaggtcctggtcatggtggtcaggtgatgattagcaata
gctatctggatggtagctataccgaaatttatccggaaatcaccgaagatgaagcaggtctgaaaacgatgttaacgttttagctttccggg
tggcaccgcaagccatgcagcaccggaaactccgggtagcattcatgaaggtggtgaactgggttatgcactgagccatgccaccggtgc
aattctggataatccgaatgttattgcagcaaccgttattggtgatggtgaagcagaaaccggtccgctgcagcaggttggtttagcaattct
tttatcaatccggttaatgatggtgccgttctgccgattattcatctgaacggtgcaaaaatttccaacccgaccattctgagccgtaaaagcaa
tcaagaactggaaaactattttagcggtctggtgggaaccgctgtttgttgaaggtgacgatccgaaactgatgcatccgctgatggcaaa
aaaacggatgaagccattgagaagattcaggtgattcaggcagcgcacgtaaacataaagcaagcgaagcaaccgtccggtttggcc
gatgctgattgttcgtaccccgaaaggttggacaggtcctaaagattggaatggcgaagtgtggaaggtagctttcgtgcacatcaggttcc
gattccggtgaatgccctgaatatgacccatatcgataaactggaagcatggctgaccagctatcatccggaagaactgtttgataaaaacg
gcaaaatcctggaagaaattcgtgccctggcaccgaaaggcctgaaacgtatggcagttcatccgattaccaatggtggtattaatccgcgt
accctgaaactgagcagctgggaaaaatttgccaccaaatttgaaaaccctggccgattaaaggtcaggatatgatcgaactgggcaaat
atttcgcagaaattatcaccctgaacaaggataactttcgcattttttggtccggatgaaaccaaatccaatcgtatgaatgccgtgttttaatgtga
ccaaacgtcagtggctggaaaaaatcgcaccgacctatgatgaatggatgagtccggaaggtcgtgttattgatagccagctgagcgaaca
tcaggcagaaggttttctggaaggttatgttattaccggtcgccatggtgttttttgcaagctatgaagcatttctgcgtgttgtggatagtatgct
gacccagcatatgaaatggatgaagaaaagcctggaactgccgtggcgtaaagattttccgagcctgaatgtgattgcgaccagcaccgc
atttcagcaggatcataatggttatacccatcaggatccgggtctgctgtgggtcatctggcagataaacgtccggaactgattcgtgaatatctg
cctgcagataccaattgcctgctggcaaccatgaaaaagcactgaaagatcgtaatgctgatcaacctgattgtgcaagcaaacagctc
gtgaacagttttatagcgttgaagaagccagcgaactggtacagaaaggctataaaatcattaattgggccagcaacgtgagcaaaaatga
agaaccggatgttgtgtttgcagcagccggtgttgaaccgaatctggaagctctggcagccattagtattctgaacaaagaattcccgaacct
gaaaatccgttttgtgaatgttctggatctgctgaagctgaaaagccgaaacatgatccggcgcattagcgacgaagaatttgatcagat
cttcaccaaaaacaaaccgatcatctttgcctttcatggttatgaaggcctgctgcgtgatatctttttttgatcgccataaccataacctgatcacc
catggctatcgtgaaaatggcgatatcaccaccagttttgatattcgtcagctgagtcatatggatcgctttcatattgcaaaagatgcagcaat
tgcagccctgggtaaagatggcgaaatgttgcgaaaaatggacagcaaactgcaagaacataccagttatgttcgcgagtatggctat
gatctgccggaagttgttaattggaaatggaccaatctgaaaccgattaaa (SEQ ID NO: 77)

Nucleic acid sequence encoding for a phosphoketolase enzyme from Streptococcus agalactiae
NEM316
atgagcgagttcgacaccaaaagctatctggaaaaactggatgcatggtggcgtgcagcaaaactatattagcgcagcacagatgtatctga
aagataatccgctgctgcgtcgtgaactggttgaaaatgacctgaaagttcatccgattggtcattggggcaccgttccgggtcagaatttttat
ctatgcacatctgaatcgtgccatcaacaaatatgatctggacatgttttatatcgaaggtcctggtcatggtggtcaggttatggttagcaata
gttatctggatggtagctataccgaactgaatccgaatattgaacagaccgaagatggttttaaacagctgtgcaaaatctttagctttccggt
ggtattgcaagccatgcagcaccggaaacaccgggtagcattcatgaaggtggcgaactggttatgcactgagccatgccaccggtgca
attctggataacccggatgttattgcagcaaccgttattggtgatggtgaaggcgaaaccggtccgctgatgcaggttggctgagcaatac
ctttattaacccggttaatgatggtgcagttctgccgatcttttatctgaatggcggtaaaatttcataatccgaccatctttgaacgcaaaaccga
tgaagaactgtcccagttttttgaaggtctggttgggaaaccgatttttgcagatgttgttgaactgagtgaagatcatgcagccgcacatgca
ctgttttgcagaaaaattagatcaggccatccaagagattaaaaaccattcagcagcgaagcacgtcagaaaccggcagaagaagcaattcag
gcaaaatttccggttctggttgcacgtattccgaaaggttggacaggtccgaaagcatgggaaggcaccccgattgaaggcggttttcgtgc
acatcaggttccgattccggttgatgccatcatatggaacatgttgatagcctgctgagctggctgcagagctatcgtccggaagaattatt
gatgaaagcggcaaaatcgtggatgaaattgcagccattagcccgaaaggcgatcgtcgtatgagcatgaacccgattaccaatgcaggt
attgttaaagcaatggataccgcagattggaaaaaattcgccctggatattaatgtgccaggccagattatggcacaggatatgattgaattg
gcaaatatgcagcgatctggtggatgcaaatccggataattttcgtattttttggtccggatgaaaccgaaaagcaatcgtctgcaagaagttttt
acccgtaccagccgtcagtggctgggtcgtcgtaaaccggattatgatgaagcactgagtccggcaggtcgtgttattgattcacagctgag
cgaacatcaggcagaaggttttctggaaggtctatgttctgaccggtcgtcatggttttttttgcaagctatgaaagctttctgcgtgttgtggatag
tatggttacccagcactttaaatggctgcgtaaaagcaaaacccataccacctggcgtaaaaactatccggcactgaatctgattgccgcaa
gcaccgttttcagcaggatcataatggttatacccatcaggatccgggtattctgacccatctggccgatgaaacgaaaaatatccgtgaaga
gcagcaatcatcagcagctgtttgtgcatggttatcgtgaaaaaggatgatattaccacccgttgatatgcgtgtatatcagaactggatcgttttcatctg
gccaggatgccgcactggcaagcctgggtaatgaagcccaggcattagtgatgaaatgaatcagatggtggcctatcaccaaagatattatccgtgaacatgg
tgatgatattccggaagttcagaattggaaatgggaaaacattaaa (SEQ ID NO: 78)

Nucleic acid sequence encoding for a phosphoketolase enzyme from Mycoplasma agalactiae
PG2
atgaaaaaagccatgattttgatagcaaagaatatctgaatctggttgatgcatggtggcgtg

```
ggtggcaccgcaagccatgcagcaccggaatgtccgggtagcattcatgaaggtggtgaactgggttatagcctgagtcatgcagccggt
gcagttctggataatccggatgttattgccgcaaccgttattggtgatggtgaaagcgaaaccggtccgctgagcgcaggttggtttattaac
agctttatcaatccggcaaatgatggtgccgttctgccgattctgcatgttaatggtggtaaaattagcaaccgaccatttggagccgtcgta
gcaatgaagaactggttagctattttaccggtgccggttggaaaccgttttattgttgaaggtaatgagccggaatatatgcatcatgaaatggc
aaaagcactggatgcaagcgttgaactgattaaacagtatcaggccgaagcacgtaaaaatggtgcaaataaagcaaaacgtccgcagtg
gccgatgattgttctgaaaagcccgaaaggttggacaggtccgaaagaatggaatcatgaagcaattgaaggttcctttcgtgcacatcagg
ttccggttccagttagcgcagaaaaaaatgcagcatattgatgcactggaaaattggctgcgtagctatcgtccggaagaactttttgatgaaaa
tgcccagctgaaaccggaaattgcagcaattgcaccgaaaaggcgatcgtcgtatgggtaaaaacccgattgcaaatggtggcattaatccg
cgtgcaattaatgttggtgattggaccaaatttgccctggatatcaaacagcctggcaaagttattaatcaggatatggttaccctgggcagct
atctgggcgaactgagcctgctgaataaagataatttttcgtgttgggtccggatgaacataaaagcaatcgtctgtatgagatgttcaaagt
taccgatcgtcagtggctggatcgtatcgatgaaaaatatgatgaatttctgagcagcgtgggtcgcattattgatagccagctgagcgaaca
tcaggcagaaggtatgctggaaggttatgttctgaccggtcgcatggtgttttttgcaagctatgaaagctttctgcgtgttgtggatagcatgc
tgacccaacatatgaagtgggttaaaaaagcgctggacattccgtggcgtaatgattatccgagcctgaatgtgattgcaaccagtaatgcat
ttcagcaggatcataatggttatacccatcaggatcctggtctgattggccatctggcagataaacgtccagaactgatccgtgaatatttacc
ggcagataccaatacctgctggcaaccatggccaaagccctgcaggatcgtaacgtgattaatctgattatcagcagtaaacagccacgc
catcagttttttagtattgaagaagcaaccgagctggtcgaaaaaggcattaaaatcattgattgggccagcaacattaagccgaacgaaga
accggatctggtggttgcagccagcggtacagaaagcaccattgaaagcctggccaccattacctacctgcgtgcccattttccggaactg
aaaatccgttttgttaatgtgctggatctgctgaagctgcgtcatccgagtattgatcctcgtggtctgagcgatagcgaatttgatagtatcttc
acgaaagacaaaccgatcctgtttgcctttcatggttatgaagccattctgcgcgatatcttttttcctgcgttcaaaccataacattatcacccat
ggctatcgtgaaaatggcgatattaccaccgcattttgatattcgtctgctgagtgaaatggatcgctttcatatgaccgcaaatgttgcaaaaaa
actggcaccggttgttggcgaaagcaaagcaaatgaactggtgaaactgatggaagataaaatcaaagaacaccgtgcctatatcaaaga
gtatggcaccgatctgccggaagttaaagaatgggaatggacccccgtataaa (SEQ ID NO: 79)
```

Nucleic acid sequence encoding for a phosphoketolase enzyme from *Streptococcus gordonii* str. *Challis* substr. CH1
```
atgaccaccgactataacagcaaagcctatctggaaaaagttgatgcatggtggcgtgcagcaaactatattagcgcagcacagatgtatct
gaaagataatccgctgctgaaacgtgatgttgttgcaaatgacctgaaagcacatccgattggtcattggggcaccgttccgggtcagaattt
tatctatgcacatctgaatcgcaccatcaacaaatatgatctggaacatgtttatatcgaaggtccggtcatggtggtcaggttatggttagcaa
tagttatctggatggtagctataccgaactgaatccgaatattccgcagaatgaagagggttttaaacacctgtgtaaaatcttttagctttccgg
gtggtattgcaagccatgcagcaccggaaacaccgggtagcattcatgaaggtggtgaactgggttatgcactgagtcatgcagccggtg
caattctggataacccggatgttattgcagcaaccgttattggtgatggtgaagcgaaaccggtccgctgatggcaggttggctgagcaat
acctttattaacccggttaatgatggtgccattctgccgatctgtttatctgaatggcggtaaaattcataatccgaccatctttgaacgcaaaacc
gatgaagaactgacccgttttttgaaggtcgggttggaaaccgattttttgcagatgttattaccgcaattagcgaaaatcatgaagcagcatg
cactgtttgcagccaaactggatgaagcaattgaagagatcaaaaaagttcaggcagaagcacgtaaaggtagcgcagaagaagcaacc
caggcaattttttccggttctggttgcacgtattccgaaaggttggacaggtccgaaaagctgggaaggcaccccgattgaaggcggttttcg
tgcacatcaggttccgattccggttgatgccatcatatggaacatgttgacgcactgctgaattggctgaaaagctatcgtccggaagaactt
tttgatgaaagcggtaaagttctgccggaaattgccgcaattgcctaaaggtgatcgtgtgcatataccggtgcaagccatgaacccgattacaatgccggt
gttattaaacctatggataccgcagattggaaaaaacacgcactgaaatttggcactccgggtgaaattgttgcacaggatatgatcgaattc
ggtaaatatgcaaccgatctggtgatgcaaatccggataattttcgtatttttggtccggacgaaaccaaaagtaatcgtctgcaagaagtttt
tacccgtaccagccgtcagtggctgggtcgtatgcgtcctgaatatgatgaagccctgagtccggcaggtcgtgttattgatagccagctga
gcgaacatcaggccgaaggtatgctggaaggttatgttctgaccggtcgcatggttttttttgcaagctatgaaagctttctgcgtgttgtggat
agcatggttacccagcacttaaatggctgcgtaaatgtaaaacccataccacctggcgtaaaaactatccggcactgaatctgattgcaacc
agcaccgttttcagcaggatcataatggttatacccatcaggatccgggtattctgacccatctggcagaaaaaactccggaatttatccgtg
aatatctgcctgcagataccaatagcctgctggcagttatggataaagcatttaaagccgaggataaggtgaacctgattgtgaccagtaaac
atccgcgtcacgcagtttttatagtgccgaaaggcggaggaactggttcgtgaaggctataaaatgattgatgggccagcaccgtgagcaa
caacgaagaaccggatgtggtttttgccgcagcaggcacagaaccgaatctggaagcactggcagcagttagcattctgcacaaagcctt
ccggaactgaaaattcgttttgtgaatgtggtggacattctgaaactgcgtcatccgagcgttgatgcgcgtggtctgagcgacgaagaattt
gatcaggtgtttaccaccgataaaccggttatctttgcctttcatggttatgaaggcatgatccgcgatatcttttttaaccgccataaccataatc
tgcgcgttcatgcctatcgtgaaaatggtgatattaccaccccgtttgatatgcgtgttatgtcagaactggatcgttttcatctggcccaggatg
ccgcaaatgcagccctgggtgaagatgcagcggttttttagcgcaaaaatggatgaaaccgttgcatatcataacgcctatattcgcgaaaat
ggggatgatattccggaagttcagaattggaaatgggaaaacattaacaaa (SEQ ID NO: 80)
```

Nucleic acid sequence encoding for a phosphoketolase enzyme from *Kingella oralis* ATCC 51147
```
atgcagaacacccagtttgacacaccggaatatctggcaaaagttgatgcatggtggcgtgcagcaaactatattagcgcagcacagatgt
atctgaaagataatccgctgctgaaaaaaccgctgaccgcaaatgatgttaaagcacatccgattggtcattggggcaccgttccgggtcag
aattttatctatgcacatctgaatcgtgccatcaacaaatatgatctggaacatgtgttttatatcgaaggtccggttcatggtggtcaggttatggtta
gcaatagctatctgtgatcataccgatatctatccggaaatttacccaggatgaagcaggtctgaaaaagctgtgtaaaatctttttagcttt
ccgggtggtattgcaagccatgcagcaccggaaacaccgggtagcattcatgaaggtggtgaactgggttatgcactgagccatgccttg
gtgcagttctggataacccgaacattattgcagcagcagttattggtgatggtgaagcagaaaccggtccgctgtgtgcaggttggtttggta
ataccttttattaacccggttaatgatggtgccgtgctgccgattctgtacctgaatggtggtaaaattcataatccgaccattctggcacgtaaa
accgatgccgaactgaccgtatttttaacggtatggttcgggaaccgattttttgtttgaagttagcgatcgcagcgatagccatgccgattatgg
cacagaaactggatgaccagtgttgaacgtattctggccatttggcaggatgtcacgtagccgtagcgccaatgatgcaaccatgcctcgttg
gcctgttctggttgcccgtattccgaaaggttggacaggtccgaaaacctggaatggcgaaccgatcgaaggcggttttcgtgcacatcag
gttccgattccgaccaatagtcatgatatgagcaccgcagatgcactggaagcatggctgcgtagctatcgtccggaagaactgtttgatgat
aatggtcgtttcctggataaattggcgtgaaattagccccgaaaggcgcaaaacgtatgagcgttcatccgatcaccaatggcggtgttgcacc
gaaagcactggttatgccgattgacccaaacatgccctgaaaattgcaccccctggcaggatgccaggatgccaggatatgattgaatggt
cgtctgatggcagatgttattaccgccaatccggataactttcgtatttttggtccggatgaaaccaaaagcaatcgtctgaatgaagtgttcaa
agtgaccaatcgtcagtggctgggtgttcgtgatgcagcctatgatgaatggattgcaccggttggtcgtgttattgatagcagctgagcga
acatcaggcagaaggttttctggaaggttatgttctgaccggtcgtcatggttttttttgcaagctatgaaagctttctgcgtgttgtggatagcat
gattacacagcactttaagtggctgcgcaaatgcaaaaccccatgcaccgtggcgtaaagattatccgagcctgaatctgattgcaaccagca
ccgttttttcagcaggatcataatggttataccccatcaggatcagcagttatgagcgaagcactgaccagccgtgatcgtattaacctgattgttagcagtaaacatc
tgcgtccgcagtttatagcgcagatgaagccaaagaactggttcgtgaaggctataaaatcattgaatgggcaagcacctgtcatgacggt
gaaccggatgttgtgatcgcagcggcaggcaccgaaccgaatatggaagcctggcagcaattaatgttctgcacaaacattacccggaa
atgaaaatccgctttatcaacgtggtggatattctgaaactgcgtcatccgagcattgatccgcgtggtctgagtgatgaagcgtttgatgccc
tgtttacccgtgataaaccggttgtttttgctttcatggctatgagaatatggtgcgcgatatcttttttccgcgtcataatcgtaatgtgcgcatcc
```

-continued

SEQUENCES atggttatcgtgaaaatggtgatattaccaccccgtttgatatgcgtgttctgtcagaaatggatcgttttcatgttgcaaaagatgccgcacag
gcagtttatggtgagaaagcagcagattttgccaacaaaatggacgaaaccattcagtttcatcgtagctacattcgcgaacatggtaaagat
attccggaagttgcagaatggaaatggcagccgctggccaaa (SEQ ID NO: 81)

Nucleic acid sequence encoding for a phosphoketolase enzyme from *Mycoplasma fermentans*
M64
atgaacaaaaaagaatttgatagcaaagaatatctggaaaaggttgatgcatggtggcgtgcagcaaattatctgagcgttggtcagatttat
ctgcgtaataatccgctgctgaaacatccgctgaccagtgatgatgttaaagtttatccgattggtcattggggcaccattagcggtcagaattt
tgcatatgcacatctgaatcgcgtgatcaacaaatatgatctgaatatgttctacatcgaaggtccgggtcatggtggtcaggttatgaccagc
aatagctatctggatggtagctataccgaactgtttccgcatgttacccaggatgaagcaggtatgcagcacctgttaaatactttagctttcc
gggtggcaccgcaagccatgccgcaccggaaacaccgggtagcattcatgaaggtggtgaactgggttatagcattagccatgcaaccg
gtgcaattctggataatccggatgttattgcagcaaccattgttggtgatggtgaagcagaaaccggtccgctggcgaccagctggtttagca
atagtttatcaatccggttaatgatggtgccgttctgccgattctgcatctgaacggtggtaaaattagcaatccgaccattctgagccgtaaa
agcaatgaagaactgcagcagtattttcgtggtatgggtgggaaccgcattttgttgaaggtgataaaccggaagtaatgcatgaactgatg
gcaaaaccctggatagcgtgattgaagaaattcagagcattcagaccaaagcccgtaaaaaaccggcagataaagcaaaacgtccggtt
tggccgatgattgttctgcgtaccccgaaaggttggacaggtccgaaaagctggaataaagaagcaattgaaggtagcttttcgtgcacatca
ggttccgctgccgatcaatgcagaaaatatggaacatgcagatgccctggaaaaatggctgcgtagctatcgtccggaagaactttttgata
aaaaaggcaaactggtgaaagagattgcagccattgcacctaaaggtaaacgtcgtatgggtatgaatccgattaccaatggtggcattaat
ccgaaagttatgaaactgggtgattggcgtaaatttgccctgcattttgatcgtcctggtagcgttgttgcacaggatatggttgagctgggca
cctattttgcagatctggttaaacgcaatccggaaaattttcgtattttttgtccggacgaaaccaaaagtaatcgtctgtataacctgttcaaag
tgaccaatcgtcagtggatggaacgcattgatagtaaactggatgaggcactgagtccggttggtcgtattattgatagccagctgagcgaa
catcaggcacagggttttctggaaggttatgttctgaccggtcgtcatggcattttttgcaagctatgaaagctttctgcgtgttgtggatagcatg
gtgacccagcatatgaaatggttacgtaaagccaaagaaatcaactggcgcaaagattatccgtccctgaatattatggcaaccagcaccg
cctttcagcaggatcataatggttataccatcaggatccgggtattatcggtcatggcggataaacgtccagaactgattcgtgaatacct
gcctgcagataccaataccctgctggcagttatggataaagccttttaccgaacgcaatgtgattaatctgattgtgagcagcaaacagcctcg
ccatcagttttatagcgttgaagaagccgaaacgctggttgaaaaaggtctggatattatcgattgggcaagtacctgtagccgtaatgaaac
tccggatctggtggttgttgccagcggcaccgaaccgaatctggaagcactggccaccattttctattctgaacaaagaatacccgagcatga
aaatccgttttgtgaatgttgttgatctgctgaagctgcgtcatccgaaaattgatccgcgtggtctgagtgatgaagaattcgatgaaatcttta
ccaaagataagccggtgctgtttgcctttcatgttttgaaggcattctgcgcgatattttcttttgatcgccataaccataaccgattgcacatg
gttatcgcgaaaatggtgatatcacaaccagctttgatattcgtcagctgtcacatatggatcgttttcacatggcaagtgatgcagcagcagc
cgtttttggtagctcaaaagcgaaagaattcatggacaaaatggaagaaaccattcagtttcacaacaagtatattcgcgaagtgggcaccg
atattccggaagtgaaaaattggaaatgggaaggcctgattaaa (SEQ ID NO: 82)

Nucleic acid sequence encoding for a phosphoketolase enzyme from *Granulicatella adiacens*
ATCC 49175
atgacccagtttgacacaccggaatatctggcaaaagttgatgcatggtggcgtgcagcaaactatattagcgttgcacagatgtatctgaaa
gataatccgctgctgcgtcgtccgattcagaaagaagatgttaaactgcatccgattggtcattggggcaccattgcaggtcagaattttatct
atgcacatctgaatcgtgccatcaacaaatatgatctggacatgttttatatcgaaggtccgggtcatggtggtcaggttatggttagcaatagc
tatctggatggtagctataccgaactgtatccgcagattacccaggatgaagcaggtttttaaacagctgtgcaaaatctttagctttccgggtg
gtattgcaagccatgcagcaccggaaacaccgggtagcattcatgaaggtggtgaactgggttatagcctgagccatgccaccggtgcag
ttctggataaccgaatgttattgcagcagcagtttattggtgatggtgaagcagaaaccggcagcaggttggtttagtaataccttt
attaacccggttaatgatggtgccgttctgccgattctgtacctgaatggcggtaaaattcataatcgaccattctggcacgtcgtaccgatg
aagaactgacacagttttttaacggtctgggttgggatccgattttttgttgaaggcaccgatccggaaaaagttcatccgctgatggcagcaa
aactggatgaggcaattgaaaaaattcaggccatccagaaagaggcacgcgcaaatcagccgaagaggcaaccatgccgcattggcct
gttctggttgttcgtaccccgaaaggttggacaggtccgaaaagaatcatgaacctgattgaaggcggttttcgtgcacatcaggttccg
attccggttagcggtgaagccatggaacatgttgatgccctggttgattggctgaaaagctatcgtccggaagaactttttgatgaaatggc
aaactggtgaaagaaattgcagccattagccctaaaggtccgcgtcgtatgagtatgaatccgattaccaatgccggtgttgttaaaccgatg
gaaattaccgattggaccaaacatgcaatcgataccagcaaaccgggtgcaattcaaaaacaggatatgatcgaattcggcaaatttgcag
ccgatctggttaaagcaaatccggataattttcggcattttcggtccggatgcagaaccaaaagtaatcgtctgaacgaagtgtttaaagccaccaa
tcgtcagtgggttggtcgtcgtgatgaaagctatgatgaatggattagtccggtgggtcgtgttattgatagcagctgagcgaacatcaggc
agaaggttttctggaaggttatgttctgaccggtcgtcatggttttttttgccagctatgaaagttttctgcgtgttgtggatagcatgattacacag
cactttaaatggctgcgtaaagccaaaacccatgcaccgtggcgtaaaaactatccgagcctgaatctgattgcaaccagcaccgttttcag
caggatcataatggttataccatcaggatccggggtctgctgacccatctggcagaaaaaaccggaatttgtgcgtgaatatttaccggca
gataccaatagtctgatggccgttatggcagaagcactgagcagcgaagataaaatcaacctgattgtgagcagtaaacatccgcgtccgc
agttttatagcgttgaagaagcaaaagaactggtcagcgaaggctataaagtgattgattgggcaagcaccgtgaaagaaggtgaagaac
cggacgttgtgatcgcagcagccggtacagaaccgaatctggaagccctggcaggtattagcattctgcacaaacagtttccggaactgaa
aatccgttttatcaacgtggtggatattctgaaactgcgtttcaccgaaagtggatccgcgtggtctgagcgacgaagaattttgataaactgttta
ccaccgataaaccggtggtttttgttttcatggttaatgaaggtatgatccgcgacctgttttttgatccgcaataaccataacgatgcatatccatg
gctatcgcgaaaatggtgatattaccaccccgtttgatatgcgtgttctgagtgaaatggatcgcttcatgttgcaaaagatgcagccgttgca
gtgtatggtgaaaaagcaagcgaatttgccgctaaaatggacgaaaccgttgaatttcatcacagctatattcgtgaacatggtgaggatattc
cggaagttgttagctggcagtgggaaaatgtgaacaaa (SEQ ID NO: 83)

Nucleic acid sequence encoding for a phosphoketolase enzyme from *Mycoplasma hominis*
ATCC 23114
atgattagcaaaatctatgatgataaaaagtatctggaaaaaatggataaatggtttcgcgcagcaaattatctgggtgtttgtcagatgtatctg
cgtgataatccgctgctgaaaaaaccgctgaccagcaatgatatcaaactgtatccgattggtcattggggcaccgttccgggtcagaattt
atctataccatctgaatcgctgcaagaaatatgatctgaatatgttctacatcgaaggtcctggtggtggcagttatggttgattagtaat
agctatctggatggcagctagcgaaattatccggaaattagccaggatgaagcaggtctggccaaatgttttaaacgttttagctttccgg
gtggcaccgcaagccatgcagcaccggaaacaccgggtagcattcatgaaggtggtgaactgggtttatagcattagccatggcaccggt
gcaattctggataacccggatgtttattgtgcagcagttgttggtgatggtgaagcagaaaccggtccgctggcgaccagctggtttagcaat
gcctttattaacccggttaatgatggtgccattctgccgattctgcatctgaacggtggtaaaattagcaatccgaccctgctgagccgtaaac
cgaaagaagaaatcaaaaaaatacttttgaaggcctgggctggaatccggattttgtttgaatggtcagaagataagagcaaccttgatatgcat
gaactgatggcaaaaagcctgataagcgcattgaaagcatcaaagaaattcaggcagaagcacgtaaaaaacctgcagaagaagcaac
ccgtccgacctggccgatgattgttctgcgtaccccgaaaggttggacaggtccgaaacagtggaataatgaagcaattgaaggtagctttc
gtgcacatcaggttccgattccggttagcgcctttaaaatggaaaagattgccgatcttgagaaatggctgaaaagctacaaaccggaagaa
ctgtttgatgaaatggcacgatcataaaagaaatccgtgatctggctccggaaggtctgaaacgtatgcagttaacccgattaccaatggt
ggtattgatagcaaacctctgaaactgcaggattggaaaaagtacgcactgaaaattgattatccgggtgaaattaaagcacaggatatggc -continued

SEQUENCES cgaaatggccaaatttgcagcagatatcatgaaagataaccctagcagctttcgcgttttttggtccggatgaaaccaaaagcaatcgtatgttt
gccctgtttaatgtgaccaatcgtcagtggctggaaccggttagtaagaaatacgatgaatggattagtccggcaggtcgcattattgattcac
agctgagcgaacatcagtgtgaaggttttctggaaggttatgttctgaccggtcgtcatggttttttttgcaagctatgaagcattctgcgtgttgt
ggatagcatgctgacccaacatatgaaatggatcaaaaaggcaagcgaactgagctggcgtaaaacctatccgagcctgaacattattgca
accagtaatgcatttcagcaggatcataatggttatacgcatcaggatccgggtctgctgggtcatctggcagataaacgtccagaaattatc
cgtgaatatctgcctgcagataccaatagcctgctggccggttatgaataaagcactgaccgaacgtaatgtgattaatctgattgttgcaagca
aacagcctcgcgaacagttttttaccgttgaagatgcagaggaactgctggaaaagggttataaagttgttccgtgggcaagcaatattagc
gaaaatgaagaaccggatattgtgtttgccagcagcggtgttgaaccgaatatcgaaagtctggcgcaattagcctgatcaatcaagaata
tcctcatctgaaaatccgctatgtgtatgtgctggatctgctgaagctgcgtagtcgtaaaatcgatccgcgtggtattagtgatgaagagtttg
ataaagtgtttaccaaaaacaaaccgattatctttgcctttcatggctttgagggactgctgcgcgatattttctttacccgtagcaaccataacct
gattgcacatggttatcgtgaaaacggtgatatcacaaccagctttgatattcgtcagctgagtgagatggatcgttatcatattgcaaaagatg
ctgccgaagccgtgtatgtaaagatgcaaaagcatttatgaacaaactggatcagaaactggaataccaccgcaactatatcgatgagtat
ggctatgatatgccggaagttgtggaatggaaatggaagaacatcaataaagaaaat (SEQ ID NO: 84)

Nucleic acid sequence encoding for a phosphoketolase enzyme from Mycoplasma crocodyli
MP145
atgaaaaaaaccgtgtatgataccgaactgtatattgagaaactggatgcatggtttcgtgcagcaaattatctgagcgttggtcagatgtatct
gcgtaataatccgctgctgcgtaacaaaattaccaaagatgatgtgaaagtgtatccgattggtcattggggcaccattccgggtcagaattt
gcatatgcacatctgaatcgcgtgatcaacaaatatgatctgaatatgttctacatcgaaggtcctggtcatggtggtcaggttatgaccagca
atagctatctggatggtagctatacagaactgttttccgcatgtttacccaggatctggacggtatgaaacacctgttaaatactttagctttccgg
gtggcaccgcaagccatgcagcaccggaaacaccgggtagcattcatgaaggtggtgaactgggttatagcctgagccatgccaccggt
gcaattctggataatccgaatgttattgcagcaaccattgttggtgatggtgaaagcgaaaccggtccgctggcagcaggttggtttagcaat
agtttatcaatccggttaatgatggtgccgttctgccgattctgcatctgaacggtggtaaaattagcaatccgaccattctgtgtcgcaaaag
caatgaagaactgaccaactattttctggggtatgggttgggaaagcattttttgttgaaggtgaagatgtgcagaaaatgcataaactgatggca
accaaactggactatgccattgaacgtattctgagcattcagaaagaagcccgtaaaggtaaagcagaagaggccacccgtccgctgtgg
ccgatgattgttctgcgtacccccgaaaggttggacaggtccgcagaaatggaatagcgatcagattgtgggtagcttcgtgcccatcaggtt
ccgattccggtgaatagtgaaaatatgacccatattgatgccctggttgattggctgaaaagctataatgttgataacctgttcgataaaaagg
gcaaactggttccggaaattgccgaaatcgcaccggtgggtgatcgtcgtatgggtatgaatccggtgaccaatggtggcctgaatccgcg
taatctggcactgccgaattggcaggattttgcactgaatctgtgaaaaacctgtgcaaaaattgcacaggatatggttgagctgggtcctat
tttgcaaaagtgatggaaatgaataaagataattttcgcctgttcggtccggatgaaaccaaaagtaatcgtctgtttaacgtgttcaaagttac
cagccgtcagtggctggaaccgattaacccgctgtttgatgaagcactgagtccggcaggtcgtgttattgatagccagctgagcgaacatc
aggcagaaggttttctggaaggttatgttctgaccggtcgccatggtgttttgcaagctatgaaagctttctgcgtgttgtggatagcatgctg
acccagcatatgaaatggctgaagaaagcaaatgatgttagctgcgcgataattatccgagcctgaatgtgatctgaaccaaagaatttccgaaactg
aaaattcgcttcgtgaatgtggttgacctgatgaaactgcgtcatccgagcattgatccgcgtggtattaccgataaagaattcgacaaaatctt
tacgaaagacaagccggttctgtttgcctttcatggttatgaaggtatcctgcgcgatatctttttcaaacgcaataaccataacctgatcgcac
atggctatcgtgaaaatggtgatatcacaaccagctttgatattcgccagctgtcacatatggatcgttttcatatggcagcaagcgcagcagt
tgcagcgctgggcaaaaagccaatgcatttgaaacaaaaatgctggaaaccatcgattttcacaccaaatatatccgcgaatacggcacc
gatattccggaagttaaagaatggaagtggaatcctctggttcgcaaa (SEQ ID NO: 85)

Nucleic acid sequence encoding for a phosphoketolase enzyme from Neisseria sp. oral taxon
014 str. F0314
atgagcgcacagtatgatagcgcagattatctgaataaagttgatgcatggtggcgtgcagcaaaactatattagcgttgcacagatgtacctg
aaagataatccgctgctgatgcgtccgattcaggcaagtgatgttaaagcacatccgattggtcattggggcaccattgcaggtcagaattttt
atctatgcacatctgaatcgtgccatcaacaaatatgatctgaacatgttctatatcgaaggtccgggtcatggtggtcaggttatggttagcaa
tagctatctggatggtagctatagcgaaatctatcccgaatattacccaggatgaagcaggtctgaaacagctgtgtaaaatctttagctttccg
ggtggtattgcaagccatgcagcaccggaaacaccgggtagcattcatgaaggtggtgaactgggttatgcactgagccatgccgttggtg
cagttctggataacccggatgttattgcagcaaccgttattggtgatggtgaagcagaaccggtccgctgagcgcaggttggtttagcaat
gtttttatcaatccggttaatgatggtgccgtgctgccgattctgtatctgaacggtggtaaaattcataacccgaccattctggcacgtaaagt
gatgaaagcctgcgtctgtattttgaaggtctgggttgggatcagttttttgttgaagccaccgattatgcaacccaccccataaagttatggcaca
gaaactggatgaggccatcgaaaaaatcaaagccattcagaccaaagcacgtcaggtaaagccgaagaggcagttatgccgaaatggc
ctgttctggttcacgtctgccgaaaggttggacaggtccgaaagtgtggaatggtgaaccgattgaaggcggtttttcgtgcacatcaggttc
ctattccggcaagcagccatgatatggccaccgttgatagcctggttgaatggctgaaaagctatcgtccggaagaactgtttcgatgcaaatg
gcacctttaaagcagaactgcgtgaaaattagcccgaaaggcgatcgtcgtatgagcaccaatccgattaccaatggtggcattaatccgcgt
cctctgaataccgcagattggaaaaaattcgcactggataatagcgatcgtggtatattggccaggatatgattgaattttggcaaatatg
cagccgaactggttaaagcgaatccggataattttcgtatttccggtccggatgaaaccaaaagcaatcgtatgaacgaagtgttcaaagtga
ccaatcgtcagtggctggaaccgatcgataaagcatatgatgaatggatgagtccggcaggtcgtgttattgatagtcagctgagcgaacat
caggcagaaggttttctggaaggttatgttctgaccggtcgtcatggttttttttgcaagctatgaaagctttctgcgtgttgtggatagcatggca
acccagcactttaaatggctgcgtaaataaaacccatgcaccgtcgtggcgtaaatccgtcactgaatctgattgcaaccagcaccgttt
ttcagcaggatcataatggttatacccatcaggatccgggtatgctgacccatctggcagaaaaaaaccggaatttatccgtgaatatctgc
ctgcagatgccaatagcctgctggccgttatgagcgaagttctgagcagcaaagataaagtgaacctgatcgttagcagtaaacatcctcgt
ccgcagttttatagtgcagcagaagcggaagaattagttcgtgaaggttacaaagttatcgattgggcaagcaccgataaaggtggcgaac
cggatgtggttattgccgcagccgcaacagaaccgaatctggaagcactggcagcaattacaattctgaacaaacagtttccggaactgaa
aatccgctttattaacgttcgtgaattctgaaactgcgtcatccctaaagtggatccggctgaccgatgaacagttcgatgcactgttta
ccaaagacaaaccggtgatttttgctttcatggctatgaaggtatgctgcgcgatatctttttttgatcgccataaccataatctgcgcatccatg
gttatcgtgaaaatggtgatattaccaccccgtttgatatgcgtgttctgagtgaaatggatcgttttcatgttgcaaaagatgcagccctggca
gtttatggtgacaaagcacaggattttgccaaaaaaatggacgataccctggcatttcatcacagctatattcgcgaaatggcgaagatattc
cggaagttcgtaattggaaatgggaagccctgaaa (SEQ ID NO: 86)

Nucleic acid sequence encoding for a phosphoketolase enzyme from Eremococcus coleocola
ACS 139 V Col8
atgaccgtggactacaacagcaaagaatatctgaccctggttgataaatggtggcgtgcagcaaattatctgagcgttggtcagatgtttctg
cgtgataatccgctgctgcaagaagaggttaccgcagatcatgttaaactgaatccgattggtcattggggcaccattggtggcagaattttt
ctgtatgcacatctgaatcgcattatcaacaagtataatgtgaatatgttttatatcgaaggcctggtcatggtggtcaggttatggttaccaat

SEQUENCES agctatctggatggtagctataccgaacgttatccggaatttacccaggatattgccggtatgaaaaaactgtttaaaaccttcagctttccggg
tggtattggtagccatgcagcaccggaaacaccgggtagcatgcatgaaggtggtgaactgggttatgcactgagccatgccaccggtgc
aattctggataacccggatgttattgcagcaaccgttgttggtgatggtgaagcagaaaccggtccgctggcagcaggttggttttagcaatgt
ttttatcaatccggtttcagatggtgcagttctgccgattctgtatctgaatggtggtaaaattgcaaacccgaccattctggcacgtaaaagca
atgaggatctgaccaaatatttcgaaggtatgggttggaaaccgtatattgttgaaggcaccgatccggaacaggttcatccgattatggcaa
aagttctggatgaagtgattgaagaaattcaggccattcaggcagaagcccgtaaaggtaaagccgaagatgcaaaaatgccgcattggc
cgatgatcctgtatcgtaccccgaaaggttggacaggtccggaagaagttgaaggtaaaacaattcagggtagctttcgtgcacatcaggtt
ccgattccggttagcggtcgtaatatggaagatattgatctgctgatcaactggctgaaaagctatggtcctgaagaactgttcaccgaaaat
ggcgaactggtagatgaactgaaagaatttgcaccgaaaggcgatcatcgtatggcaatgaacccgctgaccaatggcggtaatccgaaa
ccgctgaatatgccgaattggaaagattatgccctggaaattggcacccctggtagcaaagatgcacaggatatgattgaatttggtggttttg
cgcgtgatatcgtgaaagaaaatccggaaaactttcgcattttggtccggatgaaaccaaaagtaatcgcctgaataaagtgtttgaagtga
ccaatcgtcagtggctggaaccgattagcgaaaaatttgatgaaaacattcagcaagcggtcgcgttattgatagccagctgagcgaacat
cagaatcagggttttctggaagcatatgttctgaccggtcgtcatggttttttttgcaagctatgaaagcttttttcgtacggtggatagcatgatta
cccagcactttaaatggattcgcaaaagcgcaaaacatagctggcgtaaaccttatcagagcctgaatctgattagcgcaagcaccgttttc
agcaggatcataatggttatacccatcaggatccgggtctgctgacccatattggtgaaaaacacggtgaatatatgcgtgcatatctgcctg
cagataccaattcactgctggcagttatggataaaagcattcgcagcgaaaacgtgattaactatgttgtgaccagcaaacatccgcgtccgc
agttttttttacagcagatgaagccgaggaactggttaatgaaggtctgaaagttatcgattgggccagtaccgttaaagataatgaagaaccg
gatgtggttattgccgcagccggtacagaaccgaattttgaagcaattgcagcgatttcctatctggttaaagccttccggaactgaagattc
gttttgttaatgtggttgacctgtttcgtctgcgtagtccggaaattgatccgcgtggtctgagtgatgatgaattcgatgcaatcttcaccaaag
ataaaccggtgtttttttgcctttcatagctacgaaggcatgctgaaaagacatcttttttacccgtcataaccataatctgtacgcccatggttatcg
tgagaatggtgaaattaccaccccgtttgatatgcgcgttctgaatgaactggatcgtttttcatctgagtgcacatgttgcagatgttgtgatgg
tgataaagcccgtgattatgttgccgaaatgaaagggaaagttcaagaacatcgtgattacgtggaagaatatggtgccgatatgccggaag
tagaagattggaaatgggaggatatcaaa (SEQ ID NO: 87)

Nucleic acid sequence encoding for a phosphoketolase enzyme from Aerococcus urinae ACS
120-V-Col10a
atgaccgactttgacagcaaagcctatctggataaagttgatgcatggtggcgtgcagcaaattatctgagcgttggtcagatgtatctgcgt
gataatccgctgctggatcgtgaagttaccgcagatgatatcaaaattaccccgattggtcattggggcaccattgcaggtcagaattttgttta
tgcacatctgaatcgcgtgatcaacaaatatgatctgaatatgttctacatcgaaggtccgggtcatggtggtcaggttatgcaggcaaatgc
atacctggatggcacctggaccgaacattatccggaatatccgcagaataaagaaggcatgcagaagttcttcaaatatttcagctttccggg
tggcaccggtagccatgcaaccgcagaaattccgggtagcattcatgaaggtggtgaactgggttatagcctgagtcatgccaccggtgca
attctggacaatccggatgttattgcagcaaccgttattggtgatggtgaagcgaaaccggtccgctggcagcaagctggctgagcaata
gctttattaacccggttaccgatggtgcagttctgccgattctgtatctgaatggtggtaaaattgcaaacccgaccattctggcagctaaaag
caatgaagatctgattaaatactttcagggtctgggttgggatccgatggttgttgaaggtaatgatccggaaaaagttcatccgctgatggca
aaaacccctggatcaggcaattgaaaaaatcaaaagcattcagggtgaagcccgtaaaggtagtgcagatgaagcaaccatgggccattgg
ccgatgatcctgtatcgtaccccgaaaggttggacaggtccgaaagcatgggaaggcaatgatattgaaggttcatttcgtgcacatcaggtt
tccgattccggttaatgcagaaaatatggaacatgtggatgccctgattgattggctgaaaagctatctcgcggaagaactgtttaccgaaga
aggtcagctgcgtcctgaaattgccgaaattgcaccgaaaggcgatcagcgtatgcaagcaatccgattacagatggtggcattgatccg
aaaccgctggacctgccggattggcgtgattatgcactggatttttgaaacacccgggtgaacgtgatgcacaggatatgattgaaatgggtgg
ttatgccgcaggcgttatcgaaaaaaatcctgataactttcgcatcttcggtccggatgaaaccaaaagtaatcgtctgaacaaagtgttcaat
gtgaccaaacgtcagtggctggaaccgattaaagataactatgatgaatggatggaccgggtcgtgttattgatagccagctgagcg
aacatcagatggaaggttttctggaagcatataccctgaccggtcgtcatggttttttttgcaagctatgaagcatttattcgtaccggtatagc
atgattacccagcactttaaatggatcgcgaagcaagcgagtataaatggcataaaccgtatcagagcctgaacctgattagcagcagca
ccgcatttcagcaggatcataatggttatacccatcaggatccgggtctgctgacccatctggcagaaaaaaaaggtgaatttgtgcgtgcat
atctgcctgcagataccaatagcctgctgcagcagttatggacaaagcactgagcaacaatgtgattaactatattgtgaccagcaaacat
ccgcgtccgcagttttttagcgttgaagaagcagaagagttcgtcgataaaggctataaagtatcgattgggcaagcaccgtggaagagg
gcgaagaaccggatggtgattgcagccagcggcaccgaaccgaccgttgaaaccattgccaccattagctatctgcatgaagcctttcc
ggaactgaaaattcgttatgttaatgtggtggatctgtatcgcctgcgtcatccgaatatcgatccgcgtggtctgagtgatgaagaatttgatg
ccgttttcaccaaagataaaccggtgttttttgcctttcatagctttgaaaagacatcttcttttgatcgccataaccataaacctgtat
ccgcatggttatcgtgaggaaggtgccattaccaccccgtttgatatgcgtgttctgaatgaactggatcgcttttcattttgcagcacatgttgc
cgaagttgtgtatggtgataaagcccaggattttatcgatcagatgaatgccaaagtggaagaacatcgtgcgtatattgttgaatatggcacc
gatatgccggaagtgaaagaatggaaatggcagccgctgaaaaaa (SEQ ID NO: 88)

Nucleic acid sequence encoding for a phosphoketolase enzyme from Kingella kingae ATCC
23330
atgaccaacaaaacccagttcgacacaccggaatatctgggtaaagttgatgcatggtggcgtgcagcaaactatattagcgttgcacagat
gtatctgaaagataatccgctgctgaaaacaccgctggttgcaaatgatgttaaagcacatccgattggtcattggggcaccgttccgggtca
gaattttatctatgcacatctgaatcgtgccatcaacaaatatgatgtggacatgtttttatatcgaaggtcctgtgcatggtggtcaggttatggtt
agcaatagctatctggatggtagctataccgaaatctatccggataatacccaggataccgcaggtctgaaaaaactgtgtaaaatcttagct
ttccgggtggtattgcaagccatgcagcaccggaaacaccgggtagcattcatgaaggtggtgaactgggttatgcactgagccatgcctt
ggtgcagttctggataacccgaatgttattgcagcagcagttattggtgatggtgaagcagaaaccggtccgctgtgtgcaggttggtttggt
aatacctttattaacccggttaatgatggtgccgtgctgccgattctgtatctgaatggtggtaaaattcataatccgaccattctggcacgtaa
aaccgatgaagaactgaaacagtatttttaacgtatgggttggaaccgattttttgtggatgttaacaacgtggataactatcacgaaattatg
agccagaaagtggatgaagccgttgaacatattctgagcattggcagaccgcacgtacccagaaagccgaagatgcaaccatgccgcat
tggcctgttctggttgcccgtattccgaaaggttggacaggtccgaaaacctggcatggcgaaccgatcgaaggcggttttcgtgcacatca
ggttccgattccggcaagcagccatgatattggaaaccgcaggcgaactggaaaaatggctgcgtagctatcgtccggaagaacttttttgat
gataatggttgcttcctggatagcggcgtgatatcagcccgaaagcgcaaaacgtatgagcgttcatccgatcaccaatggcggtaatt
ccgaaagcactggttatgccgattggaccagcatgcactggaaattggtgttccaggtagccaggatgcacaggatatggttgaatgtg
gtcgtctgatggcagatgttgttaccgccaaatccgaataactttcgtattttttggtccggacgaaaccaaaagcaatcgtctgaatcaggtttttc
aggttaccaaacgtcagtggctgggtcgccgtgatgaagcatatgatgaatggattgcaccggttggtcgtgttattgatagccagctgagc
gaacatcaggcagaaggttttctggaaggttatgttctgaccggtcgtcatggtttttttgcaagctatgaaagcttttttcgtgtggtggatagc
atgattacgcagcacttttaaatggttcgcaaatgtaaaacccacgcagtggcgtaatgattatccgagcctgaactctgattgcaaccagc
accgtgtttcaggatcataatggctataccatcaggatccgggtctgctgacccatctggcagaaaaaaaaaccggaatttgtgcgtga
atatttaccggcagatagcaataccctgatgcccgttatgagcgaagcactgaccagccgtgatcgtattaacctgattgttagcagtaaaca
tctgcgtccgcagttttttcaatgcagaagaagcaaaagaactggttcgcgaaggctataaagtgattgattgggcaagcacctgtcatgacg
gtgaaccggatgttgtgatcgcagccgcaggcaccgaaccgaatatggaagccctggcagcaattagcattctgcacaaacagtttccgg
aactgaagattcgttttatcaacgttgtggatatcctgaaactgcgtcatccgagcattgatccgcgtggtctgagtgatgaacagtttgatgca

SEQUENCES ctgtttacccaagaaaaacctgtggtgttttgctttcatggttatgaaggtatgattcgcgacctgttttttccgcgtgcaaaccataatgttcgtat
tcatggctatcgcgaaaatggcgatattacaaccccgtttgatatgcgtgttctgtcagaaatggatcgttttcatgttgccaaagatgccgcac
aggcagtttatggtgataaagcaagcgaattcgccaaaaaaatgggtgaaaccgttgcatttcatcgttcctatattcgtgaacatggcaccg
atattccggaagttgcagaatggaaatggcagccgctggccaaa (SEQ ID NO: 89)

Nucleic acid sequence encoding for a phosphoketolase enzyme from *Streptococcus criceti* HS 6
atgaataccaacttcgatagcagcgattacctgaataaagttgatgcatggtggcgtgcagcaaactatattagcgcagcagatgtatctg
aaagataatccgctgctgcgtcgtgaagttgcagcagaagatctgaaaagccatccgattggtcattggggcaccgttccgggtcagaattt
tatctatgcacatctgctgcgctccatcaacaaatatgatctggatatgttctatatcgaaggtcctggtcatggtggtcaggttatggttagcaa
tagctatctggatggtagctataccgaactgaatccgcagattagccagaccgaagagggtctgaaacagctgtgtaaaatctttagctttcc
gggtggtattgcaagccatgcagcaccggaaacacccgggtagcattcatgaaggtggtgaactggggttatgcactgagccatgccaccgg
tgcagttctggataacccggatgttattgcagcaaccgttattggtgatggtgaaagcgaaaccgttccgctgatggcaggttggctgagca
ataccttttattaacccggttaatgatggtgccgttctgccgattcattttctgaatggtggcaaaattcataatccgaccatctttgaacgtaaaag
cgacgatgaactgaaagcctttttttaccggtctgggttggaaaccgatttttgcagatgttaccgcatttgcaagcgatcatgcagccgcacat
aaactgtttgcagccaaactggatgaagccattgaagaaattcgtaacattcaggcaaaagcccgtaaaggtagcgcagatgaagcaacc
atgcctgcatggcctgttattgttgcacgtattccgaaaggttggacaggtccgaaaagctggaaaggcaccccgattgaaggcggttggc
gtgcccatcaggttccgattccggttgatagccatcatatggaacatgttgatgccctgctggattggctgaaaagttatcagccggaagaac
tgttcgatgcagaaggtcatctgaaatcagaagtggcagccctgagcccgaaaggcaatcgtcgtatgagcatgaatccgattaccaatgc
cggtgttattaaaccgatggatacagccgattggaaaaaacgtgcatttgatattcagacccctggtgaaattgttgcccaggatatgattgaa
tttggcaaatatgccgcagatctggttgaagcaaatccggataaattttcgtattttttggtccggatgaaagcaaaagcaatcgcctgaatgaag
tgtttaccaaaaccaatcgtcagtggatgggtcgtcgtgatccgagctatgatgaatggctgagtccggcaggtcgtgttattgatagtcagct
gagcgaacatcaggccgaaggttttctggaaggttatgttctgaccggtcgtcatggttttttttgccagctatgaaagctttctgcgtgttgtgg
ataccatgattacccagcactttaaatggctgcgtaaaagtaaaacccataccacctggcgtaaaaactatccgagcctgaatctgattgcaa
ccagcaccgtttttcagcaggatcataatggttatacacatcaggatcgcgggtgtgctgacccatctgagtgaaaaaactccggaaatatatcc
gtgaatatctgcctgcagataccaatagcctgctggcggttatggataaagcatttaaagatgaggacaaaattaacctgatcgtgaccagca
aacatccgcgtccgcagttttatagcgttgaagaagcaagcgaactggtcgaaaaaggctataaagtgattgattgggcaagcaccgtgca
ggcaaatgaagaaccggatgtggttttgccgcagcaggcacagaaccgaatctggaagcactggcagcaattagcattctgcacaaaac
ctttccgagtctgaaaattcgtttttgtgaacgtggtggatattctgaaactgcgtcatccggacctggatccgcgtggtctgtctgatgaagaat
ttgataaagtgttcacgaaagacaagccggtgatctttcgcatttcatgcatatgaaggtgatccgcgatatcttttttcgtcgccataaccata
atctgcatgtgcatggttatcgcgaaaatggtgatattaccaccccgtttgatatgcgtgttatgtcagaactggatcgttttcatctggcacagg
atgccgcactgaccaccctgggtgaaaagcacaggcatttagcgcaaaaatggatgaaccgttgcctatcacaaagattatattcgtgaa
catggggatgatattccggaagtgcagaattggcagtgggaaaatctggacgaa (SEQ ID NO: 90)

Nucleic acid sequence encoding for a phosphoketolase enzyme from *Streptococcus criceti* HS 6
atgaccgagttcgacgacaaagattatctggcaaaagttgatgcatggtggcgtgcagcaaactatattagcgttgcacagatgtatctgaaa
gataatccgctgctgcgtcgtgaagttagcaaagaagatgttaaagttcatccgattggtcattggggcaccattgcaggtcagaatttttatcta
tgcacatctgaatcgcgtgatcaacaaattcgatctgaacatgttttatatcgaaggtccgggtcatggtggtcaggttatggttagcaatagct
atattgatggcagctataccgaacgtcatccgaatattacccaggatgaagatggtctgaaacagctgtgtaaaatctttagctttccgggtgg
tattgcaagccatgcagcaccggaaacaccgggtagcattcatgaaggtggtgaactgggttatgcactgagccatgccaccggtgcaatt
ctggataacccggatgttattgcagcaaccgttattggtgatggtgaagcagaaaccggtccgctgaatgcaggttggtttagtaataccttta
ttaacccggttaatgatggtgcattctgccgattctgtacctgaatggtggtaaaattcataatccgaccattctgagccgtaaaaccgatga
agaactgacccacctgtttcagggtctgggttggaaccgtatttttgttgaaggtaatgatccggaagttatccatagcagatggccgaaac
cctggataaagttatcgaaaaaatcaagaccattcagacccaggcacgtcagaaacctgcagaagaggcacagcaggcacagtggcctg
ttctgattgttcgtaccccgaaaggttggacaggtccgaaagaatggaatggtgaaccgattgaaggcggttttcgtgcacatcaggttccga
ttccggttgaagcaggtcatatggaacatatcgatgccctgaccggtctgaaaagctatcgtccggaagaactttttgatgagaaaggct
atgtgaaagaagagattcgcgttatttcaccgaaaggcaatcgtcgtatgagcatgaatccgattaccaatgccgtattgtgaaaaaactgg
atctggcagattggcgtaaacatgcaattgataccagcaaaccgggttccattatgaaacaggatatgatcgaattcggcaaatatgcagca
gatctggttaaagcaaatccggataactttcgtattttcggtccggatgaaaccaaaagcaatgcctgaataatgttttttaccgcaaccaatcg
tcagtggctggcaccgcgtgataaaagttatgatgaatggattagtccggtgggtcgtgttatttattgataccgagcgaacatcaggcag
aaggttttctgaaaggttatgttctgaccggtcgtcatggttttttttgcaagctatgaaagctttctgcgtgttgtggatagcatgattacacagca
ctttaaatggctgcgtaaaagcaaaacccatacggattgcgcaaaaactatccgagcctgaatctgattgcaaccagcaccgttttttcagca
ggatcataatggttatacccatcaggatccgggtctgctgacccatctggcggaaaaaacccagaatatgttcgtgaatatctgcctgcaga
ttccaatagcctgtttgcagttatggccctggcagacagaagtgaaagcatttaaagatgggcagcatgatcatgatggcgaaccggatattg
tatagcgtggcagaagcacaagaactggtaaaagaaggctacaaagtaattgattgggcgcagcaatgatcatgatggcgaaccggatattg
tttttgcagccgcaggcaccgaaccgaatctggaagtctgcaggtattagcctgctgcacaaagcatttccagaagtgaaaattcgctttat
caacgtggtggatattctgaaactgcgcagcccgaaagtggatccgcgtggtctgagtgatgaagcatttaacaaactgttcaccaccgata
aaccgatcgttttttgcctatcatggttatgaaggtcagattcgtgacctgttttttaaccgcgataaccacaaagtgtatatccatggctatcgcg
aaaatggtgatattaccaccccgtttgatgtgttatgagcgaaatggatcgctttcatattgcaaaagaagcagcacaggccgttctgg
gtgataaagcacaggtttttgcccaagaaatggcagataaactggcatatcataccgcctatattcgtgaacatggtgatgatatcccggaa
gtgcagaattggcagtgggaaaccattgat (SEQ ID NO: 91)

Nucleic acid sequence encoding for a phosphoketolase enzyme from *Mycoplasma columbinum* SF7
atgagcaaaaccaattttgatagcaaaaaatacctggataagatccatgcatggtggcgtgcagcaaattatctgagcgttggtcagatgtat
ctgaaaaataacccgctgctgcaagaaccgctgaaagatgaagatatcaaaatctatccgattggtcattggggcaccattccgggtcagaa
tctgatttatgcacatctgaatcgcgtgatcaacaaatatgatctgaatatgttctacatcgaaggtcctggtcatggtggtcaggttatgattag
caatagctatctggatggtagctataccgaactgtttccggaaattacccagatctggcaggtctgaataaaatgtttaaacgcttagctttc
cgggtggcaccgcaagccatgcagcaccggaaacaccgggtagcattcatgaaggtggtgaactgggttatgcactgagccatgccacc
ggtcaattctggataatccggatgttattgcagcaaccgttattggtgatggtgaagcagaaaccggtccgctgatggcaggttggtatagc
agcagctttattaacccggttaatgatggcaccgttctgccgattctgcatattaatggtggtaaaattagcaacccgaccattctggcacgtaa
aaccgataaagaaatttaaacagctgctggcaggctttggttgggaagcaattttttgttgaagccgatgttttcgtccggaagccattcatctga
gcatgcaaaagcattttgaaaaccatccatgaaattcagcgtattcagcgcaaaacacgtgaaaattagccagaaatcatgcaaaacgtcc
gatttggcctgcactggttgttcgtaccccgaaaggttggacctgtccgcataaaatttgatgataaagtgtatgaaggtagctttcgtagccat
caggttccgctggcagttagcagcgaaaataccaccaaaaaaagttgatctggtgaattggctggaaagctataaaccgcgtgaactgttcaa
tcaggatggtcatttaaagccattatgccgaaattgcaccgaaaggcaataaacgtatggcaatgaatccgattaccaacggtggtattaat
ccgaaaaatctggatctgccgaattgggaacagtttgccattgattttcgataaaccgggtgccattaaagcacaggatatggttagcgcagg
cacctggtttgcagatgtgattaaacgtaatccgaccaactttcgtatctttggtccggatgaaaccaaaagcaatgtctgtttgatgtgctga

```
aaaccaccaatcgtcagtggttagaacgtgttgattatgacctggatgaaaacatcggtccggcaggtcgtgttattgatagccagctgagc
gaacatcaggcagaaggttttctggaaggttatgttctgaccggtcgtcatggtatgtttgcaagctatgaaagctttctgcgtgttgtggatag
catgctgacccagcatatgaaatgggtgcaaaagcgaaaaaagtgcattggcatgattatccgagcctgaatgtgattgcaaccagca
ccgcatttcagcaggatcataatggttatacacatcaggatccgggtattctgggtcatctggccgataaaaaaccggaactgattcgtgaat
atctgcctgcagatagcaatacctgctggccgtgctggataaagcttttaaagaacgtgatgtcatcaacctgattgtggcaagcaaacagc
ctcgtgaacagtggtttagcccacgtgaagcaaatattctggttaaaaatgggctgaaagttattagctgggcaagcacctgtaccctggaag
aagaaccggatctggttgtggcagcaggtacagaaccgaacactggaagcactggcagcaattagttatctgaatgaaaaattcccga
ccctgaaaatccgttttgttaatgttgtagacctgctgaaactgcgtcatccgagcattgatccgcgtggtctgagcaattatgaattcgatagc
atctttaccaaggacaaaccgatcctgtttgcctttcatggttatgaagccctgattcgcgatattttcttcctgcgcaataaccataatctgcaca
ttcatggctatcgcgaaatggtgatattaccacgagctttgatattcgtctgatgagcgaaatggatcgttttcatatggcacagaccgcagc
aaaagccgttctgggttacgataaagcaaaaagcttcgtcgataaaatgcaggacaaaatcgatcagcataatgcctacatcaaagaacatg
gcatcgatatggatgaagttcgctattggacatggaaaggcctgaacaaa (SEQ ID NO: 92)

Amino acid sequence of Enterococcus gallinarum PKL
METTFDTQEYFDKMNAWWRAANYLSVGQIYLKDNPLLRRPIEEKDLKVNPIGHWGTIA
GQNFIYTHLNRVINKYDLNMFYIEGPGHGGQVMVSNAYLDGSYTEIYPEVTQDEAGMQ
HLFKIFSFPGGIASHAAPETPGSIHEGGELGYSIAHGTGAVLDNPDVIAAVVVGDGEAET
GPLAGSWFSNTFINPVNDGAVLPILHLNGAKISNPTILARKSDEDLTKYFEGMGWTPYFV
EGDDPATVHPQMARALDRAVEQIKAIQTKARQGKADEAVMPHWPVLIVRTPKGWTGP
KIWEGEPIEGGFRAHQVPIPVNAHQMEHVDALIDWLKSYKPEELFDESGRIKAEIQELAP
KGQQRMAMNPITNGGIDPQPLKITDWRQHAIDIGVPGSTTAQDMMEFGKFARDLIVENP
TNFRIFGPDEAKSNRLNHVFEVTNRQWLEPKQPNYDEWLSATGRVIDSQLSEHQAEGFL
EGYVLTGRHGFFASYESFLRVVDSMITQHFKWTRKSKELPWRHAYPSLNLIASSTVFQQ
DHNGYTHQDPGIMTHIAEKKAEFVRVYLPADANSLMAVMAETFQTEEQINLIVSSKHPR
PQFYTAEEAEILVKDGLKIIDWASTDQGEPDLVIAAAGTEPNLEALAAVSLLNEAFPELK
IRFINVVDLLKIRHPDVDPRGLTDEEFEAYFTKDKPIIFAFHGYEGLIRDIFFGRKNQRLHI
HGYRENGDITTPFDMRILSELDRFHLAKDGAEWVYGEQAADFAQRMTETVAYHYDFIR
ENGYDIAEVQDWQWKPLK (SEQ ID NO: 93)

Amino acid sequence of codon optimized Clostridium acetobutylicum PKL
MQSIIGKHKDEGKITPEYLKKIDAYWRAANFISVGQLYLLDNPLLREPLKPEHLKRKVV
GHWGTIPGQNFIYAHLNRVIKKYDLDMIYVSGPGHGGQVMVSNSYLDGTYSEVYPNVS
RDLNGLKKLCKQFSFPGGISSHMAPETPGSINEGGELGYSLAHSFGAVFDNPDLITACVV
GDGEAETGPLATSWQANKFLNPVTDGAVLPILHLNGYKISNPTVLSRIPKDELEKFFEGN
GWKPYFVEGEDPETMHKLMAETLDIVTEEILNIQKNARENNDCSRPKWPMIVLRTPKG
WTGPKFVDGVPNEGSFRAHQVPLAVDRYHTENLDQLEEWLKSYKPEELFDENYRLIPE
LEELTPKGNKRMAANLHANGGLLLRELRTPDPRDYAVDVPTPGSTVKQDMIELGKYVR
DVVKLNEDTRNPRIFGPDETMSNRLWAVFEGTKRQWLSEIKEPNDEFLSNDGRIVDSML
SEHLCEGWLEGYLLTGRHGFFASYEAFLRIVDSMITQHGKWLKVTSQLPWRKDIASLNL
IATSNVWQQDHNGYTHQDPGLLGHIVDKKPEIVRAYLPADANTLLAVFDKCLHTKHKI
NLLVTSKHPRQQWLTMDQAVKHVEQGISIWDWASNDKGQEPDVVIASCGDTPTLEAL
AAVTILHEHLPELKVRFVNVVDMMKLLPENEHPHGLSDKDYNALFTTDKPVIFAFHGF
AHLINQLTYHRENRNLHVHGYMEEGTITTPFDMRVQNKLDRFNLVKDVVENLPQLGNR
GAHLVQLMNDKLVEHNQYIREVGEDLPEITNWQWHV (SEQ ID NO: 94)

L. gray mvaE nucleic acid sequence
ATGGTTAAAGACATTGTAATAATTGATGCCCTCCGTACTCCCATCGGTAAGTACCGC
GGTCAGCTCTCAAAGATGACGCGGTGGAATTGGGAACCGCAGTTACAAAGGCTCT
GTTCGAGAAGAACGACCAGGTCAAAGACCATGTAGAACAAGTCATTTTTTGGCAACG
TTTTACAGGCAGGGAACGGCCAGAATCCCGCCCGTCAGATCGCCCTTAATTCTGGCC
TGTCCGCAGAGATACCGGCTTGACTATTAACCAGGTGTGTGGTTCTGGCCTGAAAG
CAATAAGCATGGCGCGCCAACAGATCCTACTCGGAGAAGCGGAAGTAATAGTAGCA
GGAGGTATCGAATCCATGACGAATGCGCCGAGTATTACATATTATAATAAAGAAGA
AGACACCCTCTCAAAGCCTGTTCCTACGATGACCTTCGATGGTCTGACCGACGCGTT
TAGCGGAAAGATTATGGGTTTAACAGCCGAAATGTTGCCGAACAGTACGGCGTAT
CACGTGAGGCCCAGGACGCCTTTGCGTATGGATCGCAGATGAAAGCAGCAAAGGCC
CAAGAACAGGGCCATTTTCGCAGCTGAAATACTGCCTCTTGAAATAGGGGACGAAGT
TATTACTCAGGACGAGGGGGTTCGTCAAGAGACCACCCTCGAAAAATTAAGTCTGC
TTCGGACCATTTTTAAAGAAGATGGTACTGTTACAGCGGGCAACGCCTCAACGATC
AATGATGGCGCCTCAGCCGTGATCATTGCATCAAAGGAGTTTGCTGAGACAAACCA
GATTCCCTACCTTGCGATCGTACATGATATTACAGAGATAGGCATTGATCCATCAAT
AATGGGCATTGCTCCCGTGAGTGCGATCAATAAACTGATCGATCGTAACCAAATTA
GCATGGAAGAAATCGATCTCTTTGAAATTAATGAGGCATTTGCAGCATCCTCGGTGG
TAGTTCAAAAAGAGTTAAGCATTCCCGATGAAAAGATCAATATTGGCGGTTCCGGT
ATTGCACTAGGCCATCCTCTTGGCGCCACAGGAGCGCGCATTGTAACCACCCTAGCG
CACCAGTTGAAACGTACACACGGACGCTATGGTATTGCCTCCCTGTGCATTGGCGGT
GGCCTTGGCCTAGCAATATTAATAGAAGTGCCTCAGGAAGATCAGCCGGTTAAAAA
ATTTTATCAATTGGCCCGTGAGGACCGTCTGGCTAGACTTCAGGAGCAAGCCGTGAT
CAGCCCAGCTACAAAACATGTACTGGCAGAAATGACACTTCCTGAAGATATTGCCG
ACAATCTGATCGAAAATCAAATATCTGAAATGGAAATCCCTCTTGGTGTGGCTTTGA
ATCGAGGGTCAATGATAAGAGTTTATACCATCCCACTAGCAACTGAGGAACCGAGT
GTAATCGCTGCCTGTAATAATGGTGCAAAAATGGCAAACCACCTGGGCGGTTTTCA
GTCAGAATTAAAAGATGGTTTCCTGCGTGGGCAAATTGTACTTATGAACGTCAAAG
AACCCGCAACTATCGAGCATACGATCACGGCAGAGAAGCGGCAATTTTTCGTGCC
GCAGCGCAGTCACATCCATCGATTGTGAAACGAGGTGGGGGTCTAAAAGAGATAGT
AGTGCGTACGTTCGATGATGATCCGACGTTCCTGTCTATTGATCTGATAGTTGATAC
TAAAGACGCAATGGGCGCTAACATCATTAACACCATTCTCGAGGGTGTAGCCGGCT
```

| SEQUENCES |
|---|
| TTCTGAGGGAAATCCTTACCGAAGAAATTCTGTTCTCTATTTTATCTAATTACGCAA<br>CCGAATCAATTGTGACCGCCAGCTGTCGCATACCTTACGAAGCACTGAGTAAAAAA<br>GGTGATGGTAAACGAATCGCTGAAAAAGTGGCTGCTGCATCTAAATTTGCCCAGTT<br>AGATCCTTATCGAGCTGCAACCCACAACAAAGGTATTATGAATGGTATTGAGGCCG<br>TCGTTTTGGCCTCAGGAAATGACACACGGGCGGTCGCGGCAGCCGCACATGCGTAT<br>GCTTCACGCGATCAGCACTATCGGGGCTTAAGCCAGTGGCAGGTTGCAGAAGGCGC<br>GTTACACGGGGAGATCAGTCTACCACTTGCACTCGGCAGCGTTGGCGGTGCAATTG<br>AGGTCTTGCCTAAAGCGAAGGCGGCATTCGAAATCATGGGGATCACAGAGGCGAAG<br>GAGCTGGCAGAAGTCACAGCTGCGGTAGGGCTGGCGCAAAACCTGGCGGCGTTAAG<br>AGCGCTTGTTAGTGAAGGAATACAGCAAGGTCACATGTCGCTCCAGGCTCGCTCTCT<br>TGCATTATCGGTAGGTGCTACAGGCAAGGAAGTTGAAATCCTGGCCGAAAAATTAC<br>AGGGGCTCTCGTATGAATCAGGCGAACGCTCAGACCATACTCGCAGAGATCAGATCG<br>CAAAAGTTGAATTGTGA (SEQ ID NO: 95) |

*E. faecium* mvaE nucleic acid sequence
ATGAAAGAAGTGGTTATGATTGATGCGGCTCGCACACCCATTGGGAAATACAGAGG
TAGTCTTAGTCCTTTTACAGCGGTGGAGCTGGGGACACTGGTCACGAAAGGGCTGCT
GGATAAAACAAAGCTTAAGAAAGACAAGATAGACCAAGTGATATTCGGCAATGTG
CTTCAGGCAGGAAACGGACAAAACGTTGCAAGACAAATAGCCCTGAACAGTGGCTT
ACCAGTTGACGTGCCGGCGATGACTATTAACGAAGTTTGCGGGTCCGGAATGAAAG
CGGTGATTTTAGCCCGCCAGTTAATACAGTTAGGGGAGGCAGAGTTGGTCATTGCA
GGGGGTACGGAGTCAATGTCACAAGCACCCATGCTGAAACCTTACCAGTCAGAGAC
CAACGAATACGGAGAGCCGATATCATCAATGGTTAATGACGGGCTGACGGATGCGT
TTTCCAATGCTCACATGGGTCTTACTGCCAAAAGGTGGCGACCCAGTTTTCAGTGT
CGCGCGAGGAACAAGACCGGTACGCATTGTCCAGCCAATTGAAAGCAGCGCACGCG
GTTGAAGCCGGGGTGTTCTCAGAAGAGATTATTCCGGTTAAGATTAGCGACGAGGA
TGTCTTGAGTGAAGACGAGGCAGTAAGAGGCAACAGCACTTTGGAAAAACTGGGCA
CCTTGCGGACGGTGTTTTCTGAAGAGGGCACGGTTACCGCTGCAATGCTTCACCGC
TGAATGACGGCGCTAGTGTCGTGATTCTTGCATCAAAAGAATACGCGGAAAACAAT
AATCTGCCTTACCTGGCGACGATAAAGGAGGTTGCGGAAGTTGGTATCGATCCTTCT
ATCATGGGTATTGCCCCAATAAAGGCCATTCAAAAGTTAACAGATCGGTCGGGCAT
GAACCTGTCCACGATTGATCTGTTCGAAATTAATGAAGCATTCGCCGGCATCTAGCAT
TGTTGTTTCTCAAGAGCTGCAATTGGACGAAGAAAAAGTGAATATCTATGGCGGGG
CGATAGCTTTAGGCCATCCAATCGGCGCAAGCGGAGCCCGGATACTGACAACCTTA
GCATACGGCCTCCTGCGTGAGCAAAAGCGTTATGGTATTGCGTCATTATGTATCGGC
GGTGGTCTTGGTCTGGCCGTGCTGTTAGAAGCTAATATGGAGCAGACCCACAAAGA
CGTTCAGAAGAAAAAGTTTTACCAGCTTACCCCCTCCGAGCGGAGATCGCAGCTTAT
CGAGAAGAACGTTCTGACTCAAGAAACGGCACTTATTTTCCAGGAGCAGACGTTGT
CCGAAGAACTGTCCGATACATGATTGAGAATCAGGTCTCCGAAGTGGAAATTCCA
ATGGGAATTGCACAAAATTTTCAGATTAATGGCAAGAAAAAATGGATTCCTATGGC
GACTGAAGAACCTTCAGTAATAGCGGCAGCATCGAACGGCGCCAAAATCTGCGGGA
ACATTTGCGCGAAACGCCTCAGCGGCTTATGCGCGGGCAGATTGTCCTGTCTGGCA
AATCAGAATATCAAGCCGTGATAAATGCCGTGAATCATCGCAAAGAAGAACTGATT
CTTTGCGCAAACGAGTCGTACCCGAGTATTGTTAAACGCGGGGAGGTGTTCAGGA
TATTTCTACGCGGGAGTTTATGGGTTCTTTTCACGCGTATTTCAATCGACTTTCTG
GTGGACGTCAAGGACGCAATGGGGCAAACATGATCAACTCTATTCTCGAAAGCGT
TGCAAATAAACTGCGTGAATGGTTCCCGGAAGAGGAAATACTGTTCTCCATCCTGTC
AAACTTCGCTACGGAGTCCCTGGCATCTGCATGTTGCGAGATTCCTTTTGAAAGACT
TGGTCGTAACAAAGAAATTGGTGAACAGATCGCCAAGAAAATTCAACAGGCAGGG
GAATATGCTAAGCTTGACCCTTACCGCGCGGCAACCCATAACAAGGGGATTATGAA
CGGTATCGAAGCCGTCGTTGCCGCAACGGGAAACGACACACGGGCTGTTTCCGCTT
CTATTCACGCATACGCCGCCCGTAATGGCTTGTACCAAGGTTTAACGGATTGGCAGA
TCAAGGGCGATAAACTGGTTGGTAAATTAACAGTCCCACTGGCTGTGGCGACTGTC
GGTGGCGCGTCGAACATATTACCAAAAGCCAAAGCTTCCCTCGCCATGCTGGATATT
GATTCCGCAAAAGAACTGGCCCAAGTGATCGCCGCGGTAGGTTAGCACAGAATCT
GGCGGCGTTACGTGCATTAGTGACAGAAGGCATTCAGAAAGGACACATGGGCTTGC
AAGCACGTTCTTTAGCGATTTCGATAGGTGCCATCGGTGAGGAGATAGAGCAAGTC
GCGAAAAAACTGCGTGAAGCTGAAAAAATGAATCAGCAAACGGCAATACAGATTTT
AGAAAAAATTCGCGAGAAATGA (SEQ ID NO: 96)

*E. gallinarum* mvaE nucleic acid sequence
ATGGAAGAAGTGGTAATTATAGATGCACGTCGGACTCCGATTGGTAAATATCACGG
GTCGTTGAAGAAGTTTTCAGCGGTGGCGCTGGGGACGGCCGTGGCTAAAGACATGT
TCGAACGCAACCAGAAAATCAAAGAGGAGATCGCGCAGGTCATAATTGGTAATGTC
TTGCAGGCAGGAAATGGCCAGAACCCCGCGCGGCAAGTTGCTCTTCAATCAGGGTT
GTCCGTTGACATTCCCGCTTCTACAATTAACGAGGTTTGTGGGTCTGGTTTGAAAGC
TATCTTGATGGGCATGGAACAAATCCAACTCGGCAAAGCGCAAGTAGTGCTGGCAG
GCGGCATTGAATCAATGACAAATGCGCCAAGCCTGTCCCACTATAACAAGGCGGAG
GATACGTATAGTGTCCCAGTGTCGAGCATGACACTGGATGGTCTGACAGACGCATTT
TCTAGTAAACCTATGGGATTAACAGCGGAAAACGTCGCACAGCGCTACGGTATCTC
CCGTGAGGCGCAAGATCAATTCGCATATCAATCTCAGATGAAAGCAGCAAAAGCGC
AGGCAGAAAACAAATTCGCTAAGGAAATTGTGCCACTGGCGGGTGAAACTAAAACC
ATCACAGCTGACGAAGGGATCAGATCCCAAACAACGATGAGAAACTGGCAAGTCT
CAAACCTGTTTTTAAAACCGATGGCACTGTAACCGCAGGGAATGCTAGCACCATTA
ATGACGGGGCCGCCCTTGTGCTGCTTGCTAGCAAAACTTACTGCGAAACTAATGAC
ATACCGTACCTTGCGACAATCAAAGAAATTGTTGAAGTTGGAATCGATCCGGAGAT
TATGGGCATCTCTCCGATAAAGCGATACAAACATTGTTACAAAATCAAAAGTTA

| SEQUENCES |
|---|
| GCCTCGAAGATATTGGAGTTTTTGAAATAAATGAAGCCTTTGCCGCAAGTAGCATA<br>GTGGTTGAATCTGAGTTGGGATTAGATCCGGCTAAAGTTAACCGTTATGGGGGTGGT<br>ATATCCTTAGGTCATGCAATTGGGGCAACCGGCGCTCGCCTGGCCACTTCACTGGTG<br>TATCAAATGCAGGAGATACAAGCACGTTATGGTATTGCGAGCCTGTGCGTTGGTGG<br>TGGACTTGGACTGGCAATGCTTTTAGAACGTCCAACTATTGAGAAGGCTAAACCGA<br>CAGACAAAAAGTTCTATGAATTGTCACCAGCTGAACGGTTGCAAGAGCTGGAAAAT<br>CAACAGAAAATCAGTTCTGAAACTAAACAGCAGTTATCTCAGATGATGCTTGCCGA<br>GGACACTGCAAACCATTTGATAGAAAATCAAATATCAGAGATTGAACTCCCAATGG<br>GCGTCGGGATGAACCTGAAGGTTGATGGGAAAGCCTATGTTGTGCCAATGGCGACG<br>GAAGAGCCGTCCGTCATCGCGGCCATGTCTAATGGTGCCAAAATGGCCGGCGAAAT<br>TCACACTCAGTCGAAAGAACGGCTGCTCAGAGGTCAGATTGTTTTCAGCGCGAAGA<br>ATCCGAATGAAATCGAACAGAATAGCTGAGAACCAAGCTTTGATTTTCGAACGT<br>GCCGAACAGTCCTATCCTTCCATTGTGAAAAGAGAGGGAGGTCTCCGCCGCATTGC<br>ACTTCGTCATTTTCCTGCCGATTCTCAGCAGGAGTCTGCGGACCAGTCCACATTTTA<br>TCAGTGGACCTTTTTGTAGATGTGAAAGACGCGATGGGGGCAAATATCATAAATGC<br>AATACTTGAGGGCGTCGCAGCCCTGTTTCGCGAATGGTTCCCCAATGAGGGAATTCT<br>TTTTTCTATTCTCTCGAACTTGGCTACGGAGAGCTTAGTCACGGCTGTTTGTGAAGTC<br>CCATTTAGTGCACTTAGCAAGAGAGGTGGTGCAACGGTGGCCCAGAAAATTGTGCA<br>GGCGTCGCTCTTCGCAAAGACAGACCCATACCGCGCAGTGACCCACAACAAAGGGA<br>TTATGAACGGTGTAGAGGCTGTTATGCTTGCCACAGGCAACGACACGCGCAGTC<br>TCAGCCGCTTGTCATGGATACGCAGCGCGCACCGGTAGCTATCAGGGTCTGACTAA<br>CTGGACGATTGAGTCGGATCGCCTGGTAGGCGAGATAACACTGCCGCTGGCCATCG<br>CTACAGTTGGAGGCGCTACCAAAGTGTTGCCCAAAGCTCAAGCGGCACTGGAGATT<br>AGTGATGTTCACTCTTCTCAAGAGCTTGCAGCCTTAGCGGCGTCAGTAGGTTTAGTA<br>CAAAATCTCGCGGCCCTGCGCGCACTGGTTTCCGAAGGTATACAAAAAGGGCACAT<br>GTCCATGCAAGCCCGGTCTCTCGCAATCGCGGTCGGTGCTGAAAAAGCCGAGATCG<br>AGCAGGTCGCCGAAAAGTTGCGGCAGAACCCGCCAATGAATCAGCAGCAGGCGCTC<br>CGTTTTCTTGGCGAGATCCGCGAACAATGA (SEQ ID NO: 97) |
| *E. casseliflavus* mvaE nucleic acid sequence<br>ATGGAAGAAGTTGTCATCATTGACGCACTGCGTACTCCAATAGGAAAGTACCACGG<br>TTCGCTGAAAGATTACACAGCTGTTGAACTGGGGACAGTAGCAGCAAAGGCGTTGC<br>TGGCACGAAATCAGCAAGCAAAAGAACACATAGCGCAAGTTATTATTGGCAACGTC<br>CTGCAAGCCGGAAGTGGGCAGAATCCAGGCCGACAAGTCAGTTTACAGTCAGGATT<br>GTCTTCTGATATCCCCGCTAGCACGATCAATGAAGTGTGTGGCTCGGGTATGAAAGC<br>GATTCTGATGGGTATGGAGCAAATTCAGCTGAACAAAGCCTCTGTGGTCTTAACAG<br>GCGGAATTGAAAGCATGACCAACGCGCCGCTGTTTAGTTATTACAACAAGGCTGAG<br>GATCAATATTCGGCGCCGGTTAGCACAATGATGCACGATGGTCTAACAGATGCTTTC<br>AGTTCCAAACCAATGGGCTTAACCGCAGAGACCGTCGCTGAGAGATATGGAATTAC<br>GCGTAAGGAACAAGATGAATTTGCTTATCACTCTCAAATGAAGGCGGCCAAAGCCC<br>AGGCGGCGAAAAAGTTTGATCAGGAAATTGTACCCCTGACGGAAAAATCCGGAACG<br>GTTCTCCAGGACGAAGGCATCAGAGCCGCGACAACAGTCGAGAAGCTAGCTGAGCT<br>TAAAAACGGTGTTCAAAAAGACGGAACAGTTACAGCGGGTAACGCCTCTACGATAA<br>ATGATGGCGCTGCTATGGTATTAATAGCATCAAAATCTTATTGCGAAGAACACCAG<br>ATTCCTTATCTGGCCGTTATAAAGGAGATCGTTGAGGTGGGTTTTGCCCCCGAAATA<br>ATGGGTATTTCCCCCATTAAGGCTATAGACACCCTGCTGAAAAATCAAGCACTGACC<br>ATAGAGGATATAGGAATATTTGAGATTAATGAAGCCTTTGCTGCGAGTTCGATTGTG<br>GTAGAACGCGAGTTGGGCCTGGACCCCAAAAAAGTTAATCGCTATGCGGTTGGTAT<br>ATCACTCGGCCACGCAATTGGGGCGACGGGAGCTCGCATTGCGACGACCGTTGCTT<br>ATCAGCTGAAAGATACCCAGGAGCGCTACGGTATAGCTTCCTTATGCGTTGGTGGG<br>GGTCTTGGATTGGCGATGCTTCTGGAAAACCCATCGGCCACTGCCTCACAAACTAAT<br>TTTGATGAGGAATCTGCTTCCGAAAAAACTGAGAAGAAGAAGTTTTATGCGCTAGC<br>TCCTAACGAACGCTTAGCGTTTTTGGAAGCCCAAGGCGCTATTACCGCTGCTGAAAC<br>CCTGGTCTTCCAGGAGATGACCTTAAACAAAGAGACAGCCAATCACTTAATCGAAA<br>ACCAAATCAGCGAAGTTGAAATTCCTTTAGGCGTGGGCCTGAACTTACAGGTGAAT<br>GGGAAAGCGTATAATGTTCCTCTGGCCACGGAGGAACCGTCCGTTATCGCTGCGAT<br>GTCGAATGGCGCCAAAATGGCTGGTCCTATTACAACAACAAGTCAGGAGAGGCTGT<br>TACGGGGTCAGATTGTCTTCATGGACGTACAGGACCCAGAAGCAATATTAGCGAAA<br>GTTGAATCCGAGCAAGCTACCATTTTCGCGGTGGCAAATGAAACATACCCGTCTATC<br>GTGAAAAGAGGAGGAGGTCTGCGTAGAGTCATTGGCAGGAATTTCAGTCCGGCCGA<br>AAGTGACTTAGCCACGGCGTATGTATCAATTGACCTGATGGTAGATGTTAAGGATG<br>CAATGGGTGCTAATATCATCAATAGTATCCTAGAAGGTGTTGCGGAATTGTTTAGAA<br>AATGGTTCCCAGAAGAAGAAATCCTGTTCTCAATTCTCTCCAATCTCGCGACAGAAA<br>GTCTGGTAACGGCGACGTGCTCAGTTCCGTTTGATAAATTGTCCAAAACTGGGAATG<br>GTCGACAAGTAGCTGGTAAAATAGTGCACGCGGCGGACTTTGCTAAGATAGATCCA<br>TACAGAGCTGCCACACACAATAAAGGTATTATGAATGGCGTTGAAGCGTTAATCTT<br>AGCCACCGGTAATGACACCCGTGCGGTGTCGGCTGCATGCCACGGTTACGCGGCAC<br>GCAATGGGCGAATGCAAGGGCTTACCTCTTGGACGATTATCGAAGATCGGCTGATA<br>GGCTCTATCACATTACCTTTGGCTATTGCGACAGTGGGGGTGCCACAAAAATCTTG<br>CCAAAAGCACAGGCCGCCCTGGCGCTAACTGGCGTTGAGACGGCGTCGGAACTGGC<br>CAGCCTGGCGGCGAGTGTGGGATTAGTTCAAAATTTGGCCGCTTTACGAGCACTAGT<br>GAGCGAGGGCATTCAGCAAGGGCACATGAGTATGCAAGCTAGATCCCTGGCCATTA<br>GCGTAGGTGCGAAAGGTACTGAAATAGAGCAACTAGCTGCGAAGCTGAGGGCAGC<br>GACGCAAATGAATCAGGAGCAGGCTCGTAAATTTCTGACCGAAATAAGAAATTAA<br>(SEQ ID NO: 98) |

*L. grayi* mvaS nucleic acid sequence
ATGACCATGAACGTTGGAATCGATAAAATGTCATTCTTTGTTCCACCTTACTTTGTG
GACATGACTGATCTGGCAGTAGCACGGGATGTCGATCCCAATAAGTTTCTGATTGGT
ATTGGCCAGGACCAGATGGCAGTTAATCCGAAAACGCAGGATATTGTGACATTTGC
CACAAATGCTGCCAAAAACATACTGTCAGCTGAGGACCTTGATAAAATTGATATGG
TCATAGTCGGCACCGAGAGTGGAATCGATGAATCCAAAGCGAGTGCCGTAGTGCTT
CACAGGTTGCTCGGTATCCAGAAGTTTGCTCGCTCCTTTGAAATCAAAGAAGCCTGT
TATGGGGGTACCGCGGCTTTACAGTTCGCTGTAAACCACATTAGGAATCATCCTGAA
TCAAAGGTTCTTGTAGTTGCATCAGATATCGCGAAATACGGCCTGGCTTCTGGAGGT
GAACCAACGCAAGGTGCAGGCGCTGTGGCTATGCTCGTCTCAACTGACCCTAAGAT
CATTGCTTTCAACGACGATAGCCTCGCGCTTACACAAGATATCTATGACTTCTGGCG
ACCAGTTGGACATGACTATCCTATGGTCGACGGGCCTCTTAGTACAGAGACCTACAT
CCAGTCATTTCAGACCGTATGGCAGGAATACACAAAACGGTCGCAGCATGCACTGG
CAGACTTTGCTGCCCTTAGCTTTCATATCCCGTATACTAAAATGGGCAAAAAGGCGC
TGCTTGCAATCCTTGAAGGCGAATCAGAGGAGGCTCAGAACCGTATACTAGCAAAA
TATGAAAAGAGTATAGCCTACTCCAGAAAGGCGGGTAACCTGTATACCGGTAGCCT
GTATCTAGGACTTATTTCACTTCTGGAAAATGCAGAAGACCTTAAAGCTGGTGATTT
AATAGGCCTCTTTTCTTACGGTTCCGGTGCTGTTGCGGAGTTTTTCTCAGGAAGGCT
GGTTGAGGACTATCAGGAACAGCTACTTAAAACAAAACATGCCGAACAGCTGGCCC
ATAGAAAGCAACTGACAATCGAGGAGTACGAAACGATGTTCTCCGATCGCTTGGAC
GTGGACAAAGACGCCGAATACGAAGACACATTAGCTTATAGCATTTCGTCAGTCCG
AAACACCGTACGTGAGTACAGGAGTTGA (SEQ ID NO: 99)

*E. faecium* mvaS nucleic acid sequence
ATGAAAATCGGTATTGACCGTCTGTCCTTCTTCATCCCGAATTTGTATTTGGACATG
ACTGAGCTGGCAGAATCACGCGGGGATGATCCAGCTAAATATCATATTGGAATCGG
ACAAGATCAGATGGCAGTGAATCGCGCAAACGAGGACATCATAACACTGGGTGCA
AACGCTGCGAGTAAGATCGTGACAGAGAAAGACCGCGAGTTGATTGATATGGTAAT
CGTTGGCACGGAATCAGGAATTGACCACTCCAAAGCAAGCGCCGTGATTATTCACC
ATCTCCTTAAAATTCAGTCGTTCGCCCGTTCTTTCGAGGTAAAAGAAGCTTGCTATG
GCGGAACTGCTGCCCTGCACATGGCGAAGGAGTATGTCAAAAATCATCCGGAGCGT
AAGGTCTTGGTAATTGCGTCAGACATCGCGCGTTATGGTTTGGCCAGCGGAGGAGA
AGTTACTCAAGGCGTGGGGGCCGTAGCCATGATGATTACACAAAACCCCCGGATTC
TTTCGATTGAAGACGATAGTGTTTTTCTCACAGAGGATATCTATGATTTCTGGCGGC
CTGATTACTCCGAGTTCCCTGTAGTGGACGGGCCCCTTTCAAACTCAACGTATATAG
AGAGTTTTCAGAAAGTTTGGAACCGGCACAAGGAATTGTCCGGAAGAGGGCTGGAA
GATTATCAAGCTATTGCTTTTCACATACCCTATACGAAGATGGGTAAGAAAGCGCTC
CAGAGTGTTTTAGACCAAACCGATGAAGATAACCAGGAGCGCTTAATGGCTAGATA
TGAGGAGTCTATTCGCTATAGCCGGAGAATTGGTAACCTGTACACAGGCAGCTTGT
ACCTTGGTCTTACAAGCGTTGTTGGAAAACTCTAAAAGTTTACAACCGGGAGATCGG
ATCGGCCTCTTTTCCTATGGCAGTGGTGCGGTGTCCGAGTTCTTTACCGGGTATTTAG
AAGAAAATTACCAAGAGTACCTGTTCGCTCAAAGCCATCAAGAAATGCTGGATAGC
CGGACTCGGATTACGGTCGATGAATACGAGACCATCTTTTCAGAGACTCTGCCAGA
ACATGGTGAATGCGCCGAATATACGAGCGACGTCCCCTTTTCTATAACCAAGATTGA
GAACGACATTCGTTATTATAAAATCTGA (SEQ ID NO: 100)

*E. gallinarum* mvaS nucleic acid sequence
ATGAACGTCGGCATTGACAAAATTAATTTTTTCGTTCCACCGTATTATCTGGATATG
GTCGACCTGGCCCACGCACGCGAAGTGGACCCGAACAAATTTACAATTGGAATTGG
ACAGGATCAGATGGCTGTGAGCAAAAGACGCACGATATCGTAACATTCGCGGCTA
GTGCCGCGAAGGAAATTTTAGAACCTGAGGACTTGCAAGCTATAGACATGGTTATA
GTTGGTACCGAATCGGGCATTGACGAGAGCAAAGCATCCGCGGTCGTTTTACATCG
TTTGTTGGGCGTACAACCTTTCGCTCGCAGTTTTGAAATTAAAGAAGCCTGTTACGG
GGCAACCGCAGGCATTCAGTTTGCCAAGACTCATATACAAGCGAACCCGGAGAGCA
AGGTCCTGGTAATTGCAAGCGATATAGCTCGGTATGGTCTTCGGTCAGGTGGAGAG
CCCACACAAGGCGCAGGGGCAGTTGCTATGCTTCTCACGGCAAATCCCAGAATCCT
GACCTTCGAAAACGACAATCTGATGTTAACGCAGGATATTTATGACTTCTGGAGACC
ACTTGGTCACGCTTACCCTATGGTAGATGGCCACCTTTCCAATCAAGTCTATATTGA
CAGTTTTAAGAAGGTCTGGCAAGCACATTGCGAACGCAATCAAGCTTCTATATCCG
ACTATGCCGCGATTAGTTTTCATATTCCGTATACAAAAATGGGTAAGAAAGCCCTGC
TCGCTGTTTTTGCAGATGAAGTGGAAACTGAACAGGAACGCGTTATGGCACGGTAT
GAAGAGTCTATCGTATATTCACGCCGGATCGGCAACTTGTATACGGGATCATTGTAC
CTGGGGCTGATATCCTTATTGGAAAACAGTTCTCACCTGTCGGCGGGCGACCGGATA
GGATTGTTTAGTTATGGGAGTGGCGCTGTCAGCGAATTTTTCTCCGGTCGTTTAGTG
GCAGGCTATGAAAATCAATTGAACAAAGAGGCGCATACCCAGCTCCTGGATCAGCG
TCAGAAGCTTTCCATCGAAGAGTATGAGGCGATTTTTACAGATTCCTTAGAAATTGA
TCAGGATGCAGCGTTCTCGGATGACCTGCCATATTCCATCCGCGAGATAAAAAACA
CGATTCGGTACTATAAGGAGAGCTGA (SEQ ID NO: 101)

*E. casseliflavus* mvaS nucleic acid sequence
ATGAACGTTGGAATTGATAAAATCAATTTTTTCGTTCCGCCCTATTTCATTGATATGG
TGGATCTCGCTCATGCAAGAGAAGTTGACCCCAACAAGTTCACTATAGGAATAGGC
CAAGATCAGATGGCAGTAAACAAGAAAACGCAAGATATCGTAACGTTCGCGATGCA
CGCCGCGAAGGATATTCTGACTAAGGAAGATTTACAGGCCATAGATATGGTAATAG
TGGGGACTGAGTCTGGGATCGACGAGAGCAAGGCAAGTGCTGTCGTATTGCATCGG
CTTTTAGGTATTCAGCCTTTTGCGCGCTCCTTTGAAATTAAGGAGGCATGCTATGGG

| SEQUENCES |
|---|
| GCCACTGCCGGCCTTCAGTTTGCAAAAGCTCATGTGCAGGCTAATCCCCAGAGCAA
GGTCCTGGTGGTAGCTTCCGATATAGCACGCTACGGACTGGCATCCGGAGGAGAAC
CGACTCAAGGTGTAGGTGCTGTGGCAATGTTGATTTCCGCTGATCCAGCTATCTTGC
AGTTAGAAAATGATAATCTCATGTTGACCCAAGATATATACGATTTTTGGCGCCCGG
TCGGGCATCAATATCCTATGGTAGACGGCCATCTGTCTAATGCCGTCTATATAGACA
GCTTTAAACAAGTCTGGCAAGCACATTGCGAGAAAAACCAACGGACTGCTAAAGAT
TATGCTGCATTGTCGTTCCATATTCCGTACACGAAAATGGGTAAGAAAGCTCTGTTA
GCGGTTTTTGCGGAGGAAGATGAGACAGAACAAAAGCGGTTAATGGCACGTTATGA
AGAATCAATTGTATACAGTCGTCGGACTGGAAATCTGTATACTGGCTCACTCTATCT
GGGCCTGATTTCCTTACTGGAGAATAGTAGCAGTTTACAGGCGAACGATCGCATAG
GTCTGTTTAGCTATGGTTCAGGGGCCGTTGCGGAATTTTTCAGTGGCCTCTTGGTAC
CGGGTTACGAGAACAATTAGCGCAAGCTGCCCATCAAGCTCTTCTGGACGACCGG
CAAAAACTGACTATCGCAGAGTACGAAGCCATGTTTAATGAAACCATTGATATTGA
TCAGGACCAGTCATTTGAGGATGACTTACTGTACTCCATCAGAGAGATCAAAAACA
CTATTCGCTACTATAACGAGGAGAATGAATAA (SEQ ID NO: 102) |

Amino acid sequence of acetoacetyl-CoA synthase
MTDVRFRIIGTGAYVPERIVSNDEVGAPAGVDDDWITRKTGIRQRRWAADDQATSDLA
TAAGRAALKAAGITPEQLTVIAVATSTPDRPQPPTAAYVQHHLGATGTAAFDVNAVCS
GTVFALSSVAGTLVYRGGYALVIGADLYSRILNPADRKTVVLFGDGAGAMVLGPTSTG
TGPIVRRVALHTFGGLTDLIRVPAGGSRQPLDTDGLDAGLQYFAMDGREVRRFVTEHLP
QLIKGFLHEAGVDAADISHFVPHQANGVMLDEVFGELHLPRATMHRTVETYGNTGAAS
IPITMDAAVRAGSFRPGELVLLAGFGGGMAASFALIEW (SEQ ID NO: 103)

L. lactis PKL nucleic acid sequence
atgaccgagtataacagcgaggcctatctgaaaaaactggataaatggtggcgtgcagcaacctatctgggtgcaggtatgattttctgaaa
gaaaatccgctgtttagcgttaccggcaccccgattaaagcagaaaatctgaaagccaatccgattggtcattgggcaccgttagcggtca
gacctttctgtatgcacatgcaaatcgtctgatcaacaaatatgatcagaaaatgttttatatgggtggtccgggtcatggtggtcaggcaatg
gttgttccgagctatctggatggtagctataccgaagcatatccggaaattacccaggatctggaaggtatgagccgtctgtttaaacgttta
gctttccgggtggtattggtagccatataccgcacagcaccgggtagcctgcatgaaggtggtgaactgggttatgttctgagccatgca
accggtgcaattctggatcagccggaacaaattgcatttgcatttgttggtgatggtgaaacccggtccgctgatgaccagctggc
ataccatcaaatttatcaaccgaaaaacgatggtgccattctgccgatcctggatctgaatggctttaaaatcagcaatccgaccctgtttgc
acgtaccagtgatgttgatattcgcaaattttttcgaaggcctgggctatagtccgcgttatattgaaatgatgatattcacgactatatggccta
ccataaactggcagcagaagttttttgataaagccatcgaagatatccatcagatccagaaagatgcccgtgaagataatcgttatcagaatg
gtgaaatttccggcatggccgattgttattgcacgtctgccgaaaggttggggtggccctcgttataatgattggagcggtccgaaatttgatg
gtaaaggtatgccgattgaacatagctttcgtgccacaggttccgctgccgctgagcagcaaaaatatgggcaccctgccggaatttgtta
aatgatgacctcatatcagcctgaaaacactgtttaatgcagatggttcactgaaagaggaactgcgcgattttgcaccgaaaggcgaaatg
cgtatggcaagtaatccggttaccaatggtggtgttgatagcagcaatctggttctgccggattggcaagaatttgcaaacccgattagcgaa
ataatcgtggtaaactgctgccggacaccaatgataatatggatatgaatgtgctgagcaagtattttgccgaaatcgttaaactgaatccga
cacgttttcgcctgtttggtccggatgaaaccatgagcaatcgttttttgggaaatgttcaaagtgaccaatcgtcagtggatgcaggttatcaaa
aatccgaacgatgaattcattagtccggaaggtcgtattattgatagccagtgagcgaacatcaggcagaaggttggctggaaggctatac
cctgaccggtcgtaccggtgcctttcaagctatgaaagcttctgcgtgttgtgatagcatgctgacccagcatttcaaatggattcgtcag
gcagccgaccagaaatggcgtcatgattatccgagcctgaatgttattagcaccagcaccgttttcagcaggatcataatggttataccatc
aggatccgggtatgctgacacatctggcagagaaaaaagcgatttatccgtcagtatctgcctgccgatggtaatccctgctggcagtgt
tgatcgtgcatttcaggatcgtagcaaaatcaatcatattgtggcaagcaaacagcctcgtcagcagtggtttaccaaagaagaagccgag
aaactggccaccgatggcattgcaaccattgattgggcgacaccgcaaagatggagcagttgatctggttttttgcaagtgccggtg
cagaaccgaccattgaaacctggcagcctgcatctgtaatgaagtgtttccgcaggcaaaatttcgctatgttaatgttgttgagctggg
tcgtctgcagaaaaagaaaggtgcactgaatcaagaacgtgaactgtccgatgaagaatctgagaaatatttcggtccgagcggtacaccg
gttatttttggttttcatggttatgaggatctgattgaaagcatctttatcagcgtggtcatgatggcctgatcgttcatggctatcgcgaagatgg
tgatattaccacccacctatgatatgcgtgtttatagcgaactggatcgttttcatcaggccattgatgcaatgcaggtactgtatgtgaatcgcaa
agttaatcagggtctggccaaagcatttatcgatcgtatgaaacgtaccctggtgaaacattttgaagtgacccgtaatgaaggcgtggatatt
ccggattttaccgaatgggtttggagcgatctgaagaaa (SEQ ID NO: 104)

L. lactis PKL amino acid sequence
MTEYNSEAYL KKLDKWWRAA TYLGAGMIFL KENPLFSVTG TPIKAENLKA
NPIGHWGTVS GQTFLYAHAN RLINKYDQKM FYMGGPGHGG QAMVVPSYLD
GSYTEAYPEI TQDLEGMSRL FKRFSFPGGI GSHMTAQTPG SLHEGGELGY
VLSHATGAIL DQPEQIAFAV VGDGEAETGP LMTSWHSIKF INPKNDGAIL
PILDLNGFKI SNPTLFARTS DVDIRKFFEG LGYSPRYIEN DDIHDYMAYH
KLAAEVFDKA IEDIHQIQKD AREDNRYQNG EIPAWPIVIA RLPKGWGGPR
YNDWSGPKFD GKGMPIEHSF RAHQVPLPLS SKNMGTLPEF VKWMTSYQPE
TLFNADGSLK EELRDFAPKG EMRMASNPVT NGGVDSSNLV LPDWQEFANP
ISENNRGKLL PDTNDNMDMN VLSKYFAEIV KLNPTRFRLF GPDETMSNRF
WEMFKVTNRQ WMQVIKNPND EFISPEGRII DSQLSEHQAE GWLEGYTLTG
RTGAFASYES FLRVVDSMLT QHFKWIRQAA DQKWRHDYPS LNVISTSTVF
QQDHNGYTHQ DPGMLTHLAE KKSDFIRQYL PADGNTLLAV FDRAFQDRSK
INHIVASKQP RQQWFTKEEA EKLATDGIAT IDWASTAKDG EAVDLVFASA
GAEPTIETLA ALHLVNEVFP QAKFRYVNVV ELGRLQKKKG ALNQERELSD
EEFEKYFGPS GTPVIFGFHG YEDLIESIFY QRGHDGLIVH GYREDGDITT
TYDMRVYSEL DRFHQAIDAM QVLYVNRKVN QGLAKAFIDR MKRTLVKHFE
VTRNEGVDIP DFTEWVWSDL KK (SEQ ID NO: 105)

What is claimed is:

1. A microorganism capable of increased carbon flux through the phosphoketolase pathway compared to a control microorganism not expressing a heterologous phosphoketolase, wherein the microorganism comprises: (i) a heterologous nucleic acid sequence encoding a polypeptide having phosphoketolase activity, wherein the polypeptide comprises at least 65% sequence identity to SEQ ID NO:8 or SEQ ID NO: 11; and (ii) one or more nucleic acids encoding one or more polypeptides of the complete mevalonate (MVA) pathway, wherein (1) the microorganism comprising the polypeptide having phosphoketolase activity of (i) has a Performance Index value of greater than 1.0 in one or more of the following parameters: (a) cell growth on glucose, (b) cell growth on xylose, (c) production of intracellular acetyl-phosphate or (d) cell growth on glucose-6-phosphate, wherein the Performance Index value is calculated as activity per unit relative to a corresponding cell expressing a phosphoketolase from *E. gallinarum*; or (2) the polypeptide having phosphoketolase activity of (i) has a Performance Index value of greater than 1.0 in one or more of the following parameters: (e) protein solubility, (f) protein expression, or (g) fructose-6-phosphate (F6P) Specific Activity, wherein the Performance Index value is calculated as activity per unit relative to a phosphoketolase from *E. gallinarum*.

2. The microorganism of claim 1, wherein the polypeptide comprises at least 90% sequence identity to a polypeptide selected from the group consisting of SEQ ID NO:23, SEQ ID NO: 24, SEQ ID NO: 25, SEQ ID NO: 26, SEQ ID NO: 27, SEQ ID NO: 28, SEQ ID NO: 29, SEQ ID NO: 30, and SEQ ID NO: 31.

3. The microorganism of claim 1, wherein the polypeptide comprises at least 90% sequence identity to a polypeptide selected from the group consisting of SEQ ID NO:32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, and SEQ ID NO: 46.

4. The microorganism of claim 1, wherein culturing of the microorganism in a suitable media increases one or more of an intracellular amount of erythrose 4-phosphate, an intracellular amount of glyceraldehyde 3-phosphate, or an intracellular amount phosphate compared to a control microorganism not expressing a heterologous phosphoketolase.

5. The microorganism of claim 1, wherein the polypeptide having phosphoketolase activity is capable of synthesizing glyceraldehyde 3-phosphate and acetyl phosphate from xylulose 5-phosphate.

6. The microorganism of claim 1, wherein the polypeptide having phosphoketolase activity is capable of synthesizing erythrose 4-phosphate and acetyl phosphate from fructose 6-phosphate.

7. The microorganism of claim 1, wherein the one or more polypeptides of the complete MVA pathway is selected from (a) acetyl-CoA acetyltransferase; (b) 3-hydroxy-3 methylglutaryl-CoA synthase; (c) 3-hydroxy-3 methylglutaryl-CoA reductase; (d) mevalonate kinase; (e) phosphomevalonate kinase; and (f) diphosphomevalonate decarboxylase.

8. The microorganism of claim 1, further comprising a heterologous nucleic acid encoding an isoprene synthase polypeptide, wherein culturing of the microorganism in a suitable media provides for the production of isoprene with a Performance Index value of greater than 1.0 in one or more of the following parameters: (h) isoprene yield or (i) isoprene specific productivity.

9. The microorganism of claim 1, wherein culturing of the microorganism in a suitable media provides for the production of isoprenoid precursors.

10. The microorganism of claim 1, further comprising a heterologous nucleic acid encoding a polyprenyl pyrophosphate synthase polypeptide, wherein culturing of the microorganism in a suitable media provides for the production of isoprenoids.

11. The microorganism of claim 1, wherein culturing of the microorganism in a suitable media provides for the production of an acetyl CoA-derived metabolite.

12. The microorganism of claim 1, wherein the microorganisms are gram-positive bacterial cells, gram-negative bacterial cells, fungal cells, filamentous fungal cells, algal cells or yeast cells.

13. The microorganism of claim 1, wherein the microorganisms are selected from the group consisting of *Corynebacteria, Bacillus subtilis, Streptomyces lividans, Streptomyces coelicolor, Streptomyces griseus, Escherichia coli, Pantoea citrea, Trichoderma reesei, Aspergillus oryzae* and *Aspergillus niger, Saccharomyces cerevisiae* and *Yarrowia lipolytica*.

14. The microorganism of claim 9, wherein the isoprenoid precursor is MVA.

15. The microorganism of claim 11, wherein the acetyl CoA-derived metabolite is selected from the group consisting of polyketides, polyhydroxybutyrate, fatty alcohols, and fatty acids.

16. The microorganism of claim 11, wherein the acetyl CoA-derived metabolite is selected from the group consisting of acetone, isopropanol, isobutene, and propene.

17. A method of producing isoprene comprising: (a) culturing the microorganism of claim 8 under conditions suitable for producing isoprene and (b) producing isoprene.

18. A method of producing an isoprenoid precursor comprising: (a) culturing the microorganism of claim 9 under conditions suitable for producing an isoprenoid precursor and (b) producing an isoprenoid precursor.

19. A method of producing an isoprenoid comprising: (a) culturing the microorganism of claim 10 under conditions suitable for producing an isoprenoid and (b) producing an isoprenoid.

20. A method of producing an acetyl CoA-derived metabolite comprising: (a) culturing the microorganism of claim 11 under conditions suitable for producing an acetyl CoA-derived metabolite and (b) producing an acetyl CoA-derived metabolite.

* * * * *

SEQUENCE LISTING

<160> NUMBER OF SEQ ID NOS: 142

<210> SEQ ID NO 1
<211> LENGTH: 823
<212> TYPE: PRT
<213> ORGANISM: Mycobacterium gilvum Spyr1

<400> SEQUENCE: 1

Met Thr Thr Ala Thr Thr Ala Glu Arg Arg Pro Leu Ser Asp Gln Asp
1               5                   10                  15

Val Asp Arg Leu Asp Arg Trp Trp Arg Ala Ala Asn Tyr Leu Ser Val
                20                  25                  30

Gly Gln Ile Tyr Leu Leu Asp Asn Pro Leu Leu Arg Thr Pro Leu Thr
            35                  40                  45

Arg Glu Asp Val Lys Pro Arg Leu Leu Gly His Trp Gly Thr Thr Pro
    50                  55                  60

Gly Leu Asn Phe Leu Tyr Ala His Leu Asn Arg Ala Ile Ala Gln Arg
65                  70                  75                  80

Gln Gln Ser Thr Ile Tyr Val Thr Gly Pro Gly His Gly Gly Pro Gly
                85                  90                  95

Leu Val Ala Asn Ala Tyr Leu Asp Gly Thr Tyr Ser Glu Ile Tyr Ser
                100                 105                 110

Asp Ile Thr Gln Asp Asp Glu Gly Leu Arg Arg Leu Phe Arg Gln Phe
            115                 120                 125

Ser Phe Pro Gly Gly Ile Pro Ser His Val Ala Pro Glu Thr Pro Gly
    130                 135                 140

Ser Ile His Glu Gly Gly Glu Leu Gly Tyr Ala Leu Ser His Ala Tyr
145                 150                 155                 160

Gly Ala Ala Phe Asp Asn Pro Asp Leu Leu Val Ala Ala Val Val Gly
                165                 170                 175

Asp Gly Glu Ala Glu Thr Gly Pro Leu Ala Thr Ser Trp His Ser Asn
                180                 185                 190

Lys Phe Val Asn Ala Ala Lys Asp Gly Ala Val Leu Pro Ile Leu His
            195                 200                 205

Leu Asn Gly Tyr Lys Ile Ala Asn Pro Thr Leu Leu Ala Arg Ile Pro
    210                 215                 220

Thr Asp Glu Leu Arg Ala Leu Met Val Gly Tyr Gly His His Pro Tyr
225                 230                 235                 240

Phe Phe Glu Val Pro Asp Asp Glu Gly Gly Pro Gly Val Asp His Ala
                245                 250                 255

Asp Ala His Arg Arg Phe Ala Arg Leu Leu Asp Asp Val Leu Asp Glu
                260                 265                 270

Ile Ala Asp Ile Lys Thr Arg Ala Arg Glu Gly Asp Glu Ser Arg Pro
            275                 280                 285

Ala Trp Pro Met Ile Val Phe Arg Thr Pro Lys Gly Trp Thr Gly Pro
    290                 295                 300

Asp Tyr Ile Asp Gly Lys Lys Thr Thr Gly Ser Trp Arg Ala His Gln
305                 310                 315                 320

Val Pro Leu Ser Asn Ala Arg Asp Thr Lys Glu His Leu Ala Val Leu
                325                 330                 335

Ser Asp Trp Leu Ser Ser Tyr Arg Pro Asp Glu Leu Phe Asp Ala Asp
                340                 345                 350

Gly Arg Leu Leu Pro Glu Ile Ala Glu Leu Ala Pro Ser Gly Gln Leu
            355                 360                 365

```
Arg Met Ser Asp Asn Ala His Ala Asn Gly Gly Leu Leu Lys Asp
    370                 375                 380

Leu Arg Leu Pro Asp Phe Arg Glu Tyr Ala Val Asp Val Pro Ala Pro
385                 390                 395                 400

Gly Ala Thr Val Ala Glu Ala Thr Arg Val Leu Gly Gln Trp Leu Thr
                    405                 410                 415

Glu Val Ile Arg Leu Asn Pro Asp Asn Phe Arg Ile Phe Gly Pro Asp
                420                 425                 430

Glu Thr Ala Ser Asn Arg Leu Gln Ala Val Tyr Asp Ala Thr Asp Lys
                435                 440                 445

Gln Trp Asn Ala Glu Phe Phe Gly Ala Glu Val Asp Glu His Leu Ala
450                 455                 460

Arg Ala Gly Arg Val Val Glu Met Leu Ser Glu His Gln Cys Gln Gly
465                 470                 475                 480

Trp Leu Glu Gly Tyr Leu Leu Thr Gly Arg His Gly Leu Phe Asn Cys
                485                 490                 495

Tyr Glu Ala Phe Ile His Ile Val Asp Ser Met Leu Asn Gln His Ala
                500                 505                 510

Lys Trp Leu Lys Val Thr Asn His Ile Pro Trp Arg Arg Pro Ile Ala
            515                 520                 525

Ser Leu Asn Tyr Leu Leu Ser Ser His Val Trp Arg Gln Asp His Asn
530                 535                 540

Gly Phe Ser His Gln Asp Pro Gly Phe Ile Asp His Val Val Asn Lys
545                 550                 555                 560

Ser Ala Lys Val Val Arg Val Tyr Leu Pro Pro Asp Ala Asn Thr Leu
                565                 570                 575

Leu Ser Thr Tyr Asp His Cys Leu Arg Ser Arg Gln Tyr Val Asn Val
                580                 585                 590

Val Val Ser Gly Lys Gln Pro Ser Pro Asn Phe Leu Thr Met Glu Gln
            595                 600                 605

Ala Val Ala His Cys Thr Arg Gly Leu Gly Ile Trp Glu Trp Ala Gly
            610                 615                 620

Ser Glu Glu Leu Gly Thr Asp Pro Asp Val Val Leu Ala Ser Ala Gly
625                 630                 635                 640

Asp Ile Pro Thr Leu Glu Ala Leu Ala Ala Asp Ile Leu Arg Gln
                645                 650                 655

His Leu Pro Asp Leu Lys Val Arg Phe Val Asn Val Asp Leu Met
                660                 665                 670

Arg Leu Gln Asp Ser Thr Glu His Pro His Gly Leu Pro Asp Arg Asp
                675                 680                 685

Phe Asp Met Ile Phe Thr Thr Asp Arg Pro Ile Ile Phe Ala Tyr His
    690                 695                 700

Gly Tyr Pro Trp Leu Ile His Arg Leu Thr Tyr Arg Arg Ala Gly His
705                 710                 715                 720

Asp Asn Leu His Val Arg Gly Tyr Lys Glu Glu Gly Thr Thr Thr Thr
                725                 730                 735

Pro Phe Asp Met Val Met Leu Asn Asp Leu Asp Arg Tyr His Leu Val
                740                 745                 750

Met Asp Val Ile Asp Arg Val Pro Ser Leu Gly Ser Thr Cys Ala Ala
                755                 760                 765

Leu Arg Gln Gln Met Ala Asp Lys Arg Ile Ala Ala Arg Glu Tyr Thr
770                 775                 780

Arg Ala His Gly Glu Asp Ile Pro Glu Val Lys Asp Trp Val Trp Pro
```

```
                785                 790                 795                 800
Ala Ala Arg Glu Ser Gly Phe Gly Thr Ala Gly Ala Asp Gly Ala Ser
                    805                 810                 815

Ser Thr Gly Gly Asp Asn Glu
                    820

<210> SEQ ID NO 2
<211> LENGTH: 788
<212> TYPE: PRT
<213> ORGANISM: Shewanella baltica OS185

<400> SEQUENCE: 2

Met Thr Gln Ile His Glu Ile Asn Ala Leu Lys Lys Tyr Val Arg Ala
1               5                   10                  15

Thr Asn Phe Leu Ala Thr Ser Gln Ile Tyr Leu Lys Gln Asn Val Leu
                20                  25                  30

His Lys Arg Pro Leu Ala His Thr Asp Ile Lys Pro Arg Leu Leu Gly
            35                  40                  45

His Trp Gly Thr Cys Pro Gly Ile Asn Phe Val Tyr Ala Asn Ile Asn
        50                  55                  60

Arg Leu Ile Val Lys His Asn Arg Ser Phe Ile Tyr Leu Val Gly Pro
65                  70                  75                  80

Gly His Gly Phe Pro Ala Val Gln Ala Asn Leu Phe Met Glu Gly Ser
                85                  90                  95

Leu Ser His Phe Tyr Pro Glu Thr Ile Pro Tyr Asn Glu Thr Gly Ile
            100                 105                 110

Glu Asp Ile Cys Lys Lys Phe Ser Ala Ala Tyr Gly Tyr Pro Ser His
        115                 120                 125

Ala Asn Pro Glu Ala Pro Gly Gln Ile Leu Glu Gly Gly Glu Leu Gly
    130                 135                 140

Tyr Ser Leu Ser Val Gly Trp Gly Ala Val Leu Asp Asn Pro Asp Leu
145                 150                 155                 160

Ile Ala Thr Val Leu Ile Gly Asp Gly Glu Ala Glu Thr Gly Pro Leu
                165                 170                 175

Ala Ala Ser Trp Tyr Ala Asn Arg Leu Val Ser Pro Ala Thr Ser Gly
            180                 185                 190

Ala Val Leu Pro Ile Val His Ile Asn Gly Tyr Lys Ile Ser Gly Pro
        195                 200                 205

Thr Arg Met Gly Arg Met Ser His Glu Glu Leu Asp Leu Glu Phe Arg
    210                 215                 220

Gly Leu Gly Tyr Phe Pro Ile Ile Val Asp Asn Glu Leu Glu Glu Asp
225                 230                 235                 240

Ile Tyr Val Gln Met Thr Asn Ala Met Asp Thr Ala Tyr Ala Met Ile
                245                 250                 255

Asn Asp Ile Gln Arg Arg Ala Arg Ser Gly Glu Asp Val Val Lys Pro
            260                 265                 270

Lys Trp Pro Val Ile Leu Met Arg Thr Ala Lys Gly Trp Thr Gly Val
        275                 280                 285

Ser Glu Tyr Lys Gly Lys Lys Leu Glu Gly Asn Cys Glu Ser His Gln
    290                 295                 300

Val Ile Val Asn Lys Cys Ala Thr Asp Lys Gly His Leu Asp Ala Leu
305                 310                 315                 320

Asp Asn Trp Leu Ala Ser Tyr His Phe Gln Glu Leu Tyr Gln Met Asn
                325                 330                 335
```

-continued

Asp Lys Gly Glu Leu Ile Phe Asp Ala Asp Ile Cys Ser Leu Ile Pro
                340                 345                 350

Pro Lys Gln Leu Ala Cys Gly Arg Gln His Leu Thr Tyr Gly Gly Glu
                355                 360                 365

Val Val Arg Ala Leu Thr Asn Pro Asp Leu Glu Lys Leu Ser Tyr Gly
            370                 375                 380

Pro Glu Val Pro Arg Gly His Arg Gly Tyr Ser Met Leu Lys Met Gly
385                 390                 395                 400

Glu Trp Met Arg Asp Ala Phe Lys Leu Asn Arg Asp Gln Arg Asn Leu
                405                 410                 415

Arg Ile Phe Ser Pro Asp Glu Thr Tyr Ser Asn Gln Leu Gln Ala Val
                420                 425                 430

Phe Glu Glu Thr Asp Arg Ala Trp Gln Trp Pro Ile Glu Ser Trp Asp
                435                 440                 445

Glu Asp Met Ser Arg Glu Gly Arg Val Ile Glu Leu Leu Ser Glu Asn
            450                 455                 460

Leu Leu Phe Gly Met Leu His Gly Tyr Thr Val Thr Gly Arg His Gly
465                 470                 475                 480

Met Phe Pro Thr Tyr Glu Ser Phe Ser Gln Val Ile Ser Ser Met Ala
                485                 490                 495

Asp Gln Tyr Cys Lys Tyr Val Tyr Ala Ser Gln Gly Val His Phe Arg
                500                 505                 510

Lys Pro Leu Pro Ser Cys Asn Val Val Leu Ser Ser Leu Leu Glu Arg
                515                 520                 525

Gln Asp His Asn Gly Tyr Ser His Gln Asn Pro Ser Phe Leu Gly Ala
            530                 535                 540

Met Leu Glu Lys His Pro Lys Ile Ile Ser Ala Tyr Leu Pro Ala Asp
545                 550                 555                 560

Ala Asn Ser Thr Leu Val Tyr Thr Glu Arg Ala Tyr Ala Asp Arg Asp
                565                 570                 575

Lys Leu Asn Ile Leu Val Ala Gly Lys Lys Glu Leu Pro Gln Trp Leu
                580                 585                 590

Ser Leu Glu Glu Ala Arg Lys Gln Ala Lys Asp Gly Val Met Val Trp
                595                 600                 605

Asp Phe Ala Ser Asp Glu Asn Pro Asp Ile Val Leu Ala Gly Cys Gly
            610                 615                 620

Asp Tyr Val Thr Gln Glu Cys Met Ala Ser Leu Val Leu Ile Arg Glu
625                 630                 635                 640

Leu Leu Pro Arg Val Lys Ile Arg Phe Val Ser Val Thr Glu Leu Ser
                645                 650                 655

Ser Asp Gly Leu Gly Ser Arg Lys Phe Lys Glu Lys Pro Trp Leu Met
                660                 665                 670

Asp Glu Ile Phe Thr Gln Asp Lys Gly Val Val Phe Asn Tyr His Gly
            675                 680                 685

Tyr Pro Asn Thr Ile Lys Lys Leu Ile Phe Asp Tyr Lys Gly Ser Arg
690                 695                 700

Arg Phe Arg Ile Lys Gly Tyr Glu Glu Gly Ser Thr Thr Thr Pro
                705             710                 715                 720

Phe Asp Met Gly Val Arg Asn Gly Thr Ser Arg Tyr His Leu Val Ile
                725                 730                 735

Asp Met Ala Tyr Lys Leu Phe Gln Gln Gly Val Ile Asp Glu Thr Met
            740                 745                 750

His Val Ser Ile Thr Thr Asp Met Leu Gln Arg Leu Val Asp His Arg

```
                755                 760                 765
Asn Tyr Ile Lys Ala Asn Gly Val Asp Pro Ile Glu Ile Glu Asn Trp
    770                 775                 780

Ile Trp Thr Arg
785

<210> SEQ ID NO 3
<211> LENGTH: 795
<212> TYPE: PRT
<213> ORGANISM: Lactobacillus rhamnosus LMS2-1

<400> SEQUENCE: 3

Met Ser Met Asp Thr Lys Val Lys Thr Val Asp Tyr Ser Ser Lys Glu
1               5                   10                  15

Tyr Phe Asp Lys Met Thr Ala Tyr Trp Arg Ala Ala Asn Tyr Val Ser
            20                  25                  30

Val Gly Gln Leu Tyr Leu Lys Asp Asn Pro Leu Leu Glu Arg Pro Leu
        35                  40                  45

Lys Ser Glu Asp Val Lys Pro His Pro Ile Gly His Trp Gly Thr Ile
    50                  55                  60

Ala Gly Gln Asn Phe Ile Tyr Thr His Leu Asn Arg Val Ile Asn Lys
65                  70                  75                  80

Tyr Asp Leu Asn Met Phe Tyr Ile Glu Gly Pro Gly His Gly Gly Gln
                85                  90                  95

Val Met Val Ser Asn Ser Tyr Leu Asp Gly Ser Tyr Ser Glu Ile Tyr
            100                 105                 110

Pro Arg Val Ser Gln Asp Lys Glu Gly Met Lys Asn Leu Phe Thr Gln
        115                 120                 125

Phe Ser Trp Pro Gly Gly Val Ala Ser His Ala Ser Ala Gln Thr Pro
    130                 135                 140

Gly Ser Ile His Glu Gly Gly Glu Leu Gly Tyr Ala Leu Ser His Ala
145                 150                 155                 160

Thr Gly Ala Ile Leu Asp Asn Pro Asp Val Ile Ala Ala Val Val Thr
                165                 170                 175

Gly Asp Gly Glu Thr Glu Thr Gly Pro Leu Ala Ala Ser Trp Phe Ser
            180                 185                 190

Asn Thr Phe Ile Asn Pro Ile Ser Asp Gly Ala Ile Leu Pro Ile Val
        195                 200                 205

His Met Asn Gly Phe Lys Ile Ser Asn Pro Thr Ile Leu Ser Arg Lys
    210                 215                 220

Ser Asp Glu Asp Leu Thr Lys Tyr Phe Glu Gly Met Gly Trp Lys Pro
225                 230                 235                 240

Tyr Phe Val Glu Gly Asp Asp Pro Thr Lys Leu Asn Pro Glu Met Ala
                245                 250                 255

Lys Val Met Asp Ala Ala Ile Glu Glu Ile Lys Ala Ile Gln Lys His
            260                 265                 270

Ala Arg Glu Thr Gly Asp Thr Thr Met Pro His Trp Pro Val Ile Ile
        275                 280                 285

Phe Arg Ser Pro Lys Gly Trp Thr Gly Pro Lys Ser Trp Asn Gly Glu
    290                 295                 300

Pro Ile Glu Gly Ser Phe Arg Ala His Gln Ile Pro Ile Pro Val Asp
305                 310                 315                 320

Ala Glu Asp Met Glu His Ala Asp Ser Leu Ala Gly Trp Leu Lys Ser
                325                 330                 335
```

```
Tyr His Pro Glu Glu Leu Phe Asp Glu Asn Gly Lys Leu Ile Pro Glu
            340                 345                 350

Leu Ala Ala Leu Pro Pro Lys Gly Asp Lys Arg Met Ala Ala Asn Pro
            355                 360                 365

Ile Thr Asn Gly Gly Leu Asp Pro Lys Pro Leu Val Leu Pro Asp Tyr
            370                 375                 380

Arg Lys Tyr Ala Leu Asp Asn Lys Glu His Gly Lys Gln Ile Lys Gln
385                 390                 395                 400

Asp Met Ile Val Trp Ser Asp Tyr Leu Arg Asp Leu Ile Lys Leu Asn
                405                 410                 415

Pro His Asn Phe Arg Ile Phe Gly Pro Asp Glu Thr Met Ser Asn Arg
            420                 425                 430

Leu Tyr Ser Leu Phe Glu Val Thr Asn Arg Gln Trp Leu Glu Pro Ile
            435                 440                 445

Lys Glu Pro Ala Asp Gln Tyr Leu Ala Pro Ala Gly Arg Ile Ile Asp
            450                 455                 460

Ser Gln Leu Ser Glu His Gln Ser Glu Gly Phe Asn Glu Gly Tyr Thr
465                 470                 475                 480

Leu Thr Gly Arg His Gly Leu Phe Thr Ser Tyr Glu Ala Phe Leu Arg
                485                 490                 495

Val Val Asp Ser Met Leu Thr Gln His Phe Lys Trp Ile Arg Lys Ala
            500                 505                 510

His Glu Glu Pro Trp His Lys Ala Tyr Pro Ser Leu Asn Val Val Ser
            515                 520                 525

Thr Ser Thr Ser Phe Gln Gln Asp His Asn Gly Tyr Thr His Gln Asp
530                 535                 540

Pro Gly Ile Leu Thr His Met Ala Glu Lys Lys Ala Glu Tyr Ile Arg
545                 550                 555                 560

Glu Tyr Leu Pro Ala Asp Ala Asn Ser Leu Leu Ala Ile Ser Pro Lys
                565                 570                 575

Leu Phe Ser Ser Gln Asn Thr Val Asn Val Leu Ile Thr Ser Lys Gln
            580                 585                 590

Pro Arg Pro Gln Phe Tyr Ser Ile Asp Glu Ala Thr Val Leu Ala Asn
            595                 600                 605

Ala Gly Leu Lys Arg Ile Asp Trp Ala Ser Asn Asp Asp Gly Val Glu
            610                 615                 620

Pro Asp Val Val Ile Ala Ala Gly Thr Glu Pro Asn Met Glu Ser
625                 630                 635                 640

Leu Ala Ala Ile Asn Leu Leu His Asp Ala Phe Pro Asp Leu Lys Ile
                645                 650                 655

Arg Phe Ile Asn Val Leu Asp Leu Leu Lys Leu Arg Ser Pro Glu Ile
            660                 665                 670

Asp Pro Arg Gly Leu Ser Asp Ala Glu Phe Asn Ser Tyr Phe Thr Thr
            675                 680                 685

Asp Lys Pro Ile Leu Phe Ala Tyr His Gly Phe Glu Gly Leu Ile Arg
            690                 695                 700

Asp Ile Phe Phe Thr Arg Gln Asn Arg Asn Val Leu Ile His Gly Tyr
705                 710                 715                 720

Arg Glu Glu Gly Asp Ile Thr Thr Pro Phe Asp Met Arg Val Leu Asn
                725                 730                 735

Glu Leu Asp Arg Phe His Leu Ala Lys Asp Val Ile Gln His Val Pro
            740                 745                 750

Ala Tyr Ala Glu Lys Ala Ala Ala Phe Val Gln Lys Met Asp Asp Thr
```

```
              755                 760                 765
Leu Gln Tyr His His Asp Phe Ile Arg Ala Asn Gly Glu Asp Ile Pro
    770                 775                 780

Glu Val Gln Glu Trp Thr Trp Lys Ser Ile Lys
785                 790                 795

<210> SEQ ID NO 4
<211> LENGTH: 799
<212> TYPE: PRT
<213> ORGANISM: Lactobacillus crispatus ST1

<400> SEQUENCE: 4

Met Ala Val Asp Tyr Asp Ser Lys Asp Tyr Leu Lys Ser Val Asp Ala
1               5                   10                  15

Tyr Trp Arg Ala Ala Asn Tyr Leu Ser Val Gly Gln Leu Phe Leu Met
                20                  25                  30

Lys Asn Pro Leu Leu Lys Thr Pro Leu Val Ala Glu Asp Val Lys Pro
            35                  40                  45

Lys Pro Ile Gly His Trp Gly Thr Ile Ala Pro Gln Asn Phe Ile Tyr
        50                  55                  60

Ala His Leu Asn Arg Val Leu Lys Lys Tyr Asp Leu Asn Met Phe Tyr
65                  70                  75                  80

Ile Glu Gly Ser Gly His Gly Gly Gln Val Met Val Ser Asn Ser Tyr
                85                  90                  95

Leu Asp Gly Ser Tyr Thr Glu Arg Tyr Pro Glu Ile Thr Gln Asp Glu
                100                 105                 110

Lys Gly Met Ala Lys Leu Phe Lys Arg Phe Ser Phe Pro Gly Gly Val
            115                 120                 125

Ala Ser His Ala Ala Pro Glu Thr Pro Gly Ser Ile His Glu Gly Gly
        130                 135                 140

Glu Leu Gly Tyr Ser Leu Ser His Gly Thr Gly Ala Val Leu Asp Asn
145                 150                 155                 160

Pro Asp Val Ile Ala Ala Val Glu Ile Gly Asp Gly Glu Ala Glu Thr
                165                 170                 175

Gly Pro Leu Ala Ala Ser Trp Phe Ser Asp Lys Phe Ile Asn Pro Ile
                180                 185                 190

Lys Asp Gly Ala Val Leu Pro Ile Leu Gln Ile Asn Gly Phe Lys Ile
            195                 200                 205

Ser Asn Pro Thr Ile Val Ser Arg Met Ser Asp Gln Glu Leu Thr Glu
        210                 215                 220

Tyr Phe Arg Gly Met Gly Trp Asp Pro His Phe Val Ser Val Phe Lys
225                 230                 235                 240

Gly Gly Arg Phe Asp Gly Glu Lys Asp Pro Met Gln Val His Glu Glu
                245                 250                 255

Met Ala Lys Thr Met Asp Glu Val Ile Glu Glu Ile Lys Ala Ile Gln
                260                 265                 270

Lys His Ala Arg Glu Asn Asn Asp Ala Thr Leu Pro His Trp Pro Met
            275                 280                 285

Ile Ile Phe Gln Cys Pro Lys Gly Trp Thr Gly Pro Lys Lys Asp Leu
        290                 295                 300

Asp Gly Asn Pro Ile Glu Asn Ser Phe Arg Ala His Gln Ile Pro Ile
305                 310                 315                 320

Pro Val Ala Gln Gly Asp Met Glu His Ala Asp Met Leu Thr Asp Trp
                325                 330                 335
```

```
Leu Glu Ser Tyr Lys Pro Glu Glu Leu Phe Asn Glu Asp Gly Ser Pro
            340                 345                 350

Lys Glu Ile Val Thr Glu Asn Thr Ala Lys Gly Asp His Arg Met Ala
            355                 360                 365

Met Asn Pro Ile Thr Asn Gly Gly Ile Asp Pro Lys Arg Leu Asn Leu
            370                 375                 380

Pro Asp Tyr Arg Lys Phe Ala Leu Lys Phe Asp Lys Pro Gly Ser Val
385                 390                 395                 400

Glu Ala Gln Asp Met Val Glu Trp Ala Lys Tyr Leu Asp Glu Val Ala
                405                 410                 415

Lys Leu Asn Pro Thr Thr Phe Arg Gly Phe Gly Pro Asp Glu Ser Lys
            420                 425                 430

Ser Asn Arg Leu Phe Gln Leu Leu Asp Asp Gln Lys Arg Gln Trp Glu
            435                 440                 445

Pro Glu Val His Glu Pro Asn Asp Glu Asn Leu Ala Pro Ser Gly Arg
            450                 455                 460

Val Ile Asp Ser Gln Leu Ser Glu His Gln Asp Glu Gly Phe Leu Glu
465                 470                 475                 480

Gly Tyr Val Leu Thr Gly Arg His Gly Phe Phe Ala Thr Tyr Glu Ala
                485                 490                 495

Phe Gly Arg Val Val Asp Ser Met Leu Thr Gln His Met Lys Trp Leu
                500                 505                 510

Arg Lys Ala Lys Glu Gln Tyr Trp Arg His Asp Tyr Pro Ser Leu Asn
            515                 520                 525

Phe Val Ala Thr Ser Thr Val Phe Gln Gln Asp His Asn Gly Tyr Thr
            530                 535                 540

His Gln Asp Pro Gly Ile Leu Thr His Leu Tyr Glu Lys Asn Arg Pro
545                 550                 555                 560

Asp Leu Val His Glu Tyr Leu Pro Ser Asp Thr Asn Thr Leu Leu Ala
                565                 570                 575

Val Gly Asp Lys Ala Leu Gln Asp Arg Glu Cys Ile Asn Val Leu Val
            580                 585                 590

Thr Ser Lys Gln Pro Arg Pro Gln Trp Phe Ser Ile Glu Glu Ala Lys
            595                 600                 605

Lys Leu Val Asp Lys Gly Leu Gly Tyr Ile Asp Trp Ala Ser Thr Asp
            610                 615                 620

Lys Gly Ala Lys Pro Asp Val Val Phe Ala Ser Thr Glu Thr Glu Pro
625                 630                 635                 640

Thr Ile Glu Thr Leu Ala Ala Ile Asp Ile Leu His Lys Lys Phe Pro
                645                 650                 655

Asp Leu Lys Ile Arg Tyr Ile Asn Val Val Asp Val Met Lys Leu Met
                660                 665                 670

Asp Pro Lys Asp Asn Lys Asn Gly Leu Ser Thr Glu Glu Phe Asp Arg
            675                 680                 685

Leu Phe Pro Lys Asp Val Pro Val Ile Phe Ala Trp His Gly Tyr Lys
            690                 695                 700

Ser Met Met Glu Ser Ile Trp Phe Ala Arg Lys Arg Tyr Asn Val His
705                 710                 715                 720

Ile His Cys Tyr Glu Glu Asn Gly Asp Ile Thr Thr Pro Phe Asp Met
                725                 730                 735

Arg Val Leu Asn His Leu Asp Arg Phe Asp Leu Ala Lys Asp Ala Val
            740                 745                 750

Glu Ser Ile Asp Lys Leu Lys Gly Lys Asn Ala Asp Phe Ile Ser His
```

```
                755                 760                 765
Met Asp Asp Leu Leu Glu Lys His His Gln Tyr Ile Arg Asp Asn Gly
                770                 775                 780
Lys Asp Met Pro Glu Val Thr Glu Trp Gln Trp Ser Gly Leu Lys
785                 790                 795

<210> SEQ ID NO 5
<211> LENGTH: 825
<212> TYPE: PRT
<213> ORGANISM: Bifidobacterium longum subsp. longum JDM301

<400> SEQUENCE: 5

Met Thr Ser Pro Val Ile Gly Thr Pro Trp Lys Lys Leu Asn Ala Pro
1               5                   10                  15

Val Ser Glu Glu Ala Leu Glu Gly Val Asp Lys Tyr Trp Arg Val Ala
                20                  25                  30

Asn Tyr Leu Ser Ile Gly Gln Ile Tyr Leu Arg Ser Asn Pro Leu Met
                35                  40                  45

Lys Glu Pro Phe Thr Arg Glu Asp Val Lys His Arg Leu Val Gly His
            50                  55                  60

Trp Gly Thr Thr Pro Gly Leu Asn Phe Leu Ile Gly His Ile Asn Arg
65                  70                  75                  80

Phe Ile Ala Asp His Gly Gln Asn Thr Val Ile Ile Met Gly Pro Gly
                85                  90                  95

His Gly Gly Pro Ala Gly Thr Ser Gln Ser Tyr Leu Asp Gly Thr Tyr
                100                 105                 110

Thr Glu Thr Phe Pro Lys Ile Thr Lys Asp Glu Ala Gly Leu Gln Lys
            115                 120                 125

Phe Phe Arg Gln Phe Ser Tyr Pro Gly Gly Ile Pro Ser His Phe Ala
130                 135                 140

Pro Glu Thr Pro Gly Ser Ile His Glu Gly Gly Glu Leu Gly Tyr Ala
145                 150                 155                 160

Leu Ser His Ala Tyr Gly Ala Ile Met Asp Asn Pro Ser Leu Phe Val
                165                 170                 175

Pro Ala Ile Val Gly Asp Gly Glu Ala Glu Thr Gly Pro Leu Ala Thr
                180                 185                 190

Gly Trp Gln Ser Asn Lys Leu Val Asn Pro Arg Thr Asp Gly Ile Val
            195                 200                 205

Leu Pro Ile Leu His Leu Asn Gly Tyr Lys Ile Ala Asn Pro Thr Ile
            210                 215                 220

Leu Ser Arg Ile Ser Asp Glu Glu Leu His Glu Phe Phe His Gly Met
225                 230                 235                 240

Gly Tyr Glu Pro Tyr Glu Phe Val Ala Gly Phe Asp Asp Glu Asp His
                245                 250                 255

Met Ser Ile His Arg Arg Phe Ala Glu Leu Trp Glu Thr Ile Trp Asp
                260                 265                 270

Glu Ile Cys Asp Ile Lys Ala Ala Ala Gln Thr Asp Asn Val His Arg
            275                 280                 285

Pro Phe Tyr Pro Met Leu Ile Phe Arg Thr Pro Lys Gly Trp Thr Cys
290                 295                 300

Pro Lys Tyr Ile Asp Gly Lys Lys Thr Glu Gly Ser Trp Arg Ala His
305                 310                 315                 320

Gln Val Pro Leu Ala Ser Ala Arg Asp Thr Glu Ala His Phe Glu Val
                325                 330                 335
```

Leu Lys Asn Trp Leu Glu Ser Tyr Lys Pro Glu Glu Leu Phe Asp Ala
                340                 345                 350

Asn Gly Ala Val Lys Asp Val Leu Ala Phe Met Pro Lys Gly Glu
            355                 360                 365

Leu Arg Ile Gly Ala Asn Pro Asn Ala Asn Gly Gly Val Ile Arg Asp
        370                 375                 380

Asp Leu Lys Leu Pro Asn Leu Glu Asp Tyr Glu Val Lys Glu Val Ala
385                 390                 395                 400

Glu Tyr Gly His Gly Trp Gly Gln Leu Glu Ala Thr Arg Arg Leu Gly
                405                 410                 415

Val Tyr Thr Arg Asp Ile Ile Lys Asn Asn Pro Arg Asp Phe Arg Ile
            420                 425                 430

Phe Gly Pro Asp Glu Thr Ala Ser Asn Arg Leu Gln Ala Ser Tyr Glu
        435                 440                 445

Val Thr Asn Lys Gln Trp Asp Ala Gly Tyr Ile Ser Asp Glu Val Asp
    450                 455                 460

Glu His Met His Val Ser Gly Gln Val Val Glu Gln Leu Ser Glu His
465                 470                 475                 480

Gln Met Glu Gly Phe Leu Glu Ala Tyr Leu Leu Thr Gly Arg His Gly
                485                 490                 495

Ile Trp Ser Ser Tyr Glu Ser Phe Val His Val Ile Asp Ser Met Leu
            500                 505                 510

Asn Gln His Ala Lys Trp Leu Glu Ala Thr Val Arg Glu Ile Pro Trp
        515                 520                 525

Arg Lys Pro Ile Ala Ser Met Asn Leu Leu Val Ser Ser His Val Trp
530                 535                 540

Arg Gln Asp His Asn Gly Phe Ser His Gln Asp Pro Gly Val Thr Ser
545                 550                 555                 560

Val Leu Leu Asn Lys Cys Phe His Asn Asp His Val Ile Gly Ile Tyr
                565                 570                 575

Phe Ala Thr Asp Ala Asn Met Leu Leu Ala Ile Ala Glu Lys Cys Tyr
            580                 585                 590

Lys Ser Thr Asn Lys Ile Asn Ala Ile Ile Ala Gly Lys Gln Pro Ala
        595                 600                 605

Ala Thr Trp Leu Thr Leu Asp Glu Ala Arg Ala Glu Leu Glu Lys Gly
    610                 615                 620

Ala Ala Ala Trp Asp Trp Ala Ser Thr Ala Lys Asn Asn Asp Glu Ala
625                 630                 635                 640

Glu Val Val Leu Ala Ala Gly Asp Val Pro Thr Gln Glu Ile Met
                645                 650                 655

Ala Ala Ser Asp Lys Leu Lys Glu Leu Gly Val Lys Phe Lys Val Val
            660                 665                 670

Asn Val Ala Asp Leu Leu Ser Leu Gln Ser Ala Lys Glu Asn Asp Glu
        675                 680                 685

Ala Leu Thr Asp Glu Glu Phe Ala Asp Ile Phe Thr Ala Asp Lys Pro
    690                 695                 700

Val Leu Phe Ala Tyr His Ser Tyr Ala His Asp Val Arg Gly Leu Ile
705                 710                 715                 720

Tyr Asp Arg Pro Asn His Asp Asn Phe Asn Val His Gly Tyr Glu Glu
                725                 730                 735

Glu Gly Ser Thr Thr Thr Pro Tyr Asp Met Val Arg Val Asn Arg Ile
            740                 745                 750

Asp Arg Tyr Glu Leu Thr Ala Glu Ala Leu Arg Met Ile Asp Ala Asp

```
            755                 760                 765
Lys Tyr Ala Asp Lys Ile Asp Glu Leu Glu Lys Phe Arg Asp Glu Ala
770                 775                 780

Phe Gln Phe Ala Val Asp Lys Gly Tyr Asp His Pro Asp Tyr Thr Asp
785                 790                 795                 800

Trp Val Tyr Ser Gly Val Asn Thr Asp Lys Lys Gly Ala Val Thr Ala
                805                 810                 815

Thr Ala Ala Thr Ala Gly Asp Asn Glu
                820                 825

<210> SEQ ID NO 6
<211> LENGTH: 817
<212> TYPE: PRT
<213> ORGANISM: Leuconostoc citreum KM20

<400> SEQUENCE: 6

Met Ala Asp Phe Asp Ser Lys Glu Tyr Leu Glu Leu Val Asp Lys Trp
1               5                   10                  15

Trp Arg Ala Thr Asn Tyr Leu Ser Ala Gly Met Ile Phe Leu Lys Ser
                20                  25                  30

Asn Pro Leu Phe Ser Val Thr Asn Thr Pro Ile Gln Ala Glu Asp Val
                35                  40                  45

Lys Val Lys Pro Ile Gly His Trp Gly Thr Ile Ser Gly Gln Thr Phe
50                  55                  60

Leu Tyr Ala His Ala Asn Arg Leu Ile Asn Lys Tyr Asp Leu Asn Met
65                  70                  75                  80

Phe Tyr Ile Gly Gly Pro Gly His Gly Gly Gln Val Met Val Thr Asn
                85                  90                  95

Ala Tyr Leu Asp Gly Glu Tyr Thr Glu Asp Tyr Pro Glu Ile Thr Gln
                100                 105                 110

Asp Leu Glu Gly Met Ser Arg Leu Phe Lys Arg Phe Ser Phe Pro Gly
                115                 120                 125

Gly Ile Gly Ser His Met Thr Ala Gln Thr Pro Gly Ser Leu His Glu
130                 135                 140

Gly Gly Glu Leu Gly Tyr Ser Leu Ser His Ala Phe Gly Ala Val Leu
145                 150                 155                 160

Asp Asn Pro Asp Gln Ile Ala Phe Ala Val Val Gly Asp Gly Glu Ala
                165                 170                 175

Glu Thr Gly Pro Ser Met Thr Ser Trp His Ser Thr Lys Phe Leu Asn
                180                 185                 190

Ala Lys Asn Asp Gly Ala Val Leu Pro Ile Leu Asp Leu Asn Gly Phe
                195                 200                 205

Lys Ile Ser Asn Pro Thr Ile Phe Ser Arg Met Ser Asp Glu Glu Ile
210                 215                 220

Thr Lys Phe Phe Glu Gly Leu Gly Tyr Ser Pro Arg Phe Ile Glu Asn
225                 230                 235                 240

Asp Asp Ile His Asp Tyr Ala Ala Tyr His Glu Leu Ala Ala Lys Val
                245                 250                 255

Leu Asp Gln Ala Ile Glu Asp Ile Gln Ala Ile Gln Lys Asp Ala Arg
                260                 265                 270

Glu Asn Gly Lys Tyr Glu Asp Gly Thr Ile Pro Ala Trp Pro Val Ile
                275                 280                 285

Ile Ala Arg Leu Pro Lys Gly Trp Gly Gly Pro Thr His Asp Glu Asp
290                 295                 300
```

```
Gly Asn Pro Ile Glu Asn Ser Phe Arg Ala His Gln Val Pro Leu Pro
305                 310                 315                 320

Leu Ala Gln Asn Lys Leu Glu Thr Leu Ser Gln Phe Glu Asp Trp Met
            325                 330                 335

Asn Ser Tyr Lys Pro Glu Glu Leu Phe Asn Ala Asp Gly Ser Leu Lys
        340                 345                 350

Asp Glu Leu Lys Ala Ile Ala Pro Lys Gly Asp Lys Arg Met Ser Ala
    355                 360                 365

Asn Pro Ile Ala Asn Gly Gly Arg Arg Gly Glu Glu Ala Thr Asp
370                 375                 380

Leu Thr Leu Pro Asp Trp Arg Gln Phe Thr Asn Asp Ile Thr Asn Glu
385                 390                 395                 400

Asn Arg Gly His Glu Leu Pro Lys Val Thr Gln Asn Met Asp Met Thr
                405                 410                 415

Thr Leu Ser Asn Tyr Leu Glu Glu Val Ala Lys Leu Asn Pro Thr Ser
            420                 425                 430

Phe Arg Val Phe Gly Pro Asp Glu Thr Met Ser Asn Arg Leu Trp Ser
        435                 440                 445

Leu Phe Asn Thr Thr Asn Arg Gln Trp Met Glu Glu Val Lys Glu Pro
450                 455                 460

Asn Asp Gln Tyr Val Gly Pro Glu Gly Arg Ile Ile Asp Ser Gln Leu
465                 470                 475                 480

Ser Glu His Gln Ala Glu Gly Trp Leu Glu Gly Tyr Thr Leu Thr Gly
                485                 490                 495

Arg Val Gly Ile Phe Ala Ser Tyr Glu Ser Phe Leu Arg Val Val Asp
        500                 505                 510

Thr Met Val Thr Gln His Phe Lys Trp Leu Arg His Ala Ser Glu Gln
    515                 520                 525

Ala Trp Arg Asn Asp Tyr Pro Ser Leu Asn Leu Ile Ala Thr Ser Thr
530                 535                 540

Ala Phe Gln Gln Asp His Asn Gly Tyr Thr His Gln Asp Pro Gly Met
545                 550                 555                 560

Leu Thr His Leu Ala Glu Lys Lys Ser Asn Phe Ile Arg Glu Tyr Leu
                565                 570                 575

Pro Ala Asp Gly Asn Ser Leu Leu Ala Val Gln Asp Arg Ala Phe Ser
            580                 585                 590

Glu Arg His Lys Val Asn Leu Ile Ile Ala Ser Lys Gln Pro Arg Gln
        595                 600                 605

Gln Trp Phe Thr Ala Asp Glu Ala Asp Glu Leu Ala Asn Glu Gly Leu
    610                 615                 620

Lys Ile Ile Asp Trp Ala Ser Thr Ala Pro Ser Gly Asp Val Asp Ile
625                 630                 635                 640

Thr Phe Ala Ser Ser Gly Thr Glu Pro Thr Ile Glu Thr Leu Ala Ala
                645                 650                 655

Leu Trp Leu Ile Asn Gln Ala Phe Pro Glu Val Lys Phe Arg Tyr Val
            660                 665                 670

Asn Val Val Glu Leu Leu Arg Leu Gln Lys Lys Ser Glu Ser His Met
        675                 680                 685

Asn Asp Glu Arg Glu Leu Ser Asp Ala Glu Phe Asn Lys Phe Gln
    690                 695                 700

Ala Asp Lys Pro Val Ile Phe Gly Phe His Ala Tyr Glu Asp Leu Ile
705                 710                 715                 720

Glu Ser Phe Phe Phe Glu Arg Lys Phe Lys Gly Asp Val Tyr Val His
```

```
                    725                 730                 735
Gly Tyr Arg Glu Asp Gly Asp Ile Thr Thr Thr Tyr Asp Met Arg Val
                740                 745                 750

Tyr Ser Lys Leu Asp Arg Phe His Gln Ala Lys Glu Ala Ala Glu Ile
            755                 760                 765

Leu Ser Ala Asn Ser Thr Ile Asp Gln Ala Ala Asp Thr Phe Ile
        770                 775                 780

Glu Lys Met Asp Ala Thr Leu Ala Lys His Phe Glu Val Thr Arg Asn
785                 790                 795                 800

Glu Gly Arg Asp Ile Glu Glu Phe Thr Asp Trp Asn Trp Ser Ala Leu
                805                 810                 815

Lys

<210> SEQ ID NO 7
<211> LENGTH: 795
<212> TYPE: PRT
<213> ORGANISM: Bradyrhizobium sp. S23321

<400> SEQUENCE: 7

Met Asn Gln Gln Gln Ser Ala Leu Ser Arg Ser Asp Leu Asp Leu
1               5                   10                  15

Leu Asp Arg Tyr Trp Arg Ala Ala Asn Tyr Leu Ser Val Gly Gln Ile
                20                  25                  30

Tyr Leu Leu Asp Asn Pro Leu Leu Arg Glu Pro Leu Arg Pro Glu His
            35                  40                  45

Ile Lys Pro Arg Leu Leu Gly His Trp Gly Thr Thr Pro Gly Leu Asn
        50                  55                  60

Phe Ile Tyr Ala His Leu Asn Arg Val Ile Arg Ala Leu Asp Leu Ser
65                  70                  75                  80

Val Leu Tyr Val Cys Gly Pro Gly Asn Gly Gly Pro Gly Met Val Ala
                85                  90                  95

Asn Thr Tyr Leu Glu Gly Ser Tyr Ser Glu Ile Tyr Pro Asn Ile Ala
            100                 105                 110

Arg Asp Thr Asp Gly Leu Arg Lys Leu Phe Arg Gln Phe Ser Phe Pro
        115                 120                 125

Gly Gly Ile Pro Ser His Ala Ala Pro Glu Thr Pro Gly Ser Ile His
130                 135                 140

Glu Gly Gly Glu Leu Gly Tyr Ala Leu Val His Ala Tyr Gly Ala Ala
145                 150                 155                 160

Phe Asp Asn Pro Asp Leu Ile Val Ala Cys Val Val Gly Asp Gly Glu
                165                 170                 175

Ala Glu Thr Gly Pro Leu Ala Ala Ser Trp His Ser Asn Lys Phe Leu
            180                 185                 190

Asn Pro Val His Asp Gly Ala Val Leu Pro Ile Leu His Leu Asn Gly
        195                 200                 205

Tyr Lys Ile Ala Asn Pro Thr Val Leu Gly Arg Met Arg Asp Glu Glu
210                 215                 220

Ile Arg Asp Leu Phe Arg Gly Phe Gly His Glu Pro Leu Phe Val Glu
225                 230                 235                 240

Gly Asp Asp Pro Thr Leu Met His Gln Ala Met Ala Asp Ala Phe Asp
                245                 250                 255

Val Ala Phe Ala Arg Ile Arg Ser Ile Gln Gln His Ala Arg Asp Gly
            260                 265                 270

Arg Lys Glu Ile Glu Arg Pro Arg Trp Pro Met Ile Val Leu Arg Ser
```

-continued

```
                275                 280                 285
Pro Lys Gly Trp Thr Gly Pro Lys Glu Val Asp Gly Leu Lys Val Glu
290                 295                 300
Gly Phe Trp Arg Ala His Gln Val Pro Val Ala Gly Cys Arg Glu Asn
305                 310                 315                 320
Pro Ala His Leu Lys Ile Leu Glu Asp Trp Met Arg Ser Tyr Glu Pro
                325                 330                 335
Glu Lys Leu Phe Asp Ala Ser Gly Ala Leu Ile Pro Glu Leu Gln Ala
                340                 345                 350
Leu Ala Pro Glu Gly Asn Arg Arg Met Gly Ala Asn Pro His Ala Asn
                355                 360                 365
Gly Gly Leu Leu Lys Lys Glu Leu Lys Leu Pro Asp Phe Arg Ser Phe
370                 375                 380
Ala Leu Glu Val Pro Gln Pro Gly Gly Val Thr Gly Glu Ala Thr Arg
385                 390                 395                 400
Glu Leu Gly Lys Phe Leu Arg Asp Val Ile Arg Leu Asn Ala Ala Glu
                405                 410                 415
Arg Asn Phe Arg Ile Met Gly Pro Asp Glu Thr Ala Ser Asn Arg Leu
                420                 425                 430
Asp Ala Val Phe Glu Glu Thr Glu Arg Val Trp Met Glu Pro Ile Glu
                435                 440                 445
Pro Tyr Asp Val His Leu Ala Gln Asp Gly Arg Val Met Glu Val Leu
450                 455                 460
Ser Glu His Leu Cys Gln Gly Trp Leu Glu Gly Tyr Leu Leu Thr Gly
465                 470                 475                 480
Arg His Gly Phe Phe Ser Cys Tyr Glu Ala Phe Ile His Ile Val Asp
                485                 490                 495
Ser Met Phe Asn Gln His Ala Lys Trp Leu Lys Val Thr Arg His Leu
                500                 505                 510
Pro Trp Arg Arg Pro Ile Ala Ser Leu Asn Tyr Leu Leu Thr Ser His
                515                 520                 525
Val Trp Arg Gln Asp His Asn Gly Phe Ser His Gln Asp Pro Gly Phe
530                 535                 540
Val Asp Leu Val Ala Asn Lys Lys Ala Asp Ile Val Arg Ile Tyr Phe
545                 550                 555                 560
Pro Pro Asp Ala Asn Thr Leu Leu Trp Ile Ala Asp His Cys Leu Arg
                565                 570                 575
Thr Tyr Asn Arg Ile Asn Val Ile Val Ala Gly Lys Gln Pro Ala Pro
                580                 585                 590
Gln Trp Leu Ser Met Gln Asp Ala Ala Thr His Cys Asp Ala Gly Ile
                595                 600                 605
Gly Ile Trp Ser Trp Ala Gly Asn Glu Asp Ala Thr Gly Glu Pro His
                610                 615                 620
Val Val Met Ala Cys Ala Gly Asp Val Pro Thr Leu Glu Thr Leu Ala
625                 630                 635                 640
Ala Val Asp Leu Leu Arg Lys Ala Leu Pro Asp Leu Lys Ile Arg Val
                645                 650                 655
Val Asn Val Val Asp Leu Met Thr Leu Gln Pro Lys Glu Gln His Pro
                660                 665                 670
His Gly Leu Ser Asp Arg Asp Phe Asp Ser Leu Phe Thr Ser Asp Lys
                675                 680                 685
Pro Val Ile Phe Ala Tyr His Gly Tyr Pro His Leu Ile His Arg Leu
                690                 695                 700
```

```
Thr Tyr Asn Arg Thr Asn His Ala Gly Leu His Val Arg Gly Phe Ile
705                 710                 715                 720

Glu Glu Gly Thr Thr Thr Pro Phe Asp Met Val Val Leu Asn Glu
            725                 730                 735

Leu Asp Arg Tyr His Leu Ala Ile Glu Ala Ile Glu Arg Val Pro Gly
            740                 745                 750

Leu Ala Ala Arg Ala Ala Ala Val Lys Gln Gln Phe Arg Asp Ala Leu
                755                 760                 765

Ile Glu His Ser His Tyr Ile Arg Glu His Gly Glu Asp Met Pro Glu
            770                 775                 780

Ile Arg Asp Trp Val Trp Pro Gly Lys Thr Gly
785                 790                 795

<210> SEQ ID NO 8
<211> LENGTH: 781
<212> TYPE: PRT
<213> ORGANISM: Enterococcus faecium E1039

<400> SEQUENCE: 8

Met Asp Tyr Ser Ser Lys Glu Tyr Phe Asp Lys Met Thr Ala Trp Trp
1               5                   10                  15

Arg Ala Ala Asn Tyr Leu Ser Val Gly Gln Leu Tyr Leu Lys Asp Asn
                20                  25                  30

Pro Leu Leu Arg Arg Thr Leu Lys Pro Glu Asp Val Lys Lys His Pro
            35                  40                  45

Ile Gly His Trp Gly Thr Ile Pro Gly Gln Asn Phe Ile Tyr Val His
    50                  55                  60

Leu Asn Arg Val Ile Asn Lys Tyr Asp Leu Asn Met Phe Tyr Ile Glu
65                  70                  75                  80

Gly Pro Gly His Gly Gly Gln Val Met Val Ser Asn Ala Tyr Leu Asp
                85                  90                  95

Gly Ser Tyr Thr Glu Ile Tyr Pro Glu Val Thr Glu Asp Glu Thr Gly
            100                 105                 110

Met Gln Lys Leu Phe Lys Arg Phe Ser Phe Pro Gly Gly Ile Ala Ser
        115                 120                 125

His Ala Ala Pro Glu Thr Pro Gly Ser Ile His Glu Gly Gly Glu Leu
    130                 135                 140

Gly Tyr Ser Leu Ser His Ala Val Gly Ala Val Leu Asp Asn Pro Glu
145                 150                 155                 160

Val Ile Ser Ala Val Ile Gly Asp Gly Glu Ala Glu Thr Gly Pro
                165                 170                 175

Leu Ala Gly Ser Trp Phe Ser Asn Val Phe Ile Asn Pro Val Ile Asp
            180                 185                 190

Gly Ala Val Leu Pro Ile Leu His Leu Asn Gly Ala Lys Ile Ala Asn
        195                 200                 205

Pro Thr Ile Leu Ala Arg Lys Ser Asp Gly Glu Leu Ala Asn Tyr Phe
    210                 215                 220

Asn Gly Leu Gly Trp Glu Pro Phe Phe Ile Glu Gly Asn Asp Pro Glu
225                 230                 235                 240

Lys Leu Asn Pro Val Met Ala Glu Lys Met Asp Gln Ala Ile Glu Lys
                245                 250                 255

Ile Lys Ser Ile Gln Lys Glu Ala Arg Leu Lys Thr Ala Thr Asp Val
            260                 265                 270

Val Met Pro Lys Trp Pro Val Leu Ile Val Arg Thr Pro Lys Gly Trp
```

```
            275                 280                 285
Thr Gly Glu Pro Ile Glu Gly Thr Phe Arg Ala His Gln Val Pro Ile
        290                 295                 300
Pro Val Asp Gln Glu His Met Asp His Ala Asp Ala Leu Leu Arg Trp
305                 310                 315                 320
Leu Lys Ser Tyr Glu Pro Glu Lys Leu Phe Asp Ala Gln Gly Arg Ile
                325                 330                 335
Leu Glu Glu Ile Arg Glu Ile Ala Pro Thr Gly Asp Gln Arg Met Ala
            340                 345                 350
Lys Asn Pro Ile Thr Asn Gly Gly Ile Asp Pro Lys Pro Leu Ile Met
        355                 360                 365
Pro Asp Trp Lys Lys Tyr Thr Leu Gln Phe Glu Lys Pro Gly Ser Ile
370                 375                 380
Lys Ala Glu Asp Met Thr Glu Leu Gly Lys Phe Val Arg Glu Ile Ile
385                 390                 395                 400
Glu Lys Asn Pro Glu Asn Phe Arg Ile Phe Gly Pro Asp Glu Thr Lys
                405                 410                 415
Ser Asn Arg Leu Asn Gln Val Phe Lys Thr Thr Asn Arg Gln Trp Met
            420                 425                 430
Glu Lys Ile Glu Pro Glu Asn Asp Glu Trp Leu Ser Pro Ser Gly Arg
        435                 440                 445
Val Ile Asp Ser Gln Leu Ser Glu His Gln Asp Glu Gly Phe Leu Glu
    450                 455                 460
Gly Tyr Val Leu Thr Gly Arg His Gly Phe Phe Ala Ser Tyr Glu Ser
465                 470                 475                 480
Phe Leu Arg Val Val Asp Ser Met Leu Thr Gln His Phe Lys Trp Met
                485                 490                 495
Arg Lys Ser His Asp Leu Ser Trp Arg Asn Asp Tyr Pro Ser Leu Asn
            500                 505                 510
Leu Ile Ala Ser Ser Thr Val Phe Gln Gln Asp His Asn Gly Tyr Ser
        515                 520                 525
His Gln Asp Pro Gly Ile Leu Thr His Leu Ala Glu Lys Lys Ala Glu
    530                 535                 540
Phe Ile Arg Glu Tyr Leu Pro Ala Asp Ala Asn Thr Leu Leu Ala Val
545                 550                 555                 560
Met Asp Lys Ala Phe Arg Ser Ser Glu Lys Ile Asn Leu Ile Ile Ser
                565                 570                 575
Ser Lys His Pro Arg Ala Gln Phe Tyr Ser Ala Glu Glu Ala Ala Val
            580                 585                 590
Leu Val Asn Glu Gly Leu Lys Ile Ile Asp Trp Ala Ser Thr Ala Lys
        595                 600                 605
Glu Glu Glu Pro Glu Leu Val Ile Ala Ala Gly Thr Glu Ser Asn
    610                 615                 620
Leu Glu Ala Leu Ala Ala Val Thr Leu Leu Glu Glu Phe Pro Lys
625                 630                 635                 640
Leu Lys Ile Arg Phe Ile Asn Val Val Asp Leu Leu Lys Leu Arg His
                645                 650                 655
Pro Ser Gln Asp Pro Arg Gly Leu Ser Asp Glu Phe Asp Gln Tyr
            660                 665                 670
Phe Thr Lys Asp Lys Pro Ile Leu Phe Ala Phe His Gly Tyr Glu Thr
        675                 680                 685
Leu Val Arg Thr Ile Phe Phe Asp Arg His Asn His His Leu Met Ile
    690                 695                 700
```

His Gly Tyr Lys Glu Asn Gly Asp Ile Thr Thr Pro Phe Asp Met Arg
705                 710                 715                 720

Val Val Asn Glu Leu Asp Arg Tyr His Leu Ala Lys Asp Ala Ala Leu
                725                 730                 735

Lys Ile Lys Gly Ser Gln Ala Glu Asp Phe Ala Glu Lys Met Asp Gln
            740                 745                 750

Lys Leu Gln Glu His Gln Asn Tyr Ile Arg Glu Asn Gly Ile Asp Leu
        755                 760                 765

Pro Glu Val Leu Asp Trp Lys Trp Lys Asn Leu Asp Gln
    770                 775                 780

<210> SEQ ID NO 9
<211> LENGTH: 789
<212> TYPE: PRT
<213> ORGANISM: Brucella microti CCM 4915

<400> SEQUENCE: 9

Met Pro Ala Lys Gly Pro Leu Thr Pro Gln Gln Leu Ser Leu Ile Asn
1               5                   10                  15

Arg Tyr Trp Arg Ala Ala Asn Tyr Leu Ser Val Gly Gln Ile Tyr Leu
            20                  25                  30

Met Lys Asn Pro Leu Leu Arg Glu Pro Leu Gln Pro Glu His Ile Lys
        35                  40                  45

Pro Arg Leu Leu Gly His Trp Gly Thr Thr Pro Gly Leu Asn Phe Ile
    50                  55                  60

Tyr Ala His Leu Asn Arg Ile Ile Gln Gln Arg Asn Ala Asn Val Ile
65                  70                  75                  80

Tyr Ile Cys Gly Pro Gly His Gly Gly Pro Gly Met Val Ala Asn Thr
            85                  90                  95

Tyr Leu Glu Gly Thr Tyr Ser Glu Ile Tyr Pro Ala Ile Ser Glu Asp
            100                 105                 110

Glu Ala Gly Met Glu Arg Leu Phe Arg Gln Phe Ser Phe Pro Gly Gly
        115                 120                 125

Ile Pro Ser His Ala Ala Pro Glu Thr Pro Gly Ser Ile His Glu Gly
    130                 135                 140

Gly Glu Leu Gly Tyr Ala Leu Val His Ala Tyr Gly Ala Ala Phe Asp
145                 150                 155                 160

Asn Pro Asp Leu Val Val Ala Cys Val Val Gly Asp Gly Glu Ala Glu
                165                 170                 175

Thr Gly Ala Leu Ala Thr Ser Trp His Ser Asn Lys Phe Leu Asn Pro
            180                 185                 190

Ala Arg Asp Gly Ala Val Leu Pro Ile Leu His Leu Asn Gly Tyr Lys
        195                 200                 205

Ile Ala Asn Pro Thr Val Leu Ala Arg Leu Ser Asp Asp Leu Asp
    210                 215                 220

Asn Leu Phe Arg Gly Tyr Gly Tyr Glu Pro Phe Phe Val Glu Gly Ser
225                 230                 235                 240

Glu Pro Ala Asp Met His Gln Lys Met Ala Ala Thr Leu Asp Thr Ile
                245                 250                 255

Phe Gln Arg Ile Gln Asp Ile Lys Lys Asn Ala Asp Val His Ser Pro
            260                 265                 270

Glu Arg Pro Arg Trp Pro Met Ile Ile Leu Arg Ser Pro Lys Gly Trp
        275                 280                 285

Thr Gly Pro Lys Thr Val Asp Gly Leu Val Val Glu Asn Tyr Trp Arg

```
            290                 295                 300
Ala His Gln Val Pro Val Ala Asn Cys Arg Glu Asn Asp Ala His Arg
305                 310                 315                 320

Lys Ile Leu Glu Asp Trp Met Lys Ser Tyr Asp Pro Ser Asp Leu Phe
                325                 330                 335

Asp Glu Lys Gly Ala Leu Lys Pro Glu Leu Arg Ala Leu Ala Pro Lys
                340                 345                 350

Gly Glu Ala Arg Met Gly Ala Asn Pro His Ala Asn Gly Gly Leu Leu
                355                 360                 365

Arg Lys Glu Leu His Met Pro Asp Phe Arg Gln Tyr Ala Val Asn Val
        370                 375                 380

Thr Glu Pro Gly Ala Ile Glu Ala Gln Ser Thr Lys Ile Leu Gly Asp
385                 390                 395                 400

Phe Leu Arg Asp Val Met Lys Leu Asn Glu Thr Glu Lys Asn Phe Arg
                405                 410                 415

Ile Phe Gly Pro Asp Glu Thr Ala Ser Asn Arg Leu Gly Ser Val Leu
                420                 425                 430

Glu Ala Thr Asn Arg Val Trp Met Ala Glu Thr Leu Asp Met Asp Asp
        435                 440                 445

His Leu Ala Ala Asp Gly Arg Val Met Glu Val Leu Ser Glu His Leu
        450                 455                 460

Cys Gln Gly Trp Leu Glu Gly Tyr Leu Leu Ser Gly Arg His Gly Phe
465                 470                 475                 480

Phe Ser Cys Tyr Glu Ala Phe Ile His Ile Ile Asp Ser Met Phe Asn
                485                 490                 495

Gln His Ala Lys Trp Leu Gln Val Ala Arg Glu Leu Glu Trp Arg Lys
                500                 505                 510

Pro Ile Ser Ser Leu Asn Tyr Leu Leu Thr Ser His Val Trp Arg Gln
        515                 520                 525

Asp His Asn Gly Phe Ser His Gln Asp Pro Gly Phe Val Asp Leu Val
        530                 535                 540

Ala Asn Lys Ser Ala Asp Ile Val Arg Val Tyr Phe Pro Pro Asp Ala
545                 550                 555                 560

Asn Thr Leu Leu Trp Val Gly Asp His Cys Leu Lys Thr Trp Asn Arg
                565                 570                 575

Val Asn Val Ile Val Ala Gly Lys Gln Pro Glu Pro Gln Trp Leu Thr
                580                 585                 590

Met Ala Glu Ala Glu Lys His Cys Glu Ala Gly Leu Gly Ile Trp Glu
        595                 600                 605

Trp Ala Gly Thr Glu Asp Gly Leu Glu Pro Asp Ile Val Met Ala Cys
        610                 615                 620

Ala Gly Asp Val Pro Thr Met Glu Thr Leu Ala Val Asp Leu Leu
625                 630                 635                 640

Arg Gln Ser Leu Pro His Leu Arg Ile Arg Val Val Asn Val Val Asp
                645                 650                 655

Leu Met Val Leu Gln Ser Pro His Gln His Pro His Gly Ile Ser Asp
                660                 665                 670

Glu Glu Phe Asp Arg Met Phe Thr Asn Arg Pro Val Ile Phe Ala
                675                 680                 685

Tyr His Gly Tyr Pro Tyr Leu Ile His Arg Leu Val Tyr Lys Arg Thr
        690                 695                 700

Asn His Ser Asn Phe His Val Arg Gly Phe Ile Glu Gln Gly Thr Thr
705                 710                 715                 720
```

```
Thr Thr Pro Phe Asp Met Thr Val Leu Asn Glu Leu Asp Arg Phe His
            725                 730                 735

Leu Ala Met Glu Ala Val Glu Arg Leu Pro Leu Gly Glu Ser Val Ala
            740                 745                 750

Lys Pro Leu Ile Asp Asn Phe Thr Glu Lys Leu Ala Leu His Lys Asp
            755                 760                 765

Tyr Ile Arg Gln His Gly Glu Asp Met Pro Glu Ile Arg Asp Trp Lys
770                 775                 780

Trp Thr Trp Pro Arg
785

<210> SEQ ID NO 10
<211> LENGTH: 786
<212> TYPE: PRT
<213> ORGANISM: Lactobacillus salivarius ATCC 11741

<400> SEQUENCE: 10

Met Thr Asp Tyr Ser Ser Gln Glu Tyr Leu Asp Lys Leu Asp Ala Tyr
1               5                   10                  15

Trp Arg Ala Ala Asn Tyr Val Ser Val Gly Gln Leu Tyr Leu Lys Asp
            20                  25                  30

Asn Pro Leu Leu Arg Arg Pro Leu Lys Ala Glu Asp Val Lys Val Lys
            35                  40                  45

Pro Ile Gly His Trp Gly Thr Ile Ala Gly Gln Asn Phe Ile Tyr Ala
        50                  55                  60

His Leu Asn Arg Val Ile Asn Lys Tyr Asp Leu Asn Met Phe Tyr Val
65                  70                  75                  80

Glu Gly Pro Gly His Gly Gly Gln Val Met Val Ser Asn Ser Tyr Leu
                85                  90                  95

Asp Gly Ser Tyr Ser Glu Ile Tyr Pro Glu Ile Ser Gln Asp Glu Gln
            100                 105                 110

Gly Met Lys Arg Leu Phe Lys Arg Phe Ser Phe Pro Gly Gly Val Ala
        115                 120                 125

Ser His Ala Ala Pro Glu Thr Pro Gly Ser Ile His Glu Gly Gly Glu
    130                 135                 140

Leu Gly Tyr Ser Ile Ser His Ser Val Gly Ala Val Leu Asp Asn Pro
145                 150                 155                 160

Asp Leu Ile Val Ala Ala Val Val Gly Asp Gly Glu Ala Glu Thr Gly
                165                 170                 175

Pro Leu Ala Ala Ser Trp Gln Ser Asn Lys Phe Ile Asn Pro Ile His
            180                 185                 190

Asp Gly Ala Val Leu Pro Ile Leu Asp Leu Asn Gly Phe Lys Ile Ser
        195                 200                 205

Asn Pro Thr Ile Leu Ser Arg Glu Ser Asp Glu Thr Leu Thr Lys Tyr
    210                 215                 220

Phe Glu Gly Met Gly Trp His Pro Ile Phe Val Glu Gly Asp Asp Pro
225                 230                 235                 240

Lys Leu Met His Pro Ala Met Ala Lys Ala Met Asp Glu Ala Ile Glu
                245                 250                 255

Glu Ile Lys Ala Ile Gln Lys Asn Ala Arg Glu Asn Asn Asp Pro Ser
            260                 265                 270

Leu Pro Ala Trp Pro Val Ile Ile Phe Arg Ala Pro Lys Gly Trp Thr
        275                 280                 285

Gly Pro Lys Glu Trp Asp Gly Glu Pro Ile Glu Lys Ser Phe Arg Ala
```

```
            290                 295                 300
His Gln Ile Pro Ile Pro Val Asp Gln Asn Asp Met Gln His Ala Asp
305                 310                 315                 320

Ala Leu Val Asp Trp Leu Glu Ser Tyr Lys Pro Glu Glu Leu Phe Asp
                325                 330                 335

Glu Asn Gly Lys Leu Lys Ala Glu Ile Ala Glu Ile Thr Pro Lys Gly
            340                 345                 350

Asp Lys Arg Met Ala Ala Asn Pro His Thr Asn Pro Gly Lys Leu Ile
        355                 360                 365

Arg Glu Val Ile Lys Pro Asp Phe Arg Asp Phe Ala Val Asp Thr Ser
    370                 375                 380

Val Pro Gly Lys Glu Val Ala Gln Asp Met Thr Val Leu Gly Lys Tyr
385                 390                 395                 400

Leu Glu Lys Val Leu Ser Asp Asn Arg His Asn Tyr Arg Val Phe Gly
                405                 410                 415

Pro Asp Glu Thr Met Ser Asn Arg Leu Ala Pro Ile Phe Asp Val Thr
            420                 425                 430

Lys Arg Gln Trp Leu Ala Glu Ile Lys Glu Pro Asn Asp Gln Tyr Leu
        435                 440                 445

Ala Pro Ser Gly Gln Val Ile Asp Ser Gln Leu Ser Glu His Gln Ala
    450                 455                 460

Glu Gly Phe Leu Glu Gly Tyr Val Leu Thr Gly Arg His Gly Phe Phe
465                 470                 475                 480

Ala Ser Tyr Glu Ser Phe Leu Arg Val Val Asp Ser Met Leu Thr Gln
                485                 490                 495

His Phe Lys Trp Leu Arg Lys Ala Thr Glu Gln Pro Trp Arg Thr Ser
            500                 505                 510

Ile Pro Ser Leu Asn Val Ile Ala Thr Ser Thr Val Phe Gln Gln Asp
        515                 520                 525

His Asn Gly Tyr Thr His Gln Asp Pro Gly Ile Leu Gly His Leu Ala
    530                 535                 540

Asp Lys Lys Pro Glu Tyr Ile Arg Glu Tyr Leu Pro Ala Asp Ala Asn
545                 550                 555                 560

Ser Leu Leu Ala Val Phe Asp Lys Thr Ile Asn Asp Arg Asp Lys Ile
                565                 570                 575

Asn Leu Ile Val Ala Ser Lys His Pro Arg Gln Gln Phe Tyr Ser Ala
            580                 585                 590

Ala Glu Ala Lys Glu Leu Val Asp Lys Gly Leu Lys Ile Ile Asp Trp
        595                 600                 605

Ala Ser Thr Asp Lys Asn Ala Glu Pro Asp Val Val Ile Ala Ala Ala
    610                 615                 620

Gly Thr Glu Pro Asn Leu Glu Ala Leu Ala Ala Ile Ser Ile Leu His
625                 630                 635                 640

Glu Lys Leu Pro Asp Leu Lys Ile Arg Phe Ile Asn Val Val Asp Ile
                645                 650                 655

Leu Lys Leu Arg Ser Pro Lys Val Asp Pro Arg Gly Leu Ser Asp Asp
            660                 665                 670

Glu Phe Asp Ala Tyr Phe Thr Lys Asp Lys Pro Val Ile Phe Ala Phe
        675                 680                 685

His Gly Tyr Glu Gly Leu Leu Arg Asp Ile Phe Tyr Tyr Arg His Asn
    690                 695                 700

His Asn Val Ala Phe His Gly Tyr Arg Glu Asn Gly Asp Ile Thr Thr
705                 710                 715                 720
```

```
Pro Phe Asp Met Arg Val Leu Ser Gln Met Asp Arg Phe Asp Leu Val
            725                 730                 735

Lys Ser Val Ala Leu Ser Leu Pro Asp Ala Asp Lys Tyr Gly Gln Leu
            740                 745                 750

Val Ala Glu Met Asp Ala Lys Val Ala Lys His His Gln Tyr Ile Arg
            755                 760                 765

Asp Glu Gly Thr Asp Leu Pro Glu Val Glu Asn Trp Glu Trp Lys Pro
            770                 775                 780

Leu Asp
785

<210> SEQ ID NO 11
<211> LENGTH: 755
<212> TYPE: PRT
<213> ORGANISM: Streptococcus agalactiae COH1

<400> SEQUENCE: 11

Met Ser Glu Phe Asp Thr Lys Ser Tyr Leu Glu Lys Leu Asp Ala Trp
1               5                   10                  15

Trp Arg Ala Ala Asn Tyr Ile Ser Ala Ala Gln Met Tyr Leu Lys Asp
            20                  25                  30

Asn Pro Leu Leu Arg Arg Glu Leu Val Glu Asn Asp Leu Lys Val His
            35                  40                  45

Pro Ile Gly His Trp Gly Thr Val Pro Gly Gln Asn Phe Ile Tyr Ala
        50                  55                  60

His Leu Asn Arg Ala Ile Asn Lys Tyr Asp Leu Asp Met Phe Tyr Ile
65                  70                  75                  80

Glu Gly Pro Gly His Gly Gly Gln Val Met Val Ser Asn Ser Tyr Leu
                85                  90                  95

Asp Gly Ser Tyr Thr Glu Leu Asn Pro Asn Ile Glu Gln Thr Glu Asp
            100                 105                 110

Gly Phe Lys Gln Leu Cys Lys Ile Phe Ser Phe Pro Gly Gly Ile Ala
            115                 120                 125

Ser His Ala Ala Pro Glu Thr Pro Gly Ser Ile His Glu Gly Gly Glu
        130                 135                 140

Leu Gly Tyr Ala Leu Ser His Ala Thr Gly Ala Ile Leu Asp Asn Pro
145                 150                 155                 160

Asp Val Ile Ala Ala Thr Val Ile Gly Asp Gly Glu Gly Glu Thr Gly
            165                 170                 175

Pro Leu Met Ala Gly Trp Leu Ser Asn Thr Phe Ile Asn Pro Val Asn
            180                 185                 190

Asp Gly Ala Val Leu Pro Ile Phe Tyr Leu Asn Gly Gly Lys Ile His
            195                 200                 205

Asn Pro Thr Ile Phe Glu Arg Lys Thr Asp Glu Glu Leu Ser Gln Phe
        210                 215                 220

Phe Glu Gly Leu Gly Trp Lys Pro Ile Phe Ala Asp Val Val Glu Leu
225                 230                 235                 240

Ser Glu Asp His Ala Ala Ala His Ala Leu Phe Ala Glu Lys Leu Asp
                245                 250                 255

Gln Ala Ile Gln Glu Ile Lys Thr Ile Gln Ser Glu Ala Arg Gln Lys
            260                 265                 270

Pro Ala Glu Glu Ala Ile Gln Ala Lys Phe Pro Val Leu Val Ala Arg
            275                 280                 285

Ile Pro Lys Gly Trp Thr Gly Pro Lys Ala Trp Glu Gly Thr Pro Ile
```

```
                290             295             300
Glu Gly Gly Phe Arg Ala His Gln Val Pro Ile Pro Val Asp Ala His
305             310             315             320

His Met Glu His Val Asp Ser Leu Leu Ser Trp Leu Gln Ser Tyr Arg
            325             330             335

Pro Glu Glu Leu Phe Asp Glu Asn Gly Lys Ile Val Asp Glu Ile Ala
            340             345             350

Ala Ile Ser Pro Lys Gly Asp Arg Arg Met Ser Met Asn Pro Ile Thr
            355             360             365

Asn Ala Gly Ile Val Lys Ala Met Asp Thr Ala Asp Trp Lys Lys Phe
            370             375             380

Ala Leu Asp Ile Asn Val Pro Gly Gln Ile Met Ala Gln Asp Met Ile
385             390             395             400

Glu Phe Gly Lys Tyr Ala Ala Asp Leu Val Asp Ala Asn Pro Asp Asn
            405             410             415

Phe Arg Ile Phe Gly Pro Asp Glu Thr Lys Ser Asn Arg Leu Gln Glu
            420             425             430

Val Phe Thr Arg Thr Ser Arg Gln Trp Leu Gly Arg Lys Pro Asp
            435             440             445

Tyr Asp Glu Ala Leu Ser Pro Ala Gly Arg Val Ile Asp Ser Gln Leu
            450             455             460

Ser Glu His Gln Ala Glu Gly Phe Leu Glu Gly Tyr Val Leu Thr Gly
465             470             475             480

Arg His Gly Phe Phe Ala Ser Tyr Glu Ser Phe Leu Arg Val Val Asp
            485             490             495

Ser Met Val Thr Gln His Phe Lys Trp Leu Arg Lys Ser Lys Thr His
            500             505             510

Thr Thr Trp Arg Lys Asn Tyr Pro Ala Leu Asn Leu Ile Ala Ala Ser
            515             520             525

Thr Val Phe Gln Gln Asp His Asn Gly Tyr Thr His Gln Asp Pro Gly
            530             535             540

Ile Leu Thr His Leu Ala Glu Lys Thr Pro Glu Tyr Ile Arg Glu Tyr
545             550             555             560

Leu Pro Ala Asp Thr Asn Ser Leu Leu Ala Val Met Asp Lys Ala Phe
            565             570             575

Lys Ala Glu Asp Lys Ile Asn Leu Ile Val Thr Ser Lys His Pro Arg
            580             585             590

Pro Gln Phe Tyr Ser Ile Ala Glu Ala Glu Leu Val Ala Glu Gly
            595             600             605

Tyr Lys Val Ile Asp Trp Ala Ser Asn Val Ser Leu Asn Gln Glu Pro
            610             615             620

Asp Val Val Phe Ala Ala Gly Thr Glu Pro Asn Leu Glu Ala Leu
625             630             635             640

Ala Ala Ile Ser Ile Leu His Lys Ala Phe Pro Glu Leu Lys Ile Arg
            645             650             655

Phe Val Asn Val Leu Asp Ile Leu Lys Leu Arg His Pro Ser Gln Asp
            660             665             670

Ala Arg Gly Leu Ser Asp Glu Glu Phe Asn Lys Val Phe Thr Thr Asp
            675             680             685

Lys Pro Val Ile Phe Ala Phe His Gly Tyr Glu Asp Met Ile Arg Asp
            690             695             700

Ile Phe Phe Ser Arg His Asn His Asn Leu His Thr His Gly Tyr Arg
705             710             715             720
```

```
Glu Asn Gly Asp Ile Thr Thr Pro Phe Asp Met Arg Val Met Ser Glu
                725                 730                 735

Leu Asp Arg Phe His Leu Ala Gln Asp Ala Ala Leu Ala Ser Leu Gly
            740                 745                 750

Ile Lys His
        755

<210> SEQ ID NO 12
<211> LENGTH: 800
<212> TYPE: PRT
<213> ORGANISM: Rhodococcus imtechensis RKJ300

<400> SEQUENCE: 12

Met Thr Asp Gly Arg Gln Val Gly Ser Gln Asp Ser Asp Gly His Tyr
1               5                   10                  15

Ser Asp Ser Asp Leu Asp Leu Asp Leu Arg Trp Trp Ala Ala Ala Asn
            20                  25                  30

Tyr Leu Thr Val Ala Gln Ile Tyr Leu Gln Asp Asn Ala Leu Leu Arg
        35                  40                  45

Ala Pro Leu Arg Pro Glu His Ile Lys Pro Arg Leu Leu Gly His Trp
    50                  55                  60

Gly Thr Ser Pro Gly Leu Ser Met Ile Tyr Ala Leu Leu Asn Arg Leu
65                  70                  75                  80

Ile Arg Arg Thr Asp Thr Asp Cys Leu Tyr Val Thr Gly Pro Gly His
                85                  90                  95

Gly Gly Pro Ala Leu Val Ala Ala Thr Tyr Leu Glu Gly Thr Tyr Ser
            100                 105                 110

Glu Val Tyr Pro Gly Val Ser Arg Asp Ala Ala Gly Ile His Arg Leu
        115                 120                 125

Cys Arg Gln Phe Ser Thr Pro Gly Gly Ile Pro Ser His Val Ser Val
    130                 135                 140

Gln Thr Pro Gly Ser Ile His Glu Gly Gly Glu Leu Gly Tyr Ala Leu
145                 150                 155                 160

Ala His Ala Ala Gly Ala Ala Phe Asp His Pro Asn Leu Leu Val Ala
                165                 170                 175

Cys Val Ile Gly Asp Gly Glu Ala Glu Thr Gly Pro Leu Ser Gly Ser
            180                 185                 190

Trp Lys Leu Pro Ala Phe Leu Asn Pro Glu Arg Asp Gly Ala Val Leu
        195                 200                 205

Pro Ile Leu His Val Asn Gly Ala Lys Ile Ala Gly Pro Thr Val Tyr
    210                 215                 220

Gly Arg Ser Ser Asp Ala Asp Val Glu Ala Phe Leu Gly Gly Gln Gly
225                 230                 235                 240

Trp Ala Pro Thr Val Val Ser Gly Asp Asp Pro Arg His Val Phe Pro
                245                 250                 255

Ala Leu His Arg Ala Leu Thr Asp Ala His Ala Ala Ile Ser Asp Leu
            260                 265                 270

Gln Arg Glu Ala Arg Ala Gly Arg Arg Ser Ala Ala Lys Trp Pro Ala
        275                 280                 285

Ile Val Leu Arg Thr Pro Lys Gly Trp Thr Gly Pro Arg Thr Val Asp
    290                 295                 300

Gly Val Leu Val Glu Gly Thr His Arg Ala His Gln Val Pro Leu Ser
305                 310                 315                 320

Gly Val Arg Thr Asp Glu Ala His Leu Arg Gln Leu Glu Glu Trp Met
```

```
                    325                 330                 335
Arg Ser Tyr Gly Pro Gly Glu Leu Phe Asp Ser Ser Gly Ala Leu Val
                340                 345                 350
Pro Asp Leu Glu Arg Leu Ala Pro Gln Gly Asp Lys Arg Met Gly Ser
                355                 360                 365
Ser Pro Tyr Ala Asn Gly Gly Arg Leu Arg Ala Asp Leu Pro Val Pro
            370                 375                 380
Pro Leu Glu Lys Tyr Ala Leu Ala Ile Glu Lys Pro Gly Thr Thr Leu
385                 390                 395                 400
His Glu Thr Thr Arg Val Leu Gly Glu Leu Leu Arg Asp Leu Tyr Ala
                405                 410                 415
Ala Thr Ala Thr Pro Asp Gly Gly Tyr Phe Arg Leu Phe Cys Pro
                420                 425                 430
Asp Glu Thr Ala Ser Asn Arg Leu Gly Ala Val Phe Glu Val Thr Asp
                435                 440                 445
Arg Cys Trp Gln Leu Pro Val Thr Asp Tyr Asp Asp Gly Leu Ser Ala
            450                 455                 460
Arg Gly Arg Val Met Glu Val Leu Ser Glu His Leu Cys Glu Gly Trp
465                 470                 475                 480
Leu Glu Gly Tyr Leu Leu Ser Gly Arg His Gly Leu Phe Ala Ser Tyr
                485                 490                 495
Glu Ala Phe Ala Met Val Ser Val Ser Met Leu Val Gln His Thr Lys
                500                 505                 510
Trp Leu Gln His Ala Val Asp Leu Pro Trp Arg Ala Pro Val Ala Ser
                515                 520                 525
Leu Asn Val Leu Leu Thr Ser Thr Cys Trp Arg Asn Asp His Asn Gly
            530                 535                 540
Phe Ser His Gln Gly Pro Gly Met Ile Asp Ala Val Ile Pro Leu Ala
545                 550                 555                 560
Pro Asp Val Val Arg Ile Trp Leu Pro Pro Asp Ser Asn Thr Leu Leu
                565                 570                 575
Ser Ile Ala Asp His Cys Leu Arg Ser Thr Asp His Val Asn Leu Ile
                580                 585                 590
Val Val Asp Lys Gln Pro His Leu Gln Tyr Leu Thr Leu Ala Glu Ala
            595                 600                 605
His Ala His Cys Ala Ala Gly Ala Ser Val Trp Glu Trp Ala Gly Thr
                610                 615                 620
Glu Gly Ala Val Gly Ala Asp Pro Asp Val Val Leu Ala Ala Ala Gly
625                 630                 635                 640
Asp Val Pro Thr Gln Glu Ile Leu Ala Ala Gln Leu Leu Arg Glu
                645                 650                 655
His Thr Pro Asp Leu Val Thr Arg Val Val Asn Val Val Asp Leu Met
                660                 665                 670
Gly Leu Leu Thr Pro Thr Glu His Pro His Gly Phe Asp Ala Arg Met
            675                 680                 685
Phe Leu Asp Leu Phe Thr Ala Asp Thr Asp Val Val Phe Ala Phe His
                690                 695                 700
Gly Tyr Ser Arg Ala Val His Glu Leu Ile His Gly Arg Pro Ala Pro
705                 710                 715                 720
Asp Arg Phe His Val Arg Gly Phe Ser Glu Gln Gly Thr Thr Thr Thr
                725                 730                 735
Pro Phe Asp Met Val Val Leu Asn Arg Met Ser Arg Tyr His Leu Val
                740                 745                 750
```

Leu Glu Ala Leu Arg Arg Thr Arg Arg Glu Pro Ala Gly Ala Gly Glu
                755                 760                 765

Leu Ala Asp Phe Cys Leu Arg Gln Leu Glu Arg His Gly Glu Tyr Val
                770                 775                 780

Val Ala His Leu Glu Asp Met Pro Glu Val Arg Asp Trp Thr Trp Ser
785                 790                 795                 800

<210> SEQ ID NO 13
<211> LENGTH: 797
<212> TYPE: PRT
<213> ORGANISM: Burkholderia xenovorans LB400

<400> SEQUENCE: 13

Met Ala Glu Ala Ser Ser Arg Pro Thr Pro Gln Val Leu Asp Ala
1               5                   10                  15

Asp Thr Leu Arg Asn Met Asp Arg Tyr Trp Arg Ala Cys Asn Tyr Leu
                20                  25                  30

Ser Ala Gly Met Ile Tyr Leu Arg Asp Asn Pro Leu Leu Arg Glu Pro
            35                  40                  45

Leu Lys Pro Glu His Ile Lys Asn Arg Leu Leu Gly His Trp Gly Ser
    50                  55                  60

Asp Pro Gly Gln Ser Phe Leu Val His Leu Asn Arg Leu Ile Arg
65              70                  75                  80

Lys Leu Asp Leu Asn Val Ile Tyr Val Ala Gly Pro Gly His Gly Ala
                85                  90                  95

Pro Ala Thr Leu Ala His Cys Tyr Leu Glu Gly Tyr Ser Glu Ile
            100                 105                 110

Tyr Pro Asp Arg Ser Glu Asp Glu Ala Gly Met Gln Arg Phe Phe Arg
        115                 120                 125

Gln Phe Ser Phe Pro Gly Gly Ile Gly Ser His Cys Thr Pro Glu Thr
130                 135                 140

Pro Gly Ser Ile His Glu Gly Gly Glu Leu Gly Tyr Ser Leu Ser His
145                 150                 155                 160

Gly Tyr Gly Ala Ala Phe Asp Asn Pro Asp Leu Ile Val Thr Val Met
                165                 170                 175

Ile Gly Asp Gly Glu Ala Glu Thr Gly Pro Leu Ala Thr Ser Trp His
            180                 185                 190

Ser Asn Lys Phe Leu Asn Pro Val Arg Asp Gly Ala Val Leu Pro Val
    195                 200                 205

Leu His Leu Asn Gly Tyr Lys Ile Ala Asn Pro Thr Ile Leu Ala Arg
210                 215                 220

Ile Pro Arg Glu Glu Leu Glu Ala Leu Leu Thr Gly Tyr Gly His Lys
225                 230                 235                 240

Pro Tyr Phe Val Glu Gly Asp Asp Pro Ala Val Met His Gln Gln Met
                245                 250                 255

Ala Ala Thr Leu Glu Gln Cys Ile Gly Glu Ile Arg Ala Ile Gln Gln
            260                 265                 270

His Ala Arg Ala Asn Asn Asp Ala Thr Arg Pro Arg Trp Pro Met Ile
        275                 280                 285

Val Leu Arg Ser Pro Lys Gly Trp Thr Gly Pro Lys Glu Val Asp Gly
    290                 295                 300

His Lys Val Glu Gly Ser Trp Arg Ala His Gln Val Pro Val Leu Asp
305                 310                 315                 320

Pro Val Thr Asn Gly Lys Ser Leu Lys Leu Val Glu Asn Trp Met Arg

```
                    325                 330                 335
Ser Tyr Glu Pro Glu Ser Leu Phe Asp Glu Ala Gly Arg Leu Val Glu
                340                 345                 350
Glu Leu Arg Glu Leu Ala Pro Lys Gly Ala Arg Ile Ser Ala Asn
            355                 360                 365
Pro His Ala Asn Gly Gly Leu Leu Cys Lys Thr Leu Asp Met Pro Ala
        370                 375                 380
Phe Gly Asp Tyr Ala Val Ala Val Lys Lys Pro Gly Gly Thr Tyr Thr
385                 390                 395                 400
Ser Pro Thr Glu Val Leu Gly Lys Phe Leu Cys Asp Val Met Arg Arg
                405                 410                 415
Asn Met Thr Asn Phe Arg Val Phe Gly Pro Asp Glu Thr Ala Ser Asn
                420                 425                 430
Lys Leu Thr Ala Ile Tyr Glu Ala Ser Glu Lys Thr Trp Leu Ala Gln
            435                 440                 445
Thr Glu Pro Ser Asp Ala Asp Gly Gly Asp Leu Ala Val Asp Gly Arg
        450                 455                 460
Val Met Glu Met Leu Ser Glu His Thr Leu Glu Gly Trp Phe Glu Gly
465                 470                 475                 480
Tyr Val Leu Thr Gly Arg His Gly Leu Phe Ala Thr Tyr Glu Ala Phe
                485                 490                 495
Val His Val Ile Asp Ser Met Phe Asn Gln His Ala Lys Trp Leu Glu
                500                 505                 510
Lys Ala Lys Arg Asp Leu Gly Trp Arg Gln Pro Val Pro Ser Ile Asn
            515                 520                 525
Leu Leu Ile Thr Ser Leu Val Trp Arg Gln Asp His Asn Gly Phe Thr
        530                 535                 540
His Gln Asp Pro Gly Phe Leu Asp Val Val Thr Asn Lys Ser Pro Asp
545                 550                 555                 560
Val Val Arg Ile Tyr Leu Pro Pro Asp Ala Asn Cys Leu Leu Ser Val
                565                 570                 575
Ala Asp His Cys Leu Arg Ser Arg Asp Tyr Val Asn Val Ile Val Ala
                580                 585                 590
Asp Lys Gln Pro His Leu Gln Tyr Leu Asp Met Asp Ala Ala Val Ile
            595                 600                 605
His Cys Thr Lys Gly Ile Gly Ile Trp Asp Trp Ala Ser Thr Asp Gln
        610                 615                 620
Gly Val Glu Pro Asp Val Val Ile Ala Ser Ala Gly Asp Ile Ala Thr
625                 630                 635                 640
Met Glu Ala Leu Ala Ala Val Gln Ile Leu Lys Glu Arg Phe Ala Asp
                645                 650                 655
Leu Lys Ile Arg Phe Val Asn Val Val Asp Leu Phe Arg Leu Met Pro
            660                 665                 670
Glu His Ala His Pro His Gly Leu Ser Asn Arg Asp Phe Asp Ser Leu
        675                 680                 685
Phe Thr Ala Thr Lys Pro Val Ile Phe Asn Phe His Ser Tyr Ala Ser
        690                 695                 700
Leu Val His Lys Leu Thr Tyr Asn Arg Thr Asn His Asp Asn Leu His
705                 710                 715                 720
Val His Gly Tyr His Glu Lys Gly Asn Ile Asn Thr Pro Leu Glu Leu
                725                 730                 735
Ala Ile Ile Asn Gln Val Asp Arg Phe Ser Leu Ala Ile Asp Val Ile
                740                 745                 750
```

```
Asp Arg Val Pro Lys Leu Arg Gly Val Gly Asp His Ala Lys Glu Trp
        755                 760                 765

Leu Arg Gly Gln Val Ile Glu His Leu Ala Tyr Ala His Ala Glu Gly
        770                 775                 780

Ile Asp Arg Glu Glu Ile Arg Asn Trp Thr Trp Lys Gly
785                 790                 795

<210> SEQ ID NO 14
<211> LENGTH: 787
<212> TYPE: PRT
<213> ORGANISM: Mycobacterium intracellulare ATCC 13950

<400> SEQUENCE: 14

Met Thr His Ala Thr Ala Leu Ser Asp Asp Glu Leu Ala Leu Ile Asp
1               5                   10                  15

Lys Tyr Trp Arg Ala Ala Asn Tyr Leu Ser Val Gly Gln Ile Tyr Leu
            20                  25                  30

Leu Asp Asn Pro Leu Leu Thr Glu Pro Leu Thr Ile Asp His Val Lys
        35                  40                  45

Pro Arg Leu Leu Gly His Trp Gly Thr Thr Pro Gly Leu Asn Leu Val
    50                  55                  60

Tyr Ala His Leu Asn Arg Val Ile Arg His Arg Asp Ala Asp Val Ile
65                  70                  75                  80

Tyr Val Thr Gly Pro Gly His Gly Gly Pro Gly Leu Val Ala Asn Ala
                85                  90                  95

Tyr Leu Glu Gly Thr Tyr Ser Glu Val Tyr Thr Gly Ile Glu Glu Asp
            100                 105                 110

Thr Glu Gly Leu Arg Lys Leu Phe Arg Gln Phe Ser Phe Pro Gly Gly
        115                 120                 125

Ile Pro Ser His Val Ala Ala Gln Thr Pro Gly Ser Ile His Glu Gly
    130                 135                 140

Gly Glu Leu Gly Tyr Ala Leu Val His Ala Tyr Gly Ala Ala Leu Asp
145                 150                 155                 160

Asn Pro Tyr Leu Val Val Ala Cys Val Val Gly Asp Gly Glu Ala Glu
                165                 170                 175

Thr Gly Pro Leu Ala Ala Ser Trp His Ser Asn Lys Phe Leu Asn Pro
            180                 185                 190

Val Thr Asp Gly Ala Val Leu Pro Ile Leu Ala Leu Asn Gly Tyr Lys
        195                 200                 205

Ile Ala Asn Pro Thr Val Leu Ala Arg Ile Pro His Ala Glu Leu Glu
    210                 215                 220

Ser Leu Leu Arg Gly Tyr Gly Tyr Arg Pro Ile Thr Val Ala Gly Asp
225                 230                 235                 240

Asp Pro Ala Asp Val His Arg Gln Leu Ala Ala Ala Leu Asp Asp Ala
                245                 250                 255

Phe Asp Asp Ile Ala Ala Ile Gln Ser Ala Ala Arg Gly Gly Asn Gly
            260                 265                 270

Val Glu Arg Pro Val Trp Pro Met Ile Val Leu Arg Thr Pro Lys Gly
        275                 280                 285

Trp Thr Gly Pro Lys Met Val Asp Gly Lys Lys Val Glu Gly Thr Trp
    290                 295                 300

Arg Ser His Gln Val Pro Leu Ala Ala Thr Arg Asp Asn Pro Glu His
305                 310                 315                 320

Arg Ala Gln Leu Glu Glu Trp Leu Arg Ser Tyr Gly Pro Gly Glu Leu
```

-continued

```
                325                 330                 335
Phe Asp Glu Asn Gly Arg Leu Arg Pro Glu Leu Arg Ala Leu Ala Pro
                340                 345                 350
Ser Gly Asp Arg Arg Met Ser Ala Asn Pro His Ala Asn Gly Gly Leu
                355                 360                 365
Leu Leu His Asp Leu Asp Leu Pro Asp Phe Arg Asp Tyr Ala Val Ala
                370                 375                 380
Val Glu Arg Pro Ala Ala Val Thr His Glu Ala Thr Arg Val Leu Gly
385                 390                 395                 400
Gly Phe Leu Arg Asp Val Ile Ala Arg Asn Lys Asp Arg Phe Arg Leu
                405                 410                 415
Met Gly Pro Asp Glu Thr Ala Ser Asn Arg Leu Asp Ala Val Tyr Gly
                420                 425                 430
Ser Thr Asp Lys Val Trp Leu Ser Glu Ile Glu Pro Asp Asp Glu His
                435                 440                 445
Leu Ala Pro Asp Gly Arg Val Met Glu Val Leu Ser Glu His Leu Cys
                450                 455                 460
Gln Gly Trp Leu Glu Gly Tyr Leu Leu Thr Gly Arg His Gly Leu Phe
465                 470                 475                 480
Asn Cys Tyr Glu Ala Phe Val His Ile Val Asp Ser Met Leu Asn Gln
                485                 490                 495
His Ala Lys Trp Leu Ala Thr Ser Arg Glu Leu Pro Trp Arg Arg Pro
                500                 505                 510
Ile Ala Ser Leu Asn Tyr Leu Leu Ser Ser His Val Trp Arg Gln Asp
                515                 520                 525
His Asn Gly Ala Ser His Gln Asp Pro Gly Phe Ile Asp Leu Val Ala
                530                 535                 540
Asn Lys Arg Pro Glu Leu Thr Arg Val Tyr Leu Pro Pro Asp Gly Asn
545                 550                 555                 560
Thr Leu Leu Ser Val Ala Asp His Cys Leu Arg Ser Arg Asp Tyr Ile
                565                 570                 575
Asn Val Ile Val Ala Gly Lys Gln Pro Ala Leu Ala Tyr Leu Asp Met
                580                 585                 590
Asp Glu Ala Val Ala His Cys Thr Arg Gly Leu Gly Ile Trp Glu Trp
                595                 600                 605
Ala Ser Thr Ala Thr Asp Asp Pro Asp Val Val Leu Ala Cys Ala Gly
                610                 615                 620
Asp Ile Pro Thr Leu Glu Thr Leu Ala Ala Asp Ile Leu Arg Ser
625                 630                 635                 640
Glu Leu Pro Glu Leu Ala Val Arg Val Val Asn Val Val Asp Leu Met
                645                 650                 655
Arg Leu Gln Pro Asp Thr Glu His Pro His Gly Leu Pro Asp Arg Glu
                660                 665                 670
Phe Asp Ala Leu Phe Thr Pro Asp Arg Pro Val Ile Phe Ala Tyr His
                675                 680                 685
Gly Tyr Pro Trp Leu Ile His Arg Leu Thr Tyr Ser Arg Thr Asn His
                690                 695                 700
Ala His Met His Val Arg Gly Phe Lys Glu Arg Gly Thr Thr Thr Thr
705                 710                 715                 720
Pro Phe Asp Met Val Met Leu Asn Asp Leu Asp Arg Phe His Leu Val
                725                 730                 735
Met Asp Val Ile Asp Arg Val Asp Gly Leu Ala Ser Arg Ala Ala Met
                740                 745                 750
```

```
Leu Arg Gln Arg Met Val Asp Ala Arg Leu Ala Ala Arg Met Tyr Thr
        755                 760                 765

Arg Glu His Gly Glu Asp Asp Pro Lys Ile Ser Gly Trp Thr Trp Gly
    770                 775                 780

Pro Ser Asp
785

<210> SEQ ID NO 15
<211> LENGTH: 789
<212> TYPE: PRT
<213> ORGANISM: Nitrosomonas sp. Is79A3

<400> SEQUENCE: 15

Met Lys Lys Asn Thr Lys Leu Leu Ser Pro Glu Leu Leu His Lys Met
1               5                   10                  15

Asp Ala Tyr Trp Arg Ala Ala Asn Tyr Leu Ser Val Gly Gln Ile Tyr
            20                  25                  30

Leu Tyr Asp Asn Pro Leu Leu Lys Gln Pro Leu Lys Leu Ala His Ile
        35                  40                  45

Lys Pro Arg Leu Leu Gly His Trp Gly Thr Thr Pro Gly Leu Asn Phe
    50                  55                  60

Ile Tyr Val His Leu Asn Arg Ile Ile Lys Glu His Asp Leu Asn Val
65                  70                  75                  80

Ile Tyr Ile Thr Gly Pro Gly His Gly Gly Pro Gly Leu Val Ala Asn
                85                  90                  95

Thr Tyr Leu Glu Gly Thr Tyr Ser Glu Val Tyr Pro Asn Ile Ser Gln
            100                 105                 110

Asp Glu Asp Gly Met Gln Arg Leu Phe Lys Gln Phe Ser Phe Pro Gly
        115                 120                 125

Gly Ile Pro Ser His Val Ala Pro Glu Thr Pro Gly Ser Ile His Glu
    130                 135                 140

Gly Gly Glu Leu Gly Tyr Ser Leu Ser His Ala Phe Gly Ala Ala Phe
145                 150                 155                 160

Asp Asn Pro Gly Leu Leu Val Ala Cys Val Val Gly Asp Gly Glu Ala
                165                 170                 175

Glu Thr Gly Pro Leu Ala Thr Ser Trp His Ser Asn Lys Phe Leu Asn
            180                 185                 190

Pro Val His Asp Gly Ala Val Leu Pro Ile Leu His Leu Asn Gly Tyr
        195                 200                 205

Lys Ile Ala Gly Pro Thr Val Leu Ala Arg Ile Pro Cys Asp Glu Leu
    210                 215                 220

Glu Ala Leu Phe Arg Gly Tyr Gly Tyr Thr Pro Tyr Phe Ile Glu Gly
225                 230                 235                 240

Asp Asp Pro Leu Glu Met His Gln Arg Met Ala Ala Thr Leu Asp Ala
                245                 250                 255

Val Ile Ala Asn Ile Gln Ser Ile Gln Arg Asp Ala Arg Thr His Gly
            260                 265                 270

Phe Thr Lys Arg Pro His Trp Pro Met Ile Ile Leu Arg Ser Pro Lys
        275                 280                 285

Gly Trp Thr Gly Pro Lys Val Val Asp Gly Lys Pro Thr Glu Gly Thr
    290                 295                 300

Phe Arg Ser His Gln Val Pro Met Gly Asp Met Ser Gln Pro Gly His
305                 310                 315                 320

Val Lys Ile Leu Glu Lys Trp Leu Lys Ser Tyr Arg Pro Gln Glu Leu
```

```
            325                 330                 335
Phe Asp Glu Thr Gly Lys Leu Leu Ala Glu Leu Ala Glu Leu Ala Pro
        340                 345                 350
Gln Gly Ala Arg Arg Met Gly Ala Asn Pro His Ala Asn Gly Gly Met
        355                 360                 365
Leu Leu Arg Asp Leu Arg Leu Pro Asp Phe Arg Asp Tyr Ala Val Lys
        370                 375                 380
Val Ala Asn Pro Gly Thr Val Ser Ala Glu Ala Thr Arg Thr Gln Gly
385                 390                 395                 400
Glu Phe Ile Arg Asp Val Val Lys Leu Asn Ala Thr Asn Phe Arg Val
        405                 410                 415
Phe Ser Pro Asp Glu Thr Ala Ser Asn Arg Trp Gly Ala Val Phe Glu
        420                 425                 430
Val Thr Asn Arg Cys Ser Thr Ala Glu Ile Val Pro Gly Asp His
        435                 440                 445
Val Ala Pro Asp Gly Arg Val Met Glu Met Leu Ser Glu His Gln Cys
    450                 455                 460
Glu Gly Trp Leu Glu Gly Tyr Leu Leu Thr Gly Arg His Gly Phe Phe
465                 470                 475                 480
Ser Cys Tyr Glu Ala Phe Ile His Ile Ile Asp Ser Met Phe Asn Gln
                485                 490                 495
His Ala Lys Trp Leu Lys Val Ala Asn Glu Ile Pro Trp Arg Arg Pro
        500                 505                 510
Ile Ala Ser Leu Asn Tyr Leu Leu Ser Ser His Val Trp Arg Gln Asp
        515                 520                 525
His Asn Gly Phe Ser His Gln Asp Pro Gly Phe Ile Asp His Val Ile
    530                 535                 540
Asn Lys Lys Ala Glu Ile Ile Arg Ile Tyr Leu Pro Pro Asp Ala Asn
545                 550                 555                 560
Thr Leu Leu Ser Val Thr Asp His Cys Leu Arg Ser Arg Asn Tyr Val
                565                 570                 575
Asn Val Ile Val Ala Gly Lys Gln Pro Gln Pro Gln Trp Leu Asp Met
            580                 585                 590
Asp Ala Ala Ile Lys His Cys Thr Ala Gly Ile Gly Ile Trp Glu Trp
        595                 600                 605
Ala Ser Asn Asp Gln Gly Glu Glu Pro Asp Val Val Met Ala Cys Ala
        610                 615                 620
Gly Asp Ala Pro Thr Ile Glu Thr Leu Ala Ala Val Glu Leu Leu Trp
625                 630                 635                 640
Lys His Phe Pro Glu Leu Lys Ile Arg Val Ile Asn Val Val Asp Leu
                645                 650                 655
Met Ser Leu Gln Pro Gln Ser Glu His Pro His Gly Leu Ser Asp Lys
            660                 665                 670
Asp Phe Asp Gly Leu Phe Thr Lys Asp Lys Pro Ile Ile Phe Ala Tyr
            675                 680                 685
His Gly Tyr Pro Trp Leu Ile His Arg Leu Thr Tyr Arg Arg Thr Asn
        690                 695                 700
His Asp Asn Leu His Val Arg Gly Tyr Lys Glu Glu Gly Thr Thr Ser
705                 710                 715                 720
Thr Pro Phe Asp Met Val Val Met Asn Asp Leu Asp Arg Phe His Leu
                725                 730                 735
Val Ala Asp Val Ile Asp Arg Val Pro Gln Leu Gly Ser Arg Ala Ala
            740                 745                 750
```

Tyr Val Lys Gln Ala Ile Arg Asp Lys Leu Ile Glu His Lys Gln Tyr
            755                 760                 765

Ile Asn Gln Tyr Gly Glu Asp Met Pro Glu Ile Arg Asn Trp Lys Trp
    770                 775                 780

Lys Gly Ser Ser Val
785

<210> SEQ ID NO 16
<211> LENGTH: 825
<212> TYPE: PRT
<213> ORGANISM: Schizosaccharomyces pombe 972h-

<400> SEQUENCE: 16

Met Ala Thr Gln Asn Asp Ile Pro Asn Ser Thr Pro Glu Asp Leu Ala
1               5                   10                  15

Lys Gln Val Glu Ile Ala Glu Lys His Pro Asp Pro Ala Met Pro
            20                  25                  30

Ser Arg Leu Pro Asp Ser Leu Lys Thr Leu Glu Ala Lys Ile Asp Thr
        35                  40                  45

Ser Lys Ile Thr Asp Glu Glu Val Ala Asn Val His Arg Phe Gln Arg
50                  55                  60

Ala Cys Asp Tyr Leu Ala Ala Ser Leu Ile Phe Leu Ser Asn Gly Leu
65                  70                  75                  80

Tyr Thr Gly Gly Asp Leu Glu Glu Lys Asp Ile Lys Thr Arg Leu Leu
                85                  90                  95

Gly His Trp Gly Thr Cys Pro Gly Leu Ser Ile Val Tyr Ser His Cys
            100                 105                 110

Asn Arg Ile Ile Asn Lys Tyr Asp Leu Asn Met Leu Phe Val Val Gly
        115                 120                 125

Pro Gly His Gly Ala Pro Ala Ile Leu Ser Ala Leu Phe Leu Glu Asp
130                 135                 140

Ser Leu Gly Pro Phe Tyr Pro Arg Tyr Gln Phe Thr Lys Glu Gly Leu
145                 150                 155                 160

Asn Asn Leu Ile Asn Thr Phe Ser Leu Pro Gly Gly Phe Pro Ser His
                165                 170                 175

Val Asn Ala Glu Val Pro Gly Ala Ile His Glu Gly Gly Glu Leu Gly
            180                 185                 190

Tyr Ala Leu Ser Val Ser Tyr Gly Ala Val Leu Asp Arg Pro Asp Leu
        195                 200                 205

Ile Val Thr Cys Val Val Gly Asp Gly Glu Ala Glu Thr Gly Pro Thr
210                 215                 220

Ala Thr Ser Trp His Ala His Lys Phe Leu Asp Pro Ala Glu Ser Gly
225                 230                 235                 240

Ala Val Ile Pro Val Leu Glu Leu Asn Gly Tyr Lys Ile Ser Glu Arg
                245                 250                 255

Thr Ile Tyr Gly Cys Met Asp Asp Ser Glu Leu Leu Ser Leu Phe Ser
            260                 265                 270

Gly Phe Gly Tyr Glu Val Ala Ile Val Asn Asp Thr Pro Asp Gln Asn
        275                 280                 285

Arg Val Met Ala Ala Thr Met Asp Trp Ala Val Glu Arg Ile His Asp
290                 295                 300

Ile Gln His Arg Ala Arg Val Asn Arg Glu Glu Ile Lys Pro Arg Trp
305                 310                 315                 320

Pro Met Ile Ile Leu Arg Thr Pro Lys Gly Lys Gly Cys Pro Lys Tyr

-continued

```
                    325                 330                 335
Leu Asn Gly Lys Phe Leu Glu Gly Thr Phe Arg Ala His Gln Val Pro
                340                 345                 350
Leu Lys Leu Ala Arg Thr Asp Thr Asn Gln Arg Asn Leu Leu Lys Asp
                355                 360                 365
Trp Leu Asn Ser Tyr Asn Cys Gln Asp Phe Leu Asp Glu His Gly Leu
            370                 375                 380
Pro Thr Lys Gly Ile Thr Glu His Leu Pro Pro Arg Glu Lys Arg Met
385                 390                 395                 400
Gly Gln Arg His Glu Thr Tyr Asn Ser Tyr Leu Pro Leu Lys Val Pro
                405                 410                 415
Asp Trp Lys Lys Tyr Gly Val Lys Lys Gly Glu Thr Thr Ser Ala Thr
                420                 425                 430
Ser Val Val Gly Gln Tyr Leu Asp Glu Leu Leu Val Thr Asn Asp Ser
                435                 440                 445
Thr Leu Arg Ile Phe Ser Pro Asp Glu Leu Glu Ser Asn Lys Leu Asp
            450                 455                 460
Gly Ala Leu Lys His Ser Tyr Arg Thr Met Gln Thr Asp Pro Glu Leu
465                 470                 475                 480
Met Ala Lys Arg Gly Arg Val Thr Glu Val Leu Ser Glu His Leu Cys
                    485                 490                 495
Gln Gly Phe Met Gln Gly Tyr Thr Leu Thr Gly Arg Thr Ala Ile Phe
                500                 505                 510
Pro Ser Tyr Glu Ala Phe Met Thr Ile Val Val Ser Met Leu Val Gln
            515                 520                 525
Tyr Ser Lys Phe Leu Lys Met Gly Leu Glu Thr Gly Trp His Gly Lys
        530                 535                 540
Phe Gly Ser Leu Asn Tyr Val Thr Ser Ser Thr Trp Ala Arg Gln Glu
545                 550                 555                 560
His Asn Gly Phe Ser His Gln Ser Pro Arg Phe Ile Thr Thr Met Leu
                565                 570                 575
Ser Leu Lys Pro Gly Val Ser Arg Val Tyr Phe Pro Pro Asp Ala Asn
                580                 585                 590
Cys Phe Leu Ala Thr Val Ala Arg Cys Met Lys Ser Glu Asn Thr Ile
            595                 600                 605
Asn Leu Met Val Ser Ser Lys Asn Pro Gln Pro Ala Tyr Leu Ser Val
        610                 615                 620
Glu Glu Ala Glu His His Cys Lys Ala Gly Ala Ser Val Trp Lys Phe
625                 630                 635                 640
Ala Ser Thr Asp Asn Gly Glu Asn Pro Asp Val Val Ile Ala Gly Val
                645                 650                 655
Gly Asn Glu Ile Met Phe Glu Val Val Lys Ala Ala Glu Met Leu Gln
                660                 665                 670
Asn Asp Ile Pro Glu Leu Arg Val Arg Val Ile Asn Val Thr Asp Leu
            675                 680                 685
Met Val Leu Ser Ser Leu His Pro His Gly Met Asn Pro Ala Glu Phe
        690                 695                 700
Asp Ser Leu Phe Thr Lys Asp Arg His Val His Phe Asn Tyr His Gly
705                 710                 715                 720
Tyr Val Met Asp Leu Lys Ala Leu Leu Phe Asp Arg Ile Gln Gly Thr
                725                 730                 735
Arg Val Thr Met Glu Gly Tyr Arg Glu Glu Gly Thr Thr Thr Pro
                740                 745                 750
```

```
Phe Asn Met Met Met Cys Asn Asn Thr Ser Arg Tyr His Val Ala Arg
        755                 760                 765

Met Ala Leu Gln His Ala Leu His Asn Pro Thr Val Ala Val Asn Cys
770                 775                 780

Asn Met Leu Cys Ala Lys Tyr Ala Trp Lys Leu Glu Glu Ile Glu Asn
785                 790                 795                 800

Tyr Ile Met Glu Asn Lys Asp Asp Pro Glu Ile Tyr Ala Ala Pro
            805                 810                 815

Val Phe Lys Asn Lys Thr Ser Thr Leu
            820                 825

<210> SEQ ID NO 17
<211> LENGTH: 788
<212> TYPE: PRT
<213> ORGANISM: Leuconostoc mesenteroides subsp. mesenteroides J18

<400> SEQUENCE: 17

Met Asn Ile Asp Ser Thr Asp Tyr Leu Asn Asn Leu Asp Ala Tyr Trp
1               5                   10                  15

Arg Ala Thr Asn Tyr Leu Ser Val Gly Gln Leu Tyr Leu Leu Asp Asn
            20                  25                  30

Pro Leu Leu Lys Glu Lys Leu Thr Ala Glu Gln Val Lys Ile His Pro
        35                  40                  45

Ile Gly His Trp Gly Thr Ile Pro Ser Gln Asn Phe Ile Tyr Ala His
    50                  55                  60

Leu Asn Arg Ala Ile Asn Lys Phe Asn Leu Asn Met Phe Tyr Ile Glu
65                  70                  75                  80

Gly Pro Gly His Gly Gly Gln Val Met Ile Ser Asn Ala Tyr Leu Asp
                85                  90                  95

Gly Ser Tyr Thr Glu Ala Phe Pro Glu Ile Thr Gln Asp Glu Ala Gly
            100                 105                 110

Met Gln Lys Met Phe Lys Arg Phe Ser Phe Pro Gly Gly Val Ala Ser
        115                 120                 125

His Ala Asp Pro Lys Val Pro Gly Ser Ile His Glu Gly Gly Ala Leu
    130                 135                 140

Gly Tyr Ser Ile Leu His Gly Ala Gly Ala Val Leu Asp Asn Pro Asp
145                 150                 155                 160

Leu Ile Ala Ala Val Val Gly Asp Gly Glu Ala Glu Thr Ala Pro
                165                 170                 175

Leu Ala Thr Ser Trp His Val Asn Lys Phe Leu Asn Pro Lys Asn Asp
            180                 185                 190

Gly Thr Val Leu Pro Ile Leu Asn Leu Asn Gly Phe Lys Ile Ala Asn
        195                 200                 205

Pro Thr Val Leu Ser Arg Glu Ser Asp Glu Thr Leu Thr Glu Tyr Phe
    210                 215                 220

His Ser Leu Gly Trp His Pro Tyr Phe Val Ser Ser Phe Asp Lys Pro
225                 230                 235                 240

Ile Met Gln Val His Glu Glu Met Ala Lys Thr Met Asp Thr Val Phe
                245                 250                 255

Thr Glu Ile Lys Asp Ile Arg Glu Lys Ala Val Gln Gln Thr Asn Glu
            260                 265                 270

Glu Ile Thr Arg Pro Leu Trp Pro Met Ile Val Leu Arg Ser Pro Lys
        275                 280                 285

Gly Trp Thr Gly Pro Lys Thr Trp Asp Asp Asn Pro Ile Glu Asn Ser
```

```
            290                 295                 300
Phe Arg Ala His Gln Ile Pro Ile Pro Ala Asp Gln Asn His Pro Glu
305                 310                 315                 320

Tyr Ile Pro Gln Leu Val Asp Trp Leu Gln Ser Tyr Lys Pro Asp Glu
                325                 330                 335

Leu Phe Asp Glu Asn Gly Gln Leu Thr Gln Ser Ile Gln Glu Val Leu
                340                 345                 350

Pro Lys Lys Glu Leu Arg Met Ala Asn Asn Ser Val Thr Asn Ala Gly
                355                 360                 365

Lys Ile Lys Pro Leu Ile Leu Pro Asp Ile Asp Asn Tyr Leu Val Glu
                370                 375                 380

Asn Asn Gln Pro Gly Asn Asn Leu Ala Gln Asp Ala Ile Leu Leu Gly
385                 390                 395                 400

Asp Tyr Leu Arg Asp Ile Ile Lys Leu Asn Pro Thr Asn Phe Arg Gly
                405                 410                 415

Phe Gly Pro Asp Glu Thr Ala Ser Asn Arg Phe Gln Asp Ile Phe Glu
                420                 425                 430

Thr Thr Asn Arg Gln Trp Leu Leu Pro Ile Lys Glu Pro Asn Asp Gln
                435                 440                 445

Phe Met Ala Pro Glu Gly Arg Ile Ile Asp Ser Met Leu Ser Glu His
            450                 455                 460

Tyr Asp Glu Gly Met Leu Glu Ala Tyr Thr Leu Thr Gly Arg His Gly
465                 470                 475                 480

Phe Phe Ala Ser Tyr Glu Val Phe Ile Arg Glu Val Asp Asp Met Ile
                485                 490                 495

Val Gln His Phe Lys Trp Leu Asn His Ser His Asp Val Ser Trp Arg
                500                 505                 510

Lys Asp Val Pro Ala Leu Asn Ile Ile Ala Asp Ser Thr Val Phe Gln
                515                 520                 525

Gln Asp His Asn Gly Tyr Ser His Gln Asp Pro Gly Val Thr Thr Met
                530                 535                 540

Leu Tyr Glu Lys Gln Pro Asp Phe Ile Arg Glu Phe Phe Pro Ala Asp
545                 550                 555                 560

Ala Asn Ser Leu Val Ala Thr Phe Glu His Ala Ala Gln Ala Thr Gln
                565                 570                 575

Gln Ile Asn Tyr Ile Val Ala Ser Lys His Pro Arg Leu Gln Trp Phe
                580                 585                 590

Ser Pro Thr Glu Ala Lys Gln Leu Val Thr Gln Gly Leu Arg Val Ile
                595                 600                 605

Asp Trp Ala Ser Thr Asp Lys Gly Glu Lys Pro Asp Ile Ile Ile Ser
                610                 615                 620

Ser Ala Gly Ser Glu Pro Thr Thr Glu Ser Leu Ala Ala Ile Gln Ile
625                 630                 635                 640

Leu His Glu His Ile Pro Ser Leu Lys Ile Arg Tyr Ile Asn Val Leu
                645                 650                 655

Asp Leu Phe Lys Leu Arg Ala Asp Ala Ser Tyr Gly Leu Ser Asp Asp
                660                 665                 670

Glu Phe Asp Ala Tyr Phe Thr Asp Thr Pro Val Leu Phe Ala Phe
                675                 680                 685

His Gly Tyr Glu Pro Met Ile Glu Ser Ile Phe Phe Lys Arg His Asn
                690                 695                 700

His His Leu Ala Val His Gly Tyr Arg Glu Val Gly Asp Ile Thr Thr
705                 710                 715                 720
```

Pro Phe Asp Met Arg Val Leu Asn Lys Ile Asp Arg Phe Asn Leu Val
            725                 730                 735

Lys Ala Ala Ile Asn Leu Leu Pro Glu Asn Ile Arg Thr Lys Gln Ala
            740                 745                 750

Ala Leu Val Gln Glu Met Thr Asp Lys Leu Asp Leu His Val Ala Tyr
            755                 760                 765

Thr Arg Ser Lys Gly Thr Asp Leu Pro Glu Val Glu Asp Trp Arg Trp
770                 775                 780

Gln Pro Leu Lys
785

<210> SEQ ID NO 18
<211> LENGTH: 694
<212> TYPE: PRT
<213> ORGANISM: Streptomyces sp. SA3_actG

<400> SEQUENCE: 18

Met Ser Asp Ala Ser Val Ser Ala Val Ala Asp Ala Leu Asp Tyr Leu
1               5                   10                  15

Cys Leu Ala Gln Leu Tyr Leu Arg Glu Asn Pro Leu Leu Ala Arg Pro
            20                  25                  30

Leu Thr Ser Ala His Val Lys Trp Arg Pro Ala Gly His Trp Gly Val
            35                  40                  45

Cys Pro Pro Val Asn Arg Met Leu Ala Leu Gly Pro Val Gln Ala
            50                  55                  60

Ser Val Pro Asp Gly Tyr Glu Leu Arg Val Leu His Gly Ala Gly His
65                  70                  75                  80

Ala Gly Pro Ser Ala Leu Ala His Ala Tyr Leu Thr Gly Arg Leu Gly
                85                  90                  95

Arg Val Tyr Pro Asp Leu Ile Gln Ser Pro Ala Gly Leu Leu Glu Leu
                100                 105                 110

Val Ser Gly Phe Pro Arg Pro Glu Thr Gly Gly Glu Ile Thr Pro Met
            115                 120                 125

Ile Pro Gly His Leu His Thr Gly Gly Gln Leu Gly Ala Ala Leu Ala
            130                 135                 140

Ile Gly Gln Gly Thr Val Leu Asp Ala Pro Arg Arg Leu Thr Val Ala
145                 150                 155                 160

Leu Leu Gly Asp Gly Glu Cys Glu Thr Gly Thr Thr Ala Ala Ser Trp
                165                 170                 175

Leu Ala Ser Arg Ala Leu Arg Gly Thr Gly Asp His Gly Thr Val Leu
            180                 185                 190

Pro Val Val Leu Leu Asn Gly Met Arg Met Gly Gly Pro Ser Val Leu
            195                 200                 205

Ser Thr Leu Ser Arg Asp Glu Leu Thr Ala Tyr Phe Thr Gly Leu Gly
            210                 215                 220

His Gln Pro Val Tyr Ser Asp Gly Leu Asp Ile Ala Gln Leu Arg Gln
225                 230                 235                 240

Ala Ile Ala Glu Ala Val Ala Asp Ala Arg Pro Leu Gly Val Pro Gly
                245                 250                 255

Pro Ser Ser Val Leu Val Leu Thr Leu Glu Lys Gly Tyr Gly Ala Pro
            260                 265                 270

Ala Gly Leu Ala Ala Thr Pro Ala Val His Lys Thr Pro Leu His Asp
            275                 280                 285

Pro Ala Ser Val Pro Ser Glu Phe Asp Leu Leu Ser Glu Trp Leu Ala

```
              290                 295                 300
Ser Tyr Arg Pro Ala Gln Leu Leu Thr Pro Gly Gly Arg Pro Arg Pro
305                 310                 315                 320

His Leu Leu Pro Ala Leu Pro Arg Pro Arg Pro Glu Pro Gly Gly Leu
                325                 330                 335

Ser Ala Pro Arg Gly Cys Ile Ala Ala Ser Thr Gln Val Ala Asp His
            340                 345                 350

Ala Ser Gly Arg Ala Phe Ala Gln Val Val Pro Asp Val Leu Arg Ala
        355                 360                 365

Arg Ala Ala Gln Gly Pro Phe Arg Val Phe Ser Pro Asp Glu Leu Ala
    370                 375                 380

Ser Asn Arg Ile Asp Leu Thr Asp Gly Gln Gly Arg Thr Val Pro Trp
385                 390                 395                 400

Ala Val Glu Val Leu Ser Glu Glu Leu Cys His Ala Trp Ala Gln Gly
                405                 410                 415

Tyr Thr Glu Thr Gly Arg His Ala Leu Val Ala Thr Tyr Glu Ala Phe
            420                 425                 430

Ala Pro Ile Thr Leu Ser Leu Val Gln Gln Gln Leu Lys His Arg Ser
        435                 440                 445

Ala Arg Arg His Ala Gly Leu Ala Pro Leu Pro Ser Leu Val Tyr Leu
    450                 455                 460

Leu Thr Ser Leu Gly Trp His Asn Thr Phe Thr His Gln Asn Pro Ser
465                 470                 475                 480

Leu Ala Thr Ala Leu Leu Ala Gly Gly Asp Pro Ser Val His Val Leu
                485                 490                 495

Thr Pro Ala Asp Pro Ala Arg Ala Ala Ala Leu Thr Phe Ala Leu
            500                 505                 510

Arg Lys Leu Asp Arg Cys Thr Leu Val Ile Ala Asp Lys His Ala Thr
        515                 520                 525

Val Gln His Pro Leu Glu Thr Leu Asp Glu Glu Leu Arg His Gly Met
    530                 535                 540

Ala Ile Trp Pro His Leu Ser Ala Pro Gly Pro Glu Glu Pro Asp Leu
545                 550                 555                 560

Ile Leu Ala Ser Ala Gly Asp Leu Pro Ala Glu Val Leu Thr Thr Leu
                565                 570                 575

Ala Arg Arg Leu Arg Asp Asp Arg Arg Glu Leu Arg Leu Arg Tyr Val
            580                 585                 590

His Ile His Asp Leu Thr Ala Leu Ala Glu Glu Asp Thr Arg Ser Leu
        595                 600                 605

Ala Leu Gly Pro Ala Ala Phe Thr His His Phe Gly Thr Thr Ala Pro
    610                 615                 620

Leu Val Leu Ala Thr Ser Gly His Pro Ala Asp Ile His Ala Leu Phe
625                 630                 635                 640

Gly Arg Arg His Pro Gly Pro Arg Leu Thr Val Leu Gly Tyr Arg Asp
                645                 650                 655

Pro Gly Arg Pro Val Ser Gln Thr His Leu Arg Gln Leu Cys Gly Leu
            660                 665                 670

Asp Asp Thr Ser Leu Trp His Leu Ala Thr Thr Leu Ile Asp Ala Ser
        675                 680                 685

Lys Glu Ile Pro Ala Pro
    690

<210> SEQ ID NO 19
```

<211> LENGTH: 796
<212> TYPE: PRT
<213> ORGANISM: Lactobacillus buchneri ATCC 11577

<400> SEQUENCE: 19

```
Met Thr Val Asp Tyr Asp Ser Lys Glu Tyr Leu Asp Leu Leu Asp Lys
1               5                   10                  15

Tyr Trp Arg Ala Ala Asn Tyr Leu Ser Val Gly Gln Leu Tyr Leu Arg
            20                  25                  30

Asp Asn Pro Leu Leu Lys Arg Pro Leu Lys Ser Asp Val Lys Ile
        35                  40                  45

Lys Pro Ile Gly His Trp Gly Thr Ile Val Ser Gln Asn Phe Ile Tyr
50                  55                  60

Ala Gln Leu Asn Arg Ala Ile Asn Lys Tyr Asp Leu Asn Met Phe Tyr
65                  70                  75                  80

Ile Glu Gly Ser Gly His Gly Gly Gln Val Met Val Ser Asn Ser Tyr
                85                  90                  95

Leu Asp Gly Ser Tyr Ser Asp Ile Tyr Pro Asn Ile Ser Gln Asp Glu
            100                 105                 110

Lys Gly Met Gln Lys Leu Phe Lys Gln Phe Ser Phe Pro Gly Gly Val
        115                 120                 125

Ala Ser His Ala Ala Pro Glu Thr Pro Gly Ser Ile His Glu Gly Gly
130                 135                 140

Glu Leu Gly Tyr Ser Leu Ser His Gly Thr Gly Ala Ile Leu Asp Asn
145                 150                 155                 160

Pro Asp Val Ile Ala Ala Val Glu Ile Gly Asp Gly Glu Ser Glu Thr
                165                 170                 175

Gly Pro Leu Ala Ala Ser Trp Phe Ser Asp Lys Phe Ile Asn Pro Ile
            180                 185                 190

Thr Asp Gly Ala Val Leu Pro Ile Ile Asn Met Asn Gly Phe Lys Ile
        195                 200                 205

Ser Asn Pro Thr Ile Leu Ser Arg Met Ser Asp Ala Asp Leu Thr Asp
210                 215                 220

Tyr Phe Lys Gly Met Gly Trp Glu Ala His Phe Val Glu Ala Thr Ala
225                 230                 235                 240

Asp Thr Asp His Ala Lys Val Glu Ala Glu Phe Ala Lys Thr Leu Asp
                245                 250                 255

Thr Val Ile Glu Lys Ile Lys Ser Ile Gln Lys Asn Ala Arg Glu Asn
            260                 265                 270

Glu Thr Pro Asp Asn Val Lys Leu Pro Val Trp Pro Met Ile Ile Phe
        275                 280                 285

Arg Ser Pro Lys Gly Trp Thr Gly Pro Lys Lys Asp Leu Asp Gly Asn
290                 295                 300

Pro Ile Glu Gly Ser Phe Arg Ala His Gln Val Pro Ile Pro Val Asp
305                 310                 315                 320

Ala Asn Asp Met Glu His Ala Asp Glu Leu Val Asp Trp Leu Lys Ser
                325                 330                 335

Tyr Lys Pro Glu Glu Leu Phe Asp Glu Asn Gly Thr Leu Lys Pro Glu
            340                 345                 350

Leu Arg Ala Leu Ala Pro Lys Gly Glu Gln Arg Met Ser Val Asn Pro
        355                 360                 365

Ile Thr Asn Gly Gly Ile Lys Pro Glu Pro Leu Lys Leu Pro Asn Val
370                 375                 380

Arg Asp Phe Glu Val Lys Phe Asp Lys Arg Gly Thr Glu Gln Lys Gln
```

```
                385                 390                 395                 400
            Asp Met Ile Glu Trp Ser Lys Trp Leu Asp Ala Val Ala Lys Leu Asn
                            405                 410                 415

Pro Thr Thr Phe Arg Gly Phe Gly Pro Asp Glu Thr Lys Ser Asn Arg
                            420                 425                 430

Leu Tyr Ser Leu Leu Asp Asp Gly Lys Arg Gln Trp Met Glu Asp Ile
                        435                 440                 445

His Glu Pro Tyr Asp Glu Asp Leu Ala Asn His Gly Arg Val Ile Asp
                450                 455                 460

Ser Gln Leu Ser Glu His Gln Ala Glu Gly Trp Leu Glu Gly Tyr Val
            465                 470                 475                 480

Leu Thr Gly Arg His Gly Phe Phe Ala Thr Tyr Glu Ser Phe Gly Arg
                            485                 490                 495

Val Val Asp Ser Met Leu Thr Gln His Phe Lys Trp Leu Arg Lys Ala
                            500                 505                 510

Ser Glu Gln Tyr Trp Arg Lys Gln Tyr Pro Ser Leu Asn Phe Val Asp
                        515                 520                 525

Thr Ser Thr Val Phe Gln Gln Asp His Asn Gly Tyr Thr His Gln Asp
                530                 535                 540

Pro Gly Leu Leu Thr His Leu Ala Glu Lys Lys Pro Glu Phe Ile Arg
            545                 550                 555                 560

Glu Tyr Leu Pro Ala Asp Ala Asn Glu Leu Leu Ala Val Gly Asp Ser
                            565                 570                 575

Ala Phe Arg Thr Tyr Glu Lys Ile Asn Leu Ile Val Thr Ser Lys His
                            580                 585                 590

Pro Arg Arg Gln Trp Tyr Ser Met Asp Glu Ala Gln Asn Leu Val Lys
                        595                 600                 605

Asn Gly Leu Gly Tyr Ile Asp Trp Ala Ser Thr Asp Gln Gly Gln Glu
                610                 615                 620

Pro Asp Val Val Phe Ala Ala Gly Ser Glu Pro Asn Leu Glu Ala
            625                 630                 635                 640

Leu Ala Ala Ile Ser Ile Leu Asn Lys Glu Phe Pro Glu Leu Lys Ile
                            645                 650                 655

Arg Phe Ile Asn Val Val Asp Ile Leu Lys Leu Asn Ser Pro Lys Lys
                            660                 665                 670

Asp Pro Arg Gly Leu Ser Asp Glu Phe Asp Asn Leu Phe Thr Thr
                        675                 680                 685

Asp Lys Pro Val Ile Phe Ala Trp His Gly Phe Glu Asp Met Ile Lys
                690                 695                 700

Asp Ile Phe Phe Asp Arg His Asn His Asn Leu Tyr Val His Gly Tyr
            705                 710                 715                 720

Arg Glu Asn Gly Asp Ile Thr Thr Pro Phe Asp Met Arg Val Leu Asn
                            725                 730                 735

Glu Leu Asp Arg Phe His Leu Ala Ala Asp Ala Ile Arg His Ile Pro
                            740                 745                 750

Ala Tyr Ala Val Lys Gly Gly Tyr Phe Ile Gln Arg Met Asn Asn Ile
                        755                 760                 765

Val Asp Lys His Asn Arg Tyr Ile Arg Glu Val Gly Thr Asp Leu Pro
                770                 775                 780

Glu Val Thr Ser Trp Asn Trp Glu Pro Leu Asn Lys
            785                 790                 795

<210> SEQ ID NO 20
```

```
<211> LENGTH: 792
<212> TYPE: PRT
<213> ORGANISM: Streptomyces ghanaensis ATCC 14672

<400> SEQUENCE: 20
```

| | | | | | | | | | | | | | | |
|---|---|---|---|---|---|---|---|---|---|---|---|---|---|---|
|Met|Pro|Glu|Ala|Pro|Asp|Thr|Arg|Thr|Val|Leu|Ser|Asp|Glu|Leu|
|1| | | |5| | | | |10| | | | |15|
|Arg|Thr|Leu|Asp|Ala|His|Trp|Arg|Ala|Ala|Asn|Tyr|Leu|Ala|Ala|Gly|
| | | | |20| | | | |25| | | | |30|
|Gln|Ile|Tyr|Leu|Leu|Ala|Asn|Pro|Leu|Leu|Thr|Glu|Pro|Leu|Arg|Pro|
| | |35| | | | |40| | | | |45| | |
|Glu|His|Ile|Lys|Pro|Arg|Leu|Leu|Gly|His|Trp|Gly|Thr|Ser|Pro|Gly|
|50| | | | |55| | | | |60| | | | |
|Leu|Asn|Leu|Val|Tyr|Thr|His|Leu|Asn|Arg|Val|Ile|Ala|Gly|Arg|Gly|
|65| | | | |70| | | | |75| | | | |80|
|Leu|Asp|Ala|Leu|Cys|Ile|Trp|Gly|Pro|Gly|His|Gly|Gly|Pro|Ser|Val|
| | | | |85| | | | |90| | | | |95| |
|Leu|Ala|Asn|Ser|Trp|Leu|Glu|Gly|Ser|Tyr|Gly|Glu|Thr|Tyr|Pro|Asp|
| | | |100| | | | |105| | | | |110| | |
|Val|Gly|Arg|Asp|Ala|Ala|Gly|Met|Glu|Arg|Leu|Phe|Arg|Gln|Phe|Ser|
| | |115| | | | |120| | | | |125| | | |
|Phe|Pro|Gly|Gly|Val|Pro|Ser|His|Val|Ala|Pro|Glu|Val|Pro|Gly|Ser|
|130| | | | |135| | | | |140| | | | |
|Val|His|Glu|Gly|Gly|Glu|Leu|Gly|Tyr|Ser|Leu|Ala|His|Ala|Tyr|Gly|
|145| | | | |150| | | | |155| | | | |160|
|Ala|Ala|Leu|Asp|His|Pro|Gly|Leu|Leu|Val|Ala|Cys|Val|Ile|Gly|Asp|
| | | | |165| | | | |170| | | | |175| |
|Gly|Glu|Ala|Glu|Thr|Gly|Pro|Leu|Ala|Ala|Ser|Trp|His|Ser|Asn|Lys|
| | | |180| | | | |185| | | | |190| | |
|Phe|Leu|Asp|Pro|Val|His|Asp|Gly|Ala|Val|Leu|Pro|Ile|Leu|His|Leu|
| | |195| | | | |200| | | | |205| | | |
|Asn|Gly|Tyr|Lys|Ile|Ala|Asn|Pro|Thr|Val|Leu|Ala|Arg|Leu|Pro|Glu|
| |210| | | | |215| | | | |220| | | | |
|Asp|Glu|Leu|Asp|Ser|Leu|Leu|Arg|Gly|Tyr|Gly|His|Glu|Pro|Ile|His|
|225| | | | |230| | | | |235| | | | |240|
|Val|Ser|Gly|Asp|Asp|Pro|Ala|Ala|Val|His|Arg|Ala|Met|Ala|His|Ala|
| | | |245| | | | |250| | | | |255| | |
|Met|Asp|Thr|Ala|Leu|Asp|Arg|Ile|Ala|Glu|Val|Gln|Arg|Ala|Ala|Arg|
| | |260| | | | |265| | | | |270| | | |
|Glu|Asp|Gly|Val|Thr|Glu|Arg|Ala|Arg|Thr|Pro|Val|Ile|Val|Leu|Arg|
| |275| | | | |280| | | | |285| | | | |
|Thr|Pro|Lys|Gly|Trp|Thr|Gly|Pro|Ala|Glu|Val|Asp|Gly|Lys|Pro|Val|
|290| | | | |295| | | | |300| | | | | |
|Glu|Gly|Thr|Trp|Arg|Ala|His|Gln|Val|Pro|Leu|Ala|Gly|Val|Arg|Asp|
|305| | | | |310| | | | |315| | | | |320|
|Asn|Pro|Glu|His|Leu|Arg|Gln|Leu|Glu|Ala|Trp|Leu|Arg|Ser|Tyr|Arg|
| | | | |325| | | | |330| | | | |335| |
|Pro|Glu|Glu|Leu|Phe|Asp|Asp|Ala|Gly|Arg|Pro|Val|Ala|Asp|Val|Leu|
| | | |340| | | | |345| | | | |350| | |
|Ala|Cys|Leu|Pro|Glu|Gly|Asp|Arg|Arg|Leu|Gly|Ser|Thr|Pro|Tyr|Ala|
| | |355| | | | |360| | | | |365| | | |
|Asn|Gly|Gly|Leu|Leu|Val|Arg|Glu|Leu|Pro|Met|Pro|Ala|Leu|Asp|Asp|
| |370| | | | |375| | | | |380| | | | |
|Phe|Ala|Val|Pro|Val|Asp|Lys|Pro|Gly|Thr|Thr|Leu|His|Glu|Pro|Thr|

```
            385                 390                 395                 400
        Arg Ile Leu Gly Gly Leu Leu Glu Arg Ile Met Arg Asp Thr Ala Asp
                        405                 410                 415

Arg Arg Asp Phe Arg Leu Val Gly Pro Asp Glu Thr Ala Ser Asn Arg
                        420                 425                 430

Leu Glu Ala Val Tyr Asp Ala Ser Gly Lys Ala Trp Gln Ala Gly Thr
                        435                 440                 445

Leu Asp Val Asp Glu His Leu Asp Arg His Gly Arg Val Met Glu Val
                        450                 455                 460

Leu Ser Glu His Leu Cys Gln Gly Trp Leu Glu Gly Tyr Leu Leu Thr
        465                 470                 475                 480

Gly Arg His Gly Leu Phe Ser Cys Tyr Glu Ala Phe Val His Ile Val
                        485                 490                 495

Asp Ser Met Val Asn Gln His Ile Lys Trp Leu Lys Thr Ser Arg Glu
                        500                 505                 510

Leu Pro Trp Arg Ala Pro Ile Ala Ser Leu Asn Tyr Leu Leu Thr Ser
                        515                 520                 525

His Val Trp Arg Gln Asp His Asn Gly Phe Ser His Gln Asp Pro Gly
        530                 535                 540

Phe Val Asp His Val Leu Asn Lys Ser Pro Glu Val Val Arg Val Tyr
        545                 550                 555                 560

Leu Pro Pro Asp Ala Asn Thr Leu Leu Ser Val Ala Asp His Ala Leu
                        565                 570                 575

Arg Ser Arg Asp Tyr Val Asn Val Val Ala Gly Lys Gln Pro Cys
                        580                 585                 590

Phe Asp Trp Leu Ser Ile Asp Glu Ala Arg Val His Cys Ala Arg Gly
                        595                 600                 605

Ala Gly Ile Trp Glu Trp Ala Gly Thr Glu Asn Gly Gly Ala Pro Asp
                        610                 615                 620

Val Val Leu Ala Cys Ala Gly Asp Val Pro Thr Gln Glu Val Leu Ala
        625                 630                 635                 640

Ala Ala Gln Leu Leu Arg Arg His Leu Pro Glu Leu Ala Val Arg Val
                        645                 650                 655

Val Asn Val Val Asp Ile Ala Arg Leu Met Pro Arg Glu Glu His Pro
                        660                 665                 670

His Gly Met Thr Asp Phe Glu Tyr Asp Gly Leu Phe Thr Ala Asp Lys
                        675                 680                 685

Pro Val Ile Phe Ala Tyr His Gly Tyr Pro Trp Leu Ile His Arg Leu
                        690                 695                 700

Ala Tyr Arg Arg Asn Gly His Pro Asn Leu His Val Arg Gly Tyr Lys
        705                 710                 715                 720

Glu Ser Gly Thr Thr Thr Thr Pro Phe Asp Met Val Val Arg Asn Asp
                        725                 730                 735

Leu Asp Arg Tyr Arg Leu Val Met Asp Val Ile Asp Arg Val Pro Gly
                        740                 745                 750

Leu Ala Val Arg Ala Ala Val Arg Gln Arg Met Ala Asp Ala Arg
                        755                 760                 765

Thr Arg His His Ala Trp Ile Arg Glu His Gly Thr Asp Leu Pro Glu
                        770                 775                 780

Val Ala Glu Trp Ser Trp Asn Ala
        785                 790

<210> SEQ ID NO 21
```

```
<211> LENGTH: 802
<212> TYPE: PRT
<213> ORGANISM: Cyanothece sp. PCC 8802

<400> SEQUENCE: 21

Met Val Ala Thr Pro Glu Arg Pro Thr Leu Glu Gln Thr Pro Leu Ser
1               5                   10                  15

Ala Glu Glu Leu Arg Gln Ile Gln Ala Tyr Trp Arg Ala Cys Asn Tyr
            20                  25                  30

Leu Ala Val Gly Met Ile Tyr Leu Arg Asp Asn Pro Leu Leu Lys Asp
        35                  40                  45

Pro Leu Thr Glu Asp His Val Lys Asn Arg Leu Leu Gly His Trp Gly
    50                  55                  60

Ser Ser Pro Gly Leu Ser Phe Ile Tyr Ile His Leu Asn Arg Leu Ile
65                  70                  75                  80

Lys Lys Tyr Gly Leu Asp Val Ile Tyr Met Ala Gly Pro Gly His Gly
                85                  90                  95

Ala Pro Gly Ile Leu Gly Pro Val Tyr Leu Glu Gly Thr Tyr Ser Glu
            100                 105                 110

Thr Tyr Pro Asp Lys Ser Glu Asp Glu Glu Gly Met Lys Lys Phe Phe
        115                 120                 125

Lys Gln Phe Ser Phe Pro Gly Gly Ile Gly Ser His Cys Thr Pro Glu
    130                 135                 140

Thr Pro Gly Ser Ile His Glu Gly Gly Glu Leu Gly Tyr Ser Leu Ser
145                 150                 155                 160

His Ala Tyr Gly Ala Ala Leu Asp Asn Pro Asp Leu Ile Val Ala Ala
                165                 170                 175

Val Val Gly Asp Gly Glu Ala Glu Thr Gly Pro Leu Ala Thr Ala Trp
            180                 185                 190

His Ser Asn Lys Phe Ile Asn Pro Ile Arg Asp Gly Ala Val Leu Pro
        195                 200                 205

Ile Leu His Leu Asn Gly Tyr Lys Ile Ala Asn Pro Thr Ile Leu Ala
    210                 215                 220

Arg Ile Ser His Glu Glu Leu Glu Tyr Leu Phe Lys Gly Tyr Gly Tyr
225                 230                 235                 240

Lys Pro Tyr Phe Val Glu Gly Ser Asp Pro Glu Val Met His Gln Lys
                245                 250                 255

Met Ala Ala Thr Leu Glu Thr Ala Ile Ala Glu Ile Lys His Ile Gln
            260                 265                 270

Gln Glu Ala Arg Thr Ser Gly Val Ala Lys Arg Pro Ile Trp Pro Met
        275                 280                 285

Ile Val Leu Arg Ser Pro Lys Gly Trp Thr Gly Pro Ala Ser Val Asp
    290                 295                 300

Gly Lys Lys Thr Glu Asp Phe Trp Arg Ser His Gln Val Pro Leu Ser
305                 310                 315                 320

Gly Met His Gly Asn Pro Ala His Ile Lys Val Leu Glu Asp Trp Leu
                325                 330                 335

Lys Ser Tyr Thr Pro Glu Glu Leu Phe Asp Glu Asn Gly Thr Leu Ile
            340                 345                 350

Pro Glu Leu Lys Glu Leu Ala Pro Thr Gly His His Arg Met Ser Ala
        355                 360                 365

Asn Pro His Ala Asn Gly Gly Leu Leu Arg Lys Asp Leu Lys Met Pro
    370                 375                 380

Asp Phe Arg Asn Tyr Gly Val Glu Val Ala Lys Pro Gly Thr Val Glu
```

```
385                 390                 395                 400
Val Gly Asn Thr Ala Leu Leu Gly Asn Phe Leu Arg Asp Val Met Ala
                405                 410                 415

Asn Asn Met Thr Asn Phe Arg Val Phe Gly Pro Asp Glu Thr Ala Ser
                420                 425                 430

Asn Arg Leu Asn Ala Ile Tyr Glu Ile Ser Lys Lys Val Trp Met Gly
                435                 440                 445

Glu Ile Leu Pro Glu Asp Ala Asp Gly Thr Glu Ile Thr Thr Asp Gly
        450                 455                 460

Arg Val Met Glu Met Leu Ser Glu His Thr Leu Gln Gly Trp Leu Glu
465                 470                 475                 480

Gly Tyr Leu Leu Thr Gly Arg His Gly Phe His Thr Tyr Glu Ala
                485                 490                 495

Phe Ala His Val Val Asp Ser Met Phe Asn Gln His Ala Lys Trp Leu
                500                 505                 510

Asp Ile Cys Lys Asn Glu Val Pro Trp Arg Ala Ser Val Ser Ser Leu
                515                 520                 525

Asn Ile Leu Leu Ser Ser Thr Val Trp Arg Gln Asp His Asn Gly Phe
        530                 535                 540

Ser His Gln Asp Pro Gly Tyr Val Asp Leu Val Thr Asn Lys Ser Ala
545                 550                 555                 560

Asp Val Val Arg Val Tyr Phe Pro Pro Asp Ala Asn Cys Leu Leu Ser
                565                 570                 575

Val Ala Asn His Cys Leu Lys Ser Thr Asp Tyr Val Asn Val Ile Val
                580                 585                 590

Ser Asp Lys Gln Ile His Leu Gln Tyr Leu Asn Met Asp Gln Ala Ile
        595                 600                 605

Lys His Cys Thr Lys Gly Ile Gly Ile Trp Asp Trp Ala Ser Asn Asp
        610                 615                 620

Asp Cys Gly Thr Glu Pro Asp His Pro Asp Val Ile Met Ala Ser Cys
625                 630                 635                 640

Gly Asp Val Ala Thr Lys Glu Ala Leu Ala Ala Thr Ala Ile Leu Arg
                645                 650                 655

Glu Glu Phe Pro Asp Leu Lys Val Arg Phe Ile Asn Val Val Asp Leu
                660                 665                 670

Phe Lys Leu Gln Ser Glu Ile Glu His Pro His Gly Leu Ser Asp Arg
                675                 680                 685

Asp Phe Asp Asn Leu Phe Thr Lys Asp Lys Pro Ile Ile Phe Asn Phe
        690                 695                 700

His Gly Tyr Pro Trp Leu Ile His Lys Leu Thr Tyr Arg Arg Thr Asn
705                 710                 715                 720

His His Asn Leu His Val Arg Gly Tyr Lys Glu Lys Gly Asn Ile Asn
                725                 730                 735

Thr Pro Leu Glu Leu Ala Ile Asn Asn Gln Ile Asp Arg Phe Asn Leu
                740                 745                 750

Val Ile Asp Val Ile Asn Arg Val Pro Lys Leu Gly Ser Ala Ala Ala
                755                 760                 765

Tyr Val Tyr Glu Arg Met Lys Asn Ala Ile Ile Glu His Arg Ala Tyr
                770                 775                 780

Ala Tyr Glu His Gly Ile Asp Lys Pro Glu Ile Asn Asn Trp Lys Trp
785                 790                 795                 800

Pro His
```

<210> SEQ ID NO 22
<211> LENGTH: 812
<212> TYPE: PRT
<213> ORGANISM: Neosartorya fischeri NRRL 181

<400> SEQUENCE: 22

```
Met Thr Ser Lys Gly Glu Ile Glu Ser Leu Ser Ala Tyr Gly Val Ala
1               5                   10                  15

Arg Ser Thr Ile Gln Gly Thr Pro Leu Ser Gln Asp Glu Leu Arg Lys
            20                  25                  30

Met Asp Ala Tyr Phe Arg Ala Ser Met Tyr Leu Cys Leu Gly Met Leu
        35                  40                  45

Tyr Leu Arg Asp Asn Pro Leu Leu Lys Glu Pro Leu Lys Val Glu His
    50                  55                  60

Leu Lys Ala Arg Leu Leu Gly His Trp Gly Ser Asp Ala Gly Gln Ser
65                  70                  75                  80

Phe Thr Trp Ile His Met Asn Arg Leu Ile Lys Lys Tyr Asp Leu Asp
                85                  90                  95

Val Leu Phe Ile Ser Gly Pro Gly His Gly Ala Pro Gly Ile Leu Ser
            100                 105                 110

Gln Ser Tyr Leu Glu Gly Val Tyr Thr Glu Val Tyr Pro Glu Lys Thr
        115                 120                 125

Gln Asp Glu Lys Gly Leu Gln Arg Phe Phe Lys Gln Phe Ser Phe Pro
    130                 135                 140

Gly Gly Ile Gly Ser His Ala Thr Pro Glu Thr Pro Gly Ser Ile His
145                 150                 155                 160

Glu Gly Gly Glu Leu Gly Tyr Ser Ile Ser His Ala Phe Gly Thr Val
                165                 170                 175

Phe Asp His Pro Asn Leu Ile Thr Leu Thr Met Val Gly Asp Gly Glu
            180                 185                 190

Ala Glu Thr Gly Pro Leu Ala Thr Ser Trp His Ser Asn Lys Phe Leu
        195                 200                 205

Asn Pro Ile Thr Asp Gly Ala Val Leu Pro Val Leu His Leu Asn Gly
    210                 215                 220

Tyr Lys Ile Asn Asn Pro Thr Ile Leu Ala Arg Ile Ser His Glu Glu
225                 230                 235                 240

Leu Glu Met Leu Leu Lys Gly Tyr Gly Trp Thr Pro Tyr Phe Val Glu
                245                 250                 255

Gly Ser Asp Arg Glu Ser Met His Gln Ala Met Ala Ala Thr Leu Glu
            260                 265                 270

His Cys Val Leu Glu Ile Lys Lys Ile Gln Lys Gln Ala Arg Glu Ser
        275                 280                 285

Asn Lys Ala Phe Arg Pro Leu Trp Pro Met Ile Val Leu Arg Ser Pro
    290                 295                 300

Lys Gly Trp Ser Ala Pro Arg Glu Ile Asp Gly Lys Tyr Leu Glu Gly
305                 310                 315                 320

Phe Trp Arg Ala His Gln Ile Pro Ile Thr Asp Val Gln Ser Lys Pro
                325                 330                 335

Glu His Leu Lys Val Leu Glu Asn Trp Met Lys Ala Tyr Lys Pro Glu
            340                 345                 350

Glu Val Phe Asp Lys Asn Gly Thr Leu Ile Pro Glu Leu Lys Glu Leu
        355                 360                 365

Ala Pro Thr Gly Thr Ser Arg Met Ser Ala Asn Pro Val Gly Asn Gly
    370                 375                 380
```

```
Gly Leu Leu Arg Arg Pro Met Asp Leu Pro Asp Phe Arg Asp Tyr Ala
385                 390                 395                 400

Leu Thr Asp Ile Glu Pro Gly Val Thr Ile Arg Pro Ser Met Ser Asn
            405                 410                 415

Met Ser Lys Tyr Leu Arg Asp Val Val Ala Arg Asn Met Thr Thr Phe
        420                 425                 430

Arg Val Phe Gly Pro Asp Glu Thr Glu Ser Asn Lys Leu Ala Glu Ile
    435                 440                 445

Tyr Lys Ala Gly Lys Lys Val Trp Met Ala Glu Tyr Phe Lys Glu Asp
450                 455                 460

Glu Asp Gly Gly Asn Leu Asp Met Gln Gly Arg Val Met Glu Ile Leu
465                 470                 475                 480

Ser Glu His Thr Cys Glu Gly Trp Leu Glu Gly Tyr Ile Leu Ser Gly
            485                 490                 495

Arg His Gly Met Leu Asn Ser Tyr Glu Pro Phe Ile His Val Ile Asp
        500                 505                 510

Ser Met Val Asn Gln His Cys Lys Trp Ile Glu Lys Cys Leu Ala Val
    515                 520                 525

Glu Trp Arg Ala Lys Val Ser Ser Leu Asn Ile Leu Leu Thr Ala Thr
530                 535                 540

Val Trp Arg Gln Asp His Asn Gly Phe Thr His Gln Asp Pro Gly Phe
545                 550                 555                 560

Leu Asp Val Val Ala Asn Lys Ser Pro Glu Val Val Arg Ile Tyr Leu
            565                 570                 575

Pro Pro Asp Gly Asn Thr Leu Leu Ser Thr Met Asn His Cys Phe Arg
        580                 585                 590

Ser Val Asn Tyr Val Asn Val Ile Val Ala Asp Lys Gln Glu His Val
    595                 600                 605

Gln Phe Leu Asn Met Glu Glu Ala Ile Glu His Cys Thr Lys Gly Val
610                 615                 620

Gly Ile Trp Asp Trp Ala Ser Asn Asp Gln Gly Cys Glu Pro Asp Val
625                 630                 635                 640

Val Met Ala Ser Cys Gly Asp Val Ala Thr His Glu Ala Leu Ala Ala
            645                 650                 655

Thr Ala Leu Leu Arg Glu His Leu Pro Gln Leu Lys Val Arg Phe Val
        660                 665                 670

Asn Val Val Asp Leu Phe Arg Leu Ile Ser Asp Ile Asn His Pro His
    675                 680                 685

Gly Met Pro Asp Arg Gln Trp Gly Ala Ile Phe Thr Thr Asp Lys Pro
690                 695                 700

Ile Ile Phe Asn Phe His Ser Tyr Pro Trp Leu Ile His Arg Leu Thr
705                 710                 715                 720

Tyr Lys Arg Pro Gly Gln His Asn Leu His Val Arg Gly Tyr Lys Glu
            725                 730                 735

Lys Gly Asn Ile Asp Thr Pro Phe Glu Leu Ala Val Arg Asn Gln Thr
        740                 745                 750

Asp Arg Tyr Ser Leu Ala Ile Asp Ala Ile Asp Arg Ile Pro Ser Leu
    755                 760                 765

Gly Asn Thr Ala Ser Gly Val Arg Glu Arg Leu Ile Asn Leu Gln Leu
770                 775                 780

Ala Ala Lys Asn Lys Ala Phe Asp Asp Gly Ile Asp Pro Asp Tyr Ile
785                 790                 795                 800
```

Arg Asn Trp Thr Trp Asp Tyr Pro Arg Lys Lys Cys
            805                 810

<210> SEQ ID NO 23
<211> LENGTH: 787
<212> TYPE: PRT
<213> ORGANISM: Enterococcus faecium TX1330

<400> SEQUENCE: 23

Met Asp Tyr Ser Ser Lys Glu Tyr Phe Asp Lys Met Thr Ala Trp Trp
1               5                   10                  15

Arg Ala Ala Asn Tyr Leu Ser Val Gly Gln Ile Tyr Leu Lys Asp Asn
                20                  25                  30

Pro Leu Leu Arg Arg Thr Leu Lys Pro Glu Asp Val Lys Lys His Pro
            35                  40                  45

Ile Gly His Trp Gly Thr Ile Pro Gly Gln Asn Phe Ile Tyr Val His
        50                  55                  60

Leu Asn Arg Val Ile Asn Lys Tyr Asp Leu Asn Met Phe Tyr Ile Glu
65                  70                  75                  80

Gly Pro Gly His Gly Gly Gln Val Met Val Ser Asn Ala Tyr Leu Asp
                85                  90                  95

Gly Ser Tyr Thr Glu Ile Tyr Pro Glu Val Thr Glu Asp Glu Thr Gly
            100                 105                 110

Met Gln Lys Leu Phe Lys Arg Phe Ser Phe Pro Gly Gly Ile Ala Ser
        115                 120                 125

His Ala Ala Pro Glu Thr Pro Gly Ser Ile His Glu Gly Gly Glu Leu
    130                 135                 140

Gly Tyr Ser Leu Ser His Gly Val Gly Ala Val Leu Asp Asn Pro Glu
145                 150                 155                 160

Val Ile Ser Ala Val Ile Gly Asp Gly Glu Ala Glu Thr Gly Pro
                165                 170                 175

Leu Ala Gly Ser Trp Phe Ser Asn Val Phe Ile Asn Pro Val Thr Asp
            180                 185                 190

Gly Ala Val Leu Pro Ile Leu His Leu Asn Gly Ala Lys Ile Ala Asn
        195                 200                 205

Pro Thr Ile Leu Ala Arg Lys Ser Asp Gly Glu Leu Ala Asn Tyr Phe
    210                 215                 220

Asn Gly Leu Gly Trp Glu Pro Phe Phe Ile Glu Gly Asn Asp Pro Glu
225                 230                 235                 240

Lys Leu Asn Pro Val Met Ala Glu Lys Met Asp Gln Ala Ile Glu Lys
                245                 250                 255

Ile Lys Ser Ile Gln Lys Glu Ala Arg Leu Lys Thr Ala Ala Asp Ala
            260                 265                 270

Met Met Pro Lys Trp Pro Val Leu Ile Val Arg Thr Pro Lys Gly Trp
        275                 280                 285

Thr Gly Pro Glu Glu Trp Asp Gly Glu Pro Ile Glu Gly Thr Phe Arg
    290                 295                 300

Ala His Gln Val Pro Ile Pro Val Asp Gln Glu His Met Asp His Ala
305                 310                 315                 320

Asp Ala Leu Leu Arg Trp Leu Lys Ser Tyr Glu Pro Glu Lys Leu Phe
                325                 330                 335

Asp Ala Gln Gly Arg Ile Leu Glu Glu Ile Arg Glu Ile Ala Pro Thr
            340                 345                 350

Gly Asp His Arg Met Ala Lys Asn Pro Ile Thr Asn Gly Gly Met Asp
        355                 360                 365

```
Pro Lys Pro Leu Ile Met Pro Asp Trp Lys Arg Tyr Thr Leu Gln Phe
        370                 375                 380

Glu Lys Pro Gly Ser Val Thr Ala Glu Asp Met Thr Glu Leu Gly Lys
385                 390                 395                 400

Phe Val Arg Glu Ile Ile Glu Lys Asn Pro Glu Asn Phe Arg Ile Phe
                405                 410                 415

Gly Pro Asp Glu Thr Lys Ser Asn Arg Leu Asn Gln Val Phe Lys Thr
                420                 425                 430

Thr Asn Arg Gln Trp Met Glu Lys Ile Glu Pro Glu Asn Asp Glu Trp
            435                 440                 445

Leu Ser Pro Ser Gly Arg Val Ile Asp Ser Gln Leu Ser Glu His Gln
450                 455                 460

Asp Glu Gly Phe Leu Glu Gly Tyr Val Leu Thr Gly Arg His Gly Phe
465                 470                 475                 480

Phe Ala Ser Tyr Glu Ser Phe Leu Arg Val Val Asp Ser Met Leu Thr
                485                 490                 495

Gln His Phe Lys Trp Met Arg Lys Ser Arg Asp Leu Ser Trp Arg Asn
                500                 505                 510

Asn Tyr Pro Ser Leu Asn Leu Ile Ala Ser Ser Thr Val Phe Gln Gln
            515                 520                 525

Asp His Asn Gly Tyr Ser His Gln Asp Pro Gly Ile Leu Thr His Leu
530                 535                 540

Ala Glu Lys Lys Ala Glu Phe Ile Arg Glu Tyr Leu Pro Ala Asp Ala
545                 550                 555                 560

Asn Thr Leu Leu Ala Val Met Asp Lys Ala Phe Arg Ser Ser Glu Lys
                565                 570                 575

Ile Asn Leu Ile Ile Ser Ser Lys His Pro Arg Ala Gln Phe Tyr Ser
                580                 585                 590

Ala Glu Glu Ala Ala Val Leu Val Asn Glu Gly Leu Lys Ile Ile Asp
            595                 600                 605

Trp Ala Ser Thr Ala Lys Glu Glu Pro Glu Leu Val Ile Ala Ala
            610                 615                 620

Ala Gly Thr Glu Ser Asn Leu Glu Ala Leu Ala Ala Val Thr Leu Leu
625                 630                 635                 640

Leu Glu Glu Phe Pro Lys Leu Lys Ile Arg Phe Ile Asn Val Val Asp
                645                 650                 655

Leu Leu Lys Leu Arg His Pro Ser Gln Asp Pro Arg Gly Leu Ser Asp
                660                 665                 670

Glu Glu Phe Asp Lys Tyr Phe Thr Lys Asp Lys Pro Ile Leu Phe Ala
            675                 680                 685

Phe His Gly Tyr Glu Thr Leu Ile Arg Thr Ile Phe Phe Asp Arg His
            690                 695                 700

Asn His His Leu Met Ile His Gly Tyr Lys Glu Asn Gly Asp Ile Thr
705                 710                 715                 720

Thr Pro Phe Asp Met Arg Val Val Asn Glu Leu Asp Arg Tyr His Leu
                725                 730                 735

Ala Lys Asp Ala Ala Leu Lys Ile Lys Gly Ser Gln Ala Glu Asp Phe
                740                 745                 750

Ala Lys Lys Met Asp Gln Lys Leu Gln Glu His Gln Asn Tyr Ile Arg
            755                 760                 765

Glu Asn Gly Ile Asp Leu Pro Glu Val Leu Asp Trp Lys Trp Lys Asn
770                 775                 780
```

-continued

Leu Asp Gln
785

<210> SEQ ID NO 24
<211> LENGTH: 791
<212> TYPE: PRT
<213> ORGANISM: Listeria grayi DSM 20601

<400> SEQUENCE: 24

Met Thr Asp Tyr Ser Ser Pro Asn Tyr Leu Ala Lys Val Asp Ala Trp
1               5                   10                  15

Trp Arg Ala Ala Asp Phe Ile Ser Val Gly Gln Leu Tyr Leu Lys Gly
            20                  25                  30

Asn Pro Leu Leu Arg Arg Pro Leu Glu Lys Glu Asp Leu Lys Val His
        35                  40                  45

Pro Ile Gly His Trp Gly Thr Ile Ser Gly Gln Asn Phe Ile Tyr Ala
    50                  55                  60

His Leu Asn Arg Val Ile Asn Lys Tyr Asp Leu Asn Met Phe Tyr Ile
65                  70                  75                  80

Glu Gly Pro Gly His Gly Gly Gln Val Met Val Ser Asn Ser Tyr Leu
                85                  90                  95

Asp Gly Ser Tyr Thr Asp Thr Tyr Pro Thr Ile Thr Gln Asp Glu Val
            100                 105                 110

Gly Leu Thr Lys Leu Tyr Lys Gln Phe Ser Phe Pro Gly Gly Ile Ala
        115                 120                 125

Ser His Ala Ala Pro Glu Thr Pro Gly Ser Leu His Glu Gly Gly Glu
    130                 135                 140

Leu Gly Tyr Ala Leu Ser His Ala Thr Gly Ser Ile Leu Asp Asn Pro
145                 150                 155                 160

Asp Val Ile Ala Ala Thr Val Ile Gly Asp Gly Glu Ala Glu Thr Gly
                165                 170                 175

Pro Leu Ser Ala Gly Trp Phe Ser Asn Thr Phe Ile Asn Pro Val Asn
            180                 185                 190

Asp Gly Ala Val Leu Pro Ile Leu Tyr Leu Asn Gly Ala Lys Ile Ser
        195                 200                 205

Asn Pro Thr Ile Leu Ser Arg Lys Thr Asp Lys Glu Leu Thr Ser Phe
    210                 215                 220

Phe Gln Gly Leu Gly Trp Asp Pro Ile Phe Val Glu Gly Glu Asp Pro
225                 230                 235                 240

Ala Lys Val His Pro Leu Met Ala Glu Lys Leu Asp Gln Ala Ile Glu
                245                 250                 255

Lys Ile Lys Ala Ile Gln Thr Glu Ala Arg Lys Glu Ala Ala Asp Lys
            260                 265                 270

Ala Thr Met Pro Thr Trp Pro Val Ile Leu Phe Arg Thr Pro Lys Gly
        275                 280                 285

Trp Thr Gly Pro Lys Glu Trp Asn Asn Glu Pro Ile Glu Gly Ser Phe
    290                 295                 300

Arg Ala His Gln Val Pro Ile Pro Val Asp Gln His His Phe Asp His
305                 310                 315                 320

Val Asp Ala Leu Glu Asn Trp Leu Gln Ser Tyr Arg Pro Glu Glu Leu
                325                 330                 335

Phe Thr Glu Glu Gly Ser Leu Lys Glu Ile Lys Ser Leu Ala Pro
            340                 345                 350

Lys Asn Arg Met Ala Thr Asn Pro Ile Thr Asn Gly Gly Ile Asp Pro
        355                 360                 365

Gln Pro Leu Arg Leu Pro Ser Trp Lys Asp Tyr Ala Val Glu Thr Ala
    370                 375                 380

Asn Lys Asp Val Ile Thr Gln Asp Met Ile Glu Leu Gly Gly Phe Val
385                 390                 395                 400

Arg Asp Ile Val Lys Glu Asn Pro Asp Asn Phe Arg Ile Phe Gly Pro
                405                 410                 415

Asp Glu Thr Lys Ser Asn Arg Leu Asn Lys Val Phe Glu Val Thr Asn
                420                 425                 430

Arg Gln Trp Met Ser Lys Ala Glu Phe Pro Arg Asp Glu Trp Leu Ala
                435                 440                 445

Pro Ala Gly Arg Ile Ile Asp Gly Gln Leu Ser Glu His Gln Ala Glu
    450                 455                 460

Gly Phe Leu Glu Gly Tyr Val Leu Thr Gly Arg His Gly Phe Phe Ala
465                 470                 475                 480

Ser Tyr Glu Ser Phe Leu Arg Val Val Asp Ser Met Leu Thr Gln His
                485                 490                 495

Phe Lys Trp Leu Arg Lys Ala Lys Glu Gln Thr Trp Arg Asn Ser Tyr
                500                 505                 510

Pro Ser Leu Asn Val Ile Ala Thr Ser Thr Val Phe Gln Gln Asp His
    515                 520                 525

Asn Gly Tyr Thr His Gln Asp Pro Gly Val Leu Thr His Leu Ala Glu
530                 535                 540

Lys Lys Pro Glu Phe Ile Arg Glu Tyr Leu Pro Ala Asp Thr Asn Ser
545                 550                 555                 560

Leu Leu Ala Val Met Asn Glu Ala Phe Arg Ser Glu Glu Leu Ile Asn
                565                 570                 575

Leu Ile Val Ser Ser Lys His Pro Arg Pro Gln Phe Tyr Ser Ala Glu
                580                 585                 590

Glu Ala Glu Ile Leu Val Lys Asp Gly Leu Lys Ile Ile Asp Trp Ala
    595                 600                 605

Ser Thr Val Ser Glu Ala Glu Glu Pro Asp Val Val Ile Ala Ser Ala
    610                 615                 620

Gly Thr Glu Pro Asn Leu Glu Ala Leu Ala Ala Val Thr Leu Leu Asn
625                 630                 635                 640

Glu Ala Phe Pro Ser Leu Lys Ile Arg Phe Ile Asn Ile Val Asp Ile
                645                 650                 655

Leu Lys Leu Arg His Pro Asp Ile Asp Pro Arg Gly Leu Thr Asp Glu
                660                 665                 670

Glu Phe Asp Arg Tyr Phe Thr Thr Asp Lys Pro Ile Ile Phe Ala Phe
                675                 680                 685

His Ser Tyr Glu Gly Met Val Arg Asp Ile Phe Asn Arg His Asn
    690                 695                 700

His Asn Leu Phe Ile His Gly Tyr Arg Glu Asn Gly Asp Ile Thr Thr
705                 710                 715                 720

Pro Phe Asp Met Arg Val Leu Ser Glu Met Asp Arg Phe His Leu Ala
                725                 730                 735

Lys Asp Ala Ala Glu Ala Val Tyr Gly Glu Ile Ala Thr Ser Phe Ala
                740                 745                 750

Ala Glu Met Asp Ala Val Leu Ser Lys His His Phe Ile Arg Glu
    755                 760                 765

Asn Gly Glu Asp Leu Pro Glu Val Glu Asn Trp Lys Trp Gln Ala Leu
770                 775                 780

Lys Thr Asp Leu Leu Glu Val
785             790

<210> SEQ ID NO 25
<211> LENGTH: 788
<212> TYPE: PRT
<213> ORGANISM: Enterococcus casseliflavus EC30

<400> SEQUENCE: 25

Met Lys Thr Thr Tyr Asp Thr Pro Glu Tyr Tyr Gln Lys Met Asn Ala
1               5                   10                  15

Trp Trp Arg Ala Ala Asn Tyr Leu Ser Val Gly Gln Ile Tyr Leu Lys
            20                  25                  30

Asp Asn Pro Leu Leu Arg Arg Pro Ile Glu Glu Lys Asp Leu Lys Val
        35                  40                  45

Asn Pro Ile Gly His Trp Gly Thr Ile Ala Gly Gln Asn Phe Ile Tyr
    50                  55                  60

Thr His Leu Asn Arg Val Ile Asn Lys Tyr Asp Leu Asn Met Phe Tyr
65                  70                  75                  80

Ile Glu Gly Pro Gly His Gly Gly Gln Val Met Val Ala Asn Ala Tyr
                85                  90                  95

Leu Asp Gly Ser Tyr Ser Glu Ile Tyr Pro Lys Ala Thr Gln Asp Glu
            100                 105                 110

Ala Gly Met Lys His Leu Phe Lys Thr Phe Ser Phe Pro Gly Gly Ile
        115                 120                 125

Ala Ser His Ala Ala Pro Glu Thr Pro Gly Ser Ile His Glu Gly Gly
    130                 135                 140

Glu Leu Gly Tyr Ser Ile Ala His Ala Thr Gly Ala Ile Leu Asp Asn
145                 150                 155                 160

Pro Asp Val Ile Ala Ala Val Val Val Gly Asp Gly Glu Ala Glu Thr
                165                 170                 175

Gly Pro Leu Ala Gly Ser Trp Phe Ser Asn Thr Phe Ile Asn Pro Val
            180                 185                 190

Asn Asp Gly Ala Ile Leu Pro Ile Leu His Leu Asn Gly Ala Lys Ile
        195                 200                 205

Ala Asn Pro Thr Ile Leu Ala Arg Lys Ser Asp Gln Asp Leu Thr Lys
    210                 215                 220

Tyr Phe Glu Gly Met Gly Trp Thr Pro Tyr Phe Val Glu Gly Asp Asp
225                 230                 235                 240

Pro Glu Ala Val His Pro Gln Leu Ala Gln Lys Met Asp Gln Ala Ile
                245                 250                 255

Glu Gln Ile His Ala Ile Gln Ala Glu Ala Arg Lys Gly Ser Ala Glu
            260                 265                 270

Glu Ala Ala Met Pro His Trp Pro Val Leu Ile Val Arg Thr Pro Lys
        275                 280                 285

Gly Trp Thr Gly Pro Lys Val Trp Asp Gly Glu Pro Ile Glu Gly Gly
    290                 295                 300

Phe Arg Ala His Gln Val Pro Ile Pro Val Asn Ala Lys His Met Glu
305                 310                 315                 320

His Val Asp Ala Leu Thr Asp Trp Leu Gln Ser Tyr Arg Pro Glu Glu
                325                 330                 335

Leu Phe Asp Glu Asn Gly Arg Ile Lys Ala Glu Ile Gln Glu Leu Ala
            340                 345                 350

Pro Lys Gly Glu Gln Arg Met Ala Val Asn Pro Ile Thr Asn Gly Gly
        355                 360                 365

-continued

Ile Asp Pro Gln Pro Leu Arg Leu Pro Asp Trp Gln Ala His Ala Ile
        370                 375                 380

Ala Ile Glu Thr Pro Gly Glu Thr Thr Ala Gln Asp Met Met Val Phe
385                 390                 395                 400

Gly Lys Phe Ala Arg Asp Ile Ile Lys Glu Asn Pro Asp Asn Phe Arg
                405                 410                 415

Ile Phe Gly Pro Asp Glu Ala Lys Ser Asn Arg Leu Asn His Val Phe
                420                 425                 430

Glu Val Thr Asp Arg Gln Trp Leu Glu Pro Lys His Pro Asp Tyr Asp
            435                 440                 445

Glu Trp Leu Ser Ser Val Gly Arg Val Ile Asp Ser Gln Leu Ser Glu
450                 455                 460

His Gln Ala Glu Gly Phe Leu Glu Gly Tyr Val Leu Thr Gly Arg His
465                 470                 475                 480

Gly Phe Phe Ala Ser Tyr Glu Ser Phe Leu Arg Val Val Asp Ser Met
                485                 490                 495

Ile Thr Gln His Phe Lys Trp Leu Arg Lys Ala His Asp Leu Asp Trp
                500                 505                 510

Arg Asn Pro Tyr Pro Ser Leu Asn Leu Ile Ala Ser Ser Thr Val Phe
            515                 520                 525

Gln Gln Asp His Asn Gly Tyr Thr His Gln Asp Pro Gly Ile Met Thr
        530                 535                 540

His Ile Ala Glu Lys Lys Ala Asp Phe Val Arg Val Tyr Leu Pro Ala
545                 550                 555                 560

Asp Ala Asn Ser Leu Met Ala Val Met Ala Glu Thr Leu Ala Ser Glu
                565                 570                 575

Glu Lys Ile Asn Leu Val Val Ser Ser Lys His Pro Arg Pro Gln Phe
            580                 585                 590

Tyr Ser Ala Asp Glu Ala Lys Val Leu Val Lys Asp Gly Leu Lys Val
        595                 600                 605

Ile Asp Trp Ala Ser Thr Asp Glu Gly Gln Glu Pro Asp Ile Val Ile
    610                 615                 620

Ala Ala Ala Gly Thr Glu Pro Asn Leu Glu Ala Leu Ala Ala Val Ser
625                 630                 635                 640

Leu Leu Ile Glu Ala Phe Pro Glu Leu Lys Val Arg Phe Ile Asn Val
                645                 650                 655

Val Asp Leu Leu Lys Leu Arg Arg Pro Glu Val Asp Pro Arg Gly Leu
            660                 665                 670

Ser Asp Glu Ala Phe Glu Ala Tyr Phe Thr Lys Asp Lys Pro Ile Val
        675                 680                 685

Phe Ala Phe His Gly Tyr Glu Gly Leu Ile Arg Asp Ile Phe Phe Gly
    690                 695                 700

Arg Arg Asn Gln Gln Leu His Ile His Gly Tyr Arg Glu Asn Gly Asp
705                 710                 715                 720

Ile Thr Thr Pro Phe Asp Met Arg Ile Leu Ser Glu Leu Asp Arg Phe
                725                 730                 735

His Leu Ala Lys Asp Ala Ala Glu Trp Val Tyr Gly Glu Lys Ala Thr
            740                 745                 750

Asp Phe Ala Gln Lys Met Ala Asp Thr Val Ala Tyr His His Asp Phe
        755                 760                 765

Ile Arg Glu Asn Gly Tyr Asp Ile Ala Glu Val Glu Glu Trp Glu Trp
    770                 775                 780

Lys Pro Leu Arg
785

<210> SEQ ID NO 26
<211> LENGTH: 792
<212> TYPE: PRT
<213> ORGANISM: Mycoplasma alligatoris A21JP2

<400> SEQUENCE: 26

Met Lys Lys Asn Thr Phe Asp Thr Gln Asp Tyr Leu Asp Lys Val Asp
1               5                   10                  15

Ala Trp Phe Arg Ala Ala Asn Tyr Leu Ser Val Gly Gln Met Tyr Leu
            20                  25                  30

Arg Asn Asn Pro Leu Leu Arg Ser Lys Ile Thr Ser Asp Asp Val Lys
        35                  40                  45

Val Tyr Pro Ile Gly His Trp Gly Thr Ile Pro Gly Gln Asn Phe Ala
    50                  55                  60

Tyr Ala His Leu Asn Arg Val Ile Asn Lys Tyr Asn Leu Asn Met Phe
65                  70                  75                  80

Tyr Ile Glu Gly Pro Gly His Gly Gly Gln Val Met Thr Ser Asn Ser
                85                  90                  95

Tyr Leu Asp Gly Ser Tyr Thr Glu Leu Phe Pro His Val Thr Gln Asp
            100                 105                 110

Val Ala Gly Met Lys His Leu Phe Lys Tyr Phe Ser Phe Pro Gly Gly
        115                 120                 125

Thr Ala Ser His Ala Ala Pro Glu Thr Pro Gly Ser Ile His Glu Gly
    130                 135                 140

Gly Glu Leu Gly Tyr Ser Leu Ser His Ala Thr Gly Ala Ile Leu Asp
145                 150                 155                 160

Asn Pro Asn Val Ile Ala Ala Thr Ile Val Gly Asp Gly Glu Ala Glu
                165                 170                 175

Thr Gly Pro Leu Ala Ala Ser Trp Phe Ser Asn Ser Phe Ile Asn Pro
            180                 185                 190

Val Asn Asp Gly Ala Val Leu Pro Ile Leu His Leu Asn Gly Gly Lys
        195                 200                 205

Ile Ser Asn Pro Thr Ile Leu Cys Arg Lys Ser Asn Lys Glu Leu Thr
    210                 215                 220

Asp Tyr Phe Ala Gly Met Gly Trp Glu Ala Val Phe Val Glu Gly Ser
225                 230                 235                 240

Asp Glu Lys Glu Met His Lys Val Met Ala Gln Lys Leu Asp Tyr Val
                245                 250                 255

Ile Glu Lys Ile Gln Ser Ile Gln Asn Glu Ala Arg Lys Lys Pro Ala
            260                 265                 270

Asn Gln Ala Thr Arg Pro Ile Trp Pro Met Met Val Leu Arg Thr Pro
        275                 280                 285

Lys Gly Trp Thr Gly Pro Asp Ser Trp Asn Lys Asp Lys Ile Val Gly
    290                 295                 300

Ser Phe Arg Ala His Gln Val Pro Ile Pro Val Asn Ser Ala Asn Met
305                 310                 315                 320

Glu His Ile Asp Ala Leu Leu Asp Trp Leu Lys Ser Tyr Lys Val Asp
                325                 330                 335

Asn Leu Phe Asp Lys Asn Gly Lys Leu Val Asp Glu Ile Ala Gln Ile
            340                 345                 350

Ala Pro Lys Gly Asp Gln Arg Met Gly Met Asn Pro Ile Thr Asn Gly
        355                 360                 365

-continued

Gly Leu Asn Pro Lys Lys Leu Val Met Pro Arg Trp Gln Asp Phe Ala
    370             375             380

Leu Lys Phe Ser Lys Pro Gly Glu Leu Val Asn Gln Asp Met Val Glu
385             390             395             400

Leu Gly Thr Tyr Phe Ala Lys Met Met Glu Leu Asn Lys Asp Asn Phe
            405             410             415

Arg Leu Phe Gly Pro Asp Glu Thr Lys Ser Asn Arg Leu Tyr Asn Val
        420             425             430

Phe Lys Val Thr Lys Arg Gln Trp Leu Glu Pro Ile Ser Pro Ile Leu
        435             440             445

Asp Glu Ala Leu Ser Pro Glu Gly Arg Val Ile Asp Ser Gln Leu Ser
    450             455             460

Glu His Gln Ala Glu Gly Phe Leu Gly Tyr Val Leu Thr Gly Arg
465             470             475             480

His Gly Val Phe Ala Ser Tyr Glu Ser Phe Leu Arg Val Val Asp Ser
            485             490             495

Met Leu Thr Gln His Leu Lys Trp Leu Lys Lys Ala Lys Asp Val His
        500             505             510

Trp Arg Asn Asp Tyr Pro Ser Leu Asn Val Ile Ala Thr Ser Thr Ala
    515             520             525

Phe Gln Gln Asp His Asn Gly Tyr Thr His Gln Asp Pro Gly Leu Ile
    530             535             540

Gly His Leu Ala Asp Lys Thr Pro Glu Ile Ile Arg Gln Tyr Leu Pro
545             550             555             560

Ala Asp Thr Asn Thr Leu Leu Ala Val Met Asp Lys Ser Leu Lys Glu
            565             570             575

Arg Asn Val Ile Asn His Ile Ile Ala Ser Lys Gln Pro Arg Glu Gln
        580             585             590

Phe Tyr Ser Glu Gln Glu Ala Ala Glu Leu Val Glu Lys Gly Leu Lys
    595             600             605

Val Ile Asp Trp Ala Ser Thr Thr Lys Gly Asn Glu Glu Pro Glu Leu
    610             615             620

Val Val Val Ala Ala Gly Thr Glu Pro Asn Leu Glu Ala Leu Ala Ala
625             630             635             640

Val Thr Ile Leu Asn Lys Glu Tyr Pro Ser Leu Lys Ile Arg Phe Val
            645             650             655

Asn Val Val Asp Leu Met Lys Leu Arg His Pro Ser Leu Asp Pro Arg
            660             665             670

Gly Leu Ser Asp Lys Glu Phe Asp Ala Ile Phe Thr Ser Asn Lys Pro
    675             680             685

Ile Val Phe Ala Phe His Gly Tyr Glu Gly Ile Leu Arg Asp Met Phe
    690             695             700

Phe Lys Arg Asn Asn His Asn Leu Ile Thr His Gly Tyr Arg Glu Asn
705             710             715             720

Gly Asp Ile Thr Thr Ser Phe Asp Ile Arg Gln Leu Ser His Met Asp
            725             730             735

Arg Phe His Ile Ser Ala Ser Ala Ala Lys Ala Val Tyr Gly Asn Lys
            740             745             750

Ala Gln Glu Phe Glu Asp Lys Met Ile Gln Thr Ile Asp Phe His Thr
    755             760             765

Lys Tyr Ile Arg Glu Tyr Gly Thr Asp Ile Pro Glu Val Lys Glu Trp
    770             775             780

Lys Trp Ala Asp Leu Thr Arg Lys
785                 790

<210> SEQ ID NO 27
<211> LENGTH: 785
<212> TYPE: PRT
<213> ORGANISM: Carnobacterium sp. 17-4

<400> SEQUENCE: 27

Met Lys Asn Tyr Asp Ser Lys Asp Tyr Leu Lys Val Asp Ala Phe
1               5                   10                  15

Trp Arg Ala Ala Asn Tyr Leu Ser Val Gly Gln Leu Tyr Leu Arg Asp
            20                  25                  30

Asn Pro Leu Leu Gln Arg Pro Leu Lys Ser Thr Asp Val Lys Ala His
            35                  40                  45

Pro Ile Gly His Trp Gly Thr Ile Ser Gly Gln Asn Phe Ile Tyr Ala
            50                  55                  60

His Leu Asn Arg Val Ile Asn Lys Tyr Asp Leu Asn Met Phe Tyr Ile
65                  70                  75                  80

Glu Gly Pro Gly His Gly Gly Gln Val Met Ile Ser Asn Ala Tyr Leu
                    85                  90                  95

Asp Gly Ser Tyr Thr Glu Ile Tyr Pro Asp Ile Thr Glu Asn Lys Glu
                100                 105                 110

Gly Met Lys Lys Leu Phe Lys Gln Phe Ser Ser Pro Gly Gly Val Ala
            115                 120                 125

Ser His Ala Ala Pro Glu Thr Pro Gly Ser Ile His Glu Gly Gly Glu
            130                 135                 140

Leu Gly Tyr Ser Leu Ser His Ala Thr Gly Ala Ile Leu Asp Asn Pro
145                 150                 155                 160

Asp Val Ile Ala Ala Thr Val Ile Gly Asp Gly Glu Ala Glu Thr Gly
                    165                 170                 175

Pro Leu Ala Ala Gly Trp Phe Ser Asn Asn Phe Ile Asn Pro Val Asn
                180                 185                 190

Asp Gly Ala Val Leu Pro Ile Leu Tyr Leu Asn Gly Gly Lys Ile Ser
            195                 200                 205

Asn Pro Thr Ile Leu Ala Arg Lys Ser Asn Glu Asp Leu Lys Lys Tyr
210                 215                 220

Phe Glu Gly Met Gly Trp Lys Pro Tyr Phe Val Glu Gly Thr Asp Pro
225                 230                 235                 240

Glu Lys Val His Pro Val Met Ala Asn Thr Leu Asp Val Val Ile Glu
                    245                 250                 255

Glu Ile Arg Ser Ile Gln Asn Glu Ala Arg Lys Gly Lys Ala Glu Asp
                260                 265                 270

Val Glu Met Pro His Trp Pro Val Met Ile Ile Arg Thr Pro Lys Gly
            275                 280                 285

Trp Thr Gly Pro Lys Glu Trp Asp Asn Lys Ile Glu Gly Thr Phe
290                 295                 300

Arg Ala His Gln Val Pro Ile Pro Val Asp Ala Glu His Met Glu Tyr
305                 310                 315                 320

Val Asn Lys Leu Val Asp Trp Leu Lys Ser Tyr Arg Pro Glu Glu Leu
                    325                 330                 335

Phe Thr Glu Asn Gly Lys Leu Ile Asp Asp Leu Lys Glu Leu Thr Pro
                340                 345                 350

Lys Gly Asn Lys Arg Met Ala Thr Asn Pro Ile Thr Asn Gly Gly Ile
            355                 360                 365

```
Asn Ala Lys Ala Leu Ile Ile Pro Asn Trp Lys Gln His Ala Ile Asp
        370                 375                 380

Thr Thr Ile Pro Gly Ala Val Ile Ala Gln Asp Met Asp Val Phe Gly
385                 390                 395                 400

Glu Gln Ala Arg Asp Leu Ile Val Lys Asn Pro Asn Asn Phe Arg Ile
                405                 410                 415

Phe Gly Pro Asp Glu Thr Lys Ser Asn Arg Leu Asp Lys Ile Phe Glu
            420                 425                 430

Val Thr Asn Arg Gln Trp Leu Glu Ser Lys Glu Leu Thr Asp Glu Trp
        435                 440                 445

Gln Ser Ser Ala Gly Arg Val Ile Asp Gly Gln Leu Ser Glu His Gln
450                 455                 460

Ala Glu Gly Phe Leu Glu Gly Tyr Val Leu Thr Gly Arg His Gly Phe
465                 470                 475                 480

Phe Ala Ser Tyr Glu Ser Phe Leu Arg Val Val Asp Ser Met Leu Thr
                485                 490                 495

Gln His Phe Lys Trp Leu Arg Lys Ala Thr Asp Gln Lys Trp Arg Asn
            500                 505                 510

Asn Tyr Pro Ser Leu Asn Val Ile Ala Thr Ser Thr Val Phe Gln Gln
        515                 520                 525

Asp His Asn Gly Tyr Thr His Gln Asp Pro Gly Ile Leu Thr His Leu
        530                 535                 540

Ala Glu Lys Lys Pro Glu Phe Ile Arg Glu Tyr Leu Pro Ala Asp Ala
545                 550                 555                 560

Asn Ser Leu Met Ala Val Met Asp Lys Thr Leu Gln Glu Glu Gln Leu
                565                 570                 575

Ile Asn Leu Ile Ile Ser Ser Lys His Pro Arg Pro Gln Phe Tyr Ser
            580                 585                 590

Val Glu Glu Ala Glu Ile Leu Val Lys Asp Gly Leu Lys Ile Ile Asp
        595                 600                 605

Trp Ala Ser Thr Asp Asn Asp Ser Glu Pro Asp Leu Val Ile Ala Ala
        610                 615                 620

Ala Gly Thr Glu Pro Asn Leu Glu Ala Leu Ala Ala Met Ser Ile Leu
625                 630                 635                 640

His Lys Ala Phe Pro Glu Leu Lys Ile Arg Phe Ile Asn Ile Val Asp
                645                 650                 655

Ile Leu Lys Leu Arg His Pro Asp Ile Asp Ser Arg Gly Leu Thr Asp
            660                 665                 670

Glu Lys Phe Asp Ser Tyr Phe Thr Lys Glu Gln Pro Ile Ile Phe Ala
        675                 680                 685

Phe His Gly Phe Glu Gly Leu Ile Arg Asp Ile Phe Phe Asn Arg His
        690                 695                 700

Asn His Asn Leu Arg Ile His Gly Tyr Arg Glu Asn Gly Asp Ile Thr
705                 710                 715                 720

Thr Pro Phe Asp Met Arg Val Leu Asn Glu Met Asp Arg Phe His Leu
                725                 730                 735

Ala Lys Asp Ala Ala Lys Ala Val Tyr Gly Leu Lys Ala Asn Lys Phe
            740                 745                 750

Met Gln Glu Met Glu Asn Thr Val Asn Phe His His Gln Tyr Ile Arg
        755                 760                 765

Glu Asn Gly Ile Asp Ile Pro Glu Val Ile Asn Trp Lys Trp Glu Lys
        770                 775                 780
```

Ile
785

<210> SEQ ID NO 28
<211> LENGTH: 799
<212> TYPE: PRT
<213> ORGANISM: Melissococcus plutonius ATCC 35311

<400> SEQUENCE: 28

| | | | | | | | | | | | | | | |
|---|---|---|---|---|---|---|---|---|---|---|---|---|---|---|
| Met | Glu | Lys | Asp | Lys | Tyr | Ser | Ser | Thr | Glu | Tyr | Leu | Asp | Lys | Ile | Asp |
| 1 | | | | 5 | | | | | 10 | | | | | 15 | |
| Lys | Trp | Trp | Arg | Ala | Ala | Asn | Tyr | Leu | Ser | Ile | Gly | Gln | Leu | Tyr | Leu |
| | | | 20 | | | | | 25 | | | | | 30 | | |
| Lys | Asp | Asn | Pro | Leu | Leu | Lys | Arg | Lys | Ile | Arg | Ser | Glu | Asp | Val | Lys |
| | | 35 | | | | | 40 | | | | | 45 | | | |
| Tyr | His | Pro | Ile | Gly | His | Trp | Gly | Thr | Ile | Ala | Gly | Gln | Asn | Phe | Ile |
| | 50 | | | | | 55 | | | | | 60 | | | | |
| Tyr | Ala | His | Leu | Asn | Arg | Ile | Ile | Asn | Lys | Tyr | Asp | Leu | Asn | Met | Phe |
| 65 | | | | | 70 | | | | | 75 | | | | | 80 |
| Tyr | Ile | Glu | Gly | Pro | Gly | His | Gly | Gly | Gln | Val | Met | Val | Ser | Asn | Ser |
| | | | | 85 | | | | | 90 | | | | | 95 | |
| Tyr | Leu | Asp | Gly | Ser | Tyr | Thr | Glu | Ile | Tyr | Pro | Ala | Val | Thr | Glu | Asp |
| | | | 100 | | | | | 105 | | | | | 110 | | |
| Glu | Ala | Gly | Met | Gln | Lys | Leu | Phe | Lys | Arg | Phe | Ser | Phe | Pro | Gly | Gly |
| | | 115 | | | | | 120 | | | | | 125 | | | |
| Val | Ser | Ser | His | Ala | Ala | Pro | Glu | Thr | Pro | Gly | Ser | Ile | His | Glu | Gly |
| | 130 | | | | | 135 | | | | | 140 | | | | |
| Gly | Glu | Leu | Gly | Tyr | Ser | Leu | Ser | His | Gly | Val | Gly | Ala | Ile | Leu | Asp |
| 145 | | | | | 150 | | | | | 155 | | | | | 160 |
| Asn | Pro | Glu | Val | Ile | Ser | Ala | Val | Val | Ile | Gly | Asp | Gly | Glu | Ser | Glu |
| | | | | 165 | | | | | 170 | | | | | 175 | |
| Thr | Gly | Pro | Leu | Ala | Thr | Ser | Trp | Phe | Ser | Asn | Thr | Phe | Ile | Asn | Pro |
| | | | 180 | | | | | 185 | | | | | 190 | | |
| Val | Thr | Asp | Gly | Ala | Val | Leu | Pro | Ile | Leu | His | Leu | Asn | Gly | Ala | Lys |
| | | 195 | | | | | 200 | | | | | 205 | | | |
| Ile | Ala | Asn | Pro | Thr | Ile | Leu | Gly | Arg | Lys | Ser | Asp | Lys | Glu | Leu | Glu |
| | 210 | | | | | 215 | | | | | 220 | | | | |
| Gln | Tyr | Phe | Arg | Gly | Met | Gly | Trp | Ile | Pro | Tyr | Phe | Val | Glu | Gly | Asn |
| 225 | | | | | 230 | | | | | 235 | | | | | 240 |
| Asp | Pro | Asn | Gln | Met | His | Pro | Leu | Met | Ala | Lys | Thr | Leu | Asp | Gln | Val |
| | | | | 245 | | | | | 250 | | | | | 255 | |
| Ile | Glu | Lys | Ile | His | Ser | Ile | Gln | Glu | Thr | Ala | Arg | Lys | Gln | Thr | Ala |
| | | | 260 | | | | | 265 | | | | | 270 | | |
| Glu | Thr | Ala | Ser | Ile | Gln | Lys | Trp | Pro | Leu | Ile | Val | Leu | Arg | Thr | Pro |
| | | 275 | | | | | 280 | | | | | 285 | | | |
| Lys | Gly | Trp | Thr | Gly | Pro | Lys | Glu | Trp | Asp | Gly | Lys | Pro | Ile | Glu | Val |
| | 290 | | | | | 295 | | | | | 300 | | | | |
| Thr | Phe | Arg | Ala | His | Gln | Val | Pro | Ile | Pro | Ile | Asp | Gln | Asp | His | Met |
| 305 | | | | | 310 | | | | | 315 | | | | | 320 |
| Glu | His | Val | Asp | Gln | Leu | Val | Asn | Trp | Leu | Lys | Ser | Tyr | Lys | Pro | Glu |
| | | | | 325 | | | | | 330 | | | | | 335 | |
| Glu | Leu | Phe | Asp | Glu | Thr | Gly | Arg | Leu | Asn | Ser | Glu | Ile | Arg | Ala | Ile |
| | | | 340 | | | | | 345 | | | | | 350 | | |
| Ala | Pro | Met | Asn | Asp | Lys | Arg | Met | Ala | Met | Asn | Pro | Ile | Thr | Asn | Gly |
| | | 355 | | | | | 360 | | | | | 365 | | | |

```
Gly Ile Asn Pro Lys Pro Leu Gln Met Pro Asp Trp Arg Glu Phe Asp
    370                 375                 380
Leu His Ile Ser Lys Pro Gly Glu Leu Val Ala Gln Asp Met Leu Glu
385                 390                 395                 400
Phe Gly Lys Met Val Ala Ala Ile Ile Lys Lys Asn Pro Gln Asn Phe
                405                 410                 415
Leu Ile Phe Gly Pro Asp Glu Thr Lys Ser Asn Leu Leu Asn Asp Ala
                420                 425                 430
Phe Ser Val Thr Ser Arg Gln Trp Leu Glu Pro Ile Tyr Glu Pro Gln
                435                 440                 445
Asp Glu Trp Leu Ala Pro Ser Gly Arg Ile Ile Asp Ser Gln Leu Ser
    450                 455                 460
Glu His Gln Asp Glu Gly Ile Leu Gly Tyr Val Leu Thr Gly Arg
465                 470                 475                 480
His Gly Phe Phe Ala Ser Tyr Glu Ala Phe Ile Arg Ile Val Asp Ser
                485                 490                 495
Met Ile Ala Gln His Ile Lys Trp Met Arg Lys Ala Met Asp Leu Pro
                500                 505                 510
Trp Arg Asn Gly Tyr Ser Ser Leu Asn Leu Ile Ala Ser Ser Thr Ala
                515                 520                 525
Phe Gln Gln Asp His Asn Gly Tyr Thr His Gln Asp Pro Gly Ile Leu
    530                 535                 540
Ser His Leu Ala Glu Lys Glu Ala Asp Phe Ile His Glu Tyr Val Pro
545                 550                 555                 560
Ala Asp Thr Asn Ser Leu Leu Ala Val Met Asp Lys Val Leu Lys Ser
                565                 570                 575
Gln Gly Lys Val Asn Leu Val Ile Ser Ser Lys His Pro Arg Pro Gln
                580                 585                 590
Phe Tyr Ser Pro Glu Glu Ala Gln Glu Leu Val Asn Arg Gly Leu Met
    595                 600                 605
Glu Ile Asp Trp Ala Ser Thr Val Ala Glu Asn Gly Thr Pro Glu Ile
    610                 615                 620
Val Ile Val Ala Ala Gly Thr Glu Pro Asn Met Glu Ala Leu Ala Ala
625                 630                 635                 640
Ile Asn Leu Ile Asn Gln Ser Phe Pro Lys Leu Gln Phe Arg Phe Ile
                645                 650                 655
Asn Val Val Asp Leu Leu Lys Leu Arg His Pro Ala Val Asp Ser Arg
                660                 665                 670
Gly Ile Ser Glu Val Glu Tyr Asn His Leu Phe Thr Val Asp Ser Pro
                675                 680                 685
Ile Ile Phe Val Cys Gln Gly Tyr Ser Ser Leu Ile Arg Ser Leu Phe
                690                 695                 700
Tyr Asp Arg Lys Asn Arg Pro Val Ser Ile His Ser Tyr Gln Glu Asn
705                 710                 715                 720
Gly Ala Ile Thr Thr Pro Phe Asp Met Arg Val Leu Asn Lys Ile Asp
                725                 730                 735
Arg Tyr His Leu Ala Lys Asp Ile Ala Leu Thr Ala Tyr Gly Ser Arg
                740                 745                 750
Gly Glu Asp Phe Ala Arg Ala Met Asp Thr Ile Leu Glu Lys His Asn
                755                 760                 765
Gln Tyr Ile Arg Glu Thr Gly Lys Asp Leu Pro Glu Val Leu Asn Trp
    770                 775                 780
```

```
Lys Trp Ala Pro Leu His Ile Tyr Asn Glu Asn Ile Glu Gln Asp
785                 790                 795

<210> SEQ ID NO 29
<211> LENGTH: 787
<212> TYPE: PRT
<213> ORGANISM: Tetragenococcus halophilus NBRC 12172

<400> SEQUENCE: 29

Met Ser Val Asn Ile Asp Ser Lys Glu Tyr Leu Glu Arg Met Asn Ala
1               5                   10                  15

Trp Trp Arg Ala Ala Asn Tyr Ile Ser Val Ala Gln Ile Phe Leu Arg
            20                  25                  30

Asp Asn Pro Leu Leu Arg Arg Pro Leu Glu Lys Glu Asp Ile Lys Ile
        35                  40                  45

Asn Pro Ile Gly His Trp Gly Thr Ile Ser Gly Gln Asn Phe Ile Tyr
    50                  55                  60

Val His Leu Asn Arg Val Ile Asn Lys Tyr Gly Leu Asn Met Phe Tyr
65                  70                  75                  80

Ile Glu Gly Pro Gly His Gly Gly Gln Val Met Val Ser Asn Ser Tyr
                85                  90                  95

Ile Asp Gly Ser Tyr Ser Glu Ile Tyr Pro Asp Val Thr Gln Asp Glu
            100                 105                 110

Ala Gly Leu Lys Lys Leu Phe Lys Gln Phe Ser Phe Pro Gly Gly Met
        115                 120                 125

Gly Ser His Ala Ala Pro Glu Thr Pro Gly Ser Ile His Glu Gly Gly
    130                 135                 140

Glu Leu Gly Tyr Ser Met Ser His Ala Val Gly Ala Val Leu Asp Asn
145                 150                 155                 160

Pro Asp Val Ile Ala Ala Thr Val Ile Gly Asp Gly Glu Ala Glu Thr
                165                 170                 175

Gly Pro Leu Ala Ala Ser Trp Met Ser Asn Asn Phe Ile Asn Pro Val
            180                 185                 190

Asn Asp Gly Ala Val Leu Pro Ile Leu Asn Leu Asn Gly Ala Lys Ile
        195                 200                 205

Ala Asn Pro Thr Val Leu Ala Arg Lys Ser Asp Lys Asp Leu Gln Lys
    210                 215                 220

Tyr Phe Glu Gly Leu Gly Trp Lys Pro Tyr Phe Val Glu Gly Asp Asn
225                 230                 235                 240

Pro Glu Lys Met His Pro Leu Met Ala Glu Thr Leu Asp Ala Val Ile
                245                 250                 255

Asn Glu Ile Gln Ser Ile Gln Lys Glu Ala Arg Lys Gly Ser Ala Glu
            260                 265                 270

Asp Val Thr Met Pro His Trp Pro Val Ile Val Phe Arg Thr Pro Lys
        275                 280                 285

Gly Trp Glu Gly Pro Glu Lys Trp Asp Asn Glu Gln Ile Ala Gly Thr
    290                 295                 300

Phe Arg Ala His Gln Val Pro Ile Pro Ile Asp Ala Ser His Met Glu
305                 310                 315                 320

Tyr Ala Asn Asp Leu Ala Lys Trp Leu Lys Ser Tyr Arg Pro Glu Glu
                325                 330                 335

Leu Phe Asp Glu Asn Gly Thr Ile Ile Asp Ala Ile Lys Glu Leu Ser
            340                 345                 350

Pro Lys Gly Asp Asn Arg Met Ser Val Asn Pro Ile Thr Asn Gly Gly
        355                 360                 365
```

```
Leu Asp Pro Lys Ala Leu Asn Met Pro Asp Trp His Thr His Ala Val
    370                 375                 380

Asp Thr Ser Lys Arg Gly Thr Asp Lys Ala Gln Asp Met Ser Val Leu
385                 390                 395                 400

Gly Gly Phe Ile Ala Asp Ile Met Glu Asn Asn Pro Lys Asn Phe Arg
                405                 410                 415

Ile Phe Gly Pro Asp Glu Thr Lys Ser Asn Arg Leu Asn Lys Val Phe
            420                 425                 430

Asp Val Thr Asn Arg Gln Trp Val Glu Pro Arg Glu Leu Ser Asp Glu
        435                 440                 445

Trp Gln Ser Ala Val Gly Arg Val Ile Asp Gly Gln Leu Ser Glu His
    450                 455                 460

Gln Ala Glu Gly Phe Leu Glu Gly Tyr Thr Leu Thr Gly Arg His Gly
465                 470                 475                 480

Phe Phe Ala Ser Tyr Glu Ala Phe Leu Arg Ile Val Asp Ser Met Leu
                485                 490                 495

Thr Gln His Phe Lys Trp Ile Arg Lys Ala Asn Glu Lys Ser Trp Arg
            500                 505                 510

Lys Lys Tyr Pro Ser Leu Asn Val Ile Ser Ser Thr Ala Phe Gln
        515                 520                 525

Gln Asp His Asn Gly Tyr Thr His Gln Asp Pro Gly Val Ile Thr His
    530                 535                 540

Leu Ala Glu Lys Lys Pro Glu Tyr Ile Arg Glu Tyr Phe Pro Ala Asp
545                 550                 555                 560

Ala Asn Ser Leu Met Ala Val Met Asp Lys Ala Leu Lys Asp Glu Asn
                565                 570                 575

Val Ile Asn Leu Ile Thr Ser Ser Lys His Pro Arg Pro Gln Phe Tyr
            580                 585                 590

Ser Val Glu Glu Ala Gln Glu Leu Val Asp Tyr Gly Val Lys Lys Ile
        595                 600                 605

Asp Trp Ala Ser Asn Asp Gln Asp Ser Glu Pro Asp Ile Val Phe Ala
    610                 615                 620

Ala Ala Gly Ser Glu Pro Asn Leu Glu Ala Leu Ala Ala Ile Ser Ile
625                 630                 635                 640

Leu His Glu Gln Phe Pro Glu Met Lys Ile Arg Phe Ile Asn Val Val
                645                 650                 655

Asp Leu Leu Lys Leu Arg His Pro Asp Val Asp Pro Arg Gly Leu Ser
            660                 665                 670

Asp Glu Ala Phe Asp Glu Leu Phe Thr Thr Asp Lys Pro Val Ile Phe
        675                 680                 685

Asn Phe His Gly Tyr Glu Gly Leu Ile Arg Asp Ile Phe Phe Thr Arg
    690                 695                 700

His Asn Arg Asn Leu Ser Ile His Gly Tyr Arg Glu Asp Gly Asp Ile
705                 710                 715                 720

Thr Thr Pro Phe Asp Met Arg Val Lys Asn Glu Leu Asp Arg Phe His
                725                 730                 735

Leu Ala Lys Asp Ala Ala Asn Thr Ile Tyr Ala Glu Lys Ala Ala Asp
            740                 745                 750

Phe Ile Gln Glu Met Asp Lys Thr Leu Gln Tyr His His Asp Tyr Ile
        755                 760                 765

Arg Glu Asn Gly Asp Asp Ile Ser Glu Val Gln Asn Trp Glu Trp Lys
    770                 775                 780
```

-continued

Asp Leu Lys
785

<210> SEQ ID NO 30
<211> LENGTH: 793
<212> TYPE: PRT
<213> ORGANISM: Melissococcus plutonius DAT561

<400> SEQUENCE: 30

Met Thr Lys Tyr Asp Ser Lys Glu Tyr Leu Ala Lys Val Asp Ala Phe
1               5                   10                  15

Trp Arg Ala Ala Asn Tyr Ile Ser Val Gly Gln Leu Tyr Leu Lys Asp
            20                  25                  30

Asn Pro Leu Leu Asp Arg Pro Ile Glu Thr Thr Asp Val Lys Val His
        35                  40                  45

Pro Ile Gly His Trp Gly Thr Ile Ser Gly Gln Asn Phe Ile Tyr Ala
    50                  55                  60

His Leu Asn Arg Val Ile Asn Lys Tyr Asp Leu Asn Met Phe Tyr Val
65                  70                  75                  80

Glu Gly Pro Gly His Gly Gly Gln Val Met Val Ser Asn Ser Tyr Leu
                85                  90                  95

Asp Gly Ser Tyr Thr Glu Ile Tyr Pro Glu Ile Thr Glu Asp Lys Glu
            100                 105                 110

Gly Leu Lys Lys Leu Phe Lys Gln Phe Ser Phe Pro Gly Gly Ile Ala
        115                 120                 125

Ser His Ala Ala Pro Glu Thr Pro Gly Ser Ile His Glu Gly Gly Glu
    130                 135                 140

Leu Gly Tyr Ser Ile Ser His Ala Thr Gly Ala Ile Leu Asp Asn Pro
145                 150                 155                 160

Asp Val Ile Ala Ala Thr Val Val Gly Asp Gly Glu Ala Glu Thr Gly
                165                 170                 175

Pro Leu Ser Ala Gly Trp Phe Ala Asn Thr Phe Ile Asn Pro Val Asn
            180                 185                 190

Asp Gly Ala Ile Leu Pro Ile Leu Tyr Leu Asn Gly Gly Lys Ile Ser
        195                 200                 205

Asn Pro Thr Ile Leu Glu Arg Lys Ser Asp Glu Glu Leu Thr Lys Tyr
    210                 215                 220

Phe Glu Gly Met Gly Trp Lys Pro Tyr Phe Val Glu Gly Thr Val Pro
225                 230                 235                 240

Asp Lys Val His Pro Leu Met Ala Lys Ile Leu Asp His Ile Ile Glu
                245                 250                 255

Glu Ile Lys Asp Ile Gln Lys Glu Ala Arg Lys Asp Lys Ala Glu Asn
            260                 265                 270

Ala Lys Met Pro His Trp Pro Val Leu Ile Met Arg Thr Pro Lys Gly
        275                 280                 285

Trp Thr Gly Pro Lys Ile Trp Asp Asp Glu Lys Ile Glu Gly Thr Phe
    290                 295                 300

Arg Ala His Gln Val Pro Ile Pro Val Asp Ala Glu His Met Glu His
305                 310                 315                 320

Ile Asp Ala Leu Val Asp Trp Leu Lys Ser Tyr His Pro Glu Glu Leu
                325                 330                 335

Phe Asp Lys Asn Gly Thr Leu Lys Pro Glu Leu Lys Glu Leu Val Pro
            340                 345                 350

Lys Gly Asp Arg Arg Met Ala Lys Asn Pro Ile Thr Asn Gly Gly Leu
        355                 360                 365

```
Asp Pro Lys Pro Leu Lys Met Asn Gly Trp Glu Gln His Ala Ile Asp
    370                 375                 380

Thr Ser Thr Pro Gly Met Val Thr Ala Gln Asp Met Ile Val Phe Gly
385                 390                 395                 400

Asn Tyr Val Glu Asp Leu Ile Lys Ala Asn Pro Thr Asn Phe Arg Ile
                405                 410                 415

Phe Gly Pro Asp Glu Thr Lys Ser Asn Arg Leu Asn Lys Val Phe Asp
            420                 425                 430

Ser Thr Asp Arg Gln Trp Met Glu Pro Ile Ser Asn Ala Asp Glu Trp
        435                 440                 445

Gln Ser Ser Val Gly Arg Val Ile Asp Gly Leu Ser Glu His Gln
    450                 455                 460

Ala Glu Gly Phe Leu Glu Gly Tyr Ile Leu Thr Gly Arg His Gly Phe
465                 470                 475                 480

Phe Ala Ser Tyr Glu Ser Phe Leu Arg Val Val Asp Ser Met Leu Thr
                485                 490                 495

Gln His Phe Lys Trp Leu Arg Lys Ala Lys Glu Gln Ser Trp Arg Lys
            500                 505                 510

Glu Tyr Pro Ala Leu Asn Ile Ile Ala Thr Ser Thr Val Phe Gln Gln
        515                 520                 525

Asp His Asn Gly Tyr Thr His Gln Asp Pro Gly Ile Leu Thr His Leu
    530                 535                 540

Ala Glu Lys Lys Ala Glu Tyr Ile Arg Glu Tyr Leu Pro Ala Asp Ala
545                 550                 555                 560

Asn Cys Leu Met Ala Val Met Asp Lys Ala Phe Gln Glu Asn Glu Val
                565                 570                 575

Ile Asn Leu Ile Val Ser Ser Lys His Pro Arg Pro Gln Phe Tyr Ser
            580                 585                 590

Val Thr Glu Ala Lys Glu Leu Val Asp Lys Gly Val Lys Val Ile Asp
        595                 600                 605

Trp Ala Ser Asn Asp Glu Gly Gln Thr Pro Asp Ile Val Ile Ala Ala
    610                 615                 620

Ser Gly Thr Glu Pro Asn Leu Glu Ala Leu Ala Ala Ile Thr Leu Leu
625                 630                 635                 640

Asn Lys Glu Phe Ile Asp Leu Lys Ile Arg Phe Val Asn Val Val Asp
                645                 650                 655

Ile Leu Lys Leu Arg His Pro Ser Ile Asp Pro Arg Gly Leu Thr Asp
            660                 665                 670

Glu Glu Phe Asp Ala Ile Phe Thr Lys Asp Lys Pro Ile Val Phe Ala
        675                 680                 685

Phe His Gly Phe Glu Gly Leu Ile Arg Asp Ile Phe Phe Ser Arg Ser
    690                 695                 700

Asn His Gln Leu Phe Val His Gly Tyr Arg Glu Lys Gly Asp Ile Thr
705                 710                 715                 720

Thr Pro Phe Asp Met Arg Val Leu Ser Glu Met Asp Arg Phe His Leu
                725                 730                 735

Ala Lys Asp Val Ala Asp Lys Val Tyr Asn Glu Gln Ala Ala Asp Phe
            740                 745                 750

Met Asn Arg Met Asp Glu Ile Leu Ala Phe His His Gln Tyr Ile Arg
        755                 760                 765

Lys Asn Gly Ile Asp Ile Pro Glu Val Val Asn Trp Lys Trp Glu Asp
    770                 775                 780
```

Leu Arg Lys Lys Thr Ile Cys Phe Asn
785                 790

<210> SEQ ID NO 31
<211> LENGTH: 793
<212> TYPE: PRT
<213> ORGANISM: Mycoplasma arthritidis 158L3-1

<400> SEQUENCE: 31

Met Lys Lys Thr Asn Tyr Asp Ser Asn Glu Tyr Phe Asn Leu Ile Asp
1               5                   10                  15

Lys Trp Phe Arg Ala Ala Asn Tyr Leu Ser Val Gly Gln Ile Tyr Leu
            20                  25                  30

Arg Asn Asn Pro Leu Leu Lys Thr Lys Leu Val Ala Asp Asp Val Lys
        35                  40                  45

Ile Tyr Pro Ile Gly His Trp Gly Thr Ile Pro Gly Gln Asn Phe Ile
50                  55                  60

Tyr Ala His Leu Asn Arg Val Ile Asn Lys Tyr Asp Leu Glu Met Phe
65                  70                  75                  80

Tyr Ile Glu Gly Pro Gly His Gly Gly Gln Val Met Ile Ser Asn Ser
                85                  90                  95

Tyr Leu Asp Gly Ser Tyr Thr Glu Ile Tyr Pro Glu Ile Thr Glu Asp
            100                 105                 110

Glu Ala Gly Leu Lys Thr Met Phe Lys Arg Phe Ser Phe Pro Gly Gly
        115                 120                 125

Thr Ala Ser His Ala Ala Pro Glu Thr Pro Gly Ser Ile His Glu Gly
130                 135                 140

Gly Glu Leu Gly Tyr Ala Leu Ser His Ala Thr Gly Ala Ile Leu Asp
145                 150                 155                 160

Asn Pro Asn Val Ile Ala Ala Thr Val Ile Gly Asp Gly Glu Ala Glu
                165                 170                 175

Thr Gly Pro Leu Ala Ala Gly Trp Phe Ser Asn Ser Phe Ile Asn Pro
            180                 185                 190

Val Asn Asp Gly Ala Val Leu Pro Ile Ile His Leu Asn Gly Ala Lys
        195                 200                 205

Ile Ser Asn Pro Thr Ile Leu Ser Arg Lys Ser Asn Gln Glu Leu Glu
210                 215                 220

Asn Tyr Phe Ser Gly Leu Gly Trp Glu Pro Leu Phe Val Glu Gly Asp
225                 230                 235                 240

Asp Pro Lys Leu Met His Pro Leu Met Ala Lys Lys Leu Asp Glu Ala
                245                 250                 255

Ile Glu Lys Ile Gln Met Ile Gln Ala Ser Ala Arg Lys His Lys Ala
            260                 265                 270

Ser Glu Ala Thr Arg Pro Val Trp Pro Met Leu Ile Val Arg Thr Pro
        275                 280                 285

Lys Gly Trp Thr Gly Pro Lys Asp Trp Asn Gly Glu Val Val Glu Gly
290                 295                 300

Ser Phe Arg Ala His Gln Val Pro Ile Pro Val Asn Ala Leu Asn Met
305                 310                 315                 320

Thr His Ile Asp Lys Leu Glu Ala Trp Leu Thr Ser Tyr His Pro Glu
                325                 330                 335

Glu Leu Phe Asp Lys Asn Gly Lys Ile Leu Glu Glu Ile Arg Ala Leu
            340                 345                 350

Ala Pro Lys Gly Leu Lys Arg Met Ala Val His Pro Ile Thr Asn Gly
        355                 360                 365

```
Gly Ile Asn Pro Arg Thr Leu Lys Leu Ser Ser Trp Glu Lys Phe Ala
    370                 375                 380

Thr Lys Phe Glu Thr Pro Gly Gln Ile Lys Gly Gln Asp Met Ile Glu
385                 390                 395                 400

Leu Gly Lys Tyr Phe Ala Glu Ile Ile Thr Leu Asn Lys Asp Asn Phe
                405                 410                 415

Arg Ile Phe Gly Pro Asp Glu Thr Lys Ser Asn Arg Met Asn Ala Val
                420                 425                 430

Phe Asn Val Thr Lys Arg Gln Trp Leu Glu Lys Ile Ala Pro Thr Tyr
            435                 440                 445

Asp Glu Trp Met Ser Pro Glu Gly Arg Val Ile Asp Ser Gln Leu Ser
450                 455                 460

Glu His Gln Ala Glu Gly Phe Leu Gly Tyr Val Ile Thr Gly Arg
465                 470                 475                 480

His Gly Val Phe Ala Ser Tyr Glu Ala Phe Leu Arg Val Val Asp Ser
                485                 490                 495

Met Leu Thr Gln His Met Lys Trp Met Lys Lys Ser Leu Glu Leu Pro
                500                 505                 510

Trp Arg Lys Asp Phe Pro Ser Leu Asn Val Ile Ala Thr Ser Thr Ala
            515                 520                 525

Phe Gln Gln Asp His Asn Gly Tyr Thr His Gln Asp Pro Gly Leu Leu
530                 535                 540

Gly His Leu Ala Asp Lys Arg Pro Glu Leu Ile Arg Glu Tyr Leu Pro
545                 550                 555                 560

Ala Asp Thr Asn Cys Leu Leu Ala Thr Met Glu Lys Ala Leu Lys Asp
                565                 570                 575

Arg Asn Val Ile Asn Leu Ile Val Ala Ser Lys Gln Pro Arg Glu Gln
                580                 585                 590

Phe Tyr Ser Val Glu Glu Ala Ser Glu Leu Val Gln Lys Gly Tyr Lys
            595                 600                 605

Ile Ile Asn Trp Ala Ser Asn Val Ser Lys Asn Glu Glu Pro Asp Val
610                 615                 620

Val Phe Ala Ala Gly Val Glu Pro Asn Leu Glu Ala Leu Ala Ala
625                 630                 635                 640

Ile Ser Ile Leu Asn Lys Glu Phe Pro Asn Leu Lys Ile Arg Phe Val
                645                 650                 655

Asn Val Leu Asp Leu Leu Lys Leu Lys Ser Pro Lys His Asp Pro Arg
                660                 665                 670

Gly Ile Ser Asp Glu Glu Phe Asp Gln Ile Phe Thr Lys Asn Lys Pro
            675                 680                 685

Ile Ile Phe Ala Phe His Gly Tyr Glu Gly Leu Leu Arg Asp Ile Phe
690                 695                 700

Phe Asp Arg His Asn His Asn Leu Ile Thr His Gly Tyr Arg Glu Asn
705                 710                 715                 720

Gly Asp Ile Thr Thr Ser Phe Asp Ile Arg Gln Leu Ser His Met Asp
                725                 730                 735

Arg Phe His Ile Ala Lys Asp Ala Ala Ile Ala Ala Leu Gly Lys Asp
                740                 745                 750

Gly Glu Met Phe Ala Lys Lys Met Asp Ser Lys Leu Gln Glu His Thr
            755                 760                 765

Ser Tyr Val Arg Glu Tyr Gly Tyr Asp Leu Pro Glu Val Val Asn Trp
770                 775                 780
```

```
Lys Trp Thr Asn Leu Lys Pro Ile Lys
785                 790
```

<210> SEQ ID NO 32
<211> LENGTH: 792
<212> TYPE: PRT
<213> ORGANISM: Streptococcus agalactiae NEM316

<400> SEQUENCE: 32

```
Met Ser Glu Phe Asp Thr Lys Ser Tyr Leu Glu Lys Leu Asp Ala Trp
1               5                   10                  15

Trp Arg Ala Ala Asn Tyr Ile Ser Ala Ala Gln Met Tyr Leu Lys Asp
            20                  25                  30

Asn Pro Leu Leu Arg Arg Glu Leu Val Glu Asn Asp Leu Lys Val His
        35                  40                  45

Pro Ile Gly His Trp Gly Thr Val Pro Gly Gln Asn Phe Ile Tyr Ala
    50                  55                  60

His Leu Asn Arg Ala Ile Asn Lys Tyr Asp Leu Asp Met Phe Tyr Ile
65                  70                  75                  80

Glu Gly Pro Gly His Gly Gly Gln Val Met Val Ser Asn Ser Tyr Leu
                85                  90                  95

Asp Gly Ser Tyr Thr Glu Leu Asn Pro Asn Ile Glu Gln Thr Glu Asp
            100                 105                 110

Gly Phe Lys Gln Leu Cys Lys Ile Phe Ser Phe Pro Gly Gly Ile Ala
        115                 120                 125

Ser His Ala Ala Pro Glu Thr Pro Gly Ser Ile His Glu Gly Gly Glu
    130                 135                 140

Leu Gly Tyr Ala Leu Ser His Ala Thr Gly Ala Ile Leu Asp Asn Pro
145                 150                 155                 160

Asp Val Ile Ala Ala Thr Val Ile Gly Asp Gly Glu Gly Glu Thr Gly
                165                 170                 175

Pro Leu Met Ala Gly Trp Leu Ser Asn Thr Phe Ile Asn Pro Val Asn
            180                 185                 190

Asp Gly Ala Val Leu Pro Ile Phe Tyr Leu Asn Gly Gly Lys Ile His
        195                 200                 205

Asn Pro Thr Ile Phe Glu Arg Lys Thr Asp Glu Glu Leu Ser Gln Phe
    210                 215                 220

Phe Glu Gly Leu Gly Trp Lys Pro Ile Phe Ala Asp Val Val Glu Leu
225                 230                 235                 240

Ser Glu Asp His Ala Ala Ala His Ala Leu Phe Ala Glu Lys Leu Asp
                245                 250                 255

Gln Ala Ile Gln Glu Ile Lys Thr Ile Gln Ser Glu Ala Arg Gln Lys
            260                 265                 270

Pro Ala Glu Glu Ala Ile Gln Ala Lys Phe Pro Val Leu Val Ala Arg
        275                 280                 285

Ile Pro Lys Gly Trp Thr Gly Pro Lys Ala Trp Glu Gly Thr Pro Ile
    290                 295                 300

Glu Gly Gly Phe Arg Ala His Gln Val Pro Ile Pro Val Asp Ala His
305                 310                 315                 320

His Met Glu His Val Asp Ser Leu Leu Ser Trp Leu Gln Ser Tyr Arg
                325                 330                 335

Pro Glu Glu Leu Phe Asp Glu Ser Gly Lys Ile Val Asp Glu Ile Ala
            340                 345                 350

Ala Ile Ser Pro Lys Gly Asp Arg Arg Met Ser Met Asn Pro Ile Thr
        355                 360                 365
```

-continued

```
Asn Ala Gly Ile Val Lys Ala Met Asp Thr Ala Asp Trp Lys Lys Phe
            370                 375                 380
Ala Leu Asp Ile Asn Val Pro Gly Gln Ile Met Ala Gln Asp Met Ile
385                 390                 395                 400
Glu Phe Gly Lys Tyr Ala Ala Asp Leu Val Asp Ala Asn Pro Asp Asn
                405                 410                 415
Phe Arg Ile Phe Gly Pro Asp Glu Thr Lys Ser Asn Arg Leu Gln Glu
            420                 425                 430
Val Phe Thr Arg Thr Ser Arg Gln Trp Leu Gly Arg Lys Pro Asp
            435                 440                 445
Tyr Asp Glu Ala Leu Ser Pro Ala Gly Arg Val Ile Asp Ser Gln Leu
450                 455                 460
Ser Glu His Gln Ala Glu Gly Phe Leu Glu Gly Tyr Val Leu Thr Gly
465                 470                 475                 480
Arg His Gly Phe Phe Ala Ser Tyr Glu Ser Phe Leu Arg Val Val Asp
                485                 490                 495
Ser Met Val Thr Gln His Phe Lys Trp Leu Arg Lys Ser Lys Thr His
            500                 505                 510
Thr Thr Trp Arg Lys Asn Tyr Pro Ala Leu Asn Leu Ile Ala Ala Ser
            515                 520                 525
Thr Val Phe Gln Gln Asp His Asn Gly Tyr Thr His Gln Asp Pro Gly
530                 535                 540
Ile Leu Thr His Leu Ala Glu Lys Thr Pro Glu Tyr Ile Arg Glu Tyr
545                 550                 555                 560
Leu Pro Ala Asp Thr Asn Ser Leu Leu Ala Val Met Asp Lys Ala Phe
                565                 570                 575
Lys Ala Glu Asp Lys Ile Asn Leu Ile Val Thr Ser Lys His Pro Arg
            580                 585                 590
Pro Gln Phe Tyr Ser Ile Ala Glu Ala Glu Leu Val Ala Glu Gly
            595                 600                 605
Tyr Lys Val Ile Asp Trp Ala Ser Asn Val Ser Leu Asn Gln Glu Pro
610                 615                 620
Asp Val Val Phe Ala Ala Ala Gly Thr Glu Pro Asn Leu Glu Ala Leu
625                 630                 635                 640
Ala Ala Ile Ser Ile Leu His Lys Ala Phe Pro Glu Leu Lys Ile Arg
                645                 650                 655
Phe Val Asn Val Leu Asp Ile Leu Lys Leu Arg His Pro Ser Gln Asp
            660                 665                 670
Ala Arg Gly Leu Ser Asp Glu Glu Phe Asp Lys Val Phe Thr Thr Asp
            675                 680                 685
Lys Pro Val Ile Phe Ala Phe His Ser Tyr Glu Asp Met Ile Arg Asp
690                 695                 700
Ile Phe Phe Ser Arg His Asn His Asn Leu His Thr His Gly Tyr Arg
705                 710                 715                 720
Glu Asn Gly Asp Ile Thr Thr Pro Phe Asp Met Arg Val Met Ser Glu
                725                 730                 735
Leu Asp Arg Phe His Leu Ala Gln Asp Ala Ala Leu Ala Ser Leu Gly
            740                 745                 750
Asn Glu Ala Gln Ala Phe Ser Asp Glu Met Asn Gln Met Val Ala Tyr
            755                 760                 765
His Lys Asp Tyr Ile Arg Glu His Gly Asp Asp Ile Pro Glu Val Gln
770                 775                 780
```

Asn Trp Lys Trp Glu Asn Ile Lys
785                 790

<210> SEQ ID NO 33
<211> LENGTH: 795
<212> TYPE: PRT
<213> ORGANISM: Mycoplasma agalactiae PG2

<400> SEQUENCE: 33

Met Lys Lys Ser His Asp Phe Asp Ser Lys Glu Tyr Leu Asn Leu Val
1               5                   10                  15

Asp Ala Trp Trp Arg Ala Ala Asn Tyr Leu Ser Val Gly Gln Met Tyr
            20                  25                  30

Leu Arg Asn Asn Pro Leu Leu Lys Ile Pro Leu Thr Ser Asn Asp Val
        35                  40                  45

Lys Ile Tyr Pro Ile Gly His Trp Gly Thr Val Pro Gly Gln Asn Phe
    50                  55                  60

Ile Tyr Ala His Leu Asn Arg Ile Ile Asn Lys Tyr Asp Leu Asn Met
65                  70                  75                  80

Phe Phe Ile Ser Gly Pro Gly His Gly Gln Val Ile Ala Ser Asn
                85                  90                  95

Thr Tyr Leu Asp Gly Ser Tyr Thr Glu Leu Phe Pro His Val Thr Lys
            100                 105                 110

Asp Ile Lys Gly Met Thr His Leu Phe Lys Tyr Phe Ser Phe Pro Gly
        115                 120                 125

Gly Thr Ala Ser His Ala Ala Pro Glu Cys Pro Gly Ser Ile His Glu
    130                 135                 140

Gly Gly Glu Leu Gly Tyr Ser Leu Ser His Ala Ala Gly Ala Val Leu
145                 150                 155                 160

Asp Asn Pro Asp Val Ile Ala Ala Thr Val Ile Gly Asp Gly Glu Ser
                165                 170                 175

Glu Thr Gly Pro Leu Ser Ala Gly Trp Phe Ile Asn Ser Phe Ile Asn
            180                 185                 190

Pro Ala Asn Asp Gly Ala Val Leu Pro Ile Leu His Val Asn Gly Gly
        195                 200                 205

Lys Ile Ser Asn Pro Thr Ile Trp Ser Arg Arg Ser Asn Glu Glu Leu
    210                 215                 220

Val Ser Tyr Phe Thr Gly Ala Gly Trp Lys Pro Phe Ile Val Glu Gly
225                 230                 235                 240

Asn Glu Pro Glu Tyr Met His His Glu Met Ala Lys Ala Leu Asp Ala
                245                 250                 255

Ser Val Glu Leu Ile Lys Gln Tyr Gln Ala Glu Ala Arg Lys Asn Gly
            260                 265                 270

Ala Asn Lys Ala Lys Arg Pro Gln Trp Pro Met Ile Val Leu Lys Ser
        275                 280                 285

Pro Lys Gly Trp Thr Gly Pro Lys Glu Trp Asn His Glu Ala Ile Glu
    290                 295                 300

Gly Ser Phe Arg Ala His Gln Val Pro Val Pro Val Ser Ala Glu Lys
305                 310                 315                 320

Met Gln His Ile Asp Ala Leu Glu Asn Trp Leu Arg Ser Tyr Arg Pro
                325                 330                 335

Glu Glu Leu Phe Asp Glu Asn Ala Gln Leu Lys Pro Glu Ile Ala Ala
            340                 345                 350

Ile Ala Pro Lys Gly Asp Arg Arg Met Gly Lys Asn Pro Ile Ala Asn
        355                 360                 365

-continued

```
Gly Gly Ile Asn Pro Arg Ala Ile Asn Val Gly Asp Trp Thr Lys Phe
    370             375             380

Ala Leu Asp Ile Lys Gln Pro Gly Lys Val Ile Asn Gln Asp Met Val
385             390             395             400

Thr Leu Gly Ser Tyr Leu Gly Glu Leu Ser Leu Leu Asn Lys Asp Asn
            405             410             415

Phe Arg Val Trp Gly Pro Asp Glu His Lys Ser Asn Arg Leu Tyr Glu
        420             425             430

Met Phe Lys Val Thr Asp Arg Gln Trp Leu Asp Arg Ile Asp Glu Lys
        435             440             445

Tyr Asp Glu Phe Leu Ser Ser Val Gly Arg Ile Ile Asp Ser Gln Leu
    450             455             460

Ser Glu His Gln Ala Glu Gly Met Leu Glu Gly Tyr Val Leu Thr Gly
465             470             475             480

Arg His Gly Val Phe Ala Ser Tyr Glu Ser Phe Leu Arg Val Val Asp
            485             490             495

Ser Met Leu Thr Gln His Met Lys Trp Val Lys Lys Ala Leu Asp Ile
            500             505             510

Pro Trp Arg Asn Asp Tyr Pro Ser Leu Asn Val Ile Ala Thr Ser Asn
        515             520             525

Ala Phe Gln Gln Asp His Asn Gly Tyr Thr His Gln Asp Pro Gly Leu
530             535             540

Ile Gly His Leu Ala Asp Lys Arg Pro Glu Leu Ile Arg Glu Tyr Leu
545             550             555             560

Pro Ala Asp Thr Asn Thr Leu Leu Ala Thr Met Ala Lys Ala Leu Gln
            565             570             575

Asp Arg Asn Val Ile Asn Leu Ile Ser Ser Lys Gln Pro Arg His
        580             585             590

Gln Phe Phe Ser Ile Glu Glu Ala Thr Glu Leu Val Glu Lys Gly Ile
        595             600             605

Lys Ile Ile Asp Trp Ala Ser Asn Ile Lys Pro Asn Glu Glu Pro Asp
    610             615             620

Leu Val Val Ala Ala Ser Gly Thr Glu Ser Thr Ile Glu Ser Leu Ala
625             630             635             640

Thr Ile Thr Tyr Leu Arg Ala His Phe Pro Glu Leu Lys Ile Arg Phe
            645             650             655

Val Asn Val Leu Asp Leu Leu Lys Leu Arg His Pro Ser Ile Asp Pro
            660             665             670

Arg Gly Leu Ser Asp Ser Glu Phe Asp Ser Ile Phe Thr Lys Asp Lys
        675             680             685

Pro Ile Leu Phe Ala Phe His Gly Tyr Glu Ala Ile Leu Arg Asp Ile
    690             695             700

Phe Phe Leu Arg Ser Asn His Asn Ile Ile Thr His Gly Tyr Arg Glu
705             710             715             720

Asn Gly Asp Ile Thr Thr Ala Phe Asp Ile Arg Leu Leu Ser Glu Met
            725             730             735

Asp Arg Phe His Met Thr Ala Asn Val Ala Lys Lys Leu Ala Pro Val
        740             745             750

Val Gly Glu Ser Lys Ala Asn Glu Leu Val Lys Leu Met Glu Asp Lys
    755             760             765

Ile Lys Glu His Arg Ala Tyr Ile Lys Glu Tyr Gly Thr Asp Leu Pro
770             775             780
```

```
Glu Val Lys Glu Trp Glu Trp Thr Pro Tyr Lys
785                 790                 795

<210> SEQ ID NO 34
<211> LENGTH: 794
<212> TYPE: PRT
<213> ORGANISM: Streptococcus gordonii str. Challis substr. CH1

<400> SEQUENCE: 34

Met Thr Thr Asp Tyr Asn Ser Lys Ala Tyr Leu Glu Lys Val Asp Ala
1               5                   10                  15

Trp Trp Arg Ala Ala Asn Tyr Ile Ser Ala Ala Gln Met Tyr Leu Lys
            20                  25                  30

Asp Asn Pro Leu Leu Lys Arg Asp Val Val Ala Asn Asp Leu Lys Ala
        35                  40                  45

His Pro Ile Gly His Trp Gly Thr Val Pro Gly Gln Asn Phe Ile Tyr
    50                  55                  60

Ala His Leu Asn Arg Thr Ile Asn Lys Tyr Asp Leu Asp Met Phe Tyr
65                  70                  75                  80

Ile Glu Gly Pro Gly His Gly Gly Gln Val Met Val Ser Asn Ser Tyr
                85                  90                  95

Leu Asp Gly Ser Tyr Thr Glu Leu Asn Pro Asn Ile Pro Gln Asn Glu
            100                 105                 110

Glu Gly Phe Lys His Leu Cys Lys Ile Phe Ser Phe Pro Gly Gly Ile
        115                 120                 125

Ala Ser His Ala Ala Pro Glu Thr Pro Gly Ser Ile His Glu Gly Gly
    130                 135                 140

Glu Leu Gly Tyr Ala Leu Ser His Ala Ala Gly Ala Ile Leu Asp Asn
145                 150                 155                 160

Pro Asp Val Ile Ala Ala Thr Val Ile Gly Asp Gly Glu Gly Glu Thr
                165                 170                 175

Gly Pro Leu Met Ala Gly Trp Leu Ser Asn Thr Phe Ile Asn Pro Val
            180                 185                 190

Asn Asp Gly Ala Ile Leu Pro Ile Phe Tyr Leu Asn Gly Gly Lys Ile
        195                 200                 205

His Asn Pro Thr Ile Phe Glu Arg Lys Thr Asp Glu Glu Leu Thr Leu
    210                 215                 220

Phe Phe Glu Gly Leu Gly Trp Lys Pro Ile Phe Ala Asp Val Thr Ala
225                 230                 235                 240

Ile Ser Glu Asn His Glu Ala Ala His Ala Leu Phe Ala Ala Lys Leu
                245                 250                 255

Asp Glu Ala Ile Glu Glu Ile Lys Lys Val Gln Ala Glu Ala Arg Lys
            260                 265                 270

Gly Ser Ala Glu Glu Ala Thr Gln Ala Ile Phe Pro Val Leu Val Ala
        275                 280                 285

Arg Ile Pro Lys Gly Trp Thr Gly Pro Lys Ser Trp Glu Gly Thr Pro
    290                 295                 300

Ile Glu Gly Gly Phe Arg Ala His Gln Val Pro Ile Pro Val Asp Ala
305                 310                 315                 320

His His Met Glu His Val Asp Ala Leu Leu Asn Trp Leu Lys Ser Tyr
                325                 330                 335

Arg Pro Glu Glu Leu Phe Asp Glu Ser Gly Lys Val Leu Pro Glu Ile
            340                 345                 350

Ala Ala Ile Gly Pro Lys Gly Asp Arg Arg Met Ala Met Asn Pro Ile
        355                 360                 365
```

```
Thr Asn Ala Gly Val Ile Lys Pro Met Asp Thr Ala Asp Trp Lys Lys
    370                 375                 380
His Ala Leu Lys Phe Gly Thr Pro Gly Glu Ile Val Ala Gln Asp Met
385                 390                 395                 400
Ile Glu Phe Gly Lys Tyr Ala Thr Asp Leu Val Asp Ala Asn Pro Asp
                405                 410                 415
Asn Phe Arg Ile Phe Gly Pro Asp Glu Thr Lys Ser Asn Arg Leu Gln
                420                 425                 430
Glu Val Phe Thr Arg Thr Ser Arg Gln Trp Leu Gly Arg Met Arg Pro
                435                 440                 445
Glu Tyr Asp Glu Ala Leu Ser Pro Ala Gly Arg Val Ile Asp Ser Gln
    450                 455                 460
Leu Ser Glu His Gln Ala Glu Gly Met Leu Glu Gly Tyr Val Leu Thr
465                 470                 475                 480
Gly Arg His Gly Phe Phe Ala Ser Tyr Glu Ser Phe Leu Arg Val Val
                485                 490                 495
Asp Ser Met Val Thr Gln His Phe Lys Trp Leu Arg Lys Cys Lys Thr
                500                 505                 510
His Thr Thr Trp Arg Lys Asn Tyr Pro Ala Leu Asn Leu Ile Ala Thr
                515                 520                 525
Ser Thr Val Phe Gln Gln Asp His Asn Gly Tyr Thr His Gln Asp Pro
530                 535                 540
Gly Ile Leu Thr His Leu Ala Glu Lys Thr Pro Glu Phe Ile Arg Glu
545                 550                 555                 560
Tyr Leu Pro Ala Asp Thr Asn Ser Leu Leu Ala Val Met Asp Lys Ala
                565                 570                 575
Phe Lys Ala Glu Asp Lys Val Asn Leu Ile Val Thr Ser Lys His Pro
                580                 585                 590
Arg Pro Gln Phe Tyr Ser Ala Glu Glu Ala Glu Leu Val Arg Glu
                595                 600                 605
Gly Tyr Lys Val Ile Asp Trp Ala Ser Thr Val Ser Asn Asn Glu Glu
                610                 615                 620
Pro Asp Val Val Phe Ala Ala Gly Thr Glu Pro Asn Leu Glu Ala
625                 630                 635                 640
Leu Ala Ala Val Ser Ile Leu His Lys Ala Phe Pro Glu Leu Lys Ile
                645                 650                 655
Arg Phe Val Asn Val Val Asp Ile Leu Lys Leu Arg His Pro Ser Val
                660                 665                 670
Asp Ala Arg Gly Leu Ser Asp Glu Glu Phe Asp Gln Val Phe Thr Thr
                675                 680                 685
Asp Lys Pro Val Ile Phe Ala Phe His Gly Tyr Glu Gly Met Ile Arg
                690                 695                 700
Asp Ile Phe Phe Asn Arg His Asn His Asn Leu Arg Val His Gly Tyr
705                 710                 715                 720
Arg Glu Asn Gly Asp Ile Thr Thr Pro Phe Asp Met Arg Val Met Ser
                725                 730                 735
Glu Leu Asp Arg Phe His Leu Ala Gln Asp Ala Ala Asn Ala Ala Leu
                740                 745                 750
Gly Glu Asp Ala Ala Val Phe Ser Ala Lys Met Asp Glu Thr Val Ala
                755                 760                 765
Tyr His Asn Ala Tyr Ile Arg Glu Asn Gly Asp Asp Ile Pro Glu Val
                770                 775                 780
```

-continued

```
Gln Asn Trp Lys Trp Glu Asn Ile Asn Lys
785                 790
```

<210> SEQ ID NO 35
<211> LENGTH: 791
<212> TYPE: PRT
<213> ORGANISM: Kingella oralis ATCC 51147

<400> SEQUENCE: 35

```
Met Gln Asn Thr Gln Phe Asp Thr Pro Glu Tyr Leu Ala Lys Val Asp
1               5                   10                  15

Ala Trp Trp Arg Ala Ala Asn Tyr Ile Ser Ala Ala Gln Met Tyr Leu
            20                  25                  30

Lys Asp Asn Pro Leu Leu Lys Lys Pro Leu Thr Ala Asn Asp Val Lys
        35                  40                  45

Ala His Pro Ile Gly His Trp Gly Thr Val Pro Gly Gln Asn Phe Ile
    50                  55                  60

Tyr Ala His Leu Asn Arg Ala Ile Asn Lys Tyr Asp Val Asp Met Phe
65                  70                  75                  80

Tyr Ile Glu Gly Pro Gly His Gly Gly Gln Val Met Val Ser Asn Ser
                85                  90                  95

Tyr Leu Asp His Ser Tyr Thr Asp Ile Tyr Pro Glu Ile Thr Gln Asp
            100                 105                 110

Glu Ala Gly Leu Lys Lys Leu Cys Lys Ile Phe Ser Phe Pro Gly Gly
        115                 120                 125

Ile Ala Ser His Ala Ala Pro Glu Thr Pro Gly Ser Ile His Glu Gly
    130                 135                 140

Gly Glu Leu Gly Tyr Ala Leu Ser His Ala Phe Gly Ala Val Leu Asp
145                 150                 155                 160

Asn Pro Asn Ile Ile Ala Ala Val Ile Gly Asp Gly Glu Ala Glu
                165                 170                 175

Thr Gly Pro Leu Cys Ala Gly Trp Phe Gly Asn Thr Phe Ile Asn Pro
            180                 185                 190

Val Asn Asp Gly Ala Val Leu Pro Ile Leu Tyr Leu Asn Gly Gly Lys
        195                 200                 205

Ile His Asn Pro Thr Ile Leu Ala Arg Lys Thr Asp Ala Glu Leu Thr
    210                 215                 220

Gln Tyr Phe Asn Gly Met Gly Trp Glu Pro Ile Phe Val Glu Val Ser
225                 230                 235                 240

Asp Pro Ala His Ser His Ala Ile Met Ala Gln Lys Leu Asp Glu Ala
                245                 250                 255

Val Glu Arg Ile Leu Ala Ile Trp Gln Asp Ala Arg Ser Arg Ser Ala
            260                 265                 270

Asn Asp Ala Thr Met Pro Arg Trp Pro Val Leu Val Ala Arg Ile Pro
        275                 280                 285

Lys Gly Trp Thr Gly Pro Lys Thr Trp Asn Gly Glu Pro Ile Glu Gly
    290                 295                 300

Gly Phe Arg Ala His Gln Val Pro Ile Pro Thr Asn Ser His Asp Met
305                 310                 315                 320

Ser Thr Ala Asp Ala Leu Glu Ala Trp Leu Arg Ser Tyr Arg Pro Glu
                325                 330                 335

Glu Leu Phe Asp Asp Asn Gly Arg Phe Leu Asp Lys Trp Arg Glu Ile
            340                 345                 350

Ser Pro Lys Gly Ala Lys Arg Met Ser Val His Pro Ile Thr Asn Gly
        355                 360                 365
```

```
Gly Val Ala Pro Lys Ala Leu Val Met Pro Asp Trp Thr Lys His Ala
    370             375             380

Leu Lys Ile Gly Thr Pro Gly Ser Gln Asp Ala Gln Asp Met Ile Glu
385             390             395             400

Cys Gly Arg Leu Met Ala Asp Val Ile Thr Ala Asn Pro Asp Asn Phe
            405             410             415

Arg Ile Phe Gly Pro Asp Glu Thr Lys Ser Asn Arg Leu Asn Glu Val
            420             425             430

Phe Lys Val Thr Asn Arg Gln Trp Leu Gly Val Arg Asp Ala Ala Tyr
        435             440             445

Asp Glu Trp Ile Ala Pro Val Gly Arg Val Ile Asp Ser Gln Leu Ser
    450             455             460

Glu His Gln Ala Glu Gly Phe Leu Gly Tyr Val Leu Thr Gly Arg
465             470             475             480

His Gly Phe Phe Ala Ser Tyr Glu Ser Phe Leu Arg Val Val Asp Ser
            485             490             495

Met Ile Thr Gln His Phe Lys Trp Leu Arg Lys Cys Lys Thr His Ala
            500             505             510

Pro Trp Arg Lys Asp Tyr Pro Ser Leu Asn Leu Ile Ala Thr Ser Thr
        515             520             525

Val Phe Gln Gln Asp His Asn Gly Tyr Thr His Gln Asp Pro Gly Leu
530             535             540

Leu Thr His Leu Ala Glu Lys Lys Pro Glu Phe Val Arg Glu Tyr Leu
545             550             555             560

Pro Ala Asp Ala Asn Thr Leu Leu Ala Val Met Ser Glu Ala Leu Thr
            565             570             575

Ser Arg Asp Arg Ile Asn Leu Ile Val Ser Ser Lys His Leu Arg Pro
            580             585             590

Gln Phe Tyr Ser Ala Asp Glu Ala Lys Glu Leu Val Arg Glu Gly Tyr
        595             600             605

Lys Ile Ile Glu Trp Ala Ser Thr Cys His Asp Gly Glu Pro Asp Val
    610             615             620

Val Ile Ala Ala Ala Gly Thr Glu Pro Asn Met Glu Ala Leu Ala Ala
625             630             635             640

Ile Asn Val Leu His Lys His Tyr Pro Glu Met Lys Ile Arg Phe Ile
            645             650             655

Asn Val Val Asp Ile Leu Lys Leu Arg His Pro Ser Ile Asp Pro Arg
            660             665             670

Gly Leu Ser Asp Glu Ala Phe Asp Ala Leu Phe Thr Arg Asp Lys Pro
        675             680             685

Val Val Phe Cys Phe His Gly Tyr Glu Asn Met Val Arg Asp Ile Phe
    690             695             700

Phe Pro Arg His Asn Arg Asn Val Arg Ile His Gly Tyr Arg Glu Asn
705             710             715             720

Gly Asp Ile Thr Thr Pro Phe Asp Met Arg Val Leu Ser Glu Met Asp
            725             730             735

Arg Phe His Val Ala Lys Asp Ala Ala Gln Ala Val Tyr Gly Glu Lys
            740             745             750

Ala Ala Asp Phe Ala Asn Lys Met Asp Glu Thr Ile Gln Phe His Arg
        755             760             765

Ser Tyr Ile Arg Glu His Gly Lys Asp Ile Pro Glu Val Ala Glu Trp
    770             775             780
```

```
Lys Trp Gln Pro Leu Ala Lys
785                 790
```

<210> SEQ ID NO 36
<211> LENGTH: 792
<212> TYPE: PRT
<213> ORGANISM: Mycoplasma fermentans M64

<400> SEQUENCE: 36

```
Met Asn Lys Lys Glu Phe Asp Ser Lys Glu Tyr Leu Glu Lys Val Asp
1               5                   10                  15

Ala Trp Trp Arg Ala Ala Asn Tyr Leu Ser Val Gly Gln Ile Tyr Leu
            20                  25                  30

Arg Asn Asn Pro Leu Leu Lys His Pro Leu Thr Ser Asp Asp Val Lys
        35                  40                  45

Val Tyr Pro Ile Gly His Trp Gly Thr Ile Ser Gly Gln Asn Phe Ala
    50                  55                  60

Tyr Ala His Leu Asn Arg Val Ile Asn Lys Tyr Asp Leu Asn Met Phe
65                  70                  75                  80

Tyr Ile Glu Gly Pro Gly His Gly Gly Gln Val Met Thr Ser Asn Ser
                85                  90                  95

Tyr Leu Asp Gly Ser Tyr Thr Glu Leu Phe Pro His Val Thr Gln Asp
            100                 105                 110

Glu Ala Gly Met Gln His Leu Phe Lys Tyr Phe Ser Phe Pro Gly Gly
        115                 120                 125

Thr Ala Ser His Ala Ala Pro Glu Thr Pro Gly Ser Ile His Glu Gly
    130                 135                 140

Gly Glu Leu Gly Tyr Ser Ile Ser His Ala Thr Gly Ala Ile Leu Asp
145                 150                 155                 160

Asn Pro Asp Val Ile Ala Ala Thr Ile Val Gly Asp Gly Glu Ala Glu
                165                 170                 175

Thr Gly Pro Leu Ala Thr Ser Trp Phe Ser Asn Ser Phe Ile Asn Pro
            180                 185                 190

Val Asn Asp Gly Ala Val Leu Pro Ile Leu His Leu Asn Gly Gly Lys
        195                 200                 205

Ile Ser Asn Pro Thr Ile Leu Ser Arg Lys Ser Asn Glu Glu Leu Gln
    210                 215                 220

Gln Tyr Phe Arg Gly Met Gly Trp Glu Pro His Phe Val Glu Gly Asp
225                 230                 235                 240

Lys Pro Glu Val Met His Glu Leu Met Ala Lys Thr Leu Asp Ser Val
                245                 250                 255

Ile Glu Glu Ile Gln Ser Ile Gln Thr Lys Ala Arg Lys Lys Pro Ala
            260                 265                 270

Asp Lys Ala Lys Arg Pro Val Trp Pro Met Ile Val Leu Arg Thr Pro
        275                 280                 285

Lys Gly Trp Thr Gly Pro Lys Ser Trp Asn Lys Glu Ala Ile Glu Gly
    290                 295                 300

Ser Phe Arg Ala His Gln Val Pro Leu Pro Ile Asn Ala Glu Asn Met
305                 310                 315                 320

Glu His Ala Asp Ala Leu Glu Lys Trp Leu Arg Ser Tyr Arg Pro Glu
                325                 330                 335

Glu Leu Phe Asp Lys Lys Gly Lys Leu Val Lys Glu Ile Ala Ala Ile
            340                 345                 350

Ala Pro Lys Gly Lys Arg Arg Met Gly Met Asn Pro Ile Thr Asn Gly
        355                 360                 365
```

```
Gly Ile Asn Pro Lys Val Met Lys Leu Gly Asp Trp Arg Lys Phe Ala
            370             375             380

Leu His Phe Asp Arg Pro Gly Ser Val Val Ala Gln Asp Met Val Glu
385             390             395             400

Leu Gly Thr Tyr Phe Ala Asp Leu Val Lys Arg Asn Pro Glu Asn Phe
                405             410             415

Arg Ile Phe Gly Pro Asp Glu Thr Lys Ser Asn Arg Leu Tyr Asn Leu
            420             425             430

Phe Lys Val Thr Asn Arg Gln Trp Met Glu Arg Ile Asp Ser Lys Leu
            435             440             445

Asp Glu Ala Leu Ser Pro Val Gly Arg Ile Ile Asp Ser Gln Leu Ser
450             455             460

Glu His Gln Ala Gln Gly Phe Leu Gly Tyr Val Leu Thr Gly Arg
465             470             475             480

His Gly Ile Phe Ala Ser Tyr Glu Ser Phe Leu Arg Val Val Asp Ser
                485             490             495

Met Val Thr Gln His Met Lys Trp Leu Arg Lys Ala Lys Glu Ile Asn
            500             505             510

Trp Arg Lys Asp Tyr Pro Ser Leu Asn Ile Met Ala Thr Ser Thr Ala
            515             520             525

Phe Gln Gln Asp His Asn Gly Tyr Thr His Gln Asp Pro Gly Ile Ile
530             535             540

Gly His Met Ala Asp Lys Arg Pro Glu Leu Ile Arg Glu Tyr Leu Pro
545             550             555             560

Ala Asp Thr Asn Thr Leu Leu Ala Val Met Asp Lys Ala Phe Thr Glu
            565             570             575

Arg Asn Val Ile Asn Leu Ile Val Ser Ser Lys Gln Pro Arg His Gln
            580             585             590

Phe Tyr Ser Val Glu Glu Ala Glu Thr Leu Val Glu Lys Gly Leu Asp
            595             600             605

Ile Ile Asp Trp Ala Ser Thr Cys Ser Arg Asn Glu Thr Pro Asp Leu
610             615             620

Val Val Val Ala Ser Gly Thr Glu Pro Asn Leu Glu Ala Leu Ala Thr
625             630             635             640

Ile Ser Ile Leu Asn Lys Glu Tyr Pro Ser Met Lys Ile Arg Phe Val
            645             650             655

Asn Val Val Asp Leu Leu Lys Leu Arg His Pro Lys Ile Asp Pro Arg
            660             665             670

Gly Leu Ser Asp Glu Glu Phe Asp Glu Ile Phe Thr Lys Asp Lys Pro
            675             680             685

Val Leu Phe Ala Phe His Gly Phe Glu Gly Ile Leu Arg Asp Ile Phe
            690             695             700

Phe Asp Arg His Asn His Asn Leu Ile Ala His Gly Tyr Arg Glu Asn
705             710             715             720

Gly Asp Ile Thr Thr Ser Phe Asp Ile Arg Gln Leu Ser His Met Asp
                725             730             735

Arg Phe His Met Ala Ser Asp Ala Ala Ala Val Phe Gly Ser Ser
            740             745             750

Lys Ala Lys Glu Phe Met Asp Lys Met Glu Glu Thr Ile Gln Phe His
            755             760             765

Asn Lys Tyr Ile Arg Glu Val Gly Thr Asp Ile Pro Glu Val Lys Asn
            770             775             780
```

Trp Lys Trp Glu Gly Leu Ile Lys
785                 790

<210> SEQ ID NO 37
<211> LENGTH: 789
<212> TYPE: PRT
<213> ORGANISM: Granulicatella adiacens ATCC 49175

<400> SEQUENCE: 37

Met Thr Gln Phe Asp Thr Pro Glu Tyr Leu Ala Lys Val Asp Ala Trp
1               5                   10                  15

Trp Arg Ala Ala Asn Tyr Ile Ser Val Ala Gln Met Tyr Leu Lys Asp
            20                  25                  30

Asn Pro Leu Leu Arg Arg Pro Ile Gln Lys Glu Asp Val Lys Leu His
        35                  40                  45

Pro Ile Gly His Trp Gly Thr Ile Ala Gly Gln Asn Phe Ile Tyr Ala
    50                  55                  60

His Leu Asn Arg Ala Ile Asn Lys Tyr Asp Leu Asp Met Phe Tyr Ile
65                  70                  75                  80

Glu Gly Pro Gly His Gly Gly Gln Val Met Val Ser Asn Ser Tyr Leu
                85                  90                  95

Asp Gly Ser Tyr Thr Glu Leu Tyr Pro Gln Ile Thr Gln Asp Glu Ala
            100                 105                 110

Gly Phe Lys Gln Leu Cys Lys Ile Phe Ser Phe Pro Gly Gly Ile Ala
        115                 120                 125

Ser His Ala Ala Pro Glu Thr Pro Gly Ser Ile His Glu Gly Gly Glu
    130                 135                 140

Leu Gly Tyr Ser Leu Ser His Ala Thr Gly Ala Val Leu Asp Asn Pro
145                 150                 155                 160

Asn Val Ile Ala Ala Val Ile Gly Asp Gly Glu Ala Glu Thr Gly
                165                 170                 175

Pro Leu Ala Ala Gly Trp Phe Ser Asn Thr Phe Ile Asn Pro Val Asn
            180                 185                 190

Asp Gly Ala Val Leu Pro Ile Leu Tyr Leu Asn Gly Gly Lys Ile His
        195                 200                 205

Asn Pro Thr Ile Leu Ala Arg Arg Thr Asp Glu Glu Leu Thr Gln Phe
    210                 215                 220

Phe Asn Gly Leu Gly Trp Asp Pro Ile Phe Val Glu Gly Thr Asp Pro
225                 230                 235                 240

Glu Lys Val His Pro Leu Met Ala Ala Lys Leu Asp Glu Ala Ile Glu
                245                 250                 255

Lys Ile Gln Ala Ile Gln Lys Glu Ala Arg Ala Lys Ser Ala Glu Glu
            260                 265                 270

Ala Thr Met Pro His Trp Pro Val Leu Val Arg Thr Pro Lys Gly
        275                 280                 285

Trp Thr Gly Pro Lys Glu Trp Asn His Glu Pro Ile Glu Gly Gly Phe
    290                 295                 300

Arg Ala His Gln Val Pro Ile Pro Val Ser Gly Glu Ala Met Glu His
305                 310                 315                 320

Val Asp Ala Leu Val Asp Trp Leu Lys Ser Tyr Arg Pro Glu Glu Leu
                325                 330                 335

Phe Asp Glu Asn Gly Lys Leu Val Glu Glu Ile Ala Ala Ile Ser Pro
            340                 345                 350

Lys Gly Pro Arg Arg Met Ser Met Asn Pro Ile Thr Asn Ala Gly Val
        355                 360                 365

```
Val Lys Pro Met Glu Ile Thr Asp Trp Thr Lys His Ala Ile Asp Thr
        370                 375                 380

Ser Lys Pro Gly Ala Ile Gln Lys Gln Asp Met Ile Glu Phe Gly Lys
385                 390                 395                 400

Phe Ala Ala Asp Leu Val Lys Ala Asn Pro Asp Asn Phe Arg Ile Phe
                405                 410                 415

Gly Pro Asp Glu Thr Lys Ser Asn Arg Leu Asn Glu Val Phe Lys Ala
                420                 425                 430

Thr Asn Arg Gln Trp Val Gly Arg Arg Asp Glu Ser Tyr Asp Glu Trp
            435                 440                 445

Ile Ser Pro Val Gly Arg Val Ile Asp Ser Gln Leu Ser Glu His Gln
        450                 455                 460

Ala Glu Gly Phe Leu Glu Gly Tyr Val Leu Thr Gly Arg His Gly Phe
465                 470                 475                 480

Phe Ala Ser Tyr Glu Ser Phe Leu Arg Val Val Asp Ser Met Ile Thr
                485                 490                 495

Gln His Phe Lys Trp Leu Arg Lys Ala Lys Thr His Ala Pro Trp Arg
                500                 505                 510

Lys Asn Tyr Pro Ser Leu Asn Leu Ile Ala Thr Ser Thr Val Phe Gln
            515                 520                 525

Gln Asp His Asn Gly Tyr Thr His Gln Asp Pro Gly Leu Leu Thr His
        530                 535                 540

Leu Ala Glu Lys Lys Pro Glu Phe Val Arg Glu Tyr Leu Pro Ala Asp
545                 550                 555                 560

Thr Asn Ser Leu Met Ala Val Met Ala Glu Ala Leu Ser Ser Glu Asp
                565                 570                 575

Lys Ile Asn Leu Ile Val Ser Ser Lys His Pro Arg Pro Gln Phe Tyr
                580                 585                 590

Ser Val Glu Glu Ala Lys Glu Leu Val Ser Glu Gly Tyr Lys Val Ile
            595                 600                 605

Asp Trp Ala Ser Thr Val Lys Glu Gly Glu Glu Pro Asp Val Val Ile
        610                 615                 620

Ala Ala Ala Gly Thr Glu Pro Asn Leu Glu Ala Leu Ala Gly Ile Ser
625                 630                 635                 640

Ile Leu His Lys Gln Phe Pro Glu Leu Lys Ile Arg Phe Ile Asn Val
                645                 650                 655

Val Asp Ile Leu Lys Leu Arg Ser Pro Lys Val Asp Pro Arg Gly Leu
                660                 665                 670

Ser Asp Glu Glu Phe Asp Lys Leu Phe Thr Thr Asp Lys Pro Val Val
            675                 680                 685

Phe Cys Phe His Gly Tyr Glu Gly Met Ile Arg Asp Leu Phe Phe Asp
        690                 695                 700

Arg Asn Asn His Asn Val His Ile His Gly Tyr Arg Glu Asn Gly Asp
705                 710                 715                 720

Ile Thr Thr Pro Phe Asp Met Arg Val Leu Ser Glu Met Asp Arg Phe
                725                 730                 735

His Val Ala Lys Asp Ala Ala Val Ala Val Tyr Gly Glu Lys Ala Ser
                740                 745                 750

Glu Phe Ala Ala Lys Met Asp Glu Thr Val Glu Phe His His Ser Tyr
            755                 760                 765

Ile Arg Glu His Gly Glu Asp Ile Pro Glu Val Val Ser Trp Gln Trp
        770                 775                 780
```

Glu Asn Val Asn Lys
785

<210> SEQ ID NO 38
<211> LENGTH: 796
<212> TYPE: PRT
<213> ORGANISM: Mycoplasma hominis ATCC 23114

<400> SEQUENCE: 38

Met Ile Ser Lys Ile Tyr Asp Asp Lys Lys Tyr Leu Glu Lys Met Asp
1               5                   10                  15

Lys Trp Phe Arg Ala Ala Asn Tyr Leu Gly Val Cys Gln Met Tyr Leu
            20                  25                  30

Arg Asp Asn Pro Leu Leu Lys Lys Pro Leu Thr Ser Asn Asp Ile Lys
        35                  40                  45

Leu Tyr Pro Ile Gly His Trp Gly Thr Val Pro Gly Gln Asn Phe Ile
    50                  55                  60

Tyr Thr His Leu Asn Arg Val Ile Lys Lys Tyr Asp Leu Asn Met Phe
65                  70                  75                  80

Tyr Ile Glu Gly Pro Gly His Gly Gly Gln Val Met Ile Ser Asn Ser
                85                  90                  95

Tyr Leu Asp Gly Ser Tyr Ser Glu Ile Tyr Pro Glu Ile Ser Gln Asp
            100                 105                 110

Glu Ala Gly Leu Ala Lys Met Phe Lys Arg Phe Ser Phe Pro Gly Gly
        115                 120                 125

Thr Ala Ser His Ala Ala Pro Glu Thr Pro Gly Ser Ile His Glu Gly
    130                 135                 140

Gly Glu Leu Gly Tyr Ser Ile Ser His Gly Thr Gly Ala Ile Leu Asp
145                 150                 155                 160

Asn Pro Asp Val Ile Cys Ala Ala Val Val Gly Asp Gly Glu Ala Glu
                165                 170                 175

Thr Gly Pro Leu Ala Thr Ser Trp Phe Ser Asn Ala Phe Ile Asn Pro
            180                 185                 190

Val Asn Asp Gly Ala Ile Leu Pro Ile Leu His Leu Asn Gly Gly Lys
        195                 200                 205

Ile Ser Asn Pro Thr Leu Leu Ser Arg Lys Pro Lys Glu Glu Ile Lys
    210                 215                 220

Lys Tyr Phe Glu Gly Leu Gly Trp Asn Pro Ile Phe Val Glu Trp Ser
225                 230                 235                 240

Glu Asp Lys Ser Asn Leu Asp Met His Glu Leu Met Ala Lys Ser Leu
                245                 250                 255

Asp Lys Ala Ile Glu Ser Ile Lys Glu Ile Gln Ala Glu Ala Arg Lys
            260                 265                 270

Lys Pro Ala Glu Glu Ala Thr Arg Pro Thr Trp Pro Met Ile Val Leu
        275                 280                 285

Arg Thr Pro Lys Gly Trp Thr Gly Pro Lys Gln Trp Asn Asn Glu Ala
    290                 295                 300

Ile Glu Gly Ser Phe Arg Ala His Gln Val Pro Ile Pro Val Ser Ala
305                 310                 315                 320

Phe Lys Met Glu Lys Ile Ala Asp Leu Glu Lys Trp Leu Lys Ser Tyr
                325                 330                 335

Lys Pro Glu Glu Leu Phe Asp Glu Asn Gly Thr Ile Ile Lys Glu Ile
            340                 345                 350

Arg Asp Leu Ala Pro Glu Gly Leu Lys Arg Met Ala Val Asn Pro Ile
        355                 360                 365

```
Thr Asn Gly Gly Ile Asp Ser Lys Pro Leu Lys Leu Gln Asp Trp Lys
    370             375             380

Lys Tyr Ala Leu Lys Ile Asp Tyr Pro Gly Glu Ile Lys Ala Gln Asp
385             390             395             400

Met Ala Glu Met Ala Lys Phe Ala Ala Asp Ile Met Lys Asp Asn Pro
            405             410             415

Ser Ser Phe Arg Val Phe Gly Pro Asp Glu Thr Lys Ser Asn Arg Met
        420             425             430

Phe Ala Leu Phe Asn Val Thr Asn Arg Gln Trp Leu Glu Pro Val Ser
        435             440             445

Lys Lys Tyr Asp Glu Trp Ile Ser Pro Ala Gly Arg Ile Ile Asp Ser
450             455             460

Gln Leu Ser Glu His Gln Cys Glu Gly Phe Leu Glu Gly Tyr Val Leu
465             470             475             480

Thr Gly Arg His Gly Phe Phe Ala Ser Tyr Glu Ala Phe Leu Arg Val
            485             490             495

Val Asp Ser Met Leu Thr Gln His Met Lys Trp Ile Lys Lys Ala Ser
        500             505             510

Glu Leu Ser Trp Arg Lys Thr Tyr Pro Ser Leu Asn Ile Ile Ala Thr
        515             520             525

Ser Asn Ala Phe Gln Gln Asp His Asn Gly Tyr Thr His Gln Asp Pro
    530             535             540

Gly Leu Leu Gly His Leu Ala Asp Lys Arg Pro Glu Ile Ile Arg Glu
545             550             555             560

Tyr Leu Pro Ala Asp Thr Asn Ser Leu Leu Ala Val Met Asn Lys Ala
            565             570             575

Leu Thr Glu Arg Asn Val Ile Asn Leu Ile Val Ala Ser Lys Gln Pro
        580             585             590

Arg Glu Gln Phe Phe Thr Val Glu Asp Ala Glu Glu Leu Leu Glu Lys
        595             600             605

Gly Tyr Lys Val Val Pro Trp Ala Ser Asn Ile Ser Glu Asn Glu Glu
        610             615             620

Pro Asp Ile Val Phe Ala Ser Ser Gly Val Glu Pro Asn Ile Glu Ser
625             630             635             640

Leu Ala Ala Ile Ser Leu Ile Asn Gln Glu Tyr Pro His Leu Lys Ile
            645             650             655

Arg Tyr Val Tyr Val Leu Asp Leu Leu Lys Leu Arg Ser Arg Lys Ile
        660             665             670

Asp Pro Arg Gly Ile Ser Asp Glu Glu Phe Asp Lys Val Phe Thr Lys
    675             680             685

Asn Lys Pro Ile Ile Phe Ala Phe His Gly Phe Glu Gly Leu Leu Arg
    690             695             700

Asp Ile Phe Phe Thr Arg Ser Asn His Asn Leu Ile Ala His Gly Tyr
705             710             715             720

Arg Glu Asn Gly Asp Ile Thr Thr Ser Phe Asp Ile Arg Gln Leu Ser
            725             730             735

Glu Met Asp Arg Tyr His Ile Ala Lys Asp Ala Ala Glu Ala Val Tyr
        740             745             750

Gly Lys Asp Ala Lys Ala Phe Met Asn Lys Leu Asp Gln Lys Leu Glu
        755             760             765

Tyr His Arg Asn Tyr Ile Asp Gly Tyr Gly Tyr Asp Met Pro Glu Val
    770             775             780
```

Val Glu Trp Lys Trp Lys Asn Ile Asn Lys Glu Asn
785                 790                 795

<210> SEQ ID NO 39
<211> LENGTH: 792
<212> TYPE: PRT
<213> ORGANISM: Mycoplasma crocodyli MP145

<400> SEQUENCE: 39

Met Lys Lys Thr Val Tyr Asp Thr Glu Leu Tyr Ile Glu Lys Leu Asp
1               5                   10                  15

Ala Trp Phe Arg Ala Ala Asn Tyr Leu Ser Val Gly Gln Met Tyr Leu
            20                  25                  30

Arg Asn Asn Pro Leu Leu Arg Asn Lys Ile Thr Lys Asp Asp Val Lys
        35                  40                  45

Val Tyr Pro Ile Gly His Trp Gly Thr Ile Pro Gly Gln Asn Phe Ala
    50                  55                  60

Tyr Ala His Leu Asn Arg Val Ile Asn Lys Tyr Asp Leu Asn Met Phe
65                  70                  75                  80

Tyr Ile Glu Gly Pro Gly His Gly Gly Gln Val Met Thr Ser Asn Ser
                85                  90                  95

Tyr Leu Asp Gly Ser Tyr Thr Glu Leu Phe Pro His Val Thr Gln Asp
            100                 105                 110

Leu Asp Gly Met Lys His Leu Phe Lys Tyr Phe Ser Phe Pro Gly Gly
        115                 120                 125

Thr Ala Ser His Ala Ala Pro Glu Thr Pro Gly Ser Ile His Glu Gly
    130                 135                 140

Gly Glu Leu Gly Tyr Ser Leu Ser His Ala Thr Gly Ala Ile Leu Asp
145                 150                 155                 160

Asn Pro Asn Val Ile Ala Ala Thr Ile Val Gly Asp Gly Glu Ser Glu
                165                 170                 175

Thr Gly Pro Leu Ala Ala Gly Trp Phe Ser Asn Ser Phe Ile Asn Pro
            180                 185                 190

Val Asn Asp Gly Ala Val Leu Pro Ile Leu His Leu Asn Gly Gly Lys
        195                 200                 205

Ile Ser Asn Pro Thr Ile Leu Cys Arg Lys Ser Asn Glu Glu Leu Thr
    210                 215                 220

Asn Tyr Phe Leu Gly Met Gly Trp Glu Ala Ile Phe Val Glu Gly Glu
225                 230                 235                 240

Asp Val Gln Lys Met His Lys Leu Met Ala Thr Lys Leu Asp Tyr Ala
                245                 250                 255

Ile Glu Arg Ile Leu Ser Ile Gln Lys Glu Ala Arg Lys Gly Lys Ala
            260                 265                 270

Glu Glu Ala Thr Arg Pro Leu Trp Pro Met Ile Val Leu Arg Thr Pro
        275                 280                 285

Lys Gly Trp Thr Gly Pro Gln Lys Trp Asn Ser Asp Gln Ile Val Gly
    290                 295                 300

Ser Phe Arg Ala His Gln Val Pro Ile Pro Val Asn Ser Glu Asn Met
305                 310                 315                 320

Thr His Ile Asp Ala Leu Val Asp Trp Leu Lys Ser Tyr Asn Val Asp
                325                 330                 335

Asn Leu Phe Asp Lys Lys Gly Lys Leu Val Pro Glu Ile Ala Glu Ile
            340                 345                 350

Ala Pro Val Gly Asp Arg Arg Met Gly Met Asn Pro Val Thr Asn Gly
        355                 360                 365

```
Gly Leu Asn Pro Arg Asn Leu Ala Leu Pro Asn Trp Gln Asp Phe Ala
    370                 375                 380
Leu Asn Leu Glu Lys Pro Gly Ala Lys Ile Ala Gln Asp Met Val Glu
385                 390                 395                 400
Leu Gly Ser Tyr Phe Ala Lys Val Met Glu Met Asn Lys Asp Asn Phe
                405                 410                 415
Arg Leu Phe Gly Pro Asp Glu Thr Lys Ser Asn Arg Leu Phe Asn Val
            420                 425                 430
Phe Lys Val Thr Ser Arg Gln Trp Leu Glu Pro Ile Asn Pro Leu Phe
        435                 440                 445
Asp Glu Ala Leu Ser Pro Ala Gly Arg Val Ile Asp Ser Gln Leu Ser
    450                 455                 460
Glu His Gln Ala Glu Gly Phe Leu Gly Tyr Val Leu Thr Gly Arg
465                 470                 475                 480
His Gly Val Phe Ala Ser Tyr Glu Ser Phe Leu Arg Val Val Asp Ser
                485                 490                 495
Met Leu Thr Gln His Met Lys Trp Leu Lys Lys Ala Asn Asp Val Ser
            500                 505                 510
Trp Arg Asn Asp Tyr Pro Ser Leu Asn Val Ile Ala Thr Ser Thr Ala
        515                 520                 525
Phe Gln Gln Asp His Asn Gly Tyr Thr His Gln Asp Pro Gly Leu Ile
    530                 535                 540
Gly His Leu Ala Asp Lys Thr Pro Glu Leu Ile Arg Gln Tyr Leu Pro
545                 550                 555                 560
Ala Asp Thr Asn Thr Leu Leu Ala Val Met Asp Lys Ser Leu Thr Glu
                565                 570                 575
Arg Asn Val Ile Asn His Ile Ile Ala Ser Lys Gln Pro Arg Glu Gln
            580                 585                 590
Phe Tyr Ser Ala Lys Glu Ala Ala Glu Leu Val Glu Lys Gly Leu Lys
        595                 600                 605
Val Ile Lys Trp Ala Ser Thr Val Glu Gly Asn Asp Glu Pro Asp Leu
    610                 615                 620
Val Val Ala Ala Ala Gly Thr Glu Pro Asn Leu Glu Ala Leu Ala Ala
625                 630                 635                 640
Ile Thr Ile Leu Asn Lys Glu Phe Pro Lys Leu Lys Ile Arg Phe Val
                645                 650                 655
Asn Val Val Asp Leu Met Lys Leu Arg His Pro Ser Ile Asp Pro Arg
            660                 665                 670
Gly Ile Thr Asp Lys Glu Phe Asp Lys Ile Phe Thr Lys Asp Lys Pro
        675                 680                 685
Val Leu Phe Ala Phe His Gly Tyr Glu Gly Ile Leu Arg Asp Ile Phe
    690                 695                 700
Phe Lys Arg Asn Asn His Asn Leu Ile Ala His Gly Tyr Arg Glu Asn
705                 710                 715                 720
Gly Asp Ile Thr Thr Ser Phe Asp Ile Arg Gln Leu Ser His Met Asp
                725                 730                 735
Arg Phe His Met Ala Ala Ser Ala Ala Val Ala Ala Leu Gly Lys Lys
            740                 745                 750
Ala Asn Ala Phe Glu Thr Lys Met Leu Glu Thr Ile Asp Phe His Thr
        755                 760                 765
Lys Tyr Ile Arg Glu Tyr Gly Thr Asp Ile Pro Glu Val Lys Glu Trp
    770                 775                 780
```

-continued

```
Lys Trp Asn Pro Leu Val Arg Lys
785                 790

<210> SEQ ID NO 40
<211> LENGTH: 789
<212> TYPE: PRT
<213> ORGANISM: Neisseria sp. oral taxon 014 str. F0314

<400> SEQUENCE: 40

Met Ser Ala Gln Tyr Asp Ser Ala Asp Tyr Leu Asn Lys Val Asp Ala
1               5                   10                  15

Trp Trp Arg Ala Ala Asn Tyr Ile Ser Val Ala Gln Met Tyr Leu Lys
            20                  25                  30

Asp Asn Pro Leu Leu Met Arg Pro Ile Gln Ala Ser Asp Val Lys Ala
        35                  40                  45

His Pro Ile Gly His Trp Gly Thr Ile Ala Gly Gln Asn Phe Ile Tyr
    50                  55                  60

Ala His Leu Asn Arg Ala Ile Asn Lys Tyr Asp Leu Asn Met Phe Tyr
65                  70                  75                  80

Ile Glu Gly Pro Gly His Gly Gly Gln Val Met Val Ser Asn Ser Tyr
                85                  90                  95

Leu Asp Gly Ser Tyr Ser Glu Ile Tyr Pro Asn Ile Thr Gln Asp Glu
            100                 105                 110

Ala Gly Leu Lys Gln Leu Cys Lys Ile Phe Ser Phe Pro Gly Gly Ile
        115                 120                 125

Ala Ser His Ala Ala Pro Glu Thr Pro Gly Ser Ile His Glu Gly Gly
    130                 135                 140

Glu Leu Gly Tyr Ala Leu Ser His Ala Val Gly Ala Val Leu Asp Asn
145                 150                 155                 160

Pro Asp Val Ile Ala Ala Thr Val Ile Gly Asp Gly Glu Ala Glu Thr
                165                 170                 175

Gly Pro Leu Ser Ala Gly Trp Phe Ser Asn Val Phe Ile Asn Pro Val
            180                 185                 190

Asn Asp Gly Ala Val Leu Pro Ile Leu Tyr Leu Asn Gly Gly Lys Ile
        195                 200                 205

His Asn Pro Thr Ile Leu Ala Arg Lys Ser Asp Glu Ser Leu Arg Leu
    210                 215                 220

Tyr Phe Glu Gly Leu Gly Trp Asp Pro Ile Phe Val Glu Ala Thr Asp
225                 230                 235                 240

Tyr Ala Thr Thr His Lys Val Met Ala Gln Lys Leu Asp Glu Ala Ile
                245                 250                 255

Glu Lys Ile Lys Ala Ile Gln Thr Lys Ala Arg Ala Gly Lys Ala Glu
            260                 265                 270

Glu Ala Val Met Pro Lys Trp Pro Val Leu Val Ala Arg Leu Pro Lys
        275                 280                 285

Gly Trp Thr Gly Pro Lys Val Trp Asn Gly Glu Pro Ile Glu Gly Gly
    290                 295                 300

Phe Arg Ala His Gln Val Pro Ile Pro Ala Ser Ser His Asp Met Ala
305                 310                 315                 320

Thr Val Asp Ser Leu Val Glu Trp Leu Lys Ser Tyr Arg Pro Glu Glu
                325                 330                 335

Leu Phe Asp Ala Asn Gly Thr Phe Lys Ala Glu Leu Arg Glu Ile Ser
            340                 345                 350

Pro Lys Gly Asp Arg Arg Met Ser Thr Asn Pro Ile Thr Asn Gly Gly
        355                 360                 365
```

```
Ile Asn Pro Arg Pro Leu Asn Thr Ala Asp Trp Lys Lys Phe Ala Leu
    370                 375                 380

Asp Asn Ser Asp Arg Gly Ser Ile Met Ala Gln Asp Met Ile Glu Phe
385                 390                 395                 400

Gly Lys Tyr Ala Ala Glu Leu Val Lys Ala Asn Pro Asp Asn Phe Arg
                405                 410                 415

Ile Phe Gly Pro Asp Glu Thr Lys Ser Asn Arg Met Asn Glu Val Phe
            420                 425                 430

Lys Val Thr Asn Arg Gln Trp Leu Glu Pro Ile Asp Lys Ala Tyr Asp
        435                 440                 445

Glu Trp Met Ser Pro Ala Gly Arg Val Ile Asp Ser Gln Leu Ser Glu
    450                 455                 460

His Gln Ala Glu Gly Phe Leu Glu Gly Tyr Val Leu Thr Gly Arg His
465                 470                 475                 480

Gly Phe Phe Ala Ser Tyr Glu Ser Phe Leu Arg Val Val Asp Ser Met
                485                 490                 495

Ala Thr Gln His Phe Lys Trp Leu Arg Lys Cys Lys Thr His Ala Pro
            500                 505                 510

Trp Arg Lys Ser Tyr Pro Ser Leu Asn Leu Ile Ala Thr Ser Thr Val
        515                 520                 525

Phe Gln Gln Asp His Asn Gly Tyr Thr His Gln Asp Pro Gly Met Leu
    530                 535                 540

Thr His Leu Ala Glu Lys Lys Pro Glu Phe Ile Arg Glu Tyr Leu Pro
545                 550                 555                 560

Ala Asp Ala Asn Ser Leu Leu Ala Val Met Ser Glu Val Leu Ser Ser
                565                 570                 575

Lys Asp Lys Val Asn Leu Ile Val Ser Ser Lys His Pro Arg Pro Gln
            580                 585                 590

Phe Tyr Ser Ala Ala Glu Ala Glu Leu Val Arg Glu Gly Tyr Lys
        595                 600                 605

Val Ile Asp Trp Ala Ser Thr Asp Lys Gly Gly Glu Pro Asp Val Val
    610                 615                 620

Ile Ala Ala Ala Ala Thr Glu Pro Asn Leu Glu Ala Leu Ala Ala Ile
625                 630                 635                 640

Thr Ile Leu Asn Lys Gln Phe Pro Glu Leu Lys Ile Arg Phe Ile Asn
                645                 650                 655

Val Val Asp Ile Leu Lys Leu Arg His Pro Lys Val Asp Pro Arg Gly
            660                 665                 670

Leu Thr Asp Glu Gln Phe Asp Ala Leu Phe Thr Lys Asp Lys Pro Val
        675                 680                 685

Ile Phe Cys Phe His Gly Tyr Glu Gly Met Val Arg Asp Ile Phe Phe
    690                 695                 700

Asp Arg His Asn His Asn Leu Arg Ile His Gly Tyr Arg Glu Asn Gly
705                 710                 715                 720

Asp Ile Thr Thr Pro Phe Asp Met Arg Val Leu Ser Glu Met Asp Arg
                725                 730                 735

Phe His Val Ala Lys Asp Ala Ala Leu Ala Val Tyr Gly Asp Lys Ala
            740                 745                 750

Gln Asp Phe Ala Lys Lys Met Asp Asp Thr Leu Ala Phe His His Ser
        755                 760                 765

Tyr Ile Arg Glu Asn Gly Glu Asp Ile Pro Glu Val Arg Asn Trp Lys
    770                 775                 780
```

Trp Glu Ala Leu Lys
785

<210> SEQ ID NO 41
<211> LENGTH: 788
<212> TYPE: PRT
<213> ORGANISM: Eremococcus coleocola ACS-139-V-Col8

<400> SEQUENCE: 41

Met Thr Val Asp Tyr Asn Ser Lys Glu Tyr Leu Thr Leu Val Asp Lys
1               5                   10                  15

Trp Trp Arg Ala Ala Asn Tyr Leu Ser Val Gly Gln Met Phe Leu Arg
            20                  25                  30

Asp Asn Pro Leu Leu Gln Glu Val Thr Ala Asp His Val Lys Leu
        35                  40                  45

Asn Pro Ile Gly His Trp Gly Thr Ile Gly Gln Asn Phe Leu Tyr
    50                  55                  60

Ala His Leu Asn Arg Ile Ile Asn Lys Tyr Asn Val Asn Met Phe Tyr
65                  70                  75                  80

Ile Glu Gly Pro Gly His Gly Gly Gln Val Met Val Thr Asn Ser Tyr
                85                  90                  95

Leu Asp Gly Ser Tyr Thr Glu Arg Tyr Pro Glu Phe Thr Gln Asp Ile
            100                 105                 110

Ala Gly Met Lys Lys Leu Phe Lys Thr Phe Ser Phe Pro Gly Gly Ile
        115                 120                 125

Gly Ser His Ala Ala Pro Glu Thr Pro Gly Ser Met His Glu Gly Gly
    130                 135                 140

Glu Leu Gly Tyr Ala Leu Ser His Ala Thr Gly Ala Ile Leu Asp Asn
145                 150                 155                 160

Pro Asp Val Ile Ala Ala Thr Val Val Gly Asp Gly Glu Ala Glu Thr
                165                 170                 175

Gly Pro Leu Ala Ala Gly Trp Phe Ser Asn Val Phe Ile Asn Pro Val
            180                 185                 190

Ser Asp Gly Ala Val Leu Pro Ile Leu Tyr Leu Asn Gly Gly Lys Ile
        195                 200                 205

Ala Asn Pro Thr Ile Leu Ala Arg Lys Ser Asn Glu Asp Leu Thr Lys
    210                 215                 220

Tyr Phe Glu Gly Met Gly Trp Lys Pro Tyr Ile Val Glu Gly Thr Asp
225                 230                 235                 240

Pro Glu Gln Val His Pro Ile Met Ala Lys Val Leu Asp Glu Val Ile
                245                 250                 255

Glu Glu Ile Gln Ala Ile Gln Ala Glu Ala Arg Lys Gly Lys Ala Glu
            260                 265                 270

Asp Ala Lys Met Pro His Trp Pro Met Ile Leu Tyr Arg Thr Pro Lys
        275                 280                 285

Gly Trp Thr Gly Pro Glu Glu Val Glu Gly Lys Thr Ile Gln Gly Ser
    290                 295                 300

Phe Arg Ala His Gln Val Pro Ile Pro Val Ser Gly Arg Asn Met Glu
305                 310                 315                 320

Asp Ile Asp Leu Leu Ile Asn Trp Leu Lys Ser Tyr Gly Pro Glu Glu
                325                 330                 335

Leu Phe Thr Glu Asn Gly Glu Leu Val Asp Glu Leu Lys Glu Phe Ala
            340                 345                 350

Pro Lys Gly Asp His Arg Met Ala Met Asn Pro Leu Thr Asn Gly Gly
        355                 360                 365

```
Asn Pro Lys Pro Leu Asn Met Pro Asn Trp Lys Asp Tyr Ala Leu Glu
    370                 375                 380

Ile Gly Thr Pro Gly Ser Lys Asp Ala Gln Asp Met Ile Glu Phe Gly
385                 390                 395                 400

Gly Phe Ala Arg Asp Ile Val Lys Glu Asn Pro Glu Asn Phe Arg Ile
                405                 410                 415

Phe Gly Pro Asp Glu Thr Lys Ser Asn Arg Leu Asn Lys Val Phe Glu
            420                 425                 430

Val Thr Asn Arg Gln Trp Leu Glu Pro Ile Ser Glu Lys Phe Asp Glu
        435                 440                 445

Asn Met Ser Ala Ser Gly Arg Val Ile Asp Ser Gln Leu Ser Glu His
    450                 455                 460

Gln Asn Gln Gly Phe Leu Glu Ala Tyr Val Leu Thr Gly Arg His Gly
465                 470                 475                 480

Phe Phe Ala Ser Tyr Glu Ser Phe Phe Arg Thr Val Asp Ser Met Ile
                485                 490                 495

Thr Gln His Phe Lys Trp Ile Arg Lys Ser Ala Lys His Ser Trp Arg
            500                 505                 510

Lys Pro Tyr Gln Ser Leu Asn Leu Ile Ser Ala Ser Thr Val Phe Gln
        515                 520                 525

Gln Asp His Asn Gly Tyr Thr His Gln Asp Pro Gly Leu Leu Thr His
    530                 535                 540

Ile Gly Glu Lys His Gly Glu Tyr Met Arg Ala Tyr Leu Pro Ala Asp
545                 550                 555                 560

Thr Asn Ser Leu Leu Ala Val Met Asp Lys Ala Phe Arg Ser Glu Asn
                565                 570                 575

Val Ile Asn Tyr Val Val Thr Ser Lys His Pro Arg Pro Gln Phe Phe
            580                 585                 590

Thr Ala Asp Glu Ala Glu Leu Val Asn Glu Gly Leu Lys Val Ile
        595                 600                 605

Asp Trp Ala Ser Thr Val Lys Asp Asn Glu Glu Pro Asp Val Val Ile
    610                 615                 620

Ala Ala Ala Gly Thr Glu Pro Asn Phe Glu Ala Ile Ala Ala Ile Ser
625                 630                 635                 640

Tyr Leu Val Lys Ala Phe Pro Glu Leu Lys Ile Arg Phe Val Asn Val
                645                 650                 655

Val Asp Leu Phe Arg Leu Arg Ser Pro Glu Ile Asp Pro Arg Gly Leu
            660                 665                 670

Ser Asp Asp Glu Phe Asp Ala Ile Phe Thr Lys Asp Lys Pro Val Phe
        675                 680                 685

Phe Ala Phe His Ser Tyr Glu Gly Met Leu Lys Asp Ile Phe Phe Thr
    690                 695                 700

Arg His Asn His Asn Leu Tyr Ala His Gly Tyr Arg Glu Asn Gly Glu
705                 710                 715                 720

Ile Thr Thr Pro Phe Asp Met Arg Val Leu Asn Glu Leu Asp Arg Phe
                725                 730                 735

His Leu Ser Ala His Val Ala Asp Val Val Tyr Gly Asp Lys Ala Arg
            740                 745                 750

Asp Tyr Val Ala Glu Met Lys Gly Lys Val Gln Glu His Arg Asp Tyr
        755                 760                 765

Val Glu Glu Tyr Gly Ala Asp Met Pro Glu Val Glu Asp Trp Lys Trp
    770                 775                 780
```

Glu Asp Ile Lys
785

<210> SEQ ID NO 42
<211> LENGTH: 789
<212> TYPE: PRT
<213> ORGANISM: Aerococcus urinae ACS-120-V-Col10a

<400> SEQUENCE: 42

Met Thr Asp Phe Asp Ser Lys Ala Tyr Leu Asp Lys Val Asp Ala Trp
1               5                   10                  15

Trp Arg Ala Ala Asn Tyr Leu Ser Val Gly Gln Met Tyr Leu Arg Asp
                20                  25                  30

Asn Pro Leu Leu Asp Arg Glu Val Thr Ala Asp Asp Ile Lys Ile Thr
            35                  40                  45

Pro Ile Gly His Trp Gly Thr Ile Ala Gly Gln Asn Phe Val Tyr Ala
        50                  55                  60

His Leu Asn Arg Val Ile Asn Lys Tyr Asp Leu Asn Met Phe Tyr Ile
65                  70                  75                  80

Glu Gly Pro Gly His Gly Gly Gln Val Met Gln Ala Asn Ala Tyr Leu
                85                  90                  95

Asp Gly Thr Trp Thr Glu His Tyr Pro Glu Tyr Pro Gln Asn Lys Glu
            100                 105                 110

Gly Met Gln Lys Phe Phe Lys Tyr Phe Ser Phe Pro Gly Gly Thr Gly
        115                 120                 125

Ser His Ala Thr Ala Glu Ile Pro Gly Ser Ile His Glu Gly Gly Glu
130                 135                 140

Leu Gly Tyr Ser Leu Ser His Ala Thr Gly Ala Ile Leu Asp Asn Pro
145                 150                 155                 160

Asp Val Ile Ala Ala Thr Val Ile Gly Asp Gly Glu Ser Glu Thr Gly
                165                 170                 175

Pro Leu Ala Ala Ser Trp Leu Ser Asn Ser Phe Ile Asn Pro Val Thr
            180                 185                 190

Asp Gly Ala Val Leu Pro Ile Leu Tyr Leu Asn Gly Gly Lys Ile Ala
        195                 200                 205

Asn Pro Thr Ile Leu Glu Arg Lys Ser Asn Glu Asp Leu Ile Lys Tyr
210                 215                 220

Phe Gln Gly Leu Gly Trp Asp Pro Met Val Val Glu Gly Asn Asp Pro
225                 230                 235                 240

Glu Lys Val His Pro Leu Met Ala Lys Thr Leu Asp Gln Ala Ile Glu
                245                 250                 255

Lys Ile Lys Ser Ile Gln Gly Glu Ala Arg Lys Gly Ser Ala Asp Glu
            260                 265                 270

Ala Thr Met Gly His Trp Pro Met Ile Leu Tyr Arg Thr Pro Lys Gly
        275                 280                 285

Trp Thr Gly Pro Lys Ala Trp Glu Gly Asn Asp Ile Glu Gly Ser Phe
290                 295                 300

Arg Ala His Gln Val Pro Ile Pro Val Asn Ala Glu Asn Met Glu His
305                 310                 315                 320

Val Asp Ala Leu Ile Asp Trp Leu Lys Ser Tyr Arg Pro Glu Glu Leu
                325                 330                 335

Phe Thr Glu Glu Gly Gln Leu Arg Pro Glu Ile Ala Glu Ile Ala Pro
            340                 345                 350

Lys Gly Asp Gln Arg Met Ala Ser Asn Pro Ile Thr Asp Gly Gly Ile
        355                 360                 365

```
Asp Pro Lys Pro Leu Asp Leu Pro Asp Trp Arg Asp Tyr Ala Leu Asp
        370                 375                 380

Phe Glu Thr Pro Gly Glu Arg Asp Ala Gln Asp Met Ile Glu Met Gly
385                 390                 395                 400

Gly Tyr Ala Ala Gly Val Ile Glu Lys Asn Pro Asp Asn Phe Arg Ile
                405                 410                 415

Phe Gly Pro Asp Glu Thr Lys Ser Asn Arg Leu Asn Lys Val Phe Asn
            420                 425                 430

Val Thr Lys Arg Gln Trp Leu Glu Pro Ile Lys Asp Asn Tyr Asp Glu
        435                 440                 445

Trp Met Ser Pro Ser Gly Arg Val Ile Asp Ser Gln Leu Ser Glu His
    450                 455                 460

Gln Met Glu Gly Phe Leu Glu Ala Tyr Thr Leu Thr Gly Arg His Gly
465                 470                 475                 480

Phe Phe Ala Ser Tyr Glu Ala Phe Ile Arg Thr Val Asp Ser Met Ile
                485                 490                 495

Thr Gln His Phe Lys Trp Met Arg Glu Ala Ser Glu Tyr Lys Trp His
            500                 505                 510

Lys Pro Tyr Gln Ser Leu Asn Leu Ile Ser Ser Thr Ala Phe Gln
        515                 520                 525

Gln Asp His Asn Gly Tyr Thr His Gln Asp Pro Gly Leu Leu Thr His
    530                 535                 540

Leu Ala Glu Lys Lys Gly Glu Phe Val Arg Ala Tyr Leu Pro Ala Asp
545                 550                 555                 560

Thr Asn Ser Leu Leu Ala Val Met Asp Lys Ala Leu Ser Ser Glu Asn
                565                 570                 575

Val Ile Asn Tyr Ile Val Thr Ser Lys His Pro Arg Pro Gln Phe Phe
            580                 585                 590

Ser Val Glu Glu Ala Glu Phe Val Asp Lys Gly Tyr Lys Val Ile
        595                 600                 605

Asp Trp Ala Ser Thr Val Glu Glu Gly Glu Pro Asp Val Val Ile
    610                 615                 620

Ala Ala Ser Gly Thr Glu Pro Thr Val Glu Thr Ile Ala Thr Ile Ser
625                 630                 635                 640

Tyr Leu His Glu Ala Phe Pro Glu Leu Lys Ile Arg Tyr Val Asn Val
                645                 650                 655

Val Asp Leu Tyr Arg Leu Arg His Pro Asn Ile Asp Pro Arg Gly Leu
            660                 665                 670

Ser Asp Glu Glu Phe Asp Ala Val Phe Thr Lys Asp Lys Pro Val Phe
        675                 680                 685

Phe Gly Phe His Ser Phe Glu Gly Leu Leu Lys Asp Ile Phe Phe Asp
    690                 695                 700

Arg His Asn His Asn Leu Tyr Pro His Gly Tyr Arg Glu Glu Gly Ala
705                 710                 715                 720

Ile Thr Thr Pro Phe Asp Met Arg Val Leu Asn Glu Leu Asp Arg Phe
                725                 730                 735

His Phe Ala Ala His Val Ala Glu Val Val Tyr Gly Asp Lys Ala Gln
            740                 745                 750

Asp Phe Ile Asp Gln Met Asn Ala Lys Val Glu Glu His Arg Ala Tyr
        755                 760                 765

Ile Val Glu Tyr Gly Thr Asp Met Pro Glu Val Lys Glu Trp Lys Trp
    770                 775                 780
```

-continued

```
Gln Pro Leu Glu Lys
785

<210> SEQ ID NO 43
<211> LENGTH: 792
<212> TYPE: PRT
<213> ORGANISM: Kingella kingae ATCC 23330

<400> SEQUENCE: 43

Met Thr Asn Lys Thr Gln Phe Asp Thr Pro Glu Tyr Leu Gly Lys Val
1               5                   10                  15

Asp Ala Trp Trp Arg Ala Ala Asn Tyr Ile Ser Val Ala Gln Met Tyr
            20                  25                  30

Leu Lys Asp Asn Pro Leu Leu Lys Thr Pro Leu Val Ala Asn Asp Val
        35                  40                  45

Lys Ala His Pro Ile Gly His Trp Gly Thr Val Pro Gly Gln Asn Phe
    50                  55                  60

Ile Tyr Ala His Leu Asn Arg Ala Ile Asn Lys Tyr Asp Val Asp Met
65                  70                  75                  80

Phe Tyr Ile Glu Gly Pro Gly His Gly Gly Gln Val Met Val Ser Asn
                85                  90                  95

Ser Tyr Leu Asp Gly Ser Tyr Thr Glu Ile Tyr Pro Asp Ile Thr Gln
            100                 105                 110

Asp Thr Ala Gly Leu Lys Lys Leu Cys Lys Ile Phe Ser Phe Pro Gly
        115                 120                 125

Gly Ile Ala Ser His Ala Ala Pro Glu Thr Pro Gly Ser Ile His Glu
    130                 135                 140

Gly Gly Glu Leu Gly Tyr Ala Leu Ser His Ala Phe Gly Ala Val Leu
145                 150                 155                 160

Asp Asn Pro Asn Val Ile Ala Ala Val Ile Gly Asp Gly Glu Ala
                165                 170                 175

Glu Thr Gly Pro Leu Cys Ala Gly Trp Phe Gly Asn Thr Phe Ile Asn
            180                 185                 190

Pro Val Asn Asp Gly Ala Val Leu Pro Ile Leu Tyr Leu Asn Gly Gly
        195                 200                 205

Lys Ile His Asn Pro Thr Ile Leu Ala Arg Lys Thr Asp Glu Glu Leu
    210                 215                 220

Lys Gln Tyr Phe Asn Gly Met Gly Trp Glu Pro Ile Phe Val Asp Val
225                 230                 235                 240

Asn Asn Val Asp Asn Tyr His Glu Ile Met Ser Gln Lys Val Asp Glu
                245                 250                 255

Ala Val Glu His Ile Leu Ser Ile Trp Gln Thr Ala Arg Thr Gln Lys
            260                 265                 270

Ala Glu Asp Ala Thr Met Pro His Trp Pro Val Leu Val Ala Arg Ile
        275                 280                 285

Pro Lys Gly Trp Thr Gly Pro Lys Thr Trp His Gly Glu Pro Ile Glu
    290                 295                 300

Gly Gly Phe Arg Ala His Gln Val Pro Ile Pro Ala Ser His Asp
305                 310                 315                 320

Met Glu Thr Ala Gly Glu Leu Glu Lys Trp Leu Arg Ser Tyr Arg Pro
                325                 330                 335

Glu Glu Leu Phe Asp Asp Asn Gly Cys Phe Leu Asp Lys Trp Arg Asp
            340                 345                 350

Ile Ser Pro Lys Gly Ala Lys Arg Met Ser Val His Pro Ile Thr Asn
        355                 360                 365
```

```
Gly Gly Ile Asn Pro Lys Ala Leu Val Met Pro Asp Trp Thr Gln His
        370                 375                 380
Ala Leu Glu Ile Gly Val Pro Gly Ser Gln Asp Ala Gln Asp Met Val
385                 390                 395                 400
Glu Cys Gly Arg Leu Met Ala Asp Val Val Thr Ala Asn Pro Asn Asn
                405                 410                 415
Phe Arg Ile Phe Gly Pro Asp Glu Thr Lys Ser Asn Arg Leu Asn Gln
                420                 425                 430
Val Phe Gln Val Thr Lys Arg Gln Trp Leu Gly Arg Arg Asp Glu Ala
                435                 440                 445
Tyr Asp Glu Trp Ile Ala Pro Val Gly Arg Val Ile Asp Ser Gln Leu
        450                 455                 460
Ser Glu His Gln Ala Glu Gly Phe Leu Glu Gly Tyr Val Leu Thr Gly
465                 470                 475                 480
Arg His Gly Phe Phe Ala Ser Tyr Glu Ser Phe Phe Arg Val Val Asp
                485                 490                 495
Ser Met Ile Thr Gln His Phe Lys Trp Leu Arg Lys Cys Lys Thr His
                500                 505                 510
Ala Ala Trp Arg Asn Asp Tyr Pro Ser Leu Asn Leu Ile Ala Thr Ser
        515                 520                 525
Thr Val Phe Gln Gln Asp His Asn Gly Tyr Thr His Gln Asp Pro Gly
        530                 535                 540
Leu Leu Thr His Leu Ala Glu Lys Lys Pro Glu Phe Val Arg Glu Tyr
545                 550                 555                 560
Leu Pro Ala Asp Ser Asn Thr Leu Met Ala Val Met Ser Glu Ala Leu
                565                 570                 575
Thr Ser Arg Asp Arg Ile Asn Leu Ile Val Ser Ser Lys His Leu Arg
                580                 585                 590
Pro Gln Phe Phe Asn Ala Glu Glu Ala Lys Glu Leu Val Arg Glu Gly
        595                 600                 605
Tyr Lys Val Ile Asp Trp Ala Ser Thr Cys His Asp Gly Glu Pro Asp
        610                 615                 620
Val Val Ile Ala Ala Gly Thr Glu Pro Asn Met Glu Ala Leu Ala
625                 630                 635                 640
Ala Ile Ser Ile Leu His Lys Gln Phe Pro Glu Leu Lys Ile Arg Phe
                645                 650                 655
Ile Asn Val Val Asp Ile Leu Lys Leu Arg His Pro Ser Ile Asp Pro
                660                 665                 670
Arg Gly Leu Ser Asp Glu Gln Phe Asp Ala Leu Phe Thr Gln Glu Lys
        675                 680                 685
Pro Val Val Phe Cys Phe His Gly Tyr Glu Gly Met Ile Arg Asp Leu
        690                 695                 700
Phe Phe Pro Arg Ala Asn His Asn Val Arg Ile His Gly Tyr Arg Glu
705                 710                 715                 720
Asn Gly Asp Ile Thr Thr Pro Phe Asp Met Arg Val Leu Ser Glu Met
                725                 730                 735
Asp Arg Phe His Val Ala Lys Asp Ala Gln Ala Val Tyr Gly Asp
                740                 745                 750
Lys Ala Ser Glu Phe Ala Lys Lys Met Gly Glu Thr Val Ala Phe His
        755                 760                 765
Arg Ser Tyr Ile Arg Glu His Gly Thr Asp Ile Pro Glu Val Ala Glu
        770                 775                 780
```

-continued

```
Trp Lys Trp Gln Pro Leu Ala Lys
785                 790

<210> SEQ ID NO 44
<211> LENGTH: 794
<212> TYPE: PRT
<213> ORGANISM: Streptococcus criceti HS-6

<400> SEQUENCE: 44

Met Asn Thr Asn Phe Asp Ser Ser Asp Tyr Leu Asn Lys Val Asp Ala
1               5                   10                  15

Trp Trp Arg Ala Ala Asn Tyr Ile Ser Ala Ala Gln Met Tyr Leu Lys
            20                  25                  30

Asp Asn Pro Leu Leu Arg Arg Glu Val Ala Ala Glu Asp Leu Lys Ser
        35                  40                  45

His Pro Ile Gly His Trp Gly Thr Val Pro Gly Gln Asn Phe Ile Tyr
    50                  55                  60

Ala His Leu Leu Arg Ser Ile Asn Lys Tyr Asp Leu Asp Met Phe Tyr
65                  70                  75                  80

Ile Glu Gly Pro Gly His Gly Gly Gln Val Met Val Ser Asn Ser Tyr
                85                  90                  95

Leu Asp Gly Ser Tyr Thr Glu Leu Asn Pro Gln Ile Ser Gln Thr Glu
            100                 105                 110

Glu Gly Leu Lys Gln Leu Cys Lys Ile Phe Ser Phe Pro Gly Gly Ile
        115                 120                 125

Ala Ser His Ala Ala Pro Glu Thr Pro Gly Ser Ile His Glu Gly Gly
    130                 135                 140

Glu Leu Gly Tyr Ala Leu Ser His Ala Thr Gly Ala Val Leu Asp Asn
145                 150                 155                 160

Pro Asp Val Ile Ala Ala Thr Val Ile Gly Asp Gly Glu Ser Glu Thr
                165                 170                 175

Gly Pro Leu Met Ala Gly Trp Leu Ser Asn Thr Phe Ile Asn Pro Val
            180                 185                 190

Asn Asp Gly Ala Val Leu Pro Ile His Phe Leu Asn Gly Gly Lys Ile
        195                 200                 205

His Asn Pro Thr Ile Phe Glu Arg Lys Ser Asp Asp Glu Leu Lys Ala
    210                 215                 220

Phe Phe Thr Gly Leu Gly Trp Lys Pro Ile Phe Ala Asp Val Thr Ala
225                 230                 235                 240

Phe Ala Ser Asp His Ala Ala His Lys Leu Phe Ala Ala Lys Leu
                245                 250                 255

Asp Glu Ala Ile Glu Glu Ile Arg Asn Ile Gln Ala Lys Ala Arg Lys
            260                 265                 270

Gly Ser Ala Asp Glu Ala Thr Met Pro Ala Trp Pro Val Ile Val Ala
        275                 280                 285

Arg Ile Pro Lys Gly Trp Thr Gly Pro Lys Ser Trp Lys Gly Thr Pro
    290                 295                 300

Ile Glu Gly Gly Trp Arg Ala His Gln Val Pro Ile Pro Val Asp Ser
305                 310                 315                 320

His His Met Glu His Val Asp Ala Leu Leu Asp Trp Leu Lys Ser Tyr
                325                 330                 335

Gln Pro Glu Glu Leu Phe Asp Ala Glu Gly His Leu Lys Ser Glu Val
            340                 345                 350

Ala Ala Leu Ser Pro Lys Gly Asn Arg Arg Met Ser Met Asn Pro Ile
        355                 360                 365
```

```
Thr Asn Ala Gly Val Ile Lys Pro Met Asp Thr Ala Asp Trp Lys Lys
    370                 375                 380

Arg Ala Phe Asp Ile Gln Thr Pro Gly Glu Ile Val Ala Gln Asp Met
385                 390                 395                 400

Ile Glu Phe Gly Lys Tyr Ala Ala Asp Leu Val Glu Ala Asn Pro Asp
                405                 410                 415

Asn Phe Arg Ile Phe Gly Pro Asp Glu Ser Lys Ser Asn Arg Leu Asn
                420                 425                 430

Glu Val Phe Thr Lys Thr Asn Arg Gln Trp Met Gly Arg Arg Asp Pro
                435                 440                 445

Ser Tyr Asp Glu Trp Leu Ser Pro Ala Gly Arg Val Ile Asp Ser Gln
    450                 455                 460

Leu Ser Glu His Gln Ala Glu Gly Phe Leu Glu Gly Tyr Val Leu Thr
465                 470                 475                 480

Gly Arg His Gly Phe Phe Ala Ser Tyr Glu Ser Phe Leu Arg Val Val
                485                 490                 495

Asp Thr Met Ile Thr Gln His Phe Lys Trp Leu Arg Lys Ser Lys Thr
                500                 505                 510

His Thr Thr Trp Arg Lys Asn Tyr Pro Ser Leu Asn Leu Ile Ala Thr
        515                 520                 525

Ser Thr Val Phe Gln Gln Asp His Asn Gly Tyr Thr His Gln Asp Pro
    530                 535                 540

Gly Val Leu Thr His Leu Ser Glu Lys Thr Pro Glu Tyr Ile Arg Glu
545                 550                 555                 560

Tyr Leu Pro Ala Asp Thr Asn Ser Leu Leu Ala Val Met Asp Lys Ala
                565                 570                 575

Phe Lys Asp Glu Asp Lys Ile Asn Leu Ile Val Thr Ser Lys His Pro
                580                 585                 590

Arg Pro Gln Phe Tyr Ser Val Glu Glu Ala Ser Glu Leu Val Glu Lys
                595                 600                 605

Gly Tyr Lys Val Ile Asp Trp Ala Ser Thr Val Gln Ala Asn Glu Glu
    610                 615                 620

Pro Asp Val Val Phe Ala Ala Gly Thr Glu Pro Asn Leu Glu Ala
625                 630                 635                 640

Leu Ala Ala Ile Ser Ile Leu His Lys Thr Phe Pro Ser Leu Lys Ile
                645                 650                 655

Arg Phe Val Asn Val Val Asp Ile Leu Lys Leu Arg His Pro Asp Leu
                660                 665                 670

Asp Pro Arg Gly Leu Ser Asp Glu Glu Phe Asp Lys Val Phe Thr Lys
            675                 680                 685

Asp Lys Pro Val Ile Phe Ala Phe His Ala Tyr Glu Gly Met Ile Arg
    690                 695                 700

Asp Ile Phe Phe Arg Arg His Asn His Asn Leu His Val His Gly Tyr
705                 710                 715                 720

Arg Glu Asn Gly Asp Ile Thr Thr Pro Phe Asp Met Arg Val Met Ser
                725                 730                 735

Glu Leu Asp Arg Phe His Leu Ala Gln Asp Ala Ala Leu Thr Thr Leu
            740                 745                 750

Gly Glu Lys Ala Gln Ala Phe Ser Ala Lys Met Asp Glu Thr Val Ala
        755                 760                 765

Tyr His Lys Asp Tyr Ile Arg Glu His Gly Asp Asp Ile Pro Glu Val
    770                 775                 780
```

-continued

Gln Asn Trp Gln Trp Glu Asn Leu Asp Glu
785                 790

<210> SEQ ID NO 45
<211> LENGTH: 787
<212> TYPE: PRT
<213> ORGANISM: Streptococcus criceti HS-6

<400> SEQUENCE: 45

Met Thr Glu Phe Asp Ser Lys Asp Tyr Leu Ala Lys Val Asp Ala Trp
1               5                   10                  15

Trp Arg Ala Ala Asn Tyr Ile Ser Val Ala Gln Met Tyr Leu Lys Asp
            20                  25                  30

Asn Pro Leu Leu Arg Arg Glu Val Ser Lys Glu Asp Val Lys Val His
        35                  40                  45

Pro Ile Gly His Trp Gly Thr Ile Ala Gly Gln Asn Phe Ile Tyr Ala
    50                  55                  60

His Leu Asn Arg Val Ile Asn Lys Phe Asp Leu Asn Met Phe Tyr Ile
65                  70                  75                  80

Glu Gly Pro Gly His Gly Gly Gln Val Met Val Ser Asn Ser Tyr Ile
                85                  90                  95

Asp Gly Ser Tyr Thr Glu Arg Tyr Pro Asn Ile Thr Gln Asp Glu Asp
            100                 105                 110

Gly Leu Lys Gln Leu Cys Lys Ile Phe Ser Phe Pro Gly Gly Ile Ala
        115                 120                 125

Ser His Ala Ala Pro Glu Thr Pro Gly Ser Ile His Glu Gly Gly Glu
    130                 135                 140

Leu Gly Tyr Ala Leu Ser His Ala Thr Gly Ala Ile Leu Asp Asn Pro
145                 150                 155                 160

Asp Val Ile Ala Ala Thr Val Ile Gly Asp Gly Glu Ala Glu Thr Gly
                165                 170                 175

Pro Leu Asn Ala Gly Trp Phe Ser Asn Thr Phe Ile Asn Pro Val Asn
            180                 185                 190

Asp Gly Ala Val Leu Pro Ile Leu Tyr Leu Asn Gly Gly Lys Ile His
        195                 200                 205

Asn Pro Thr Ile Leu Ser Arg Lys Thr Asp Glu Glu Leu Thr His Leu
    210                 215                 220

Phe Gln Gly Leu Gly Trp Glu Pro Tyr Phe Val Glu Gly Asn Asp Pro
225                 230                 235                 240

Glu Val Ile His Ser Gln Met Ala Glu Thr Leu Asp Lys Val Ile Glu
                245                 250                 255

Lys Ile Lys Thr Ile Gln Thr Gln Ala Arg Gln Lys Pro Ala Glu Glu
            260                 265                 270

Ala Gln Gln Ala Gln Trp Pro Val Leu Ile Val Arg Thr Pro Lys Gly
        275                 280                 285

Trp Thr Gly Pro Lys Glu Trp Asn Gly Glu Pro Ile Glu Gly Gly Phe
    290                 295                 300

Arg Ala His Gln Val Pro Ile Pro Val Glu Ala Gly His Met Glu His
305                 310                 315                 320

Ile Asp Ala Leu Thr Asp Trp Leu Lys Ser Tyr Arg Pro Glu Glu Leu
                325                 330                 335

Phe Asp Glu Lys Gly Tyr Val Lys Glu Glu Ile Arg Val Ile Ser Pro
            340                 345                 350

Lys Gly Asn Arg Arg Met Ser Met Asn Pro Ile Thr Asn Ala Gly Ile
        355                 360                 365

```
Val Lys Lys Leu Asp Leu Ala Asp Trp Arg Lys His Ala Ile Asp Thr
    370                 375                 380

Ser Lys Pro Gly Ser Ile Met Lys Gln Asp Met Ile Glu Phe Gly Lys
385                 390                 395                 400

Tyr Ala Ala Asp Leu Val Lys Ala Asn Pro Asp Asn Phe Arg Ile Phe
                405                 410                 415

Gly Pro Asp Glu Thr Lys Ser Asn Arg Leu Asn Asn Val Phe Thr Ala
            420                 425                 430

Thr Asn Arg Gln Trp Leu Ala Pro Arg Asp Lys Ser Tyr Asp Glu Trp
        435                 440                 445

Ile Ser Pro Val Gly Arg Val Ile Asp Ser Gln Leu Ser Glu His Gln
    450                 455                 460

Ala Glu Gly Phe Leu Glu Gly Tyr Val Leu Thr Gly Arg His Gly Phe
465                 470                 475                 480

Phe Ala Ser Tyr Glu Ser Phe Leu Arg Val Val Asp Ser Met Ile Thr
                485                 490                 495

Gln His Phe Lys Trp Leu Arg Lys Ser Lys Thr His Thr Asp Trp Arg
            500                 505                 510

Lys Asn Tyr Pro Ser Leu Asn Leu Ile Ala Thr Ser Thr Val Phe Gln
        515                 520                 525

Gln Asp His Asn Gly Tyr Thr His Gln Asp Pro Gly Leu Leu Thr His
    530                 535                 540

Leu Ala Glu Lys Thr Pro Glu Tyr Val Arg Glu Tyr Leu Pro Ala Asp
545                 550                 555                 560

Ser Asn Ser Leu Phe Ala Val Met Glu Tyr Ala Leu Ala Asp Glu Asp
                565                 570                 575

Lys Val Asn Val Ile Val Thr Ser Lys His Pro Arg Pro Gln Phe Tyr
            580                 585                 590

Ser Val Ala Glu Ala Gln Glu Leu Val Lys Glu Gly Tyr Lys Val Ile
        595                 600                 605

Asp Trp Ala Ser Asn Asp His Asp Gly Glu Pro Asp Ile Val Phe Ala
    610                 615                 620

Ala Ala Gly Thr Glu Pro Asn Leu Glu Val Leu Ala Gly Ile Ser Leu
625                 630                 635                 640

Leu His Lys Ala Phe Pro Glu Val Lys Ile Arg Phe Ile Asn Val Val
                645                 650                 655

Asp Ile Leu Lys Leu Arg Ser Pro Lys Val Asp Pro Arg Gly Leu Ser
            660                 665                 670

Asp Glu Ala Phe Asn Lys Leu Phe Thr Thr Asp Lys Pro Ile Val Phe
        675                 680                 685

Ala Tyr His Gly Tyr Glu Gly Gln Ile Arg Asp Leu Phe Phe Asn Arg
    690                 695                 700

Asp Asn His Lys Val Tyr Ile His Gly Tyr Arg Glu Asn Gly Asp Ile
705                 710                 715                 720

Thr Thr Pro Phe Asp Met Arg Val Met Ser Glu Met Asp Arg Phe His
                725                 730                 735

Ile Ala Lys Glu Ala Ala Gln Ala Val Leu Gly Asp Lys Ala Gln Gly
            740                 745                 750

Phe Ala Gln Glu Met Ala Asp Lys Leu Ala Tyr His Thr Ala Tyr Ile
        755                 760                 765

Arg Glu His Gly Asp Asp Ile Pro Glu Val Gln Asn Trp Gln Trp Glu
    770                 775                 780
```

Thr Ile Asp
785

<210> SEQ ID NO 46
<211> LENGTH: 794
<212> TYPE: PRT
<213> ORGANISM: Mycoplasma columbinum SF7

<400> SEQUENCE: 46

Met Ser Lys Thr Asn Phe Asp Ser Lys Lys Tyr Leu Asp Lys Ile His
1               5                   10                  15

Ala Trp Trp Arg Ala Ala Asn Tyr Leu Ser Val Gly Gln Met Tyr Leu
            20                  25                  30

Lys Asn Asn Pro Leu Leu Gln Glu Pro Leu Lys Asp Glu Asp Ile Lys
        35                  40                  45

Ile Tyr Pro Ile Gly His Trp Gly Thr Ile Pro Gly Gln Asn Leu Ile
    50                  55                  60

Tyr Ala His Leu Asn Arg Val Ile Asn Lys Tyr Asp Leu Asn Met Phe
65                  70                  75                  80

Tyr Ile Glu Gly Pro Gly His Gly Gly Gln Val Met Ile Ser Asn Ser
                85                  90                  95

Tyr Leu Asp Gly Ser Tyr Thr Glu Leu Phe Pro Glu Ile Thr Gln Asp
            100                 105                 110

Leu Ala Gly Leu Asn Lys Met Phe Lys Arg Phe Ser Phe Pro Gly Gly
        115                 120                 125

Thr Ala Ser His Ala Ala Pro Glu Thr Pro Gly Ser Ile His Glu Gly
    130                 135                 140

Gly Glu Leu Gly Tyr Ala Leu Ser His Ala Thr Gly Ala Ile Leu Asp
145                 150                 155                 160

Asn Pro Asp Val Ile Ala Ala Thr Val Ile Gly Asp Gly Glu Ala Glu
                165                 170                 175

Thr Gly Pro Leu Met Ala Gly Trp Tyr Ser Ser Phe Ile Asn Pro
            180                 185                 190

Val Asn Asp Gly Thr Val Leu Pro Ile Leu His Ile Asn Gly Gly Lys
        195                 200                 205

Ile Ser Asn Pro Thr Ile Leu Ala Arg Lys Thr Asp Lys Glu Ile Lys
    210                 215                 220

Gln Leu Leu Ala Gly Phe Gly Trp Glu Ala Ile Phe Val Glu Ala Asp
225                 230                 235                 240

Val Phe Arg Pro Glu Ala Ile His Leu Ser Met Ala Lys Ala Phe Asp
                245                 250                 255

Lys Ala Ile Glu Lys Ile Gln Arg Ile Gln Arg Glu Ala Arg Ala Asn
            260                 265                 270

Ser Ala Asn His Ala Lys Arg Pro Ile Trp Pro Ala Leu Val Val Arg
        275                 280                 285

Thr Pro Lys Gly Trp Thr Cys Pro His Lys Ile Asp Asp Lys Val Tyr
    290                 295                 300

Glu Gly Ser Phe Arg Ser His Gln Val Pro Leu Ala Val Ser Ser Glu
305                 310                 315                 320

Asn Thr Thr Lys Lys Val Asp Leu Val Asn Trp Leu Glu Ser Tyr Lys
                325                 330                 335

Pro Arg Glu Leu Phe Asn Gln Asp Gly Ser Phe Lys Ala His Tyr Ala
            340                 345                 350

Glu Ile Ala Pro Lys Gly Asn Lys Arg Met Ala Met Asn Pro Ile Thr
        355                 360                 365

```
Asn Gly Gly Ile Asn Pro Lys Asn Leu Asp Leu Pro Asn Trp Glu Gln
            370                 375                 380

Phe Ala Ile Asp Phe Asp Lys Pro Gly Ala Ile Lys Ala Gln Asp Met
385                 390                 395                 400

Val Ser Ala Gly Thr Trp Phe Ala Asp Val Ile Lys Arg Asn Pro Thr
                405                 410                 415

Asn Phe Arg Ile Phe Gly Pro Asp Glu Thr Lys Ser Asn Arg Leu Phe
                420                 425                 430

Asp Val Leu Lys Thr Thr Asn Arg Gln Trp Leu Glu Arg Val Asp Tyr
            435                 440                 445

Asp Leu Asp Glu Asn Ile Gly Pro Ala Gly Arg Val Ile Asp Ser Gln
        450                 455                 460

Leu Ser Glu His Gln Ala Glu Gly Phe Leu Glu Gly Tyr Val Leu Thr
465                 470                 475                 480

Gly Arg His Gly Met Phe Ala Ser Tyr Glu Ser Phe Leu Arg Val Val
                485                 490                 495

Asp Ser Met Leu Thr Gln His Met Lys Trp Val Ala Lys Ala Lys Lys
                500                 505                 510

Val His Trp Arg Asn Asp Tyr Pro Ser Leu Asn Val Ile Ala Thr Ser
            515                 520                 525

Thr Ala Phe Gln Gln Asp His Asn Gly Tyr Thr His Gln Asp Pro Gly
530                 535                 540

Ile Leu Gly His Leu Ala Asp Lys Lys Pro Glu Leu Ile Arg Glu Tyr
545                 550                 555                 560

Leu Pro Ala Asp Ser Asn Thr Leu Leu Ala Val Leu Asp Lys Ala Phe
                565                 570                 575

Lys Glu Arg Asp Val Ile Asn Leu Ile Val Ala Ser Lys Gln Pro Arg
                580                 585                 590

Glu Gln Trp Phe Ser Pro Arg Glu Ala Asn Ile Leu Val Lys Asn Gly
            595                 600                 605

Leu Lys Val Ile Ser Trp Ala Ser Thr Cys Thr Leu Glu Glu Glu Pro
        610                 615                 620

Asp Leu Val Val Ala Ala Gly Thr Glu Pro Thr Leu Glu Ala Leu
625                 630                 635                 640

Ala Ala Ile Ser Tyr Leu Asn Glu Lys Phe Pro Thr Leu Lys Ile Arg
                645                 650                 655

Phe Val Asn Val Val Asp Leu Leu Lys Leu Arg His Pro Ser Ile Asp
                660                 665                 670

Pro Arg Gly Leu Ser Asn Tyr Glu Phe Asp Ser Ile Phe Thr Lys Asp
            675                 680                 685

Lys Pro Ile Leu Phe Ala Phe His Gly Tyr Glu Ala Leu Ile Arg Asp
        690                 695                 700

Ile Phe Phe Leu Arg Asn Asn His Asn Leu His Ile His Gly Tyr Arg
705                 710                 715                 720

Glu Asn Gly Asp Ile Thr Thr Ser Phe Asp Ile Arg Leu Met Ser Glu
                725                 730                 735

Met Asp Arg Phe His Met Ala Gln Thr Ala Ala Lys Ala Val Leu Gly
                740                 745                 750

Tyr Asp Lys Ala Lys Ser Phe Val Asp Lys Met Gln Asp Lys Ile Asp
            755                 760                 765

Gln His Asn Ala Tyr Ile Lys Glu His Gly Ile Asp Met Asp Glu Val
        770                 775                 780
```

```
Arg Tyr Trp Thr Trp Lys Gly Leu Asn Lys
785                 790

<210> SEQ ID NO 47
<211> LENGTH: 797
<212> TYPE: PRT
<213> ORGANISM: Burkholderia phytofirmans PsJN

<400> SEQUENCE: 47

Met Ala Glu Ala Thr Ala His Pro Thr Pro Gln Thr Leu Asp Ala
1               5                   10                  15

Asp Thr Leu Arg Asn Met Asp Arg Tyr Trp Arg Ala Cys Asn Tyr Leu
            20                  25                  30

Ser Ala Gly Met Ile Tyr Leu Arg Asp Asn Pro Leu Leu Arg Glu Pro
                35                  40                  45

Leu Lys Pro Glu His Ile Lys Asn Arg Leu Leu Gly His Trp Gly Ser
        50                  55                  60

Asp Pro Gly Gln Ser Phe Leu Val His Leu Asn Arg Leu Ile Lys
65                  70                  75                  80

Lys Leu Asp Leu Asn Val Ile Tyr Val Ala Gly Pro Gly His Gly Ala
                85                  90                  95

Pro Ala Thr Leu Ala Asn Cys Tyr Leu Glu Gly His Tyr Ser Glu Ile
                100                 105                 110

Tyr Pro Asp Arg Ser Gln Asp Val Ala Gly Met Glu Arg Phe Phe Arg
                115                 120                 125

Gln Phe Ser Phe Pro Gly Gly Ile Gly Ser His Cys Thr Pro Glu Thr
130                 135                 140

Pro Gly Ser Ile His Glu Gly Gly Glu Leu Gly Tyr Ser Leu Ser His
145                 150                 155                 160

Gly Tyr Gly Ala Ala Phe Asp Asn Pro Asp Leu Ile Val Ala Val Met
                165                 170                 175

Ile Gly Asp Gly Glu Ala Glu Thr Gly Pro Leu Ala Thr Ser Trp His
                180                 185                 190

Ser Asn Lys Phe Leu Asn Pro Ile Arg Asp Gly Ala Val Leu Pro Val
                195                 200                 205

Leu His Leu Asn Gly Tyr Lys Ile Ala Asn Pro Thr Ile Leu Ala Arg
210                 215                 220

Ile Pro Arg Glu Glu Leu Glu Ala Leu Leu Thr Gly Tyr Gly His Lys
225                 230                 235                 240

Pro Tyr Phe Val Glu Gly Glu Asp Pro Ala Val Met His Gln Gln Met
                245                 250                 255

Ala Ala Thr Leu Glu Gln Cys Ile Gly Glu Ile Arg Ala Ile Gln Gln
                260                 265                 270

His Ala Arg Glu Ser Asn Asp Ala Ser Arg Pro Arg Trp Pro Met Ile
                275                 280                 285

Val Leu Arg Ser Pro Lys Gly Trp Thr Gly Pro Lys Glu Val Asp Gly
                290                 295                 300

His Lys Val Glu Gly Ser Trp Arg Ala His Gln Val Pro Val Leu Asp
305                 310                 315                 320

Pro Ala Thr Asn Ser Lys Ser Leu Lys Leu Val Glu Asn Trp Leu Arg
                325                 330                 335

Ser Tyr Glu Pro Glu Thr Leu Phe Asp Glu Ala Gly Arg Leu Val Lys
                340                 345                 350

Glu Leu Arg Glu Leu Ala Pro Glu Gly Ala Arg Arg Ile Ser Ala Asn
                355                 360                 365
```

```
Pro His Ala Asn Gly Gly Val Leu Cys Lys Thr Leu Ala Met Pro Pro
    370                 375                 380

Phe Arg Asp Tyr Ala Val Ala Val Lys Lys Pro Ala Gly Ser Tyr Thr
385                 390                 395                 400

Ser Pro Thr Glu Val Leu Gly Lys Phe Leu Arg Asp Val Met Arg Asn
                405                 410                 415

Asn Met Thr Asn Phe Arg Val Phe Gly Pro Asp Glu Thr Ser Ser Asn
            420                 425                 430

Lys Leu Thr Ala Ile Tyr Glu Ala Ser Glu Lys Thr Trp Leu Ala Gln
        435                 440                 445

Thr Val Pro Ser Asp Ala Asp Gly Gly Glu Leu Ala Val Asp Gly Arg
450                 455                 460

Val Met Glu Met Leu Ser Glu His Thr Leu Glu Gly Trp Phe Glu Gly
465                 470                 475                 480

Tyr Val Leu Thr Gly Arg His Gly Leu Phe Ala Thr Tyr Glu Ala Phe
                485                 490                 495

Val His Val Ile Asp Ser Met Phe Asn Gln His Ala Lys Trp Leu Glu
            500                 505                 510

Lys Ala Lys Arg Asp Leu Gly Trp Arg Gln Pro Val Pro Ser Ile Asn
        515                 520                 525

Leu Leu Ile Thr Ser Leu Val Trp Arg Gln Asp His Asn Gly Phe Thr
530                 535                 540

His Gln Asp Pro Gly Phe Leu Asp Val Val Thr Asn Lys Ser Pro Asp
545                 550                 555                 560

Val Val Arg Ile Tyr Leu Pro Pro Asp Ala Asn Cys Leu Leu Ser Val
                565                 570                 575

Ala Asp His Cys Leu Arg Ser Arg Asp Tyr Val Asn Val Ile Val Ala
            580                 585                 590

Asp Lys Gln Pro His Leu Gln Tyr Leu Asp Met Asp Ala Ala Val Thr
        595                 600                 605

His Cys Thr Lys Gly Ile Gly Ile Trp Asp Trp Ala Ser Thr Asp Gln
610                 615                 620

Gly Val Glu Pro Asp Val Val Met Ala Cys Ala Gly Asp Ile Pro Thr
625                 630                 635                 640

Met Glu Ala Leu Ala Ala Val Gln Ile Leu Lys Glu Gln Phe Ala Asp
                645                 650                 655

Leu Lys Ile Arg Phe Val Asn Val Val Asp Leu Phe Arg Leu Met Pro
            660                 665                 670

Glu His Ala His Pro His Gly Leu Ser Ser Arg Asp Phe Asp Ser Leu
        675                 680                 685

Phe Thr Thr Asp Lys Pro Val Ile Phe Asn Phe His Ser Tyr Ala Ser
690                 695                 700

Leu Val His Lys Leu Thr Tyr Asn Arg Thr Asn His Asp Asn Leu His
705                 710                 715                 720

Val His Gly Tyr His Glu Lys Gly Asn Ile Asn Thr Pro Leu Glu Leu
                725                 730                 735

Ala Ile Ile Asn Gln Val Asp Arg Phe Ser Leu Ala Ile Asp Val Ile
            740                 745                 750

Asp Arg Val Pro Arg Leu Arg Gly Val Gly Asp His Ala Lys Glu Trp
        755                 760                 765

Leu Arg Gly Gln Ile Ile Glu His Leu Ala Tyr Ala His Ala Glu Gly
770                 775                 780
```

Ile Asp Lys Glu Glu Ile Arg Asn Trp Thr Trp Lys Gly
785                 790                 795

<210> SEQ ID NO 48
<211> LENGTH: 795
<212> TYPE: PRT
<213> ORGANISM: Lactobacillus buchneri NRRL B-30929

<400> SEQUENCE: 48

Met Thr Val Asp Tyr Asp Ser Lys Glu Tyr Leu Glu Leu Val Asp Lys
1               5                   10                  15

Tyr Trp Arg Ala Ala Asn Tyr Leu Ser Val Gly Gln Leu Phe Leu Arg
            20                  25                  30

Asp Asn Pro Leu Leu Lys Arg Pro Leu Glu Ala Lys Asp Val Lys Val
        35                  40                  45

Lys Pro Ile Gly His Trp Gly Thr Ile Val Ser Gln Asn Leu Ile Tyr
50                  55                  60

Ala Glu Leu Asn Arg Val Ile Asn Lys Tyr Asp Leu Asn Met Phe Tyr
65                  70                  75                  80

Ile Glu Gly Ser Gly His Gly Gly Gln Val Met Val Ser Asn Ser Tyr
                85                  90                  95

Leu Asp Gly Ser Tyr Ser Asp Ile Tyr Pro Asn Ile Ser Gln Asp Glu
            100                 105                 110

Lys Gly Met Ala Lys Leu Phe Lys Gln Phe Ser Phe Pro Gly Gly Val
        115                 120                 125

Ala Ser His Ala Ala Pro Glu Thr Pro Gly Ser Ile His Glu Gly Gly
130                 135                 140

Glu Leu Gly Tyr Ser Leu Ser His Gly Thr Gly Ala Ile Leu Asp Asn
145                 150                 155                 160

Pro Asp Val Ile Ala Ala Val Glu Ile Gly Asp Gly Glu Ser Glu Thr
                165                 170                 175

Gly Pro Leu Ala Ala Ser Trp Phe Ser Asp Lys Phe Ile Asn Pro Ile
            180                 185                 190

Thr Asp Gly Ala Val Leu Pro Ile Ile Asn Met Asn Gly Phe Lys Ile
        195                 200                 205

Ser Asn Pro Thr Ile Leu Ser Arg Met Ser Asp Glu Asp Leu Thr Ser
210                 215                 220

Tyr Phe Lys Gly Met Gly Trp Asp Pro Tyr Phe Val Glu Ala Thr Ala
225                 230                 235                 240

Asp Thr Asp His Ala Lys Val Glu Glu Glu Phe Ala Lys Thr Leu Asp
                245                 250                 255

His Val Ile Glu Glu Ile Lys Ser Ile Gln Lys Asn Ala Arg Glu Asn
            260                 265                 270

Glu Thr Pro Asp Asn Val Lys Leu Pro Asn Trp Pro Met Ile Ile Phe
        275                 280                 285

Arg Ser Pro Lys Gly Trp Thr Gly Pro Lys Lys Asp Leu Asp Gly Asn
290                 295                 300

Pro Ile Glu Gly Ser Phe Arg Ala His Gln Val Pro Ile Pro Val Ala
305                 310                 315                 320

Ala Gly Ser Met Glu His Lys Asp Leu Leu Asn Asp Trp Leu Lys Ser
                325                 330                 335

Tyr Lys Pro Glu Glu Leu Phe Asp Glu Asn Gly Thr Val Lys Pro Glu
            340                 345                 350

Ile Arg Ala Val Ala Pro Lys Gly Asp Lys Arg Met Ser Val Asn Pro
        355                 360                 365

Ile Thr Asn Gly Gly Ile Lys Pro Glu Pro Leu Lys Leu Pro Asp Val
    370                 375                 380

Arg Asn Phe Glu Val Lys Phe Asp Arg Gly Val Thr Gln Lys Gln Asp
385                 390                 395                 400

Met Ile Glu Trp Ser Asn Trp Leu Glu Lys Val Ala Glu Leu Asn Pro
                405                 410                 415

Thr Ser Phe Arg Gly Phe Gly Pro Asp Glu Thr Lys Ser Asn Arg Leu
                420                 425                 430

Tyr Ser Leu Leu Asp Asp Ser Lys Arg Gln Trp Met Glu Asp Ile His
                435                 440                 445

Glu Pro Phe Asp Glu Asp Leu Ser Asn His Gly Arg Val Ile Asp Ser
    450                 455                 460

Gln Leu Ser Glu His Gln Ala Glu Gly Trp Leu Glu Gly Tyr Val Leu
465                 470                 475                 480

Thr Gly Arg His Gly Phe Phe Ala Thr Tyr Glu Ser Phe Gly Arg Val
                485                 490                 495

Val Asp Ser Met Leu Thr Gln His Phe Lys Trp Leu Arg Lys Ala Ser
                500                 505                 510

Glu Gln Tyr Trp Arg Lys Gln Tyr Pro Ser Leu Asn Phe Val Asp Thr
    515                 520                 525

Ser Thr Val Phe Gln Gln Asp His Asn Gly Tyr Thr His Gln Asp Pro
    530                 535                 540

Gly Met Leu Thr His Leu Ala Glu Lys Lys Pro Glu Phe Ile Arg Glu
545                 550                 555                 560

Tyr Leu Pro Ala Asp Ala Asn Glu Leu Leu Ala Val Gly Asp Val Ala
                565                 570                 575

Phe Arg Thr Tyr Glu Lys Ile Asn Leu Ile Val Thr Ser Lys His Pro
                580                 585                 590

Arg Arg Gln Trp Tyr Thr Met Asp Glu Ala Gln Asn Leu Val Lys Asn
    595                 600                 605

Gly Leu Gly Tyr Ile Asp Trp Ala Ser Thr Asp Gln Gly Gln Glu Pro
    610                 615                 620

Asp Val Val Phe Ala Ala Ala Gly Ser Glu Pro Asn Leu Glu Ala Leu
625                 630                 635                 640

Ala Ala Ile Ser Ile Leu Asn Lys Glu Phe Pro Glu Met Lys Ile Arg
                645                 650                 655

Phe Ile Asn Val Val Asp Leu Leu Lys Leu Arg Ser Pro Lys Val Asp
                660                 665                 670

Pro Arg Gly Leu Ser Asp Glu Glu Phe Asp Asn Leu Phe Thr Thr Asp
    675                 680                 685

Lys Pro Val Ile Phe Ala Phe His Gly Phe Glu Asp Leu Ile Lys Asp
    690                 695                 700

Ile Phe Phe Asp Arg His Asn His Asn Leu His Val His Gly Tyr Arg
705                 710                 715                 720

Glu Asn Gly Asp Ile Thr Thr Pro Phe Asp Met Arg Val Leu Asn Gln
                725                 730                 735

Leu Asp Arg Phe Asp Leu Ala Lys Glu Ala Val Gln Asp Ile Pro Ala
                740                 745                 750

Tyr Thr Val Lys Gly Gly Tyr Phe Ile Gln Arg Met Asn Asp Met Val
                755                 760                 765

Asp Lys His Asn Ala Tyr Ile Arg Gln Glu Gly Thr Asp Leu Pro Glu
    770                 775                 780

```
Val Val Asp Trp Lys Trp Glu Gly Leu Lys Lys
785             790             795
```

<210> SEQ ID NO 49
<211> LENGTH: 826
<212> TYPE: PRT
<213> ORGANISM: Bifidobacterium gallicum DSM 20093

<400> SEQUENCE: 49

```
Met Thr Ser Pro Val Ile Gly Thr Pro Trp Gln Lys Leu Asn Arg Pro
1               5                   10                  15

Val Ser Glu Glu Ala Ile Glu Gly Met Asp Lys Tyr Trp Arg Ala Ser
            20                  25                  30

Asn Tyr Met Ser Ile Gly Gln Ile Tyr Leu Arg Ser Asn Pro Leu Met
        35                  40                  45

Lys Glu Pro Phe Thr Arg Asp Asp Val Lys Tyr Arg Leu Val Gly His
    50                  55                  60

Trp Gly Thr Thr Pro Gly Leu Asn Phe Leu Leu Ala His Ile Asn Arg
65                  70                  75                  80

Leu Ile Ala Asp His Gln Gln Asn Thr Val Phe Ile Met Gly Pro Gly
                85                  90                  95

His Gly Gly Pro Ala Gly Thr Ala Gln Ser Tyr Leu Asp Gly Thr Tyr
            100                 105                 110

Thr Glu Tyr Tyr Pro Asn Ile Thr Lys Asp Glu Glu Gly Leu Gln Lys
        115                 120                 125

Phe Phe Arg Gln Phe Ser Tyr Pro Gly Gly Ile Pro Ser His Phe Ala
    130                 135                 140

Pro Glu Thr Pro Gly Ser Ile His Glu Gly Gly Glu Leu Gly Tyr Ala
145                 150                 155                 160

Leu Ser His Ala Tyr Gly Ala Val Met Asn Asn Pro Ser Leu Phe Val
                165                 170                 175

Pro Cys Ile Val Gly Asp Gly Glu Ala Glu Thr Gly Pro Leu Ala Thr
            180                 185                 190

Gly Trp Gln Ser Asn Lys Leu Val Asn Pro Arg Thr Asp Gly Ile Val
        195                 200                 205

Leu Pro Ile Leu His Leu Asn Gly Tyr Lys Ile Ala Asn Pro Thr Ile
    210                 215                 220

Leu Ala Arg Val Ser Asp Glu Glu Leu His Asp Phe Phe Arg Gly Leu
225                 230                 235                 240

Gly Tyr His Pro Tyr Glu Phe Val Ala Gly Phe Asp Asn Glu Asp His
                245                 250                 255

Leu Ser Ile His Arg Arg Phe Ala Glu Leu Phe Glu Thr Ile Phe Asp
            260                 265                 270

Glu Ile Cys Asp Ile Lys Ala Ala Ala Asn Thr Asp Asp Met Thr Arg
        275                 280                 285

Pro Phe Tyr Pro Met Leu Ile Phe Arg Thr Pro Lys Gly Trp Thr Cys
    290                 295                 300

Pro Lys Phe Ile Asp Gly Lys Lys Thr Glu Gly Ser Trp Arg Ala His
305                 310                 315                 320

Gln Val Pro Leu Ala Ser Ala Arg Asp Thr Glu Ala His Phe Glu Val
                325                 330                 335

Leu Lys Asn Trp Met Ala Ser Tyr Lys Pro Glu Glu Leu Phe Asp Asp
            340                 345                 350

Lys Gly Ala Ile Lys Asp Asp Val Val Asp Phe Met Pro Lys Gly Asp
        355                 360                 365
```

```
Leu Arg Ile Gly Ala Asn Pro Asn Ala Asn Gly Gly Val Ile Arg Glu
    370                 375                 380

Glu Leu Asp Leu Pro Ala Leu Glu Asn Tyr Glu Val Lys Glu Val Lys
385                 390                 395                 400

Glu Phe Gly His Gly Trp Gly Gln Leu Glu Ala Thr Arg Lys Leu Gly
                405                 410                 415

Glu Tyr Thr Arg Asp Ile Ile Lys Asn Asn Pro Asp Ser Phe Arg Ile
                420                 425                 430

Phe Gly Pro Asp Glu Thr Ala Ser Asn Arg Leu Gln Ala Ser Tyr Glu
        435                 440                 445

Val Thr Asn Lys Gln Trp Asp Asn Gly Tyr Leu Ser Lys Asp Leu Val
    450                 455                 460

Asp Glu His Met Ala Val Thr Gly Gln Val Thr Glu Gln Leu Ser Glu
465                 470                 475                 480

His Gln Cys Glu Gly Phe Leu Glu Ala Tyr Leu Leu Thr Gly Arg His
                485                 490                 495

Gly Ile Trp Ser Ser Tyr Glu Ser Phe Val His Val Ile Asp Ser Met
                500                 505                 510

Leu Asn Gln His Ala Lys Trp Leu Glu Ala Thr Val Arg Glu Ile Pro
    515                 520                 525

Trp Arg Lys Pro Ile Ser Ser Met Asn Leu Leu Val Ser Ser His Val
    530                 535                 540

Trp Arg Gln Asp His Asn Gly Phe Ser His Gln Asp Pro Gly Val Thr
545                 550                 555                 560

Ser Val Leu Leu Asn Lys Thr Phe Asn Asn Asp His Val Ile Gly Leu
                565                 570                 575

Tyr Phe Ala Thr Asp Ala Asn Val Leu Leu Ala Ile Ala Glu Lys Cys
                580                 585                 590

Tyr Lys Ser Thr Asn Met Ile Asn Ala Ile Val Ala Gly Lys Gln Pro
                595                 600                 605

Ala Ala Thr Trp Thr Thr Leu Asp Glu Ala Arg Glu Leu Val Ala Lys
        610                 615                 620

Gly Ala Gly Glu Phe Glu Trp Ala Ser Asn Val Lys Thr Asn Asp Glu
625                 630                 635                 640

Ala Glu Ile Val Leu Ala Ser Ala Gly Asp Val Pro Thr Gln Glu Leu
                645                 650                 655

Met Ala Ala Asp Arg Leu Asn Lys Leu Gly Val Lys Phe Lys Val
        660                 665                 670

Val Asn Val Val Asp Leu Ile Lys Leu Gln Ser Ala Lys Glu Asn Asp
    675                 680                 685

Gln Ala Leu Ser Asp Ala Glu Phe Ala Glu Leu Phe Thr Glu Asp Lys
    690                 695                 700

Pro Val Leu Phe Ala Tyr His Ser Tyr Ala His Asp Val Arg Gly Leu
705                 710                 715                 720

Ile Phe Asp Arg Pro Asn His Asp Asn Phe Asn Val Val Gly Tyr Lys
                725                 730                 735

Glu Gln Gly Ser Thr Thr Thr Pro Tyr Asp Met Val Arg Val Asn Asp
                740                 745                 750

Ile Asp Arg Tyr Glu Leu Thr Ala Thr Ala Leu Arg Met Ile Asp Ala
            755                 760                 765

Asp Lys Tyr Ala Asp Glu Ile Lys Lys Leu Glu Asp Phe Arg Ile Glu
    770                 775                 780
```

```
Ala Tyr Gln Phe Ala Val Asp Asn Gly Tyr Asp Ile Pro Asp Tyr Thr
            785                 790                 795                 800

Asp Trp Val Trp Pro Gly Val Lys Thr Asp Leu Pro Gly Ala Val Ser
                    805                 810                 815

Ala Thr Ala Ala Thr Ala Gly Asp Asn Glu
            820                 825

<210> SEQ ID NO 50
<211> LENGTH: 825
<212> TYPE: PRT
<213> ORGANISM: Bifidobacterium dentium Bd1

<400> SEQUENCE: 50

Met Thr Ser Pro Val Ile Gly Thr Pro Trp Lys Lys Leu Asn Ala Pro
1               5                   10                  15

Val Ser Glu Glu Ala Ile Glu Gly Val Asp Lys Tyr Trp Arg Ala Ala
            20                  25                  30

Asn Tyr Leu Ser Ile Gly Gln Ile Tyr Leu Arg Ser Asn Pro Leu Met
        35                  40                  45

Lys Glu Pro Phe Thr Arg Glu Asp Val Lys His Arg Leu Val Gly His
    50                  55                  60

Trp Gly Thr Thr Pro Gly Leu Asn Phe Leu Ile Gly His Ile Asn Arg
65                  70                  75                  80

Leu Ile Ala Asp His Gln Gln Asn Thr Val Ile Ile Met Gly Pro Gly
                85                  90                  95

His Gly Gly Pro Ala Gly Thr Ala Gln Ser Tyr Leu Asp Gly Thr Tyr
            100                 105                 110

Thr Glu Tyr Phe Pro Asn Ile Thr Lys Asp Glu Ala Gly Leu Gln Lys
        115                 120                 125

Phe Phe Arg Gln Phe Ser Tyr Pro Gly Gly Ile Pro Ser His Tyr Ala
    130                 135                 140

Pro Glu Thr Pro Gly Ser Ile His Glu Gly Gly Glu Leu Gly Tyr Ala
145                 150                 155                 160

Leu Ser His Ala Tyr Gly Ala Val Met Asn Asn Pro Ser Leu Phe Val
                165                 170                 175

Pro Ala Ile Val Gly Asp Gly Glu Ala Glu Thr Gly Pro Leu Ala Thr
            180                 185                 190

Gly Trp Gln Ser Asn Lys Leu Val Asn Pro Arg Thr Asp Gly Ile Val
        195                 200                 205

Leu Pro Ile Leu His Leu Asn Gly Tyr Lys Ile Ala Asn Pro Thr Ile
    210                 215                 220

Leu Ser Arg Ile Ser Asp Glu Glu Leu His Glu Phe Phe His Gly Met
225                 230                 235                 240

Gly Tyr Glu Pro Tyr Glu Phe Val Ala Gly Phe Asp Asn Glu Asp His
                245                 250                 255

Leu Ser Ile His Arg Arg Phe Ala Glu Leu Phe Glu Thr Val Phe Asp
            260                 265                 270

Glu Ile Cys Asp Ile Lys Ala Ala Gln Thr Asp Asp Met Thr Arg
        275                 280                 285

Pro Phe Tyr Pro Met Ile Ile Phe Arg Thr Pro Lys Gly Trp Thr Cys
    290                 295                 300

Pro Lys Phe Ile Asp Gly Lys Lys Thr Glu Gly Ser Trp Arg Ser His
305                 310                 315                 320

Gln Val Pro Leu Ala Ser Ala Arg Asp Thr Glu Ala His Phe Glu Val
                325                 330                 335
```

```
Leu Lys Asn Trp Leu Glu Ser Tyr Lys Pro Glu Leu Phe Asp Ala
            340                 345                 350

Asn Gly Ala Val Lys Pro Glu Val Thr Ala Phe Met Pro Thr Gly Glu
            355                 360                 365

Leu Arg Ile Gly Glu Asn Pro Asn Ala Asn Gly Gly Arg Ile Arg Glu
        370                 375                 380

Glu Leu Asn Leu Pro Ala Leu Glu Asp Tyr Glu Val Lys Glu Val Ala
385                 390                 395                 400

Glu Tyr Gly His Gly Trp Gly Gln Leu Glu Ala Thr Arg Arg Leu Gly
                405                 410                 415

Val Tyr Thr Arg Asp Ile Ile Lys Asn Asn Pro Asp Ser Phe Arg Ile
            420                 425                 430

Phe Gly Pro Asp Glu Thr Ala Ser Asn Arg Leu Gln Ala Ala Tyr Asp
            435                 440                 445

Val Thr Asn Lys Gln Trp Asp Ala Gly Tyr Leu Ser Ala Gln Val Asp
            450                 455                 460

Glu His Met Ala Val Thr Gly Gln Val Thr Glu Gln Leu Ser Glu His
465                 470                 475                 480

Gln Met Glu Gly Phe Leu Glu Ala Tyr Leu Leu Thr Gly Arg His Gly
                485                 490                 495

Ile Trp Ser Ser Tyr Glu Ser Phe Val His Val Ile Asp Ser Met Leu
            500                 505                 510

Asn Gln His Ala Lys Trp Leu Glu Ala Thr Val Arg Glu Ile Pro Trp
            515                 520                 525

Arg Lys Pro Ile Ser Ser Met Asn Leu Leu Val Ser Ser His Val Trp
            530                 535                 540

Arg Gln Asp His Asn Gly Phe Ser His Gln Asp Pro Gly Val Thr Ser
545                 550                 555                 560

Val Leu Leu Asn Lys Cys Phe Asn Asn Asp His Val Ile Gly Ile Tyr
                565                 570                 575

Phe Pro Val Asp Ser Asn Met Leu Leu Ala Val Ala Glu Lys Cys Tyr
            580                 585                 590

Lys Ser Thr Asp Met Ile Asn Ala Ile Ile Ala Gly Lys Gln Pro Ala
            595                 600                 605

Ala Thr Trp Leu Thr Leu Asp Glu Ala Arg Ala Glu Leu Glu Lys Gly
            610                 615                 620

Ala Ala Glu Trp Glu Trp Ala Ser Thr Ala Lys Ser Asn Asp Glu Ala
625                 630                 635                 640

Gln Ile Val Leu Ala Ser Ala Gly Asp Val Pro Ala Gln Glu Ile Met
                645                 650                 655

Ala Ala Ala Asp Lys Leu Asp Ala Met Gly Ile Lys Phe Lys Val Val
            660                 665                 670

Asn Val Val Asp Leu Val Lys Leu Gln Ser Thr Lys Glu Asn Asp Glu
            675                 680                 685

Ala Ile Ser Asp Ala Asp Phe Ala Asp Leu Phe Thr Glu Asp Lys Pro
            690                 695                 700

Val Leu Phe Ala Tyr His Ser Tyr Ala Arg Asp Val Arg Gly Leu Ile
705                 710                 715                 720

Tyr Asp Arg Pro Asn His Asp Asn Phe Asn Val His Gly Tyr Glu Glu
                725                 730                 735

Gln Gly Ser Thr Thr Pro Tyr Asp Met Val Arg Val Asn Asn Ile
            740                 745                 750
```

-continued

```
Asp Arg Tyr Glu Leu Val Ala Glu Ala Leu Arg Met Ile Asp Ala Asp
        755                 760                 765
Lys Tyr Ala Asp Lys Ile Asp Glu Leu Glu Ala Phe Arg Lys Glu Ala
    770                 775                 780
Phe Gln Phe Ala Val Asp Asn Gly Tyr Asp His Pro Asp Tyr Thr Asp
785                 790                 795                 800
Trp Val Tyr Ser Gly Val Asn Thr Asn Lys Gln Gly Ala Val Ser Ala
                805                 810                 815
Thr Ala Ala Thr Ala Gly Asp Asn Glu
            820                 825

<210> SEQ ID NO 51
<211> LENGTH: 825
<212> TYPE: PRT
<213> ORGANISM: Bifidobacterium bifidum IPLA 20015

<400> SEQUENCE: 51

Met Thr Ser Pro Val Ile Gly Thr Pro Trp Lys Lys Leu Asn Ala Pro
1               5                   10                  15
Val Ser Glu Glu Ala Leu Glu Gly Val Asp Lys Tyr Trp Arg Val Ala
            20                  25                  30
Asn Tyr Leu Ser Ile Gly Gln Ile Tyr Leu Arg Ser Asn Pro Leu Met
        35                  40                  45
Lys Glu Pro Phe Thr Arg Glu Asp Val Lys His Arg Leu Val Gly His
    50                  55                  60
Trp Gly Thr Thr Pro Gly Leu Asn Phe Leu Ile Gly His Ile Asn Arg
65                  70                  75                  80
Phe Ile Ala Asp His Gly Gln Asn Thr Val Phe Ile Met Gly Pro Gly
                85                  90                  95
His Gly Gly Pro Ala Gly Thr Ser Gln Ser Tyr Leu Asp Gly Thr Tyr
            100                 105                 110
Thr Glu Thr Tyr Pro Asn Ile Thr Lys Asp Glu Ala Gly Leu Gln Lys
        115                 120                 125
Phe Phe Arg Gln Phe Ser Tyr Pro Gly Gly Ile Pro Ser His Phe Ala
    130                 135                 140
Pro Glu Thr Pro Gly Ser Ile His Glu Gly Gly Glu Leu Gly Tyr Ala
145                 150                 155                 160
Leu Ser His Ala Tyr Gly Ala Ile Met Asp Asn Pro Ser Leu Phe Val
                165                 170                 175
Pro Cys Ile Val Gly Asp Gly Glu Ala Glu Thr Gly Pro Leu Ala Thr
            180                 185                 190
Gly Trp Gln Ser Asn Lys Leu Val Asn Pro Arg Thr Asp Gly Ile Val
        195                 200                 205
Leu Pro Ile Leu His Leu Asn Gly Tyr Lys Ile Ala Asn Pro Thr Ile
    210                 215                 220
Leu Ser Arg Ile Ser Asp Glu Glu Leu His Glu Phe Phe His Gly Met
225                 230                 235                 240
Gly Tyr Glu Pro Tyr Glu Phe Val Ala Gly Phe Asp Asp Glu Asp His
                245                 250                 255
Met Ser Ile His Arg Arg Phe Ala Glu Leu Phe Glu Ser Val Trp Asp
            260                 265                 270
Glu Ile Cys Asp Ile Lys Ala Ala Ala Asn Thr Asp Asn Met His Arg
        275                 280                 285
Pro Phe Tyr Pro Met Ile Ile Phe Arg Thr Pro Lys Gly Trp Thr Cys
    290                 295                 300
```

```
Pro Lys Tyr Ile Asp Gly Lys Thr Glu Gly Ser Trp Arg Ala His
305                 310                 315                 320

Gln Val Pro Leu Ala Ser Ala Arg Asp Thr Glu Ala His Phe Glu Val
            325                 330                 335

Leu Lys Asn Trp Leu Glu Ser Tyr Lys Pro Glu Glu Leu Phe Asp Ala
            340                 345                 350

Asn Gly Ala Val Lys Asp Val Leu Ala Phe Met Pro Lys Gly Glu
            355                 360                 365

Leu Arg Ile Gly Ala Asn Pro Asn Ala Asn Gly Gly Val Ile Arg Lys
370                 375                 380

Asp Leu Val Leu Pro Ala Leu Glu Asp Tyr Glu Val Lys Glu Val Lys
385                 390                 395                 400

Glu Phe Gly His Gly Trp Gly Gln Leu Glu Ala Thr Arg Arg Leu Gly
            405                 410                 415

Val Tyr Thr Arg Asp Ile Ile Lys Asn Asn Met His Asp Phe Arg Ile
            420                 425                 430

Phe Gly Pro Asp Glu Thr Ala Ser Asn Arg Leu Gln Ala Ser Tyr Glu
            435                 440                 445

Val Thr Asn Lys Gln Trp Asp Ala Gly Tyr Ile Ser Asp Glu Val Asp
            450                 455                 460

Glu His Met His Val Ser Gly Gln Val Glu Gln Leu Ser Glu His
465                 470                 475                 480

Gln Met Glu Gly Phe Leu Glu Ala Tyr Leu Leu Thr Gly Arg His Gly
            485                 490                 495

Ile Trp Ser Ser Tyr Glu Ser Phe His Val Ile Asp Ser Met Leu
            500                 505                 510

Asn Gln His Ala Lys Trp Leu Glu Ala Thr Val Arg Glu Ile Pro Trp
            515                 520                 525

Arg Lys Pro Ile Ala Ser Met Asn Leu Leu Val Ser Ser His Val Trp
530                 535                 540

Arg Gln Asp His Asn Gly Phe Ser His Gln Asp Pro Gly Val Thr Ser
545                 550                 555                 560

Val Leu Leu Asn Lys Cys Phe His Asn Asp His Val Ile Gly Ile Tyr
            565                 570                 575

Phe Ala Thr Asp Ala Asn Met Leu Leu Ala Ile Ala Glu Lys Cys Tyr
            580                 585                 590

Lys Ser Thr Asn Lys Ile Asn Ala Ile Ile Ala Gly Lys Gln Pro Ala
            595                 600                 605

Ala Thr Trp Leu Thr Leu Asp Glu Ala Arg Ala Glu Leu Ala Lys Gly
            610                 615                 620

Ala Ala Ala Trp Asp Trp Ala Ser Thr Ala Lys Thr Asn Asp Glu Ala
625                 630                 635                 640

Gln Val Val Leu Ala Ala Gly Asp Val Pro Thr Gln Glu Ile Met
            645                 650                 655

Ala Ala Ser Asp Lys Leu Lys Ala Leu Gly Ile Lys Phe Lys Val Val
            660                 665                 670

Asn Val Ala Asp Leu Leu Ser Leu Gln Ser Ala Lys Glu Asn Asp Glu
            675                 680                 685

Ala Leu Thr Asp Glu Glu Phe Ala Asp Ile Phe Thr Ala Asp Lys Pro
            690                 695                 700

Val Leu Phe Ala Tyr His Ser Tyr Ala His Asp Val Arg Gly Leu Ile
705                 710                 715                 720
```

Tyr Asp Arg Pro Asn His Asp Asn Phe Asn Val His Gly Tyr Glu Glu
             725                 730                 735

Glu Gly Ser Thr Thr Thr Pro Tyr Asp Met Val Arg Val Asn Glu Leu
         740                 745                 750

Asp Arg Tyr Glu Leu Thr Ala Glu Ala Leu Arg Met Ile Asp Ala Asp
             755                 760                 765

Lys Tyr Ala Asp Glu Ile Gln Lys Leu Glu Asp Phe Arg Gln Glu Ala
         770                 775                 780

Phe Gln Phe Ala Val Asp Lys Gly Tyr Asp His Pro Asp Tyr Thr Asp
785                 790                 795                 800

Trp Val Tyr Ser Gly Val Lys Thr Asp Lys Lys Gly Ala Val Thr Ala
                 805                 810                 815

Thr Ala Thr Ala Gly Asp Asn Glu
             820                 825

<210> SEQ ID NO 52
<211> LENGTH: 2469
<212> TYPE: DNA
<213> ORGANISM: Mycobacterium gilvum Spyr1

<400> SEQUENCE: 52

| | | |
|---|---|---|
| atgaccaccg ccaccaccgc agaacgtcgt ccgctgagcg atcaggatgt tgatcgtctg | 60 |
| gatcgttggt ggcgtgcagc aaattatctg agcgttggtc agatttatct gctggataat | 120 |
| ccgctgctgc gtacaccgct gacccgtgaa gatgttaaac cgcgtctgct gggtcattgg | 180 |
| ggcaccacac cgggtctgaa tttctgtat gcacatctga atcgtgcaat tgcccagcgt | 240 |
| cagcagagca ccatttatgt taccggtccg ggtcatggtg gtcctggtct ggttgcaaat | 300 |
| gcatatctgg atgcacccta tagcgaaatt tacagcgata ttacccagga tgatgaaggt | 360 |
| ctgcgtcgtc tgtttcgtca gtttagcttt ccgggtggta ttccgagcca tgttgcaccg | 420 |
| gaaactccgg gtagcattca tgaaggtggt gaactgggtt atgcactgag ccatgcatat | 480 |
| ggtgcagcat ttgataaccc ggacctgctg gttgccgcag ttgttggtga tggtgaagca | 540 |
| gaaacaggtc cgctggcaac cagctggcat agcaacaaat tgtgaatgc agccaaagat | 600 |
| ggtgccgttc tgccgattct gcatctgaac ggctataaaa tcgcaaatcc gaccctgctg | 660 |
| gcacgcattc cgaccgatga actgcgtgca ctgatggttg ttatggtca tcatccgtat | 720 |
| tttttcgaag ttccggatga cgaaggcggt ccaggtgtgg atcatgcaga tgcccatcgt | 780 |
| cgttttgcac gtctgttaga tgatgttctg atgaaattg ccgatatcaa aacccgtgca | 840 |
| cgcgaaggtc atgaaagccg tccggcatgg ccgatgattg tttttcgtac cccgaaaggt | 900 |
| tggacgggtc cggattatat tgatggcaaa aaaaccaccg gtagctggcg tgcccatcag | 960 |
| gttccgctgt caaatgcacg tgataccaaa gaacatctgg cagttctgag tgattggctg | 1020 |
| agcagctatc gtcctgatga gctgtttgat gccgatggtc gcctgctgcc ggaaattgca | 1080 |
| gaactggcac cgagcggtca gctgcgtatg agcgataatg cacatgcaaa tggcggtctg | 1140 |
| ctgctgaaag atctgcgtct gccggatttt cgtgaatatg cagttgatgt tccggcaccg | 1200 |
| ggtgcaaccg ttgccgaagc aacccgtgtt ctgggtcagt ggctgaccga agttattcgt | 1260 |
| ctgaatccgg ataactttcg catttttggt ccagatgaaa ccgcaagcaa tcgtctgcag | 1320 |
| gcagtttatg atgcaaccga taaacagtgg aacgccgaat ttttggtgc ggaagttgat | 1380 |
| gaacacctgg cacgtgcagg tcgtgttgtt gaaatgctga gtgaacatca gtgtcagggt | 1440 |
| tggctggaag gttacctgct gaccggtcgt catggtctgt ttaattgtta tgaagccttt | 1500 |

```
atccacatcg tggatagcat gctgaaccag cacgcaaaat ggctgaaagt taccaatcat    1560
attccgtggc gtcgtcctat tgcaagcctg aattatcttc tgagcagtca tgtttggcgt    1620
caggatcata atggttttag tcatcaggat ccgggtttta ttgatcacgt tgtgaataaa    1680
agcgccaaag ttgtgcgtgt gtatctgcct ccggatgcca atacactgct gagtacctat    1740
gatcattgtc tgcgtagccg tcagtatgtt aatgttgttg ttagcggtaa acagccgagc    1800
ccgaactttc tgaccatgga acaggccgtt gcacattgta cccgtggcct gggtattttgg   1860 gaatgggcag gtagcgaaga actgggcaca gatccggatg tggttctggc aagtgccggt    1920
gatattccta ccctggaagc actggcagca gcagatattc tgcgccagca tctgcctgat    1980
ctgaaagtgc gttttgttaa cgttgtggat ctgatgcgcc tgcaggatag caccgaacat    2040
ccgcatggcc tgccagatcg tgattttgat atgattttta ccaccgatcg tccgatcatc    2100
tttgcctatc atggttatcc gtggctgatt catcgtctga cctatcgtcg tgccggtcat    2160
gataatctgc atgttcgtgg ttataaagaa gaaggtacaa ccaccacccc gttcgatatg    2220
gttatgctga atgatttaga tcgctatcac ctggtcatgg atgtgattga tcgtgtgccg    2280
agcctgggtt caacctgtgc agccttacgc cagcagatgg cagataaacg tattgcagct    2340
cgcgaatata cccgtgcgca tggcgaagat attccggaag ttaaagattg ggtttggcct    2400
gcagcacgtg aaagcggttt tggtacagcc ggtgcggatg tgcgagcag caccggtggt    2460 gataatgaa                                                            2469

<210> SEQ ID NO 53
<211> LENGTH: 2364
<212> TYPE: DNA
<213> ORGANISM: Shewanella baltica OS185

<400> SEQUENCE: 53
atgacccaga tccatgaaat taatgccctg aaaaaatacg tgcgtgccac caattttctg      60
gcaaccagcc agatttatct gaaacagaat gttctgcaca acgtccgct ggcacatacc     120 gatatcaaac cgcgtctgct gggtcattgg ggcacctgtc cgggtattaa ctttgtttat    180
gcaaacatta accgcctgat cgtgaaacat aatcgcagct ttatctatct ggttggtccg    240
ggtcatggtt ttccggcagt tcaggcaaac ctgtttatgg aaggtagcct gagccatttt    300
tatccggaaa ccattccgta taatgaaacc ggcattgaag atatttgcaa aaaattcagc    360
gcagcctatg gttatccgag ccatgcaaat ccggaagcac cgggtcagat tctggaaggt    420
ggtgaactgg gttatagcct gtcagttggt tggggtgcag ttctggataa tccggatctg    480
attgcaaccg ttctgattgg tgatggtgaa gcagaaaccg gtcctctggc agcaagctgg    540
tatgccaatc gtctggtttc accggcaacc tcaggtgccg ttctgccgat tgttcatatt    600
aatggctata aaatcagcgg tccgacccgt atgggtcgta tgagccatga agaactggat    660
ctggaatttc gtggtctggg ctattttccg attattgtgg ataatgaact ggaagaggat    720
atttacgtgc agatgaccaa tgcaatggat accgcatatg ccatgattaa cgatattcag    780
cgtcgtgcac gtagcggtga agatgttgtt aaaccgaaat ggcctgttat tctgatgcgt    840
accgcaaaag ttggaccggt gttagcgaa tacaaaggca aaaaacttga aggcaattgc    900
gaaagccatc aggtgattgt gaataaatgt gcaaccgata aaggtcatct ggatgcactg    960
gataactggc tggcaagcta tcattttcaa gaactgtatc agatgaacga caaaggcgaa    1020 ctgattttg atgccgatat ctgcagcctg attccgccta acagctggc atgtggtcgt    1080 cagcatctga cctatggtgg cgaagttgtt cgtgcactga ccaatccgga cctggaaaaa   1140
```

```
ctgagctatg gtccggaagt tccgcgtggt catcgtggtt atagtatgct gaaaatgggt      1200
gaatggatgc gtgatgcctt taaactgaat cgtgatcagc gtaatctgcg catttttct      1260 ccggatgaaa cctatagcaa tcagctgcag gcagttttg aagaaaccga tcgtgcatgg       1320
cagtggccga ttgaaagctg ggatgaggat atgagtcgtg aaggtcgtgt tattgaactg      1380
ctgagcgaaa atctgctgtt tggtatgctg catggttata ccgttaccgg tcgtcatggt      1440
atgtttccga cctatgaaag ctttagccag gttattagca gcatggccga tcagtattgc      1500
aaatatgtgt atgcaagcca gggtgtgcat tttcgtaaac cgctgccgag ctgtaatgtt      1560
gttctgagca gcctgctgga acgtcaggat cataatggtt attcacatca gaatccgagc      1620
tttctgggtg ccatgttaga aaaacatccg aaaattatca gcgcatatct gcctgcagat      1680
gcaaatagca ccctggttta taccgaacgt gcctatgcag atcgtgataa gctgaatatt      1740
ctggttgccg aaaaaaaga actgccgcag tggctgagcc tggaagaagc acgtaaacag      1800
gcaaaagatg gtgttatggt ttgggatttt gccagtgatg aaaacccgga tattgtgctg      1860
gcaggttgtg gtgattatgt tacccaagaa tgtatggcca gcctggtgct gattcgtgaa      1920
ctgttaccgc gtgttaaaat tcgttttgtt agcgttaccg aactgagcag tgatggcctg      1980
ggtagccgta aattcaaaga aaaaccgtgg ctgatggatg aaattttcac ccaggataaa      2040
ggcgtggtgt ttaactatca tggctatccg aataccatca aaaagctgat cttcgactat      2100
aaaggcagcc gtcgttttcg cattaaaggc tatgaagaag aaggtagtac caccaccccg      2160
tttgatatgg gtgttcgtaa tggcaccagc cgctatcatc tggtgatcga tatggcatat      2220
aaactgtttc agcagggcgt gattgatgaa acaatgcatg tgagcattac caccgacatg      2280
ctgcagcgtc tggtggatca tcgtaattac attaaagcca atggtgtgga tccgatcgaa      2340
atcgaaaatt ggatttggac ccgt                                              2364

<210> SEQ ID NO 54
<211> LENGTH: 2385
<212> TYPE: DNA
<213> ORGANISM: Lactobacillus rhamnosus LMS2-1

<400> SEQUENCE: 54
atgagcatgg acaccaaagt gaaaaccgtt gattatagca gcaaagaata ttttgacaaa        60
atgaccgcat attggcgtgc agcaaattat gttagcgttg tcagctgta tctgaaagat        120 aatccgctgc tggaacgtcc gctgaaaagc gaagatgtta aaccgcatcc gattggtcat       180 tgggcacca ttgcaggtca gaattttatc tatacccatc tgaatcgcgt gatcaacaaa        240
tatgatctga atatgttcta catcgaaggt ccgggtcatg gtggtcaggt tatggttagc       300
aatagctatc tggatggtag ctatagcgaa atttatccgc gtgttagcca ggataaagaa       360
ggtatgaaaa acctgtttac ccagtttagc tggcctggtg tgttgcaag ccatgcaagc       420 gcacagacac cgggtagcat tcatgaaggt ggtgaactgg ttatgcact gagccatgcc       480 accggtgcaa ttctggataa cccggatgtt attgcagcag ttgttaccgg tgatggtgaa       540
accgaaaccg gtccgctggc agcaagctgg tttagtaata cctttattaa cccgattagc      600
gacggtgcca tcctgccgat tgttcatatg aatggcttta aaatcagcaa cccgaccatt      660
ctgagccgta aagtgatga agatctgacc aaatatttcg aaggcatggg ttggaaaccg       720 tatttttgttg aaggtgatga tccgaccaaa ctgaatccgg aaatggcaaa agttatggat     780
gcagccattg aagaaattaa agccatccag aaacatgccc gtgaaacagg tgataccacc      840
```

```
atgccgcatt ggcctgttat tatctttcgt agcccgaaag gttggacagg tccgaaaagc    900
tggaatggcg aaccgattga aggtagcttt cgtgcacatc agattccgat tccggttgat    960
gccgaagata tggaacatgc agatagcctg gcaggttggc tgaaatcata tcatccggaa   1020
gaactgtttg atgagaacgg taaactgatc cctgaactgg cagccctgcc tccgaaaggc   1080
gataaacgta tggcagccaa tccgattacc aatggtggcc tggatccgaa acctctggtt   1140
ctgccggatt atcgtaaata tgccctggat aataaagaac acggcaagca gattaaacag   1200
gacatgattg tttggagcga ttatctgcgt gatctgatta aactgaaccc gcataacttt   1260
cgtattttcg gtccggatga aaccatgagc aatcgtctgt atagcctgtt gaagttacc    1320
aatcgtcagt ggctggaacc gatcaaagaa cctgcagatc agtatctggc accggcaggt   1380
cgtattattg atagccagct gagcgaacat cagagcgaag ttttaatga aggttatacc    1440
ctgaccggtc gtcatggtct gtttacaagc tatgaagcat ttctgcgtgt tgttgatagc   1500
atgctgaccc agcactttaa atggattcgt aaagcacatg aagaaccgtg gcataaagca   1560
tatccgagcc tgaatgttgt tagcaccagc accagttttc agcaggatca taatggttat   1620
acacatcagg atccgggtat tctgaccccat atggcagaaa aaaagcgga atatattcgc   1680
gagtatctgc cagcagatgc caatagcctg ctggcaatta gtccgaaact gtttagcagc   1740
cagaataccg ttaatgttct gatcaccagc aaacagcctc gtccgcagtt ttatagtatt   1800
gatgaagcca ccgttctggc aaatgcaggt ctgaaacgta ttgattgggc aagcaatgat   1860
gatggtgttg aaccggatgt ggtgattgca gccgcaggca ccgaaccgaa tatggaaagt   1920
ctggctgcaa ttaatctgct gcatgatgca tttccggatc tgaaaattcg ctttatcaat   1980
gtgctggatc tgctgaaact gcgttcaccg gaaattgatc ctcgtggtct gagtgatgca   2040
gaatttaaca gctatttcac caccgataaa ccgatcctgt tgcctatca tggttttgaa   2100
ggtctgattc gcgatatttt ctttacccgt cagaatcgta acgtgctgat tcatggttat   2160
cgtgaagagg gtgatattac caccccgttt gatatgcgtg ttctgaatga actggatcgt   2220
tttcatctgg ccaaagatgt gattcagcat gttccggcat atgcggaaaa agcagcagca   2280
tttgttcaga aaatggatga taccctgcag tatcaccatg attttattcg tgcaaatggt   2340
gaggatattc cggaagttca agaatggacc tggaaaagca ttaaa                  2385
```

<210> SEQ ID NO 55
<211> LENGTH: 2397
<212> TYPE: DNA
<213> ORGANISM: Lactobacillus crispatus ST1

<400> SEQUENCE: 55

```
atggccgtgg attatgatag caaagactat ctgaaaagcg tggatgcata ttggcgtgca     60
gcaaattatc tgagcgttgg tcagctgttt ctgatgaaaa tccgctgct gaaaacaccg    120
ctggttgcag aagatgttaa accgaaaccg attggtcatt ggggcaccat tgcaccgcag    180
aattttatct atgcacatct gaatcgtgtt ctgaaaaagt acgatctgaa tatgttctat    240
atcgaaggta gcggtcatgg tggtcaggtt atggttagca atagttatct ggatggtagc    300
tataccgaac gctatccgga aattacccag gatgagaaag gtatggcaaa actgtttaaa    360
cgctttagct ttccgggtgg tgttgcaagc catgcagcac cggaaacacc gggtagcatt    420
catgaaggtg gtgaactggg ttatagcctg agccatggca ccggtgcagt tctggataat    480
ccggatgtta ttgcagcagt tgaaattggt gatggtgaag cagaaaccgg tccgctggca    540
gcaagctggt ttagcgataa attcattaac ccgattaaag atggtgccgt tctgccgatt    600
```

```
ctgcagatca atggctttaa aatcagcaat ccgaccattg ttagccgtat gagcgatcaa    660
gaactgaccg aatattttcg tggtatgggt tgggatccgc attttgttag cgttttaaa    720 ggtggtcgtt tcgatggcga aaaagatccg atgcaggttc acgaagaaat ggccaaaacc    780
atggatgaag tgatcgaaga gattaaggcc attcagaaac atgcgcgtga aaataatgat    840
gcaaccctgc cgcattggcc gatgattatc tttcagtgtc cgaaaggttg acaggtccg    900 aaaaaagatt tagatggtaa tccgatcgaa aacagctttc gtgcacatca gattccgatt    960
ccggttgcac agggtgatat ggaacatgca gatatgctga cagattggct ggaaagctat   1020
aaaccggaag aactgttcaa tgaagatggc agcccgaaag aaattgttac cgaaaatacc   1080
gcaaaaggtg atcatcgtat ggccatgaat ccgattacca atggtggtat tgatccgaaa   1140
cgtctgaatc tgccggatta tcgtaaattt gccctgaaat tgataaaacc tggtagcgtt   1200
gaagcacagg atatggttga atgggcaaaa tatctggacg aagttgccaa actgaacccg   1260
accacctttc gcggttttgg tccggatgaa agcaaaagca atcgtctgtt tcagctgctg   1320
gatgatcaga aacgccagtg ggaacctgaa gttcatgaac cgaacgatga aaatctggca   1380
ccgagcggtc gtgttattga tagccagctg agcgaacatc aggatgaagg ttttctggaa   1440
ggttatgttc tgaccggtcg tcatggtttt tttgcaacct atgaagcatt tggtcgtgtg   1500
gtggatagca tgctgaccca gcatatgaaa tggctgcgta agccaaaga acagtactgg   1560 cgtcacgatt atccgagcct gaattttgtt gcgaccagca ccgttttca gcaggatcat   1620 aatggttata cccaccagga tccgggtatt ctgacccacc tgtatgaaaa aaatcgtccg   1680
gatctggtgc atgaatatct gccgagcgat accaataccc tgctggcagt tggtgataaa   1740
gcactgcagg atcgtgaatg tattaatgtt ctggttacca gcaaacagcc tcgtccgcag   1800
tggtttagta ttgaagaagc aaaaaaactg gtcgataaag gcctgggcta tattgattgg   1860
gcaagcacag ataaaggtgc aaaaccggat gtggttttg ccagtaccga acagaaccg   1920 acaattgaaa ccctggcagc cattgatatt ctgcataaga aatttccgga cctgaagatc   1980
cgttatatca atgttgttga cgtgatgaaa ctgatggatc cgaaggataa caaaaatggt   2040
ctgagcacgg aagaatttga tcgcctgttt ccgaaagatg ttccggttat ttttgcctgg   2100
catggctata aaagcatgat ggaaagtatt tggtttgccc gtaaacgcta taacgtgcat   2160
attcactgct atgaagaaaa cggtgatatt accaccccgt ttgatatgcg tgtgctgaat   2220
catctggatc gttttgatct ggcaaaagat gccgttgaaa gcatcgataa actgaaaggc   2280
aaaaacgccg atttttatcag ccatatggat gacctgctgg aaaaacatca tcagtatatt   2340
cgcgataacg gcaaagatat gccggaagtt acagaatggc aatggtcagg cctgaaa      2397
```

<210> SEQ ID NO 56
<211> LENGTH: 2451
<212> TYPE: DNA
<213> ORGANISM: Leuconostoc citreum KM20

<400> SEQUENCE: 56

```
atggccgatt tcgacagcaa agagtatctg gaactggttg ataaatggtg gcgtgcaacc     60
aattatctga gcgcaggtat gatttttctg aaaagcaatc gctgtttag cgttaccaat    120 accccgattc aggcagaaga tgttaaagtt aaaccgattg gtcattgggg caccattagc    180
ggtcagacct ttctgtatgc acatgcaaat cgtctgatca caaatacga tctgaatatg    240 ttctatattg gcggtccggg tcatggtggt caggttatgg tgaccaatgc atatctggat    300
```

```
ggtgaatata ccgaagatta tccggaaatt acccaggatc tggaaggtat gagccgtctg    360
tttaaacgtt ttagctttcc gggtggtatt ggtagccata tgaccgcaca gacaccgggt    420
agcctgcatg aaggtggtga actgggttat agcctgagcc atgcatttgg tgcagttctg    480
gataatccgg atcagattgc atttgcagtt gttggtgatg gcgaagcaga aaccggtccg    540
agcatgacca gctggcatag caccaaattt ctgaatgcaa aaaatgatgg tgccgtgctg    600
ccgattctgg atctgaacgg ctttaaaatc agtaacccga ccattttag ccgtatgtcc    660 gatgaagaaa tcaccaagtt ttttgaaggt ctgggctata gtccgcgttt tattgaaaac    720
gatgatatcc atgattacgc agcctatcat gaactggcag caaaagtgct ggatcaggca    780
attgaagata ttcaggccat tcagaaagat gcccgtgaaa atggtaaata tgaagatggt    840
acaattccgg catggcctgt tattattgca cgtctgccga aggttgggg tggtccgacc    900 catgatgagg atggtaatcc gattgaaaat agctttcgtg cacatcaggt tccgctgccg    960
ctggcacaga taaactgga aaccctgagt cagtttgaag attggatgaa tagctacaaa    1020
ccggaagaac tgtttaatgc agatggcagc ctgaaagatg aactgaaagc aattgcaccg    1080
aaaggcgata aacgtatgag cgcaaacccg attgcaaatg gcggtcgtcg tcgtggtgaa    1140
gaagcaaccg atctgaccct gccggattgg cgtcagttta ccaatgatat aaccaatgaa    1200
aaccgtggtc acgaactgcc taaagttacc cagaatatgg atatgaccac cctgagcaat    1260
tacctggaag aagttgcaaa actgaatccg accagttttc gtgttttgg tccggatgaa    1320 accatgagca atcgcctgtg gtcactgttc aataccacca atcgtcagtg gatggaagag    1380
gtgaaagaac cgaatgatca gtatgtgggt ccggaaggtc gtattattga tagccagctg    1440
agcgaacatc aggcggaagg ttggctggaa ggctataccc tgaccggtcg tgttggtatt    1500
tttgcaagct atgaaagctt tctgcgtgtt gttgatacca tggtgacaca gcactttaaa    1560
tggctgcgtc atgcaagcga acaggcatgg cgtaatgatt atcctagcct gaatctgatt    1620
gcaaccagca ccgcatttca gcaggatcat aatggttata cccatcagga tccgggtatg    1680
ctgacccatc tggcagagaa aaaaagcaac tttatccgtg aatatctgcc tgccgatggc    1740
aatagcctgc tggcagttca ggatcgtgca tttagcgaac gtcataaagt gaacctgatt    1800
atcgcaagca aacagcctcg tcagcagtgg tttaccgcag atgaagcaga tgagctggca    1860
aatgaaggcc tgaaaattat cgattgggca agtaccgcac cgagcggtga tgttgatatt    1920 accttttgcca gcagcggcac cgaaccgaca attgaaacgc tggcagccct gtggctgatt    1980
aatcaagcat ttccggaagt gaaattccgc tatgttaatg ttgtggaact gctgcgcctg    2040
cagaaaaaat cagaaagtca tatgaatgat gagcgcgaac tgagtgatgc agagtttaac    2100 aaattttttcc aggccgataa accggtgatc tttggttttc atgcatatga ggatctgatc    2160
gagagctttt ttttcgagcg taaattcaaa ggtgatgtgt atgtgcatgg ttatcgcgaa    2220
gatggcgata ttacaaccac ctatgatatg cgtgtttaca gcaaactgga tcgttttcat    2280
caggccaaag aagcagcaga aattctgtca gcaaatagca caattgacca ggcagcagcc    2340
gataccttta tcgaaaaaat ggatgcaacc ctggccaaac attttgaagt gacccgtaat    2400
gaaggtcgcg atattgaaga atttacggat tggaattgga gcgcactgaa a              2451

<210> SEQ ID NO 57
<211> LENGTH: 2385
<212> TYPE: DNA
<213> ORGANISM: Bradyrhizobium sp. S23321

<400> SEQUENCE: 57
```

```
atgaacaatc agcagcagag cgcactgagc cgtagcgatc tggatctgct ggatcgttat      60
tggcgtgcag caaattatct gagcgttggt cagatttacc tgctggacaa tccgctgctg     120
cgtgaaccgc tgcgtccgga acacattaaa ccgcgtctgc tgggtcattg gggcaccaca     180
ccgggtctga attttatcta tgcacatctg aatcgtgtta ccgtgcact  ggacctgagc     240
gtgctgtatg tttgtggtcc gggtaatggt ggtcctggca tggttgcaaa tacctatctg     300
gaaggtagct atagcgaaat ctatccgaat attgcacgtg ataccgatgg tctgcgtaaa     360
ctgtttcgtc agtttagctt ccgggtggt  attccgagcc atgcagcacc ggaaactccg     420
ggtagcattc atgaaggtgg tgaactgggt tatgcactgg ttcatgcata tggtgcagca     480
tttgataatc cggatctgat tgttgcatgt gttgttggtg atggtgaagc agaaaccggt     540
ccgctggcag caagctggca tagcaacaaa tttctgaatc cggttcatga tggtgccgtt     600
ctgccgattc tgcatctgaa cggctataaa atcgcaaatc cgaccgttct gggtcgtatg     660
cgtgatgaag aaattcgtga tttatttcgc ggttttggtc atgaacctct gtttgttgaa     720
ggtgatgatc cgaccctgat gcaccaggca atggcagatg cctttgatgt tgcatttgca     780
cgtattcgta gcatccagca gcatgcccgt gatggtcgta agaaattga  acgtccgcgt     840
tggccgatga ttgttctgcg tagcccgaaa ggttggacag gtccgaaaga agttgacggt     900
ctgaaagtgg aaggtttctg gcgtgcccat caggttccgg ttgcaggttg tcgtgaaaat     960
cctgcccatc tgaaaattct ggaagattgg atgcgtagct atgaaccgga aaaactgttc    1020
gatgcaagcg gtgcactgat tccggaactg caggccctgg ctccggaagg taatcgtcgt    1080
atgggtgcca atccgcatgc aaatggcggt ctgctgaaaa agaactgaa  actgccggat    1140
tttcgtagct ttgccctgga agttccgcag cctggtggtg ttaccggtga agccacacgc    1200
gaactgggca aattcctgcg tgacgttatt cgtctgaatg cagcagaacg taattttcgc    1260
attatgggtc cggatgaaac cgcaagcaat cgtctggatg ccgttttga  agaaaccgaa    1320
cgtgttttgga tggaaccgat tgaaccgtat gatgttcatc tggcacagga tggtcgcgtt    1380
atggaagtgc tgagcgaaca tctgtgtcag ggttggctgg aaggctatct gctgaccggt    1440
cgtcatggtt tttttagctg ttatgaagcc tttatccaca tcgtggatag catgtttaat    1500
cagcacgcaa aatggctgaa agttacccgt catctgccgt ggcgtcgtcc gattgcaagc    1560
ctgaattatc ttctgaccag ccatgtttgg cgtcaggatc ataatggttt tagtcatcag    1620
gatcctggtt tgttgatct  ggttgccaac aaaaaagcgg atattgtgcg tatctatttt    1680
ccgcctgatg ccaataccct gctgtggatt gcagatcatt gcctgcgtac ctataatcgc    1740
attaatgtta ttgtggcagg taaacagcct gcaccgcagt ggctgagcat gcaggatgca    1800
gcaacccatt gtgatgcagg tattggtatt tggagctggg ctggtaatga agatgcaaca    1860
ggcgaaccgc atgttgttat ggcatgtgcc ggtgatgtgc cgacactgga accctggca    1920
gccgttgacc tgctgcgcaa agcactgcct gatctgaaga ttcgtgttgt taatgttgta    1980
gatctgatga cactgcagcc taaagaacag catcctcatg gtctgagcga tcgcgatttt    2040
gatagtctgt ttaccagcga taaaccggtg attttttgcct atcatggtta tccgcacctg    2100
attcatcgtc tgacatataa tcgtaccaat catgcaggtc tgcatgtgcg tggttttatt    2160
gaagaaggta caaccaccac cccgtttgat atggttgttc tgaatgaact ggatcgctat    2220
cacctggcaa ttgaagccat tgaacgcgtt ccaggtctgg cagcgcgtgc cgcagcggtt    2280
aaacagcagt ttcgtgatgc cctgattgaa catagccatt atattcgtga acacggtgaa    2340
```
gatatgccgg aaatccgcga ttgggtttgg cctggtaaaa ccggt         2385

<210> SEQ ID NO 58
<211> LENGTH: 2367
<212> TYPE: DNA
<213> ORGANISM: Brucella microti CCM 4915

<400> SEQUENCE: 58
atgcctgcaa aaggtccgct gacaccgcag cagctgagcc tgattaatcg ttattggcgt      60
gcagcaaatt atctgagcgt tggtcagatt tacctgatga aaaatccgct gctgcgtgaa     120
ccgctgcagc cggaacacat taaaccgcgt ctgctgggtc attggggcac cacaccgggt     180
ctgaatttta tctatgcaca tctgaatcgc attatccagc agcgtaatgc caatgtgatt     240
tatatctgtg gtccgggtca tggtggccct ggtatggttg caaataccta tctggaaggc     300
acctatagcg aaatttatcc ggcaattagc gaagatgaag caggtatgga acgtctgttt     360
cgtcagttta gctttccggg tggtattccg agccatgcag caccggaaac tccgggtagc     420
attcatgaag gtggtgaact gggttatgca ctggttcatg catatggtgc agcatttgat     480
aatccggatc tggttgttgc atgtgttgtt ggtgatggtg aagcagaaac cggtgcactg     540
gcaaccagct ggcatagcaa caaatttctg aatccggcac gtgatggcgc agttctgccg     600
attctgcatc tgaacggcta taaaatcgca aatccgaccg ttctggcacg tctgagtgat     660
gatgatctgg ataacctgtt cgcggttat ggttatgaac cgttttttgt tgaaggtagc      720
gaaccggcag atatgcatca gaaaatggca gcaaccctgg ataccatttt tcagcgtatt     780
caggacatca aaaaaaacgc cgatgttcat agtccggaac gtccgcgttg ccgatgatt      840
attctgcgta gcccgaaagg ttggaccggt ccgaaaaccg ttgatggtct ggtggttgaa     900
aattactggc gtgcccatca ggttccggtt gccaattgtc gtgaaaatga tgcccatcgt     960
aaaatcctgg aagattggat gaaaagctat gatccgagcg acctgtttga tgagaaaggt    1020
gccctgaaac cggaactgcg tgccctggca ccgaaaggcg aagcccgtat gggtgccaat    1080
ccgcatgcga atggtggtct gctgcgcaaa gaactgcaca tgccggattt cgccagtat    1140
gcagttaatg ttaccgaacc gggtgcaatt gaagcacaga gcaccaaaat tctgggtgat    1200
ttcctgcgtg atgtgatgaa actgaatgaa accgaaaaaa acttccgcat ttttggtccg    1260
gatgaaacag caagcaatcg tctgggtagc gttctggaag cgaccaatcg tgtttggatg    1320
gccgaaacac tggatatgga tgatcacctg gcagcagatg gtcgtgttat ggaagttctg    1380
agcgaacatc tgtgtcaggg ttggctggaa ggttatctgc tgagcggtcg tcatggtttt    1440
tttagctgtt atgaagcctt catccacatc atcgatagca tgtttaatca gcatgcaaaa    1500
tggctgcagg ttgcacgcga actggaatgg cgtaaaccga ttagcagcct gaattacctg    1560
ctgaccagcc atgtttggcg tcaggatcat aatggtttta gtcatcagga tcctggtttt    1620
gtagatctgg tggcaaataa aagcgcagat attgtgcgtg tttatttttcc gcctgatgcc    1680
aatacctgc tgtgggtggg tgatcattgc ctgaaaacct ggaatcgtgt gaatgttatt    1740
gttgcaggta acagccaga accgcagtgg ctgaccatgg cggaagccga aaacattgt     1800
gaagccggtc tgggcatttg gaatgggca ggtacagaag atggcctgga accggatatt    1860
gttatggcat gtgccggtga tgttccgacc atggaaacgc tggcagccgt ggatttactg    1920
cgtcagagcc tgccgcatct gcgtattcgt gttgttaatg tggttgatct gatggttctg    1980
cagagtccgc atcagcatcc tcatggtatt agtgatgaag aatttgatcg tatgttcacc    2040
acaaatcgtc cggtgatttt tgcctatcat ggttatccgt atctgattca ccgtctggtt    2100

```
tataaacgta ccaatcacag caattttcac gtgcgtggtt ttattgaaca gggtacaacc      2160
accaccccgt ttgatatgac cgtgctgaat gagctggatc gttttcatct ggcaatggaa      2220
gcagttgaac gcctgccact gggtgaaagc gttgcaaaac cgctgattga taactttaca      2280
gaaaaactgg cactgcacaa agattatatt cgtcagcatg cgaagatat gccggaaatt       2340 cgtgattgga aatggacctg gcctcgt                                          2367

<210> SEQ ID NO 59
<211> LENGTH: 2358
<212> TYPE: DNA
<213> ORGANISM: Lactobacillus salivarius ATCC 11741

<400> SEQUENCE: 59
atgaccgatt atagcagcca agaatacctg gataaactgg atgcatattg gcgtgcagca       60
aattatgtta gcgttggtca gctgtatctg aaagataatc cgctgctgcg tcgtccgctg      120
aaagcagaag atgttaaagt taaaccgatt ggtcattggg gcaccattgc aggtcagaat      180 tttatcctatg cacatctgaa tcgcgtgatc aacaaatatg atctgaacat gttctatgtg      240
gaaggtccgg gtcatggtgg tcaggttatg gttagcaata gctatctgga tggtagctat      300
agcgaaatct atccggaaat tagccaggat gaacagggta tgaaacgtct gtttaaacgt      360
tttagctttc cgggtggtgt tgcaagccat gcagcaccgg aaacaccggg tagcattcat      420
gaaggtggtg aactgggtta tagcattagc catagcgtgg gtgcagttct ggataacccg      480
gatctgattt ttgcagcagt tgttggtgat ggtgaagcag aaaccggtcc gctggcagca      540
agctggcaga gcaataaatt cattaatccg attcatgatg gcgcagtgct gccgattctg      600
gatctgaatg gctttaaaat cagcaatccg accattctga gccgtgaaag tgatgaaacc      660
ctgaccaaat atttcgaagg tatgggttgg catccgatct ttgttgaagg tgatgatccg      720
aaattaatgc atccggcaat ggcaaaagca atggatgaag caattgaaga gattaaagcg      780
attcagaaaa acgcacgcga aaataacgat ccgagcctgc ctgcatggcc tgttattatc      840
tttcgtgcac cgaaaggttg gacaggtccg aaagaatggg atggcgaacc gatcgaaaaa      900
agctttcgcg cacatcagat tccgattccg gttgatcaga atgatatgca gcatgcagat      960
gcactggttg attggctgga aagctataaa ccggaagaac tgtttgatga aaacggcaaa     1020
ctgaaagccg aaattgcaga aattaccccg aaaggcgata acgtatggc agccaatccg      1080 cataccaatc cgggtaaact gattcgcgaa gttatcaaac cggattttcg tgattttgca      1140
gttgatacca gcgttcctgg taaagaagtt gcacaggata tgaccgttct gggtaaatat      1200
ctggaaaaag tgctgagcga taaccgccat aattatcgtg ttttggtcc ggatgaaacg      1260 atgagcaatc gtctggcacc gatttttgat gttaccaaac gtcagtggct ggccgaaatc      1320
aaagaaccga atgatcagta tttagcaccg agcggtcagg tgattgatag ccagctgagt      1380
gaacatcagg cagaaggttt tctggaaggt tatgttctga ccggtcgtca tggtttttt      1440 gcaagctatg aaagttttct gcgtgtggtt gatagcatgc tgacccagca ctttaaatgg     1500
ctgcgtaaag caaccgaaca gccgtggcgt accagcattc cgagtctgaa tgttattgca     1560
accagcaccg ttttcagca ggatcataat ggttataccc atcaggatcc tggtattctg      1620
ggtcatctgg cagataaaaa acctgaatat atccgcgaat atctgcctgc cgatgcaaat     1680
agcctgctgg cagttttga taaaaccatt aatgaccgcg acaaaattaa cctgattgtg     1740
gcaagcaaac atccgcgtca gcagttttat agcgcagcag aagcaaaaga actggtagat     1800
```

```
aaaggcctga aaattatcga ttgggcgagc accgataaaa atgccgaacc ggatgtggtt    1860
attgccgcag caggcaccga accgaacctg gaagcactgg cagcgattag cattctgcat    1920
gaaaaactgc cggatcttaa aatccgcttt attaacgttg tggacattct gaaactgcgt    1980
agcccgaaag ttgatccgcg tggtctgagt gatgatgaat ttgatgccta tttcaccaaa    2040
gacaaaccgg tgattttgc ctttcatggt tatgaaggtc tgctgcgcga tatttctat    2100 tatcgccata accataacgt ggcctttcac ggctatcgtg aaaatggtga tattaccacc    2160
ccgtttgata tgcgtgttct gtcacagatg gatcgttttg atctggttaa aagcgttgca    2220
ctgagtctgc ctgatgccga taaatatggc cagctggttg ccgaaatgga tgcaaaagtt    2280 gcaaacatc atcagtatat ccgtgatgaa ggtacagatc tgccggaagt tgaaaattgg    2340
gaatggaaac cgctggat                                                  2358

<210> SEQ ID NO 60
<211> LENGTH: 2400
<212> TYPE: DNA
<213> ORGANISM: Rhodococcus imtechensis RKJ300

<400> SEQUENCE: 60
atgaccgatg gtcgtcaggt tggtagccag gatagtgatg gtcattatag cgatagcgat      60
ctggatctgg acctgcgttg gtgggcagca gcaaattatc tgaccgttgc acagatttat     120
ctgcaggata atgcactgct gcgtgctccg ctgcgtccgg aacacattaa accgcgtctg     180
ctgggtcatt ggggcaccag tccgggtctg agcatgattt atgccctgct gaatcgtctg     240
attcgtcgta ccgataccga ttgtctgtat gttaccggtc tggtcatgg tggtccggca     300 ctggttgcag caacctatct ggaaggcacc tatagcgaag tttatccggg tgttagccgt     360
gatgcagcag gtattcatcg tctgtgtcgt cagtttagca caccgggtgg tattccgagc     420
catgttagcg ttcagactcc gggtagcatt catgaaggtg gtgaactggg ttatgcactg     480
gcacatgcag ccggtgcagc atttgatcat ccgaatctgc tggttgcctg tgttattggt     540
gatggtgaag cagaaaccgg tccgctgagc ggtagctgga aactgcctgc atttctgaat     600
ccggaacgtg atggcgcagt tctgccgatt ctgcatgtta atggtgcaaa aattgcaggt     660
ccgaccgttt atggtcgtag ctcagatgca gatgttgaag cctttctggg tggtcagggt     720
tgggcaccga ccgtggtgag cggtgatgat ccgcgtcatg ttttttccagc actgcatcgt     780 gcactgacag atgcacatgc cgcaattagt gatctgcagc gtgaagcacg tgcaggtcgt     840
cgtagcgcag caaaatggcc tgcaattgtt ctgcgtaccc cgaaaggttg gacaggtccg     900
cgtaccgttg atggtgttct ggttgaaggt acacatcgtg cccatcaggt tccgctgtca     960
ggtgttcgca ccgatgaagc acatctgcgt cagctggaag aatggatgcg tagctatggt    1020
ccgggtgagc tgtttgatag cagcggtgcc ctggttcctg atctggaacg tctggcaccg    1080
cagggtgata aacgtatggg tagcagcccg tatgcaaatg gtggccgtct gcgtgcagat    1140
ctgccggttc cgcctctgga aaaatatgcg ctggcaattg aaaaaccggg tacaaccctg    1200
catgaaacca cccgtgtgct gggtgaatta ctgcgtgatc tgtatgcagc caccgcaaca    1260
ccggatggtg gtggttattt tcgtctgttt tgtccggatg aaaccgcaag caatcgcctg    1320
ggtgcagttt ttgaagttac cgatcgttgt tggcagctgc cggtgaccga ttatgatgat    1380
ggtctgagtg cacgtggtcg tgttatggaa gttctgagcg aacatctgtg tgaaggttgg    1440
ctggaaggtt atctgctgag tggtcgccat ggtctgtttg caagctatga agcatttgca    1500
atggttagcg tgagcatgct ggttcagcat accaaatggc tgcagcatgc agttgatctg    1560
```

```
ccttggcgtg caccggttgc aagcctgaat gtgctgctga ccagcacctg ttggcgtaat    1620
gatcataatg gttttagtca tcagggtccg ggaatgattg atgcagttat tccgctggct    1680
ccggatgttg ttcgtatttg gctgccaccg gatagcaata ccctgctgtc aattgcagat    1740
cattgcctgc gtagcaccga tcatgtgaat ctgattgttg ttgataaaca gccgcatctg    1800
cagtatctga cactggccga agcccatgca cattgtgcag cgggtgccag cgtgtgggaa    1860
tgggcaggca ccgaaggtgc ggttggtgcg atcctgatg ttgtgctggc agcggctggt     1920
gatgttccga cccaagaaat cctggcagcc gcacagctgc tgcgcgaaca tactccggat    1980
ctggttaccc gtgttgttaa tgttgtggat ctgatgggtc tgctgacgcc gaccgaacat    2040
ccgcatggtt ttgatgcacg tatgtttctg gatttgttta ccgcagatac ggatgtggtt    2100
tttgcctttc atggttatag ccgtgccgtt catgaactga ttcatggtcg ccctgcaccg    2160
gatcgttttc atgttcgcgg ttttagcgaa cagggtacga ccaccacccc gtttgatatg    2220
gttgttctga accgtatgag ccgttatcat ctggtgctgg aagcactgcg tcgcacccgt    2280
cgtgaacctg cgggtgcagg cgaactggca gattttgtc tgcgccagtt agaacgccat      2340
ggcgaatatg ttgttgcaca cctggaagat atgccggaag ttcgtgattg gacctggtca    2400
```

<210> SEQ ID NO 61
<211> LENGTH: 2391
<212> TYPE: DNA
<213> ORGANISM: Burkholderia xenovorans LB400

<400> SEQUENCE: 61

```
atggcagaag caagcagccg tccgacccct ccgcaggttc tggatgcaga taccctgcgt      60
aatatggatc gttattggcg tgcatgtaat tatctgagcg caggtatgat ttatctgcgt    120
gataatccgc tgctgcgtga accgctgaaa ccggaacaca ttaaaaaccg tctgctgggt    180
cattggggta gcgatccggg tcagagcttt ctgctggtgc atctgaatcg tctgattcgt    240
aaactggatc tgaacgtgat ttatgttgca ggtcctggtc atggtgcacc ggcaaccctg    300
gcacattgtt atctggaagg tcattatagc gaaatttatc cggatcgtag cgaagatgaa    360
gccggtatgc agcgtttttt tcgtcagttt agctttccgg tggtattgg tagccattgt      420 acaccggaaa caccgggtag cattcatgaa ggtggtgaac tgggttatag cctgagccat    480
ggttatggtc cgcatttga taacccggat ctgattgtta ccgtgatgat tggtgatggt      540
gaagcagaaa ccggtccgct ggcaaccagc tggcatagca acaaatttct gaatccggtt    600
cgtgatggcg cagttctgcc ggttctgcac ctgaatggct ataaaatcgc aaatccgacc    660
attctggcac gtattccgcg tgaagaactg gaagcactgc tgaccggcta tggtcataaa    720
ccgtatttcg ttgaaggtga tgatccggca gttatgcatc agcagatggc agccaccctg    780
gaacagtgta ttggtgaaat tcgtgcaatt cagcagcatg cacgtgcaaa taatgatgca    840
acccgtccgc gttggccgat gattgttctg cgtagcccga aaggttggac aggtccgaaa    900
gaagttgacg gccataaagt ggaaggtagc tggcgtgccc atcaggttcc ggtgctggat    960
ccggttacca atggtaaaag cctgaaactg gttgaaaatt ggatgcgtag ctatgaaccg    1020
gaaagcctgt ttgatgaagc aggtcgtctg gttgaggaac tgcgcgaact ggcaccgaaa    1080
ggcgcacgtc gtattagcgc caatccgcat gcaaatggtg gtctgctgtg taaaaccctg    1140
gatatgcctg catttggtga ttatgcagtt gcagttaaaa aaccgggtgg cacctatacc    1200
agcccgaccg aagttctggg taaattcctg tgtgatgtta tgcgtcgcaa tatgaccaat    1260
```

-continued

```
tttcgtgttt ttggtccgga tgaaaccgca agcaataaac tgaccgcaat ttatgaagcc      1320
agcgaaaaaa cctggctggc ccagaccgaa ccgagtgatg ccgatggtgg cgatctggca      1380
gttgatggtc gtgttatgga aatgctgagc gaacatacac tggaaggctg gtttgaaggt      1440
tatgttctga ccggtcgtca tggtctgttt gcaacctatg aagcatttgt gcatgtgatc      1500
gatagcatgt ttaatcagca cgcaaaatgg ctggaaaaag caaaacgtga tctgggttgg      1560
cgtcagccgg ttccgagcat taatctgctg attaccagcc tggtgtggcg tcaagatcat      1620
aatggtttta cacatcagga tcctggtttt ctggacgttg tgaccaataa atcaccggat      1680
gttgtgcgta tctatctgcc tccggatgcc aattgtctgc tgagtgttgc agatcattgc      1740
ctgcgtagtc gcgattatgt taatgttatt gttgccgata aacagccgca tctgcagtat      1800
ctggacatgg atgccgcagt tattcattgt accaaaggta ttggcatctg ggattgggca      1860
agcaccgatc agggtgttga acctgatgtt gttattgcaa gtgccggtga tattgccacc      1920
atggaagccc tggcagcagt tcagattctg aaagaacgtt ttgccgatct gaaaatccgt      1980
tttgtgaatg ttgttgacct gtttcgcctg atgccggaac atgcacatcc gcacggtctg      2040
agcaatcgtg attttgatag tctgtttacc gcaaccaaac cggtgatctt aactttcat       2100
agctatgcaa gcctggttca caaactgaca tataatcgta ccaaccatga taacctgcat      2160
gtgcatggct atcatgaaaa aggcaatatt aacacaccgc tggaactggc cattattaac      2220
caggttgatc gttttagcct ggcgattgat gtgattgatc gtgttccgaa actgcgtggt      2280
gtgggtgatc atgcaaaaga atggctgcgt ggccaggtta ttgaacatct ggcatatgca      2340
catgccgaag gcattgatcg cgaagaaatt cgcaattgga cctggaaagg t              2391
```

<210> SEQ ID NO 62
<211> LENGTH: 2361
<212> TYPE: DNA
<213> ORGANISM: Mycobacterium intracellulare ATCC 13950

<400> SEQUENCE: 62

```
atgacccatg caaccgcact gagtgatgat gaactggcac tgattgataa atactggcgt       60
gcagcaaatt atctgagcgt tggtcagatt tatctgctgg ataatccgct gctgaccgaa      120
ccgctgacca ttgatcatgt taaaccgcgt ctgctgggtc attggggcac cacaccgggt      180
ctgaatctgg tttatgcaca tctgaatcgt gttattcgtc atcgtgatgc cgatgttatt      240
tatgttaccg gtccgggtca tggtggtcct ggtctggttg caaatgcata tctggaaggc      300
acctatagcg aagtttatac cggtattgaa gaagataccg aaggtctgcg taaactgttt      360
cgtcagttta gctttccggg tggtattccg agccatgttg cagcacagac tccgggtagc      420
attcatgaag gtggtgaact gggttatgcc ctggttcatg catatggtgc agcactggat      480
aacccgtatc tggttgttgc atgtgttgtt ggtgatggtg aagcagaaac aggtccgctg      540
gcagcaagct ggcatagcaa caaatttctg aatccggtga ccgatggtgc cgttctgccg      600
attctggccc tgaatggcta taaaatcgca atccgaccg ttctggcacg tattccgcat      660
gcagaactgg aaagcctgct gcgtggttat ggttatcgtc cgattaccgt tgccggtgat      720
gatccggcag atgttcatcg tcaactgca gctgccctgg atgatgcctt tgatgatatt      780
gcagcaattc agagcgcagc acgtggtggt aatggtgttg aacgtccggt ttggccgatg      840
attgttctgc gtaccccgaa aggttggacg gtccgaaaa tggttgatgg caaaaaagtt      900
gaaggtacat ggcgtagcca tcaggttccg ttagcagcaa cccgtgataa tcctgaacat      960
cgtgcacagc tggaagaatg gctgcgtagc tatggtccag gcgaactgtt tgatgaaaat     1020
```

```
ggccgtctgc gtccggaact gcgtgcactg gcaccgagcg gtgatcgtcg tatgagcgca   1080
aacccgcatg ccaatggtgg actgctgctg cacgatctgg atctgccgga ttttcgtgat   1140
tatgcagttg cagtggaacg tcctgcagca gttacccatg aagccacccg tgttctgggt   1200
ggttttctgc gtgatgtgat tgcacgtaat aaagatcgtt ttcgcctgat gggtccggat   1260
gaaaccgcaa gcaatcgtct ggatgcagtt tatggtagca ccgataaagt ttggctgagc   1320
gaaattgaac cggatgatga gcatctggct ccgatggtc gtgtgatgga agttctgagt   1380
gaacatctgt gtcagggttg gctggaaggt tatttactga ccggtcgtca tggtctgttt   1440
aattgttatg aagcctttgt gcacatcgtg atagcatgc tgaaccagca tgcaaaatgg   1500
ctggcaacca gccgtgaact gccgtggcgt cgtcctattg caagcctgaa ttacctgctg   1560
agcagccatg tgtggcgtca ggatcataat ggtgcaagtc atcaggatcc gggttttatt   1620
gatctggtgg ccaataaacg tccagaactg acccgtgtgt atctgccacc ggatggcaat   1680
accctgctgt ctgttgcaga tcattgtctg cgttcacgcg attacattaa tgttattgtt   1740
gcaggtaaac agccagccct ggcctatctg gatatggatg aagccgttgc acattgtacc   1800
cgtggcctgg gtatttggga atgggcaagc ccgcaaccg atgatcctga tgttgtgctg   1860
gcatgtgcag gcgatattcc gaccctggaa accctggcag ccgcagatat tctgcgcagc   1920
gaactgcccg aactggccgt tcgtgttgtt aatgttgttg atctgatgcg tctgcagccg   1980
gatacagaac atccgcatgg cctgcctgat cgtgaatttg atgcactgtt tacaccggat   2040
cgtccggtga tttttgcata tcatggctat ccgtggctga tccatcgtct gacctatagt   2100
cgtaccaatc atgcacatat gcatgtgcgt ggctttaaag aacgtggtac aaccaccacc   2160
ccgtttgata tggtaatgct gaatgatctg gaccgttttc acttagttat ggatgttatc   2220
gatcgtgttg atggtctggc aagccgtgcc gcaatgctgc gtcagcgcat ggtggatgca   2280
cgtctggcag cgcgtatgta tacccgtgaa catggcgaag atgatccaaa aattagcggt   2340
tggacctggg gtccgagcga t                                             2361
```

<210> SEQ ID NO 63
<211> LENGTH: 2367
<212> TYPE: DNA
<213> ORGANISM: Nitrosomonas sp. Is79A3

<400> SEQUENCE: 63

```
atgaaaaaga ataccaagct gctgagtccg gaactgctgc acaaaatgga tgcatattgg    60
cgtgcagcaa attatctgag cgttggtcag atttatctgt atgataatcc gctgctgaaa   120
cagccgctga aactggcaca tatcaaaccg cgtctgctgg gtcattgggg caccacaccg   180
ggtctgaatt ttatctatgt tcatctgaac cgcattatca aagagcacga tctgaacgtt   240
atctatatta ccggtccggg tcatggtggt cctggtctgg ttgcaaatac ctatctggaa   300
ggcacctata gcgaagtgta tccgaatatt agccaggatg aagatggtat gcagcgtctg   360
ttcaaacagt ttagcttcc gggtggtatt ccgagccatg ttgcaccgga actccgggt   420 agcattcatg aaggtggtga actgggttat agcctgagcc atgcatttgg tgcagcattt   480
gataaccctg gctgctggt tgcctgtgtt gttggtgatg gtgaagcaga aacaggtccg   540
ctggcaacca gctggcatag caacaaattt ctgaatccgg ttcatgatgg tgcagttctg   600
ccgattctgc atctgaatgg ctataaaatc gcaggtccga ccgttctggc acgtattccg   660
tgtgatgaac tggaagcact gtttcgtggt tatggttata ccccgtatt tatcgaaggt   720
```

-continued

```
gatgatcctc tggaaatgca tcagcgtatg gcagcaaccc tggatgcagt tattgccaat      780
attcagagca ttcagcgtga tgcacgtacc catggtttta ccaaacgtcc gcattggccg      840
atgattattc tgcgtagccc gaaaggttgg acgggtccga agttgttga tggtaaaccg       900 accgaaggta catttcgtag ccatcaggtt ccgatgggtg atatgagcca gcctggtcat      960
gttaaaattc tggaaaaatg gctgaaaagc tatcgtccgc aagaactgtt tgatgaaacc     1020
ggtaaactgc tggcagaact ggccgagctg gcaccgcagg gtgcacgtcg tatgggtgca     1080
aatccgcatg caaatggtgg tatgctgctg cgtgatctgc gtctgccgga ttttcgcgat     1140
tatgccgtta agttgccaa tccgggtaca gttagcgcag aagcaacccg tacccagggt      1200
gaatttattc gtgatgttgt taaactgaac gccaccaact ttcgtgtttt tagtccggat     1260
gaaacggcaa gcaatcgttg gggtgccgtt tttgaagtta ccaatcgctg tagtaccgca     1320
gaaattgttc ctggtgatga ccatgtggct ccggatggtc gtgttatgga aatgttaagc     1380
gaacatcagt gtgaaggttg gctggaaggt tatctgctga ccggtcgtca tggcttttt      1440 agctgttatg aagcctttat ccacattatt gatagcatgt taaccagca tgccaagtgg      1500 ttaaaagtgg caaatgaaat tccgtggcgt cgtccgattg caagcctgaa ttacctgctg     1560
agcagccatg tgtggcgtca ggatcataat ggttttcac atcaggatcc gggttttatt      1620
gatcatgtga tcaacaaaaa agccgaaatt attcgcatct atctgccacc ggatgccaat     1680
accctgctgt cagttaccga tcattgtctg cgttcacgta attatgtgaa tgttattgtt     1740
gcgggtaaac agcctcagcc gcagtggctg gatatggatg ccgcaattaa acattgtaca     1800
gccggtattg gtatttggga tgggccagc aatgatcagg gcgaagaacc ggatgttgtg      1860
atggcatgtg ccggtgatgc tccgaccatt gaaacactgg cagcagttga gctgctgtgg     1920 aaacatttc ctgaactgaa aattcgcgtg attaatgtgg ttgatctgat gagcctgcag      1980
ccacagagtg aacatcctca tggtctgagc gataaagatt ttgatggtct gtttaccaag     2040
gacaagccga ttatctttgc ctatcatggt tatccgtggc tgattcatcg tctgacctat     2100
cgtcgtacca atcatgataa cctgcatgtt cgcggttata agaagaagg tacgaccagc      2160 accccgtttg atatggttgt aatgaatgat ctggatcgct tcatctggt ggcagatgtg      2220 attgatcgtg ttccgcagct gggtagccgt gcagcctatg ttaaacaggc aattcgcgat     2280
aaactgatcg aacacaaaca gtacattaac cagtatggcg aagatatgcc ggaaattcgt     2340
aattggaaat ggaaaggtag cagcgtg                                          2367
```

<210> SEQ ID NO 64
<211> LENGTH: 2475
<212> TYPE: DNA
<213> ORGANISM: Schizosaccharomyces pombe 972h-

<400> SEQUENCE: 64

```
atggccaccc agaatgatat tccgaatagc acaccggaag atctggcaaa acaggttgaa       60
attgcagaaa acatccgga tccgcctgca atgccgagcc gtctgccgga tagcctgaaa      120 acccctggaag caaaaattga taccagcaaa attaccgatg aagaggttgc aaatgtgcat      180
cgttttcagc gtgcatgtga ttatctggca gcaagcctga ttttctgag caatggtctg      240 tataccggtg gtgatctgga agagaaagat atcaaaaccc gtctgctggg tcattggggc      300
acctgtccgg gtctgagcat tgtttatagc cattgcaatc gcatcatcaa caaatacgat      360
ctgaacatgc tgtttgttgt tggtcctggt catggtgcac cggcaattct gagcgcactg      420
ttcctggaag atagtctggg tccgtttat ccgcgttatc agtttaccaa agaaggcctg      480
```

| | |
|---|---|
| aataacctga ttaacacctt tagcctgcct ggtggttttc cgagccatgt taatgccgaa | 540 |
| gttccgggtg caattcatga aggtggcgaa ctgggttatg cactgagcgt tagctatggt | 600 |
| gcagttctgg atcgtccgga tctgattgtt acctgtgttg tgggtgatgg tgaagcagaa | 660 |
| accggtccga ccgcaaccag ctggcatgca cataaatttc ttgatccggc agaaagcggt | 720 |
| gccgttattc cggttctgga actgaatggt tacaaaatta gcaacgcac cattatggt | 780 |
| tgcatggatg atagcgaact gctgagcctg tttagcggtt ttggttatga agttgccatt | 840 |
| gtgaatgata caccggatca gaatcgtgtt atggcagcca ccatggattg ggcagttgaa | 900 |
| cgtattcatg atatccagca tcgtgcacgt gttaatcgcg aagaaattaa accgcgttgg | 960 |
| ccgatgatta ttctgcgtac cccgaaaggt aaaggttgtc cgaaatatct gaatggcaaa | 1020 |
| tttctggaag gcacctttcg tgcacatcag gttccgctga aactggcacg taccgatacc | 1080 |
| aatcagcgta atctgctgaa agattggctg aatagctata actgtcagga ttttctggat | 1140 |
| gaacatggtc tgccgaccaa aggtattacc gaacatctgc ctccgcgtga aaaacgtatg | 1200 |
| ggtcagcgtc atgaaaccta taatagttat ctgccactga aagtgccgga ctggaagaaa | 1260 |
| tatggtgtta aaaaaggtga aaccaccagt gcgaccagcg tggttggcca gtatctggac | 1320 |
| gagctgctgg ttaccaatga tagcaccctg cgcatttta gtccggatga actggaaagc | 1380 |
| aataaactgg atggtgccct gaaacatagc tatcgtacca tgcagaccga tccggaactg | 1440 |
| atggccaaac gtggtcgtgt taccgaagtg ctgagtgaac acctgtgtca gggttttatg | 1500 |
| cagggttata ccctgaccgg tcgtaccgcc atttttccgt catatgaagc atttatgacc | 1560 |
| atcgttgtta gcatgctggt tcagtatagc aaattcctga aatgggtct ggaaacgggt | 1620 |
| tggcatggta aatttggtag tctgaattat gttaccagca gcacctgggc acgtcaagaa | 1680 |
| cataatggtt ttagccatca gagtccgcgt tttattacca ccatgctgag tctgaaaccg | 1740 |
| ggtgttagcc gtgtttattt tccgcctgat gcaaattgtt ttctggcaac cgttgcacgt | 1800 |
| tgtatgaaaa gcgaaaacac cattaatctg atggtcagca gtaaaaatcc gcagcctgca | 1860 |
| tatctgagcg tggaagaagc ggaacatcat tgtaaagccg gtgcaagcgt ttggaaattt | 1920 |
| gcaagcaccg ataatggtga aaatccggat gttgttattg ccggtgttgg caatgaaatc | 1980 |
| atgtttgaag ttgttaaagc agccgaaatg ctgcagaacg atatccctga actgcgtgtt | 2040 |
| cgtgtgatta atgtgaccga cctgatggtg ctgagcagtc tgcatccgca tggtatgaat | 2100 |
| cctgcagaat ttgattcact gtttacgaaa gatcgccacg tgcactttaa ctatcatggt | 2160 |
| tatgttatgg atctgaaggc actgctgttc gatcgtattc agggcacccg tgtgaccatg | 2220 |
| gaaggttatc gtgaagaagg tacaaccacc accccgttta atatgatgat gtgtaataat | 2280 |
| accagccgct atcatgttgc ccgtatggca ctgcagcatg ccctgcataa tccgaccgtt | 2340 |
| gcggttaatt gtaatatgct gtgtgcaaaa tatgcctgga aacttgaaga gatcgagaac | 2400 |
| tacatcatga aaaacaaaga tgatcctccg gaaatttatg ccgcaccggt gtttaaaaac | 2460 |
| aaaaccagta ccctg | 2475 |

<210> SEQ ID NO 65
<211> LENGTH: 2388
<212> TYPE: DNA
<213> ORGANISM: Lactobacillus buchneri ATCC 11577

<400> SEQUENCE: 65

| | |
|---|---|
| atgaccgtgg attacgatag caaagagtat ctggatctgc tggataaata ctggcgtgca | 60 |

```
gcaaattatc tgagcgttgg tcagctgtat ctgcgtgata atccgctgct gaaacgtccg    120
ctgaaaagtg atgatgttaa aatcaaaccg attggtcatt ggggcaccat tgttagccag    180
aattttatct atgcacagct gaatcgtgcc atcaacaaat atgatctgaa tatgttctat    240
attgaaggca gcggtcatgg tggtcaggtt atggttagca atagctatct ggacggtagc    300
tatagcgata tttatccgaa tattagccag gacgaaaaag gcatgcagaa actgttcaaa    360
cagtttagct ttccgggtgg tgttgcaagc catgcagcac cggaaacacc gggtagcatt    420
catgaaggtg gtgaactggg ttatagcctg agccatggca ccggtgcaat tctggataac    480
ccggatgtta ttgcagcagt tgaaattggt gatggtgaaa gcgaaaccgg tccgctggca    540
gcaagctggt ttagcgataa attcattaat ccgattaccg atggtgcagt tctgccgatt    600
attaacatga acggtttcaa aattagcaat ccgaccattc tgagccgtat gagtgatgca    660
gatctgacgg attatttcaa aggtatgggt tgggaagccc attttgttga agcaaccgca    720
gataccgatc atgcaaaagt tgaagccgaa tttgcaaaaa ccctggatac cgtgattgag    780
aaaattaaga gcatccagaa aaacgcacgc gaaaatgaaa ctccggataa tgttaaactg    840
ccggtttggc cgatgattat cttccgtagc ccgaaaggtt ggacaggtcc gaaaaaagat    900
ctggatggta acccgattga aggtagcttt cgtgcacatc aggttccgat tccggttgat    960
gcaaatgata tggaacatgc agatgaactg gttgactggc tgaaatcata taaaccggaa   1020
gaactgtttg atgaaaacgg caccctgaaa cctgaactgc gtgcactggc accgaaaggc   1080
gaacagcgta tgagcgtgaa tccgatcaca aatggtggta ttaaaccaga acctctgaaa   1140
ctgcctaatg tgcgtgattt tgaagtgaaa tttgataaac gtgggaccga gcagaaacag   1200
gatatgattg agtggtcaaa atggctggat gcagttgcaa aactgaaccc gaccaccttt   1260
cgtggttttg gtccggatga aaccaaaagc aatcgtctgt attcactgct ggacgatggt   1320
aaacgtcagt ggatggaaga tatccatgaa ccgtatgatg aggatctggc aaatcatggt   1380
cgtgttattg atagccagct gagcgaacat caggcagaag gttggctgga aggttatgtt   1440
ctgaccggtc gtcatggttt ttttgcaacc tatgaaagct ttggtcgcgt tgtggatagc   1500
atgctgaccc agcattttaa gtggctgcgt aaagcaagcg aacagtattg gcgtaaacag   1560
tatccgagcc tgaactttgt tgataccagc accgttttc agcaggatca taatggttat   1620
acccatcagg atccgggtct gctgacacat ctggcgaaaa aaaagccgga atttattcgt   1680
gaatatctgc ctgcagatgc caatgaactg ctggcagttg gtgatagcgc atttcgtaca   1740
tatgaaaaga ttaacctgat cgtgaccagc aaacatccgc gtcgccagtg gtatagtatg   1800
gatgaagcac agaatctggt gaaaaatggt ctgggctata tcgattgggc aagcaccgat   1860
cagggtcaag aaccggatgt ggttttttgca gccgcaggta gcgaaccgaa tctggaagcc   1920
ctggcagcca ttagtattct gaataaagaa ttcccggaac tgaagatccg ctttattaac   1980
gtggttgata tcctgaagct gaacagccct aaaaaggatc cgcgtggtct gtcagatgaa   2040
gaattcgata acctgttac caccgacaaa ccggtgattt ttgcatggca tggctttgag   2100
gacatgatca aagacatctt ttttgatcgc cataaccaca acctgtatgt gcatggttat   2160
cgtgaaaatg gcgatattac caccccgttt gatatgcgtg ttctgaacga actggatcgt   2220
tttcatctgg cagcggatgc cattcgtcat attccggcat atgcagttaa aggtggctat   2280
tttatccagc gcatgaacaa catcgtggat aaacataatc gctatattcg cgaagttggt   2340
acggatctgc cggaagttac cagctggaat tgggaaccgc tgaacaaa                2388
```

<210> SEQ ID NO 66
<211> LENGTH: 2376
<212> TYPE: DNA
<213> ORGANISM: Streptomyces ghanaensis ATCC 14672

<400> SEQUENCE: 66

```
atgccggaag caccggatac ccgtaccgtt ctgagtgatg aagaactgcg taccctggat      60
gcacattggc gtgcagcaaa ttatctggca gcaggtcaga tttatctgct ggcaaatccg     120
ctgctgaccg aaccgctgcg tccggaacac attaaaccgc gtctgctggg tcattggggc     180
accagtccgg gtctgaatct ggtttatacc catctgaatc gtgttattgc aggtcgtggt     240
ctggatgccc tgtgtatttg gggtcctggt catggtggtc cgagcgttct ggccaatagc     300
tggctggaag gtagctatgg tgaaacctat ccggatgttg gtcgtgatgc agccggtatg     360
gaacgtctgt ttcgtcagtt tagctttccg ggtggtgtgc cgagccatgt tgcaccggaa     420
gttccgggta gcgttcatga aggtggtgaa ctgggttata gcctggcaca tgcatatggt     480
gcagcactgg atcatccggg actgctggtt gcatgcgtta ttggtgatgg tgaagcagaa     540
accggtccgc tggcagccag ctggcatagc aacaaatttc tggatccggt tcatgatggc     600
gcagttctgc cgattctgca tctgaacggc tataaaatcg ccaatccgac cgtgctggca     660
cgtctgcctg aagatgaact ggatagcctg ctgcgtggtt atggtcatga accgattcat     720
gttagcggtg atgatccggc agcagttcat cgtgcaatgg cccatgcaat ggatactgcc     780
ctggatcgta ttgccgaagt tcagcgtgcc gcacgtgaag atggtgttac cgaacgtgca     840
cgtacaccgg ttattgttct gcgcaccccg aaaggtttgga ccggtcctgc ggaagttgat     900
ggtaaaccgg ttgaaggcac ctggcgtgcc catcaggttc tctggcagg cgttcgtgat     960
aacccggaac atctgcgtca gctggaagca tggctgcgta gctatcgtcc tgaggaactg    1020
tttgatgatg ccggtcgtcc ggttgcagat gttctggcgt gtctgccaga aggtgatcgt    1080
cgtctgggta gcaccccgta tgcaaatggt ggcctgctgg tgcgcgaact gccgatgcct    1140
gcgctggatg attttgcagt tccggttgat aaaccgggta caaccctgca tgaacctacc    1200
cgtattctgg tggtctgtt agaacgtatt atgcgtgata ccgcagatcg tcgcgatttt    1260
cgtctggttg gtccggatga aaccgcaagc aatcgtctgg aagccgttta tgatgcaagc    1320
ggtaaagcgt ggcaggcagg tacactggat gttgatgagc atctggatcg ccatggtcgt    1380
gtgatggaag ttctgagcga acacctgtgt cagggttggt tagaaggtta tttactgaca    1440
ggtcgtcatg gcctgtttag ctgttatgaa gcatttgtgc atatcgtgga tagcatggtt    1500
aaccagcata tcaaatggct gaaaaccagc cgtgaactgc catggcgtgc tccgattgca    1560
agcctgaatt acctgctgac aagccatgtg tggcgtcagg atcataatgg tttttagccat    1620
caggatccgg ttttgttga tcatgttctg aataaaagtc cggaagtggt tcgtgtgtat    1680
ctgcctccgg atgcaaatac cctgctgtca gttgccgatc atgcactgcg tagtcgtgat    1740
tatgttaatg ttgttgttgc cggtaaacag ccgtgttttg attggctgag cattgatgaa    1800
gcacgtgttc attgtgcacg tggtgcaggc atttgggaat gggcaggcac cgaaaatggc    1860
ggtgcacctg atgtggttct ggcatgtgcg ggtgatgttc cgacccaaga agtactggca    1920
gcggcacagc tgttacgtcg tcatctgccg gaactggcag ttcgtgttgt gaatgttgtg    1980
gatattgccc gtctgatgcc tcgtgaagaa catccgcatg gtatgacaga ttttgaatat    2040
gatgactgt caccgcaga caaaccggtg attttttgcct atcatggtta ccgtggctg    2100
attcaccgtc tggcctatcg tcgtaatggt catccgaatc tgcatgttcg tggttacaaa    2160
```

```
gaaagcggta cgaccaccac cccgtttgat atggttgttc gtaatgatct ggaccgttat    2220
cgcctggtaa tggatgttat tgatcgtgtt cctggtctgg ccgttcgcgc agcagccgtt    2280
cgtcagcgta tggcagatgc ccgtacccgt catcatgcat ggattcgtga acatggcacc    2340
gatttacctg aagttgcaga atggtcttgg aatgca                              2376
```

<210> SEQ ID NO 67
<211> LENGTH: 2406
<212> TYPE: DNA
<213> ORGANISM: Cyanothece sp. PCC 8802

<400> SEQUENCE: 67

```
atggttgcaa caccggaacg tccgaccctg aacagacac cgctgagcgc agaagaactg      60
cgtcagattc aggcatattg gcgtgcatgt aattatctgg cagtgggtat gatttatctg    120
cgtgataatc cgctgctgaa agatccgctg accgaagatc atgttaaaaa tcgtctgctg    180
ggtcattggg gtagcagtcc gggtctgagc tttatctata ttcatctgaa tcgcctgatc    240
aaaaaatacg gcctggatgt gatttatatg gcaggtcctg tcatggtgc accgggtatt     300 ctgggtccgg tttatctgga aggcacctat agcgaaacct atccggataa agcgaagat     360 gaagagggca tgaaaaaatt cttcaaacag tttagctttc cgggtggtat tggtagccat    420
tgtactccgg aaacaccggg ttcaattcat gaaggtggtg aactgggtta gcctgagc     480 catgcatatg gtgcagcact ggataacccg atctgattg ttgcagcagt tgttggtgat    540
ggtgaagcag aaaccggtcc gctggcaacc gcatggcata gcaataaatt cattaatccg    600
attcgtgatg gcgcagttct gccgattctg catctgaacg ctataaaat cgcaaatccg    660 accattctgg cacgtattag ccatgaggaa ctggaatacc tgtttaaagg ttatggctac    720
aaaccgtatt ttgtcgaagg tagcgatccg aagttatgc atcagaaaat ggcagcaaca    780
ctggaaaccg caattgccga aattaaacat attcagcaag aggcacgtac cagcggtgtt    840
gcaaaacgtc ctatttggcc gatgattgtt ctgcgtagcc cgaaaggttg acaggtccg    900 gcaagcgttg atggcaaaaa acggaagat tttttggcgta gccatcaggt tccgctgagt    960
ggtatgcatg taatccggc acatattaaa gttctggaag attggctgaa aagctatacc   1020
cctgaagaac tttttgatga aaacggcacc ctgattccgg aactgaaaga actggcaccg   1080
accggtcatc atcgtatgag cgccaatccg catgccaatg gtgtctgct gcgtaaagat    1140 ctgaaaatgc cggatttcg taattatggt gttgaagttg ccaaaccggg tacagttgaa    1200
gtgggtaata ccgcactgct gggcaatttt ctgcgggatg ttatggccaa taatatgacc   1260
aattttcgtg tgtttggtcc ggatgaaacc gccagcaacc gtctgaatgc aatttatgaa   1320
atcagcaaaa aagtgtggat gggcgaaatt ctgccggaag atgcagatgg tacagaaatc    1380
accaccgatg gtcgtgttat ggaaatgctg agcgaacata ccctgcaggg ctggctggaa    1440
ggttatctgc tgaccggtcg ccatggtttt tttcatacct atgaagcatt tgcccatgtg    1500
gtggatagca tgtttaatca gcatgcaaaa tggctggaca tctgcaaaaa tgaagttccg   1560
tggcgtgcca gcgttagcag cctgaatatt ctgctgagca gcaccgtttg gcgtcaggat   1620
cataatggtt ttagtcatca ggatcctggt tatgttgatc tggttaccaa taatcagcg     1680 gatgttgtgc gtgtttatttt cctccggat gcgaattgtc tgctgtcagt tgcaaatcat   1740
tgtctgaaat caaccgatta cgtgaacgtt attgttagcg ataagcagat ccatctgcag   1800
tatctgaata tggatcaggc catcaaacat tgcaccaaag gtattggcat ttgggattgg   1860
gcaagcaatg atgattgcgg tacggaaccg gatcatcctg atgttattat ggcaagctgt   1920
```

| | |
|---|---|
| ggtgatgttg caaccaaaga agcactggca gccaccgcca ttctgcgcga agaatttccg | 1980 |
| gatttaaaag tgcgttttat caacgtggtt gacctgttca aactgcagag tgaaattgaa | 2040 |
| catcctcatg gtctgagtga tcgcgatttt gataacccttt tcaccaaaga caaaccgatc | 2100 |
| atctttaact ttcatggtta tccgtggctg atccacaaac tgacctatcg tcgtaccaat | 2160 |
| catcacaatc tgcatgttcg tggttataaa gagaaaggca atattaacac tccgctggaa | 2220 |
| ctggccatta acaatcagat tgatcgtttt aacctggtga tcgatgttat caatcgtgtt | 2280 |
| ccgaaactgg gtagcgcagc agcatatgtt tatgaacgta tgaaaaacgc catcatcgaa | 2340 |
| catcgtgcat atgcctatga acatggtatt gataagcccg agattaacaa ctggaaatgg | 2400 |
| cctcat | 2406 |

<210> SEQ ID NO 68
<211> LENGTH: 2436
<212> TYPE: DNA
<213> ORGANISM: Neosartorya fischeri NRRL 181

<400> SEQUENCE: 68

| | |
|---|---|
| atgaccagca aaggcgaaat tgaaagcctg agcgcatatg gtgttgcacg tagcaccatt | 60 |
| cagggtacac cgctgagcca ggatgaactg cgtaaaatgg atgcatattt tcgtgcaagc | 120 |
| atgtatctgt gtctgggtat gctgtatctg cgtgataatc cgctgctgaa agaaccgctg | 180 |
| aaagttgaac atctgaaagc acgtctgctg ggtcattggg gtagtgatgc cggtcagagc | 240 |
| tttacctgga ttcatatgaa ccgtctgatc aaaaaatacg atctggatgt gctgtttatt | 300 |
| agcggtccgg gtcatggtgc accgggtatt ctgtcacaga gctatctgga aggtgtttat | 360 |
| accgaagttt atccggaaaa aacccaggac gaaaaaggtc tgcagcgttt tttcaaacag | 420 |
| tttagctttc cgggtggtat tggtagccat gcaacaccgg aaacaccggg ttcaattcat | 480 |
| gaaggtggtg aactgggtta tagcattagt catgcatttg caccgttttt tgatcatccg | 540 |
| aatctgatta ccctgaccat ggttggtgat ggtgaagcag aaaccggtcc gctggcaacc | 600 |
| agctggcata gcaacaaatt tctgaatccg attacagatg gtgcagttct gccggttctg | 660 |
| catctgaatg gctataaaat caataacccg accattctgg cacgcattag ccatgaagaa | 720 |
| ctggaaatgc tgttaaaagg ttatggttgg accccgtatt tgttgaaggt tagcgatcgt | 780 |
| gaaagtatgc atcaggcaat ggcagcaacc ctggaacatt gtgttctgga aattaagaag | 840 |
| atccagaaac aggcacgcga aagcaataaa gcatttcgtc cgctgtggcc gatgattgtt | 900 |
| ctgcgtagcc cgaaaggttg gagcgcaccg cgtgaaattg atggtaaata cctggaaggc | 960 |
| ttttggcgtg cacatcagat tccgatcacc gatgttcaga gcaaaccgga cacttaaaa | 1020 |
| gtgctggaaa attggatgaa agcgtataag ccggaagagg tgtttgataa aaatggcacc | 1080 |
| ctgattccgg aactgaaaga gctggcaccg accggcacca gccgtatgag cgcaaatccg | 1140 |
| gtgggtaatg tggtctgct gcgtcgtccg atggatctgc cggattttcg cgattatgca | 1200 |
| ctgaccgata ttgaaccggg tgttaccatt cgtccgagca tgagcaatat gagcaaatat | 1260 |
| ctgcgggatt tgttgcccg taatatgacc acctttcgtg ttttttggtcc ggatgaaacc | 1320 |
| gaatcaaata aactggccga aatctacaaa gccggtaaaa aggtttggat ggccgaatat | 1380 |
| ttcaaagaag atgaggacgg aggtaatctg gatatgcagg tcgtgtgat ggaaattctg | 1440 |
| agcgaacata catgtgaagg ttggctggaa ggatatattc tgagtggtcg tcatggcatg | 1500 |
| ctgaatagtt atgagccgtt tattcatgtg atcgacagca tggttaatca gcattgcaaa | 1560 |

| | |
|---|---:|
| tggattgaaa aatgcctggc agttgaatgg cgtgccaaag ttagcagcct gaatattctg | 1620 |
| ctgaccgcaa ccgtttggcg tcaggatcat aatggtttta cccatcagga tccgggtttt | 1680 |
| ctggacgttg ttgcaaataa agtccggaa gttgtgcgta tttatctgcc tccggatggc | 1740 |
| aatacccctgc tgagcaccat gaatcattgt tttcgtagcg tgaattacgt gaatgtgatt | 1800 |
| gtggcagata acaagaaca tgtgcagttt ctgaacatgg aagaagcaat tgaacattgc | 1860 |
| accaaaggtg ttggtatttg ggattgggca agcaatgatc agggttgcga accggatgtg | 1920 |
| gttatggcaa gctgtggtga tgttgcaacc catgaagccc tggcagccac cgcactgctg | 1980 |
| cgcgaacatt taccgcagtt aaaagttcgt tttgttaatg tggttgacct gtttcgtctg | 2040 |
| attagcgata ttaatcatcc gcatggtatg ccggatcgtc agtggggtgc aattttacc | 2100 |
| accgataaac cgatcatctt taactttcat agctatccgt ggctgattca tcgtctgacc | 2160 |
| tataaacgtc ctggtcagca taatctgcat gtgcgtggtt ataagaaaa aggcaatatc | 2220 |
| gatacccccgt ttgaactggc ggttcgtaat cagaccgatc gttatagcct ggccattgat | 2280 |
| gcaattgatc gtattccgag cctgggtaat accgcaagcg tgttcgtga acgcctgatt | 2340 |
| aacctgcaac tggcagcgaa aaacaaagcc tttgatgatg gtattgatcc ggattatatt | 2400 |
| cgcaattgga cctgggatta tccgcgtaaa aaatgc | 2436 |

<210> SEQ ID NO 69
<211> LENGTH: 2361
<212> TYPE: DNA
<213> ORGANISM: Enterococcus faecium TX1330

<400> SEQUENCE: 69

| | |
|---|---:|
| atggattata gcagcaaaga atattttgat aaaatgaccg catggtggcg tgcagcaaat | 60 |
| tatctgagcg ttggtcagat ttatctgaaa gataatccgc tgctgcgtcg taccctgaaa | 120 |
| ccggaagatg ttaaaaaaca cccgattggt cattgggca ccattccggg tcagaatttt | 180 |
| atctatgttc atctgaatcg cgtgatcaac aaatacgatc tgaacatgtt ttatatcgaa | 240 |
| ggtcctggtc atggtggtca ggttatggtt agcaatgcat atctggatgg tagctatacc | 300 |
| gaaatttatc cggaagttac cgaagatgaa acgggtatgc agaaactgtt taaacgtttt | 360 |
| agctttccgg gtggtattgc aagccatgca gcaccggaaa caccgggtag cattcatgaa | 420 |
| ggtggtgaac tggttatag cctgagccat ggtgttggtg cagttctgga taatcctgaa | 480 |
| gttattagcg cagttgttat tggtgatggt gaagcagaaa ccggtccgct ggcaggtagc | 540 |
| tggtttagta atgttttat caatccggtt accgatggtg cggtgctgcc gattctgcat | 600 |
| ctgaacggtg caaaaattgc aaatccgacc attctggcac gtaaaagtga tggcgaactg | 660 |
| gccaattatt tcaatggtct gggttgggaa ccgttttca ttgaaggtaa tgatccggaa | 720 |
| aaactgaatc cggtgatggc agaaaaaatg gatcaggcca ttgagaaaat caaaagcatt | 780 |
| cagaaagaag cccgtctgaa aaccgcagca gatgcaatga tgccgaaatg gcctgttctg | 840 |
| attgtgcgta ccccgaaagg ttggacaggt ccggaagaat gggatggtga gccgattgaa | 900 |
| ggcacctttc gtgcacatca ggttccgatt ccggttgatc aagaacatat ggatcatgca | 960 |
| gatgccctgc tgcgctggct gaaaagctat gaaccagaaa agctgtttga tgcacagggt | 1020 |
| cgtattctgg aagaaattcg tgaaattgca ccgaccggtg atcatcgtat ggcaaaaaat | 1080 |
| ccgattacaa atggtggtat ggatccgaaa ccgctgatta tgccggattg gaaacgttat | 1140 |
| accctgcagt ttgaaaaacc gggttcagtt accgcagaag atatgaccga actgggcaaa | 1200 |
| tttgttcgcg aaatcattga aaaaaacccg gaaaactttc gcatctttgg tccggatgaa | 1260 |

```
accaaaagca atcgtctgaa tcaggtgttt aaaaccacca atcgtcagtg gatggaaaaa      1320
attgaaccgg aaaatgatga atggctgagc ccgagcggtc gtgttattga tagccagctg      1380
agcgaacatc aggatgaagg ttttttagaa ggttatgttc tgaccggtcg ccatggtttt      1440
tttgcaagtt atgaaagctt tctgcgtgtg gttgatagca tgctgaccca gcactttaaa      1500
tggatgcgta aaagccgtga tctgagctgg cgtaataact atccgagcct gaatctgatt      1560
gcaagtagca ccgtgtttca gcaggatcat aatggttata gtcaccagga tccgggtatt      1620
ctgacccatc tggccgaaaa aaaagcagaa tttattcgtg agtatctgcc tgccgatgca      1680
aatacactgc tggccgttat ggataaagca tttcgtagca gcgaaaagat caacctgatt      1740
atcagcagta acatccgcg tgcacagttt tatagtgcag aagaagcagc cgttctggtt       1800
aatgaaggcc tgaaaattat cgattgggca agcaccgcaa agaagaaga acctgaactg       1860
gtaattgcag cagcaggcac cgaaagtaat ctggaagcac tggcagcagt tactctgctg      1920
ctggaagagt ttccgaaact gaaaatccgc tttattaacg ttgtggacct gctgaaactg      1980
cgtcatccga gtcaggatcc tcgtggtctg agtgatgaag aatttgacaa atactttacc      2040
aaagataaac cgatcctgtt tgcctttcat ggctatgaaa cactgattcg caccatctt      2100
tttgatcgcc ataatcatca tctgatgatt cacggctata agagaatgg cgatattacc       2160
accccgtttg atatgcgtgt tgtgaatgaa ctggatcgtt atcatctggc aaaagatgca      2220
gccctgaaga ttaaaggtag ccaggccgaa gattttgcca aaagatgga ccaaaaactg       2280
caagaacacc agaactatat ccgcgaaaat ggtattgatc tgccggaagt gctggactgg      2340
aaatggaaga atctggatca g                                                2361

<210> SEQ ID NO 70
<211> LENGTH: 2373
<212> TYPE: DNA
<213> ORGANISM: Listeria grayi DSM 20601

<400> SEQUENCE: 70
atgaccgatt atagcagccc gaactatctg gcaaaagttg atgcatggtg gcgtgcagca       60
gattttatca gcgttggtca gctgtatctg aaaggtaatc cgctgctgcg tcgtccgctg      120
gaaaaagaag atttaaaagt tcatccgatt ggtcattggg caccattag cggtcagaat       180
tttatctatg cacatctgaa tcgcgtgatc aacaaatatg atctgaatat gttctacatc      240
gaaggtccgg tcatggtgg tcaggttatg gttagcaata gctatctgga tggtagctat       300
accgatacct atccgaccat tacccaggat gaagttggtc tgaccaaaact gtataaacag      360
tttagctttc cgggtggtat tgcaagccat gcagcaccgg aaacaccggg tagcctgcat      420
gaaggtggta actgggtta tgcactgagc catgccaccg gtagcattct ggataatccg       480
gatgttattg cagcaaccgt tattggtgat ggtgaagcag aaaccggtcc gctgagcgca      540
ggttggttta gtaataccct tattaacccg gttaatgatg gtgcagttct gccgattctg      600
tacctgaatg gtgcaaaaat tagcaatccg acaattctga gccgcaaaac cgataaagaa      660
ctgaccagct ttttttcaggg tctgggttgg gatccgattt ttgttgaagg tgaagatcct      720
gccaaagtgc atccgctgat ggcagaaaaa ctggatcagg caattgaaaa aatcaaagcc      780
attcagaccg aagcacgtaa agaagccgca gataaagcaa ccatgccgac ctggcctgtt      840
attctgtttc gtaccccgaa aggttggaca ggtccgaaag aatggaataa tgaaccgatt      900
gaaggtagct ttcgtgcaca tcaggttccg attccggttg atcagcatca ttttgatcat      960
```

```
gttgatgccc tggaaaattg gctgcagagc tatcgtccgg aagaactgtt taccgaagaa    1020
ggtagtctga agaagaaat caaaagcctg gcaccgaaaa atcgtatggc aaccaatccg     1080
attaccaatg gtggcattga tccgcagccg ctgcgtctgc cgagctggaa agattatgca    1140
gttgaaaccg caaacaaaga tgtgattacg caggatatga ttgagctggg tggttttgtt    1200
cgtgatatcg ttaaagaaaa cccggataac tttcgcattt ttggtccgga tgaaaccaaa    1260
agcaatcgcc tgaataaagt gtttgaagtg accaatcgtc agtggatgag caaagcagaa    1320
tttccgcgtg atgaatggct ggctccggca ggtcgtatta ttgatggcca gctgagcgaa    1380
catcaggcag aaggttttct ggaaggttat gttctgaccg tcgtcatgg ttttttttgca    1440 agctatgaaa gctttctgcg tgttgttgat agcatgctga cccagcactt taaatggctg    1500
cgtaaagcaa aagaacagac ctggcgtaat agttatccga gcctgaatgt gattgcaacc    1560
agcaccgttt ttcagcagga tcataatggt tatacccatc aggatccggg tgtgctgaca    1620
catctggccg aaaaaaaacc ggaatttatc cgtgaatatc tgcctgcaga taccaatagc    1680
ctgctggcag ttatgaatga agcatttcgt agcgaggaac tgattaatct gattgtgagc    1740
agcaaacatc cgcgtccgca gttttatagc gcagaagaag ctgaaattct ggttaaagat    1800
ggcctgaaaa tcattgattg gcaagcaccc gtgagcgaag ccgaagaacc ggatgtggtt    1860
attgccagtg caggtacaga accgaatctg gaagcactgg cagcagttac cctgctgaac    1920
gaagcctttc cgtcgctgaa aattcgcttt atcaacattg tggacattct gaaactgcgc    1980
catccggata tcgatccgcg tggcctgacc gatgaagaat tgatcgtta tttcaccacg    2040 gacaaaccga tcattttgc ctttcattca tatgaaggta tggtgcgcga tatcttttt     2100 aaccgccata atcacaacct gttcatccat ggttatcgcg aaaatggtga tattaccacc    2160
ccgtttgata tgcgtgttct gagtgaaatg gatcgttttc acctggccaa agatgcagcc    2220
gaagcagttt atggtgaaat tgcgaccagt tttgccgcag aaatggacgc cgttctgtca    2280
aaacatcatc actttattcg tgaaaacggc gaagatctgc cggaagttga gaattggaaa    2340
tggcaggcac tgaaaactga cctgctggaa gtg                                  2373
```

<210> SEQ ID NO 71
<211> LENGTH: 2364
<212> TYPE: DNA
<213> ORGANISM: Enterococcus casseliflavus EC30

<400> SEQUENCE: 71

```
atgaaaacca cctacgatac ccctgagtat taccagaaaa tgaatgcatg gtggcgtgca     60
gcaaattatc tgagcgttgg tcagattttat ctgaaagata tccgctgct gcgtcgtccg    120 attgaagaaa aagacctgaa agtgaatccg attggtcatt ggggcaccat tgcaggtcag    180 aatttttatct ataccccatct gaatcgcgtg atcaacaaat atgatctgaa tatgttctac    240
atcgaaggtc cgggtcatgg tggtcaggtt atggttgcaa atgcatatct ggatggtagc    300
tatagcgaaa tctatccgaa agcaacccag gatgaagcag gtatgaaaca cctgtttaaa    360
acctttagct ttccgggtgg tattgcaagc catgcagcac cggaaacacc gggtagcatt    420
catgaaggtg gtgaactggg ttatagcatt gcacatgcaa ccggtgcaat tctggataac    480
ccggatgtta ttgcagcagt tgttgttggt gatggtgaag cagaaaccgg tccgctggca    540
ggtagctggt ttagcaatac ctttattaac ccggttaacg atggtgccat tctgccgatt    600
ctgcatctga cggtgcaaa aattgcaaat ccgaccattc tggcacgtaa aagcgatcag    660
gatctgacca atatttcga aggtatgggt tggacccccgt attttgttga aggtgatgat    720
```

```
ccggaagcag ttcatccgca gctggcacaa aaaatggatc aggcaattga gcagattcat    780
gcaattcagg cagaagcccg taaaggttca gccgaagagg cagcaatgcc gcattggcct    840
gttctgattg ttcgtacccc gaaaggttgg acaggtccga agtttggga tggcgaaccg      900 atcgaaggcg gttttcgtgc acatcaggtt ccgattccgg ttaatgcaaa acatatggaa    960
catgttgatg cactgaccga ttggctgcag agctatcgtc cggaagaact gtttgatgaa    1020
aatggtcgta ttaaggccga atccaagaa ctggcaccga aggcgaaca gcgtatggca      1080 gttaacccga ttaccaatgg cggtattgat cctcagccgc tgcgtctgcc ggattggcag    1140
gcacatgcca ttgcaattga aactccgggt gaaaccaccg cacaggatat gatggttttt    1200
ggtaaatttg cccgtgatat tatcaaagag aacccggaca ttttcgcat ttttggtcct      1260 gatgaagcca aaagcaatcg tctgaatcat gtgtttgaag ttaccgatcg tcagtggctg    1320
gaaccgaaac atccggatta tgatgaatgg ctgagcagcg tgggtcgtgt tattgatagc    1380
cagctgagcg aacatcaggc cgaaggtttt ctggaaggtt atgttctgac cggtcgccat    1440 ggctttttg caagctatga aagctttctg cgtgttgtgg atagcatgat tacccagcac    1500
tttaaatggc tgcgtaaagc acatgatctg gattggcgta atccgtatcc gagcctgaat    1560
ctgattgcaa gtagcaccgt ttttcagcag gatcataatg ttataccca ccaggatccg    1620 ggtattatga cccatattgc agaaaaaaaa gccgattttg tgcgtgttta tctgcctgca    1680
gatgcaaata gcctgatggc cgttatggcc gaaaccctgg caagcgaaga aaagattaat    1740
ctggttgtta gcagcaaaca tcctcgtccg cagtttttata gcgcagatga agcgaaagtt    1800
ctggtgaaag atggtctgaa agttatcgat tgggcaagca ccgatgaagg tcaagaaccg    1860
gatattgtga ttgcagccgc aggtacagaa ccgaatctgg aagcactggc agccgttagc    1920
ctgctgattg aagcatttcc ggaactgaaa gtccgtttta tcaatgttgt tgacctgctg    1980
aaactgcgtc gccctgaagt tgatccgcgt ggtctgagcg acgaagcctt tgaagcctat    2040
tttaccaaag ataagccgat cgtgtttgcc tttcatggtt atgaaggcct gattcgcgat    2100 atctttttg gccgtcgtaa tcagcagctg catattcatg gctatcgcga aaacggcgat    2160
attaccaccc cgtttgatat gcgtattctg tcagaactgg atcgttttca tctggcaaaa    2220
gatgcagcag aatgggttta tggtgaaaaa gccacagatt ttgcacagaa gatggcagat    2280
accgttgcat atcatcatga tttatccgc gagaacggtt atgatattgc cgaagttgaa    2340
gaatgggaat ggaaaccgct gcgc                                          2364
```

<210> SEQ ID NO 72
<211> LENGTH: 2376
<212> TYPE: DNA
<213> ORGANISM: Mycoplasma alligatoris A21JP2

<400> SEQUENCE: 72

```
atgaaaaaga ataccttcga tacccaggac tatctggata agttgatgc atggtttcgt       60 gcagcaaatt atctgagcgt tggtcagatg tatctgcgta ataatccgct gctgcgtagc    120
aaaattacca gtgatgatgt taaagtgtat ccgattggtc attggggcac cattccgggt    180
cagaattttg catatgcaca tctgaatcgc gtgatcaaca atacaatct gaatatgttc      240 tacatcgaag gtcctggtca tggtggtcag gttatgacca gcaatagcta cctggatggt    300
agctataccg aactgtttcc gcatgtgacc caggatgttg caggtatgaa acacctgttt    360
aagtatttta gctttccggg tggcaccgca agccatgcag caccggaaac accgggtagc    420
```

```
attcatgaag gtggtgaact gggttatagc ctgagccatg ccaccggtgc aatcctggat    480
aatccgaatg ttattgcagc aaccattgtt ggtgatggtg aagcagaaac cggtccgctg    540
gcagcaagct ggtttagcaa tagttttatc aatccggtta atgatggtgc cgttctgccg    600
attctgcatc tgaacggtgg taaaattagc aatccgacca ttctgtgtcg caaaagcaat    660
aaagaactga ccgattattt tgccggtatg ggttgggaag cagttttgt tgaaggtagt    720 gatgagaaag aaatgcacaa agttatggcc cagaaactgg attatgtgat cgaaaaaatt    780
cagagcattc agaacgaggc acgtaaaaaa ccggcaaatc aggcaacccg tccgatttgg    840
ccgatgatgg ttctgcgtac cccgaaaggt tggacaggtc cggatagctg aataaagat    900 aaaattgtgg gtagctttcg tgcccatcag gttccgattc cggtgaatag cgcaaatatg    960
gaacatattg atgcactgct ggattggctg aaatcctata agtggataa cctgttcgac   1020 aaaaatggca actggttga tgaaattgca cagattgcac cgaaaggcga tcagcgtatg   1080
ggtatgaatc cgattaccaa tggtggcctg aacccgaaaa aactggtaat gcctcgttgg   1140
caggattttg cactgaaatt ttcaaaaccg ggtgagctgg ttaatcagga tatggttgag   1200
ctgggcacct attttgcaaa aatgatggaa ctgaacaagg caactttcg tctgtttggt   1260 cctgatgaaa ccaaaagtaa tcgcctgtat aacgtgttca agtgaccaa acgtcagtgg   1320 ctggaaccga ttagccctat tctggatgaa gcactgagtc cggaaggtcg tgttattgat   1380
agccagctga gcaacatca ggcagaaggt tttctggaag ttatgttct gaccggtcgc   1440 catggtgttt ttgcaagcta tgaaagcttt ctgcgtgttg tggatagtat gctgacccag   1500
cacctgaaat ggctgaagaa agcaaaagat gttcattggc gtaatgatta tccgagcctg   1560
aatgtgattg cgaccagcac cgcatttcag caggatcata atggttatac acatcaggat   1620
ccgggtctga ttggccatct ggcagataaa actccggaaa ttattcgtca gtatctgcct   1680
gcagatacca ataccctgct ggcagttatg gataaaagcc tgaagaacg caacgtgatt   1740 aaccatatca ttgcaagcaa acagcctcgc gaacagtttt atagcgaaca agaagcagca   1800
gaactggtag aaaaaggtct gaaagtaatt gattgggcaa gcaccaccaa aggtaatgaa   1860
gaaccggaac tggtggttgt tgcagcaggc accgaaccga atctggaagc cctggcagcc   1920
gtgacgattc tgaacaaaga gtatccgtca ctgaaaatcc gttttgtgaa tgtggttgat   1980
ctgatgaagc tgcgtcatcc gagtctggat ccgcgtggtc tgagcgataa agaatttgat   2040
gcaattttca ccagcaacaa gccgattgtg tttgcctttc atggttatga aggtattctg   2100
cgcgacatgt ttttcaaacg caataaccat aatctgatca cccatggcta tcgcgaaaat   2160
ggtgatatca caaccagctt tgatattcgc cagctgtcac atatggatcg ctttcatatt   2220
agcgcaagcg cagcaaaagc ggtgtatggt aataaagcac aagagttcga ggacaaaatg   2280
atccagacca ttgatttcca caccaaatat atccgtgaat atggcaccga tattcccgaa   2340
gttaaagaat ggaaatgggc agatctgacc cgtaaa                             2376
```

```
<210> SEQ ID NO 73
<211> LENGTH: 2355
<212> TYPE: DNA
<213> ORGANISM: Carnobacterium sp. 17-4

<400> SEQUENCE: 73
atgaaaaact atgatagcaa agattatctg aaaaaagtgg acgcattttg cgtgcagca     60 aattatctgt cagttggtca gctgtatctg cgtgataatc cgctgctgca gcgtccgctg    120
aaaagcaccg atgttaaagc acatccgatt ggtcattggg caccattag cggtcagaat    180
```

-continued

```
tttatctatg cacatctgaa tcgcgtgatc aacaaatatg atctgaatat gttctacatc    240
gaaggtccgg gtcatggtgg tcaggttatg attagcaatg catatctgga tggtagctat    300
accgaaatct atccggatat caccgaaaac aaagaaggca tgaagaaact gttcaagcag    360
tttagcagtc cgggtggtgt tgcaagccat gcagcaccgg aaacaccggg tagcattcat    420
gaaggtggtg aactgggtta tagcctgagc catgccaccg gtgcaattct ggataacccg    480
gatgttattg cagcaaccgt tattggtgat ggtgaagcag aaaccggtcc gctggcagca    540
ggttggttta gcaataattt cattaatccg gtgaatgatg gtgccgttct gccgattctg    600
tacctgaatg gtggtaaaat tagtaacccg accattctgg cacgtaaaag caatgaagat    660
ctgaagaaat atttcgaggg tatgggttgg aaaccgtatt tgttgaagg caccgatccg    720
gaaaaagttc atccggttat ggcaaatacc ctggatgttg ttatcgaaga aattcgcagc    780
attcagaatg aagcccgtaa aggtaaagcc gaagatgttg aaatgccgca ttggcctgtg    840
atgattattc gtaccccgaa aggttggaca ggtccgaaag aatgggataa caaaaaaatc    900
gaaggcacgt ttcgtgcaca tcaggttccg attccggttg atgcagaaca tatggaatat    960
gtgaataaac tggtggactg gctgaaatca tatcgtccgg aagaactgtt taccgaaaat   1020
ggcaaactga tcgatgacct gaaagaactg acaccgaaag gcaataaacg tatggcaacc   1080
aatccgatta ccaatggtgg cattaatgca aaagcactga ttatcccgaa ttggaaacag   1140
catgcaattg ataccaccat tccgggtgca gttattgccc aggatatgga tgttttggt    1200
gaacaggcac gtgatctgat tgttaaaaat ccgaacaact ttcgcatctt cggtccggat   1260
gaaaccaaaa gtaatcgcct ggataaaatc tttgaagtga ccaatcgtca gtggctggaa   1320
agcaaagaat taccgatga atggcagagc agcgcaggtc gtgttattga tggccagctg   1380
agcgaacatc aggcagaagg ttttctggaa ggttatgttc tgaccggtcg tcatggtttt   1440
tttgcaagct atgaaagctt tctgcgtgtt gttgatagca tgctgaccca gcactttaaa   1500
tggctgcgta aagcaaccga tcagaaatgg cgtaataact atccgagcct gaatgtgatt   1560
gcaaccagca ccgttttca gcaggatcat aatggttata cccatcagga tccgggtatt   1620
ctgacccatc tggcagaaaa aaaaccggaa tttatccgtg aatatctgcc tgcagatgca   1680
aatagtctga tggcagttat ggacaaaaca ctgcaagaag aacagctgat taacctgatc   1740
attagcagca acatccgcg tccgcagttt tatagcgttg aagaagccga aattctggtt   1800
aaagatggcc tgaaaattat cgattgggcc agtaccgata atgatagcga accggatctg   1860
gttatcgcag cagccggtac agaaccgaac ctggaagcac tggcagccat gagcattctg   1920
cacaaagcat ttccggaact gaaaatccgc tttatcaaca ttgtggacat tctgaaactg   1980
cgtcacccgg atattgatag ccgtggtctg acagatgaaa aattcgatag ctatttcacc   2040
aaagagcagc cgattatctt tgcctttcat ggctttgaag gtctgattcg cgatatcttt   2100
tttaaccgcc ataaccataa tctgcgcatt cacggttatc gtgaaaatgg tgatattacc   2160
accccgtttg atatgcgtgt tctgaatgaa atggatcgtt tcatctggc caaagatgcc   2220
gcaaaagccg tttatggtct gaaagccaac aaattcatgc aagagatgga aaacaccgtg   2280
aactttcatc atcagtatat tcgcgaaaac ggcattgata ttccggaagt gattaactgg   2340
aaatgggaaa aaatc                                                    2355
```

<210> SEQ ID NO 74
<211> LENGTH: 2397
<212> TYPE: DNA

<213> ORGANISM: Melissococcus plutonius ATCC 35311

<400> SEQUENCE: 74
atggaaaaag ataaatacag cagcaccgag tacctggaca aaattgataa atggtggcgt 60
gcagcaaact atctgagcat tggtcagctg tatctgaaag ataatccgct gctgaaacgt 120
aaaattcgta gcgaggatgt taaatatcat ccgattggtc attggggcac cattgcaggt 180
cagaatttta tctatgcaca tctgaaccgc attatcaaca aatacgatct gaatatgttt 240
tatatcgagg gtccgggtca tggtggtcag gttatggtta gcaatagcta tctggatggt 300
agctataccg aaatttatcc ggcagttacc gaagatgaag caggtatgca gaaactgttt 360
aaacgtttta gctttccggg tggtgttagc agccatgccg caccggaaac accgggtagc 420
attcatgaag gtggtgaact gggttatagc ctgagccatg gtgttggtgc aattctggat 480
aacccggaag ttattagcgc agttgttatt ggtgatggtg aaagcgaaac cggtccgctg 540
gcgaccagct ggtttagtaa tacctttatt aacccggtta ccgatggtgc cgttctgccg 600
attctgcatc tgaatggtgc aaaaattgca aatccgacca ttctgggtcg taaaagcgat 660
aaagaactgg aacagtattt tcgtggtatg ggttggattc cgtattttgt ggaaggtaat 720
gatccgaatc agatgcatcc gctgatggca aaaaccctgg atcaggtgat tgaaaaaatc 780
cacagcattc aagaaaccgc acgtaaacag accgcagaaa cagcaagtat tcagaaatgg 840
cctctgattg ttctgcgtac cccgaaaggt tggacaggtc cgaaagaatg ggatggtaaa 900
ccgattgaag ttacctttcg tgcacatcag gttccgattc cgattgatca ggatcatatg 960
gaacatgttg atcagctggt gaattggctg aaaagctata aaccggaaga actgtttgat 1020
gaaacaggtc gtctgaatag cgaaattcgt gccattgcac cgatgaatga taaacgtatg 1080
gcaatgaatc cgattaccaa tggtggtatt aatccgaaac cgctgcagat gccggattgg 1140
cgtgaatttg atctgcatat tagcaaaccg ggtgagctgg ttgcacagga tatgctggaa 1200
tttggtaaaa tggttgcagc catcatcaaa aaaaacccgc agaactttct gatctttggt 1260
ccggatgaaa ccaaaagcaa tctgctgaat gatgcattta gcgttaccag ccgtcagtgg 1320
ctggaaccga tttatgaacc tcaggatgaa tggctggcac cgtcaggtcg tattattgat 1380
agccagctga gcgaacatca ggacgaaggt attctggaag gttatgttct gaccggtcgt 1440
catggttttt ttgcaagcta tgaagccttt attcgcatcg tggatagcat gattgcccag 1500
catatcaaat ggatgcgtaa agcaatggat ctgccgtggc gtaatggtta tagtagcctg 1560
aatctgattg caagcagtac cgcatttcag caggatcaca atggctatac ccaccaggat 1620
ccgggtatcc tgagtcatct ggcagaaaaa gaagcagatt ttatccacga atatgtgcct 1680
gcagatacca atagcctgct ggcagttatg gataaagttc tgaaaagtca gggcaaagtg 1740
aatctggtga ttagctcaaa acatccgcgt ccgcagtttt atagccctga agaagcacaa 1800
gaattagtta atcgtggcct gatggaaatt gattgggcaa gcaccgttgc agaaaatggc 1860
actccggaaa ttgtgattgt tgccgcaggc accgaaccga atatggaagc actggcagca 1920
attaatctga tcaatcagag ttttccgaaa ctgcagttcc gctttatcaa tgttgtggat 1980
ttactgaaac tgcgtcatcc tgcagttgat tcaagaggta ttagcgaagt ggaatataac 2040
cacctgttta ccgttgattc cccgattatc tttgtttgtc agggttattc aagcctgatt 2100
cgcagcctgt tctatgatcg taaaaatcgt ccggttagca tccatagcta ccaagaaaac 2160
ggtgccatta ccaccccgtt tgatatgcgt gttctgaata aaatcgatcg ttatcacctg 2220
gccaaagata ttgcactgac cgcatatggt agccgtggtg aagattttgc acgtgccatg 2280

```
gataccatcc tggaaaaaca caatcagtat attcgcgaaa cgggtaaaga tctgcctgaa    2340
gtgctgaatt ggaaatgggc tccgctgcat atctataacg aaaacattga acaggat      2397

<210> SEQ ID NO 75
<211> LENGTH: 2361
<212> TYPE: DNA
<213> ORGANISM: Tetragenococcus halophilus NBRC 12172

<400> SEQUENCE: 75
atgagcgtga acatcgacag caaagaatat ctggaacgta tgaatgcatg gtggcgtgca      60
gcaaactata ttagcgttgc acagattttt ctgcgtgata tccgctgct gcgtcgtccg      120 ctggaaaaag aagatatcaa aattaacccg attggtcatt ggggcaccat tagcggtcag     180
aattttatct atgttcatct gaaccgcgtg atcaacaaat atggtctgaa catgttttat     240
atcgaaggtc cgggtcatgg tggtcaggtt atggttagca atagctatat tgatggcagc    300
tatagcgaaa tctatccgga tgttacccag gatgaagcag gtctgaaaaa actgttcaaa    360
cagtttagct ttccgggtgg tatgggtagc catgcagcac cggaaacacc gggtagcatt    420
catgaaggtg tgaactggg ttatagcatg agccatgccg ttggtgcagt tctggataat     480
cctgatgtta ttgcagcaac cgttattggt gatggtgaag cagaaaccgg tcctctggca    540
gcaagctgga tgagcaataa tttcattaat ccggtgaatg atggcgcagt gctgccgatt    600
ctgaatctga tggtgcaaa aattgcaaat ccgaccgttc tggcacgtaa aagcgataaa     660
gatctgcaga atactttga aggtctgggt tggaaaccgt attttgtgga aggtgataac     720
ccggaaaaaa tgcatccgct gatggccgaa accctggatg cagttattaa cgaaattcag    780
agcattcaga agaagcccg taaaggttca gccgaagatg tgaccatgcc gcattggcct     840
gttattgttt ttcgtacccc gaaaggttgg gaaggtccag aaaaatggga taatgagcag    900
attgcaggca cctttcgtgc acatcaggtt ccgattccga ttgatgcaag ccatatggaa    960
tatgcaaatg atctggcaaa atggctgaaa agctatcgtc cggaagaact gtttgatgaa   1020
aatggcacaa ttattgatgc gattaaagaa ctgagtccga aggcgataa tcgcatgagt    1080 gttaatccga ttaccaatgg tggcctggat ccgaaagcac tgaatatgcc tgattggcat    1140
acccatgcag ttgataccag caaacgtggc accgataaag cacaggatat gagcgttctg    1200
ggtggtttta ttgccgatat tatggaaaac aacccgaaga actttcgcat tttggtccg    1260 gatgaaacca aaagcaatcg cctgaataaa gttttgatg tgacaaatcg tcagtgggtt    1320
gaacctcgtg aactgtcaga tgaatggcag agcgcagttg gtcgtgtgat cgatggtcag    1380
ctgagcgaac atcaggcaga aggttttctg gaaggctata ccctgaccgg tcgtcatggt    1440 tttttgcaa gctatgaagc atttctgcgc attgttgata gcatgctgac ccagcacttt    1500
aaatggattc gtaaagccaa tgaaaaaagc tggcgcaaaa aatacccgag cctgaatgtg   1560
attagcagca gtaccgcatt tcagcaggat cataatggtt ataccatca ggatccgggt    1620 gtgattaccc atctggcaga aaaaaaaccg gaatatatcc gcgaatattt tccggcagat   1680
gcaaatagcc tgatggcggt tatggataaa gccctgaaag atgaaaacgt cattaacctg    1740
attacctcga gcaaacatcc gcgtccgcag ttttatagcg ttgaagaagc acaagaactg   1800
gtcgattatg gcgtgaaaaa aatcgattgg gcaagcaatg atcaggatag cgaaccggat    1860
attgtgtttg cagcagcagg tagtgaaccg aatctggaag cactggcagc gattagcatt    1920
ctgcatgaac agtttccgga aatgaaaatc cgctttatca atgttgtgga cctgctgaaa    1980
```

```
ctgcgtcatc cagatgttga tccgcgtggt ctgagtgatg aagcctttga tgagctgttt    2040
accacagata aaccggtgat ctttaacttt catggttatg aaggcctgat tcgcgatatc    2100
ttttttaccc gtcataatcg taatctgagc atccatggct atcgtgaaga tggtgatatt    2160
accaccccgt ttgatatgcg tgttaaaaat gaactggatc gctttcatct ggccaaagat    2220
gcagccaata ccattatgc cgaaaaagca gccgatttca tccaagaaat ggacaaaacc    2280
ctgcagtatc accatgatta tattcgcgaa aacggtgatg atatcagcga agttcagaat    2340
tgggaatgga agacctgaa a                                               2361
```

<210> SEQ ID NO 76
<211> LENGTH: 2379
<212> TYPE: DNA
<213> ORGANISM: Melissococcus plutonius DAT561

<400> SEQUENCE: 76

```
atgaccaaat atgatagcaa agaatatctg gccaaagtgg atgcattttg gcgtgcagca      60
aactatatta gcgttggtca gctgtatctg aaagataatc cgctgctgga tcgtccgatt     120
gaaaccaccg atgttaaagt tcatccgatt ggtcattggg caccattag cggtcagaat     180 tttatctatg cacatctgaa tcgcgtgatc aacaaatacg atctgaacat gttttatgtg     240
gaaggtccgg gtcatggtgg tcaggttatg gttagcaata gctatctgga tggtagctat     300
accgaaatct atccggaaat caccgaagat aaagagggtc tgaaaaaact gttcaaacag     360
tttagctttc cgggtggtat tgcaagccat gcagcaccgg aaactccggg tagcattcat     420
gaaggtggtg aactgggtta tagcattagc catgccaccg tgcaattct ggataaccg     480 gatgttattg cagcaaccgt tgttggtgat ggtgaagcag aaaccggtcc gctgagcgca     540
ggttggtttg caaataccttt tattaacccg gttaacgatg tgccattct gccgattctg     600 tacctgaatg gtggtaaaaat tagcaatccg accattctgg aacgcaaaag tgatgaagaa     660
ctgaccaagt attttgaagg tatgggttgg aaaccgtatt ttgttgaagg caccgttccg     720
gataaagtgc atcctctgat ggcaaaaatc ctggatcata tcatcgaaga aatcaaagat     780
attcagaaag aagcccgtaa agacaaagcc gaaaatgcaa aaatgccgca ttggcctgtt     840
ctgattatgc gtacccgaa aggttggaca ggtccgaaaa tttgggatga tgaaaaaatt     900
gagggcacct tcgtgcaca tcaggttccg attccggttg atgcagaaca tatggaacat     960
attgatgcac tggttgattg gctgaaaagc tatcatccgg aagaactttt tgataaaaac    1020 ggcacccctga aaccggaact gaaagaactg gttccgaaag cgatcgtcg tatggccaaa    1080 aacccgatta ccaatggtgg cctggatccg aaaccgctga aaatgaatgg ttgggaacag    1140
catgcaattg ataccagcac accgggtatg gttaccgcac aggatatgat tgttttgggc    1200
aattatgtcg aagatctgat caaagcaaac ccgaccaatt tcgtattttt tggtccggat    1260
gaaaccaaaa gcaatcgcct gaataaagtg tttgatagca ccgatcgtca gtggatggaa    1320
ccgattagta atgcagatga atggcagagc agcgtgggtc gtgttattga tggccagctg    1380
agcgaacatc aggcagaagg ttttctggaa ggttatattc tgaccggtcg tcatggtttt    1440
tttgcaagct atgaaagctt tctgcgtgtt gtggatagca tgctgaccca gcactttaaa    1500
tggctgcgta agcaaaaga acagagctgg cgtaaagagt atccggcact gaacattatt    1560
gcaaccagca ccgttttttca gcaggatcat aatggttata cccatcagga tccgggtatc    1620
ctgacccatc tggcagaaaa aaaagcagaa tatatccgtg aatacctgcc tgcagatgca    1680
aattgcctga tggccgttat ggataaagcc tttcaagaaa acgaagtgat taacctgatt    1740
```

```
gtgagcagta acatccgcg tccgcagttt tatagcgtta ccgaagccaa agaattggtt    1800
gataaaggcg tgaaagtgat tgattgggca agcaatgatg aaggtcagac accggatatt    1860
gtgattgcag cgagcggcac cgaaccgaat ctggaagcac tggcagcaat taccctgctg    1920
aacaaagagt ttattgatct gaaaatccgc ttcgtgaacg tggtggatat cctgaaactg    1980
cgtcatccga gcattgatcc gcgtggtctg accgatgaag agtttgatgc aatttttcacc   2040 aaggacaaac cgattgtgtt tgcctttcat ggctttgaag cctgattcg cgatatcttt     2100 tttagccgta gcaatcatca gctgtttgtg catggttatc gtgaaaaagg tgatattacc    2160
accccgtttg atatgcgtgt tctgagtgaa atggatcgtt ttcacctggc aaaagatgtt    2220
gccgacaaag tgtataatga acaggcagcc gatttttatga atcgcatgga tgaaattctg    2280
gcctttcacc atcagtatat tcgcaaaaac ggtatcgata ttccggaagt ggttaactgg    2340
aaatgggagg atctgcgcaa aaaaacgatt tgctttaat                            2379
```

<210> SEQ ID NO 77
<211> LENGTH: 2379
<212> TYPE: DNA
<213> ORGANISM: Mycoplasma arthritidis 158L3-1

<400> SEQUENCE: 77

```
atgaaaaaaa ccaattatga tagcaatgaa tatttcaatc tgattgataa atggtttcgc      60
gcagccaatt atctgagcgt tggtcagatt tatctgcgta taatccgct gctgaaaacc      120 aaactggttg cagatgatgt taaaatctat ccgattggtc attggggcac cattccgggt      180
cagaatttta tctatgcaca tctgaatcgc gtgattaaca atacgatct ggaaatgttc      240 tatatcgaag tcctggtca tggtggtcag gtgatgatta gcaatagcta tctggatggt      300
agctataccg aaatttatcc ggaaatcacc gaagatgaag caggtctgaa aacgatgttt      360 aaacgttttta gctttccggg tggcaccgca agccatgcag caccggaaac tccgggtagc      420
attcatgaag gtggtgaact gggttatgca ctgagccatg ccaccggtgc aattctggat      480
aatccgaatg ttattgcagc aaccgttatt ggtgatggtg aagcagaaac cggtccgctg      540
gcagcaggtt ggtttagcaa ttcttttatc aatccggtta atgatggtgc cgttctgccg      600
attattcatc tgaacggtgc aaaaattttcc aaccccgacca ttctgagccg taaaagcaat      660
caagaactgg aaaactattt tagcggtctg ggttgggaac cgctgtttgt tgaaggtgac      720
gatccgaaac tgatgcatcc gctgatggca aaaaaactgg atgaagccat tgagaagatt      780
cagatgattc aggcaagcgc acgtaaacat aaagcaagcg aagcaacccg tccggttttgg      840 ccgatgctga ttgttcgtac cccgaaaggt tggacaggtc ctaaagattg aatggcgaa      900 gttgtggaag gtagctttcg tgcacatcag gttccgattc cggtgaatgc cctgaatatg      960
acccatatcg ataaactgga agcatggctg accagctatc atccggaaga actgtttgat      1020
aaaaacggca aatcctgga agaaattcgt gccctggcac cgaaaggcct gaaacgtatg      1080
gcagttcatc cgattaccaa tggtggtatt aatccgcgta ccctgaaact gagcagctgg      1140 gaaaaattg ccaccaaatt tgaaacccct ggccagatta aggtcagga tatgatcgaa      1200 ctgggcaaat atttcgcaga aattatcacc ctgaacaagg ataactttcg cattttttggt      1260 ccggatgaaa ccaaatccaa tcgtatgaat gccgtgttta atgtgaccaa acgtcagtgg      1320
ctggaaaaaa tcgcaccgac ctatgatgaa tggatgagtc cggaaggtcg tgttattgat      1380
agccagctga gcgaacatca ggcagaaggt tttctggaag gttatgttat taccggtcgc      1440
```

```
catggtgttt ttgcaagcta tgaagcattt ctgcgtgttg tggatagtat gctgacccag    1500
catatgaaat ggatgaagaa aagcctggaa ctgccgtggc gtaaagattt tccgagcctg    1560
aatgtgattg cgaccagcac cgcatttcag caggatcata atggttatac ccatcaggat    1620
ccgggtctgc tgggtcatct ggcagataaa cgtccggaac tgattcgtga atatctgcct    1680
gcagatacca attgcctgct ggcaaccatg gaaaaagcac tgaaagatcg taatgtgatc    1740
aacctgattg tggcaagcaa acagcctcgt gaacagtttt atagcgttga agaagccagc    1800
gaactggtac agaaaggcta taaatcatt aattgggcca gcaacgtgag caaaaatgaa    1860
gaaccggatg ttgtgtttgc agcagccggt gttgaaccga atctggaagc tctggcagcc    1920
attagtattc tgaacaaaga attcccgaac ctgaaaatcc gttttgtgaa tgttctggat    1980
ctgctgaagc tgaaaagccc gaaacatgat ccgcgtggca ttagcgacga agaatttgat    2040
cagatcttca ccaaaaacaa accgatcatc tttgcctttc atggttatga aggcctgctg    2100
cgtgatatct tttttgatcg ccataaccat aacctgatca cccatggcta tcgtgaaaat    2160
ggcgatatca ccaccagttt tgatattcgt cagctgagtc atatggatcg ctttcatatt    2220
gcaaaagatg cagcaattgc agccctgggt aaagatggcg aaatgtttgc gaaaaaaatg    2280
gacagcaaac tgcaagaaca taccagttat gttcgcgagt atggctatga tctgccggaa    2340
gttgttaatt ggaaatggac caatctgaaa ccgattaaa                           2379
```

<210> SEQ ID NO 78
<211> LENGTH: 2376
<212> TYPE: DNA
<213> ORGANISM: Streptococcus agalactiae NEM316

<400> SEQUENCE: 78

```
atgagcgagt tcgacaccaa aagctatctg gaaaaactgg atgcatggtg gcgtgcagca     60
aactatatta gcgcagcaca gatgtatctg aaagataatc cgctgctgcg tcgtgaactg    120
gttgaaaatg acctgaaagt tcatccgatt ggtcattggg gcaccgttcc gggtcagaat    180
tttatctatg cacatctgaa tcgtgccatc aacaaatatg atctggacat gttttatatc    240
gaaggtcctg gtcatggtgg tcaggttatg gttagcaata gttatctgga tggtagctat    300
accgaactga atccgaatat tgaacagacc gaagatggtt ttaaacagct gtgcaaaatc    360
tttagctttc cgggtggtat tgcaagccat gcagcaccgg aaacaccggg tagcattcat    420
gaaggtggcg aactgggtta tgcactgagc catgccaccg gtgcaattct ggataacccg    480
gatgttattg cagcaaccgt tattggtgat ggtgaaggcg aaaccggtcc gctgatggca    540
ggttggctga gcaataccct tattaacccg gttaatgatg gtgcagttct gccgatcttt    600
tatctgaatg gcgtaaaaat tcataatccg accatctttg aacgcaaaac cgatgaagaa    660
ctgtcccagt tttttgaagg tctgggttgg aaaccgattt tgcagatgt tgttgaactg    720 agtgaagatc atgcagccgc acatgcactg tttgcagaaa aattagatca ggccatccaa    780
gagattaaaa ccattcagag cgaagcacgt cagaaaccgg cagaagaagc aattcaggca    840
aaatttccgg ttctggttgc acgtattccg aaaggttgga caggtccgaa agcatgggaa    900
ggcaccccga ttgaaggcgg ttttcgtgca catcaggttc cgattccggt tgatgcccat    960
catatggaac atgttgatag cctgctgagc tggctgcaga gctatcgtcc ggaagaatta    1020
tttgatgaaa gcggcaaaat cgtggatgaa attgcagcca ttagcccgaa aggcgatcgt    1080
cgtatgagca tgaacccgat taccaatgca ggtattgtta aagcaatgga taccgcagat    1140
tggaaaaaat tcgccctgga tattaatgtg ccaggccaga ttatggcaca ggatatgatt    1200
```

-continued

```
gaatttggca aatatgcagc ggatctggtg gatgcaaatc cggataattt tcgtatttt    1260 ggtccggatg aaacgaaaag caatcgtctg caagaagttt ttacccgtac cagccgtcag    1320
tggctgggtc gtcgtaaacc ggattatgat gaagcactga gtccggcagg tcgtgttatt    1380
gattcacagc tgagcgaaca tcaggcagaa ggttttctgg aaggttatgt tctgaccggt    1440
cgtcatggtt tttttgcaag ctatgaaagc tttctgcgtg ttgtggatag tatggttacc    1500
cagcacttta atggctgcg taaaagcaaa acccatacca cctggcgtaa aaactatccg    1560
gcactgaatc tgattgccgc aagcaccgtt tttcagcagg atcataatgg ttatacccat    1620
caggatccgg gtattctgac ccatctggcc gaaaaaactc cggaatatat tcgtgaatat    1680
ctgcctgcag ataccaatag tctgctggca gttatggata agcatttaa agccgaggac    1740 aagattaacc tgattgtgac cagcaaacat ccgcgtccgc agtttatag cattgcagaa    1800 gccgaagaac ttgttgccga aggctataaa gtgattgatt gggcaagcaa tgttagcctg    1860
aatcaagaac cggatgtggt ttttgccgca gcaggcacag aaccgaatct ggaagccctg    1920
gcagcaatta gcattctgca caaagccttt ccggaactga aaattcgttt tgtgaatgtg    1980
ctggacattg tgaaactgcg tcatccgagc caggatgcac gtggtctgag cgacgaagaa    2040
tttgataaag tgtttaccac cgataagccg gtgatctttg catttcattc ctacgaagat    2100
atgatccgcg atatcttttt tagccgtcat aatcacaatc tgcatacccca tggttatcgc    2160 gaaaatggtg atattaccac cccgtttgat atgcgtgtta tgtcagaact ggatcgtttt    2220
catctggcgc aggatgccgc actgcaaagc ctgggtaatg aagcccaggc atttagtgat    2280
gaaatgaatc agatggtggc ctatcacaaa gattatatcc gtgaacatgg tgatgatatt    2340
ccggaagttc agaattggaa atgggaaaac attaaa                              2376
```

<210> SEQ ID NO 79
<211> LENGTH: 2385
<212> TYPE: DNA
<213> ORGANISM: Mycoplasma agalactiae PG2

<400> SEQUENCE: 79

```
atgaaaaaaa gccatgattt tgatagcaaa gaatatctga atctggttga tgcatggtgg      60
cgtgcagcaa attatctgag cgttggtcag atgtatctgc gtaataatcc gctgctgaaa     120
attccgctga ccagcaatga tgttaaaatc tatccgattg gtcattgggg caccgttccg     180
ggtcagaatt ttatctatgc acatctgaac cgcattatca caaatacga tctgaatatg     240 ttttttatca gcggtcctgg tcatggtggt caggttattg caagcaatac ctatctggat     300
ggtagctata ccgaactgtt tccgcatgtt accaaagata ttaaaggtat gacccacctg     360
ttcaaatact ttagctttcc gggtggcacc gcaagccatg cagcaccgga atgtccgggt     420
agcattcatg aaggtggtga actgggttat agcctgagtc atgcagccgg tgcagttctg     480
gataatccgg atgttattgc cgcaaccgtt attggtgatg tgaaagcga accggtccg     540 ctgagcgcag gttggtttat taacagcttt atcaatccgg caaatgatgg tgccgttctg     600
ccgattctgc atgttaatgg tgtaaaaatt agcaacccga ccatttggag ccgtcgtagc     660
aatgaagaac tggttagcta ttttaccggt gccggttgga accgtttat tgttgaaggt     720 aatgagccgg aatatatgca tcatgaaatg gcaaaagcac tggatgcaag cgttgaactg     780
attaaacagt atcaggccga agcacgtaaa aatggtgcaa ataaagcaaa acgtccgcag     840
tggccgatga ttgttctgaa aagcccgaaa ggttggacag gtccgaaaga atggaatcat     900
```

```
gaagcaattg aaggttcctt tcgtgcacat caggttccgg ttccagttag cgcagaaaaa   960
atgcagcata ttgatgcact ggaaaattgg ctgcgtagct atcgtccgga agaactttt   1020
gatgaaaatg cccagctgaa accggaaatt gcagcaattg caccgaaagg cgatcgtcgt  1080
atgggtaaaa acccgattgc aaatggtggc attaatccgc gtgcaattaa tgttggtgat  1140
tggaccaaat ttgccctgga tatcaaacag cctggcaaag ttattaatca ggatatggtt  1200
accctgggca gctatctggg cgaactgagc ctgctgaata agataatttt cgtgtttgg   1260
ggtccggatg aacataaaag caatcgtctg tatgagatgt caaagttac cgatcgtcag   1320
tggctggatc gtatcgatga aaatatgat gaatttctga gcagcgtggg tcgcattatt   1380
gatagccagc tgagcgaaca tcaggcagaa ggtatgctgg aaggttatgt tctgaccggt  1440
cgccatggtg tttttgcaag ctatgaaagc tttctgcgtg ttgtggatag catgctgacc  1500
caacatatga agtgggttaa aaaagcgctg acattccgt ggcgtaatga ttatccgagc   1560
ctgaatgtga ttgcaaccag taatgcattt cagcaggatc ataatggtta acccatcag   1620
gatcctggtc tgattggcca tctggcagat aaacgtccag aactgatccg tgaatattta  1680
ccggcagata ccaataccct gctggcaacc atggccaaag ccctgcagga tcgtaacgtg  1740
attaatctga ttatcagcag taaacagcca cgccatcagt tttttagtat tgaagaagca  1800
accgagctgg tcgaaaaagg cattaaaatc attgattggg ccagcaacat taagccgaac  1860
gaagaaccgg atctggtggt tgcagccagc ggtacagaaa gcaccattga aagcctggcc  1920
accattacct acctgcgtgc ccattttccg gaactgaaaa tccgttttgt taatgtgctg  1980
gatctgctga gctgcgtca tccgagtatt gatcctcgtg gtctgagcga tagcgaattt  2040
gatagtatct tcacgaaaga caaaccgatc ctgtttgcct tcatggttat tgaagccatt  2100
ctgcgcgata tctttttcct gcgttcaaac cataacatta tcacccatgg ctatcgtgaa  2160
aatggcgata ttaccaccgc atttgatatt cgtctgctga gtgaaatgga tcgctttcat  2220
atgaccgcaa atgttgcaaa aaaactggca ccggttgttg gcgaaagcaa agcaaatgaa  2280
ctggtgaaaac tgatggaaga taaaatcaaa gaacaccgtg cctatatcaa agagtatggc  2340
accgatctgc cggaagttaa agaatgggaa tggaccccgt ataaa              2385

<210> SEQ ID NO 80
<211> LENGTH: 2382
<212> TYPE: DNA
<213> ORGANISM: Streptococcus gordonii str. Challis substr. CH1

<400> SEQUENCE: 80
atgaccaccg actataacag caaagcctat ctggaaaaag ttgatgcatg gtggcgtgca   60
gcaaactata ttagcgcagc acagatgtat ctgaaagata tccgctgct gaaacgtgat  120
gttgttgcaa atgacctgaa agcacatccg attggtcatt ggggcaccgt tccgggtcag  180
aattttatct atgcacatct gaatcgcacc atcaacaaat atgatctgga catgttttat  240
atcgaaggtc ctggtcatgg tggtcaggtt atggttagca atagttatct ggatggtagc  300
tataccgaac tgaatccgaa tattccgcag aatgaagagg ttttaaaaca cctgtgtaaa  360
atctttagct ttccgggtgg tattgcaagc catgcagcac ggaaacacc gggtagcatt   420
catgaaggtg gtgaactggg ttatgcactg agtcatgcag ccggtgcaat tctggataac  480
ccggatgtta ttgcagcaac cgttattggt gatggtgaag cgaaaccggt tccgctgatg  540
gcaggttggc tgagcaatac ctttattaac ccggttaatg atggtgccat tctgccgatc  600
tttttatctga atggcggtaa aattcataat ccgaccatct ttgaacgcaa aaccgatgaa  660
```

```
gaactgaccc tgtttttgta aggtctgggt tggaaaccga tttttgcaga tgttaccgca      720
attagcgaaa atcatgaagc agcacatgca ctgtttgcag ccaaactgga tgaagcaatt      780
gaagagatca aaaagttca  ggcagaagca cgtaaaggta gcgcagaaga agcaacccag      840 gcaattttc  cggttctggt tgcacgtatt ccgaaaggtt ggacaggtcc gaaaagctgg      900
gaaggcaccc cgattgaagg cggttttcgt gcacatcagg ttccgattcc ggttgatgcc      960
catcatatgg aacatgttga cgcactgctg aattggctga aaagctatcg tccgaagaa     1020 cttttgatg  aaagcggtaa agttctgccg gaaattgccg caattggtcc taaaggtgat     1080
cgtcgtatgg caatgaaccc gattaccaat gccggtgtta ttaaacctat ggataccgca     1140
gattggaaaa aacacgcact gaaatttggc actccgggtg aaattgttgc acaggatatg     1200
atcgaattcg gtaaatatgc aaccgatctg gtggatgcaa atccgataa  ttttcgtatt     1260 tttggtccgg acgaaaccaa agtaatcgt  ctgcaagaag ttttacccg  taccagccgt     1320 cagtggctgg tcgtatgcg  tcctgaatat gatgaagccc tgagtccggc aggtcgtgtt     1380
attgatagcc agctgagcga acatcaggcc gaaggtatgc tggaaggtta tgttctgacc     1440
ggtcgtcatg gttttttgc  aagctatgaa agctttctgc gtgttgtgga tagcatggtt     1500
acccagcact ttaaatggct gcgtaaatgt aaaacccata ccacctggcg taaaaactat     1560
ccggcactga atctgattgc aaccagcacc gttttcagc  aggatcataa tggttatacc     1620
catcaggatc cgggtattct gacccatctg gcagaaaaaa ctccggaatt tatccgtgaa     1680
tatctgcctg cagataccaa tagcctgctg gcagttatgg ataaagcatt taaagccgag     1740
gataaggtga acctgattgt gaccagtaaa catccgcgtc gcagttttta tagtgccgaa     1800
gaagcggagg aactggttcg tgaaggctat aaagtgattg attgggcaag caccgtgagc     1860
aacaacgaag aaccggatgt ggttttgcc  gcagcaggca cagaaccgaa tctggaagca     1920
ctggcagcag ttagcattct gcacaaagcc tttccggaac tgaaaattcg ttttgtgaat     1980
gtggtggaca ttctgaaact cgtcatccg  agcgttgatg cgcgtggtct gagcgacgaa     2040
gaatttgatc agtgtttac  caccgataaa ccggttatct ttgcctttca tggttatgaa     2100
ggcatgatcc gcgatatctt tttaaccgc  ataaccata  atctgcgcgt tcatggctat     2160
cgtgaaaatg gtgatattac caccccgttt gatatgcgtg ttatgtcaga actggatcgt     2220
tttcatctgg cccaggatgc cgcaaatgca gccctgggtg aagatgcagc ggtttttagc     2280
gcaaaaatgg atgaaaccgt tgcatatcat aacgcctata ttcgcgaaaa tggggatgat     2340
attccggaag ttcagaattg gaaatgggaa aacattaaca aa                        2382
```

<210> SEQ ID NO 81
<211> LENGTH: 2373
<212> TYPE: DNA
<213> ORGANISM: Kingella oralis ATCC 51147

<400> SEQUENCE: 81

```
atgcagaaca cccagtttga cacaccggaa tatctggcaa agttgatgc  atggtggcgt       60 gcagcaaact atattagcgc agcacagatg tatctgaaag ataatccgct gctgaaaaaa      120
ccgctgaccg caaatgatgt taaagcacat ccgattggtc attggggcac cgttccgggt      180
cagaatttta tctatgcaca tctgaatcgt gccatcaaca aatatgatgt ggacatgttt      240
tatatcgaag gtcctggtca tgtggtcag  gttatggtta gcaatagcta tctggatcat      300
agctataccg atatctatcc ggaaattacc caggatgaag caggtctgaa aaagctgtgt      360
```

```
aaaatcttta gctttccggg tggtattgca agccatgcag caccggaaac accgggtagc    420
attcatgaag gtggtgaact gggttatgca ctgagccatg cctttggtgc agttctggat    480
aacccgaaca ttattgcagc agcagttatt ggtgatggtg aagcagaaac cggtccgctg    540
tgtgcaggtt ggtttggtaa tacctttatt aacccggtta atgatggtgc cgtgctgccg    600
attctgtacc tgaatggtgg taaaattcat aatccgacca ttctggcacg taaaaccgat    660
gccgaactga cccagtattt taacggtatg ggttgggaac cgattttgt tgaagttagc    720
gatccggcac atagccatgc gattatggca cagaaactgg atgaggcagt tgaacgtatt    780
ctggccattt ggcaggatgc acgtagccgt agcgccaatg atgcaaccat gcctcgttgg    840
cctgttctgg ttgcccgtat tccgaaaggt tggacaggtc cgaaaacctg aatggcgaa    900
ccgatcgaag gcggttttcg tgcacatcag gttccgattc cgaccaatag tcatgatatg    960
agcaccgcag atgcactgga agcatggctg cgtagctatc gtccggaaga actgtttgat    1020
gataatggtc gtttcctgga taatggcgt gaaattagcc cgaaaggcgc aaaacgtatg    1080
agcgttcatc cgatcaccaa tggcggtgtt gcaccgaaag cactggttat gccggattgg    1140
accaaacatg ccctgaaaat tggcaccct ggtagccagg atgcccagga tatgattgaa    1200
tgtggtcgtc tgatggcaga tgttattacc gccaatccgg ataactttcg tattttggt    1260
ccggatgaaa ccaaaagcaa tcgtctgaat gaagtgttca agtgaccaa tcgtcagtgg    1320
ctgggtgttc gtgatgcagc ctatgatgaa tggattgcac cggttggtcg tgttattgat    1380
agccagctga gcgaacatca ggcagaaggt tttctggaag gttatgttct gaccggtcgt    1440
catggttttt ttgcaagcta tgaaagcttt ctgcgtgttg tggatagcat gattacacag    1500
cactttaagt ggctgcgcaa atgcaaaacc catgcaccgt ggcgtaaaga ttatccgagc    1560
ctgaatctga ttgcaaccag caccgttttt cagcaggatc ataatggtta tacccatcag    1620
gatccgggtc tgctgaccca tctggcagaa aaaaaacctg aatttgtgcg cgaatattta    1680
ccggcagatg ccaatacccct gctggcagtt atgagcgaag cactgaccag ccgtgatcgt    1740
attaacctga ttgttagcag taaacatctg cgtccgcagt tttatagcgc agatgaagcc    1800
aaagaactgg ttcgtgaagg ctataaaatc attgaatggg caagcacctg tcatgacggt    1860
gaaccggatg ttgtgatcgc agcggcaggc accgaaccga atatggaagc cctggcagca    1920
attaatgttc tgcacaaaca ttacccggaa atgaaaatcc gctttatcaa cgtggtggat    1980
attctgaaac tgcgtcatcc gagcattgat ccgcgtggtc tgagtgatga agcgtttgat    2040
gccctgttta cccgtgataa accggttgtt ttttgctttc atggctatga gaatatggtg    2100
cgcgatatct ttttttccgcg tcataatcgt aatgtgcgca tccatggtta tcgtgaaaat    2160
ggtgatatta ccaccccgtt tgatatgcgt gttctgtcag aaatggatcg ttttcatgtt    2220
gcaaaagatg ccgcacaggc agtttatggt gagaaagcag cagattttgc caacaaaatg    2280
gacgaaacca ttcagtttca tcgtagctac attcgcgaac atggtaaaga tattccggaa    2340
gttgcagaat ggaaatggca gccgctggcc aaa                                2373
```

<210> SEQ ID NO 82
<211> LENGTH: 2376
<212> TYPE: DNA
<213> ORGANISM: Mycoplasma fermentans M64

<400> SEQUENCE: 82

```
atgaacaaaa aagaatttga tagcaaagaa tatctggaaa aggttgatgc atggtggcgt     60
gcagcaaatt atctgagcgt tggtcagatt tatctgcgta ataatccgct gctgaaacat    120
```

```
ccgctgacca gtgatgatgt taaagtttat ccgattggtc attggggcac cattagcggt      180
cagaattttg catatgcaca tctgaatcgc gtgatcaaca aatatgatct gaatatgttc      240
tacatcgaag gtccgggtca tggtggtcag gttatgacca gcaatagcta tctggatggt      300
agctataccg aactgtttcc gcatgttacc caggatgaag caggtatgca gcacctgttt      360
aaatacttta gctttccggg tggcaccgca agccatgccg caccggaaac accgggtagc      420
attcatgaag tggtgaact gggttatagc attagccatg caaccggtgc aattctggat       480
aatccggatg ttattgcagc aaccattgtt ggtgatggtg aagcagaaac cggtccgctg      540
gcgaccagct ggtttagcaa tagttttatc aatccggtta tgatggtgc cgttctgccg       600 attctgcatc tgaacggtgg taaaattagc aatccgacca ttctgagccg taaaagcaat      660
gaagaactgc agcagtattt tcgtggtatg ggttgggaac cgcattttgt tgaaggtgat      720
aaaccggaag taatgcatga actgatggca aaaaccctgg atagcgtgat tgaagaaatt      780
cagagcattc agaccaaagc ccgtaaaaaa ccggcagata agcaaaacg tccggtttgg       840 ccgatgattg ttctgcgtac cccgaaaggt tggacaggtc cgaaaagctg gaataaagaa      900
gcaattgaag gtagctttcg tgcacatcag gttccgctgc cgatcaatgc agaaaatatg      960
gaacatgcag atgccctgga aaaatggctg cgtagctatc gtccggaaga acttttgat      1020 aaaaaaggca actggtgaa agagattgca gccattgcac ctaaaggtaa acgtcgtatg      1080
ggtatgaatc cgattaccaa tggtggcatt aatccgaaag ttatgaaact gggtgattgg      1140
cgtaaatttg ccctgcattt tgatcgtcct ggtagcgttg ttgcacagga tatggttgag      1200
ctgggcacct attttgcaga tctggttaaa cgcaatccgg aaaattttcg tattttggt       1260 ccggacgaaa ccaaaagtaa tcgtctgtat aacctgttca agtgaccaa tcgtcagtgg      1320 atggaacgca ttgatagtaa actggatgag gcactgagtc cggttggtcg tattattgat      1380
agccagctga gcgaacatca ggcacagggt tttctggaag gttatgttct gaccggtcgt      1440 catggcatt ttgcaagcta tgaaagcttt ctgcgtgttg tggatagcat ggtgacccag       1500
catatgaaat ggttacgtaa agccaaagaa atcaactggc gcaaagatta tccgtccctg      1560
aatattatgg caaccagcac cgcctttcag caggatcata atggttatac ccatcaggat      1620
ccgggtatta tcggtcatat ggcggataaa cgtccagaac tgattcgtga atacctgcct      1680
gcagatacca atccctgct ggcagttatg gataaagcct ttaccgaacg caatgtgatt       1740
aatctgattg tgagcagcaa acagcctcgc catcagtttt atagcgttga agaagccgaa      1800
acgctggttt aaaaaggtct ggatattatc gattgggcaa gtacctgtag ccgtaatgaa      1860
actccggatc tggtggttgt tgccagcggc accgaaccga atctggaagc actggccacc      1920
atttctattc tgaacaaaga atacccgagc atgaaaatcc gttttgtgaa tgttgttgat      1980
ctgctgaagc tgcgtcatcc gaaaattgat ccgcgtggtc tgagtgatga agaattcgat      2040
gaaatcttta ccaaagataa gccggtgctg tttgcctttc atggttttga aggcattctg      2100
cgcgatattt tctttgatcg ccataaccat aacctgattg cacatggtta tcgcgaaaat      2160
ggtgatatca caaccagctt tgatattcgt cagctgtcac atatggatcg tttcacatg       2220 gcaagtgatg cagcagcagc cgttttggt agctcaaaag cgaaagaatt catggacaaa       2280
atggaagaaa ccattcagtt tcacaacaag tatattcgcg aagtgggcac cgatattccg      2340
gaagtgaaaa attggaaatg ggaaggcctg attaaa                                2376

<210> SEQ ID NO 83
```

<211> LENGTH: 2367
<212> TYPE: DNA
<213> ORGANISM: Granulicatella adiacens ATCC 49175

<400> SEQUENCE: 83

```
atgacccagt tgacacacc ggaatatctg gcaaaagttg atgcatggtg gcgtgcagca      60
aactatatta gcgttgcaca gatgtatctg aaagataatc cgctgctgcg tcgtccgatt    120
cagaaagaag atgttaaact gcatccgatt ggtcattggg gcaccattgc aggtcagaat    180
tttatctatg cacatctgaa tcgtgccatc aacaaatatg atctggacat gttttatatc    240
gaaggtccgg tcatggtgg tcaggttatg gttagcaata gctatctgga tggtagctat    300
accgaactgt atccgcagat tacccaggat gaagcaggtt taaacagct gtgcaaaatc    360
tttagctttc cgggtggtat tgcaagccat gcagcaccgg aaacaccggg tagcattcat    420
gaaggtggtg aactgggtta tagcctgagc catgccaccg gtgcagttct ggataacccg    480
aatgttattg cagcagcagt tattggtgat ggtgaagcag aaaccggtcc gctggcagca    540
ggttggttta gtaatacctt tattaacccg gttaatgatg gtgccgttct gccgattctg    600
tacctgaatg gcgtaaaaat tcataatccg accattctgg cacgtcgtac cgatgaagaa    660
ctgacacagt tttttaacgg tctgggttgg atccgatttt tgttgaagg caccgatccg    720
gaaaaagttc atccgctgat ggcagcaaaa ctggatgagg caattgaaaa aattcaggcc    780
atccagaaag aggcacgcgc aaaatcagcc gaagaggcaa ccatgccgca ttggcctgtt    840
ctggttgttc gtaccccgaa aggttggaca ggtccgaaag aatggaatca tgaaccgatt    900
gaaggcggtt ttcgtgcaca tcaggttccg attccggtta gcggtgaagc catgaacat     960
gttgatgccc tggttgattg gctgaaaagc tatcgtccgg aagaactttt tgatgaaaat   1020
ggcaaactgg tggaagaaat tgcagccatt agccctaaag tccgcgtcg tatgagtatg   1080
aatccgatta ccaatgccgg tgttgttaaa ccgatggaaa ttaccgattg gaccaaacat   1140
gcaatcgata ccagcaaacc gggtgcaatt caaaaacagg atatgatcga attcggcaaa   1200
tttgcagccg atctggttaa agcaaatccg gataattttc gcattttcgg tccggatgaa   1260
accaaaagta tcgtctgaa cgaagtgttt aaagccacca atcgtcagtg ggttggtcgt   1320
cgtgatgaaa gctatgatga atggattagt ccggtgggtc gtgttattga tagccagctg   1380
agcgaacatc aggcagaagg ttttctggaa ggttatgttc tgaccggtcg tcatggtttt   1440
tttgccagct atgaaagttt tctgcgtgtt gtggatagca tgattacaca gcacttttaaa   1500
tggctgcgta aagccaaaac ccatgcaccg tggcgtaaaa actatccgag cctgaatctg   1560
attgcaacca gcaccgtttt tcagcaggat cataatggtt ataccatca ggatccgggt   1620
ctgctgaccc atctggcaga aaaaaaaccg gaatttgtgc gtgaatattt accggcagat   1680
accaatagtc tgatggccgt tatggcagaa gcactgagca gcgaagataa aatcaacctg   1740
attgtgagca gtaaacatcc gcgtccgcag ttttatagcg ttgaagaagc aaaagaactg   1800
gtcagcgaag gctataaagt gattgattgg gcaagcaccg tgaaagaagg tgaagaaccg   1860
gacgttgtga tcgcagcagc cggtacagaa ccgaatctgg aagccctggc aggtattagc   1920
attctgcaca acagtttcc ggaactgaaa atccgttttta tcaacgtggt ggatattctg   1980
aaactgcgtt caccgaaagt ggatccgcgt ggtctgagcg acgaagaatt tgataaactg   2040
tttaccaccg ataaaccggt ggtgtttttgt tttcatggtt atgaaggtat gatccgcgac   2100
ctgtttttg atcgcaataa ccataacgtg catatccatg gctatcgcga aaatggtgat   2160
attaccacc gtttgatat gcgtgttctg agtgaaatgg atcgctttca tgttgcaaaa   2220
```

-continued

| | |
|---|---|
| gatgcagccg ttgcagtgta tggtgaaaaa gcaagcgaat ttgccgctaa aatggacgaa | 2280 |
| accgttgaat ttcatcacag ctatattcgt gaacatggtg aggatattcc ggaagttgtt | 2340 |
| agctggcagt gggaaaatgt gaacaaa | 2367 |

<210> SEQ ID NO 84
<211> LENGTH: 2388
<212> TYPE: DNA
<213> ORGANISM: Mycoplasma hominis ATCC 23114

<400> SEQUENCE: 84

| | |
|---|---|
| atgattagca aaatctatga tgataaaaag tatctggaaa aatggataaa atggtttcgc | 60 |
| gcagcaaatt atctgggtgt ttgtcagatg tatctgcgtg ataatccgct gctgaaaaaa | 120 |
| ccgctgacca gcaatgatat caaactgtat ccgattggtc attggggcac cgttccgggt | 180 |
| cagaatttta tctatacccca tctgaatcgc gtgatcaaga aatatgatct gaatatgttc | 240 |
| tacatcgaag gtcctggtca tggtggtcag gttatgatta gtaatagcta tctggatggc | 300 |
| agctatagcg aaatttatcc ggaaattagc caggatgaag caggtctggc caaaatgttt | 360 |
| aaacgtttta gctttccggg tggcaccgca agccatgcag caccggaaac accgggtagc | 420 |
| attcatgaag gtggtgaact gggttatagc attagccatg gcaccggtgc aattctggat | 480 |
| aacccggatg ttatttgtgc agcagttgtt ggtgatggtg aagcagaaac cggtccgctg | 540 |
| gcgaccagct ggtttagcaa tgcctttatt aacccggtta atgatggtgc cattctgccg | 600 |
| attctgcatc tgaacggtgg taaaattagc aatccgaccc tgctgagccg taaaccgaaa | 660 |
| gaagaaatca aaaaatactt tgaaggcctg ggctggaatc cgattttttgt tgaatggtca | 720 |
| gaagataaga gcaacctgga tatgcatgaa ctgatggcaa aaagcctgga taaagccatt | 780 |
| gaaagcatca agaaattca ggcagaagca cgtaaaaaac ctgcagaaga agcaacccgt | 840 |
| ccgacctggc cgatgattgt tctgcgtacc ccgaaaggtt ggacaggtcc gaaacagtgg | 900 |
| aataatgaag caattgaagg tagctttcgt gcacatcagg ttccgattcc ggttagcgcc | 960 |
| tttaaaatgg aaaagattgc cgatcttgag aaatggctga aaagctacaa accggaagaa | 1020 |
| ctgtttgatg aaaatggcac gatcataaaa gaaatccgtg atctggctcc ggaaggtctg | 1080 |
| aaacgtatgg cagttaaccc gattaccaat ggtggtattg atagcaaacc tctgaaactg | 1140 |
| caggattgga aaaagtacgc actgaaaatt gattatccgg gtgaaattaa agcacaggat | 1200 |
| atggccgaaa tggccaaatt tgcagcagat atcatgaaag ataacccctag cagcttttcgc | 1260 |
| gttttttggtc cggatgaaac caaaagcaat cgtatgtttg ccctgtttaa tgtgaccaat | 1320 |
| cgtcagtggc tggaaccggt tagtaagaaa tacgatgaat ggattagtcc ggcaggtcgc | 1380 |
| attattgatt cacagctgag cgaacatcag tgtgaaggtt ttctggaagg ttatgttctg | 1440 |
| accggtcgtc atggttttttt tgcaagctat gaagcatttc tgcgtgttgt ggatagcatg | 1500 |
| ctgacccaac atatgaaatg gatcaaaaag gcaagcgaac tgagctggcg taaaacctat | 1560 |
| ccgagcctga acattattgc aaccagtaat gcatttcagc aggatcataa tggttatacg | 1620 |
| catcaggatc cgggtctgct gggtcatctg gcagataaac gtccagaaat tatccgtgaa | 1680 |
| tatctgcctg cagataccaa tagcctgctg gcggttatga taaaagcact gaccgaacgt | 1740 |
| aatgtgatta atctgattgt tgcaagcaaa cagcctcgcg aacagttttt taccgttgaa | 1800 |
| gatgcagagg aactgctgga aagggttat aaagttgttc cgtgggcaag caatattagc | 1860 |
| gaaaatgaag aaccggatat tgtgtttgcc agcagcggtg ttgaaccgaa tatcgaaagt | 1920 |

| | |
|---|---|
| ctggcagcaa ttagcctgat caatcaagaa tatcctcatc tgaaaatccg ctatgtgtat | 1980 |
| gtgctggatc tgctgaagct gcgtagtcgt aaaatcgatc cgcgtggtat tagtgatgaa | 2040 |
| gagtttgata aagtgtttac caaaaacaaa ccgattatct ttgcctttca tggctttgag | 2100 |
| ggactgctgc gcgatatttt ctttacccgt agcaaccata acctgattgc acatggttat | 2160 |
| cgtgaaaacg gtgatatcac aaccagcttt gatattcgtc agctgagtga gatggatcgt | 2220 |
| tatcatattg caaaagatgc tgccgaagcc gtgtatggta agatgcaaaa agcatttatg | 2280 |
| aacaaactgg atcagaaact ggaataccac cgcaactata tcgatgagta tggctatgat | 2340 |
| atgccggaag ttgtggaatg gaaatggaag aacatcaata agaaaat | 2388 |

<210> SEQ ID NO 85
<211> LENGTH: 2376
<212> TYPE: DNA
<213> ORGANISM: Mycoplasma crocodyli MP145

<400> SEQUENCE: 85

| | |
|---|---|
| atgaaaaaaa ccgtgtatga taccgaactg tatattgaga aactggatgc atggtttcgt | 60 |
| gcagcaaatt atctgagcgt tggtcagatg tatctgcgta taatccgct gctgcgtaac | 120 |
| aaaattacca aagatgatgt gaaagtgtat ccgattggtc attggggcac cattccgggt | 180 |
| cagaattttg catatgcaca tctgaatcgc gtgatcaaca atatgatct gaatatgttc | 240 |
| tacatcgaag gtcctggtca tggtggtcag gttatgacca gcaatagcta tctggatggt | 300 |
| agctatacag aactgtttcc gcatgttacc caggatctgg acggtatgaa acacctgttt | 360 |
| aaatacttta gctttccggg tggcaccgca agccatgcag caccggaaac accgggtagc | 420 |
| attcatgaag gtggtgaact gggttatagc ctgagccatg ccaccggtgc aattctggat | 480 |
| aatccgaatg ttattgcagc aaccattgtt ggtgatggtg aaagcgaaac cggtccgctg | 540 |
| gcagcaggtt ggtttagcaa tagttttatc aatccggtta tgatggtgc cgttctgccg | 600 |
| attctgcatc tgaacggtgg taaaattagc aatccgacca ttctgtgtcg caaaagcaat | 660 |
| gaagaactga ccaactattt tctgggtatg ggttgggaag ccatttttgt tgaaggtgaa | 720 |
| gatgtgcaga aaatgcataa actgatggca accaaactgg actatgccat tgaacgtatt | 780 |
| ctgagcattc agaaagaagc ccgtaaaggt aaagcagaag aggccacccg tccgctgtgg | 840 |
| ccgatgattg ttctgcgtac cccgaaaggt tggacaggtc gcagaaatg gaatagcgat | 900 |
| cagattgtgg gtagctttcg tgcccatcag gttccgattc cggtgaatag tgaaaatatg | 960 |
| acccatattg atgccctggt tgattggctg aaaagctata atgttgataa cctgttcgat | 1020 |
| aaaaagggca aactggttcc ggaaattgcc gaaatcgcac cggtgggtga tcgtcgtatg | 1080 |
| ggtatgaatc cggtgaccaa tggtggcctg aatccgcgta tctggcact gccgaattgg | 1140 |
| caggattttg cactgaatct ggaaaaacct ggtgcaaaaa ttgcacagga tatggttgag | 1200 |
| ctgggttcct atttttgcaaa agtgatgaa atgaataaag ataattttcg cctgttcggt | 1260 |
| ccggatgaaa ccaaaagtaa tcgtctgttt aacgtgttca agttaccag ccgtcagtgg | 1320 |
| ctggaaccga ttaacccgct gtttgatgaa gcactgagtc cggcaggtcg tgttattgat | 1380 |
| agccagctga gcgaacatca ggcagaaggt tttctggaag ttatgttct gaccggtcgc | 1440 |
| catggtgttt ttgcaagcta tgaaagcttt ctgcgtgttg tggatagcat gctgacccag | 1500 |
| catatgaaat ggctgaagaa agcaaatgat gttagctggc gtaatgatta tccgagcctg | 1560 |
| aatgtgattg cgaccagcac cgcatttcag caggatcata tggttatac acatcaggat | 1620 |
| ccgggtctga ttggccatct ggcagataaa actccggaac tgattcgtca gtatctgcct | 1680 |

```
gcagatacca ataccctgct ggcagttatg gataaaagcc tgaccgaacg taacgtgatt    1740
aaccatatca ttgcaagcaa acagcctcgc gaacagtttt atagcgcaaa agaagcagca    1800
gaactggttg aaaaaggtct gaaagtgatt aaatgggcaa gcaccgtgga aggtaatgat    1860
gaaccggatc tggttgttgc agcagcaggc accgaaccga acctggaagc cctggcagcc    1920
attacgattc tgaacaaaga atttccgaaa ctgaaaattc gcttcgtgaa tgtggttgac    1980
ctgatgaaac tgcgtcatcc gagcattgat ccgcgtggta ttaccgataa agaattcgac    2040
aaaatcttta cgaaagacaa gccggttctg tttgccttc atggttatga aggtatcctg    2100
cgcgatatct ttttcaaacg caataaccat aacctgatcg cacatggcta tcgtgaaaat    2160
ggtgatatca caaccagctt tgatattcgc cagctgtcac atatggatcg ttttcatatg    2220
gcagcaagcg cagcagttgc agcgctgggc aaaaaagcca atgcatttga aacaaaaatg    2280
ctggaaacca tcgattttca caccaaatat atccgcgaat acggcaccga tattccggaa    2340
gttaaagaat ggaagtggaa tcctctggtt cgcaaa    2376
```

<210> SEQ ID NO 86
<211> LENGTH: 2367
<212> TYPE: DNA
<213> ORGANISM: Neisseria sp. oral taxon 014 str. F0314

<400> SEQUENCE: 86

```
atgagcgcac agtatgatag cgcagattat ctgaataaag ttgatgcatg gtggcgtgca      60
gcaaactata ttagcgttgc acagatgtac ctgaaagata tccgctgct gatgcgtccg     120 attcaggcaa gtgatgttaa agcacatccg attggtcatt ggggcaccat tgcaggtcag     180
aattttatct atgcacatct gaatcgtgcc atcaacaaat atgatctgaa catgttctat     240
atcgaaggtc cgggtcatgg tggtcaggtt atggttagca atagctatct ggatggtagc     300
tatagcgaaa tctatccgaa tattacccag gatgaagcag gtctgaaaca gctgtgtaaa     360
atctttagct ttccgggtgg tattgcaagc catgcagcac cggaaacacc gggtagcatt     420
catgaaggtg gtgaactggg ttatgcactg agccatgccg ttggtgcagt tctggataac     480
ccggatgtta ttgcagcaac cgttattggt gatggtgaag cagaaaccgg tccgctgagc     540
gcaggttggt ttagcaatgt ttttatcaat ccggttaatg atggtgccgt gctgccgatt     600
ctgtatctga cggtggtaa aattcataac ccgaccattc tggcacgtaa agtgatgaa     660 agcctgcgtc tgtattttga aggtctgggt tgggatccga ttttgttga agccaccgat     720 tatgcaacca cccataaagt tatggcacag aaactggatg aggccatcga aaaaatcaaa     780
gccattcaga ccaaagcacg tgcaggtaaa gccgaagagg cagttatgcc gaaatggcct     840
gttctggttg cacgtctgcc gaaaggttgg acaggtccga aatgtggaa tggtgaaccg     900 attgaaggcg ttttcgtgc acatcaggtt cctattccgg caagcagcca tgatatggcc     960
accgttgata gcctggttga atggctgaaa agctatcgtc cggaagaact gttgatgca    1020 aatggcacct ttaaagcaga actgcgtgaa attagcccga aaggcgatcg tcgtatgagc    1080
accaatccga ttaccaatgg tggcattaat ccgcgtcctc tgaataccgc agattggaaa    1140
aaattcgcac tggataatag cgatcgtggt agtattatgg cccaggatat gattgaattt    1200
ggcaaatatg cagccgaact ggttaaagcg aatccggata ttttcgtat ttcggtccg     1260 gatgaaacca aaagcaatcg tatgaacgaa gtgttcaaag tgaccaatcg tcagtggctg    1320
gaaccgatcg ataaagcata tgatgaatgg atgagtccgg caggtcgtgt tattgatagt    1380
```

-continued

| | |
|---|---|
| cagctgagcg aacatcaggc agaaggtttt ctggaaggtt atgttctgac cggtcgtcat | 1440 |
| ggttttttg caagctatga aagctttctg cgtgttgtgg atagcatggc aacccagcac | 1500 |
| tttaaatggc tgcgtaaatg taaaacccat gcaccgtggc gtaaatcata ccgtcactg | 1560 |
| aatctgattg caaccagcac cgttttcag caggatcata atggttatac ccatcaggat | 1620 |
| ccgggtatgc tgacccatct ggcagaaaaa aaaccggaat ttatccgtga atatctgcct | 1680 |
| gcagatgcca atagcctgct ggccgttatg agcgaagttc tgagcagcaa agataaagtg | 1740 |
| aacctgatcg ttagcagtaa acatcctcgt ccgcagtttt atagtgcagc agaagcggaa | 1800 |
| gaattagttc gtgaaggtta caaagttatc gattgggcaa gcaccgataa aggtggcgaa | 1860 |
| ccggatgtgg ttattgccgc agccgcaaca gaaccgaatc tggaagcact ggcagcaatt | 1920 |
| acaattctga caaacagtt tccggaactg aaaatccgct ttattaacgt ggtggatatt | 1980 |
| ctgaaactgc gtcatcctaa agtggatccg cgtggtctga ccgatgaaca gttcgatgca | 2040 |
| ctgtttacca agacaaacc ggtgattttt tgctttcatg gctatgaagg tatggtgcgc | 2100 |
| gatatcttt ttgatcgcca taaccataat ctgcgcatcc atggttatcg tgaaaatggt | 2160 |
| gatattacca ccccgtttga tatgcgtgtt ctgagtgaaa tggatcgttt tcatgttgca | 2220 |
| aaagatgcag ccctggcagt ttatggtgac aaagcacagg attttgccaa aaaaatggac | 2280 |
| gataccctgg catttcatca cagctatatt cgcgaaaatg gcgaagatat tccggaagtt | 2340 |
| cgtaattgga aatgggaagc cctgaaa | 2367 |

<210> SEQ ID NO 87
<211> LENGTH: 2364
<212> TYPE: DNA
<213> ORGANISM: Eremococcus coleocola ACS-139-V-Col8

<400> SEQUENCE: 87

| | |
|---|---|
| atgaccgtgg actacaacag caaagaatat ctgaccctgg ttgataaatg gtggcgtgca | 60 |
| gcaaattatc tgagcgttgg tcagatgttt ctgcgtgata tccgctgct gcaagaagag | 120 |
| gttaccgcag atcatgttaa actgaatccg attggtcatt ggggcaccat tggtggccag | 180 |
| aattttctgt atgcacatct gaatcgcatt atcaacaagt ataatgtgaa tatgttttat | 240 |
| atcgaaggcc ctggtcatgg tggtcaggtt atggttacca atagctatct ggatggtagc | 300 |
| tataccgaac gttatccgga atttacccag gatattgccg gtatgaaaaa actgtttaaa | 360 |
| accttcagct ttccgggtgg tattggtagc catgcagcac cggaaacacc gggtagcatg | 420 |
| catgaaggtg gtgaactggg ttatgcactg agccatgcca ccggtgcaat tctggataac | 480 |
| ccggatgtta ttgcagcaac cgttgttggt gatggtaag cagaaaccgg tccgctggca | 540 |
| gcaggttggt ttagcaatgt ttttatcaat ccggtttcag atggtgcagt tctgccgatt | 600 |
| ctgtatctga tggtggtaa aattgcaaac ccgaccattc tggcacgtaa aagcaatgag | 660 |
| gatctgacca atatttcga aggtatgggt tggaaaccgt atattgttga aggcaccgat | 720 |
| ccggaacagg ttcatccgat tatggcaaaa gttctggatg aagtgattga agaaattcag | 780 |
| gccattcagg cagaagcccg taaaggtaaa gccgaagatg caaaaatgcc gcattggccg | 840 |
| atgatcctgt atcgtacccc gaaaggttgg acaggtccgg aagaagttga aggtaaaaca | 900 |
| attcagggta gctttcgtgc acatcaggtt ccgattccgg ttagcggtcg taatatggaa | 960 |
| gatattgatc tgctgatcaa ctggctgaaa agctatggtc ctgaagaact gttcaccgaa | 1020 |
| aatggcgaac tggtagatga actgaaagaa tttgcaccga aaggcgatca tcgtatggca | 1080 |
| atgaacccgc tgaccaatgg cggtaatccg aaaccgctga atatgccgaa ttggaaagat | 1140 |

```
tatgccctgg aaattggcac ccctggtagc aaagatgcac aggatatgat tgaatttggt    1200
ggttttgcgc gtgatatcgt gaaagaaaat ccggaaaact ttcgcatttt tggtccggat    1260
gaaaccaaaa gtaatcgcct gaataaagtg tttgaagtga ccaatcgtca gtggctggaa    1320
ccgattagcg aaaaatttga tgaaaacatg tcagcaagcg gtcgcgttat tgatagccag    1380
ctgagcgaac atcagaatca gggttttctg aagcatatg ttctgaccgg tcgtcatggt    1440
ttttttgcaa gctatgaaag ctttttcgt acggtggata gcatgattac ccagcacttt    1500
aaatggattc gcaaaagcgc aaaacatagc tggcgtaaac cttatcagag cctgaatctg    1560
attagcgcaa gcaccgtttt tcagcaggat cataatggtt atacccatca ggatccgggt    1620
ctgctgaccc atattggtga aaaacacggt gaatatatgc gtgcatatct gcctgcagat    1680
accaattcac tgctggcagt tatggataaa gcatttcgca gcgaaaacgt gattaactat    1740
gttgtgacca gcaaacatcc gcgtccgcag ttttttacag cagatgaagc cgaggaactg    1800
gttaatgaag gtctgaaagt tatcgattgg gccagtaccg ttaaagataa tgaagaaccg    1860
gatgtggtta ttgccgcagc cggtacagaa ccgaattttg aagcaattgc agcgatttcc    1920
tatctggtta aagcctttcc ggaactgaag attcgttttg ttaatgtggt tgacctgttt    1980
cgtctgcgta gtccggaaat tgatccgcgt ggtctgagtg atgatgaatt cgatgcaatc    2040
ttcaccaaag ataaaccggt gttttttgcc tttcatagct acgaaggcat gctgaaagac    2100 atcttttta cccgtcataa ccataatctg tacgcccatg gttatcgtga aatggtgaa     2160 attaccaccc cgtttgatat gcgcgttctg aatgaactgg atcgttttca tctgagtgca    2220
catgttgcag atgttgtgta tggtgataaa gcccgtgatt atgttgccga atgaaagggg    2280
aaagttcaag aacatcgtga ttacgtggaa gaatatggtg ccgatatgcc ggaagtagaa    2340
gattggaaat gggaggatat caaa                                          2364

<210> SEQ ID NO 88
<211> LENGTH: 2367
<212> TYPE: DNA
<213> ORGANISM: Aerococcus urinae ACS-120-V-Col10a

<400> SEQUENCE: 88
atgaccgact ttgacagcaa agcctatctg gataaagttg atgcatggtg gcgtgcagca      60
aattatctga gcgttggtca gatgtatctg cgtgataatc cgctgctgga tcgtgaagtt     120
accgcagatg atatcaaaat taccccgatt ggtcattggg gcaccattgc aggtcagaat     180
tttgtttatg cacatctgaa tcgcgtgatc aacaaatatg atctgaatat gttctacatc     240
gaaggtccgg gtcatggtgg tcaggttatg caggcaaatg catacctgga tggcacctgg     300
accgaacatt atccggaata tccgcagaat aaagaaggca tgcagaagtt cttcaaatat     360
ttcagctttc cgggtggcac cggtagccat gcaaccgcag aaattccggg tagcattcat     420
gaaggtggta aactgggtta tagcctgagt catgccaccg gtgcaattct ggacaatccg     480
gatgttattg cagcaaccgt tattggtgat ggtgaaagcg aaaccggtcc gctggcagca     540
agctggctga gcaatagctt tattaacccg gttaccgatg gtgcagttct gccgattctg     600
tatctgaatg gtggtaaaat tgcaaacccg accattctgg aacgtaaaag caatgaagat     660
ctgattaaat actttcaggg tctgggttgg gatccgatgg ttgttgaagg taatgatccg     720
gaaaaagttc atccgctgat ggcaaaaacc ctggatcagg caattgaaaa atcaaaagc     780 attcagggtg aagcccgtaa aggtagtgca gatgaagcaa ccatgggcca ttggccgatg     840
```

| | |
|---|---|
| atcctgtatc gtaccccgaa aggttggaca ggtccgaaag catgggaagg caatgatatt | 900 |
| gaaggttcat ttcgtgcaca tcaggttccg attccggtta atgcagaaaa tatggaacat | 960 |
| gtggatgccc tgattgattg gctgaaaagc tatcgtccgg aagaactgtt taccgaagaa | 1020 |
| ggtcagctgc gtcctgaaat tgccgaaatt gcaccgaaag cgatcagcg tatggcaagc | 1080 |
| aatccgatta cagatggtgg cattgatccg aaaccgctgg acctgccgga ttggcgtgat | 1140 |
| tatgcactgg attttgaaac accgggtgaa cgtgatgcac aggatatgat tgaaatgggt | 1200 |
| ggttatgccg caggcgttat cgaaaaaaat cctgataact ttcgcatctt cggtccggat | 1260 |
| gaaaccaaaa gtaatcgtct gaacaaagtg ttcaatgtga ccaaacgtca gtggctggaa | 1320 |
| ccgattaaag ataactatga tgaatggatg agcccgagcg tcgtgttat tgatagccag | 1380 |
| ctgagcgaac atcagatgga aggttttctg gaagcatata ccctgaccgg tcgtcatggt | 1440 |
| ttttttgcaa gctatgaagc atttattcgt accgtggata gcatgattac ccagcacttt | 1500 |
| aaatggatgc gcgaagcaag cgagtataaa tggcataaac cgtatcagag cctgaacctg | 1560 |
| attagcagca gcaccgcatt tcagcaggat cataatggtt ataccatca ggatccgggt | 1620 |
| ctgctgaccc atctggcaga aaaaaaggt gaatttgtgc gtgcatatct gcctgcagat | 1680 |
| accaatagcc tgctggcagt tatggacaaa gcactgagca gcgaaaatgt gattaactat | 1740 |
| attgtgacca gcaaacatcc gcgtccgcag ttttttagcg ttgaagaagc agaagagttc | 1800 |
| gtcgataaag gctataaagt tatcgattgg gcaagcaccg tggaagaggg cgaagaaccg | 1860 |
| gatgtggtga ttgcagccag cggcaccgaa ccgaccgttg aaaccattgc caccattagc | 1920 |
| tatctgcatg aagcctttcc ggaactgaaa attcgttatg ttaatgtggt ggatctgtat | 1980 |
| cgcctgcgtc atccgaatat cgatccgcgt ggtctgagtg atgaagaatt tgatgccgtt | 2040 |
| ttcaccaaag ataaaccggt gttttttggc tttcatagct ttgaaggcct gctgaaagat | 2100 |
| atcttctttg atcgccataa ccataacctg tatccgcatg gttatcgtga ggaaggtgcc | 2160 |
| attaccaccc cgtttgatat gcgtgttctg aatgaactgg atcgctttca ttttgcagca | 2220 |
| catgttgccg aagttgtgta tggtgataaa gcccaggatt ttatcgatca gatgaatgcc | 2280 |
| aaagtggaag aacatcgtgc gtatattgtt gaatatggca ccgatatgcc ggaagtgaaa | 2340 |
| gaatggaaat ggcagccgct ggaaaaaa | 2367 |

<210> SEQ ID NO 89
<211> LENGTH: 2376
<212> TYPE: DNA
<213> ORGANISM: Kingella kingae ATCC 23330

<400> SEQUENCE: 89

| | |
|---|---|
| atgaccaaca aaacccagtt cgacacaccg gaatatctgg gtaaagttga tgcatggtgg | 60 |
| cgtgcagcaa actatattag cgttgcacag atgtatctga agataatcc gctgctgaaa | 120 |
| acaccgctgg ttgcaaatga tgttaaagca catccgattg gtcattgggg caccgttccg | 180 |
| ggtcagaatt ttatctatgc acatctgaat cgtgccatca caaatatga tgtggacatg | 240 |
| ttttatatcg aaggtcctgg tcatggtggt caggttatgg ttagcaatag ctatctggat | 300 |
| ggtagctata ccgaaatcta tccggatatt acccaggata ccgcaggtct gaaaaaactg | 360 |
| tgtaaaatct ttagctttcc gggtggtatt gcaagccatg cagcaccgga acaccgggt | 420 |
| agcattcatg aaggtggtga actgggttat gcactgagcc atgcctttgg tgcagttctg | 480 |
| gataacccga tgttattgc agcagcagtt attggtgatg tgaagcaga aaccggtccg | 540 |
| ctgtgtgcag gttggtttgg taataccttt attaacccgg ttaatgatgg tgccgtgctg | 600 |

```
ccgattctgt acctgaatgg tggtaaaatt cataatccga ccattctggc acgtaaaacc      660
gatgaagaac tgaaacagta ttttaacggt atgggttggg aaccgatttt tgtggatgtt      720
aacaacgtgg ataactatca cgaaattatg agccagaaag tggatgaagc cgttgaacat      780
attctgagca tttggcagac cgcacgtacc cagaaagccg aagatgcaac catgccgcat      840
tggcctgttc tggttgcccg tattccgaaa ggttggacag gtccgaaaac ctggcatggc      900
gaaccgatcg aaggcggttt tcgtgcacat caggttccga ttccggcaag cagccatgat      960
atggaaaccg caggcgaact ggaaaaatgg ctgcgtagct atcgtccgga agaacttttt     1020
gatgataatg gttgcttcct ggataagtgg cgtgatatta gcccgaaagg cgcaaaacgt     1080
atgagcgttc atccgatcac caatggtggc attaatccga aagcactggt tatgccggat     1140
tggacccagc atgcactgga aattggtgtt ccaggtagcc aggatgcaca ggatatggtt     1200
gaatgtggtc gtctgatggc agatgttgtt accgcaaatc cgaataactt tcgtattttt     1260
ggtccggaca aaaccaaaag caatcgtctg aatcaggttt ttcaggttac caaacgtcag     1320
tggctgggtc gccgtgatga agcatatgat gaatggattg caccggttgg tcgtgttatt     1380
gatagccagc tgagcgaaca tcaggcagaa ggttttctgg aaggttatgt tctgaccggt     1440
cgtcatggtt tttttgcaag ctatgaaagc tttttcgtg tggtggatag catgattacg     1500 cagcactttta aatggcttcg caaatgtaaa acccacgcag catggcgtaa tgattatccg     1560
agcctgaatc tgattgcaac cagcaccgtg tttcagcagg atcataatgg ctatacccat     1620
caggatccgg gtctgctgac ccatctggca gaaaaaaaac cggaatttgt gcgtgaatat     1680
ttaccggcag atagcaatac cctgatggcc gttatgagcg aagcactgac cagccgtgat     1740
cgtattaacc tgattgttag cagtaaacat ctgcgtccgc agttttttcaa tgcagaagaa     1800 gcaaaagaac tggttcgcga aggctataaa gtgattgatt gggcaagcac ctgtcatgac     1860
ggtgaaccgg atgttgtgat cgcagccgca ggcaccgaac cgaatatgga agccctggca     1920
gcaattagca ttctgcacaa acagtttccg gaactgaaga ttcgttttat caacgttgtg     1980
gatatcctga actgcgtca tccgagcatt gatccgcgtg gtctgagtga tgaacagttt     2040
gatgcactgt ttacccaaga aaaacctgtg tgttttttgct ttcatggtta tgaaggtatg     2100
attcgcgacc tgttttttcc gcgtgcaaac cataatgttc gtattcatgg ctatcgcgaa     2160
aatggcgata ttacaacccc gtttgatatg cgtgttctgt cagaaatgga tcgttttcat     2220
gttgccaaag atgccgcaca ggcagtttat ggtgataaag caagcgaatt cgccaaaaaa     2280
atgggtgaaa ccgttgcatt tcatcgttcc tatattcgtg aacatggcac cgatattccg     2340
gaagttgcag aatggaaatg gcagccgctg gccaaa                               2376
```

<210> SEQ ID NO 90
<211> LENGTH: 2382
<212> TYPE: DNA
<213> ORGANISM: Streptococcus criceti HS-6

<400> SEQUENCE: 90

```
atgaatacca acttcgatag cagcgattac ctgaataaag ttgatgcatg gtggcgtgca       60
gcaaactata ttagcgcagc acagatgtat ctgaaagata atccgctgct gcgtcgtgaa      120
gttgcagcag aagatctgaa aagccatccg attggtcatt ggggcaccgt tccgggtcag      180
aattttatct atgcacatct gctgcgctcc atcaacaaat atgatctgga tatgttctat      240
atcgaaggtc ctggtcatgg tggtcaggtt atggttagca atagctatct ggatggtagc      300
```

```
tataccgaac tgaatccgca gattagccag accgaagagg gtctgaaaca gctgtgtaaa    360
atctttagct ttccgggtgg tattgcaagc catgcagcac cggaaacacc gggtagcatt    420
catgaaggtg gtgaactggg ttatgcactg agccatgcca ccggtgcagt tctggataac    480
ccggatgtta ttgcagcaac cgttattggt gatggtgaaa gcgaaaccgg tccgctgatg    540
gcaggttggc tgagcaatac ctttattaac ccggttaatg atggtgccgt tctgccgatt    600
cattttctga tggtggcaa aattcataat ccgaccatct ttgaacgtaa aagcgacgat    660
gaactgaaag ccttttttac cggtctgggt tggaaaccga ttttttgcaga tgttaccgca    720
tttgcaagcg atcatgcagc cgcacataaa ctgtttgcag ccaaactgga tgaagccatt    780
gaagaaattc gtaacattca ggcaaaagcc cgtaaaggta gcgcagatga agcaaccatg    840
cctgcatggc ctgttattgt tgcacgtatt ccgaaaggtt ggacaggtcc gaaaagctgg    900
aaaggcaccc cgattgaagg cggttggcgt gcccatcagg ttccgattcc ggttgatagc    960
catcatatgg aacatgttga tgccctgctg gattggctga aaagttatca gccggaagaa   1020
ctgttcgatg cagaaggtca tctgaaatca gaagtggcag ccctgagccc gaaaggcaat   1080
cgtcgtatga gcatgaatcc gattaccaat gccggtgtta ttaaaccgat ggatacagcc   1140
gattggaaaa acgtgcatt tgatattcag accccctggtg aaattgttgc ccaggatatg   1200
attgaatttg gcaaatatgc cgcagatctg gttgaagcaa atccggataa ttttcgtatt   1260
tttggtccgg atgaaagcaa aagcaatcgc ctgaatgaag tgtttaccaa aaccaatcgt   1320
cagtggatgg gtcgtcgtga tccgagctat gatgaatggc tgagtccggc aggtcgtgtt   1380
attgatagtc agctgagcga acatcaggcc gaaggttttc tggaaggtta tgttctgacc   1440
ggtcgtcatg gttttttgc cagctatgaa agctttctgc gtgttgtgga taccatgatt   1500
acccagcact ttaaatggct gcgtaaaagt aaaacccata ccacctggcg taaaaactat   1560
ccgagcctga atctgattgc aaccagcacc gttttttcagc aggatcataa tggttataca   1620
catcaggatc cgggtgtgct gacccatctg agtgaaaaaa ctccggaata tatccgtgaa   1680
tatctgcctg cagataccaa tagcctgctg gcggttatgg ataaagcatt taaagatgag   1740
gacaaaatta acctgatcgt gaccagcaaa catccgcgtc cgcagttttta tagcgttgaa   1800
gaagcaagcg aactggtcga aaaaggctat aaagtgattg attgggcaag caccgtgcag   1860
gcaaatgaag aaccggatgt ggttttttgcc gcagcaggca cagaaccgaa tctggaagca   1920
ctggcagcaa ttagcattct gcacaaaacc tttccgagtc tgaaaattcg ttttgtgaac   1980
gtggtggata ttctgaaact gcgtcatccg gacctggatc cgcgtggtct gtctgatgaa   2040
gaatttgata agtgttcac gaaagacaag ccggtgatct ttgcatttca tgcatatgaa   2100
ggtatgatcc gcgatatctt ttttcgtcgc cataaccata atctgcatgt gcatggttat   2160
cgcgaaaatg gtgatattac cacccccgttt gatatgcgtg ttatgtcaga actggatcgt   2220
tttcatctgg cacaggatgc cgcactgacc accctgggtg aaaaagcaca ggcatttagc   2280
gcaaaaatgg atgaaaccgt tgcctatcac aaagattata ttcgtgaaca tggggatgat   2340
attccggaag tgcagaattg gcagtgggaa aatctggacg aa                      2382
```

```
<210> SEQ ID NO 91
<211> LENGTH: 2361
<212> TYPE: DNA
<213> ORGANISM: Streptococcus criceti HS-6

<400> SEQUENCE: 91
atgaccgagt tcgacagcaa agattatctg gcaaaagttg atgcatggtg gcgtgcagca    60
```

```
aactatatta gcgttgcaca gatgtatctg aaagataatc cgctgctgcg tcgtgaagtt    120
agcaaagaag atgttaaagt tcatccgatt ggtcattggg gcaccattgc aggtcagaat    180
tttatctatg cacatctgaa tcgcgtgatc aacaaattcg atctgaacat gttttatatc    240
gaaggtccgg tcatggtgg tcaggttatg gttagcaata gctatattga tggcagctat     300
accgaacgct atccgaatat tacccaggat gaagatggtc tgaaacagct gtgtaaaatc    360
tttagctttc cgggtggtat tgcaagccat gcagcaccgg aaacaccggg tagcattcat    420
gaaggtggtg aactgggtta tgcactgagc catgccaccg gtgcaattct ggataacccg    480
gatgttattg cagcaaccgt tattggtgat ggtgaagcag aaaccggtcc gctgaatgca    540
ggttggttta gtaataccct tattaacccg gttaatgatg gtgcagttct gccgattctg    600
tacctgaatg gcgtaaaaat tcataatccg accattctga gccgtaaaac cgatgaagaa    660
ctgacccacc tgtttcaggg tctgggttgg gaaccgtatt ttgttgaagg taatgatccg    720
gaagttatcc atagccagat ggccgaaacc ctggataaag ttatcgaaaa aatcaagacc    780
attcagaccc aggcacgtca gaaacctgca gaagaggcac agcaggcaca gtggcctgtt    840
ctgattgttc gtaccccgaa aggttggaca ggtccgaaag aatggaatgg tgaaccgatt    900
gaaggcggtt ttcgtgcaca tcaggttccg attccggttg aagcaggtca tatggaacat    960
atcgatgccc tgaccgattg gctgaaaagc tatcgtccgg aagaactttt tgatgagaaa   1020
ggctatgtga agaagagat cgcgttatt tcaccgaaag gcaatcgtcg tatgagcatg      1080
aatccgatta ccaatgccgg tattgtgaaa aaactggatc tggcagattg gcgtaaacat   1140
gcaattgata ccagcaaacc gggttccatt atgaaacagg atatgatcga attcggcaaa   1200
tatgcagcag atctggttaa agcaaatccg gataactttc gtattttcgg tccggatgaa   1260
accaaaagca atcgcctgaa taatgttttt accgcaacca atcgtcagtg gctggcaccg   1320
cgtgataaaa gttatgatga atggattagt ccggtgggtc gtgttattga tagtcagctg   1380
agcgaacatc aggcagaagg ttttctggaa ggttatgttc tgaccggtcg tcatggtttt   1440
tttgcaagct atgaaagctt tctgcgtgtt gtggatagca tgattacaca gcactttaaa   1500
tggctgcgta aaagcaaaac ccatacggat tggcgcaaaa actatccgag cctgaatctg   1560
attgcaacca gcaccgtttt tcagcaggat cataatggtt ataccatca ggatccgggt    1620 ctgctgaccc atctggcgga aaaaccccca gaatatgttc gtgaatatct gcctgcagat   1680
tccaatagcc tgtttgcagt tatggaatat gccctggcag acgaagataa agtgaatgtg   1740
attgtgacca gtaaacatcc gcgtccgcag ttttatagcg tggcagaagc acaagaactg   1800
gtaaaagaag gctacaaagt aattgattgg gccagcaatg atcatgatgg cgaaccggat   1860 attgttttg cagccgcagg caccgaaccg aatctggaag ttctggcagg tattagcctg    1920
ctgcacaaag catttccaga agtgaaaatt cgctttatca acgtggtgga tattctgaaa   1980
ctgcgcagcc cgaaagtgga tccgcgtggt ctgagtgatg aagcatttaa caaactgttc   2040
accaccgata aaccgatcgt ttttgcctat catggttatg aaggtcagat tcgtgacctg   2100
ttttttaacc gcgataacca caaagtgtat atccatggct atcgcgaaaa tggtgatatt   2160
accaccccgt tgatatgcg tgttatgagc gaaatggatc gctttcatat tgcaaaagaa    2220
gcagcacagg ccgttctggg tgataaagca cagggttttg cccaagaaat ggcagataaa   2280
ctggcatatc ataccgccta tattcgtgaa catggtgatg atatcccgga agtgcagaat   2340
tggcagtggg aaaccattga t                                             2361
```

<210> SEQ ID NO 92
<211> LENGTH: 2382
<212> TYPE: DNA
<213> ORGANISM: Mycoplasma columbinum SF7

<400> SEQUENCE: 92

| | | | | | |
|---|---|---|---|---|---|
| atgagcaaaa | ccaattttga | tagcaaaaaa | tacctggata | agatccatgc | atggtggcgt | 60 |
| gcagcaaatt | atctgagcgt | tggtcagatg | tatctgaaaa | ataacccgct | gctgcaagaa | 120 |
| ccgctgaaag | atgaagatat | caaaatctat | ccgattggtc | attggggcac | cattccgggt | 180 |
| cagaatctga | tttatgcaca | tctgaatcgc | gtgatcaaca | aatatgatct | gaatatgttc | 240 |
| tacatcgaag | gtcctggtca | tggtggtcag | gttatgatta | gcaatagcta | tctggatggt | 300 |
| agctataccg | aactgtttcc | ggaaattacc | caggatctgg | caggtctgaa | taaaatgttt | 360 |
| aaacgcttta | gctttccggg | tggcaccgca | agccatgcag | caccggaaac | accgggtagc | 420 |
| attcatgaag | tggtgaact | gggttatgca | ctgagccatg | ccaccggtgc | aattctggat | 480 |
| aatccggatg | ttattgcagc | aaccgttatt | ggtgatggtg | aagcagaaac | cggtccgctg | 540 |
| atggcaggtt | ggtatagcag | cagctttatt | aacccggtta | atgatggcac | cgttctgccg | 600 |
| attctgcata | ttaatggtgg | taaaattagc | aacccgacca | ttctggcacg | taaaaccgat | 660 |
| aaagaaatta | acagctgct | ggcaggcttt | ggttgggaag | caattttgt | tgaagccgat | 720 |
| gtttttcgtc | cggaagccat | tcatctgagc | atggcaaaag | catttgataa | agccatcgaa | 780 |
| aaaattcagc | gtattcagcg | cgaagcacgt | gcaaatagcg | caaatcatgc | aaaacgtccg | 840 |
| atttggcctg | cactggttgt | tcgtaccccg | aaaggttgga | cctgtccgca | taaaattgat | 900 |
| gataaagtgt | atgaaggtag | cttcgtagc | catcaggttc | cgctggcagt | tagcagcgaa | 960 |
| aataccacca | aaaagttga | tctggtgaat | tggctggaaa | gctataaacc | gcgtgaactg | 1020 |
| ttcaatcagg | atggttcatt | taaagcccat | tatgccgaaa | ttgcaccgaa | aggcaataaa | 1080 |
| cgtatggcaa | tgaatccgat | taccaacggt | ggtattaatc | cgaaaaatct | ggatctgccg | 1140 |
| aattgggaac | agtttgccat | tgatttcgat | aaaccgggtg | ccattaaagc | acaggatatg | 1200 |
| gttagcgcag | gcacctggtt | tgcagatgtg | attaaacgta | atccgaccaa | ctttcgtatc | 1260 |
| tttggtccgg | atgaaaccaa | aagcaatcgt | ctgtttgatg | tgctgaaaac | caccaatcgt | 1320 |
| cagtggttag | aacgtgttga | ttatgacctg | gatgaaaaca | tcggtccggc | aggtcgtgtt | 1380 |
| attgatagcc | agctgagcga | acatcaggca | gaaggtttc | tggaaggtta | tgttctgacc | 1440 |
| ggtcgtcatg | gtatgtttgc | aagctatgaa | agctttctgc | gtgttgtgga | tagcatgctg | 1500 |
| acccagcata | tgaaatgggt | tgcaaaagcg | aaaaaagtgc | attggcgtaa | tgattatccg | 1560 |
| agcctgaatg | tgattgcaac | cagcaccgca | tttcagcagg | atcataatgg | ttatacacat | 1620 |
| caggatccgg | gtattctggg | tcatctggcc | gataaaaaac | cggaactgat | tcgtgaatat | 1680 |
| ctgcctgcag | atagcaatac | cctgctggcc | gtgctggata | agcttttaa | agaacgtgat | 1740 |
| gtcatcaacc | tgattgtggc | aagcaaacag | cctcgtgaac | agtggtttag | cccacgtgaa | 1800 |
| gcaaatattc | tggttaaaaa | tgggctgaaa | gttattagct | gggcaagcac | ctgtaccctg | 1860 |
| gaagaagaac | cggatctggt | tgtggcagca | gcaggtacag | aaccgacact | ggaagcactg | 1920 |
| gcagcaatta | gttatctgaa | tgaaaaattc | ccgaccctga | aaatccgttt | tgttaatgtt | 1980 |
| gtagacctgc | tgaaactgcg | tcatccgagc | attgatccgc | gtggtctgag | caattatgaa | 2040 |
| ttcgatagca | tctttaccaa | ggacaaaccg | atcctgtttg | cctttcatgg | ttatgaagcc | 2100 |
| ctgattcgcg | atattttctt | cctgcgcaat | aaccataatc | tgcacattca | tggctatcgc | 2160 |

```
gaaaatggtg atattaccac gagctttgat attcgtctga tgagcgaaat ggatcgtttt    2220
catatggcac agaccgcagc aaaagccgtt ctgggttacg ataaagcaaa aagcttcgtc    2280
gataaaatgc aggacaaaat cgatcagcat aatgcctaca tcaaagaaca tggcatcgat    2340
atggatgaag ttcgctattg gacatggaaa ggcctgaaca aa                       2382
```

<210> SEQ ID NO 93
<211> LENGTH: 787
<212> TYPE: PRT
<213> ORGANISM: Enterococcus gallinarum

<400> SEQUENCE: 93

```
Met Glu Thr Thr Phe Asp Thr Gln Glu Tyr Phe Asp Lys Met Asn Ala
1               5                   10                  15

Trp Trp Arg Ala Ala Asn Tyr Leu Ser Val Gly Gln Ile Tyr Leu Lys
            20                  25                  30

Asp Asn Pro Leu Leu Arg Arg Pro Ile Glu Glu Lys Asp Leu Lys Val
        35                  40                  45

Asn Pro Ile Gly His Trp Gly Thr Ile Ala Gly Gln Asn Phe Ile Tyr
    50                  55                  60

Thr His Leu Asn Arg Val Ile Asn Lys Tyr Asp Leu Asn Met Phe Tyr
65                  70                  75                  80

Ile Glu Gly Pro Gly His Gly Gly Gln Val Met Val Ser Asn Ala Tyr
                85                  90                  95

Leu Asp Gly Ser Tyr Thr Glu Ile Tyr Pro Glu Val Thr Gln Asp Glu
            100                 105                 110

Ala Gly Met Gln His Leu Phe Lys Ile Phe Ser Phe Pro Gly Gly Ile
        115                 120                 125

Ala Ser His Ala Ala Pro Glu Thr Pro Gly Ser Ile His Glu Gly Gly
    130                 135                 140

Glu Leu Gly Tyr Ser Ile Ala His Gly Thr Gly Ala Val Leu Asp Asn
145                 150                 155                 160

Pro Asp Val Ile Ala Ala Val Val Val Gly Asp Gly Glu Ala Glu Thr
                165                 170                 175

Gly Pro Leu Ala Gly Ser Trp Phe Ser Asn Thr Phe Ile Asn Pro Val
            180                 185                 190

Asn Asp Gly Ala Val Leu Pro Ile Leu His Leu Asn Gly Ala Lys Ile
        195                 200                 205

Ser Asn Pro Thr Ile Leu Ala Arg Lys Ser Asp Glu Asp Leu Thr Lys
    210                 215                 220

Tyr Phe Glu Gly Met Gly Trp Thr Pro Tyr Phe Val Glu Gly Asp Asp
225                 230                 235                 240

Pro Ala Thr Val His Pro Gln Met Ala Arg Ala Leu Asp Arg Ala Val
                245                 250                 255

Glu Gln Ile Lys Ala Ile Gln Thr Lys Ala Arg Gln Gly Lys Ala Asp
            260                 265                 270

Glu Ala Val Met Pro His Trp Pro Val Leu Ile Val Arg Thr Pro Lys
        275                 280                 285

Gly Trp Thr Gly Pro Lys Ile Trp Glu Gly Glu Pro Ile Glu Gly Gly
    290                 295                 300

Phe Arg Ala His Gln Val Pro Ile Pro Val Asn Ala His Gln Met Glu
305                 310                 315                 320

His Val Asp Ala Leu Ile Asp Trp Leu Lys Ser Tyr Lys Pro Glu Glu
                325                 330                 335
```

```
Leu Phe Asp Glu Ser Gly Arg Ile Lys Ala Glu Ile Gln Glu Leu Ala
            340                 345                 350

Pro Lys Gly Gln Gln Arg Met Ala Met Asn Pro Ile Thr Asn Gly Gly
            355                 360                 365

Ile Asp Pro Gln Pro Leu Lys Ile Thr Asp Trp Arg Gln His Ala Ile
370                 375                 380

Asp Ile Gly Val Pro Gly Ser Thr Thr Ala Gln Asp Met Met Glu Phe
385                 390                 395                 400

Gly Lys Phe Ala Arg Asp Leu Ile Val Glu Asn Pro Thr Asn Phe Arg
            405                 410                 415

Ile Phe Gly Pro Asp Glu Ala Lys Ser Asn Arg Leu Asn His Val Phe
            420                 425                 430

Glu Val Thr Asn Arg Gln Trp Leu Glu Pro Lys Gln Pro Asn Tyr Asp
            435                 440                 445

Glu Trp Leu Ser Ala Thr Gly Arg Val Ile Asp Ser Gln Leu Ser Glu
            450                 455                 460

His Gln Ala Glu Gly Phe Leu Glu Gly Tyr Val Leu Thr Gly Arg His
465                 470                 475                 480

Gly Phe Phe Ala Ser Tyr Glu Ser Phe Leu Arg Val Val Asp Ser Met
                485                 490                 495

Ile Thr Gln His Phe Lys Trp Thr Arg Lys Ser Lys Glu Leu Pro Trp
            500                 505                 510

Arg His Ala Tyr Pro Ser Leu Asn Leu Ile Ala Ser Ser Thr Val Phe
            515                 520                 525

Gln Gln Asp His Asn Gly Tyr Thr His Gln Asp Pro Gly Ile Met Thr
            530                 535                 540

His Ile Ala Glu Lys Lys Ala Glu Phe Val Arg Val Tyr Leu Pro Ala
545                 550                 555                 560

Asp Ala Asn Ser Leu Met Ala Val Met Ala Glu Thr Phe Gln Thr Glu
                565                 570                 575

Glu Gln Ile Asn Leu Ile Val Ser Ser Lys His Pro Arg Pro Gln Phe
            580                 585                 590

Tyr Thr Ala Glu Glu Ala Glu Ile Leu Val Lys Asp Gly Leu Lys Ile
            595                 600                 605

Ile Asp Trp Ala Ser Thr Asp Gln Gly Glu Pro Asp Leu Val Ile Ala
610                 615                 620

Ala Ala Gly Thr Glu Pro Asn Leu Glu Ala Leu Ala Ala Val Ser Leu
625                 630                 635                 640

Leu Asn Glu Ala Phe Pro Glu Leu Lys Ile Arg Phe Ile Asn Val Val
                645                 650                 655

Asp Leu Leu Lys Ile Arg His Pro Asp Val Asp Pro Arg Gly Leu Thr
            660                 665                 670

Asp Glu Glu Phe Glu Ala Tyr Phe Thr Lys Asp Lys Pro Ile Ile Phe
            675                 680                 685

Ala Phe His Gly Tyr Glu Gly Leu Ile Arg Asp Ile Phe Phe Gly Arg
            690                 695                 700

Lys Asn Gln Arg Leu His Ile His Gly Tyr Arg Glu Asn Gly Asp Ile
705                 710                 715                 720

Thr Thr Pro Phe Asp Met Arg Ile Leu Ser Glu Leu Asp Arg Phe His
                725                 730                 735

Leu Ala Lys Asp Gly Ala Glu Trp Val Tyr Gly Glu Gln Ala Ala Asp
            740                 745                 750
```

```
Phe Ala Gln Arg Met Thr Glu Thr Val Ala Tyr His Tyr Asp Phe Ile
            755                 760                 765

Arg Glu Asn Gly Tyr Asp Ile Ala Glu Val Gln Asp Trp Gln Trp Lys
            770                 775                 780

Pro Leu Lys
785

<210> SEQ ID NO 94
<211> LENGTH: 796
<212> TYPE: PRT
<213> ORGANISM: Clostridium acetobutylicum

<400> SEQUENCE: 94

Met Gln Ser Ile Ile Gly Lys His Lys Asp Glu Gly Lys Ile Thr Pro
1               5                   10                  15

Glu Tyr Leu Lys Lys Ile Asp Ala Tyr Trp Arg Ala Ala Asn Phe Ile
            20                  25                  30

Ser Val Gly Gln Leu Tyr Leu Leu Asp Asn Pro Leu Leu Arg Glu Pro
        35                  40                  45

Leu Lys Pro Glu His Leu Lys Arg Lys Val Val Gly His Trp Gly Thr
    50                  55                  60

Ile Pro Gly Gln Asn Phe Ile Tyr Ala His Leu Asn Arg Val Ile Lys
65                  70                  75                  80

Lys Tyr Asp Leu Asp Met Ile Tyr Val Ser Gly Pro Gly His Gly Gly
                85                  90                  95

Gln Val Met Val Ser Asn Ser Tyr Leu Asp Gly Thr Tyr Ser Glu Val
            100                 105                 110

Tyr Pro Asn Val Ser Arg Asp Leu Asn Gly Leu Lys Lys Leu Cys Lys
        115                 120                 125

Gln Phe Ser Phe Pro Gly Gly Ile Ser Ser His Met Ala Pro Glu Thr
    130                 135                 140

Pro Gly Ser Ile Asn Glu Gly Gly Glu Leu Gly Tyr Ser Leu Ala His
145                 150                 155                 160

Ser Phe Gly Ala Val Phe Asp Asn Pro Asp Leu Ile Thr Ala Cys Val
                165                 170                 175

Val Gly Asp Gly Glu Ala Glu Thr Gly Pro Leu Ala Thr Ser Trp Gln
            180                 185                 190

Ala Asn Lys Phe Leu Asn Pro Val Thr Asp Gly Ala Val Leu Pro Ile
        195                 200                 205

Leu His Leu Asn Gly Tyr Lys Ile Ser Asn Pro Thr Val Leu Ser Arg
    210                 215                 220

Ile Pro Lys Asp Glu Leu Glu Lys Phe Phe Glu Gly Asn Gly Trp Lys
225                 230                 235                 240

Pro Tyr Phe Val Glu Gly Glu Asp Pro Glu Thr Met His Lys Leu Met
                245                 250                 255

Ala Glu Thr Leu Asp Ile Val Thr Glu Glu Ile Leu Asn Ile Gln Lys
            260                 265                 270

Asn Ala Arg Glu Asn Asn Asp Cys Ser Arg Pro Lys Trp Pro Met Ile
        275                 280                 285

Val Leu Arg Thr Pro Lys Gly Trp Thr Gly Pro Lys Phe Val Asp Gly
    290                 295                 300

Val Pro Asn Glu Gly Ser Phe Arg Ala His Gln Val Pro Leu Ala Val
305                 310                 315                 320

Asp Arg Tyr His Thr Glu Asn Leu Asp Gln Leu Glu Glu Trp Leu Lys
                325                 330                 335
```

```
Ser Tyr Lys Pro Glu Glu Leu Phe Asp Glu Asn Tyr Arg Leu Ile Pro
            340                 345                 350

Glu Leu Glu Glu Leu Thr Pro Lys Gly Asn Lys Arg Met Ala Ala Asn
            355                 360                 365

Leu His Ala Asn Gly Gly Leu Leu Arg Glu Leu Arg Thr Pro Asp
370                 375                 380

Phe Arg Asp Tyr Ala Val Asp Val Pro Thr Pro Gly Ser Thr Val Lys
385                 390                 395                 400

Gln Asp Met Ile Glu Leu Gly Lys Tyr Val Arg Asp Val Val Lys Leu
                405                 410                 415

Asn Glu Asp Thr Arg Asn Phe Arg Ile Phe Gly Pro Asp Glu Thr Met
            420                 425                 430

Ser Asn Arg Leu Trp Ala Val Phe Glu Gly Thr Lys Arg Gln Trp Leu
            435                 440                 445

Ser Glu Ile Lys Glu Pro Asn Asp Glu Phe Leu Ser Asn Asp Gly Arg
450                 455                 460

Ile Val Asp Ser Met Leu Ser Glu His Leu Cys Glu Gly Trp Leu Glu
465                 470                 475                 480

Gly Tyr Leu Leu Thr Gly Arg His Gly Phe Phe Ala Ser Tyr Glu Ala
                485                 490                 495

Phe Leu Arg Ile Val Asp Ser Met Ile Thr Gln His Gly Lys Trp Leu
            500                 505                 510

Lys Val Thr Ser Gln Leu Pro Trp Arg Lys Asp Ile Ala Ser Leu Asn
            515                 520                 525

Leu Ile Ala Thr Ser Asn Val Trp Gln Gln Asp His Asn Gly Tyr Thr
530                 535                 540

His Gln Asp Pro Gly Leu Leu Gly His Ile Val Asp Lys Lys Pro Glu
545                 550                 555                 560

Ile Val Arg Ala Tyr Leu Pro Ala Asp Ala Asn Thr Leu Leu Ala Val
                565                 570                 575

Phe Asp Lys Cys Leu His Thr Lys His Lys Ile Asn Leu Leu Val Thr
            580                 585                 590

Ser Lys His Pro Arg Gln Gln Trp Leu Thr Met Asp Gln Ala Val Lys
            595                 600                 605

His Val Glu Gln Gly Ile Ser Ile Trp Asp Trp Ala Ser Asn Asp Lys
610                 615                 620

Gly Gln Glu Pro Asp Val Val Ile Ala Ser Cys Gly Asp Thr Pro Thr
625                 630                 635                 640

Leu Glu Ala Leu Ala Ala Val Thr Ile Leu His Glu His Leu Pro Glu
                645                 650                 655

Leu Lys Val Arg Phe Val Asn Val Val Asp Met Met Lys Leu Leu Pro
            660                 665                 670

Glu Asn Glu His Pro His Gly Leu Ser Asp Lys Asp Tyr Asn Ala Leu
            675                 680                 685

Phe Thr Thr Asp Lys Pro Val Ile Phe Ala Phe His Gly Phe Ala His
690                 695                 700

Leu Ile Asn Gln Leu Thr Tyr His Arg Glu Asn Arg Asn Leu His Val
705                 710                 715                 720

His Gly Tyr Met Glu Glu Gly Thr Ile Thr Thr Pro Phe Asp Met Arg
                725                 730                 735

Val Gln Asn Lys Leu Asp Arg Phe Asn Leu Val Lys Asp Val Val Glu
            740                 745                 750
```

Asn Leu Pro Gln Leu Gly Asn Arg Gly Ala His Leu Val Gln Leu Met
    755                 760                 765

Asn Asp Lys Leu Val Glu His Asn Gln Tyr Ile Arg Glu Val Gly Glu
    770                 775                 780

Asp Leu Pro Glu Ile Thr Asn Trp Gln Trp His Val
785                 790                 795

<210> SEQ ID NO 95
<211> LENGTH: 2439
<212> TYPE: DNA
<213> ORGANISM: Listeria grayi

<400> SEQUENCE: 95

```
atggttaaag acattgtaat aattgatgcc ctccgtactc ccatcggtaa gtaccgcggt      60
cagctctcaa agatgacggc ggtggaattg ggaaccgcag ttacaaaggc tctgttcgag     120
aagaacgacc aggtcaaaga ccatgtagaa caagtcattt ttggcaacgt tttacaggca     180
gggaacggcc agaatcccgc ccgtcagatc gcccttaatt ctggcctgtc cgcagagata     240
ccggcttcga ctattaacca ggtgtgtggt tctggcctga agcaataag catggcgcgc      300 caacagatcc tactcggaga gcggaagta atagtagcag gaggtatcga atccatgacg      360
aatgcgccga gtattacata ttataataaa gaagaagaca ccctctcaaa gcctgttcct     420
acgatgacct tcgatggtct gaccgacgcg tttagcggaa agattatggg tttaacagcc     480
gaaaatgttg ccgaacagta cggcgtatca cgtgaggccc aggacgcctt tgcgtatgga     540
tcgcagatga aagcagcaaa ggcccaagaa cagggcattt tcgcagctga aatactgcct     600
cttgaaatag gggacgaagt tattactcag gacgaggggg ttcgtcaaga gaccaccctc     660
gaaaaattaa gtctgcttcg gaccattttt aaagaagatg gtactgttac agcgggcaac     720
gcctcaacga tcaatgatgg cgcctcagcc gtgatcattg catcaaagga gtttgctgag     780
acaaaccaga ttccctacct tgcgatcgta catgatatta cagagatagg cattgatcca     840
tcaataatgg gcattgctcc cgtgagtgcg atcaataaac tgatcgatcg taaccaaatt     900
agcatggaag aaatcgatct ctttgaaatt aatgaggcat ttgcagcatc ctcggtggta     960
gttcaaaaag agttaagcat tcccgatgaa agatcaata ttggcggttc cggtattgca    1020
ctaggccatc ctcttggcgc cacaggagcg cgcattgtaa ccaccctagc gcaccagttg    1080
aaacgtacac acggacgcta tggtattgcc tccctgtgca ttggcggtgg ccttggccta    1140
gcaatattaa tagaagtgcc tcaggaagat cagccggtta aaaaatttta tcaattggcc    1200
cgtgaggacc gtctggctag acttcaggag caagccgtga tcagcccagc tacaaaacat    1260
gtactggcag aaatgacact tcctgaagat attgccgaca atctgatcga aaatcaaata    1320
tctgaaatgg aaatccctct tggtgtggct ttgaatctga gggtcaatga taagagttat    1380
accatcccac tagcaactga ggaaccgagt gtaatcgctg cctgtaataa tggtgcaaaa    1440
atggcaaacc acctgggcgg ttttcagtca gaattaaaag atggtttcct gcgtgggcaa    1500
attgtactta tgaacgtcaa agaacccgca actatcgagc atacgatcac ggcagagaaa    1560
gcggcaattt ttcgtgccgc agcgcagtca catccatcga ttgtgaaacg aggtgggggt    1620
ctaaaagaga tagtagtgcg tacgttcgat gatgatccga cgttcctgtc tattgatctg    1680
atagttgata ctaaagacgc aatgggcgct aacatcatta acaccattct cgagggtgta    1740
gccggctttc tgagggaaat ccttaccgaa gaattctgt tctctatttt atctaattac    1800
gcaaccgaat caattgtgac cgccagctgt cgcataccct acgaagcact gagtaaaaaa    1860
```

```
ggtgatggta acgaatcgc tgaaaaagtg gctgctgcat ctaaatttgc ccagttagat    1920
ccttatcgag ctgcaaccca caacaaaggt attatgaatg gtattgaggc cgtcgttttg    1980
gcctcaggaa atgacacacg ggcggtcgcg gcagccgcac atgcgtatgc ttcacgcgat    2040
cagcactatc ggggcttaag ccagtggcag gttgcagaag gcgcgttaca cggggagatc    2100
agtctaccac ttgcactcgg cagcgttggc ggtgcaattg aggtcttgcc taaagcgaag    2160
gcggcattcg aaatcatggg gatcacagag gcgaaggagc tggcagaagt cacagctgcg    2220
gtagggctgg cgcaaaacct ggcggcgtta agagcgcttg ttagtgaagg aatacagcaa    2280
ggtcacatgt cgctccaggc tcgctctctt gcattatcgg taggtgctac aggcaaggaa    2340
gttgaaatcc tggccgaaaa attacagggc tctcgtatga atcaggcgaa cgctcagacc    2400
atactcgcag agatcagatc gcaaaaagtt gaattgtga                          2439
```

<210> SEQ ID NO 96
<211> LENGTH: 2442
<212> TYPE: DNA
<213> ORGANISM: Enterococcus faecium

<400> SEQUENCE: 96

```
atgaaagaag tggttatgat tgatgcggct cgcacaccca ttgggaaata cagaggtagt      60
cttagtcctt ttacagcggt ggagctgggg acactggtca cgaaagggct gctggataaa     120
acaaagctta gaaagacaa gatagaccaa gtgatattcg gcaatgtgct tcaggcagga     180
aacggacaaa acgttgcaag acaaatagcc ctgaacagtg gcttaccagt tgacgtgccg     240
gcgatgacta ttaacgaagt ttgcgggtcc ggaatgaaag cggtgatttt agcccgccag     300
ttaatacagt taggggaggc agagttggtc attgcagggg gtacggagtc aatgtcacaa     360
gcacccatgc tgaaacctta ccagtcagag accaacgaat acggagagcc gatatcatca     420
atggttaatg acgggctgac ggatgcgttt tccaatgctc acatgggtct tactgccgaa     480
aaggtggcga cccagttttc agtgtcgcgc gaggaacaag accggtacgc attgtccagc     540
caattgaaag cagcgcacgc ggttgaagcc ggggtgttct cagaagagat tattccggtt     600
aagattagcg acgaggatgt cttgagtgaa gacgaggcag taagaggcaa cagcactttg     660
gaaaaactgg caccttgcg acggtgtttt tctgaagagg gcacggttac cgctggcaat     720
gcttcaccgc tgaatgacgg cgctagtgtc gtgattcttg catcaaaaga atacgcggaa     780
aacaataatc tgccttacct ggcgacgata aaggaggttg cggaagttgg tatcgatcct     840
tctatcatgg gtattgcccc aataaaggcc attcaaaagt taacagatcg gtcgggcatg     900
aacctgtcca cgattgatct gttcgaaatt aatgaagcat cgcggcatc tagcattgtt     960 gtttctcaag agctgcaatt ggacgaagaa aaagtgaata tctatggcgg ggcgatagct    1020
ttaggccatc caatcggcgc aagcggagcc cggatactga caaccttagc atacggcctc    1080
ctgcgtgagc aaaagcgtta tggtattgcg tcattatgta tcggcggtgg tcttggtctg    1140
gccgtgctgt agaagctaa tatggagcag acccacaaag acgttcagaa gaaaaagtttt    1200 taccagctta cccccttccga gcggagatcg cagcttatcg agaagaacgt tctgactcaa    1260
gaaacggcac ttatttttcca ggagcagacg ttgtccgaag aactgtccga tcacatgatt    1320
gagaatcagg tctccgaagt ggaaattcca atgggaattg cacaaaattt tcagattaat    1380
ggcaagaaaa aatggattcc tatggcgact gaagaacctt cagtaatagc ggcagcatcg    1440 aacgcgcca aatctgcgg gaacattgc gcggaaacgc ctcagcggct tatgcgcggg    1500
cagattgtcc tgtctggcaa atcagaatat caagccgtga taaatgccgt gaatcatcgc    1560
```

```
aaagaagaac tgattctttg cgcaaacgag tcgtacccga gtattgttaa acgcggggga   1620
ggtgttcagg atatttctac gcgggagttt atgggttctt ttcacgcgta tttatcaatc   1680
gactttctgg tggacgtcaa ggacgcaatg ggggcaaaca tgatcaactc tattctcgaa   1740
agcgttgcaa ataaactgcg tgaatggttc ccggaagagg aaatactgtt ctccatcctg   1800
tcaaacttcg ctacggagtc cctggcatct gcatgttgcg agattccttt gaaagactt    1860 ggtcgtaaca agaaattgg tgaacagatc gccaagaaaa ttcaacaggc aggggaatat    1920
gctaagcttg acccttaccg cgcggcaacc cataacaagg ggattatgaa cggtatcgaa   1980
gccgtcgttg ccgcaacggg aaacgacaca cgggctgttt ccgcttctat tcacgcatac   2040
gccgcccgta atggcttgta ccaaggttta acggattggc agatcaaggg cgataaactg   2100
gttggtaaat taacagtccc actggctgtg gcgactgtcg gtggcgcgtc gaacatatta   2160
ccaaaagcca agcttccct cgccatgctg gatattgatt ccgcaaaaga actggcccaa    2220
gtgatcgccg cggtaggttt agcacagaat ctggcggcgt tacgtgcatt agtgacagaa   2280
ggcattcaga aggacacat gggcttgcaa gcacgttctt tagcgatttc gataggtgcc    2340
atcggtgagg agatagagca agtcgcgaaa aaactgcgtg aagctgaaaa aatgaatcag   2400
caaacggcaa tacagatttt agaaaaaatt cgcgagaaat ga                      2442

<210> SEQ ID NO 97
<211> LENGTH: 2448
<212> TYPE: DNA
<213> ORGANISM: Enterococcus gallinarum

<400> SEQUENCE: 97
atggaagaag tggtaattat agatgcacgt cggactccga ttggtaaata tcacgggtcg     60
ttgaagaagt tttcagcggt ggcgctgggg acggccgtgg ctaaagacat gttcgaacgc   120
aaccagaaaa tcaaagagga gatcgcgcag gtcataattg gtaatgtctt gcaggcagga   180
aatggccaga accccgcgcg gcaagttgct cttcaatcag ggttgtccgt tgacattccc   240
gcttctacaa ttaacgaggt ttgtgggtct ggtttgaaag ctatcttgat gggcatggaa   300
caaatccaac tcggcaaagc gcaagtagtg ctggcaggcg gcattgaatc aatgacaaat   360
gcgccaagcc tgtcccacta taacaaggcg gaggatacgt atagtgtccc agtgtcgagc   420
atgacactgg atggtctgac agacgcattt tctagtaaac ctatgggatt aacagcggaa   480
aacgtcgcac agcgctacgg tatctcccgt gaggcgcaag atcaattcgc atatcaatct   540
cagatgaaag cagcaaaagc gcaggcagaa acaaattcg ctaaggaaat tgtgccactg    600
gcgggtgaaa ctaaaaccat cacagctgac gaagggatca gatcccaaac aacgatggag   660
aaactggcaa gtctcaaacc tgtttttaaa accgatggca ctgtaaccgc agggaatgct   720
agcaccatta tgacggggc cgcccttgtg ctgcttgcta gcaaaactta ctgcgaaact    780
aatgacatac cgtaccttgc gacaatcaaa gaaattgttg aagttggaat cgatccggag   840
attatgggca tctctccgat aaaagcgata caaacattgt acaaaatca aaaagttagc     900 ctcgaagata ttggagtttt tgaaataaat gaagcctttg ccgcaagtag catagtggtt   960
gaatctgagt tgggattaga tccggctaaa gttaaccgtt atggggtgg tatatcctta   1020 ggtcatgcaa ttgggcaac cggcgctcgc ctggccactt cactggtgta tcaaatgcag   1080
gagatacaag cacgttatgg tattgcgagc ctgtgcgttg gtggtggact tggactggca   1140 atgctttag aacgtccaac tattgagaag gctaaaccga cagacaaaaa gttctatgaa    1200
```

```
ttgtcaccag ctgaacggtt gcaagagctg gaaaatcaac agaaaatcag ttctgaaact    1260
aaacagcagt tatctcagat gatgcttgcc gaggacactg caaaccattt gatagaaaat    1320
caaatatcag agattgaact cccaatgggc gtcgggatga acctgaaggt tgatgggaaa    1380
gcctatgttg tgccaatggc gacggaagag ccgtccgtca tcgcggccat gtctaatggt    1440
gccaaaatgg ccggcgaaat tcacactcag tcgaaagaac ggctgctcag aggtcagatt    1500
gttttcagcg cgaagaatcc gaatgaaatc gaacagagaa tagctgagaa ccaagctttg    1560
attttcgaac gtgccgaaca gtcctatcct tccattgtga aaagagaggg aggtctccgc    1620
cgcattgcac ttcgtcattt tcctgccgat tctcagcagg agtctgcgga ccagtccaca    1680 ttttatcag tggacctttt tgtagatgtg aaagacgcga tgggggcaaa tatcataaat    1740
gcaatacttg agggcgtcgc agccctgttt cgcgaatggt tccccaatga ggaaattctt    1800
ttttctattc tctcgaactt ggctacggag agcttagtca cggctgtttg tgaagtccca    1860
tttagtgcac ttagcaagag aggtggtgca acggtggccc agaaaattgt gcaggcgtcg    1920
ctcttcgcaa agacagaccc ataccgcgca gtgacccaca caaagggat tatgaacggt    1980 gtagaggctg ttatgcttgc cacaggcaac gacacgcgcg cagtctcagc cgcttgtcat    2040
ggatacgcag cgcgcaccgg tagctatcag ggtctgacta actggacgat tgagtcggat    2100
cgcctggtag cgagataac actgccgctg ccatcgcta cagttggagg cgctaccaaa    2160
gtgttgccca agctcaagc ggcactggag attagtgatg ttcactcttc tcaagagctt    2220
gcagccttag cggcgtcagt aggtttagta caaaatctcg cggccctgcg cgcactggtt    2280
tccgaaggta tacaaaaagg gcacatgtcc atgcaagccc ggtctctcgc aatcgcggtc    2340
ggtgctgaaa agccgagat cgagcaggtc gccgaaaagt tgcggcagaa cccgccaatg    2400
aatcagcagc aggcgctccg ttttcttggc gagatccgcg aacaatga               2448

<210> SEQ ID NO 98
<211> LENGTH: 2475
<212> TYPE: DNA
<213> ORGANISM: Enterococcus casseliflavus

<400> SEQUENCE: 98
atggaagaag ttgtcatcat tgacgcactg cgtactccaa taggaaagta ccacggttcg      60
ctgaaagatt acacagctgt tgaactgggg acagtagcag caaaggcgtt gctggcacga     120
aatcagcaag caaaagaaca catagcgcaa gttattattg gcaacgtcct gcaagccgga     180
agtgggcaga atccaggccg acaagtcagt ttacagtcag gattgtcttc tgatatcccc     240
gctagcacga tcaatgaagt gtgtggctcg ggtatgaaag cgattctgat gggtatggag     300
caaattcagc tgaacaaagc ctctgtggtc ttaacaggcg gaattgaaag catgaccaac     360
gcgccgctgt ttagttatta caacaaggct gaggatcaat attcggcgcc ggttagcaca     420
atgatgcacg atggtctaac agatgctttc agttccaaac caatgggctt aaccgcagag     480
accgtcgctg agagatatgg aattacgcgt aaggaacaag atgaatttgc ttatcactct     540
caaatgaagg cggccaaagc ccaggcggcg aaaaagtttg atcaggaaat tgtaccoctg     600 acggaaaaat ccggaacggt tctccaggac gaaggcatca gagccgcgac aacagtcgag     660
aagctagctg agcttaaaac ggtgttcaaa aaagacggaa cagttacagc gggtaacgcc     720
tctacgataa atgatggcgc tgctatggta ttaatagcat caaatcttta ttgcgaagaa     780
caccagattc cttatctggc cgttataaag gagatcgttg aggtgggttt tgcccccgaa     840
ataatgggta tttccccat taaggctata gacaccctgc tgaaaaatca agcactgacc     900
```

```
atagaggata taggaatatt tgagattaat gaagcctttg ctgcgagttc gattgtggta      960
gaacgcgagt tgggcctgga ccccaaaaaa gttaatcgct atggcggtgg tatatcactc     1020
ggccacgcaa ttggggcgac gggagctcgc attgcgacga ccgttgctta tcagctgaaa     1080
gatacccagg agcgctacgg tatagcttcc ttatgcgttg gtggggtct tggattggcg      1140 atgcttctgg aaaacccatc ggccactgcc tcacaaacta attttgatga ggaatctgct     1200
tccgaaaaaa ctgagaagaa gaagttttat gcgctagctc taacgaacg cttagcgttt      1260 ttggaagccc aaggcgctat taccgctgct gaaaccctgg tcttccagga gatgaccta     1320 aacaaagaga cagccaatca cttaatcgaa aaccaaatca gcgaagttga aattccttta     1380
ggcgtgggcc tgaacttaca ggtgaatggg aaagcgtata atgttcctct ggccacggag     1440
gaaccgtccg ttatcgctgc gatgtcgaat ggcgccaaaa tggctggtcc tattacaaca    1500
acaagtcagg agaggctgtt acggggtcag attgtcttca tggacgtaca ggacccagaa     1560
gcaatattag cgaaagttga atccgagcaa gctaccattt cgcggtggc aaatgaaaca      1620 tacccgtcta tcgtgaaaag aggaggaggt ctgcgtagag tcattggcag gaatttcagt     1680
ccggccgaaa gtgacttagc cacggcgtat gtatcaattg acctgatggt agatgttaag     1740
gatgcaatgg gtgctaatat catcaatagt atcctagaag gtgttgcgga attgtttaga     1800
aaatggttcc cagaagaaga aatcctgttc tcaattctct ccaatctcgc gacagaaagt     1860
ctggtaacgg cgacgtgctc agttccgttt gataaattgt ccaaaactgg gaatggtcga     1920
caagtagctg gtaaaatagt gcacgcggcg gactttgcta agatagatcc atacagagct     1980
gccacacaca ataaaggtat tatgaatggc gttgaagcgt taatcttagc caccggtaat     2040
gacacccgtg cggtgtcggc tgcatgccac ggttacgcgg cacgcaatgg gcgaatgcaa     2100
gggcttacct cttggacgat tatcgaagat cggctgatag gctctatcac attacctttg     2160
gctattgcga cagtgggggg tgccacaaaa atcttgccaa aagcacaggc cgccctggcg     2220
ctaactggcg ttgagacggc gtcggaactg gccagcctgg cggcgagtgt gggattagtt     2280
caaaatttgg ccgctttacg agcactagtg agcgagggca ttcagcaagg gcacatgagt     2340
atgcaagcta gatccctggc cattagcgta ggtgcgaaag gtactgaaat agagcaacta     2400
gctgcgaagc tgagggcagc gacgcaaatg aatcaggagc aggctcgtaa atttctgacc     2460
gaaataagaa attaa                                                      2475
```

<210> SEQ ID NO 99
<211> LENGTH: 1158
<212> TYPE: DNA
<213> ORGANISM: Listeria grayi

<400> SEQUENCE: 99

```
atgaccatga acgttggaat cgataaaatg tcattctttg ttccacctta ctttgtggac       60
atgactgatc tggcagtagc acgggatgtc gatcccaata agtttctgat tggtattggc      120
caggaccaga tggcagttaa tccgaaaacg caggatattg tgacatttgc cacaaatgct      180
gccaaaaaca tactgtcagc tgaggacctt gataaaattg atatggtcat agtcggcacc      240
gagagtggaa tcgatgaatc caaagcgagt gccgtagtgc ttcacaggtt gctcggtatc      300
cagaagtttg ctcgctcctt tgaaatcaaa gaagcctgtt atggggggtac gcgggcttta     360 cagttcgctg taaaccacat taggaatcat cctgaatcaa aggttcttgt agttgcatca     420
gatatcgcga aatacggcct ggcttctgga ggtgaaccaa cgcaaggtgc aggcgctgtg     480
```

```
gctatgctcg tctcaactga ccctaagatc attgctttca acgacgatag cctcgcgctt    540
acacaagata tctatgactt ctggcgacca gttggacatg actatcctat ggtcgacggg    600
cctcttagta cagagaccta catccagtca tttcagaccg tatggcagga atacacaaaa    660
cggtcgcagc atgcactggc agactttgct gcccttagct ttcatatccc gtatactaaa    720
atgggcaaaa aggcgctgct tgcaatcctt gaaggcgaat cagaggaggc tcagaaccgt    780
atactagcaa aatatgaaaa gagtatagcc tactccagaa aggcgggtaa cctgtatacc    840
ggtagcctgt atctaggact tatttcactt ctggaaaatg cagaagacct aaagctggt     900 gatttaatag gcctcttttc ttacggttcc ggtgctgttg cggagttttt ctcaggaagg    960
ctggttgagg actatcagga acagctactt aaaacaaaac atgccgaaca gctggcccat   1020
agaaagcaac tgacaatcga ggagtacgaa acgatgttct ccgatcgctt ggacgtggac   1080
aaagacgccg aatacgaaga cacattagct tatagcattt cgtcagtccg aaacaccgta   1140
cgtgagtaca ggagttga                                                  1158
```

<210> SEQ ID NO 100
<211> LENGTH: 1155
<212> TYPE: DNA
<213> ORGANISM: Enterococcus faecium

<400> SEQUENCE: 100

```
atgaaaatcg gtattgaccg tctgtccttc ttcatcccga atttgtattt ggacatgact     60
gagctggcag aatcacgcgg ggatgatcca gctaaatatc atattggaat cggacaagat    120
cagatggcag tgaatcgcgc aaacgaggac atcataacac tgggtgcaaa cgctgcgagt    180
aagatcgtga cagagaaaga ccgcgagttg attgatatgg taatcgttgg cacggaatca    240
ggaattgacc actccaaagc aagcgccgtg attattcacc atctccttaa aattcagtcg    300
ttcgcccgtt ctttcgaggt aaaagaagct tgctatggcg gaactgctgc cctgcacatg    360
gcgaaggagt atgtcaaaaa tcatccggag cgtaaggtct tggtaattgc gtcagacatc    420
gcgcgttatg gtttggccag cggaggagaa gttactcaag gcgtgggggc cgtagccatg    480
atgattacac aaaacccccg gattctttcg attgaagacg atagtgtttt tctcacagag    540
gatatctatg atttctggcg gcctgattac tccgagttcc ctgtagtgga cgggccccttt    600 tcaaactcaa cgtatatagaa gagttttcag aaagtttgga accggcacaa ggaattgtcc    660
ggaagagggc tggaagatta tcaagctatt gcttttcaca tacccatatac gaagatgggt    720 aagaaagcgc tccagagtgt tttagaccaa accgatgaag ataaccagga gcgcttaatg    780
gctagatatg aggagtctat tcgctatagc cggagaattg gtaacctgta cacaggcagc    840
ttgtaccttg gtcttacaag cttgttggaa aactctaaaa gtttacaacc gggagatcgg    900
atcggcctct tttcctatgg cagtggtgcg gtgtccgagt tctttaccgg gtatttagaa    960
gaaaattacc aagagtacct gttcgctcaa agccatcaag aaatgctgga tagccggact   1020
cggattacgg tcgatgaata cgagaccatc ttttcagaga ctctgccaga acatggtgaa   1080
tgcgccgaat atacgagcga cgtcccctttt tctataacca agattgagaa cgacattcgt   1140
tattataaaa tctga                                                    1155
```

<210> SEQ ID NO 101
<211> LENGTH: 1155
<212> TYPE: DNA
<213> ORGANISM: Enterococcus gallinarum

<400> SEQUENCE: 101

-continued

```
atgaacgtcg gcattgacaa aattaatttt ttcgttccac cgtattatct ggatatggtc    60
gacctggccc acgcacgcga agtggacccg aacaaattta caattggaat tggacaggat   120
cagatggctg tgagcaaaaa gacgcacgat atcgtaacat tcgcggctag tgccgcgaag   180
gaaattttag aacctgagga cttgcaagct atagacatgg ttatagttgg taccgaatcg   240
ggcattgacg agagcaaagc atccgcggtc gttttacatc gtttgttggg cgtacaacct   300
ttcgctcgca gttttgaaat taaagaagcc tgttacgggg caaccgcagg cattcagttt   360
gccaagactc atatacaagc gaacccggag agcaaggtcc tggtaattgc aagcgatata   420
gctcggtatg gtcttcggtc aggtggagag cccacacaag gcgcagggc agttgctatg    480 cttctcacgg caaatcccag aatcctgacc ttcgaaaacg acaatctgat gttaacgcag   540
gatatttatg acttctggag accacttggt cacgcttacc ctatggtaga tggccacctt   600
tccaatcaag tctatattga cagttttaag aaggtctggc aagcacattg cgaacgcaat   660
caagcttcta tatccgacta tgccgcgatt agttttcata ttccgtatac aaaaatgggt   720
aagaaagccc tgctcgctgt ttttgcagat gaagtggaaa ctgaacagga acgcgttatg   780
gcacggtatg aagagtctat cgtatattca cgccggatcg gcaacttgta tacgggatca   840
ttgtacctgg ggctgatatc cttattggaa acagttctc acctgtcggc gggcgaccgg    900
ataggattgt ttagttatgg gagtggcgct gtcagcgaat tttctccgg tcgtttagtg     960 gcaggctatg aaaatcaatt gaacaaagag gcgcataccc agctcctgga tcagcgtcag  1020 aagcttttcca tcgaagagta tgaggcgatt tttacagatt ccttagaaat tgatcaggat  1080
gcagcgttct cggatgacct gccatattcc atccgcgaga taaaaaacac gattcggtac   1140
tataaggaga gctga                                                    1155
```

<210> SEQ ID NO 102
<211> LENGTH: 1161
<212> TYPE: DNA
<213> ORGANISM: Enterococcus casseliflavus

<400> SEQUENCE: 102

```
atgaacgttg gaattgataa aatcaatttt ttcgttccgc cctatttcat tgatatggtg    60
gatctcgctc atgcaagaga agttgacccc aacaagttca ctataggaat aggccaagat   120
cagatggcag taaacaagaa aacgcaagat atcgtaacgt tcgcgatgca cgccgcgaag   180
gatattctga ctaaggaaga tttacaggcc atagatatgg taatagtggg gactgagtct   240
gggatcgacg agagcaaggc aagtgctgtc gtattgcatc ggcttttagg tattcagcct   300
tttgcgcgct ccttttgaaat taaggaggca tgctatgggg ccactgccgg ccttcagttt   360
gcaaaagctc atgtgcaggc taatcccag agcaaggtcc tggtggtagc ttccgatata   420
gcacgctacg gactggcatc cggaggagaa ccgactcaag gtgtaggtgc tgtggcaatg   480
ttgatttccg ctgatccagc tatcttgcag ttagaaaatg ataatctcat gttgacccaa   540
gatatatacg attttggcg cccggtcggg catcaatatc ctatggtaga cggccatctg   600
tctaatgccg tctatataga cagctttaaa caagtctggc aagcacattg cgagaaaaac   660
caacggactc taaagatta tgctgcattg tcgttccata ttccgtacac gaaaatgggt   720
aagaaagctc tgttagcggt ttttgcggag gaagatgaga cagaacaaaa gcggttaatg   780
gcacgttatg aagaatcaat tgtatacagt cgtcggactg gaaatctgta tactggctca   840
ctctatctgg gcctgatttc cttactggag aatagtagca gtttacaggc gaacgatcgc   900
```

```
ataggtctgt ttagctatgg ttcaggggcc gttgcggaat ttttcagtgg cctcttggta    960
ccgggttacg agaaacaatt agcgcaagct gcccatcaag ctcttctgga cgaccggcaa   1020
aaactgacta tcgcagagta cgaagccatg tttaatgaaa ccattgatat tgatcaggac   1080
cagtcatttg aggatgactt actgtactcc atcagagaga tcaaaaacac tattcgctac   1140
tataacgagg agaatgaata a                                            1161
```

<210> SEQ ID NO 103  
<211> LENGTH: 329  
<212> TYPE: PRT  
<213> ORGANISM: Streptomyces sp. CL190

<400> SEQUENCE: 103

```
Met Thr Asp Val Arg Phe Arg Ile Ile Gly Thr Gly Ala Tyr Val Pro
1               5                   10                  15

Glu Arg Ile Val Ser Asn Asp Glu Val Gly Ala Pro Ala Gly Val Asp
            20                  25                  30

Asp Asp Trp Ile Thr Arg Lys Thr Gly Ile Arg Gln Arg Arg Trp Ala
        35                  40                  45

Ala Asp Asp Gln Ala Thr Ser Asp Leu Ala Thr Ala Ala Gly Arg Ala
    50                  55                  60

Ala Leu Lys Ala Ala Gly Ile Thr Pro Glu Gln Leu Thr Val Ile Ala
65                  70                  75                  80

Val Ala Thr Ser Thr Pro Asp Arg Pro Gln Pro Pro Thr Ala Ala Tyr
                85                  90                  95

Val Gln His His Leu Gly Ala Thr Gly Thr Ala Ala Phe Asp Val Asn
            100                 105                 110

Ala Val Cys Ser Gly Thr Val Phe Ala Leu Ser Ser Val Ala Gly Thr
        115                 120                 125

Leu Val Tyr Arg Gly Gly Tyr Ala Leu Val Ile Gly Ala Asp Leu Tyr
130                 135                 140

Ser Arg Ile Leu Asn Pro Ala Asp Arg Lys Thr Val Val Leu Phe Gly
145                 150                 155                 160

Asp Gly Ala Gly Ala Met Val Leu Gly Pro Thr Ser Thr Gly Thr Gly
                165                 170                 175

Pro Ile Val Arg Arg Val Ala Leu His Thr Phe Gly Gly Leu Thr Asp
            180                 185                 190

Leu Ile Arg Val Pro Ala Gly Gly Ser Arg Gln Pro Leu Asp Thr Asp
        195                 200                 205

Gly Leu Asp Ala Gly Leu Gln Tyr Phe Ala Met Asp Gly Arg Glu Val
    210                 215                 220

Arg Arg Phe Val Thr Glu His Leu Pro Gln Leu Ile Lys Gly Phe Leu
225                 230                 235                 240

His Glu Ala Gly Val Asp Ala Ala Asp Ile Ser His Phe Val Pro His
                245                 250                 255

Gln Ala Asn Gly Val Met Leu Asp Glu Val Phe Gly Glu Leu His Leu
            260                 265                 270

Pro Arg Ala Thr Met His Arg Thr Val Glu Thr Tyr Gly Asn Thr Gly
        275                 280                 285

Ala Ala Ser Ile Pro Ile Thr Met Asp Ala Ala Val Arg Ala Gly Ser
    290                 295                 300

Phe Arg Pro Gly Glu Leu Val Leu Leu Ala Gly Phe Gly Gly Gly Met
305                 310                 315                 320

Ala Ala Ser Phe Ala Leu Ile Glu Trp
```

<210> SEQ ID NO 104
<211> LENGTH: 2466
<212> TYPE: DNA
<213> ORGANISM: Lactococcus lactis

<400> SEQUENCE: 104

```
atgaccgagt ataacagcga ggcctatctg aaaaaactgg ataaatggtg gcgtgcagca      60
acctatctgg gtgcaggtat gatttttctg aaagaaaatc cgctgtttag cgttaccggc     120
accccgatta aagcagaaaa tctgaaagcc aatccgattg gtcattgggg caccgttagc     180
ggtcagacct ttctgtatgc acatgcaaat cgtctgatca caaatatga tcagaaaatg     240
ttttatatgg gtggtccggg tcatggtggt caggcaatgg ttgttccgag ctatctggat     300
ggtagctata ccgaagcata tccggaaatt acccaggatc tggaaggtat gagccgtctg     360
tttaaacgtt ttagctttcc gggtggtatt ggtagccata tgaccgcaca gacaccgggt     420
agcctgcatg aaggtggtga actgggttat gttctgagcc atgcaaccgg tgcaattctg     480
gatcagccgg aacaaattgc atttgcagtt gttggtgatg gtgaagccga accggtccg     540
ctgatgacca gctggcatag catcaaattt atcaacccga aaaacgatgg tgccattctg     600
ccgatcctgg atctgaatgg cttttaaaatc agcaatccga ccctgtttgc acgtaccagt     660
gatgttgata ttcgcaaatt tttcgaaggc ctgggctata gtccgcgtta tattgaaaat     720
gatgatattc acgactatat ggcctaccat aaactggcag cagaagtttt tgataaagcc     780
atcgaagata tccatcagat ccagaaagat gcccgtgaag ataatcgtta tcagaatggt     840
gaaattccgg catggccgat tgttattgca cgtctgccga aaggttgggg tggccctcgt     900
tataatgatt ggagcggtcc gaaatttgat ggtaaaggta tgccgattga acatagcttt     960
cgtgcacatc aggttccgct gccgctgagc agcaaaata tgggcacccct gccggaattt    1020
gttaaatgga tgacctcata tcagcctgaa acactgttta atgcagatgg ttcactgaaa    1080
gaggaactgc gcgattttgc accgaaaggc gaaatgcgta tggcaagtaa tccggttacc    1140
aatggtggtt tgatagcag caatctggtt ctgccggatt ggcaagaatt tgcaaacccg    1200
attagcgaaa ataatcgtgg taaactgctg ccggacacca tgataatat ggatatgaat    1260
gtgctgagca gtattttgc cgaaatcgtt aaactgaatc cgacacgttt tcgcctgttt    1320
ggtccggatg aaaccatgag caatcgtttt tgggaaatgt tcaaagtgac caatcgtcag    1380
tggatgcagg ttatcaaaaa tccgaacgat gaattcatta gtccggaagg tcgtattatt    1440
gatagccagc tgagcgaaca tcaggcagaa ggttggctgg aaggctatac cctgaccggt    1500
cgtaccggtg cctttgcaag ctatgaaagc tttctgcgtg ttgtggatag catgctgacc    1560
cagcatttca aatggattcg tcaggcagcc gaccagaaat ggcgtcatga ttatccgagc    1620
ctgaatgtta ttagcaccag caccgttttt cagcaggatc ataatggtta tacccatcag    1680
gatccgggta tgctgacaca tctggcagag aaaaaaagcg atttttatccg tcagtatctg    1740
cctgccgatg gtaataccct gctggcagtg tttgatcgtg catttcagga tcgtagcaaa    1800
atcaatcata ttgtggcaag caaacagcct cgtcagcagt ggtttaccaa agaagaagcc    1860
gagaaactgg ccaccgatgg cattgcaacc attgattggg cgagcaccgc aaaagatggc    1920
gaagcagttg atctggtttt tgcaagtgcc ggtgcagaac cgaccattga aaccctggca    1980
gccctgcatc tggttaatga agtgtttccg caggcaaaat ttcgctatgt taatgttgtt    2040
gagctgggtc gtctgcagaa aaagaaaggt gcactgaatc aagaacgtga actgtccgat    2100
```

```
gaagaattcg agaaatattt cggtccgagc ggtacaccgg ttattttttgg ttttcatggt    2160 tatgaggatc tgattgaaag catctttttat cagcgtggtc atgatggcct gatcgttcat    2220
ggctatcgcg aagatggtga tattaccacc acctatgata tgcgtgttta tagcgaactg    2280
gatcgttttc atcaggccat tgatgcaatg caggtactgt atgtgaatcg caaagttaat    2340
cagggtctgg ccaaagcatt tatcgatcgt atgaaacgta ccctggtgaa acattttgaa    2400
gtgacccgta atgaaggcgt ggatattccg gattttaccg aatgggtttg gagcgatctg    2460
aagaaa                                                                2466
```

<210> SEQ ID NO 105
<211> LENGTH: 822
<212> TYPE: PRT
<213> ORGANISM: Lactococcus lactis

<400> SEQUENCE: 105

```
Met Thr Glu Tyr Asn Ser Glu Ala Tyr Leu Lys Lys Leu Asp Lys Trp
1               5                   10                  15

Trp Arg Ala Ala Thr Tyr Leu Gly Ala Gly Met Ile Phe Leu Lys Glu
            20                  25                  30

Asn Pro Leu Phe Ser Val Thr Gly Thr Pro Ile Lys Ala Glu Asn Leu
        35                  40                  45

Lys Ala Asn Pro Ile Gly His Trp Gly Thr Val Ser Gly Gln Thr Phe
    50                  55                  60

Leu Tyr Ala His Ala Asn Arg Leu Ile Asn Lys Tyr Asp Gln Lys Met
65                  70                  75                  80

Phe Tyr Met Gly Gly Pro Gly His Gly Gln Ala Met Val Val Pro
                85                  90                  95

Ser Tyr Leu Asp Gly Ser Tyr Thr Glu Ala Tyr Pro Glu Ile Thr Gln
            100                 105                 110

Asp Leu Glu Gly Met Ser Arg Leu Phe Lys Arg Phe Ser Phe Pro Gly
        115                 120                 125

Gly Ile Gly Ser His Met Thr Ala Gln Thr Pro Gly Ser Leu His Glu
    130                 135                 140

Gly Gly Glu Leu Gly Tyr Val Leu Ser His Ala Thr Gly Ala Ile Leu
145                 150                 155                 160

Asp Gln Pro Glu Gln Ile Ala Phe Ala Val Val Gly Asp Gly Glu Ala
                165                 170                 175

Glu Thr Gly Pro Leu Met Thr Ser Trp His Ser Ile Lys Phe Ile Asn
            180                 185                 190

Pro Lys Asn Asp Gly Ala Ile Leu Pro Ile Leu Asp Leu Asn Gly Phe
        195                 200                 205

Lys Ile Ser Asn Pro Thr Leu Phe Ala Arg Thr Ser Asp Val Asp Ile
    210                 215                 220

Arg Lys Phe Phe Glu Gly Leu Gly Tyr Ser Pro Arg Tyr Ile Glu Asn
225                 230                 235                 240

Asp Asp Ile His Asp Tyr Met Ala Tyr His Lys Leu Ala Ala Glu Val
                245                 250                 255

Phe Asp Lys Ala Ile Glu Asp Ile His Gln Ile Gln Lys Asp Ala Arg
            260                 265                 270

Glu Asp Asn Arg Tyr Gln Asn Gly Glu Ile Pro Ala Trp Pro Ile Val
        275                 280                 285

Ile Ala Arg Leu Pro Lys Gly Trp Gly Gly Pro Arg Tyr Asn Asp Trp
    290                 295                 300
```

```
Ser Gly Pro Lys Phe Asp Gly Lys Gly Met Pro Ile Glu His Ser Phe
305                 310                 315                 320

Arg Ala His Gln Val Pro Leu Pro Leu Ser Ser Lys Asn Met Gly Thr
            325                 330                 335

Leu Pro Glu Phe Val Lys Trp Met Thr Ser Tyr Gln Pro Glu Thr Leu
            340                 345                 350

Phe Asn Ala Asp Gly Ser Leu Lys Glu Glu Leu Arg Asp Phe Ala Pro
            355                 360                 365

Lys Gly Glu Met Arg Met Ala Ser Asn Pro Val Thr Asn Gly Gly Val
370                 375                 380

Asp Ser Ser Asn Leu Val Leu Pro Asp Trp Gln Glu Phe Ala Asn Pro
385                 390                 395                 400

Ile Ser Glu Asn Asn Arg Gly Lys Leu Leu Pro Asp Thr Asn Asp Asn
            405                 410                 415

Met Asp Met Asn Val Leu Ser Lys Tyr Phe Ala Glu Ile Val Lys Leu
            420                 425                 430

Asn Pro Thr Arg Phe Arg Leu Phe Gly Pro Asp Glu Thr Met Ser Asn
            435                 440                 445

Arg Phe Trp Glu Met Phe Lys Val Thr Asn Arg Gln Trp Met Gln Val
450                 455                 460

Ile Lys Asn Pro Asn Asp Glu Phe Ile Ser Pro Glu Gly Arg Ile Ile
465                 470                 475                 480

Asp Ser Gln Leu Ser Glu His Gln Ala Glu Gly Trp Leu Glu Gly Tyr
            485                 490                 495

Thr Leu Thr Gly Arg Thr Gly Ala Phe Ala Ser Tyr Glu Ser Phe Leu
            500                 505                 510

Arg Val Val Asp Ser Met Leu Thr Gln His Phe Lys Trp Ile Arg Gln
            515                 520                 525

Ala Ala Asp Gln Lys Trp Arg His Asp Tyr Pro Ser Leu Asn Val Ile
            530                 535                 540

Ser Thr Ser Thr Val Phe Gln Gln Asp His Asn Gly Tyr Thr His Gln
545                 550                 555                 560

Asp Pro Gly Met Leu Thr His Leu Ala Glu Lys Lys Ser Asp Phe Ile
            565                 570                 575

Arg Gln Tyr Leu Pro Ala Asp Gly Asn Thr Leu Leu Ala Val Phe Asp
            580                 585                 590

Arg Ala Phe Gln Asp Arg Ser Lys Ile Asn His Ile Val Ala Ser Lys
            595                 600                 605

Gln Pro Arg Gln Gln Trp Phe Thr Lys Glu Glu Ala Glu Lys Leu Ala
            610                 615                 620

Thr Asp Gly Ile Ala Thr Ile Asp Trp Ala Ser Thr Ala Lys Asp Gly
625                 630                 635                 640

Glu Ala Val Asp Leu Val Phe Ala Ser Ala Gly Ala Glu Pro Thr Ile
            645                 650                 655

Glu Thr Leu Ala Ala Leu His Leu Val Asn Glu Val Phe Pro Gln Ala
            660                 665                 670

Lys Phe Arg Tyr Val Asn Val Val Glu Leu Gly Arg Leu Gln Lys Lys
            675                 680                 685

Lys Gly Ala Leu Asn Gln Glu Arg Glu Leu Ser Asp Glu Glu Phe Glu
690                 695                 700

Lys Tyr Phe Gly Pro Ser Gly Thr Pro Val Ile Phe Gly Phe His Gly
705                 710                 715                 720
```

```
Tyr Glu Asp Leu Ile Glu Ser Ile Phe Tyr Gln Arg Gly His Asp Gly
            725                 730                 735

Leu Ile Val His Gly Tyr Arg Glu Asp Gly Asp Ile Thr Thr Thr Tyr
        740                 745                 750

Asp Met Arg Val Tyr Ser Glu Leu Asp Arg Phe His Gln Ala Ile Asp
            755                 760                 765

Ala Met Gln Val Leu Tyr Val Asn Arg Lys Val Asn Gln Gly Leu Ala
        770                 775                 780

Lys Ala Phe Ile Asp Arg Met Lys Arg Thr Leu Val Lys His Phe Glu
785                 790                 795                 800

Val Thr Arg Asn Glu Gly Val Asp Ile Pro Asp Phe Thr Glu Trp Val
            805                 810                 815

Trp Ser Asp Leu Lys Lys
        820

<210> SEQ ID NO 106
<211> LENGTH: 125
<212> TYPE: DNA
<213> ORGANISM: Enterobacteria phage lambda

<400> SEQUENCE: 106
aattcatata aaaacatac agataaccat ctgcggtgat aaattatctc tggcggtgtt      60
gacataaata ccactggcgg tgatactgag cacatcagca ggacgcactg accaccatga     120
aggtg                                                                 125

<210> SEQ ID NO 107
<211> LENGTH: 32
<212> TYPE: DNA
<213> ORGANISM: Artificial Sequence
<220> FEATURE:
<223> OTHER INFORMATION: Synthetic Construct

<400> SEQUENCE: 107
ctgtattcat gacgagtcct gttattggca cc                                   32

<210> SEQ ID NO 108
<211> LENGTH: 31
<212> TYPE: DNA
<213> ORGANISM: Artificial Sequence
<220> FEATURE:
<223> OTHER INFORMATION: Synthetic Construct

<400> SEQUENCE: 108
ctctatgaat tctcactcgt tgtcgccagc g                                    31

<210> SEQ ID NO 109
<211> LENGTH: 51
<212> TYPE: DNA
<213> ORGANISM: Artificial Sequence
<220> FEATURE:
<223> OTHER INFORMATION: Synthetic Construct

<400> SEQUENCE: 109
taaggaggaa taaaccatgc aaagtataat aggaaaacat aaggatgaag g              51

<210> SEQ ID NO 110
<211> LENGTH: 45
<212> TYPE: DNA
<213> ORGANISM: Artificial Sequence
<220> FEATURE:
<223> OTHER INFORMATION: Synthetic Construct
```

<400> SEQUENCE: 110
ttctagaaag cttcgttata catgccactg ccaattagtt atttc                              45

<210> SEQ ID NO 111
<211> LENGTH: 38
<212> TYPE: DNA
<213> ORGANISM: Artificial Sequence
<220> FEATURE:
<223> OTHER INFORMATION: Synthetic Construct

<400> SEQUENCE: 111
tgataacgaa taagagctcg agatctgcag ctggtacc                                     38

<210> SEQ ID NO 112
<211> LENGTH: 51
<212> TYPE: DNA
<213> ORGANISM: Artificial Sequence
<220> FEATURE:
<223> OTHER INFORMATION: Synthetic Construct

<400> SEQUENCE: 112
gactcgtcat ggtttattcc tccttattta atcgatacat taatatatac c                      51

<210> SEQ ID NO 113
<211> LENGTH: 37
<212> TYPE: DNA
<213> ORGANISM: Artificial Sequence
<220> FEATURE:
<223> OTHER INFORMATION: Synthetic Construct

<400> SEQUENCE: 113
ggaataaacc atgacgagtc cagttattgg aacaccc                                      37

<210> SEQ ID NO 114
<211> LENGTH: 36
<212> TYPE: DNA
<213> ORGANISM: Artificial Sequence
<220> FEATURE:
<223> OTHER INFORMATION: Synthetic Construct

<400> SEQUENCE: 114
tctcgagctc ttattcgtta tcacccgcag tagcgg                                       36

<210> SEQ ID NO 115
<211> LENGTH: 38
<212> TYPE: DNA
<213> ORGANISM: Artificial Sequence
<220> FEATURE:
<223> OTHER INFORMATION: Synthetic Construct

<400> SEQUENCE: 115
cgacaacgag taagagctcg agatctgcag ctggtacc                                     38

<210> SEQ ID NO 116
<211> LENGTH: 51
<212> TYPE: DNA
<213> ORGANISM: Artificial Sequence
<220> FEATURE:
<223> OTHER INFORMATION: Synthetic Construct

<400> SEQUENCE: 116
gagaggtcat ggtttattcc tccttattta atcgatacat taatatatac c                      51

<210> SEQ ID NO 117
<211> LENGTH: 36

```
<212> TYPE: DNA
<213> ORGANISM: Artificial Sequence
<220> FEATURE:
<223> OTHER INFORMATION: Synthetic Construct

<400> SEQUENCE: 117
ggaataaacc atgacctctc cagtaattgg cactcc                              36

<210> SEQ ID NO 118
<211> LENGTH: 32
<212> TYPE: DNA
<213> ORGANISM: Artificial Sequence
<220> FEATURE:
<223> OTHER INFORMATION: Synthetic Construct

<400> SEQUENCE: 118
tctcgagctc ttactcgttg tcgcctgccg tg                                  32

<210> SEQ ID NO 119
<211> LENGTH: 38
<212> TYPE: DNA
<213> ORGANISM: Artificial Sequence
<220> FEATURE:
<223> OTHER INFORMATION: Synthetic Construct

<400> SEQUENCE: 119
cgataatgaa taagagctcg agatctgcag ctggtacc                            38

<210> SEQ ID NO 120
<211> LENGTH: 51
<212> TYPE: DNA
<213> ORGANISM: Artificial Sequence
<220> FEATURE:
<223> OTHER INFORMATION: Synthetic Construct

<400> SEQUENCE: 120
gagaagtcat ggtttattcc tccttattta atcgatacat taatatatac c             51

<210> SEQ ID NO 121
<211> LENGTH: 36
<212> TYPE: DNA
<213> ORGANISM: Artificial Sequence
<220> FEATURE:
<223> OTHER INFORMATION: Synthetic Construct

<400> SEQUENCE: 121
ggaataaacc atgacttctc ccgtgattgg tactcc                              36

<210> SEQ ID NO 122
<211> LENGTH: 34
<212> TYPE: DNA
<213> ORGANISM: Artificial Sequence
<220> FEATURE:
<223> OTHER INFORMATION: Synthetic Construct

<400> SEQUENCE: 122
tctcgagctc ttattcatta tcgcccgccg tagc                                34

<210> SEQ ID NO 123
<211> LENGTH: 38
<212> TYPE: DNA
<213> ORGANISM: Artificial Sequence
<220> FEATURE:
<223> OTHER INFORMATION: Synthetic Construct

<400> SEQUENCE: 123
```
gctgaaaaaa taagagctcg agatctgcag ctggtacc                                    38

<210> SEQ ID NO 124
<211> LENGTH: 51
<212> TYPE: DNA
<213> ORGANISM: Artificial Sequence
<220> FEATURE:
<223> OTHER INFORMATION: Synthetic Construct

<400> SEQUENCE: 124
ccactgtcat ggtttattcc tccttattta atcgatacat taatatatac c                     51

<210> SEQ ID NO 125
<211> LENGTH: 46
<212> TYPE: DNA
<213> ORGANISM: Artificial Sequence
<220> FEATURE:
<223> OTHER INFORMATION: Synthetic Construct

<400> SEQUENCE: 125
ggaataaacc atgacagtgg actatgactc aaaagagtac ttagag                           46

<210> SEQ ID NO 126
<211> LENGTH: 36
<212> TYPE: DNA
<213> ORGANISM: Artificial Sequence
<220> FEATURE:
<223> OTHER INFORMATION: Synthetic Construct

<400> SEQUENCE: 126
tctcgagctc ttattttttc agcccttccc atttcc                                      36

<210> SEQ ID NO 127
<211> LENGTH: 38
<212> TYPE: DNA
<213> ORGANISM: Artificial Sequence
<220> FEATURE:
<223> OTHER INFORMATION: Synthetic Construct

<400> SEQUENCE: 127
ctggaaaggt taagagctcg agatctgcag ctggtacc                                    38

<210> SEQ ID NO 128
<211> LENGTH: 51
<212> TYPE: DNA
<213> ORGANISM: Artificial Sequence
<220> FEATURE:
<223> OTHER INFORMATION: Synthetic Construct

<400> SEQUENCE: 128
cttcagccat ggtttattcc tccttattta atcgatacat taatatatac c                     51

<210> SEQ ID NO 129
<211> LENGTH: 32
<212> TYPE: DNA
<213> ORGANISM: Artificial Sequence
<220> FEATURE:
<223> OTHER INFORMATION: Synthetic Construct

<400> SEQUENCE: 129
ggaataaacc atggctgaag ccactgccca tc                                          32

<210> SEQ ID NO 130
<211> LENGTH: 39
<212> TYPE: DNA
<213> ORGANISM: Artificial Sequence
<220> FEATURE:
<223> OTHER INFORMATION: Synthetic Construct

<400> SEQUENCE: 130
tctcgagctc ttaacctttc caggtccaat tccggattt        39

<210> SEQ ID NO 131
<211> LENGTH: 38
<212> TYPE: DNA
<213> ORGANISM: Artificial Sequence
<220> FEATURE:
<223> OTHER INFORMATION: Synthetic Construct

<400> SEQUENCE: 131
atggcatgta taagagctcg agatctgcag ctggtacc        38

<210> SEQ ID NO 132
<211> LENGTH: 51
<212> TYPE: DNA
<213> ORGANISM: Artificial Sequence
<220> FEATURE:
<223> OTHER INFORMATION: Synthetic Construct

<400> SEQUENCE: 132
ttgattgcat ggtttattcc tccttattta atcgatacat taatatatac c        51

<210> SEQ ID NO 133
<211> LENGTH: 34
<212> TYPE: DNA
<213> ORGANISM: Artificial Sequence
<220> FEATURE:
<223> OTHER INFORMATION: Synthetic Construct

<400> SEQUENCE: 133
ggaataaacc atgcaatcaa tcatcggcaa acac        34

<210> SEQ ID NO 134
<211> LENGTH: 38
<212> TYPE: DNA
<213> ORGANISM: Artificial Sequence
<220> FEATURE:
<223> OTHER INFORMATION: Synthetic Construct

<400> SEQUENCE: 134
tctcgagctc ttatacatgc cattgccagt ttgtgatc        38

<210> SEQ ID NO 135
<211> LENGTH: 28
<212> TYPE: DNA
<213> ORGANISM: Artificial Sequence
<220> FEATURE:
<223> OTHER INFORMATION: Synthetic Construct

<400> SEQUENCE: 135
catgcgagca tgatccagag atttctga        28

<210> SEQ ID NO 136
<211> LENGTH: 28
<212> TYPE: DNA
<213> ORGANISM: Artificial Sequence
<220> FEATURE:
<223> OTHER INFORMATION: Synthetic Construct

<400> SEQUENCE: 136
gcttgtccgc aaacggacat atcaaggt        28

```
<210> SEQ ID NO 137
<211> LENGTH: 24
<212> TYPE: DNA
<213> ORGANISM: Artificial Sequence
<220> FEATURE:
<223> OTHER INFORMATION: Synthetic Construct

<400> SEQUENCE: 137
cagctcccat gagcgaagcg gagt                                          24

<210> SEQ ID NO 138
<211> LENGTH: 24
<212> TYPE: DNA
<213> ORGANISM: Artificial Sequence
<220> FEATURE:
<223> OTHER INFORMATION: Synthetic Construct

<400> SEQUENCE: 138
gacgcgtcag cgtcgcatcc ggca                                          24

<210> SEQ ID NO 139
<211> LENGTH: 27
<212> TYPE: DNA
<213> ORGANISM: Artificial Sequence
<220> FEATURE:
<223> OTHER INFORMATION: Synthetic Construct

<400> SEQUENCE: 139
gctgcgatcg actgactatc gcaccga                                       27

<210> SEQ ID NO 140
<211> LENGTH: 27
<212> TYPE: DNA
<213> ORGANISM: Artificial Sequence
<220> FEATURE:
<223> OTHER INFORMATION: Synthetic Construct

<400> SEQUENCE: 140
cagacgcctg gcccacgttg tggatca                                       27

<210> SEQ ID NO 141
<211> LENGTH: 27
<212> TYPE: DNA
<213> ORGANISM: Artificial Sequence
<220> FEATURE:
<223> OTHER INFORMATION: Synthetic Construct

<400> SEQUENCE: 141
gcagcggacg ggcgagtaga ttgcgca                                       27

<210> SEQ ID NO 142
<211> LENGTH: 25
<212> TYPE: DNA
<213> ORGANISM: Artificial Sequence
<220> FEATURE:
<223> OTHER INFORMATION: Synthetic Construct

<400> SEQUENCE: 142
gtgatctaca acacgcctta tctat                                         25
```